(12) United States Patent
Noguchi et al.

(10) Patent No.: US 12,295,947 B2
(45) Date of Patent: *May 13, 2025

(54) TETRAHYDROQUINOLINE DERIVATIVES AS P2X7 RECEPTOR ANTAGONISTS

(71) Applicants: RaQualia Pharma Inc., Nagoya (JP); Asahi Kasei Pharma Corporation, Tokyo (JP)

(72) Inventors: Hirohide Noguchi, Nagoya (JP); Yoshimasa Arano, Nagoya (JP); Kazuo Ando, Nagoya (JP); Kazuki Toyoshima, Tokyo (JP); Toshihiko Sone, Tokyo (JP); Koki Matsubara, Tokyo (JP)

(73) Assignees: RaQualia Pharma Inc., Nagoya (JP); Asahi Kasei Pharma Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,423

(22) Filed: Jul. 22, 2022

(65) Prior Publication Data

US 2023/0149382 A1    May 18, 2023

Related U.S. Application Data

(63) Continuation of application No. 17/112,097, filed on Dec. 4, 2020, now Pat. No. 11,439,633, which is a continuation of application No. 16/491,119, filed as application No. PCT/JP2018/009627 on Mar. 13, 2018, now Pat. No. 11,077,100.

(30) Foreign Application Priority Data

Mar. 13, 2017 (JP) .................. 2017-047794

(51) Int. Cl.
    *C07D 215/20*   (2006.01)
    *A61K 31/47*    (2006.01)
    *C07D 215/06*   (2006.01)

(52) U.S. Cl.
    CPC ............ *A61K 31/47* (2013.01); *C07D 215/06* (2013.01)

(58) Field of Classification Search
    CPC .. C07D 471/04; C07D 215/20; A61K 31/437; A61K 31/47; A61P 25/00; A61P 29/00; A61P 35/00; A61P 37/00; A61P 25/02
    USPC .................. 546/118, 169, 152; 514/303, 311
    See application file for complete search history.

(56) References Cited

U.S. PATENT DOCUMENTS

| 6,956,047 B1 | 10/2005 | Chen |
| 7,125,880 B1 | 10/2006 | Chen |
| 11,077,100 B2 | 8/2021 | Noguchi |

FOREIGN PATENT DOCUMENTS

| WO | 2001/07051 | 2/2001 |
| WO | 2001/53263 | 7/2001 |
| WO | 2001/57023 | 8/2001 |
| WO | 2004/106305 | 12/2004 |
| WO | 2005/009968 | 2/2005 |
| WO | 2005/070891 | 8/2005 |
| WO | 2008/005368 | 1/2008 |
| WO | 2008/100867 | 8/2008 |
| WO | 2008/116814 | 10/2008 |
| WO | 2008/124153 | 10/2008 |
| WO | 2009/064449 | 5/2009 |
| WO | 2009/089057 | 7/2009 |
| WO | 2010/137351 | 12/2010 |
| WO | 2013/014587 | 1/2013 |
| WO | 2013/062964 | 5/2013 |
| WO | 2013/108227 | 7/2013 |
| WO | 2013/169563 | 11/2013 |
| WO | 2014/025651 | 2/2014 |
| WO | 2014/097140 | 6/2014 |
| WO | 2014/115072 | 7/2014 |
| WO | 2014/115078 | 7/2014 |
| WO | 2014/152604 | 9/2014 |
| WO | 2015/187905 | 12/2015 |
| WO | 2016/019228 | 2/2016 |
| WO | 2016/039983 | 3/2016 |

OTHER PUBLICATIONS

Australian Office Action for Australian Application No. 2018235561, dated Jan. 17, 2020.
Basso, et al., "Behavioral profile of P2X7 receptor knockout mice in animal models of depression and anxiety: Relevance for neuropsychiatric disorders," Behavioural Brian Research, vol. 198, pp. 83-90, 2009.
Canadian Office Action for Canadian Application No. 3,049,192, dated Jul. 29, 2020.
Capuron, et al., "Immune System to Brain Signaling: Neuropsychopharmacological Implications," Pharmacology & Therapeutics, vol. 130, No. 2, pp. 226-238, May 2011.
Chessell, et al., "Disruption of the P2X7 purinoceptor gene abolishes chronic inflammatory and neuropathic pain," Pain, vol. 114, pp. 386-396, 2005.
Dantzer, "Cytokine, Sickness Behavior, and Depression," Immunology and Allergy Clinics of North America, vol. 29, No. 2, pp. 247-264, May 2009.
Duan, et al., "P2X7 Receptors: Properties and Relevance to CNS Function," Glia, vol. 54, pp. 738-746, 2006.
Extended European Search Report for European Application No. 18768497.2, dated Nov. 12, 2020.
Ferrari, et al., "The P2X7 Receptor: A Key Player in IL-1 Processing and Release," The Journal of Immunology, vol. 176, pp. 3877-3883, 2006.
File Registry of STN, RN 115271-77-7, Entered STN: Jul. 16, 1988.
File Registry on STN, RN 58111-53-8, Entered STN: Nov. 16, 1984.
Guile, et al., "Antagonists of the P2X7 Receptor: From Lead Identification to Drug Development," Journal of Medicinal Chemistry, vol. 52, No. 10, pp. 3123-3141, May 28, 2009.

(Continued)

*Primary Examiner* — Charanjit Aulakh
(74) *Attorney, Agent, or Firm* — Gabriel Magallanes

(57) ABSTRACT

The present invention relates to tetrahydroquinoline derivatives of the present invention or a pharmaceutically acceptable salt thereof or a prodrug thereof, processes for their preparation, pharmaceutical compositions containing them and their use in the treatment of various disorders which are mediated via the P2X7 receptor.

6 Claims, No Drawings

(56) References Cited

OTHER PUBLICATIONS

Gunosewoyo, et al. "P2X purinergic receptor ligands: recently patented compounds," Expert Opinion on Therapeutic Patents, vol. 20, No. 5, pp. 625-646, 2010.

Indian Office Action for Indian Application No. 201917029117, dated Mar. 11, 2020, with English translation.

International Preliminary Report on Patentability and English translation of the Written Opinion of the International Searching Authority for International Application No. PCT/JP2018/009627, dated Sep. 26, 2019.

International Search Report for PCT/JP2018/009627 (PCT/ISA/210) mailed on Jun. 12, 2018.

Japanese Office Action for Japanese Application No. 2019-550864, dated Jul. 7, 2020, with English translation.

Japanese Office Action for Japanese Application No. 2019-550864, dated Oct. 6, 2020, with English translation.

Muller, et al., "A Potential Role for P2X7R in Allergic Airway Inflammation in Mice and Humans," American Journal of Respiratory Cell and Molecular Biology, vol. 44, pp. 456-464, 2011.

North, "Molecular Physiology of P2X Receptors," Physiological Reviews, vol. 82, pp. 1013-1067, 2002.

Parvathenani, et al., "P2X7 Mediates Superoxice Production in Primary Microglia and is Up-regulated in a Transgenec Mouse Model of Alzheimer's Disease," The Journal of Biological Chemistry, vol. 278, No. 15, pp. 13309-13317, Apr. 11, 2003.

Russian Office Action and Search Report dated Feb. 19, 2020, for corresponding Russian Patent Application No. 2019131685, with English translation.

Skaper, et al., "The P2X7 purinergic receptor: from physiology to neurological disorders," The FASEB Journal, vol. 24, pp. 337-345, Feb. 2010.

Surprenant, et al., "Signaling at P2X Receptors," Annual Review of Physiology, vol. 71, pp. 333-359, 2009.

Surprenant, et al. "The Cytolytic P2Z Receptor for Extracellular ATP Identified as a P2X Receptor (P2X7)," Science, vol. 272, pp. 735-738, May 3, 1996.

Virginio, et al., "Kinetics of cell lysis, dye uptake and permeability changes in cells expressing the rat P2X7 receptor," Journal of Physiology, vol. 519.2, pp. 335-346, 1999.

Written Opinion of the International Searching Authority for PCT/JP2018/009627 (PCT/ISA/237) mailed on Jun. 12, 2018.

TETRAHYDROQUINOLINE DERIVATIVES AS P2X7 RECEPTOR ANTAGONISTS

RELATED APPLICATIONS

This application is a continuation of copending U.S. patent application Ser. No. 17/112,097 filed on Dec. 4, 2020, which is a continuation of U.S. Pat. No. 11,077,100, which issued on Aug. 3, 2021, which is the National Phase filed under 35 U.S.C. § 371 of International Application No. PCT/JP2018/009627, filed on Mar. 13, 2018, which claims the benefit under 35 U.S.C. § 119(a) to Patent Application No. 2017-047794, filed in Japan on Mar. 13, 2017, all of which are hereby expressly incorporated by reference into the present application.

TECHNICAL FIELD

This invention relates to tetrahydroquinoline derivatives that act as modulators of the P2X7 receptor. The present invention also relates to processes for the preparation of the compounds, pharmaceutical compositions containing the compounds, and to their use in the treatment of a wide range of diseases, syndromes, and disorders, which are associated with P2X7 receptor activity such as diseases of the autoimmune and inflammatory system, diseases of the nervous and neuro-immune system, diseases involved with neuroinflammation of the Central Nervous System (CNS) or diseases of the cardiovascular, metabolic, gastrointestinal and urogenital systems.

BACKGROUND ART

The P2X7 receptors (P2RX7) belong to the family of P2X ionotropic receptors that are activated by extracellular nucleotides, in particular adenosine triphosphate (ATP). P2X7 receptor is distinguished from other P2X family members by the high concentrations (mM range) of ATP required to activate it and by its ability to form a large pore upon prolonged or repeated stimulation (NPL 1 to NPL 3: North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (NPL 4 to NPL 6: Duan and Neary, Glia 2006, 54, 738-746; Skaper et al, FASEB J 2009, 24, 337-345; Surprenant and North, Annu. Rev. Physiol. 2009, 71, 333-359).

P2X7 receptor is located on many cell types, especially ones known to be involved in inflammatory and immune processes. Activation of the P2X7 receptor by extracellular nucleotides, in particular adenosine triphosphate, leads to the release of proinflammatory cytokines IL-1 beta and IL-18 (NPL 7: Muller, et al., Am. J. Respir. Cell Mol. Biol. 2011, 44, 456-464), giant cell formation (macrophages/microglial cells), degranulation (mast cells) and L-selectin shedding (lymphocytes) (NPL 8 to NPL 9: Ferrari et al., J. Immunol. 2006, 176, 3877-3883; Surprenant and North, Annu. Rev. Physiol. 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knockout mice. These mice demonstrate the role of P2X7 in the development and maintenance of pain, as these mice are protected from the development of both adjuvant-induced inflammatory pain and partial nerve ligation induced neuropathic pain (NPL 10: Chessell et al., Pain 2005, 114, 386-396). In addition, P2X7 knockout mice also exhibit an anti-depressant phenotype based on reduced immobility in forced swim and tail suspension tests (NPL 11: Basso et al., Behav. Brain Res. 2009, 198, 83-90). Moreover, the P2X7 pathway is linked to the release of the proinflammatory cytokine, IL-1 beta, which has been linked to precipitation of mood disorders in humans (NPL 12 to NPL 13: Dantzer, Immunol. Allergy Clin. North Am. 2009, 29, 247-264; Capuron and Miller, Pharmacol. Ther. 2011, 130, 226-238). In addition, in murine models of Alzheimer's disease, P2X7 was upregulated around amyloid plaques indicating a role of this target in such pathology as well (NPL 14: Parvathenani et al., J. Biol. Chem. 2003, 278, 13309-13317).

There is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition, a recent report suggests a link between P2X7 receptor and chronic, inflammatory and neuropathic pain (NPL 15: Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in the treatment of a wide range of diseases, syndromes, and disorders, which are associated with P2X7 receptor activity such as diseases of the autoimmune and inflammatory system, diseases of the nervous and neuro-immune system, diseases involved with neuroinflammation of the CNS or diseases of the cardiovascular, metabolic, gastrointestinal and urogenital systems.

Several reviews on small molecule inhibitors of P2X7 which have been published are: NPL 16: Guile, S. D., et al., J. Med. Chem, 2009, 52, 3123-3141; and NPL 17: Gunosewoyo, H. and Kassiou, M., Exp Opin, 2010, 20, 625-646.

International patent application PTL 1: WO 2013/108227 purportedly describes aza-bicyclic pyridine derivatives as a P2X7 receptor antagonist. The chemical structures are dihydrofuropyridine derivatives and dihydropyranopyridine derivatives, which are quite different from tetrahydroquinoline derivatives of the present invention. They neither disclose nor suggest teterhydroquinoline derivatives.

Recently, PTL 2: WO 2016/039983 and PTL3: WO 2016/019228 also disclose aza-bicyclic compounds with P2X7 receptor antagonistic activities. Each chemical structure is triazolopyrazine derivative and indolizine derivative, respectively, which is quite different from a tetrahydroquinoline derivative of the present invention.

CITATION LIST

Patent Literature

{PTL 1} WO 2013/108227
{PTL 2} WO 2016/039983
{PTL 3} WO 2016/019228

Non Patent Literature

{NPL 1} North, R. A., Physiol. Rev. 2002, 82(4), 1013-67
{NPL 2} Surprenant, A., Rassendren, F. et al., Science 1996, 272(5262), 735-8
{NPL 3} Virginio, C., MacKenzie, A. et al., J. Physiol., 1999, 519, 335-46
{NPL 4} Duan and Neary, Glia 2006, 54, 738-746
{NPL 5} Skaper et al, FASEB J 2009, 24, 337-345
{NPL 6} Surprenant and North, Annu. Rev. Physiol. 2009, 71, 333-359
{NPL 7} Muller, et al. Am. J. Respir. Cell Mol. Biol. 2011, 44, 456-464
{NPL 8} Ferrari et al., J. Immunol. 2006, 176, 3877-3883
{NPL 9} Surprenant and North, Annu. Rev. Physiol. 2009, 71, 333-359
{NPL 10} Chessell et al., Pain 2005, 114, 386-396
{NPL 11} Basso et al., Behav. Brain Res. 2009, 198, 83-90
{NPL 12} Dantzer, Immunol. Allergy Clin. North Am. 2009, 29, 247-264
{NPL 13} Capuron and Miller, Pharmacol. Ther. 2011, 130, 226-238
{NPL 14} Parvathenani et al., J. Biol. Chem. 2003, 278, 13309-13317
{NPL 15} Chessell, I. P., Hatcher, J. P. et al., Pain, 2005, 114(3), 386-96
{NPL 16} Guile, S. D., et al., J. Med. Chem, 2009, 52, 3123-3141
{NPL 17} Gunosewoyo, H. and Kassiou, M., Exp Opin, 2010, 20, 625-646

SUMMARY OF INVENTION

Technical Problem

There is a need in the art for P2X7 antagonists that can be used to treat a disease, syndrome, or condition in a mammal including human, wherein the disease, syndrome, or condition is affected by the modulation of P2X7 receptors, such as diseases of the autoimmune and inflammatory system; diseases of the nervous and neuro-immune system; diseases involved with, and without, neuroinflammation of the CNS; diseases of the cardiovascular, metabolic, gastrointestinal and urogenital systems; skeletal disorders, diseases involving the secretory function of exocrine glands and glaucoma, Glomerulonephritis, Chaga's Disease, chlamydia, neuroblastoma, Tuberculosis, Polycystic Kidney Disease, cancer, and acne.

It is an objective of the invention to provide new P2X7 receptor antagonists that are good drug candidates. P2X7 antagonists should be well absorbed from the GI tract and should be metabolically stable and possess favorable pharmacokinetic properties. They should be non-toxic. Furthermore, the ideal drug candidate would exist in a physical form that is stable, non-hygroscopic and easily formulated. In particular, it has been desired that compounds would have to bind potently to the P2X7 receptor and show functional activity as antagonists. Also it has been desired that compounds would have favorable pharmacokinetic properties.

Solution to Problem

With respect to other compounds disclosed in the art, the compounds of the present invention may show less toxicity, good absorption and distribution, good solubility, less plasma protein binding, less drug-drug interaction, good metabolic stability. The present invention provides novel compounds which have excellent P2X7 antagonistic activities as well as excellent pharmacokinetic properties.

In addition, the tetrahydroquinoline derivatives of the present invention show an excellent selectivity for the P2X7 channel as compared with other P2X families, especially P2X1 channel. Involvement of P2X1 against auto regulation in kidney has been reported in P2X1 antagonist (NF 279) (Purinergic Signalling (2012) 8: 375-417). Thus, selective P2X7 compounds of the present invention lead to improvements in the side-effect profile.

The present invention provides the following items.

[1] A compound represented by the following formula (I):

[Chem. 1]

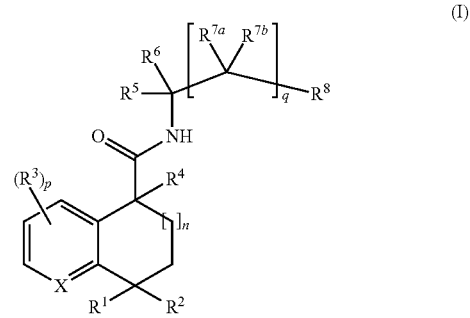

or a prodrug thereof or a pharmaceutically acceptable salt thereof,
wherein:
X is N or N-oxide;
n is 0 or 1; preferably n is 1;
$R^1$ is selected from the group consisting of:
(1) hydrogen, (2) halogen, (3) hydroxyl, (4) —$NH_2$, (5) —NH—$C_{1-6}$ alkyl and (6) —$S(O)_m$—$C_{1-6}$ alkyl; wherein m is independently 0, 1 or 2;
$R^2$ is selected from the group consisting of:
(1) hydrogen, (2) halogen, (3) $C_{1-6}$ alkyl and (4) —O—$C_{1-6}$ alkyl; wherein the $C_{1-6}$ alkyl or the —O—$C_{1-6}$ alkyl is unsubstituted or substituted with one or more substituents independently selected from the group consisting of: halogen, hydroxyl, —O—$C_{1-6}$ alkyl, —CN, —$NR^{9a}R^{10a}$, —(C=O)—$R^{9a}$, —(C=O)—$NR^{9a}R^{10a}$ and —$S(O)_m$—$R^{9a}$; wherein m is independently 0, 1 or 2;

$R^1$ may form =CH$_2$ or =O with $R^2$; or $R^1$ may form a 3 to 7 membered ring with $R^2$ which may contain one or more independently selected from the group consisting of: nitrogen atom, oxygen atom, sulfur atom and carbonyl group; wherein the 3 to 7 membered ring is unsubstituted or substituted one or more with C$_{1-6}$ alkyl;

$R^3$ is independently selected from the group consisting of:

(1) hydrogen, (2) halogen, (3) C$_{1-6}$ alkyl and (4) —O—C$_{1-6}$alkyl; preferably $R^3$ is hydrogen at 4-position against X;

p is 0, 1, 2 or 3; preferably p is 0 or 1;

when p is 2 or 3, each $R^3$ is the same or different;

$R^4$ is selected from the group consisting of:

(1) hydrogen, (2) halogen and (3) hydroxyl;

$R^5$ is hydrogen or C$_{1-6}$ alkyl;

$R^6$ is selected from the group consisting of:

(1) hydrogen, (2) C$_{1-6}$ alkyl, (3) hydroxyC$_{1-6}$ alkyl, (4) C$_{1-6}$ alkoxy C$_{1-6}$ alkyl and (5) heterocyclyl C$_{1-6}$ alkyl;

preferably $R^6$ is selected from the group consisting of (1) hydrogen and (2) C$_{1-6}$ alkyl;

$R^5$ may form a saturated 3 to 7 membered ring with $R^6$ which may contain a nitrogen atom, an oxygen atom, a sulfur atom or a double bond; or a saturated or unsaturated bicyclic 9 to 10 membered ring with $R^6$ which may contain a nitrogen atom, an oxygen atom or a sulfur atom; wherein the saturated 3 to 7 membered ring or the saturated or unsaturated bicyclic 9 to 10 membered ring is optionally substituted with 1 to 6 substituents independently selected from the group consisting of: (1) hydroxyl, (2) halogen, (3) —O-aryl and (4) —O—C$_{1-6}$ alkylaryl; preferably $R^5$ may form a saturated or unsaturated bicyclic 9 to 10 membered ring with $R^6$ which may contain a nitrogen atom, an oxygen atom or a sulfur atom; wherein the saturated or unsaturated bicyclic 9 to 10 membered ring is optionally substituted with 1 to 6 substituents independently selected from the group consisting of: (1) hydroxyl, (2) halogen and (3) —O-aryl;

$R^{7a}$ and $R^{7b}$ are independently selected from the group consisting of:

(1) hydrogen, (2) halogen, (3) hydroxyl, (4) C$_{1-6}$ alkyl and (5) —NR$^{9b}$R$^{10b}$; preferably $R^{7a}$ and $R^{7b}$ are independently selected from the group consisting of (1) hydrogen, (4) C$_{1-6}$ alkyl and (5) —NR$^{9b}$R$^{10b}$;

$R^{7a}$ may form a 3 to 7 membered ring with $R^5$ which may contain a nitrogen atom or an oxygen atom; or $R^{7a}$ may form a 3 to 7 membered ring with $R^{7b}$ which may contain a nitrogen atom or an oxygen atom;

q is 0 or 1; preferably q is 0;

$R^1$ is selected from the group consisting of:

(1) hydrogen, (2) C$_{1-6}$ alkyl, (3) —O—C$_{1-6}$ alkyl, (4) C$_{2-6}$ alkenyl, (5) C$_{3-10}$ cycloalkyl, (6) —NR$^{9b}$R$^{10b}$: wherein the C$_{1-6}$ alkyl, the —O—C$_{1-6}$ alkyl, the C$_{2-6}$ alkenyl, the C$_{3-10}$ cycloalkyl or the —NR$^{9b}$R$^{10b}$ is unsubstituted or substituted with one or more substituents independently selected from the group consisting of: halogen and hydroxyl; (7) heterocyclyl, (8) aryl, (9) —O—C$_{1-6}$ alkylaryl, (10) —O-aryl, (11) heteroaryl and (12) aryl substituted heteroaryl:

wherein the heterocyclyl, the aryl, the —O—C$_{1-6}$ alkylaryl, the —O-aryl, the heteroaryl or the aryl-substituted heteroaryl is unsubstituted or substituted with one or more substituents independently selected from the group consisting of: halogen, hydroxyl, —O—C$_{1-6}$ alkyl, —O—C$_{1-6}$ haloalkyl, —C$_{3-7}$ cycloalkyl, —O—C$_{3-7}$ cycloalkyl, hydroxyl-C$_{1-6}$ alkoxy, —CN, —NR$^{9b}$R$^{10b}$, —(C=O)—R$^{9b}$, —(C=O)—NR$^{9b}$R$^{10b}$, —NR$^{9b}$—(C=O)—R$^{10b}$, —NR$^{11}$—(C=O)—NR$^{9b}$R$^{10b}$, —NR$^{9b}$—(C=O)—OR$^{10b}$, —NR$^{9b}$—S(O)$_m$—R$^{10b}$, —NR$^{11}$—S(O)$_m$—NR$^{9b}$R$^{10b}$, —S(O)$_m$—R$^{9b}$ and C$_{1-6}$ alkyl which may be substituted one or more with halogen, hydroxyl, —O—C$_{1-6}$ alkyl or NR$^{9b}$R$^{10b}$;

wherein m is independently 0, 1 or 2;

preferably $R^1$ is selected from the group consisting of: (1) hydrogen, (2) C$_{1-6}$ alkyl, (5) C$_{3-10}$ cycloalkyl, wherein the C$_{1-6}$ alkyl or the C$_{3-10}$ cycloalkyl is unsubstituted or substituted with one or more substituents independently selected from the group consisting of: halogen and hydroxyl; (7) heterocyclyl, (8) aryl, (9) —O—C$_{1-6}$ alkylaryl, (10) —O-aryl, (11) heteroaryl and (12) aryl-substituted heteroaryl, wherein the heterocyclyl, the aryl, the —O—C$_{1-6}$ alkylaryl, the —O-aryl, the heteroaryl or the aryl-substituted heteroaryl is unsubstituted or substituted with one or more substituents independently selected from the group consisting of: halogen, hydroxyl, —O—C$_{1-6}$ alkyl, —O—C$_{1-6}$ haloalkyl, —CN and C$_1$-6 alkyl which may be substituted one or more with halogen, hydroxyl, —O—C$_{1-6}$ alkyl or NR$^{9b}$R$^{10b}$;

more preferably, $R^1$ is selected from the group consisting of:

2,4-dichloro-3-fluorophenyl, 2-chloro-3,4-difluorophenyl, 2,3,4-trifluorophenyl, 2-chloro-4-fluorophenyl, 2,4-dichlorophenyl, 4-chloro-2,6-difluorophenyl, 2-chloro-4,6-difluorophenyl, 2,4-dichloro-6-fluorophenyl, 2,3-dichlorophenyl, 2-chloro-3-(trifluoromethyl)phenyl, 2,4-dichloro-6-(hydroxymethyl)phenyl and 2-chloro-4-fluoro-6-(hydroxymethyl)phenyl;

$R^{9a}$, $R^{9b}$, $R^{10a}$, $R^{10b}$ or $R^{11}$ is independently selected from the group consisting of:

(1) hydrogen, (2) hydroxyl, (3) C$_{1-6}$ alkyl and (4) hydroxyC$_{1-6}$ alkyl;

$R^{9a}$ may form a 4 to 7 membered ring with $R^{10a}$ which may contain one or more independently selected from the group consisting of: nitrogen atom, oxygen atom, sulfur atom and double bond, wherein the 4 to 7 membered ring is optionally substituted with 1 to 6 substituents independently selected from the group consisting of: (1) hydroxyl, (2) halogen, (3) C$_{1-6}$ alkyl and (4) —O—C$_{1-6}$ alkyl;

$R^{9b}$ may form a 4 to 7 membered ring with $R^{10b}$ which may contain one or more independently selected from the group consisting of: nitrogen atom, oxygen atom, sulfur atom and double bond, wherein the 4 to 7 membered ring is optionally substituted with 1 to 6 substituents independently selected from the group consisting of: (1) hydroxyl, (2) halogen and (3) C$_{1-6}$ alkyl.

[2] The compound according to [1]:

or a prodrug thereof or a pharmaceutically acceptable salt thereof, wherein:

X is N;

$R^5$ is hydrogen or C$_{1-6}$ alkyl;

$R^6$ is selected from the group consisting of:

(1) hydrogen and (2) C$_{1-6}$ alkyl;

$R^5$ may form a saturated or unsaturated bicyclic 9 to 10 membered ring with $R^6$ which may contain a nitrogen atom, an oxygen atom or a sulfur atom; wherein the saturated or unsaturated bicyclic 9 to 10 membered ring is optionally substituted with 1 to 6 substituents independently selected from the group consisting of: (1) hydroxyl, (2) halogen and (3) —O-aryl;

$R^{7a}$ and $R^{7b}$ are independently selected from the group consisting of: (1) hydrogen, (4) $C_{1-6}$ alkyl and (5) —$NR^{9b}R^{10b}$;

$R^{7a}$ may form a 3 to 7 membered ring with $R^5$ which may contain a nitrogen atom or an oxygen atom; or $R^{7a}$ may form a 3 to 7 membered ring with $R^{7b}$ which may contain a nitrogen atom or an oxygen atom;

$R^1$ is selected from the group consisting of:

(1) hydrogen, (2) $C_{1-6}$ alkyl, (5) $C_{3-10}$ cycloalkyl, wherein the $C_{1-6}$ alkyl or the $C_{3-10}$ cycloalkyl is unsubstituted or substituted with one or more substituents independently selected from the group consisting of: halogen and hydroxyl; (7) heterocyclyl, (8) aryl, (9) —O—$C_{1-6}$ alkylaryl, (10) —O-aryl, (11) heteroaryl and (12) aryl-substituted heteroaryl, wherein the heterocyclyl, the aryl, the —O—$C_{1-6}$ alkylaryl, the —O-aryl, the heteroaryl or the aryl-substituted heteroaryl is unsubstituted or substituted with one or more substituents independently selected from the group consisting of: halogen, hydroxyl, —O—$C_{1-6}$ alkyl, —O—$C_{1-6}$ haloalkyl, —CN and $C_{1-6}$ alkyl which may be substituted one or more with halogen, hydroxyl, —O—$C_{1-6}$ alkyl or $NR^{9b}R^{10b}$.

[3] A compound represented by the following formula (M):

[Chem. 2]

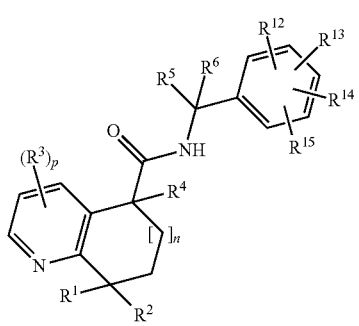

(M)

or a prodrug thereof or a pharmaceutically acceptable salt thereof, wherein:

n is 0 or 1; preferably n is 1;

$R^1$ is selected from the group consisting of:

(1) hydrogen, (2) halogen, (3) hydroxyl, (4) —$NH_2$, (5) —NH—$C_{1-6}$ alkyl and (6) —$S(O)_mC_{1-6}$ alkyl;

wherein m is independently 0, 1 or 2;

$R^2$ is selected from the group consisting of:

(1) hydrogen, (2) halogen, (3) $C_{1-6}$ alkyl and (4) —O—$C_{1-6}$ alkyl; wherein the $C_{1-6}$ alkyl or the —O—$C_{1-6}$ alkyl is unsubstituted or substituted with one or more substituents independently selected from the group consisting of: halogen, hydroxyl, —O—$C_{1-6}$ alkyl, —CN, —$NR^{9a}R^{10a}$, —(C=O)—$R^{9a}$, —(C=O)—$NR^{9a}R^{10a}$ and —$S(O)_m$—$R^{9a}$; wherein m is independently 0, 1 or 2;

$R^1$ may form =$CH_2$ or =O with $R^2$; or $R^1$ may form a 3 to 7 membered ring with $R^2$ which may contain one or more independently selected from the group consisting of: nitrogen atom, oxygen atom, sulfur atom and carbonyl group; where the 3 to 7 membered ring is unsubstituted or substituted one or more with $C_{1-6}$ alkyl;

$R^3$ is independently selected from the group consisting of:

(1) hydrogen, (2) halogen, (3) $C_{1-6}$ alkyl and (4) —O—$C_{1-6}$alkyl;

preferably $R^3$ is hydrogen at 4-position against X;

p is 0, 1, 2 or 3; preferably p is 0 or 1;

when p is 2 or 3, each $R^3$ is the same or different;

$R^4$ is selected from the group consisting of:

(1) hydrogen, (2) halogen and (3) hydroxyl;

$R^5$ is hydrogen or $C_{1-6}$ alkyl;

$R^6$ is selected from the group consisting of:

(1) hydrogen, (2) $C_{1-6}$ alkyl, (3) hydroxy$C_{1-6}$ alkyl, (4) $C_{1-6}$ alkoxy $C_{1-6}$ alkyl and (5) heterocyclyl $C_{1-6}$ alkyl;

preferably $R^6$ is selected from the group consisting of (1) hydrogen and (2) $C_{1-6}$ alkyl;

$R^5$ may form a saturated 3 to 7 membered ring with $R^6$ which may contain a nitrogen atom, an oxygen atom, a sulfur atom or a double bond; wherein the saturated 3 to 7 membered ring is optionally substituted with 1 to 6 substituents independently selected from the group consisting of: (1) hydroxyl, (2) halogen, (3) —O-aryl and (4) —O—$C_{1-6}$ alkylaryl;

preferably $R^5$ may form a saturated 3 to 7 membered ring with $R^6$ which may contain a nitrogen atom, an oxygen atom, a sulfur atom or a double bond; wherein the saturated 3 to 7 membered ring is optionally substituted with 1 to 6 substituents independently selected from the group consisting of: (1) hydroxyl, (2) halogen and (3) —O-aryl;

$R^{9a}$, $R^{9b}$, $R^{10a}$ or $R^{10b}$ is independently selected from the group consisting of:

(1) hydrogen, (2) hydroxyl, (3) $C_{1-6}$ alkyl and (4) hydroxy$C_{1-6}$ alkyl;

$R^{9a}$ may form a 4 to 7 membered ring with $R^{10a}$ which may contain a nitrogen atom or an oxygen atom; wherein the 4 to 7 membered ring is optionally substituted with 1 to 6 substituents independently selected from the group consisting of: (1) hydroxyl, (2) halogen, (3) $C_{1-6}$ alkyl and (4) —O—$C_{1-6}$ alkyl;

$R^{9b}$ may form a 4 to 7 membered ring with $R^{10b}$ which may contain a nitrogen atom or an oxygen atom; wherein the 4 to 7 membered ring is optionally substituted with 1 to 6 substituents independently selected from the group consisting of: (1) hydroxyl, (2) halogen and (3) $C_{1-6}$ alkyl;

$R^{12}$, $R^{13}$, $R^{14}$ and $R^{15}$ are independently selected from the group consisting of:

(1) hydrogen, (2) hydroxyl, (3) halogen, (4) $C_{1-6}$ alkyl, (5) —O—$C_{1-6}$ alkyl and (6) CN; wherein the $C_{1-6}$ alkyl or the —O—$C_{1-6}$ alkyl is unsubstituted or substituted with one or more substituents independently selected from the group consisting of: halogen, hydroxyl, —O—$C_{1-6}$ alkyl and $NR^{9b}R^{10b}$; or $R^{12}$ may form a 5 to 7 membered ring with $R^5$ which may contain one or more independently selected from the group consisting of: nitrogen atom and oxygen atom.

[4] The compound according to [3]:

or a prodrug thereof or a pharmaceutically acceptable salt thereof, wherein:

n is 1;

$R^1$ is hydrogen or hydroxyl;

$R^2$ is methyl which is unsubstituted or substituted with one or more substituents independently selected from the group consisting of: halogen, hydroxyl, —O—$C_{1-6}$ alkyl, —CN and —$NR^{9a}R^{10a}$;

p is 0;

$R^4$ is hydrogen or fluoro;

$R^5$ and $R^6$ are independently selected from the group consisting of: (1) hydrogen and (2) $C_{1-6}$ alkyl;

$R^{12}$, $R^{13}$ and $R^{14}$ are independently selected from the group consisting of: (1) hydrogen, (3) halogen, and (4) $C_{1-3}$ alkyl which may be substituted one or more with hydroxyl;

$R^{15}$ is hydrogen.

[5] A compound which is selected from the group following or a prodrug thereof or a pharmaceutically acceptable salt thereof, N-(2,4-dichloro-6-methylbenzyl)-8-oxo-5,6,7,8-tetrahydroquinoline-5-carboxamide;
N-(2-chloro-3-(trifluoromethyl)benzyl)-8-oxo-5,6,7,8-tetrahydroquinoline-5-carboxamide;
N-(2,3-dichlorobenzyl)-8-oxo-5,6,7,8-tetrahydroquinoline-5-carboxamide;
N-(2,4-dichloro-6-(hydroxymethyl)benzyl)-8-oxo-5,6,7,8-tetrahydroquinoline-5-carboxamide;
N-(cycloheptylmethyl)-8-oxo-5,6,7,8-tetrahydroquinoline-5-carboxamide;
N-(2,4-dichloro-6-methylbenzyl)-8-hydroxy-5,6,7,8-tetrahydroquinoline-5-carboxamide;
N-(2-chloro-3-(trifluoromethyl)benzyl)-8-hydroxy-5,6,7,8-tetrahydroquinoline-5-carboxamide;
N-(2,3-dichlorobenzyl)-8-hydroxy-5,6,7,8-tetrahydroquinoline-5-carboxamide;
N-(2,4-dichloro-6-(hydroxymethyl)benzyl)-8-hydroxy-5,6,7,8-tetrahydroquinoline-5-carboxamide;
N-(2,4-dichloro-6-(methoxymethyl)benzyl)-8-hydroxy-5,6,7,8-tetrahydroquinoline-5-carboxamide;
N-(2,4-dichloro-6-methylbenzyl)-7-methylene-6,7-dihydro-5H-cyclopenta[b]pyridine-5-carboxamide;
N-(2,4-dichloro-6-methylbenzyl)-5-fluoro-8-oxo-5,6,7,8-tetrahydroquinoline-5-carboxamide;
N-(2-chloro-3-(trifluoromethyl)benzyl)-5-fluoro-8-oxo-5,6,7,8-tetrahydroquinoline-5-carboxamide;
N-(2,4-dichloro-6-(hydroxymethyl)benzyl)-5-fluoro-8-oxo-5,6,7,8-tetrahydroquinoline-5-carboxamide;
N-(2,4-dichloro-6-methylbenzyl)-5-hydroxy-8-oxo-5,6,7,8-tetrahydroquinoline-5-carboxamide;
N-(2,4-dichloro-6-methylbenzyl)-7-oxo-6,7-dihydro-5H-cyclopenta[b]pyridine-5-carboxamide;
N-(2-chloro-3-(trifluoromethyl)benzyl)-7-oxo-6,7-dihydro-5H-cyclopenta[b]pyridine-5-carboxamide;
N-(2,4-dichloro-6-methylbenzyl)-5-fluoro-8-hydroxy-5,6,7,8-tetrahydroquinoline-5-carboxamide;
N-(2-chloro-3-(trifluoromethyl)benzyl)-5-fluoro-8-hydroxy-5,6,7,8-tetrahydroquinoline-5-carboxamide;
N-(2,4-dichloro-6-(hydroxymethyl)benzyl)-5-fluoro-8-hydroxy-5,6,7,8-tetrahydroquinoline-5-carboxamide;
N-(2,3-dichlorobenzyl)-5-fluoro-8-hydroxy-5,6,7,8-tetrahydroquinoline-5-carboxamide;
N-(2,4-dichlorobenzyl)-5-fluoro-8-hydroxy-5,6,7,8-tetrahydroquinoline-5-carboxamide;
N-(2,4-dichloro-6-(methoxymethyl)benzyl)-5-fluoro-8-hydroxy-5,6,7,8-tetrahydroquinoline-5-carboxamide;
N-(2,4-dichloro-6-methylbenzyl)-5,8-dihydroxy-5,6,7,8-tetrahydroquinoline-5-carboxamide;
N-(2-chloro-3-(trifluoromethyl)benzyl)-5,8-dihydroxy-5,6,7,8-tetrahydroquinoline-5-carboxamide;
N-(2,4-dichloro-6-methylbenzyl)-7-hydroxy-6,7-dihydro-5H-cyclopenta[b]pyridine-5-carboxamide;
N-(2-chloro-3-(trifluoromethyl)benzyl)-7-hydroxy-6,7-dihydro-5H-cyclopenta[b]pyridine-5-carboxamide;
N-(2,3-dichlorobenzyl)-7-hydroxy-6,7-dihydro-5H-cyclopenta[b]pyridine-5-carboxamide;
N-(2,4-dichlorobenzyl)-5-fluoro-7-hydroxy-6,7-dihydro-5H-cyclopenta[b]pyridine-5-carboxamide;
2-(5-(((2,4-dichloro-6-methylbenzyl)carbamoyl)-5,6,7,8-tetrahydroquinolin-8-yl)acetic acid;
2-(5-(((2-chloro-3-(trifluoromethyl)benzyl)carbamoyl)-5,6,7,8-tetrahydroquinolin-8-yl) acetic acid;
(2-amino-2-oxoethyl)-N-(2-chloro-3-(trifluoromethyl)benzyl)-5,6,7,8-tetrahydroquinoline-5-carboxamide;
N-(2,4-dichloro-6-methylbenzyl)-8-hydroxy-8-(hydroxymethyl)-5,6,7,8-tetrahydroquinoline-5-carboxamide;
N-(2,4-dichloro-6-methylbenzyl)-5-fluoro-8-hydroxy-8-(hydroxymethyl)-5,6,7,8-tetrahydroquinoline-5-carboxamide;
N-(2-chloro-3-(trifluoromethyl)benzyl)-5-fluoro-8-hydroxy-8-(hydroxymethyl)-5,6,7,8-tetrahydroquinoline-5-carboxamide;
N-(2,3-dichlorobenzyl)-5-fluoro-8-hydroxy-8-(hydroxymethyl)-5,6,7,8-tetrahydroquinoline-5-carboxamide;
N-(2,4-dichlorobenzyl)-5-fluoro-8-hydroxy-8-(hydroxymethyl)-5,6,7,8-tetrahydroquinoline-5-carboxamide;
N-(2,4-dichlorobenzyl)-5-fluoro-7-hydroxy-7-(hydroxymethyl)-6,7-dihydro-5H-cyclopenta[b]pyridine-5-carboxamide;
N-(2,4-dichloro-6-methylbenzyl)-5-fluoro-8-hydroxy-8-(methoxymethyl)-5,6,7,8-tetrahydroquinoline-5-carboxamide;
N-(2-chloro-3-(trifluoromethyl)benzyl)-5-fluoro-8-hydroxy-8-(methoxymethyl)-5,6,7,8-tetrahydroquinoline-5-carboxamide;
(5S*,8S*)—N-(2,4-dichlorobenzyl)-5-fluoro-8-hydroxy-8-(methoxymethyl)-5,6,7,8-tetrahydroquinoline-5-carboxamide;
(5S*,8S*)—N-(2-chloro-4-fluorobenzyl)-5-fluoro-8-hydroxy-8-(methoxymethyl)-5,6,7,8-tetrahydroquinoline-5-carboxamide;
8-(aminomethyl)-N-(2,4-dichloro-6-methylbenzyl)-8-hydroxy-5,6,7,8-tetrahydroquinoline-5-carboxamide;
N-(2,4-dichloro-6-methylbenzyl)-8-hydroxy-8-((methylamino)methyl)-5,6,7,8-tetrahydroquinoline-5-carboxamide;
8-(aminomethyl)-N-(2,4-dichloro-6-methylbenzyl)-5-fluoro-8-hydroxy-5,6,7,8-tetrahydroquinoline-5-carboxamide;
N-(2,4-dichloro-6-methylbenzyl)-5-fluoro-8-hydroxy-8-((methylamino)methyl)-5,6,7,8-tetrahydroquinoline-5-carboxamide;
N-(2,4-dichloro-6-methylbenzyl)-8-((dimethylamino)methyl)-5-fluoro-8-hydroxy-5,6,7,8-tetrahydroquinoline-5-carboxamide; 8-(aminomethyl)-N-(2-chloro-3-(trifluoromethyl)benzyl)-5-fluoro-8-hydroxy-5,6,7,8-tetrahydroquinoline-5-carboxamide;
N-(2-chloro-3-(trifluoromethyl)benzyl)-5-fluoro-8-hydroxy-8-((methylamino)methyl)-5,6,7,8-tetrahydroquinoline-5-carboxamide;
N-(2-chloro-3-(trifluoromethyl)benzyl)-8-((dimethylamino)methyl)-5-fluoro-8-hydroxy-5,6,7,8-tetrahydroquinoline-5-carboxamide;
(5S*,8R*)—N-(2,4-dichlorobenzyl)-5-fluoro-8-hydroxy-8-((3-hydroxyazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-((3-hydroxyazetidin-yl)methyl)-5,6,7,8-tetrahydroquinoline-5-carboxamide;

(5S*,8R*)—N-(2-chloro-4-fluorobenzyl)-5-fluoro-8-hydroxy-8-((3-methoxyazetidin-yl)methyl)-5,6,7,8-tetrahydroquinoline-5-carboxamide;
(5S*,8R*)—N-(2-chloro-4-fluorobenzyl)-5-fluoro-8-hydroxy-8-((3-hydroxy-3-methylazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-((3-methoxy-3-methylazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-(((2-hydroxyethyl)amino)methyl)-5,6,7,8-tetrahydroquinoline-5-carboxamide;
(5S*,8R*)—N-(2-chloro-4-fluorobenzyl)-5-fluoro-8-hydroxy-8-(((2-hydroxyethyl)(meth yl)amino)methyl)-5,6,7,8-tetrahydroquinoline-5-carboxamide;
N-(2-chloro-3-(trifluoromethyl)benzyl)-5-fluoro-8-hydroxy-8-methyl-5,6,7,8-tetrahydroquinoline-5-carboxamide;
(5S*,8R*)-8-amino-N-(2,4-dichlorobenzyl)-5-fluoro-8-(hydroxymethyl)-5,6,7,8-tetrahydroquinoline-5-carboxamide;
(5S*,8S*)-8-amino-N-(2,4-dichlorobenzyl)-5-fluoro-8-(hydroxymethyl)-5,6,7,8-tetrahydroquinoline-5-carboxamide;
(3R*,5'S*)—N-(2,4-dichlorobenzyl)-5'-fluoro-5-oxo-6',7'-dihydro-5'H-spiro[morpholine-3,8'-quinoline]-5'-carboxamide;
(3S*,5'S*)—N-(2,4-dichlorobenzyl)-5'-fluoro-5-oxo-6',7'-dihydro-5'H-spiro[morpholine-3,8'-quinoline]-5'-carboxamide;
(5S,8S)—N-(2,4-dichloro-6-methylbenzyl)-8-hydroxy-5,6,7,8-tetrahydroquinoline-5-carboxamide;
(5R,8S)—N-(2,4-dichloro-6-methylbenzyl)-8-hydroxy-5,6,7,8-tetrahydroquinoline-5-carboxamide;
(5S,8S)—N-(2,4-dichlorobenzyl)-8-hydroxy-5,6,7,8-tetrahydroquinoline-5-carboxamide;
(5R,8S)—N-(2,4-dichlorobenzyl)-8-hydroxy-5,6,7,8-tetrahydroquinoline-5-carboxamide (5S,8S)—N-(2-chloro-4-fluorobenzyl)-8-hydroxy-5,6,7,8-tetrahydroquinoline-5-carboxamide;
(5R,8S)—N-(2-chloro-4-fluorobenzyl)-8-hydroxy-5,6,7,8-tetrahydroquinoline-5-carboxamide;
(5S,8S)—N-(2,4-dichloro-6-fluorobenzyl)-8-hydroxy-5,6,7,8-tetrahydroquinoline-5-carboxamide;
(5R,8S)—N-(2,4-dichloro-6-fluorobenzyl)-8-hydroxy-5,6,7,8-tetrahydroquinoline-5-carboxamide;
(5S,8S)-8-hydroxy-N-(2,3,4-trifluorobenzyl)-5,6,7,8-tetrahydroquinoline-5-carboxamide;
(5R,8S)-8-hydroxy-N-(2,3,4-trifluorobenzyl)-5,6,7,8-tetrahydroquinoline-5-carboxamide;
(5R,8S)-8-hydroxy-N-(2,4,6-trifluorobenzyl)-5,6,7,8-tetrahydroquinoline-5-carboxamide;
(5R,8S)—N-(2,4-difluorobenzyl)-8-hydroxy-5,6,7,8-tetrahydroquinoline-5-carboxamide;
(5S,8S)—N-(4-fluoro-2-(trifluoromethyl)benzyl)-8-hydroxy-5,6,7,8-tetrahydroquinoline-5-carboxamide;
(5R,8S)—N-(4-fluoro-2-(trifluoromethyl)benzyl)-8-hydroxy-5,6,7,8-tetrahydroquinoline-5-carboxamide;
(5R,8S)—N-(4-chloro-2-fluorobenzyl)-8-hydroxy-5,6,7,8-tetrahydroquinoline-5-carboxamide;
(5R,8S)—N-(4-chloro-2-fluorobenzyl)-8-hydroxy-5,6,7,8-tetrahydroquinoline-5-carboxamide;
(5R,8S)—N-(4-bromo-2-fluorobenzyl)-8-hydroxy-5,6,7,8-tetrahydroquinoline-5-carboxamide;
(5R,8S)—N-(4-bromo-2-fluorobenzyl)-8-hydroxy-5,6,7,8-tetrahydroquinoline-5-carboxamide;
(5S,8S)—N-(2-chloro-3,4-difluorobenzyl)-8-hydroxy-5,6,7,8-tetrahydroquinoline-5-carboxamide;
(5R,8S)—N-(2-chloro-3,4-difluorobenzyl)-8-hydroxy-5,6,7,8-tetrahydroquinoline-5-carboxamide;
(5S,7S)—N-(2,4-dichloro-6-methylbenzyl)-7-hydroxy-6,7-dihydro-5H-cyclopenta[b]pyridine-5-carboxamide;
(5R,8R)—N-(2,4-dichloro-6-methylbenzyl)-8-hydroxy-5,6,7,8-tetrahydroquinoline-5-carboxamide;
(5S,8R)—N-(2,4-dichloro-6-methylbenzyl)-8-hydroxy-5,6,7,8-tetrahydroquinoline-5-carboxamide;
(5S,8S)—N-(2-chloro-3-(trifluoromethyl)benzyl)-8-hydroxy-5,6,7,8-tetrahydroquinoline-5-carboxamide;
(5R,8R)—N-(2,4-dichlorobenzyl)-8-hydroxy-5,6,7,8-tetrahydroquinoline-5-carboxamide;
(5S,8R)—N-(2,4-dichlorobenzyl)-8-hydroxy-5,6,7,8-tetrahydroquinoline-5-carboxamide;
(5R,8R)—N-(2-chloro-4-fluorobenzyl)-8-hydroxy-5,6,7,8-tetrahydroquinoline-5-carboxamide;
(5S,8R)—N-(2-chloro-4-fluorobenzyl)-8-hydroxy-5,6,7,8-tetrahydroquinoline-5-carboxamide;
(5R,8R)—N-(2,4-dichloro-6-fluorobenzyl)-8-hydroxy-5,6,7,8-tetrahydroquinoline-5-carboxamide;
(5S,8R)—N-(2,4-dichloro-6-fluorobenzyl)-8-hydroxy-5,6,7,8-tetrahydroquinoline-5-carboxamide;
(5R,8R)-8-hydroxy-N-(2,3,4-trifluorobenzyl)-5,6,7,8-tetrahydroquinoline-5-carboxamide;
(5S,8R)-8-hydroxy-N-(2,3,4-trifluorobenzyl)-5,6,7,8-tetrahydroquinoline-5-carboxamide;
(5R,8R)—N-(4-chloro-2-fluorobenzyl)-8-hydroxy-5,6,7,8-tetrahydroquinoline-5-carboxamide;
(5S,8R)—N-(4-chloro-2-fluorobenzyl)-8-hydroxy-5,6,7,8-tetrahydroquinoline-5-carboxamide;
(5R,7R)—N-(2,4-dichloro-6-methylbenzyl)-7-hydroxy-6,7-dihydro-5H-cyclopenta[b]pyridine-5-carboxamide;
(5S,7R)—N-(2,4-dichloro-6-methylbenzyl)-7-hydroxy-6,7-dihydro-5H-cyclopenta[b]pyridine-5-carboxamide;
(5R,8S)—N-(2,4-dichloro-6-methylbenzyl)-5-fluoro-8-hydroxy-5,6,7,8-tetrahydroquinoline-5-carboxamide;
(5S,8R)—N-(2,4-dichloro-6-methylbenzyl)-5-fluoro-8-hydroxy-5,6,7,8-tetrahydroquinoline-5-carboxamide;
(5R,8S)—N-(2-chloro-3-(trifluoromethyl)benzyl)-5-fluoro-8-hydroxy-5,6,7,8-tetrahydroquinoline-5-carboxamide;
(5S,8R)—N-(2-chloro-3-(trifluoromethyl)benzyl)-5-fluoro-8-hydroxy-5,6,7,8-tetrahydroquinoline-5-carboxamide;
(5R,8S)—N-(2,4-dichloro-6-(hydroxymethyl)benzyl)-5-fluoro-8-hydroxy-5,6,7,8-tetrahydroquinoline-5-carboxamide;
(5S,8R)—N-(2,4-dichloro-6-(hydroxymethyl)benzyl)-5-fluoro-8-hydroxy-5,6,7,8-tetrahydroquinoline-5-carboxamide;
(5R,8S)—N-(2,4-dichlorobenzyl)-5-fluoro-8-hydroxy-5,6,7,8-tetrahydroquinoline-5-carboxamide;
(5S,8R)—N-(2,4-dichlorobenzyl)-5-fluoro-8-hydroxy-5,6,7,8-tetrahydroquinoline-5-carboxamide;
(5S,8R)—N-(2-chloro-4-fluorobenzyl)-5-fluoro-8-hydroxy-5,6,7,8-tetrahydroquinoline-5-carboxamide;
(5S,8R)-5-fluoro-8-hydroxy-N-(2,3,4-trifluorobenzyl)-5,6,7,8-tetrahydroquinoline-5-carboxamide;
(5S,8R)—N-(2,4-difluorobenzyl)-5-fluoro-8-hydroxy-5,6,7,8-tetrahydroquinoline-5-carboxamide;
(5S,8R)-5-fluoro-N-(4-fluoro-2-(trifluoromethyl)benzyl)-8-hydroxy-5,6,7,8-tetrahydroquinoline-5-carboxamide;
(5S,8R)—N-(4-chloro-2-fluorobenzyl)-5-fluoro-8-hydroxy-5,6,7,8-tetrahydroquinoline-5-carboxamide;
(5R,8S)—N-(2,6-dichloro-4-(trifluoromethyl)benzyl)-5-fluoro-8-hydroxy-5,6,7,8-tetrahydroquinoline-5-carboxamide;

(5S,8R)—N-(2,6-dichloro-4-(trifluoromethyl)benzyl)-5-fluoro-8-hydroxy-5,6,7,8-tetrahydroquinoline-5-carboxamide;
(5R,8S)—N-(2,4-dichloro-6-(difluoromethyl)benzyl)-5-fluoro-8-hydroxy-5,6,7,8-tetrahydroquinoline-5-carboxamide;
(5S,8R)—N-(2,4-dichloro-6-(difluoromethyl)benzyl)-5-fluoro-8-hydroxy-5,6,7,8-tetrahydroquinoline-5-carboxamide;
(5R,8S)—N-(2,4-dichloro-6-fluorobenzyl)-5-fluoro-8-hydroxy-5,6,7,8-tetrahydroquinoline-5-carboxamide;
(5S,8R)—N-(2,4-dichloro-6-fluorobenzyl)-5-fluoro-8-hydroxy-5,6,7,8-tetrahydroquinoline-5-carboxamide;
(5S,8R)—N-(4-bromo-2-chlorobenzyl)-5-fluoro-8-hydroxy-5,6,7,8-tetrahydroquinoline-5-carboxamide;
(5S,8R)—N—((R)-1-(2,4-dichlorophenyl)ethyl)-5-fluoro-8-hydroxy-5,6,7,8-tetrahydroquinoline-5-carboxamide;
(5R,8S)—N-(2,3-dichlorobenzyl)-5-fluoro-8-hydroxy-5,6,7,8-tetrahydroquinoline-5-carboxamide;
(5S,8R)—N-(2,3-dichlorobenzyl)-5-fluoro-8-hydroxy-5,6,7,8-tetrahydroquinoline-5-carboxamide;
(5S,8R)—N-(2-chloro-6-methylbenzyl)-5-fluoro-8-hydroxy-5,6,7,8-tetrahydroquinoline-5-carboxamide;
(5S,8R)—N-(2-chloro-4,5-difluorobenzyl)-5-fluoro-8-hydroxy-5,6,7,8-tetrahydroquinoline-5-carboxamide;
(5S,8R)-5-fluoro-8-hydroxy-N-(2,3,6-trichlorobenzyl)-5,6,7,8-tetrahydroquinoline-5-carboxamide;
(5S,8R)—N-(2-chloro-4-methylbenzyl)-5-fluoro-8-hydroxy-5,6,7,8-tetrahydroquinoline-5-carboxamide;
(5R,8R)—N-(2,4-dichloro-6-methylbenzyl)-5-fluoro-8-hydroxy-5,6,7,8-tetrahydroquino line-5-carboxamide;
(5S,8S)—N-(2,4-dichloro-6-methylbenzyl)-5-fluoro-8-hydroxy-5,6,7,8-tetrahydroquinoline-5-carboxamide;
(5R,8R)—N-(2-chloro-3-(trifluoromethyl)benzyl)-5-fluoro-8-hydroxy-5,6,7,8-tetrahydroquinoline-5-carboxamide;
(5S,8S)—N-(2-chloro-3-(trifluoromethyl)benzyl)-5-fluoro-8-hydroxy-5,6,7,8-tetrahydroquinoline-5-carboxamide;
(5R,8R)—N-(2,4-dichloro-6-(hydroxymethyl)benzyl)-5-fluoro-8-hydroxy-5,6,7,8-tetrahydroquinoline-5-carboxamide;
(5S,8S)—N-(2,4-dichloro-6-(hydroxymethyl)benzyl)-5-fluoro-8-hydroxy-5,6,7,8-tetrahydroquinoline-5-carboxamide;
(5R,8R)—N-(2,4-dichlorobenzyl)-5-fluoro-8-hydroxy-5,6,7,8-tetrahydroquinoline-5-carboxamide;
(5S,8S)—N-(2,4-dichlorobenzyl)-5-fluoro-8-hydroxy-5,6,7,8-tetrahydroquinoline-5-carboxamide;
(5R,8R)—N-(2-chloro-4-fluorobenzyl)-5-fluoro-8-hydroxy-5,6,7,8-tetrahydroquinoline-5-carboxamide;
(5S,8S)—N-(2-chloro-4-fluorobenzyl)-5-fluoro-8-hydroxy-5,6,7,8-tetrahydroquinoline-5-carboxamide;
(5R,8R)-5-fluoro-8-hydroxy-N-(2,3,4-trifluorobenzyl)-5,6,7,8-tetrahydroquinoline-5-carboxamide;
(5S,8S)-5-fluoro-8-hydroxy-N-(2,3,4-trifluorobenzyl)-5,6,7,8-tetrahydroquinoline-5-carboxamide;
(5R,8R)—N-(2,6-dichlorobenzyl)-5-fluoro-8-hydroxy-5,6,7,8-tetrahydroquinoline-5-carboxamide;
(5S,8S)—N-(2,6-dichlorobenzyl)-5-fluoro-8-hydroxy-5,6,7,8-tetrahydroquinoline-5-carboxamide;
(5R,8R)—N-(2,4-difluorobenzyl)-5-fluoro-8-hydroxy-5,6,7,8-tetrahydroquinoline-5-carboxamide;
(5S,8S)—N-(2,4-difluorobenzyl)-5-fluoro-8-hydroxy-5,6,7,8-tetrahydroquinoline-5-carboxamide;
(5S,8S)—N-(2-chloro-6-fluoro-3-methylbenzyl)-5-fluoro-8-hydroxy-5,6,7,8-tetrahydroquinoline-5-carboxamide;
(5R,8R)-5-fluoro-N-(4-fluoro-2-(trifluoromethyl)benzyl)-8-hydroxy-5,6,7,8-tetrahydroquinoline-5-carboxamide;
(5S,8S)-5-fluoro-N-(4-fluoro-2-(trifluoromethyl)benzyl)-8-hydroxy-5,6,7,8-tetrahydroquinoline-5-carboxamide;
(5R,8R)—N-(4-chloro-2-fluorobenzyl)-5-fluoro-8-hydroxy-5,6,7,8-tetrahydroquinoline-5-carboxamide;
(5S,8S)—N-(4-chloro-2-fluorobenzyl)-5-fluoro-8-hydroxy-5,6,7,8-tetrahydroquinoline-5-carboxamide;
(5R,8R)—N-(2,6-dichloro-4-(trifluoromethyl)benzyl)-5-fluoro-8-hydroxy-5,6,7,8-tetrahydroquinoline-5-carboxamide;
(5S,8S)—N-(2,6-dichloro-4-(trifluoromethyl)benzyl)-5-fluoro-8-hydroxy-5,6,7,8-tetrahydroquinoline-5-carboxamide;
(5S,8S)—N-(2,4-dichloro-6-(difluoromethyl)benzyl)-5-fluoro-8-hydroxy-5,6,7,8-tetrahydroquinoline-5-carboxamide;
(5S,8S)—N-(2-chloro-4-fluoro-6-(hydroxymethyl)benzyl)-5-fluoro-8-hydroxy-5,6,7,8-tetrahydroquinoline-5-carboxamide;
(5R,8R)—N-(2,4-dichloro-6-fluorobenzyl)-5-fluoro-8-hydroxy-5,6,7,8-tetrahydroquinoline-5-carboxamide;
(5S,8S)—N-(2,4-dichloro-6-fluorobenzyl)-5-fluoro-8-hydroxy-5,6,7,8-tetrahydroquinoline-5-carboxamide;
(5R,8R)—N-(4-bromo-2-chlorobenzyl)-5-fluoro-8-hydroxy-5,6,7,8-tetrahydroquinoline-5-carboxamide;
(5S,8S)—N-(4-bromo-2-chlorobenzyl)-5-fluoro-8-hydroxy-5,6,7,8-tetrahydroquinoline-5-carboxamide;
(5R,8R)—N—((R)-1-(2,4-dichlorophenyl)ethyl)-5-fluoro-8-hydroxy-5,6,7,8-tetrahydroquinoline-5-carboxamide;
(5R,8R)—N-(4-chloro-2-(trifluoromethyl)benzyl)-5-fluoro-8-hydroxy-5,6,7,8-tetrahydroquinoline-5-carboxamide;
(5S,8S)—N-(4-chloro-2-(trifluoromethyl)benzyl)-5-fluoro-8-hydroxy-5,6,7,8-tetrahydroquinoline-5-carboxamide;
(5R,8R)—N-(2,3-dichlorobenzyl)-5-fluoro-8-hydroxy-5,6,7,8-tetrahydroquinoline-5-carboxamide;
(5S,8S)—N-(2,3-dichlorobenzyl)-5-fluoro-8-hydroxy-5,6,7,8-tetrahydroquinoline-5-carboxamide;
(5R,8R)—N-(2-chloro-6-methylbenzyl)-5-fluoro-8-hydroxy-5,6,7,8-tetrahydroquinoline-5-carboxamide;
(5S,8S)—N-(2-chloro-6-methylbenzyl)-5-fluoro-8-hydroxy-5,6,7,8-tetrahydroquinoline-5-carboxamide;
(5R,8R)—N-(2-chloro-4,5-difluorobenzyl)-5-fluoro-8-hydroxy-5,6,7,8-tetrahydroquinoline-5-carboxamide;
(5S,8S)—N-(2-chloro-4,5-difluorobenzyl)-5-fluoro-8-hydroxy-5,6,7,8-tetrahydroquinoline-5-carboxamide;
(5R,8R)-5-fluoro-8-hydroxy-N-(2,3,6-trichlorobenzyl)-5,6,7,8-tetrahydroquinoline-5-carboxamide;
(5S,8S)-5-fluoro-8-hydroxy-N-(2,3,6-trichlorobenzyl)-5,6,7,8-tetrahydroquinoline-5-carboxamide;
(5R,8R)—N-(2-chloro-4-methylbenzyl)-5-fluoro-8-hydroxy-5,6,7,8-tetrahydroquinoline-5-carboxamide;
(5S,8S)—N-(2-chloro-4-methylbenzyl)-5-fluoro-8-hydroxy-5,6,7,8-tetrahydroquinoline-5-carboxamide;
(5S,8S)-5-fluoro-8-hydroxy-N—((S)-1-(2,3,4-trichlorophenyl)ethyl)-5,6,7,8-tetrahydroquinoline-5-carboxamide;
(5S,8S)—N-(2-chloro-3-fluorobenzyl)-5-fluoro-8-hydroxy-5,6,7,8-tetrahydroquinoline-5-carboxamide;
(5S,8S)—N-(2-chloro-3,6-difluorobenzyl)-5-fluoro-8-hydroxy-5,6,7,8-tetrahydroquinoline-5-carboxamide;
(5S,8S)—N-(2-chloro-6-fluorobenzyl)-5-fluoro-8-hydroxy-5,6,7,8-tetrahydroquinoline-5-carboxamide;
(5S,8S)—N-(2-chloro-4-methoxybenzyl)-5-fluoro-8-hydroxy-5,6,7,8-tetrahydroquinoline-5-carboxamide;
(5S,8S)—N-(2,5-dichlorobenzyl)-5-fluoro-8-hydroxy-5,6,7,8-tetrahydroquinoline-5-carboxamide;
(5S,8S)—N-(2-chloro-3,4-difluorobenzyl)-5-fluoro-8-hydroxy-5,6,7,8-tetrahydroquinoline-5-carboxamide;

(5S,8S)-5-fluoro-N-(2-fluoro-3-(trifluoromethyl)benzyl)-8-hydroxy-5,6,7,8-tetrahydroquinoline-5-carboxamide;
(5S,8S)—N-(2-chloro-4,6-difluorobenzyl)-5-fluoro-8-hydroxy-5,6,7,8-tetrahydroquinoline-5-carboxamide;
(5S,8S)—N-((3,5-dichloropyridin-2-yl)methyl)-5-fluoro-8-hydroxy-5,6,7,8-tetrahydroquinoline-5-carboxamide;
(5S,8S)-5-fluoro-N-(3-fluoro-2-(trifluoromethyl)benzyl)-8-hydroxy-5,6,7,8-tetrahydroquinoline-5-carboxamide;
(5S,8S)—N-(2-chloro-6-(trifluoromethyl)benzyl)-5-fluoro-8-hydroxy-5,6,7,8-tetrahydroquinoline-5-carboxamide;
(5S,8S)-5-fluoro-8-hydroxy-N-(2,4,6-trifluorobenzyl)-5,6,7,8-tetrahydroquinoline-5-carboxamide;
(5S,8S)—N-(5-bromo-2-chlorobenzyl)-5-fluoro-8-hydroxy-5,6,7,8-tetrahydroquinoline-5-carboxamide;
(5S,8S)—N-(4-bromo-2-fluorobenzyl)-5-fluoro-8-hydroxy-5,6,7,8-tetrahydroquinoline-5-carboxamide;
(5S,8S)—N-(4-chloro-2,3-difluorobenzyl)-5-fluoro-8-hydroxy-5,6,7,8-tetrahydroquinoline-5-carboxamide;
(5S,8S)—N-(4-chloro-2,6-difluorobenzyl)-5-fluoro-8-hydroxy-5,6,7,8-tetrahydroquinoline-5-carboxamide;
(5S,8S)—N-(3-chloro-2,4-difluorobenzyl)-5-fluoro-8-hydroxy-5,6,7,8-tetrahydroquinoline-5-carboxamide;
(5S,8S)-5-fluoro-N-(2-fluoro-6-(trifluoromethyl)benzyl)-8-hydroxy-5,6,7,8-tetrahydroquinoline-5-carboxamide;
(5S,8S)—N-(2-chloro-4-(trifluoromethyl)benzyl)-5-fluoro-8-hydroxy-5,6,7,8-tetrahydroquinoline-5-carboxamide;
(5S,8S)—N-(3-chloro-4-fluorobenzyl)-5-fluoro-8-hydroxy-5,6,7,8-tetrahydroquinoline-5-carboxamide;
(5S,8S)-5-fluoro-8-hydroxy-N—((R)-1,2,3,4-tetrahydronaphthalen-1-yl)-5,6,7,8-tetrahydroquinoline-5-carboxamide;
(5S,8S)—N-(3-chloro-2-fluorobenzyl)-5-fluoro-8-hydroxy-5,6,7,8-tetrahydroquinoline-5-carboxamide;
(5S,8S)—N-(2,4-dichlorophenethyl)-5-fluoro-8-hydroxy-5,6,7,8-tetrahydroquinoline-5-carboxamide;
(5S,8S)-5-fluoro-8-hydroxy-N-((1-morpholinocyclohexyl)methyl)-5,6,7,8-tetrahydroquinoline-5-carboxamide;
(5S,8S)—N-(3-chloro-2,6-difluorobenzyl)-5-fluoro-8-hydroxy-5,6,7,8-tetrahydroquinoline-5-carboxamide;
(5S,8S)—N-((3-chloro-5-(trifluoromethyl)pyridin-2-yl)methyl)-5-fluoro-8-hydroxy-5,6,7,8-tetrahydroquinoline-5-carboxamide;
(5S,8S)—N-(2-chlorobenzyl)-5-fluoro-8-hydroxy-5,6,7,8-tetrahydroquinoline-5-carboxamide;
(5S,8S)—N—((R)-2,3-dihydro-1H-inden-1-yl)-5-fluoro-8-hydroxy-5,6,7,8-tetrahydroquinoline-5-carboxamide;
(5S,8S)—N-(3,4-dichlorobenzyl)-5-fluoro-8-hydroxy-5,6,7,8-tetrahydroquinoline-5-carboxamide;
(5S,8S)—N-(2-chloro-6-methoxybenzyl)-5-fluoro-8-hydroxy-5,6,7,8-tetrahydroquinoline-5-carboxamide;
(5S,8S)-5-fluoro-8-hydroxy-N-(2-(trifluoromethyl)benzyl)-5,6,7,8-tetrahydroquinoline-5-carboxamide;
(5S,8S)-5-fluoro-8-hydroxy-N-(3,4,5-trifluorobenzyl)-5,6,7,8-tetrahydroquinoline-5-carboxamide;
(5S,8S)—N-(4-cyano-2-fluorobenzyl)-5-fluoro-8-hydroxy-5,6,7,8-tetrahydroquinoline-5-carboxamide;
(5S,8S)—N-(3,4-difluorobenzyl)-5-fluoro-8-hydroxy-5,6,7,8-tetrahydroquinoline-5-carboxamide;
(5S,8S)—N-(3-chloro-5-fluorobenzyl)-5-fluoro-8-hydroxy-5,6,7,8-tetrahydroquinoline-5-carboxamide (5S,8S)—N-(2-chloro-5-fluorobenzyl)-5-fluoro-8-hydroxy-5,6,7,8-tetrahydroquinoline-5-carboxamide;
(5S,8S)—N-(3-chlorobenzyl)-5-fluoro-8-hydroxy-5,6,7,8-tetrahydroquinoline-5-carboxamide;
(5S,8S)—N-(4-chloro-3-fluorobenzyl)-5-fluoro-8-hydroxy-5,6,7,8-tetrahydroquinoline-5-carboxamide;
(5S,8S)-5-fluoro-N-(2-fluoro-4-(trifluoromethoxy)benzyl)-8-hydroxy-5,6,7,8-tetrahydroquinoline-5-carboxamide;
(5S,8S)—N-(2,3-difluorobenzyl)-5-fluoro-8-hydroxy-5,6,7,8-tetrahydroquinoline-5-carboxamide;
(5S,8S)—N-(2-chloro-5-(trifluoromethyl)benzyl)-5-fluoro-8-hydroxy-5,6,7,8-tetrahydroquinoline-5-carboxamide;
(5S,8S)—N-(4-chlorobenzyl)-5-fluoro-8-hydroxy-5,6,7,8-tetrahydroquinoline-5-carboxamide;
(5S,8S)-5-fluoro-8-hydroxy-N-(4-methoxy-2-(trifluoromethyl)benzyl)-5,6,7,8-tetrahydroquinoline-5-carboxamide;
(5S,8S)—N-(3,5-dichlorobenzyl)-5-fluoro-8-hydroxy-5,6,7,8-tetrahydroquinoline-5-carboxamide;
(5S,8S)—N-((4-(4-chlorophenyl)thiazol-2-yl)methyl)-5-fluoro-8-hydroxy-5,6,7,8-tetrahydroquinoline-5-carboxamide;
(5S,8S)-5-fluoro-8-hydroxy-N-(2-(morpholinomethyl)benzyl)-5,6,7,8-tetrahydroquinoline-5-carboxamide;
(5S,8S)-5-fluoro-8-hydroxy-N-((1S,2R)-2-phenylcyclopropyl)-5,6,7,8-tetrahydroquino line-5-carboxamide;
(5S,8S)—N-(6-chloro-2-fluoro-3-methylbenzyl)-5-fluoro-8-hydroxy-5,6,7,8-tetrahydroquinoline-5-carboxamide;
(5S,8S)—N-(2,6-difluorobenzyl)-5-fluoro-8-hydroxy-5,6,7,8-tetrahydroquinoline-5-carboxamide;
(5S,8S)-5-fluoro-8-hydroxy-N—((S)-1,2,3,4-tetrahydronaphthalen-1-yl)-5,6,7,8-tetrahydroquinoline-5-carboxamide;
(5S,8S)-5-fluoro-8-hydroxy-N-(2-(3-(trifluoromethyl)phenoxy)ethyl)-5,6,7,8-tetrahydroquinoline-5-carboxamide;
(5S,8S)-5-fluoro-N-((1-(4-fluorophenyl)cyclopropyl)methyl)-8-hydroxy-5,6,7,8-tetrahydroquinoline-5-carboxamide;
(5S,8S)—N-(3,5-difluorobenzyl)-5-fluoro-8-hydroxy-5,6,7,8-tetrahydroquinoline-5-carboxamide;
(5S,8S)-5-fluoro-8-hydroxy-N-((1R,2S)-2-phenylcyclopropyl)-5,6,7,8-tetrahydroquino line-5-carboxamide;
(5S,8S)-5-fluoro-N-(2-fluorobenzyl)-8-hydroxy-5,6,7,8-tetrahydroquinoline-5-carboxamide;
(5S,8S)—N-(2-chloro-3-methoxybenzyl)-5-fluoro-8-hydroxy-5,6,7,8-tetrahydroquinoline-5-carboxamide;
(5S,8S)—N-((1S,2S)-2-(benzyloxy)cyclopentyl)-5-fluoro-8-hydroxy-5,6,7,8-tetrahydroquinoline-5-carboxamide;
(5S,8S)—N—((S)-2,3-dihydro-1H-inden-1-yl)-5-fluoro-8-hydroxy-5,6,7,8-tetrahydroquinoline-5-carboxamide;
(5S,8S)—N-(3,3-dimethylbutyl)-5-fluoro-8-hydroxy-5,6,7,8-tetrahydroquinoline-5-carboxamide;
(5S,8S)-5-fluoro-8-hydroxy-N-(2-phenoxyethyl)-5,6,7,8-tetrahydroquinoline-5-carboxamide;
(5S,8S)—N-(4,6-dichloro-2,3-dihydrobenzofuran-3-yl)-5-fluoro-8-hydroxy-5,6,7,8-tetra hydroquinoline-5-carboxamide;
(5S,8S)—N-(5,7-dichlorochroman-4-yl)-5-fluoro-8-hydroxy-5,6,7,8-tetrahydroquinoline-5-carboxamide;
(5S,8S)—N-(1-(adamantan-1-yl)ethyl)-5-fluoro-8-hydroxy-5,6,7,8-tetrahydroquinoline-5-carboxamide;
(5S,8S)—N-(2-(4-chlorophenyl)-2-(4,4-difluoropiperidin-1-yl)ethyl)-5-fluoro-8-hydroxy-5,6,7,8-tetrahydroquinoline-5-carboxamide;
(5S,8S)—N-(chroman-3-yl)-5-fluoro-8-hydroxy-5,6,7,8-tetrahydroquinoline-5-carboxamide;
(5S,8S)—N-(2-(4-chlorophenyl)propyl)-5-fluoro-8-hydroxy-5,6,7,8-tetrahydroquinoline-5-carboxamide;
(5S,8S)-5-fluoro-8-hydroxy-N-(2-morpholino-2-phenylethyl)-5,6,7,8-tetrahydroquinoline-5-carboxamide;
(5S,8S)—N-(2-(4,4-difluoropiperidin-1-yl)-2-(4-methylthiazol-5-yl)ethyl)-5-fluoro-8-hydroxy-5,6,7,8-tetrahydroquinoline-5-carboxamide;

(5S,8S)—N—((R)-1-(2-chloro-4-fluorophenyl)ethyl)-5-fluoro-8-hydroxy-5,6,7,8-tetrahydroquinoline-5-carboxamide;

(5S,8S)—N-((trans)-2-(2,4-dichlorophenyl)cyclopropyl)-5-fluoro-8-hydroxy-5,6,7,8-tetrahydroquinoline-5-carboxamide;

(5S,8S)—N—((S)-1-(2-chloro-4-fluorophenyl)ethyl)-5-fluoro-8-hydroxy-5,6,7,8-tetrahydroquinoline-5-carboxamide;

(5S,8S)—N-((4-(2,4-dichlorophenyl)tetrahydro-2H-pyran-4-yl)methyl)-5-fluoro-8-hydroxy-5,6,7,8-tetrahydroquinoline-5-carboxamide;

(5S,8S)—N-(2,4-dichlorobenzyl)-3,5-difluoro-8-hydroxy-5,6,7,8-tetrahydroquinoline-5-carboxamide;

(5S,8S)—N-(2-chloro-4-fluorobenzyl)-3,5-difluoro-8-hydroxy-5,6,7,8-tetrahydroquinoline-5-carboxamide;

(5S,8S)—N-(2,4-dichlorobenzyl)-5-fluoro-8-hydroxy-3-methyl-5,6,7,8-tetrahydroquinoline-5-carboxamide (5S,8S)—N-(2-chloro-4-fluorobenzyl)-5-fluoro-8-hydroxy-3-methyl-5,6,7,8-tetrahydroquinoline-5-carboxamide;

(5S,8S)-5-((2,4-dichlorobenzyl)carbamoyl)-5-fluoro-8-hydroxy-5,6,7,8-tetrahydroquinoline 1-oxide;

(R)—N-(2-chloro-3-(trifluoromethyl)benzyl)-5-fluoro-8-oxo-5,6,7,8-tetrahydroquinoline-5-carboxamide;

(S)—N-(2-chloro-3-(trifluoromethyl)benzyl)-5-fluoro-8-oxo-5,6,7,8-tetrahydroquinoline-5-carboxamide;

(S)—N-(2,4-dichlorobenzyl)-5-fluoro-8-oxo-5,6,7,8-tetrahydroquinoline-5-carboxamide;

(S)—N-(2-chloro-4-fluorobenzyl)-5-fluoro-8-oxo-5,6,7,8-tetrahydroquinoline-5-carboxamide;

(S)—N-(2-chloro-3-fluorobenzyl)-5-fluoro-8-oxo-5,6,7,8-tetrahydroquinoline-5-carboxamide;

(S)—N-(2,4-dichloro-6-fluorobenzyl)-5-fluoro-8-oxo-5,6,7,8-tetrahydroquinoline-5-carboxamide;

(S)—N-(2,3-dichlorobenzyl)-5-fluoro-8-oxo-5,6,7,8-tetrahydroquinoline-5-carboxamide;

(S)—N-(2-chloro-4-(trifluoromethyl)benzyl)-5-fluoro-8-oxo-5,6,7,8-tetrahydroquinoline-5-carboxamide;

(S)-5-fluoro-8-oxo-N-(2,3,4-trifluorobenzyl)-5,6,7,8-tetrahydroquinoline-5-carboxamide;

(S)—N-((3,5-dichloropyridin-2-yl)methyl)-5-fluoro-8-oxo-5,6,7,8-tetrahydroquinoline-5-carboxamide;

(5S,8S)—N-(2,4-dichlorobenzyl)-5-fluoro-8-hydroxy-8-methyl-5,6,7,8-tetrahydroquinoline-5-carboxamide;

(5S,8R)—N-(2,4-dichlorobenzyl)-5-fluoro-8-hydroxy-8-methyl-5,6,7,8-tetrahydroquinoline-5-carboxamide;

(5S,8S)-5-fluoro-8-hydroxy-8-methyl-N-(2,3,4-trifluorobenzyl)-5,6,7,8-tetrahydroquinoline-5-carboxamide;

(5S,8S)—N-(2-chloro-4-fluorobenzyl)-5-fluoro-8-hydroxy-8-methyl-5,6,7,8-tetrahydroquinoline-5-carboxamide;

(5S,8R)—N-(2-chloro-4-fluorobenzyl)-5-fluoro-8-hydroxy-8-methyl-5,6,7,8-tetrahydroquinoline-5-carboxamide;

(5S,8S)—N-(2,4-dichloro-6-(hydroxymethyl)benzyl)-5-fluoro-8-hydroxy-8-methyl-5,6,7,8-tetrahydroquinoline-5-carboxamide;

(5S,8S)—N-(2-chloro-4-fluoro-6-(hydroxymethyl)benzyl)-5-fluoro-8-hydroxy-8-methyl-5,6,7,8-tetrahydroquinoline-5-carboxamide;

(5S,8S)—N-(2,4-difluorobenzyl)-5-fluoro-8-hydroxy-8-methyl-5,6,7,8-tetrahydroquinoline-5-carboxamide;

(5S,8S)—N-(4-chloro-2-fluorobenzyl)-5-fluoro-8-hydroxy-8-methyl-5,6,7,8-tetrahydroquinoline-5-carboxamide;

(5S,8S)—N-(2,4-dichloro-6-fluorobenzyl)-5-fluoro-8-hydroxy-8-methyl-5,6,7,8-tetrahydroquinoline-5-carboxamide;

(5S,8S)—N-(2-chloro-4,6-difluorobenzyl)-5-fluoro-8-hydroxy-8-methyl-5,6,7,8-tetrahydroquinoline-5-carboxamide;

(5S,8S)—N-(4-chloro-2,3-difluorobenzyl)-5-fluoro-8-hydroxy-8-methyl-5,6,7,8-tetrahydroquinoline-5-carboxamide;

(5S,8S)—N-(3-chloro-2,4-difluorobenzyl)-5-fluoro-8-hydroxy-8-methyl-5,6,7,8-tetrahydroquinoline-5-carboxamide;

(5S,8S)—N-(4-chloro-2,6-difluorobenzyl)-5-fluoro-8-hydroxy-8-methyl-5,6,7,8-tetrahydroquinoline-5-carboxamide;

(5S,8S)—N—((R)-1-(2-chloro-4-fluorophenyl)ethyl)-5-fluoro-8-hydroxy-8-methyl-5,6,7,8-tetrahydroquinoline-5-carboxamide;

(5S,8S)—N—((S)-1-(2-chloro-4-fluorophenyl)ethyl)-5-fluoro-8-hydroxy-8-methyl-5,6,7,8-tetrahydroquinoline-5-carboxamide;

(5S,8S)—N-((3,5-dichloropyridin-2-yl)methyl)-5-fluoro-8-hydroxy-8-methyl-5,6,7,8-tetrahydroquinoline-5-carboxamide;

(5S,8S)—N-((trans)-2-(2,4-dichlorophenyl)cyclopropyl)-5-fluoro-8-hydroxy-8-methyl-5,6,7,8-tetrahydroquinoline-5-carboxamide;

(5S,8S)-5-fluoro-8-hydroxy-8-methyl-N-((1-morpholinocyclohexyl)methyl)-5,6,7,8-tetrahydroquinoline-5-carboxamide;

(5S,8R)-5-fluoro-8-hydroxy-8-methyl-N-((1-morpholinocyclohexyl)methyl)-5,6,7,8-tetrahydroquinoline-5-carboxamide;

(5S,8S)—N-(2-chloro-4-fluorobenzyl)-5-fluoro-8-hydroxy-3,8-dimethyl-5,6,7,8-tetrahydroquinoline-5-carboxamide;

(5S,8R)—N-(2,4-dichlorobenzyl)-5-fluoro-8-hydroxy-8-(((2-hydroxyethyl)(methyl)amino)methyl)-5,6,7,8-tetrahydroquinoline-5-carboxamide;

(5R,8S)—N-(2,4-dichlorobenzyl)-5-fluoro-8-hydroxy-8-(((2-hydroxyethyl)(methyl)amino)methyl)-5,6,7,8-tetrahydroquinoline-5-carboxamide;

(5R,8S)—N-(2,4-dichlorobenzyl)-5-fluoro-8-hydroxy-8-((3-hydroxyazetidin-1-yl)methy1)-5,6,7,8-tetrahydroquinoline-5-carboxamide;

(5S,8R)-8-(cyanomethyl)-N-(2,4-dichlorobenzyl)-5-fluoro-8-hydroxy-5,6,7,8-tetrahydroquinoline-5-carboxamide;

(5S,8R)—N-(2-chloro-4-fluorobenzyl)-8-(cyanomethyl)-5-fluoro-8-hydroxy-5,6,7,8-tetrahydroquinoline-5-carboxamide;

(5S,8S)—N-(2-chloro-4-fluorobenzyl)-8-(cyanomethyl)-5-fluoro-8-hydroxy-5,6,7,8-tetrahydroquinoline-5-carboxamide;

(5S,8R)-8-(cyanomethyl)-N-(2,4-dichloro-6-(hydroxymethyl)benzyl)-5-fluoro-8-hydroxy-5,6,7,8-tetrahydroquinoline-5-carboxamide;

(5S,8R)—N-(2-chloro-4-fluoro-6-(hydroxymethyl)benzyl)-8-(cyanomethyl)-5-fluoro-8-hydroxy-5,6,7,8-tetrahydroquinoline-5-carboxamide;

(5S,8S)—N-(2,4-dichlorobenzyl)-5-fluoro-8-(fluoromethyl)-8-hydroxy-5,6,7,8-tetrahydroquinoline-5-carboxamide;

(5S,8S)—N-(2-chloro-4-fluorobenzyl)-5-fluoro-8-(fluoromethyl)-8-hydroxy-5,6,7,8-tetrahydroquinoline-5-carboxamide;

(5S,8S)—N-(2,4-dichlorobenzyl)-5-fluoro-8-hydroxy-8-((methylthio)methyl)-5,6,7,8-tetrahydroquinoline-5-carboxamide;

(5S,8S)—N-(2-chloro-4-fluorobenzyl)-5-fluoro-8-hydroxy-8-((methylthio)methyl)-5,6,7,8-tetrahydroquinoline-5-carboxamide;

(5S,8S)—N-(2-chloro-4-fluorobenzyl)-5-fluoro-8-hydroxy-8-(((2-hydroxyethyl)thio)methyl)-5,6,7,8-tetrahydroquinoline-5-carboxamide;

(2R,5'S)—N-(2,4-dichlorobenzyl)-5'-fluoro-4-methyl-6',7'-dihydro-5'H-spiro[morpholine-2,8'-quinoline]-5'-carboxamide;

(5S,5'S)—N-(2,4-dichlorobenzyl)-5'-fluoro-2-oxo-6',7'-dihydro-5'H-spiro[oxazolidine-5,8'-quinoline]-5'-carboxamide;

(5R,5'S)—N-(2,4-dichlorobenzyl)-5'-fluoro-2-oxo-6',7'-dihydro-5'H-spiro[oxazolidine-5,8'-quinoline]-5'-carboxamide;

(2S,5'R)—N-(2,4-dichlorobenzyl)-5'-fluoro-5-oxo-6',7'-dihydro-5'H-spiro[morpholine-2,8'-quinoline]-5'-carboxamide;

(2S,5'S)—N-(2,4-dichlorobenzyl)-5'-fluoro-5-oxo-6',7'-dihydro-5'H-spiro[morpholine-2,8'-quinoline]-5'-carboxamide;

(2R,5'S)—N-(2,4-dichlorobenzyl)-5'-fluoro-5-oxo-6',7'-dihydro-5'H-spiro[morpholine-2,8'-quinoline]-5'-carboxamide;

(5S,8S)—N-(2-chloro-4-fluorobenzyl)-5-fluoro-8-hydroxy-8-((methylsulfinyl)methyl)-5,6,7,8-tetrahydroquinoline-5-carboxamide;

(5S,8R)—N-(2,4-dichlorobenzyl)-5-fluoro-8-hydroxy-8-((methylthio)methyl)-5,6,7,8-tetrahydroquinoline-5-carboxamide;

(5S,8S)—N-(2,4-dichlorobenzyl)-5-fluoro-8-hydroxy-8-((methylsulfonyl)methyl)-5,6,7,8-tetrahydroquinoline-5-carboxamide;

(5S,8S)—N-(2-chloro-4-fluorobenzyl)-5-fluoro-8-hydroxy-8-((methylsulfonyl)methyl)-5,6,7,8-tetrahydroquinoline-5-carboxamide;

(5S,8S)—N-(2,4-dichlorobenzyl)-5-fluoro-8-hydroxy-8-(((2-hydroxyethyl)sulfonyl)methyl)-5,6,7,8-tetrahydroquinoline-5-carboxamide;

(5S,8S)—N-(2-chloro-4-fluorobenzyl)-5-fluoro-8-hydroxy-8-(((2-hydroxyethyl)sulfonyl)methyl)-5,6,7,8-tetrahydroquinoline-5-carboxamide;

(5R,8R)—N-(2,4-dichlorobenzyl)-5-fluoro-8-hydroxy-8-(hydroxymethyl)-5,6,7,8-tetrahydroquinoline-5-carboxamide;

(5R,8S)—N-(2,4-dichlorobenzyl)-5-fluoro-8-hydroxy-8-(hydroxymethyl)-5,6,7,8-tetrahydroquinoline-5-carboxamide;

(5S,8S)—N-(2,4-dichlorobenzyl)-5-fluoro-8-hydroxy-8-(hydroxymethyl)-5,6,7,8-tetrahydroquinoline-5-carboxamide;

(5S,8R)—N-(2,4-dichlorobenzyl)-5-fluoro-8-hydroxy-8-(hydroxymethyl)-5,6,7,8-tetrahydroquinoline-5-carboxamide;

(5S,8S)—N-(2-chloro-4-fluorobenzyl)-5-fluoro-8-hydroxy-8-(hydroxymethyl)-5,6,7,8-tetrahydroquinoline-5-carboxamide;

(5S,8R)—N-(2-chloro-4-fluorobenzyl)-5-fluoro-8-hydroxy-8-(hydroxymethyl)-5,6,7,8-tetrahydroquinoline-5-carboxamide;

(5S,8S)-5-fluoro-8-hydroxy-8-(hydroxymethyl)-N-(2,3,4-trifluorobenzyl)-5,6,7,8-tetra hydroquinoline-5-carboxamide;

(5S,8R)-5-fluoro-8-hydroxy-8-(hydroxymethyl)-N-(2,3,4-trifluorobenzyl)-5,6,7,8-tetra hydroquinoline-5-carboxamide;

(5S,8S)—N-(2,4-dichloro-6-fluorobenzyl)-5-fluoro-8-hydroxy-8-(hydroxymethyl)-5,6,7,8-tetrahydroquinoline-5-carboxamide;

(5S,8R)—N-(2,4-dichloro-6-fluorobenzyl)-5-fluoro-8-hydroxy-8-(hydroxymethyl)-5,6,7,8-tetrahydroquinoline-5-carboxamide;

(5S,8S)—N-(2-chloro-3,4-difluorobenzyl)-5-fluoro-8-hydroxy-8-(hydroxymethyl)-5,6,7,8-tetrahydroquinoline-5-carboxamide;

(5S,8R)—N-(2-chloro-3,4-difluorobenzyl)-5-fluoro-8-hydroxy-8-(hydroxymethyl)-5,6,7,8-tetrahydroquinoline-5-carboxamide;

(5S,8S)—N-(4-chloro-2-fluorobenzyl)-5-fluoro-8-hydroxy-8-(hydroxymethyl)-5,6,7,8-tetrahydroquinoline-5-carboxamide;

(5S,8R)—N-(4-chloro-2-fluorobenzyl)-5-fluoro-8-hydroxy-8-(hydroxymethyl)-5,6,7,8-tetrahydroquinoline-5-carboxamide;

(5S,8S)—N-(2,4-dichloro-6-(hydroxymethyl)benzyl)-5-fluoro-8-hydroxy-8-(hydroxymethyl)-5,6,7,8-tetrahydroquinoline-5-carboxamide;

(5S,8S)—N-(2-chloro-4-fluoro-6-(hydroxymethyl)benzyl)-5-fluoro-8-hydroxy-8-(hydroxymethyl)-5,6,7,8-tetrahydroquinoline-5-carboxamide;

(5S,8S)—N-(2,4-difluorobenzyl)-5-fluoro-8-hydroxy-8-(hydroxymethyl)-5,6,7,8-tetrahydroquinoline-5-carboxamide;

(5S,8S)—N-(2,4-dichloro-3-fluorobenzyl)-5-fluoro-8-hydroxy-8-(hydroxymethyl)-5,6,7,8-tetrahydroquinoline-5-carboxamide;

(5S,8S)—N-(2,3-dichloro-4-fluorobenzyl)-5-fluoro-8-hydroxy-8-(hydroxymethyl)-5,6,7,8-tetrahydroquinoline-5-carboxamide;

(5S,8S)—N-(2-chloro-4,6-difluorobenzyl)-5-fluoro-8-hydroxy-8-(hydroxymethyl)-5,6,7,8-tetrahydroquinoline-5-carboxamide;

(5S,8S)—N-(4-chloro-2,3-difluorobenzyl)-5-fluoro-8-hydroxy-8-(hydroxymethyl)-5,6,7,8-tetrahydroquinoline-5-carboxamide;

(5S,8S)—N-(3-chloro-2,4-difluorobenzyl)-5-fluoro-8-hydroxy-8-(hydroxymethyl)-5,6,7,8-tetrahydroquinoline-5-carboxamide;

(5S,8S)—N-(4-chloro-2,6-difluorobenzyl)-5-fluoro-8-hydroxy-8-(hydroxymethyl)-5,6,7,8-tetrahydroquinoline-5-carboxamide;

(5S,8S)—N-(2,4-dichlorobenzyl)-5-fluoro-8-hydroxy-8-(hydroxymethyl)-3-methyl-5,6,7,8-tetrahydroquinoline-5-carboxamide;

(5S,8S)—N—((R)-1-(2,4-dichlorophenyl)ethyl)-5-fluoro-8-hydroxy-8-(hydroxymethyl)-5,6,7,8-tetrahydroquinoline-5-carboxamide;

(5S,8S)—N—((R)-1-(2-chloro-4-fluorophenyl)ethyl)-5-fluoro-8-hydroxy-8-(hydroxymethyl)-5,6,7,8-tetrahydroquinoline-5-carboxamide;

(5S,8R)—N—((R)-1-(2-chloro-4-fluorophenyl)ethyl)-5-fluoro-8-hydroxy-8-(hydroxymethyl)-5,6,7,8-tetrahydroquinoline-5-carboxamide;

(5S,8S)—N-((3,5-dichloropyridin-2-yl)methyl)-5-fluoro-8-hydroxy-8-(hydroxymethyl)-5,6,7,8-tetrahydroquinoline-5-carboxamide;

(5S,8S)—N-(2,4-dichlorophenethyl)-5-fluoro-8-hydroxy-8-(hydroxymethyl)-5,6,7,8-tetrahydroquinoline-5-carboxamide;

(5S,8S)—N-((trans)-2-(2,4-dichlorophenyl)cyclopropyl)-5-fluoro-8-hydroxy-8-(hydroxy methyl)-5,6,7,8-tetrahydroquinoline-5-carboxamide;

(5S,8S)—N-((4-(2,4-dichlorophenyl)tetrahydro-2H-pyran-4-yl)methyl)-5-fluoro-8-hydroxy-8-(hydroxymethyl)-5,6,7,8-tetrahydroquinoline-5-carboxamide;
(5R,8S)—N-(2,4-dichloro-6-(hydroxymethyl)benzyl)-5-fluoro-8-methoxy-5,6,7,8-tetrahydroquinoline-5-carboxamide;
(5S,8R)—N-(2,4-dichloro-6-(hydroxymethyl)benzyl)-5-fluoro-8-methoxy-5,6,7,8-tetrahydroquinoline-5-carboxamide;
(5S,8S)—N-(2,4-dichloro-6-fluorobenzyl)-5-fluoro-8-methoxy-5,6,7,8-tetrahydroquinoline-5-carboxamide;
(5S,8S)—N-(2,3-dichlorobenzyl)-5-fluoro-8-hydroxy-5,6,7,8-tetrahydroquinoline-5-carboxamide;
(5S,8S)—N-(2-chloro-4-fluorobenzyl)-5-fluoro-8-methoxy-5,6,7,8-tetrahydroquinoline-5-carboxamide;
(5S,8S)—N-(2-chloro-4-(trifluoromethyl)benzyl)-5-fluoro-8-methoxy-5,6,7,8-tetrahydroquinoline-5-carboxamide;
(5S,8S)-5-fluoro-8-methoxy-N-(2,3,4-trifluorobenzyl)-5,6,7,8-tetrahydroquinoline-5-carboxamide;
(5S,8S)—N-(4-chloro-2-fluorobenzyl)-5-fluoro-8-methoxy-5,6,7,8-tetrahydroquinoline-5-carboxamide;
(5S,8S)-5-fluoro-8-methoxy-N-(2,4,6-trifluorobenzyl)-5,6,7,8-tetrahydroquinoline-5-carboxamide;
(5S,8S)—N-(2,4-difluorobenzyl)-5-fluoro-8-methoxy-5,6,7,8-tetrahydroquinoline-5-carboxamide;
(5S,8S)—N-(2,4-dichloro-6-(hydroxymethyl)benzyl)-5-fluoro-8-(2-hydroxyethoxy)-5,6,7,8-tetrahydroquinoline-5-carboxamide;
(5S,8S)—N-(2-chloro-4-fluorobenzyl)-5-fluoro-8-(2-hydroxyethoxy)-5,6,7,8-tetrahydroquinoline-5-carboxamide;
(5S,8S)-5-fluoro-8-(2-hydroxyethoxy)-N-(2,3,4-trifluorobenzyl)-5,6,7,8-tetrahydroquinoline-5-carboxamide;
(5S,8S)—N-(4-chloro-2-fluorobenzyl)-5-fluoro-8-(2-hydroxyethoxy)-5,6,7,8-tetrahydroquinoline-5-carboxamide;
(5S,8S)—N-(2,4-difluorobenzyl)-5-fluoro-8-(2-hydroxyethoxy)-5,6,7,8-tetrahydroquinoline-5-carboxamide;
(5R,8R)—N-(2,4-dichlorobenzyl)-5-fluoro-8-(2-hydroxyethoxy)-5,6,7,8-tetrahydroquinoline-5-carboxamide;
(5S,8S)—N-(2,4-dichlorobenzyl)-8-(2,3-dihydroxypropoxy)-5-fluoro-5,6,7,8-tetrahydroquinoline-5-carboxamide;
(5S,8rac)-N-(2,4-dichlorobenzyl)-5-fluoro-8-(methylsulfonyl)-5,6,7,8-tetrahydroquinoline-5-carboxamide;
(5S,8rac)-N-(2,4-dichlorobenzyl)-5-fluoro-8-((2-hydroxyethyl)sulfonyl)-5,6,7,8-tetrahydroquinoline-5-carboxamide;
(5R,8S)—N-(2-chloro-3-(trifluoromethyl)benzyl)-5,8-difluoro-5,6,7,8-tetrahydroquinoline-5-carboxamide;
(5R,8S)—N-(2,4-dichlorobenzyl)-5,8-difluoro-5,6,7,8-tetrahydroquinoline-5-carboxamide and
(5R,8S)—N-(2,3-dichlorobenzyl)-5,8-difluoro-5,6,7,8-tetrahydroquinoline-5-carboxamide.

[6] The compound according to [5], which is selected from the group following or a prodrug thereof or a pharmaceutically acceptable salt thereof,
N-(2,3-dichlorobenzyl)-8-oxo-5,6,7,8-tetrahydroquinoline-5-carboxamide;
N-(2,4-dichloro-6-(hydroxymethyl)benzyl)-8-hydroxy-5,6,7,8-tetrahydroquinoline-5-carboxamide;
N-(2-chloro-3-(trifluoromethyl)benzyl)-7-oxo-6,7-dihydro-5H-cyclopenta[b]pyridine-5-carboxamide;
N-(2,4-dichloro-6-methylbenzyl)-5-fluoro-8-hydroxy-5,6,7,8-tetrahydroquinoline-5-carboxamide;
N-(2-chloro-3-(trifluoromethyl)benzyl)-5-fluoro-8-hydroxy-5,6,7,8-tetrahydroquinoline-5-carboxamide;
N-(2,4-dichloro-6-(hydroxymethyl)benzyl)-5-fluoro-8-hydroxy-5,6,7,8-tetrahydroquinoline-5-carboxamide;
N-(2,3-dichlorobenzyl)-5-fluoro-8-hydroxy-5,6,7,8-tetrahydroquinoline-5-carboxamide;
N-(2,4-dichlorobenzyl)-5-fluoro-8-hydroxy-5,6,7,8-tetrahydroquinoline-5-carboxamide;
N-(2-chloro-3-(trifluoromethyl)benzyl)-7-hydroxy-6,7-dihydro-5H-cyclopenta[b]pyridine-5-carboxamide;
N-(2,4-dichlorobenzyl)-5-fluoro-7-hydroxy-6,7-dihydro-5H-cyclopenta[b]pyridine-5-carboxamide;
2-(5-(((2,4-dichloro-6-methylbenzyl)carbamoyl)-5,6,7,8-tetrahydroquinolin-8-yl)acetic acid;
2-(5-((2-chloro-3-(trifluoromethyl)benzyl)carbamoyl)-5,6,7,8-tetrahydroquinolin-8-yl) acetic acid;
N-(2-chloro-3-(trifluoromethyl)benzyl)-5-fluoro-8-hydroxy-8-(hydroxymethyl)-5,6,7,8-tetrahydroquinoline-5-carboxamide;
N-(2,3-dichlorobenzyl)-5-fluoro-8-hydroxy-8-(hydroxymethyl)-5,6,7,8-tetrahydroquinoline-5-carboxamide;
N-(2,4-dichlorobenzyl)-5-fluoro-8-hydroxy-8-(hydroxymethyl)-5,6,7,8-tetrahydroquinoline-5-carboxamide;
N-(2,4-dichlorobenzyl)-5-fluoro-7-hydroxy-7-(hydroxymethyl)-6,7-dihydro-5H-cyclopenta[b]pyridine-5-carboxamide;
(5S*,8S*)—N-(2-chloro-4-fluorobenzyl)-5-fluoro-8-hydroxy-8-(methoxymethyl)-5,6,7,8-tetrahydroquinoline-5-carboxamide;
N-(2,4-dichloro-6-methylbenzyl)-8-((dimethylamino)methyl)-5-fluoro-8-hydroxy-5,6,7,8-tetrahydroquinoline-5-carboxamide;
(5S*,8R*)—N-(2,4-dichlorobenzyl)-5-fluoro-8-hydroxy-8-((3-hydroxyazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-((3-hydroxyazetidin-yl)methyl)-5,6,7,8-tetrahydroquinoline-5-carboxamide;
(5S*,8R*)—N-(2-chloro-4-fluorobenzyl)-5-fluoro-8-hydroxy-8-((3-methoxyazetidin-yl)methyl)-5,6,7,8-tetrahydroquinoline-5-carboxamide;
(5S*,8R*)—N-(2-chloro-4-fluorobenzyl)-5-fluoro-8-hydroxy-8-((3-hydroxy-3-methylazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-((3-methoxy-3-methylazetidin-1-yl)methyl)-5,6,7,8-tetrahydroquinoline-5-carboxamide;
(5S*,8R*)—N-(2-chloro-4-fluorobenzyl)-5-fluoro-8-hydroxy-8-(((2-hydroxyethyl)amino)methyl)-5,6,7,8-tetrahydroquinoline-5-carboxamide;
(5S*,8R*)—N-(2-chloro-4-fluorobenzyl)-5-fluoro-8-hydroxy-8-(((2-hydroxyethyl)(meth yl)amino)methyl)-5,6,7,8-tetrahydroquinoline-5-carboxamide;
(3R*,5'S*)—N-(2,4-dichlorobenzyl)-5'-fluoro-5-oxo-6',7'-dihydro-5'H-spiro[morpholine-3,8'-quinoline]-5'-carboxamide;
(3S*,5'S*)—N-(2,4-dichlorobenzyl)-5'-fluoro-5-oxo-6',7'-dihydro-5'H-spiro[morpholine-3,8'-quinoline]-5'-carboxamide;
(5S,8S)—N-(2,4-dichloro-6-methylbenzyl)-8-hydroxy-5,6,7,8-tetrahydroquinoline-5-carboxamide;
(5S,8S)—N-(2,4-dichlorobenzyl)-8-hydroxy-5,6,7,8-tetrahydroquinoline-5-carboxamide (5S,8S)—N-(2-chloro-4-fluorobenzyl)-8-hydroxy-5,6,7,8-tetrahydroquinoline-5-carboxamide;
(5R,8S)—N-(2-chloro-4-fluorobenzyl)-8-hydroxy-5,6,7,8-tetrahydroquinoline-5-carboxamide;
(5S,8S)—N-(2,4-dichloro-6-fluorobenzyl)-8-hydroxy-5,6,7,8-tetrahydroquinoline-5-carboxamide;

(5S,8S)-8-hydroxy-N-(2,3,4-trifluorobenzyl)-5,6,7,8-tetrahydroquinoline-5-carboxamide;
(5R,8S)-8-hydroxy-N-(2,3,4-trifluorobenzyl)-5,6,7,8-tetrahydroquinoline-5-carboxamide;
(5S,8S)-8-hydroxy-N-(2,4,6-trifluorobenzyl)-5,6,7,8-tetrahydroquinoline-5-carboxamide;
(5R,8S)—N-(2,4-difluorobenzyl)-8-hydroxy-5,6,7,8-tetrahydroquinoline-5-carboxamide;
(5S,8S)—N-(4-fluoro-2-(trifluoromethyl)benzyl)-8-hydroxy-5,6,7,8-tetrahydroquinoline-5-carboxamide;
(5R,8S)—N-(4-fluoro-2-(trifluoromethyl)benzyl)-8-hydroxy-5,6,7,8-tetrahydroquinoline-5-carboxamide;
(5S,8S)—N-(4-chloro-2-fluorobenzyl)-8-hydroxy-5,6,7,8-tetrahydroquinoline-5-carboxamide;
(5R,8S)—N-(4-chloro-2-fluorobenzyl)-8-hydroxy-5,6,7,8-tetrahydroquinoline-5-carboxamide;
(5S,8S)—N-(4-bromo-2-fluorobenzyl)-8-hydroxy-5,6,7,8-tetrahydroquinoline-5-carboxamide;
(5R,8S)—N-(4-bromo-2-fluorobenzyl)-8-hydroxy-5,6,7,8-tetrahydroquinoline-5-carboxamide;
(5S,8S)—N-(2-chloro-3,4-difluorobenzyl)-8-hydroxy-5,6,7,8-tetrahydroquinoline-5-carboxamide;
(5R,8R)—N-(2,4-dichloro-6-methylbenzyl)-8-hydroxy-5,6,7,8-tetrahydroquinoline-5-carboxamide;
(5S,8S)—N-(2-chloro-3-(trifluoromethyl)benzyl)-8-hydroxy-5,6,7,8-tetrahydroquinoline-5-carboxamide;
(5R,8R)—N-(2-chloro-4-fluorobenzyl)-8-hydroxy-5,6,7,8-tetrahydroquinoline-5-carboxamide;
(5S,8R)—N-(2-chloro-4-fluorobenzyl)-8-hydroxy-5,6,7,8-tetrahydroquinoline-5-carboxamide;
(5R,8R)—N-(2,4-dichloro-6-fluorobenzyl)-8-hydroxy-5,6,7,8-tetrahydroquinoline-5-carboxamide;
(5R,8R)-8-hydroxy-N-(2,3,4-trifluorobenzyl)-5,6,7,8-tetrahydroquinoline-5-carboxamide;
(5S,8R)-8-hydroxy-N-(2,3,4-trifluorobenzyl)-5,6,7,8-tetrahydroquinoline-5-carboxamide;
(5R,8R)—N-(4-chloro-2-fluorobenzyl)-8-hydroxy-5,6,7,8-tetrahydroquinoline-5-carboxamide;
(5R,8S)—N-(2,4-dichloro-6-methylbenzyl)-5-fluoro-8-hydroxy-5,6,7,8-tetrahydroquinoline-5-carboxamide;
(5R,8S)—N-(2,4-dichloro-6-(hydroxymethyl)benzyl)-5-fluoro-8-hydroxy-5,6,7,8-tetrahydroquinoline-5-carboxamide;
(5R,8S)—N-(2,4-dichlorobenzyl)-5-fluoro-8-hydroxy-5,6,7,8-tetrahydroquinoline-5-carboxamide;
(5S,8R)—N-(2,4-dichlorobenzyl)-5-fluoro-8-hydroxy-5,6,7,8-tetrahydroquinoline-5-carboxamide;
(5S,8R)—N-(2-chloro-4-fluorobenzyl)-5-fluoro-8-hydroxy-5,6,7,8-tetrahydroquinoline-5-carboxamide;
(5S,8R)-5-fluoro-8-hydroxy-N-(2,3,4-trifluorobenzyl)-5,6,7,8-tetrahydroquinoline-5-carboxamide;
(5S,8R)—N-(2,4-difluorobenzyl)-5-fluoro-8-hydroxy-5,6,7,8-tetrahydroquinoline-5-carboxamide;
(5S,8R)-5-fluoro-N-(4-fluoro-2-(trifluoromethyl)benzyl)-8-hydroxy-5,6,7,8-tetrahydroquinoline-5-carboxamide;
(5S,8R)—N-(4-chloro-2-fluorobenzyl)-5-fluoro-8-hydroxy-5,6,7,8-tetrahydroquinoline-5-carboxamide;
(5R,8S)—N-(2,6-dichloro-4-(trifluoromethyl)benzyl)-5-fluoro-8-hydroxy-5,6,7,8-tetrahydroquinoline-5-carboxamide;
(5S,8R)—N-(2,6-dichloro-4-(trifluoromethyl)benzyl)-5-fluoro-8-hydroxy-5,6,7,8-tetrahydroquinoline-5-carboxamide;
(5R,8S)—N-(2,4-dichloro-6-fluorobenzyl)-5-fluoro-8-hydroxy-5,6,7,8-tetrahydroquinoline-5-carboxamide;
(5S,8R)—N-(2,4-dichloro-6-fluorobenzyl)-5-fluoro-8-hydroxy-5,6,7,8-tetrahydroquinoline-5-carboxamide;

(5S,8R)—N-(4-bromo-2-chlorobenzyl)-5-fluoro-8-hydroxy-5,6,7,8-tetrahydroquinoline-5-carboxamide;
(5R,8S)—N-(2,3-dichlorobenzyl)-5-fluoro-8-hydroxy-5,6,7,8-tetrahydroquinoline-5-carboxamide;
(5S,8R)—N-(2,3-dichlorobenzyl)-5-fluoro-8-hydroxy-5,6,7,8-tetrahydroquinoline-5-carboxamide;
(5S,8R)—N-(2-chloro-6-methylbenzyl)-5-fluoro-8-hydroxy-5,6,7,8-tetrahydroquinoline-5-carboxamide;
(5S,8R)—N-(2-chloro-4,5-difluorobenzyl)-5-fluoro-8-hydroxy-5,6,7,8-tetrahydroquinoline-5-carboxamide;
(5S,8R)—N-(2-chloro-4-methylbenzyl)-5-fluoro-8-hydroxy-5,6,7,8-tetrahydroquinoline-5-carboxamide;
(5R,8R)—N-(2,4-dichloro-6-methylbenzyl)-5-fluoro-8-hydroxy-5,6,7,8-tetrahydroquino line-5-carboxamide;
(5R,8R)—N-(2-chloro-3-(trifluoromethyl)benzyl)-5-fluoro-8-hydroxy-5,6,7,8-tetrahydroquinoline-5-carboxamide;
(5R,8R)—N-(2,4-dichloro-6-(hydroxymethyl)benzyl)-5-fluoro-8-hydroxy-5,6,7,8-tetrahydroquinoline-5-carboxamide;
(5S,8S)—N-(2,4-dichloro-6-(hydroxymethyl)benzyl)-5-fluoro-8-hydroxy-5,6,7,8-tetrahydroquinoline-5-carboxamide;
(5R,8R)—N-(2,4-dichlorobenzyl)-5-fluoro-8-hydroxy-5,6,7,8-tetrahydroquinoline-5-carboxamide;
(5S,8S)—N-(2,4-dichlorobenzyl)-5-fluoro-8-hydroxy-5,6,7,8-tetrahydroquinoline-5-carboxamide;
(5R,8R)—N-(2-chloro-4-fluorobenzyl)-5-fluoro-8-hydroxy-5,6,7,8-tetrahydroquinoline-5-carboxamide;
(5S,8S)—N-(2-chloro-4-fluorobenzyl)-5-fluoro-8-hydroxy-5,6,7,8-tetrahydroquinoline-5-carboxamide;
(5R,8R)-5-fluoro-8-hydroxy-N-(2,3,4-trifluorobenzyl)-5,6,7,8-tetrahydroquinoline-5-carboxamide;
(5S,8S)-5-fluoro-8-hydroxy-N-(2,3,4-trifluorobenzyl)-5,6,7,8-tetrahydroquinoline-5-carboxamide;
(5R,8R)—N-(2,6-dichlorobenzyl)-5-fluoro-8-hydroxy-5,6,7,8-tetrahydroquinoline-5-carboxamide;
(5R,8R)—N-(2,4-difluorobenzyl)-5-fluoro-8-hydroxy-5,6,7,8-tetrahydroquinoline-5-carboxamide;
(5S,8S)—N-(2,4-difluorobenzyl)-5-fluoro-8-hydroxy-5,6,7,8-tetrahydroquinoline-5-carboxamide;
(5R,8R)-5-fluoro-N-(4-fluoro-2-(trifluoromethyl)benzyl)-8-hydroxy-5,6,7,8-tetrahydroquinoline-5-carboxamide;
(5S,8S)-5-fluoro-N-(4-fluoro-2-(trifluoromethyl)benzyl)-8-hydroxy-5,6,7,8-tetrahydroquinoline-5-carboxamide;
(5R,8R)—N-(4-chloro-2-fluorobenzyl)-5-fluoro-8-hydroxy-5,6,7,8-tetrahydroquinoline-5-carboxamide;
(5S,8S)—N-(4-chloro-2-fluorobenzyl)-5-fluoro-8-hydroxy-5,6,7,8-tetrahydroquinoline-5-carboxamide;
(5R,8R)—N-(2,6-dichloro-4-(trifluoromethyl)benzyl)-5-fluoro-8-hydroxy-5,6,7,8-tetrahydroquinoline-5-carboxamide;
(5S,8S)—N-(2,4-dichloro-6-(difluoromethyl)benzyl)-5-fluoro-8-hydroxy-5,6,7,8-tetrahydroquinoline-5-carboxamide;
(5S,8S)—N-(2-chloro-4-fluoro-6-(hydroxymethyl)benzyl)-5-fluoro-8-hydroxy-5,6,7,8-tetrahydroquinoline-5-carboxamide;
(5R,8R)—N-(2,4-dichloro-6-fluorobenzyl)-5-fluoro-8-hydroxy-5,6,7,8-tetrahydroquinoline-5-carboxamide;
(5S,8S)—N-(2,4-dichloro-6-fluorobenzyl)-5-fluoro-8-hydroxy-5,6,7,8-tetrahydroquinoline-5-carboxamide;
(5R,8R)—N-(4-bromo-2-chlorobenzyl)-5-fluoro-8-hydroxy-5,6,7,8-tetrahydroquinoline-5-carboxamide;
(5S,8S)—N-(4-bromo-2-chlorobenzyl)-5-fluoro-8-hydroxy-5,6,7,8-tetrahydroquinoline-5-carboxamide;
(5R,8R)—N-(2,3-dichlorobenzyl)-5-fluoro-8-hydroxy-5,6,7,8-tetrahydroquinoline-5-carboxamide;

(5S,8S)—N-(2,3-dichlorobenzyl)-5-fluoro-8-hydroxy-5,6,7,8-tetrahydroquinoline-5-carboxamide;
(5R,8R)—N-(2-chloro-6-methylbenzyl)-5-fluoro-8-hydroxy-5,6,7,8-tetrahydroquinoline-5-carboxamide;
(5R,8R)—N-(2-chloro-4,5-difluorobenzyl)-5-fluoro-8-hydroxy-5,6,7,8-tetrahydroquinoline-5-carboxamide;
(5R,8R)-5-fluoro-8-hydroxy-N-(2,3,6-trichlorobenzyl)-5,6,7,8-tetrahydroquinoline-5-carboxamide;
(5R,8R)—N-(2-chloro-4-methylbenzyl)-5-fluoro-8-hydroxy-5,6,7,8-tetrahydroquinoline-5-carboxamide;
(5S,8S)—N-(2-chloro-4-methylbenzyl)-5-fluoro-8-hydroxy-5,6,7,8-tetrahydroquinoline-5-carboxamide;
(5S,8S)—N-(2-chloro-3-fluorobenzyl)-5-fluoro-8-hydroxy-5,6,7,8-tetrahydroquinoline-5-carboxamide;
(5S,8S)—N-(2-chloro-3,6-difluorobenzyl)-5-fluoro-8-hydroxy-5,6,7,8-tetrahydroquinoline-5-carboxamide;
(5S,8S)—N-(2-chloro-6-fluorobenzyl)-5-fluoro-8-hydroxy-5,6,7,8-tetrahydroquinoline-5-carboxamide;
(5S,8S)—N-(2-chloro-4-methoxybenzyl)-5-fluoro-8-hydroxy-5,6,7,8-tetrahydroquinoline-5-carboxamide;
(5S,8S)—N-(2-chloro-3,4-difluorobenzyl)-5-fluoro-8-hydroxy-5,6,7,8-tetrahydroquinoline-5-carboxamide;
(5S,8S)—N-(2-chloro-4,6-difluorobenzyl)-5-fluoro-8-hydroxy-5,6,7,8-tetrahydroquinoline-5-carboxamide;
(5S,8S)-5-fluoro-N-(3-fluoro-2-(trifluoromethyl)benzyl)-8-hydroxy-5,6,7,8-tetrahydroquinoline-5-carboxamide;
(5S,8S)-5-fluoro-8-hydroxy-N-(2,4,6-trifluorobenzyl)-5,6,7,8-tetrahydroquinoline-5-carboxamide;
(5S,8S)—N-(4-bromo-2-fluorobenzyl)-5-fluoro-8-hydroxy-5,6,7,8-tetrahydroquinoline-5-carboxamide;
(5S,8S)—N-(4-chloro-2,3-difluorobenzyl)-5-fluoro-8-hydroxy-5,6,7,8-tetrahydroquinoline-5-carboxamide;
(5S,8S)—N-(4-chloro-2,6-difluorobenzyl)-5-fluoro-8-hydroxy-5,6,7,8-tetrahydroquinoline-5-carboxamide;
(5S,8S)—N-(2-chloro-4-(trifluoromethyl)benzyl)-5-fluoro-8-hydroxy-5,6,7,8-tetrahydroquinoline-5-carboxamide;
(5S,8S)—N-(3-chloro-4-fluorobenzyl)-5-fluoro-8-hydroxy-5,6,7,8-tetrahydroquinoline-5-carboxamide;
(5S,8S)-5-fluoro-8-hydroxy-N—((R)-1,2,3,4-tetrahydronaphthalen-1-yl)-5,6,7,8-tetrahydroquinoline-5-carboxamide;
(5S,8S)—N-(3-chloro-2-fluorobenzyl)-5-fluoro-8-hydroxy-5,6,7,8-tetrahydroquinoline-5-carboxamide;
(5S,8S)—N-(3-chloro-2,6-difluorobenzyl)-5-fluoro-8-hydroxy-5,6,7,8-tetrahydroquinoline-5-carboxamide;
(5S,8S)—N-((3-chloro-5-(trifluoromethyl)pyridin-2-yl)methyl)-5-fluoro-8-hydroxy-5,6,7,8-tetrahydroquinoline-5-carboxamide;
(5S,8S)—N-(2-chlorobenzyl)-5-fluoro-8-hydroxy-5,6,7,8-tetrahydroquinoline-5-carboxamide;
(5S,8S)—N—((R)-2,3-dihydro-1H-inden-1-yl)-5-fluoro-8-hydroxy-5,6,7,8-tetrahydroquinoline-5-carboxamide;
(5S,8S)—N-(3,4-dichlorobenzyl)-5-fluoro-8-hydroxy-5,6,7,8-tetrahydroquinoline-5-carboxamide;
(5S,8S)-5-fluoro-8-hydroxy-N-(2-(trifluoromethyl)benzyl)-5,6,7,8-tetrahydroquinoline-5-carboxamide;
(5S,8S)-5-fluoro-8-hydroxy-N-(3,4,5-trifluorobenzyl)-5,6,7,8-tetrahydroquinoline-5-carboxamide;
(5S,8S)—N-(4-cyano-2-fluorobenzyl)-5-fluoro-8-hydroxy-5,6,7,8-tetrahydroquinoline-5-carboxamide;
(5S,8S)—N-(3,4-difluorobenzyl)-5-fluoro-8-hydroxy-5,6,7,8-tetrahydroquinoline-5-carboxamide;
(5S,8S)—N-(3-chloro-5-fluorobenzyl)-5-fluoro-8-hydroxy-5,6,7,8-tetrahydroquinoline-5-carboxamide;
(5S,8S)—N-(2-chloro-5-fluorobenzyl)-5-fluoro-8-hydroxy-5,6,7,8-tetrahydroquinoline-5-carboxamide;
(5S,8S)—N-(3-chlorobenzyl)-5-fluoro-8-hydroxy-5,6,7,8-tetrahydroquinoline-5-carboxamide;
(5S,8S)—N-(4-chloro-3-fluorobenzyl)-5-fluoro-8-hydroxy-5,6,7,8-tetrahydroquinoline-5-carboxamide;
(5S,8S)-5-fluoro-N-(2-fluoro-4-(trifluoromethoxy)benzyl)-8-hydroxy-5,6,7,8-tetrahydroquinoline-5-carboxamide;
(5S,8S)—N-(2,3-difluorobenzyl)-5-fluoro-8-hydroxy-5,6,7,8-tetrahydroquinoline-5-carboxamide;
(5S,8S)—N-(4-chlorobenzyl)-5-fluoro-8-hydroxy-5,6,7,8-tetrahydroquinoline-5-carboxamide;
(5S,8S)—N-(3,5-dichlorobenzyl)-5-fluoro-8-hydroxy-5,6,7,8-tetrahydroquinoline-5-carboxamide;
(5S,8S)-5-fluoro-8-hydroxy-N-((1S,2R)-2-phenylcyclopropyl)-5,6,7,8-tetrahydroquinoline-5-carboxamide;
(5S,8S)—N-(2,6-difluorobenzyl)-5-fluoro-8-hydroxy-5,6,7,8-tetrahydroquinoline-5-carboxamide;
(5S,8S)-5-fluoro-8-hydroxy-N—((S)-1,2,3,4-tetrahydronaphthalen-1-yl)-5,6,7,8-tetrahydroquinoline-5-carboxamide;
(5S,8S)-5-fluoro-8-hydroxy-N-(2-(3-(trifluoromethyl)phenoxy)ethyl)-5,6,7,8-tetrahydroquinoline-5-carboxamide;
(5S,8S)—N-(3,5-difluorobenzyl)-5-fluoro-8-hydroxy-5,6,7,8-tetrahydroquinoline-5-carboxamide;
(5S,8S)-5-fluoro-8-hydroxy-N-((1R,2S)-2-phenylcyclopropyl)-5,6,7,8-tetrahydroquinoline-5-carboxamide;
(5S,8S)-5-fluoro-N-(2-fluorobenzyl)-8-hydroxy-5,6,7,8-tetrahydroquinoline-5-carboxamide;
(5S,8S)—N-(2-chloro-3-methoxybenzyl)-5-fluoro-8-hydroxy-5,6,7,8-tetrahydroquinoline-5-carboxamide;
(5S,8S)—N—((S)-2,3-dihydro-1H-inden-1-yl)-5-fluoro-8-hydroxy-5,6,7,8-tetrahydroquinoline-5-carboxamide;
(5S,8S)—N-(3,3-dimethylbutyl)-5-fluoro-8-hydroxy-5,6,7,8-tetrahydroquinoline-5-carboxamide;
(5S,8S)-5-fluoro-8-hydroxy-N-(2-phenoxyethyl)-5,6,7,8-tetrahydroquinoline-5-carboxamide;
(5S,8S)—N-(4,6-dichloro-2,3-dihydrobenzofuran-3-yl)-5-fluoro-8-hydroxy-5,6,7,8-tetrahydroquinoline-5-carboxamide;
(5S,8S)—N-(chroman-3-yl)-5-fluoro-8-hydroxy-5,6,7,8-tetrahydroquinoline-5-carboxamide;
(5S,8S)-5-fluoro-8-hydroxy-N-(2-morpholino-2-phenylethyl)-5,6,7,8-tetrahydroquinoline-5-carboxamide;
(5S,8S)—N-(2-(4,4-difluoropiperidin-1-yl)-2-(4-methylthiazol-5-yl)ethyl)-5-fluoro-8-hydroxy-5,6,7,8-tetrahydroquinoline-5-carboxamide;
(5S,8S)—N-((trans)-2-(2,4-dichlorophenyl)cyclopropyl)-5-fluoro-8-hydroxy-5,6,7,8-tetrahydroquinoline-5-carboxamide;
(5S,8S)—N-(2,4-dichlorobenzyl)-5-fluoro-8-hydroxy-3-methyl-5,6,7,8-tetrahydroquinoline-5-carboxamide;
(5S,8S)—N-(2-chloro-4-fluorobenzyl)-5-fluoro-8-hydroxy-3-methyl-5,6,7,8-tetrahydroquinoline-5-carboxamide;
(5S,8S)-5-((2,4-dichlorobenzyl)carbamoyl)-5-fluoro-8-hydroxy-5,6,7,8-tetrahydroquinoline 1-oxide;
(5S,8S)-5-fluoro-8-hydroxy-8-methyl-N-(2,3,4-trifluorobenzyl)-5,6,7,8-tetrahydroquinoline-5-carboxamide;
(5S,8S)—N-(2-chloro-4-fluorobenzyl)-5-fluoro-8-hydroxy-8-methyl-5,6,7,8-tetrahydroquinoline-5-carboxamide;
(5S,8R)—N-(2-chloro-4-fluorobenzyl)-5-fluoro-8-hydroxy-8-methyl-5,6,7,8-tetrahydroquinoline-5-carboxamide;
(5S,8S)—N-(2-chloro-4-fluoro-6-(hydroxymethyl)benzyl)-5-fluoro-8-hydroxy-8-methyl-5,6,7,8-tetrahydroquinoline-5-carboxamide;
(5S,8S)—N-(2,4-difluorobenzyl)-5-fluoro-8-hydroxy-8-methyl-5,6,7,8-tetrahydroquinoline-5-carboxamide;
(5S,8S)—N-(4-chloro-2-fluorobenzyl)-5-fluoro-8-hydroxy-8-methyl-5,6,7,8-tetrahydroquinoline-5-carboxamide;

(5S,8S)—N-(2-chloro-4,6-difluorobenzyl)-5-fluoro-8-hydroxy-8-methyl-5,6,7,8-tetrahydroquinoline-5-carboxamide;

(5S,8S)—N-(4-chloro-2,3-difluorobenzyl)-5-fluoro-8-hydroxy-8-methyl-5,6,7,8-tetrahydroquinoline-5-carboxamide;

(5S,8S)—N-(4-chloro-2,6-difluorobenzyl)-5-fluoro-8-hydroxy-8-methyl-5,6,7,8-tetrahydroquinoline-5-carboxamide;

(5S,8S)—N—((S)-1-(2-chloro-4-fluorophenyl)ethyl)-5-fluoro-8-hydroxy-8-methyl-5,6,7,8-tetrahydroquinoline-5-carboxamide;

(5S,8S)—N-((3,5-dichloropyridin-2-yl)methyl)-5-fluoro-8-hydroxy-8-methyl-5,6,7,8-tetrahydroquinoline-5-carboxamide;

(5S,8S)—N-((trans)-2-(2,4-dichlorophenyl)cyclopropyl)-5-fluoro-8-hydroxy-8-methyl-5,6,7,8-tetrahydroquinoline-5-carboxamide;

(5S,8R)—N-(2,4-dichlorobenzyl)-5-fluoro-8-hydroxy-8-(((2-hydroxyethyl)(methyl)amino) methyl)-5,6,7,8-tetrahydroquinoline-5-carboxamide;

(5R,8S)—N-(2,4-dichlorobenzyl)-5-fluoro-8-hydroxy-8-(((2-hydroxyethyl)(methyl)amino)methyl)-5,6,7,8-tetrahydroquinoline-5-carboxamide;

(5R,8S)—N-(2,4-dichlorobenzyl)-5-fluoro-8-hydroxy-8-((3-hydroxyazetidin-1-yl)methy 1)-5,6,7,8-tetrahydroquinoline-5-carboxamide;

(5S,8R)-8-(cyanomethyl)-N-(2,4-dichlorobenzyl)-5-fluoro-8-hydroxy-5,6,7,8-tetrahydroquinoline-5-carboxamide;

(5S,8R)—N-(2-chloro-4-fluorobenzyl)-8-(cyanomethyl)-5-fluoro-8-hydroxy-5,6,7,8-tetrahydroquinoline-5-carboxamide;

(5S,8S)—N-(2-chloro-4-fluorobenzyl)-8-(cyanomethyl)-5-fluoro-8-hydroxy-5,6,7,8-tetrahydroquinoline-5-carboxamide;

(5S,8R)—N-(2-chloro-4-fluoro-6-(hydroxymethyl)benzyl)-8-(cyanomethyl)-5-fluoro-8-hydroxy-5,6,7,8-tetrahydroquinoline-5-carboxamide;

(5S,8S)—N-(2,4-dichlorobenzyl)-5-fluoro-8-(fluoromethyl)-8-hydroxy-5,6,7,8-tetrahydroquinoline-5-carboxamide;

(5S,8S)—N-(2-chloro-4-fluorobenzyl)-5-fluoro-8-(fluoromethyl)-8-hydroxy-5,6,7,8-tetrahydroquinoline-5-carboxamide;

(2R,5'S)—N-(2,4-dichlorobenzyl)-5'-fluoro-4-methyl-6',7'-dihydro-5'H-spiro[morpholine-2,8'-quinoline]-5'-carboxamide;

(5S,5'S)—N-(2,4-dichlorobenzyl)-5'-fluoro-2-oxo-6',7'-dihydro-5'H-spiro[oxazolidine-5,8'-quinoline]-5'-carboxamide;

(5R,5'S)—N-(2,4-dichlorobenzyl)-5'-fluoro-2-oxo-6',7'-dihydro-5'H-spiro[oxazolidine-5,8'-quinoline]-5'-carboxamide;

(2S,5'R)—N-(2,4-dichlorobenzyl)-5'-fluoro-5-oxo-6',7'-dihydro-5'H-spiro[morpholine-2,8'-quinoline]-5'-carboxamide;

(2S,5'S)—N-(2,4-dichlorobenzyl)-5'-fluoro-5-oxo-6',7'-dihydro-5'H-spiro[morpholine-2,8'-quinoline]-5'-carboxamide;

(2R,5'S)—N-(2,4-dichlorobenzyl)-5'-fluoro-5-oxo-6',7'-dihydro-5'H-spiro[morpholine-2,8'-quinoline]-5'-carboxamide;

(5S,8S)—N-(2-chloro-4-fluorobenzyl)-5-fluoro-8-hydroxy-8-((methylsulfinyl)methyl)-5,6,7,8-tetrahydroquinoline-5-carboxamide;

(5S,8S)—N-(2-chloro-4-fluorobenzyl)-5-fluoro-8-hydroxy-8-((methylsulfonyl)methyl)-5,6,7,8-tetrahydroquinoline-5-carboxamide;

(5S,8S)—N-(2,4-dichlorobenzyl)-5-fluoro-8-hydroxy-8-(((2-hydroxyethyl)sulfonyl)methyl)-5,6,7,8-tetrahydroquinoline-5-carboxamide;

(5S,8S)—N-(2-chloro-4-fluorobenzyl)-5-fluoro-8-hydroxy-8-(((2-hydroxyethyl)sulfonyl)methyl)-5,6,7,8-tetrahydroquinoline-5-carboxamide;

(5R,8R)—N-(2,4-dichlorobenzyl)-5-fluoro-8-hydroxy-8-(hydroxymethyl)-5,6,7,8-tetrahydroquinoline-5-carboxamide;

(5R,8S)—N-(2,4-dichlorobenzyl)-5-fluoro-8-hydroxy-8-(hydroxymethyl)-5,6,7,8-tetrahydroquinoline-5-carboxamide;

(5S,8S)—N-(2,4-dichlorobenzyl)-5-fluoro-8-hydroxy-8-(hydroxymethyl)-5,6,7,8-tetrahydroquinoline-5-carboxamide;

(5S,8R)—N-(2,4-dichlorobenzyl)-5-fluoro-8-hydroxy-8-(hydroxymethyl)-5,6,7,8-tetrahydroquinoline-5-carboxamide;

(5S,8S)—N-(2-chloro-4-fluorobenzyl)-5-fluoro-8-hydroxy-8-(hydroxymethyl)-5,6,7,8-tetrahydroquinoline-5-carboxamide;

(5S,8R)—N-(2-chloro-4-fluorobenzyl)-5-fluoro-8-hydroxy-8-(hydroxymethyl)-5,6,7,8-tetrahydroquinoline-5-carboxamide;

(5S,8S)-5-fluoro-8-hydroxy-8-(hydroxymethyl)-N-(2,3,4-trifluorobenzyl)-5,6,7,8-tetra hydroquinoline-5-carboxamide;

(5S,8R)-5-fluoro-8-hydroxy-8-(hydroxymethyl)-N-(2,3,4-trifluorobenzyl)-5,6,7,8-tetra hydroquinoline-5-carboxamide;

(5S,8S)—N-(2,4-dichloro-6-fluorobenzyl)-5-fluoro-8-hydroxy-8-(hydroxymethyl)-5,6,7,8-tetrahydroquinoline-5-carboxamide;

(5S,8R)—N-(2,4-dichloro-6-fluorobenzyl)-5-fluoro-8-hydroxy-8-(hydroxymethyl)-5,6,7,8-tetrahydroquinoline-5-carboxamide;

(5S,8S)—N-(2-chloro-3,4-difluorobenzyl)-5-fluoro-8-hydroxy-8-(hydroxymethyl)-5,6,7,8-tetrahydroquinoline-5-carboxamide;

(5S,8R)—N-(2-chloro-3,4-difluorobenzyl)-5-fluoro-8-hydroxy-8-(hydroxymethyl)-5,6,7,8-tetrahydroquinoline-5-carboxamide;

(5S,8S)—N-(4-chloro-2-fluorobenzyl)-5-fluoro-8-hydroxy-8-(hydroxymethyl)-5,6,7,8-tetrahydroquinoline-5-carboxamide;

(5S,8R)—N-(4-chloro-2-fluorobenzyl)-5-fluoro-8-hydroxy-8-(hydroxymethyl)-5,6,7,8-tetrahydroquinoline-5-carboxamide;

(5S,8S)—N-(2,4-dichloro-6-(hydroxymethyl)benzyl)-5-fluoro-8-hydroxy-8-(hydroxymethyl)-5,6,7,8-tetrahydroquinoline-5-carboxamide;

(5S,8S)—N-(2-chloro-4-fluoro-6-(hydroxymethyl)benzyl)-5-fluoro-8-hydroxy-8-(hydroxymethyl)-5,6,7,8-tetrahydroquinoline-5-carboxamide;

(5S,8S)—N-(2,4-difluorobenzyl)-5-fluoro-8-hydroxy-8-(hydroxymethyl)-5,6,7,8-tetrahydroquinoline-5-carboxamide;

(5S,8S)—N-(2,4-dichloro-3-fluorobenzyl)-5-fluoro-8-hydroxy-8-(hydroxymethyl)-5,6,7,8-tetrahydroquinoline-5-carboxamide;

(5S,8S)—N-(2-chloro-4,6-difluorobenzyl)-5-fluoro-8-hydroxy-8-(hydroxymethyl)-5,6,7,8-tetrahydroquinoline-5-carboxamide;

(5S,8S)—N-(4-chloro-2,3-difluorobenzyl)-5-fluoro-8-hydroxy-8-(hydroxymethyl)-5,6,7,8-tetrahydroquinoline-5-carboxamide;
(5S,8S)—N-(3-chloro-2,4-difluorobenzyl)-5-fluoro-8-hydroxy-8-(hydroxymethyl)-5,6,7,8-tetrahydroquinoline-5-carboxamide;
(5S,8S)—N-(4-chloro-2,6-difluorobenzyl)-5-fluoro-8-hydroxy-8-(hydroxymethyl)-5,6,7,8-tetrahydroquinoline-5-carboxamide;
(5S,8S)—N—((R)-1-(2,4-dichlorophenyl)ethyl)-5-fluoro-8-hydroxy-8-(hydroxymethyl)-5,6,7,8-tetrahydroquinoline-5-carboxamide;
(5S,8S)—N—((R)-1-(2-chloro-4-fluorophenyl)ethyl)-5-fluoro-8-hydroxy-8-(hydroxymethyl)-5,6,7,8-tetrahydroquinoline-5-carboxamide;
(5S,8R)—N—((R)-1-(2-chloro-4-fluorophenyl)ethyl)-5-fluoro-8-hydroxy-8-(hydroxymethyl)-5,6,7,8-tetrahydroquinoline-5-carboxamide;
(5S,8S)—N-((3,5-dichloropyridin-2-yl)methyl)-5-fluoro-8-hydroxy-8-(hydroxymethyl)-5,6,7,8-tetrahydroquinoline-5-carboxamide;
(5S,8S)—N-((trans)-2-(2,4-dichlorophenyl)cyclopropyl)-5-fluoro-8-hydroxy-8-(hydroxy methyl)-5,6,7,8-tetrahydroquinoline-5-carboxamide;
(5S,8S)-5-fluoro-8-methoxy-N-(2,4,6-trifluorobenzyl)-5,6,7,8-tetrahydroquinoline-5-carboxamide;
(5S,8S)—N-(2,4-difluorobenzyl)-5-fluoro-8-methoxy-5,6,7,8-tetrahydroquinoline-5-carboxamide;
(5S,8S)—N-(4-chloro-2-fluorobenzyl)-5-fluoro-8-(2-hydroxyethoxy)-5,6,7,8-tetrahydroquinoline-5-carboxamide and (5S,8S)—N-(2,4-difluorobenzyl)-5-fluoro-8-(2-hydroxyethoxy)-5,6,7,8-tetrahydroquinoline-5-carboxamide.

[7] A compound represented by the following formula (L-a) or a pharmaceutically acceptable salt thereof:

[Chem. 3]

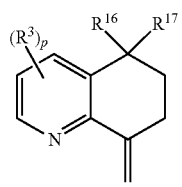

(L-a)

wherein:
$R^3$ is independently selected from the group consisting of:
(1) hydrogen, (2) halogen, (3) $C_{1-6}$ alkyl and (4) —O—$C_{1-6}$ alkyl;
preferably $R^3$ is (1) hydrogen;
p is 0, 1, 2 or 3;
when p is 2 or 3, each $R^3$ is the same or different;
$R^{16}$ is selected from the group consisting of:
(1) CN and (2) —$CO_2R^{18}$;
$R^{17}$ is selected from the group consisting of:
(1) fluoro and (2) hydroxyl; or,
$R^{16}$ may form =O with $R^{17}$;
$R^{18}$ is selected from the group consisting of:
(1) hydrogen and (2) $C_{1-6}$ alkyl.

[7-1] The compound according to [7] or a salt thereof, wherein $R^{16}$ forms =O with $R^{17}$.
[7-2] The compound according to [7] or a salt thereof, wherein $R^{17}$ is fluoro.
[7-3] The compound according to [7-2] or a salt thereof, wherein $R^{16}$ is —CN.
[7-4] The compound according to [7-2] or a salt thereof, wherein $R^{16}$ is —$CO_2R^{18}$.
[7-5] The compound according to [7] or a salt thereof, wherein $R^{16}$ is —$CO_2R^{18}$; $R^{17}$ is hydroxyl.

[8] A compound represented by the following formula (L-b) or a pharmaceutically acceptable salt thereof:

[Chem. 4]

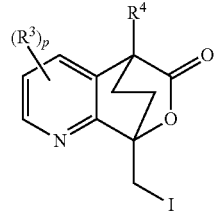

(L-b)

wherein:
$R^3$ is independently selected from the group consisting of:
(1) hydrogen, (2) halogen, (3) $C_{1-6}$ alkyl and (4) —O—$C_{1-6}$ alkyl;
preferably $R^3$ is (1) hydrogen;
p is 0, 1, 2 or 3;
when p is 2 or 3, each $R^3$ is the same or different;
$R^4$ is selected from the group consisting of:
(1) hydrogen, (2) halogen and (3) hydroxyl.

[9] A use of a compound described in any one of [1] to [6] or a pharmaceutically acceptable salt thereof or a prodrug thereof for the manufacture of a medicament for the treatment of a condition or disorder mediated by P2X7 receptor antagonistic activity.

[10] The use as described in [9], wherein the condition or disorder is selected from the group consisting of: diseases of the autoimmune and inflammatory system; diseases of the nervous and neuro-immune system; diseases involved with, and without, neuroinflammation of the Central Nervous System (CNS); diseases of the cardiovascular, metabolic, gastrointestinal and urogenital systems; skeletal disorders, diseases involving the secretory function of exocrine glands and glaucoma, Glomerulonephritis, Chaga's Disease, chlamydia, neuroblastoma, Tuberculosis, Polycystic Kidney Disease, cancer, and acne; and combinations thereof.

[11] A method for the treatment of a condition or disorder mediated by P2X7 receptor antagonistic activity in a mammalian subject, including a human, which comprises administering to a mammal in need of such treatment a therapeutically effective amount of a compound described in any one of [1] to [6] or a pharmaceutically acceptable salt thereof or a prodrug thereof.

[12] The method as described in [11], wherein the condition or disorder is selected from the group consisting of: diseases of the autoimmune and inflammatory system; diseases of the nervous and neuro-immune system; diseases involved with, and without, neuroinflammation of the Central Nervous System (CNS); diseases of the cardiovascular, metabolic, gastrointestinal and urogenital systems; skeletal disorders, diseases involving the secretory function of exocrine glands and glaucoma, Glomerulonephritis, Chaga's Disease, chlamydia, neuroblastoma, Tuberculosis, Polycystic Kidney Disease, cancer, and acne; and combinations thereof.

[13] A pharmaceutical composition comprising a compound or a pharmaceutically acceptable salt thereof or a prodrug thereof, as described in any one of [1] to [6], and a pharmaceutically acceptable carrier.

[14] The pharmaceutical composition as described in [13], further comprising another pharmacologically active agent.

[15] A compound described in any one of [1] to [6] or a pharmaceutically acceptable salt thereof or a prodrug thereof for use in the treatment of a condition or disorder mediated by P2X7 receptor antagonistic activity.

[16] A process for preparing a pharmaceutical composition, wherein the process comprises mixing a compound described in any one of [1] to [6] or a pharmaceutically acceptable salt thereof or a prodrug thereof and a pharmaceutically acceptable carrier or excipient.

Examples of conditions or disorders mediated by P2X7 receptor activity include, but are not limited to, P2X7 related diseases.

Advantageous Effects of Invention

The tetrahydroquinoline derivatives of the present invention act as modulators of the P2X7 receptor and have a number of therapeutic applications, particularly in the treatment of diseases of the autoimmune and inflammatory system, diseases of the nervous and neuro-immune system, diseases involved with neuroinflammation of the CNS or diseases of the cardiovascular, metabolic, gastrointestinal and urogenital systems. More particularly, the tetrahydroquinoline derivatives of the invention are selective P2X7 receptor antagonists. In the discussion that follows, the invention is exemplified by reference to the inhibition of P2X7 channel as the purinergic receptor.

The compounds of the present invention show the P2X7 receptor antagonistic activity. The compounds of the present invention may show less toxicity, good absorption, distribution, good solubility, less protein binding affinity other than P2X7 receptor, less drug-drug interaction, and good metabolic stability.

Especially, the present invention show excellent P2X7 antagonistic activities as well as excellent pharmacokinetic properties. In addition, they show selectivity for the P2X7 channel as compared with other P2X families, especially P2X1 channel.

DESCRIPTION OF EMBODIMENTS

As used herein, the term "alkyl" as a group or part of a group e.g. alkoxy or hydroxyalkyl refers to a straight or branched alkyl group in all isomeric forms. The term "$C_1$-$C_6$ alkyl" refers to an alkyl group, as defined above, containing at least 1 and at most 6 carbon atoms. Examples of such alkyl groups include methyl, ethyl, propyl, isopropyl, n-butyl, iso-butyl, sec-butyl, tert-butyl, n-pentyl, pentan-2-yl, pentan-3-yl, 2-methylbutyl, 3-methylbutan-2-yl, isopentyl, tert-pentyl, neopentyl, n-hexyl, hexan-2-yl, hexan-3-yl, 2-methylpentyl, 4-methylpentyl, 2-methylpentan-3-yl, 4-methylpentan-2-yl, 2-ethylbutyl, 3-methylpentyl, 3-methylpentan-2-yl, 3-methylpentan-3-yl, 2,3-dimethylbutyl, 2,3-dimethylbutan-2-yl, 3,3-dimethylbutyl, 3,3-dimethylbutan-2-yl, and 2,2-dimethylbutyl.

Examples of such alkoxy groups include methoxy, ethoxy, propoxy, iso-propoxy, butoxy, iso-butoxy, sec-butoxy, tert-butoxy, n-pentoxy, pentan-2-oxy, pentan-3-oxy, 2-methylbutoxy, 3-methylbutan-2-oxy, isopentoxy, tert-pentoxy, neopentoxy, n-hexoxy, hexan-2-oxy, hexan-3-oxy, 2-methylpentoxy, 4-methylpentoxy, 2-methylpentan-3-oxy, 4-methylpentan-2-oxy, 2-ethylbutoxy, 3-methylpentoxy, 3-methylpentan-2-oxy, 3-methylpentan-3-oxy, 2,3-dimethylbutoxy, 2,3-dimethylbutan-2-oxy, 3,3-dimethylbutoxy, 3,3-dimethylbutan-2-oxy, and 2,2-dimethylbutoxy.

The term "cycloalkyl", as used herein, means a mono-, bicyclic- or tricyclic ring, but not limited to, cyclopropyl, cyclobutyl, cyclopentyl, cyclohexyl, cycloheptyl, norbornyl, adamantyl groups and the like.

The term "alkenyl", as used herein, means a hydrocarbon radical having at least one double bond, which may be in a E- or a Z-arrangement, including, but not limited to, ethenyl, propenyl, 1-butenyl, 2-butenyl and the like.

The term "halogen" refers to fluoro (—F), chloro (—Cl), bromo (—Br) and iodo (—I).

The term "haloalkyl", as used herein, means an alkyl radical which is substituted by halogen atom(s) as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl, bromomethyl groups and the like.

The term "heterocyclyl", as used herein, means a saturated 3- to 16-membered ring which comprises one or more heteroatoms selected from nitrogen, oxygen and sulfur. For purposes of this invention, the heterocyclyl may be a monocyclic, bicyclic or tricyclic ring system, which may include fused, bridged or spiro ring systems. Examples of such heterocyclyl groups include azetidinyl, 1,4-dioxanyl, pyrrolidinyl, piperidinyl, piperazinyl, morpholinyl, tetrahydrofuranyl, thiomorpholinyl, tetrahydrothienyl, 2-oxo-pyrrolidinyl, 2-oxo-piperidinyl, 2-oxo-imidazolidinyl, 2-oxo-oxazolidinyl, quinuclidinyl, azabicyclo[3.2.1]octyl, 2-oxa-6-azaspiro[3.4]octyl and N-oxides thereof and S-oxides thereof.

The term "aryl", as used herein, means unsaturated or partially saturated mono- or bicyclic 6-15 membered ring which consists of carbon atoms.

Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S,4S)-bicyclo[2.2.2]oct-2-enyl, and (1R,4S)-bicyclo[2.2.1]hept-2-enyl. Examples of —O—$C_{1-6}$ alkylaryl include, benzyloxy.

The term "heteroaryl" as used herein, means unsaturated and partially saturated mono- or bicyclic 5-15 membered ring, preferably 6-10 membered ring, which may contain 1-4 heteroatoms selected from O, N and S:

Examples of such heteroaryl include, but are not limited to, thiophenyl, thiazolyl, isoxazolyl, pyrazolyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, triazinyl, benzofuranyl, benzothiophenyl, benzotriazolyl, indolyl, indazolyl, benzoimidazolyl, pyrrolopyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinazolinyl, phthalazinyl, quinoxalinyl, naphthyridinyl, pyridopyrimidinyl, and N-oxides thereof and S-oxides thereof.

$R^5$ may form a saturated or unsaturated bicyclic 9 to 10 membered ring with $R^6$ which may contain a nitrogen atom, an oxygen atom or a sulfur atom; Examples of such bicyclic 9 to 10 membered ring include 1,2,3,4-tetrahydronaphthalenyl, 2,3-dihydro-1H-indenyl, chromanyl, 2,3-dihydrobenzofuranyl, 1,2,3,4-tetrahydroquinolinyl, indolinyl, thiochromanyl and 2,3-dihydrobenzo[b]thiophenyl.

The substituents on the ring of the compound of the present invention may exist on the any atoms if it is chemically allowed.

The term "protecting group", as used herein, means a hydroxy or amino protecting group which is selected from typical hydroxy or amino protecting groups described in Protective Groups in Organic Synthesis Forth Edition edited by T. W. Greene et al. (John Wiley & Sons, 2006);

The terms "treating" and "treatment", as used herein, refer to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

In some cases, the symbol letter is written the corresponding English word in the present specification. For example, the symbols $\alpha$, $\beta$, and $\delta$ are written alpha, beta, and delta, respectively.

Included within the scope of the "compounds of the invention" are all salts, solvates, hydrates, complexes, polymorphs, prodrugs, radiolabeled derivatives, stereoisomers and optical isomers of the compounds of the present invention.

The compounds of the present invention can form acid addition salts thereof. It would be appreciated that for use in medicine, the salts of the compounds of the present invention should be pharmaceutically acceptable. Suitable pharmaceutically acceptable salts would be apparent to those skilled in the art and include those described in J. Pharm. Sci, 66, 1-19, 1977, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of the present invention may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of the present invention. Thus, certain derivatives of compounds of the present invention which may have little or no pharmacological activity themselves, when administered into or onto the body, can be converted into compounds of the present invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and V Stella) and Bioreversible Carriers in Drug Design, Pergamon Press, 1987 (ed. E B Roche, American Pharmaceutical Association).

Prodrugs in accordance with the invention, for example, can be produced by replacing appropriate functionalities present in the compounds of the present invention with certain moieties known to those skilled in the art as 'pro-moieties' as described, for example, in Design of Prodrugs by H Bundgaard (Elsevier, 1985). Some examples of prodrugs in accordance with the invention include:

(i) where the compound of the present invention contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the present invention contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

The compounds of the present invention, salts thereof and prodrugs thereof may be prepared in crystalline or non-crystalline form and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of the present invention and their pharmaceutically acceptable salts.

Additionally, the compounds of the present invention may be administered as prodrugs. As used herein, a "prodrug" of a compound of the present invention is a functional derivative of the compound which, upon administration to a patient, eventually liberates the compound of the present invention in vivo. Administration of a compound of the present invention as a prodrug may enable the skilled artisan to do one or more of the followings: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of the present invention, there may be some chiral carbon atoms. In such cases, compounds of the present invention exist as stereoisomers. The invention extends to all optical isomers such as stereoisomeric forms of the compounds of the present invention including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the invention can be generally prepared by carrying out the procedures disclosed in the Schemes and/or in the Examples/Intermediates below, then substituting a readily available isotopically labeled reagent for a non-isotopically labeled reagent.

The potencies and efficacies of the compounds of this invention for P2X7 can be determined by calcium influx assay performed on the human cloned receptor as described herein. Compounds of the present invention have demonstrated antagonistic activity at the P2X7 receptor, using the functional assay described herein.

Compounds of the present invention and pharmaceutically acceptable salts thereof are therefore of use in the treatment of conditions or disorders which are mediated via the P2X7 receptor. In particular the compounds of the present invention and pharmaceutically acceptable salts thereof are of use in the treatment of a wide range of diseases, syndromes, and disorders, in particular for the treatment of diseases of the autoimmune and inflammatory system; diseases of the nervous and neuro-immune system; diseases involved with, and without, neuroinflammation of the CNS; diseases of the cardiovascular, metabolic, gastrointestinal and urogenital systems; skeletal disorders, diseases involving the secretory function of exocrine glands and diseases such as glaucoma, Glomerulonephritis, Chaga's Disease, chlamydia, neuroblastoma, Tuberculosis, Polycystic Kidney Disease, cancer, and acne.

Examples of diseases of the autoimmune and inflammatory system include rheumatoid arthritis, osteoarthritis, interstitial cystitis, psoriasis, septic shock, sepsis, allergic dermatitis, idiopathic pulmonary fibrosis, allergic rhinitis, chronic obstructive pulmonary disease, airway hyper-responsiveness and asthma. Examples of asthma include allergic asthma, mild to severe asthma, and steroid resistant asthma.

Examples of diseases of the nervous and neuro-immune system include acute and chronic pain. Examples of acute and chronic pain include neuropathic pain, inflammatory pain, migraine, spontaneous pain. Examples of spontaneous pain include opioid induced pain, diabetic neuropathy, postherpetic neuralgia, low back pain, chemotherapy-induced neuropathic pain, fibromyalgia.

Examples of diseases involved with, and without, neuroinflammation of the CNS include cognition, sleep disorders, multiple sclerosis, epileptic seizures, Parkinson's disease, schizophrenia, Alzheimer's disease, Huntington's disease, Amyotrophic Lateral Sclerosis, autism, spinal cord injury and cerebral ischemia/traumatic brain injury, stress-related disorders, and mood disorders. Examples of mood disorders include major depression, major depressive disorder, treatment resistant depression, bipolar disorder, seasonal affective disorder, post natal depression, manic depression, bipolar depression, anxious depression, and anxiety. Examples of anxiety include social anxiety, post traumatic stress disorder, phobias, social phobia, special phobias, panic disorder, obsessive compulsive disorder, acute stress disorder, separation anxiety disorder, and generalized anxiety disorder.

Examples of diseases of the cardiovascular, metabolic, gastrointestinal and urogenital systems include diabetes, diabetes mellitus, thrombosis, irritable bowel disease, irritable bowel syndrome, Crohn's disease, cardiovascular diseases (such as hypertension, myocardial infarction, ischemic heart disease, ischemia), ureteric obstruction, lower urinary tract syndrome, lower urinary tract dysfunction such as incontinence, and disease after cardiac transplantation.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paraesthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostal neuralgia, mammary neuralgia, Morton's neuralgia, nasociliary neuralgia, occipital neuralgia, red neuralgia, Sluder's neuralgia, sphenopalatine neuralgia, supraorbital neuralgia, vulvodynia, or vidian neuralgia.

Antagonistic activities of the compound of the present invention against P2X7 and other P2X families can be confirmed in the suitable methods known to skilled in the art. For example, antagonistic activities of compounds of the present invention have been confirmed in $Ca^{2+}$ influx assay and electrophysiology assay.

Activities of the compound of the present invention for each disease, syndrome, and disorder described above can be confirmed in the suitable model known to skilled in the art. For example, activities of compounds of the present invention for pain are confirmed in rodent models of pain.

It is to be understood that "treatment" as used herein includes prophylaxis as well as alleviation of established symptoms as described above.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administered compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tableting lubricants (e.g. magnesium stearate, talc or silica); disintegrants (e.g. potato starch or sodium starch glycolate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of the present invention or pharmaceutically acceptable salt thereof and a sterile vehicle. Formulations for injection may be presented in unit dosage form e.g. in ampoules or in multi-dose, utilising a compound of the present invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogenfree water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and in general will also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the present invention or pharmaceutically acceptable salts thereof may also be formulated in rectal compositions such as suppositories or retention enemas, e.g. containing conventional suppository bases such as cocoa butter or other glycerides.

The compounds of the present invention or pharmaceutically acceptable salts may also be formulated as depot preparations. Such long acting formulations may be administered by implantation (for example subcutaneously or intramuscularly) or by intramuscular injection. Thus, for example, the compounds of the present invention or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds the present invention or pharmaceutically acceptable salts thereof may be formulated as solutions for administration via a suitable metered or unitary dose device or alternatively as a powder mix with a suitable carrier for administration using a suitable delivery device. Thus, the compounds of the present invention or pharmaceutically acceptable salts thereof may be formulated for oral, buccal, parenteral, topical (including ophthalmic and nasal), depot or rectal administration or in a form suitable for administration by inhalation or insufflation (through either mouth or nose). The compounds of the present invention and pharmaceutically acceptable salts thereof may be formulated for topical administration in the form of ointments, creams, gels, lotions, pessaries, aerosols or drops (e.g. eye, ear or nose drops). Ointments and creams may for example, be formulated with an aqueous or oily base with the addition of suitable thickening and/or gelling agents. Ointments for administration to the eye may be manufactured in a sterile manner using sterilized components.

A P2X7 antagonist may be usefully combined with another pharmacologically active compound, or two or more other pharmacologically active compounds, particularly in the treatment of inflammatory, pain and urological diseases or disorders. For example, a P2X7 antagonist, particularly a compound of the present invention, or a pharmaceutically acceptable salt or solvate thereof, as defined above, may be administered simultaneously, sequentially or separately in combination with one or more agents.

Such combinations offer significant advantages, including synergistic activity, in therapy.

The composition may contain from 0.1% to 99% by weight, preferably from 10% to 60% by weight, of the active material, depending on the method of administration. The dose of the compound used in the treatment of the aforementioned disorders may vary in the usual way with the seriousness of the disorders, the weight of the sufferer, and other similar factors.

A therapeutically effective amount of a compound of the present invention or a pharmaceutical composition thereof includes a dose range from about 0.05 mg to about 3000 mg, in particular from about 1 mg to about 1000 mg or, more particularly, from about 10 mg to about 500 mg of active ingredient in a regimen of about once a day or more than once a day, for example two, three or four times a day for an average (70 kg) human; although, it is apparent to one skilled in the art that the therapeutically effective amount for active compounds of the invention may vary as well the diseases, syndromes, conditions, and disorders being treated.

For oral administration, a pharmaceutical composition is preferably provided in the form of tablets containing about 0.01, about 0.1, about 1, about 10, about 50, about 100, about 150, about 200, about 250, and about 500 milligrams of the inventive compound as the active ingredient.

Advantageously, a compound of the present invention may be administered in a single daily dose, or the total daily dosage may be administered in divided doses of two, three and four times daily.

Optimal dosages of a compound of the present invention to be administered may be readily determined and may vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level.

The above dosages are thus exemplary of the average case. There can be individual instances wherein higher or lower dosage ranges are merited of course, and such are within the scope of this invention.

Compounds of the present invention may be administered in any of the foregoing compositions and dosage regimens or by means of those compositions and dosage regimens established in the art whenever use of a compound of the present invention is required for a subject in need thereof.

General Synthesis

Throughout the instant application, the following abbreviations are used with the following meanings:
AcOH: acetic acid
AIBN: 2,2'-azobis(isobutyronitrile)
BINAP: 2,2'-bis(diphenylphosphino)-1,1'-binaphthyl
BzATP: 2'(3')—O-(4-benzoylbenzoyl)adenosine-5'-triphosphate
DAST N,N-diethylaminosulfur trifluoride
d.e.: diastereomeric excess
Deoxo-Fluor (trademark): bis(2-methoxyethyl)aminosulfur trifluoride
Dess-Martin periodinane: 1,1,1-triacetoxy-1,1-dihydro-1,2-benziodoxol-3(1H)-one
DMF: N,N-dimethylformamide
DMSO: dimethylsulfoxide
DMT-MM: 4-(4,6-Dimethoxy-1,3,5-triazin-2-yl)-4-methylmorpholinium Chloride
e.e.: enantiomeric excess
EtOAc: ethyl acetate
EtOH: ethanol
ESI: electrospray ionization
Ex: example(s)
h: hour(s)
HBTU: N,N,N',N'-tetramethyl-O-(1H-benzotriazol-1-yl)uronium hexafluorophosphate
HPLC: high-performance liquid chromatography
(M)Hz: (mega)hertz
IM: intermediate(s)
LHMDS: lithium hexamethyldisilazide
mCPBA: m-chloroperbenzoic acid
MeCN: acetonitrile
MeOH: methanol
min: minute(s)
MS: mass spectrometry
n-BusP: tri-n-butylphosphine
NIS: N-iodosuccinimide
NMP: N-methyl-2-pyrrolidinone
NMR: nuclear magnetic resonance
$NaBH_4$: sodium tetrahydroborate
NaH: sodium hydride
NaHMDS: sodium hexamethyldisilazide
NBS: N-bromosuccinimide
NFSI: N-fluoro-N-(phenylsulfonyl)benzenesulfonamide
NMO: N-methylmorpholine oxide
NH gel: amino bound silica gel
Pd—C: palladium on carbon
RuCl(p-cymene)[(S,S)-Ts-DPEN]:
  [(S,S)—N-(2-amino-1,2-diphenylethyl)-p-toluenesulfonamide]chloro(p-cymene)ruthenium(II)
RuCl(p-cymene)[(R,R)-Ts-DPEN]:
  [(R,R)—N-(2-amino-1,2-diphenylethyl)-p-toluenesulfonamide]chloro(p-cymene)ruthenium(II)
SCX: super cation exchange resin
TBAF tetrabutylammonium fluoride
$T_3P$ (trademark): propylphosphonic anhydride
TBS: tert-butyldimethylsilyl
TBSCl: tert-butyldimethylsilyl chloride
TEMPO: 2,2,6,6-tetramethylpiperidine N-oxide
TFA: trifluoroacetic acid
THF: tetrahydrofuran
TLC: thin layer chromatography
TMAD: 1,1'-azobis(N,N-dimethylformamide)
TMSCl: trimethylsilyl chloride
Togni reagent: 1-trifluoromethyl-3,3-dimethyl-1,2-benziodoxole
tR: retention time
UV: ultraviolet
Xantphos 4,5-bis(diphenylphosphino)-9,9-dimethylxanthene The compounds described herein are prepared using techniques known to one skilled in the art through the reaction sequences depicted in Schemes 1-18 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

The use of "protecting groups" (PG) is well known in the art (see for example "Protective Groups in Organic Synthesis Forth Edition edited by T. W. Greene et al. (John Wiley & Sons, 2006)". For the purposes of this discussion, it will be assumed that such protecting groups are as necessary in place.

All starting materials in the following general syntheses may be commercially available or obtained by conventional methods known to those skilled in the art.

All of the 5,6,7,8-tetrahydroquinoline and 6,7-dihydro-5H-cyclopenta[b]pyridine derivatives of the formula I can be prepared by the procedures described in the general methods presented below or by the specific methods described in the Examples section and the Preparations section, or by routine modifications thereof. The present invention also encompasses any one or more of these processes for preparing the compounds of formula I, in addition to any novel intermediates used therein.

[Chem. 5]

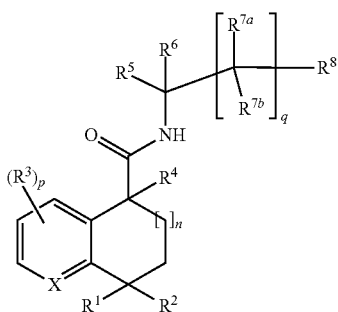

I

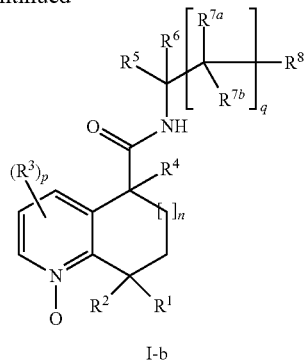

I-b

In the following general methods, X, $R^1$, $R^2$, $R^3$, $R^4$, $R^5$, $R^6$, $R^{7a}$, $R^{7b}$, $R^8$, n, p, and q are as previously defined for 5,6,7,8-tetrahydroquinoline and 6,7-dihydro-5H-cyclopenta[b]pyridine derivatives of the formula I unless otherwise stated.

Syntheses detailing the preparation of the compounds of formula I in a sequential manner are presented in the following reaction schemes. The phrase "amidation" is used here, and it means coupling a carboxylic acid with an amine using a coupling agent such as HBTU, DMT-MM, and $T_3P$ (trademark) in an inert solvent such as DMF and dichloromethane in the presence of a base such as trialkylamine at temperature of 0 to 50° C.

The following illustrates a preparation of the desired compounds of formula I (Scheme 1). X is N (II and I-a), X is N-oxide (I-b), PG is a carboxyl-protecting group, $R^1$, $R^2$, $R^3$, $R^4$, $R^5$, $R^6$, $R^{7a}$, $R^{7b}$, $R^8$, n, p, and q are as defined above.

The compounds of formula I-a can be prepared by deprotection of carboxyl-protecting group of the compounds formula II and then amidation between the compounds of formula III. Typical PG includes, but not limited to: methyl, ethyl, t-butyl. The typical deprotection methods of PG are described in above reference [Protective Groups in Organic Synthesis Forth Edition]. The following amidation method is described in above. Compounds of formula II can be prepared as described in the experimental part below. The compounds of formula I-b can be prepared by oxidation of the compounds of formula I-a with an oxidizing reagent such as mCPBA in a solvent such as halogenated hydrocarbons at temperature of −10 to 40° C.

The compounds of formula II use for the synthesis of compounds of the present invention are prepared as described in Schemes 2, 3, and 4. $R^3$, $R^4$, p, n, and PG are as defined above. The compounds of formula II can be prepared from the compounds of formula IV by the following steps; alkenylalkylation (Step 1), intramolecular Heck reaction (Step 2), alcoholysis (Step 3), nucleophilic addition (Step 4), oxidative cleavage (Step 5), and reduction (Step 6).

Scheme 1

[Chem. 6]

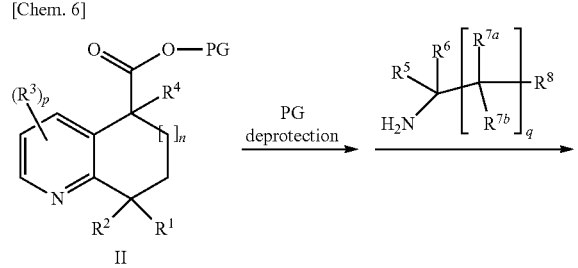

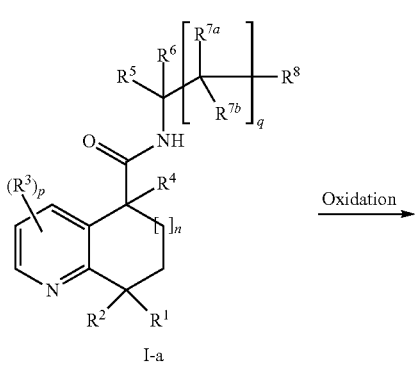

Scheme 2

[Chem. 7]

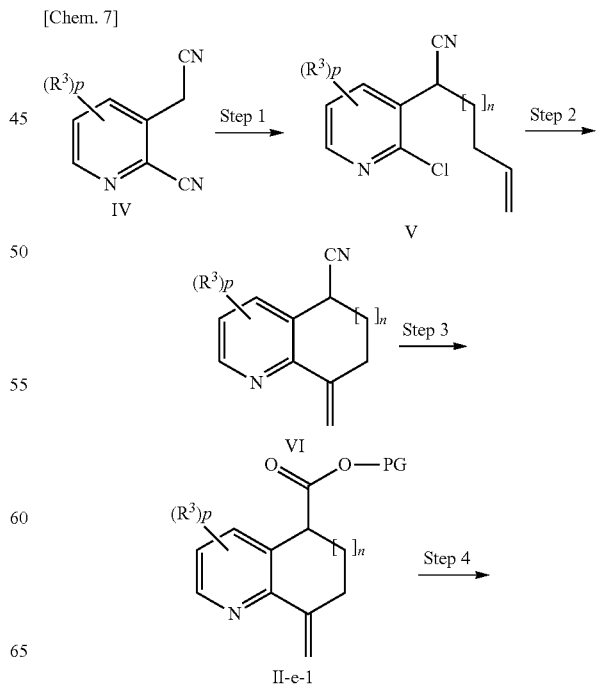

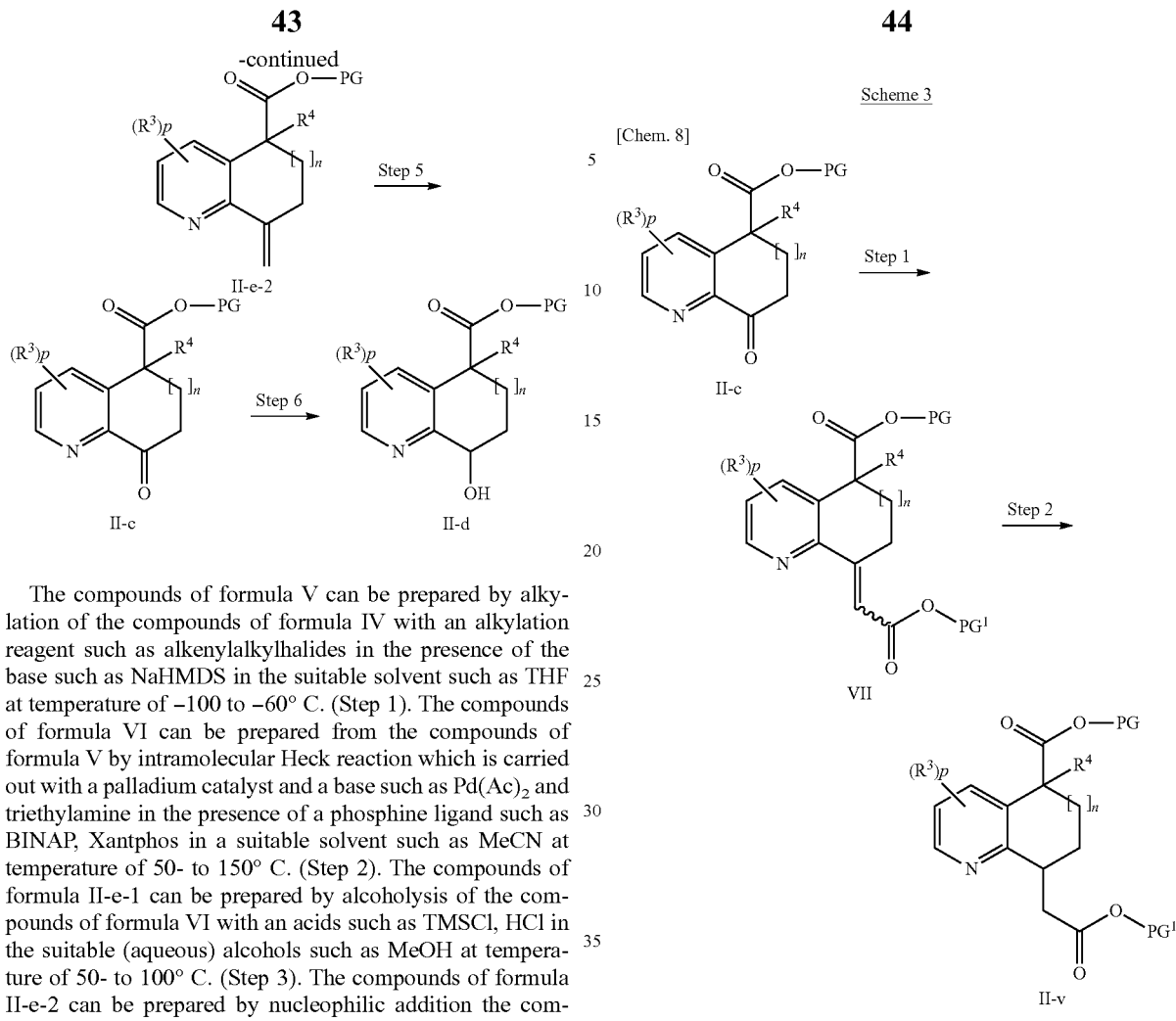

The compounds of formula V can be prepared by alkylation of the compounds of formula IV with an alkylation reagent such as alkenylalkylhalides in the presence of the base such as NaHMDS in the suitable solvent such as THF at temperature of −100 to −60° C. (Step 1). The compounds of formula VI can be prepared from the compounds of formula V by intramolecular Heck reaction which is carried out with a palladium catalyst and a base such as Pd(Ac)$_2$ and triethylamine in the presence of a phosphine ligand such as BINAP, Xantphos in a suitable solvent such as MeCN at temperature of 50- to 150° C. (Step 2). The compounds of formula II-e-1 can be prepared by alcoholysis of the compounds of formula VI with an acids such as TMSCl, HCl in the suitable (aqueous) alcohols such as MeOH at temperature of 50- to 100° C. (Step 3). The compounds of formula II-e-2 can be prepared by nucleophilic addition the compounds of formula II-e-1 with an electrophile such as NFSI or Togni reagent in the presence of a base such as NaHMDS in a suitable solvent such as THF at temperature of −100 to −60° C. (Step 4). The compounds of formula II-c can be prepared by oxidative cleavage reaction of the compounds of formula II-e-2 with an oxidizing reagent such as ozone and following treatment with a reducing agent such as dimethylsulfide or triphenylphosphine in a suitable solvent such as alcohol and/or halogenated hydrocarbons at temperature of −80 to −40° C. (Step 5). The compounds formula II-d can be prepared by reduction of the compounds formula II-c with a reducing reagent such as NaBH$_4$ in a suitable solvent such as MeOH, THF at temperature of −10 to 70° C. The alternative method for the preparation of the compounds of formula II-d from II-c by transfer hydrogenation with a hydrogen donor such as formic acid in the presence of metal catalyst such as RuCl(p-cymene)[Ts-DPEN] and a base such as triethylamine in a suitable solvent such as DMF at temperature of −10 to 70° C. (Step 6). The diastereo isomers can be separate by silica gel column chromatography or preparative TLC. In the Scheme 2, the reaction of Step 4 can be skipped to afford the compounds of formulae II-c and II-d, which are hydrogen as R$^4$.

The following illustrates a preparation of the desired compounds of formula II-v (Scheme 3). The compounds of formula II-v can be prepared from the compounds of formula II-c by the following steps; Horner-Wadsworth-Emmons (HWE) reaction (Step 1), and hydrogenation (Step 2).

The HWE reaction is carried out for preparation of the compounds of formula VII, the compounds of formula II-c treated with a trialkyl phosphono acetate such as t-butyl dimethylphosphonoacetate in the presence of a base in a suitable solvent such as THF at temperature of −40 to 50° C. (Step 1). The compounds of formula II-v can be prepared by hydrogenation of the compounds of formula VII with a hydrogen in the presence of a metal catalyst such as platinum oxide, palladium in a suitable solvent such as alcohols at temperature of 0 to 40° C.

The following illustrates a preparation of the desired compounds of formulae II-s and II-y (Scheme 4).

Scheme 4

[Chem. 9]

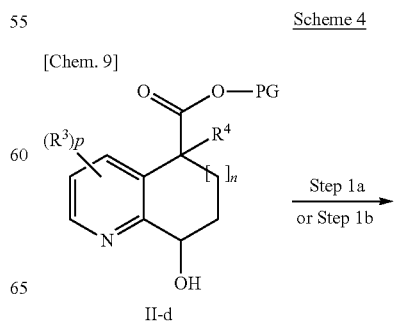

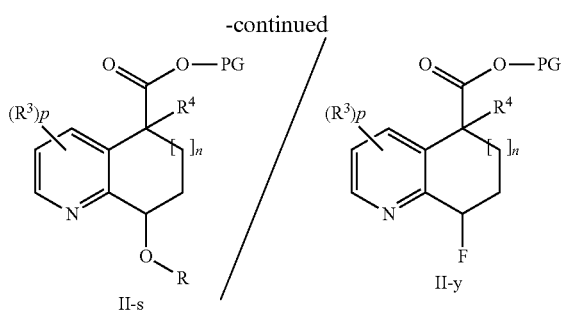

The compounds of formula II-s can be prepared by alkylation of the compounds of formula II-d with an alkylation reagent such as alkylhalides, alkenylalkylhalides in the presence of a base, and/or additives such as silver(I) oxide in a suitable solvent such as THF, NMP at temperature of −10 to 100° C. (Step 1a). The compounds of formula II-y can be prepared by deoxygenative fluorination of the compounds of formula II-d with a deoxygenative fluorination reagent such as DAST, Deoxo-Fluor (trademark) in a suitable solvent such as halogenated hydrocarbons, ethers at temperature of −50 to 20° C. (Step 1b).

Compounds of formula III, if not commercially available, can be prepared by known procedures or following procedures outlined in Scheme 5. $R^5$ and $R^6$ are hydrogen, q is 0, $R^8$ is aryl. The compounds formula III-a can be prepared from the compounds of formula VIII by the following steps; bromination (Step 1), fluorination (Step 2), and reduction (Step 3). The compounds of formula III-b can be prepared from the compounds of formula VIII by the following steps; bromination (Step 1), nucleophilic substitution (Step 4), and reduction (Step 3).

Scheme 5

[Chem. 10]

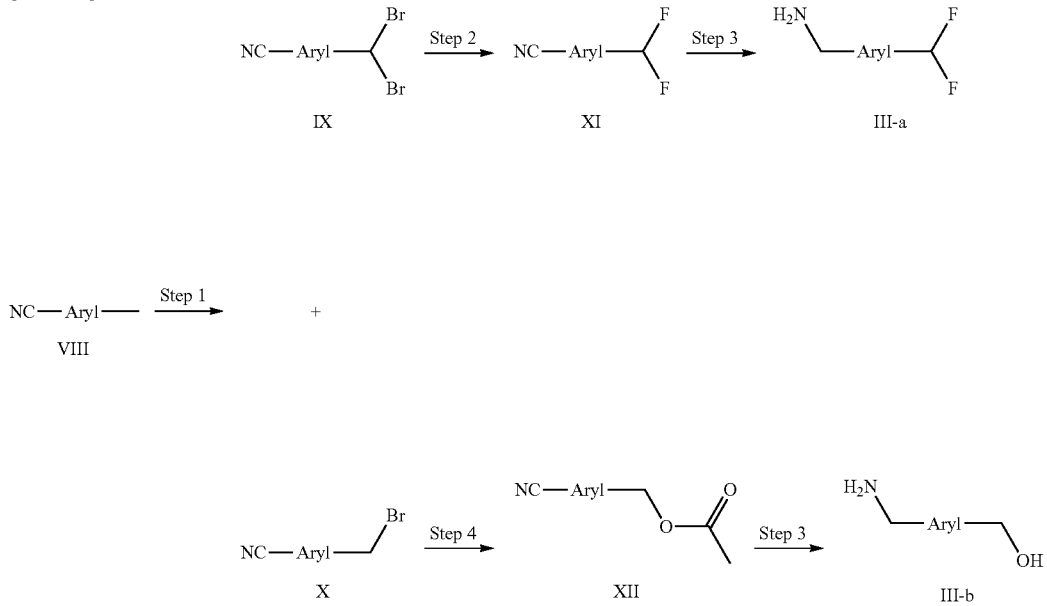

The bromination is carried out for the compounds of formula VIII with a bromine source such as NBS in the presence of a radical initiator such as AIBN in a suitable solvent such as carbon tetrachloride at temperature of 50- to 100° C. to afford the compounds of formulae IX and X (Step 1). The fluorination to the compounds of formula IX is carried out with a fluorine source such as silver tetrafluoroborate to afford the compounds of formula XI (Step 2). The compounds of formula XII can be prepared by nucleophilic substitution of the compounds of formula X with a suitable nucleophile such as sodium acetate in a suitable solvent such as AcOH at temperature of 80- to 120° C. The compounds of formulae III-a and III-b can be prepared by reduction of the compounds of formulae XI and XII with a suitable reducing reagent such as borane-THF complex in a suitable solvent such as THF at temperature of −10 to 80° C.

The following illustrates a preparation of the desired compounds of formulae I-c and I-d (Scheme 6). $R^1$ and $R^2$ form ketone (I-c) and $R^1$ is hydrogen, $R^2$ is hydroxyl (I-d), $R^3$, $R^4$, $R^5$, $R^6$, $R^{7a}$, $R^{7b}$, $R^8$, n, p, and q are as defined above.

Scheme 6

[Chem. 11]

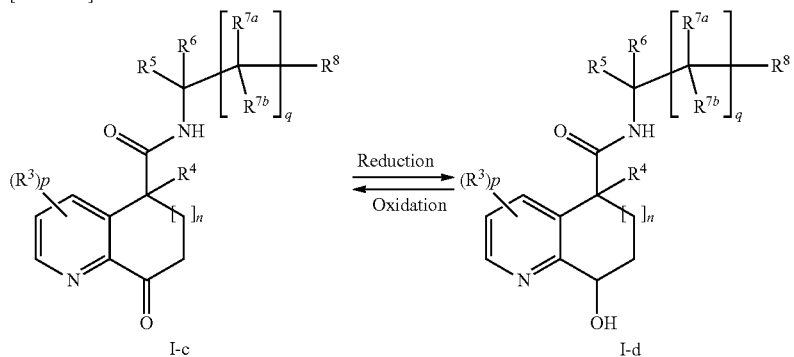

I-c ⇌ (Reduction/Oxidation) ⇌ I-d

The compounds of formula I-d can be prepared by the same procedure as described in the Step 6 in Scheme 2. The diastereoisomers of the compounds of formula I-d can be separate by silica gel column chromatography or preparative TLC. The compounds of formula I-c can be prepared by oxidation of the compounds of formula I-d with an oxidizing reagent such as Dess-Martin periodinane, TEMPO, and N-t-butylphenylsulfinimidoyl chloride in a suitable solvent such as dichloromethane, toluene at temperature of −10 to 70° C.

The following illustrates a preparation of the desired compounds of formulae I-c, and I-f (Scheme 7). $R^1$ and $R^2$ form methylene (I-e), $R^1$ and $R^2$ form ketone (I-c) and R 1 is hydroxyl, $R^2$ is hydroxymethyl (I-f), $R^3$, $R^4$, $R^5$, $R^6$, $R^{7a}$, $R^{7b}$, $R^8$, n, p, and q are as defined above.

compounds of formula I-f can be prepared by dihydroxylation of the compounds of formula I-e with an oxidizing reagent such as osmium tetroxide in the presence or absence of co-oxidants such as NMO in a suitable solvent such as alcohols and water at temperature of −10 to 60° C.

The following illustrates a preparation of the desired compounds of formulae I-g, and I-h (Scheme 8). $R^1$ and $R^2$ form ketone (I-c), $R^1$ and $R^2$ form methylene (I-e), $R^1$ and $R^2$ form epoxide (I-g), and $R^1$ is hydroxyl, $R^2$ is nucleophilic group (Nu) such as acyloxy groups, hydroxides, alkoxides, fluoride, cyano, amines, azides, sulfides (I-h), R 3, $R^4$, $R^5$, $R^6$, $R^{7a}$, $R^{7b}$, $R^8$, n, p, and q are as defined above.

Scheme 7

[Chem. 12]

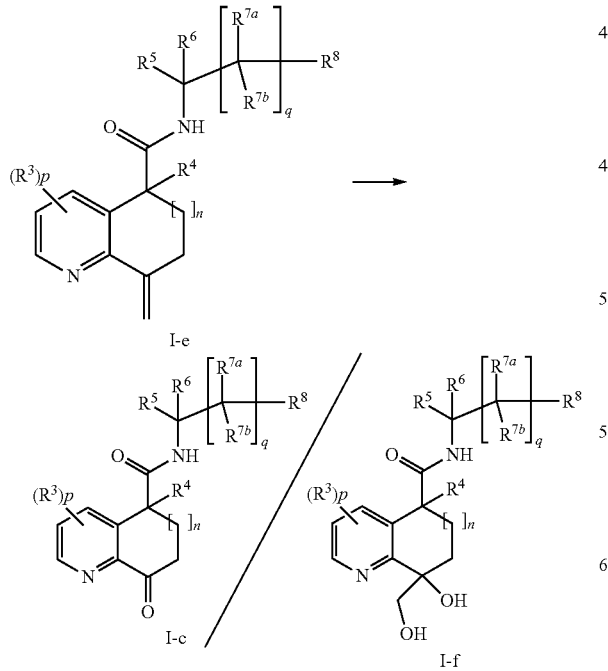

Scheme 8

[Chem. 13]

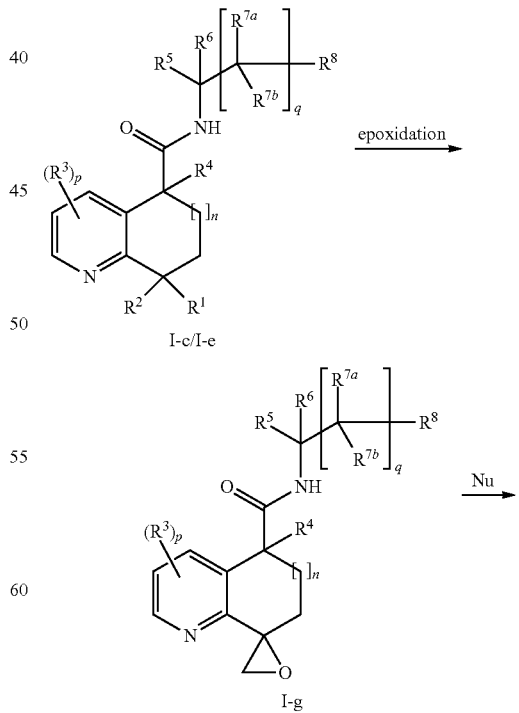

The compounds of formula I-c can be prepared by the same procedure as described in the Step 5 in Scheme 2. The -continued

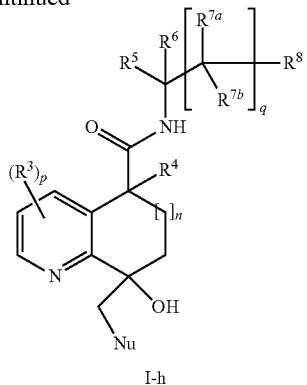

I-h

The compounds of formula I-g can be prepared by epoxidation of the compounds of formula I-e with NBS in a suitable solvent such as aqueous tert-butanol at temperature of 30- to 80° C. and then treatment with a base such as NaOH at temperature of −10 to 10° C. The compounds of formula I-g can be prepared by epoxidation of the compounds of formula I-c with a sulfur ylide reagent such as dimethyloxosulfonium methylide in a suitable solvent such as DMSO at temperature of −10 to 50° C. The diastereo isomers can be separate by silica gel column chromatography or preparative TLC. The nucleophilic addition of the compounds of formula I-g for the synthesis of the compounds of formula I-h is carried out with the nucleophiles such as alkali metal hydroxide, alkali metal alkoxide, acyloxy groups, alkali metal cyanide, alkali metal fluoride, substituted or unsubstituted alkylsulfide, and amine or the corresponding ammonium salt of nucleophiles in a suitable solvent such as halogenated hydrocarbons, ethers, aromatic hydrocarbons, amides, inert amines, sulfoxides at temperature of −80 to 100° C. in the presence or in the absence of a catalyst such as copper salts or zinc salts.

The following illustrates a preparation of the desired compounds of formulae I-i, I-j, and I-k (Scheme 9). LvG and LvG$^1$ are leaving groups such as halogen, hydroxyl, sulfonate, azide, imidazole. In the case where R$^{10a}$ is LvG$^1$ substituted C$_1$-C$_2$alkyl and Y$^1$ and Y$^2$ are hydrogen (I-h-1 and I-j) or R$^{10a}$ is hydrogen and Y$^1$ and Y$^2$ form carbonyl (I-h-1, I-i, and I-k), R$^3$, R$^4$, R$^5$, R$^6$, R$^{7a}$, R$^{7b}$, R$^8$, R$^{9a}$, n, p, and q are as defined above.

Scheme 9

[Chem. 14]

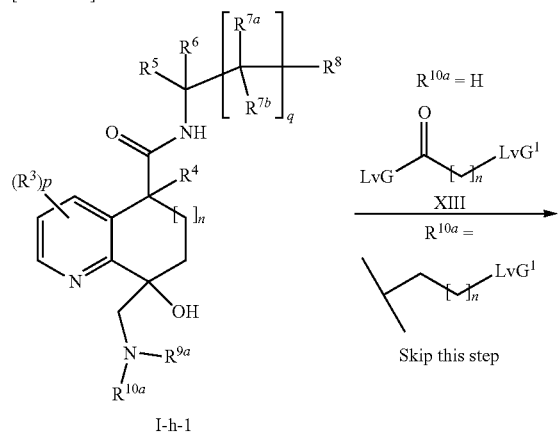

-continued

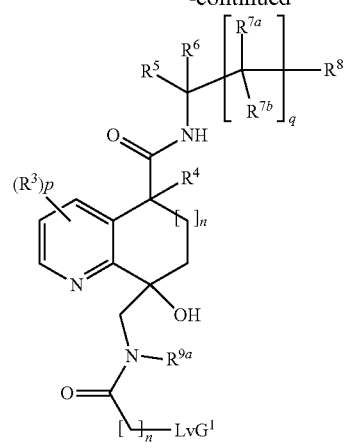

I-i

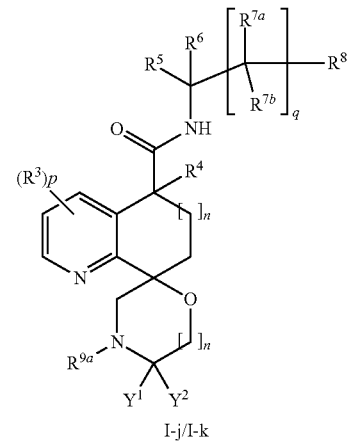

I-j/I-k

The compounds of formula I-i can be prepared by amidation of the compounds of formula I-h-1 (R$^{10a}$ is hydrogen) with a carboxylic acid XIII (LvG is hydroxyl) under "amidation" condition as described above, or with a activated carboxylic acid XIII such as acid halide (LvG is halogen) in a suitable base such as trialkylamine in a suitable solvent such as dichloromethane at temperature of −30 to 20° C. In the case where n is 0, the cyclized compounds of formula I-k can be prepared in this step without following "cyclization" step. In the case where LvG$^1$ is not hydroxyl, the compounds of formulae I-j and I-k can be prepared by cyclization of the compounds of formula I-i or I-h-1 (R$^{10a}$ is LvG$^1$ substituted C$_1$-C$_2$alkyl) in the presence of a suitable base such as potassium tert-butoxide in a suitable solvent such as alcohol and/or halogenated hydrocarbons at temperature of −20 to 50° C. In the case where LvG$^1$ is hydroxyl, the compounds of formulae I-j and I-k can be prepared by intramolecular Mitsunobu reaction of the compounds of formula I-h-1 or I-i with a Mitsunobu reagents such as N,N,N',N'-tetraalkylazodicarboxamide or dialkylazodicarboxylate in the presence of trialkylphosphine or triarylphosphine in a suitable solvent such as THF at temperature of −40 to 80° C.

The following illustrates a preparation of the desired compounds of formula I-l (Scheme 10). R$^1$ is hydroxyl, R$^2$ is C$_1$alkylthio-R$^{9a}$, m is 0 (I-h-2), or m is 1 or 2 (I-1), R$^3$, R$^4$, R$^5$, R$^6$, R$^{7a}$, R$^{7b}$, R$^8$, R$^{9a}$, n, p, and q are as defined above.

Scheme 10

[Chem. 15]

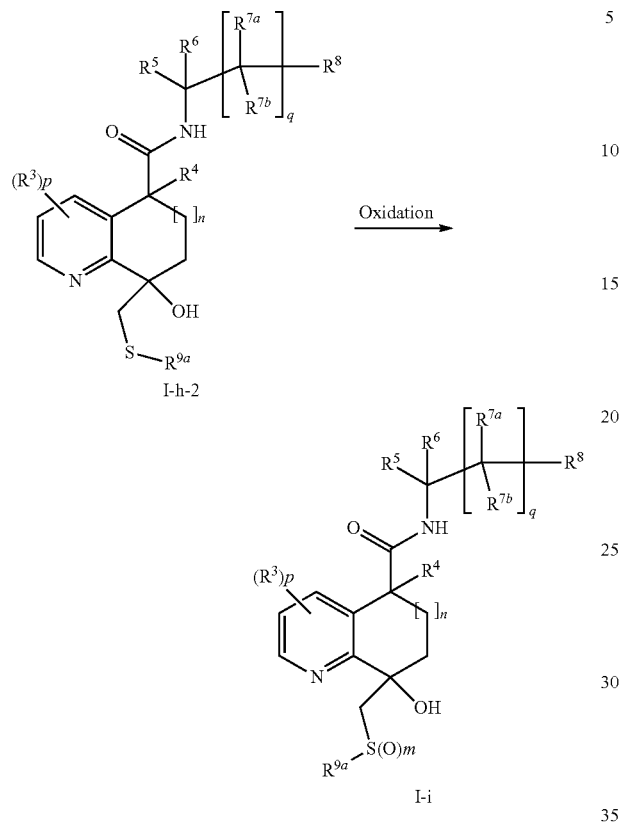

The compounds of formula I-l can be prepared by oxidation of the compounds formula I-h-2 with an oxidizing reagent such as mCPBA in a suitable solvent such as halogenated hydrocarbons at temperature of −20 to 50° C.

The following illustrates a preparation of the desired compounds of formulae I-m and I-n (Scheme 11). $R^1$ is hydroxyl, $R^2$ is $C_1$alkylazide (I-h-3), or $R^1$ and $R^2$ form aziridine (I-m), or $R^1$ is amino, $R^2$ is hydroxy$C_1$alkyl (I-n), $R^3$, $R^4$, $R^5$, $R^6$, $R^{7a}$, $R^{7b}$, $R^8$, R 9a, n, p, q, and PG are as defined above.

Scheme 11

[Chem. 16]

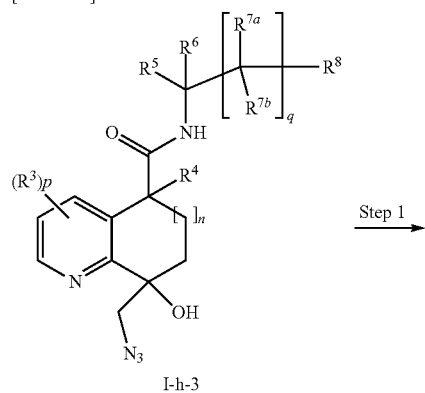

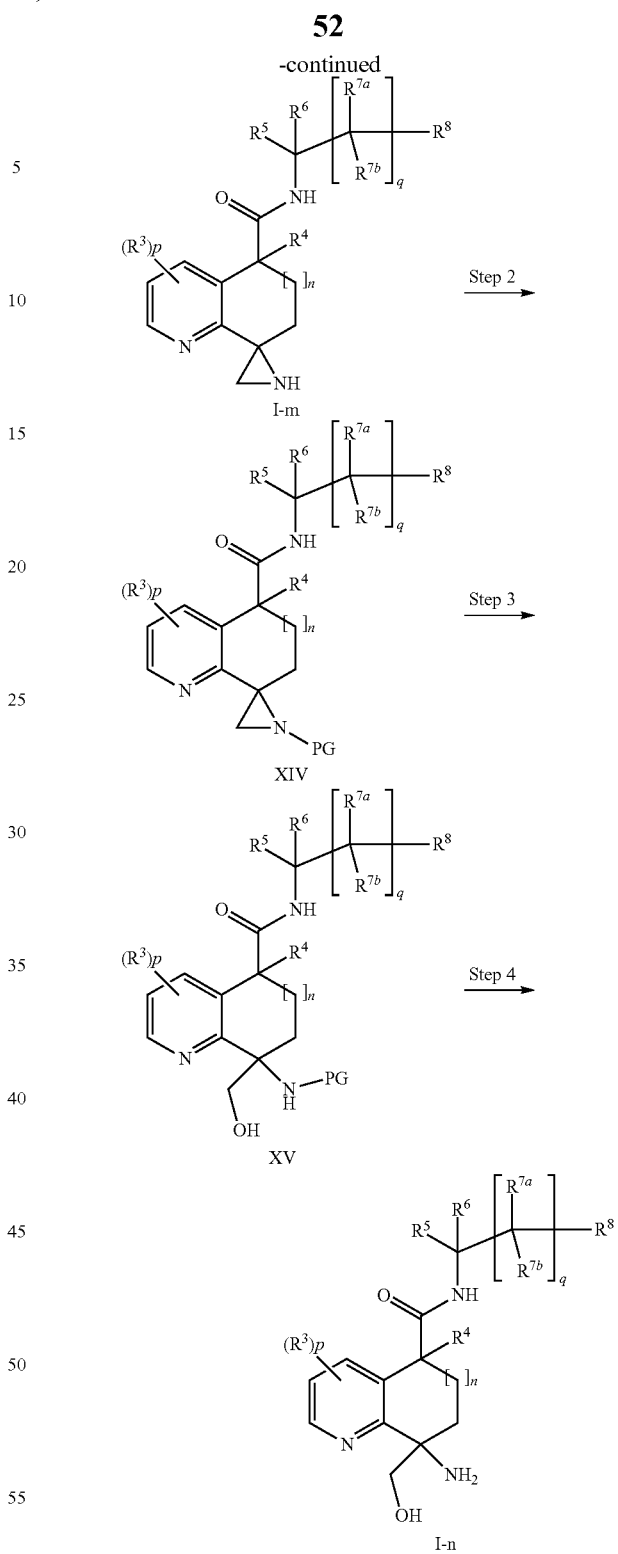

The compounds of formula I-m can be prepared by aziridine formation of the compounds formula I-h-3 with a triphenylposphine in a suitable solvent such as aqueous MeCN at temperature of 20- to 100° C. (Step 1). The compounds of formula I-n can be prepared by following reactions, protection of aziridine (Step 2), nucleophilic ring opening and hydrolysis (Step 3), and deprotection (Step 4). The suitable PG such as 2-nitrophenylsulfonyl group, the protection and deprotection reactions can be performed in the usual manner. The compounds of formula XV can be prepared by nucleophilic addition and then hydrolysis of the compounds of formula XIV with a metal carboxide such as alkali metal acetoxide in a suitable solvent such as DMF at temperature of 60- to 120° C. and followed by hydrolysis with an alkali metal hydroxide such as NaOH in a suitable solvent such as DMF at room temperature. The compounds of formula I-n can be prepared by deprotection of the compounds of formula XV by the usual manner such as 4-mercaptobenzoic acid in a suitable solvent such as DMF at temperature of 70- to 120° C.

The following illustrates a preparation of the desired compounds of formula I-o (Scheme 12). $R^1$ is amino, $R^2$ is hydroxyC$_1$alkyl (I-n), $R^3$, $R^4$, $R^5$, $R^6$, $R^{7a}$, $R^{7b}$, $R^8$, $R^{9a}$, LvG, LvG$^1$, n, p, and q are as defined above.

The compounds of formula I-o can be prepared by the same procedure as described in Scheme 9 from the compounds of formula I-n via the compounds of formula XVI.

The following illustrates a preparation of the desired compounds of formulae I-p, I-q, and I-r (Scheme 13). $R^1$ is hydrogen and $R^2$ is hydroxyl (I-d), R is methyl or phenyl, $R^2$ is thioester (I-p), $R^2$ is sulfide (I-q), $R^2$ is sulfoxide or sulfone (I-r), $R^3$, $R^4$, $R^5$, $R^6$, $R^{7a}$, $R^{7b}$, $R^8$, $R^{9a}$, m, n, p, and q are as defined above.

Scheme 12

[Chem. 17]

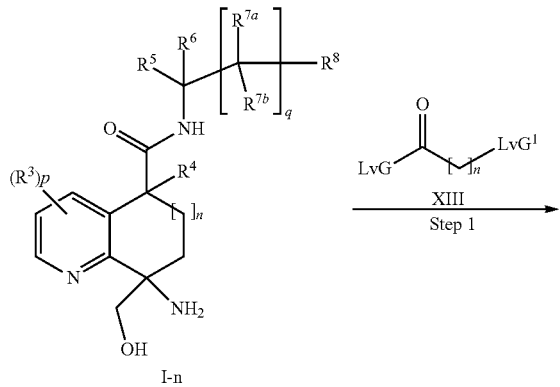

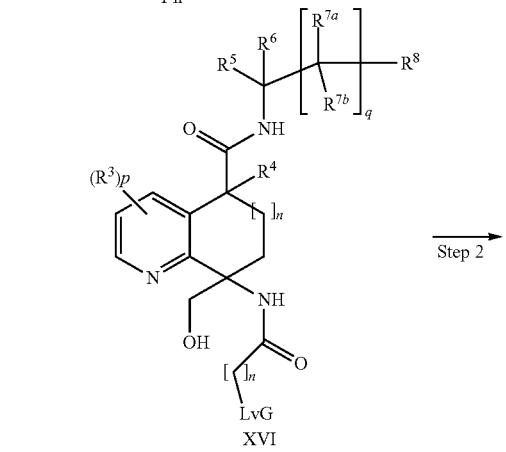

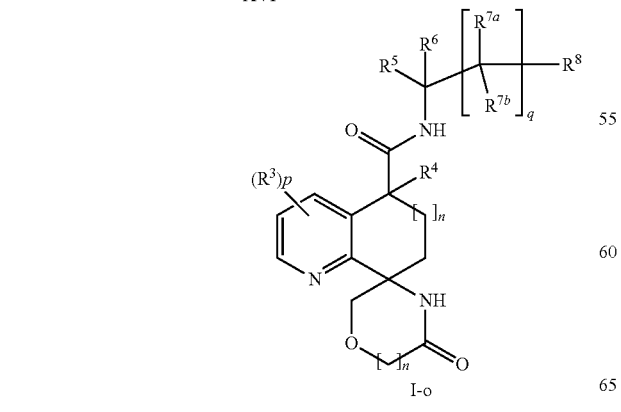

Scheme 13

[Chem. 18]

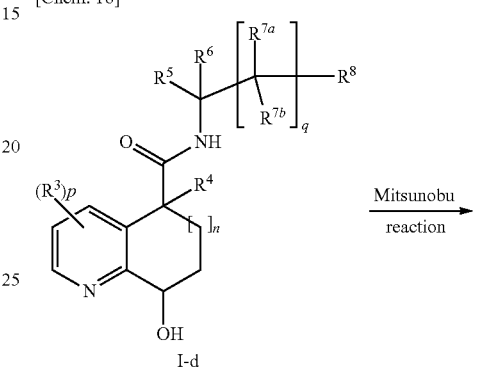

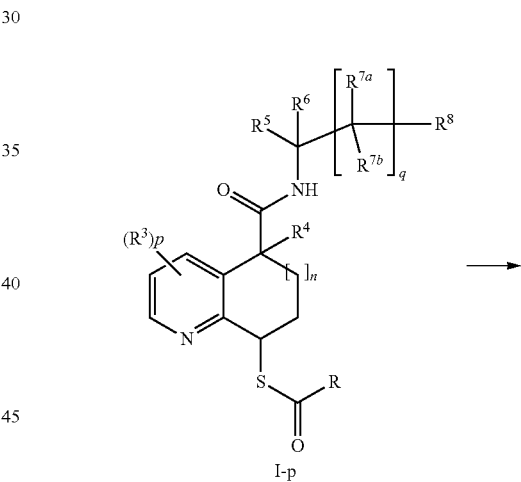

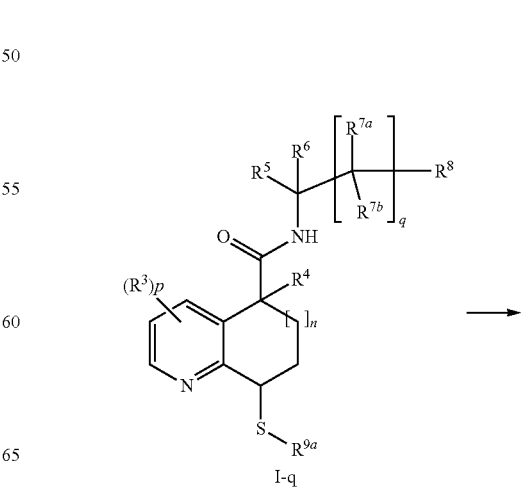

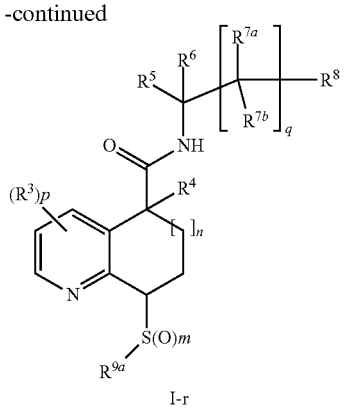

The compounds of formula I-p can be prepared by Mitsunobu reaction of the compounds of formula I-d with a thiocarboxylic acid such as thioacetic acid, thiobenzoic acid under Mitsunobu reaction condition as described above.

The compounds of formula I-q can be prepared by S-alkylation of the compounds of formula I-p with an alkylation reagent such as dimethyl sulfonate, alkylhalides in the presence of alkali metal hydroxide in a suitable solvent such as halogenated hydrocarbons, ethers, alcohols at temperature of −20 to 50° C. The compounds of formula I-r can be prepared by the same procedures as described in Scheme 10.

The following illustrates a preparation of the desired compounds of formulae I-s, I-t and I-u (Scheme 14). $R^1$ is hydrogen and $R^2$ is alkenylalkoxide (I-s), $R^2$ is hydroxyalkoxide (I-t), $R^2$ is hydroxy substituted hydroxyalkoxide (I-u), $R^4$, $R^5$, $R^6$, $R^{7a}$, $R^{7b}$, and $R^1$ are as defined above.

Scheme 14

[Chem. 19]

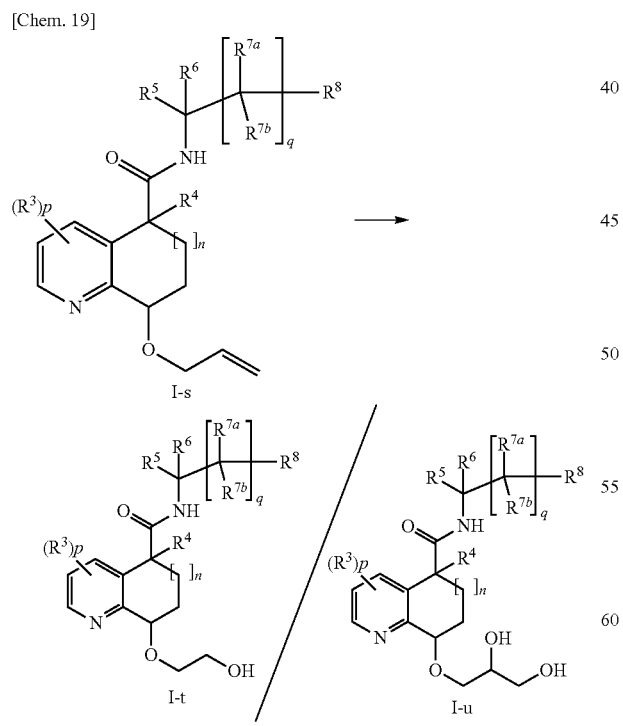

The compounds of formula I-t can be prepared by oxidation of the compounds of formula I-s with an oxidizing reagent such as ozone at temperature of −100 to −60° C. and then treated with sodium tetrahydroborate in a suitable solvent such as halogenated hydrocarbons and/or alcohols. The compounds of formula I-u can be prepared by the same procedure of the "dihydroxylation" in Scheme 7.

The following illustrates a preparation of the desired compounds of formulae I-w, and I-x (Scheme 15). $R^1$ is hydrogen and $R^2$ is "Protected carboxylic acid" alkyl (I-v), $R^2$ is carboxylic acid alkyl (I-w), $R^2$ is aminocarboxylalkyl (I-x), $R^4$, $R^5$, $R^6$, $R^{7a}$, $R^{7b}$, $R^8$, $R^{9a}$ and $R^{10a}$ are as defined above.

Scheme 15

[Chem. 20]

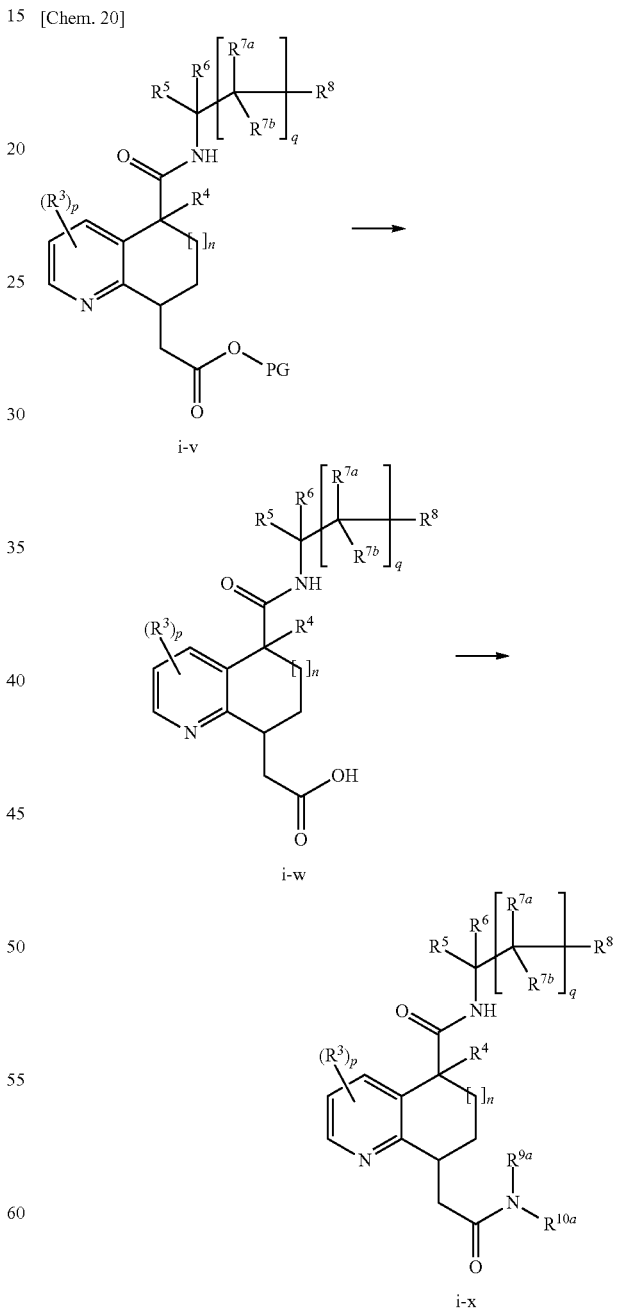

The compounds of formula I-w can be prepared by deprotection of the PG from the compounds of formula I-v.

The compounds of formula I-x can be prepared by "amidation" of the compounds of formula I-w with a coupling agent and amines. The general condition of "amidation" is described in above.

The following illustrates a preparation of the desired compounds of formula II-e-2 (Scheme 16). $R^4$ is hydroxyl or fluoro, $R^3$, p, n, and PG are as defined above. The compounds of formula II-e-2 also can be prepared from the compounds of formula XVII by the following steps; alkenylacylation (Step 1), intramolecular Heck reaction (Step 2), cyanohydrination and deoxygenative fluorination (Step 3), and alcoholysis (Step 4).

from the compounds of formula XX by the same procedure as described in Scheme 2 Step 3 (Step 4).

The following illustrates a preparation of the desired compounds of formula II-e-2 (Scheme 17). $R^3$, $R^4$, p, n, and PG are as defined above. The compounds of formula II-e-2 ($R^4$ is fluoro) also can be prepared from the compounds of formula XVII by the following steps; alkenylalkylation (Step 1), intramolecular Heck reaction (Step 2), and deoxygenative fluorination (Step 3).

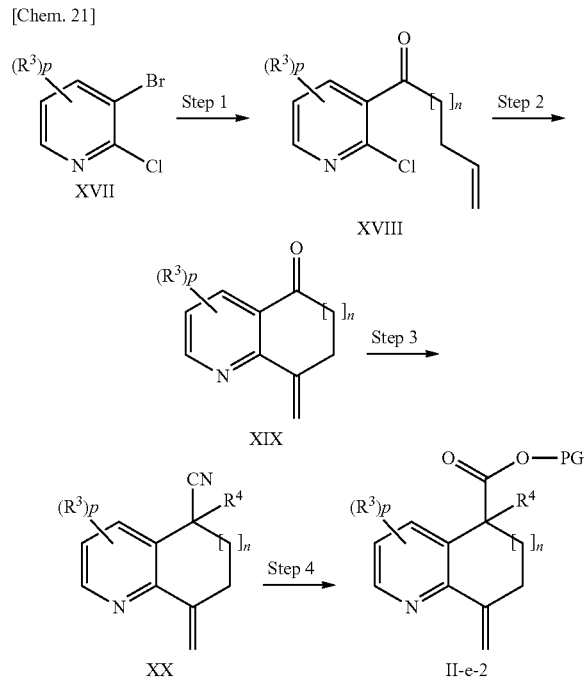

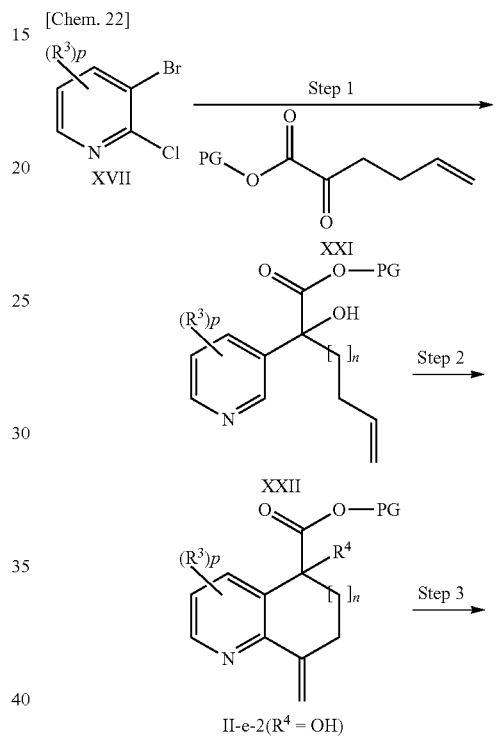

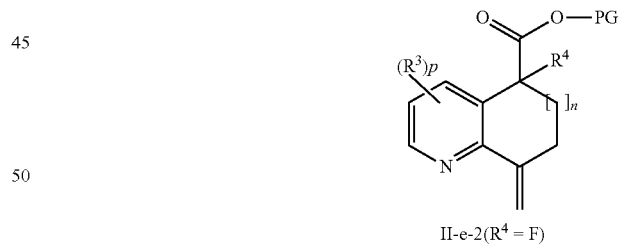

The compounds of formula XVIII can be prepared by alkenylacylation of the compounds of formula XVII, which is carried out by the following procedure. The preparation of the Grignard reagents of the compounds of formula XVII is carried out by the treatment of the compounds of formula XVII with a Turbo Grignard reagent such as 2-propylmagnesium chloride lithium chloride complex in the suitable solvent such as THF at temperature of −20 to 10° C. The compounds of formula XVIII can be prepared by the following addition of an alkenylalkylacylhalides in the suitable solvent such as THF at temperature of −50 to 0° C. (Step 1). The compounds of formula XIX can be prepared from the compounds of formula XVIII by the same procedure as described in Scheme 2 Step 2 (Step 2). The compounds of formula XX can be prepared by cyanohydrination and following deoxygenative fluorination of the compounds of formula XIX. The cyanohydrination of the compounds of formula XIX is carried out with the cyanide source such as trimethylsilyl cyanide in the presence of a catalyst such as NMO in a suitable solvent such as THF at temperature of −10 to 30° C. And then deoxygenative fluorination is carried out by the same procedure as described in Scheme 4 Step 1b (Step 3). The compounds of formula II-e-2 can be prepared The compounds of formula XXII, II-e-2 ($R^4$ is hydroxyl), and II-e-2 ($R^4$ is fluoro) can be prepared by the same procedure as described in Scheme 16 Step 1 with an alkylation reagent of XXI (Step 1), Scheme 2 Step 2 (Step 2), and Scheme 4 Step 1b (Step 3).

The following illustrates a preparation of the desired compounds of formula I-g (Scheme 18). $R^3$, $R^4$, $R^5$, $R^6$, $R^{7a}$, $R^{7b}$, $R^8$, p, n, q, and PG are as defined above. The compounds of formula I-g also can be prepared from the compounds of formula II-e-2 by the following steps; hydrolysis (Step 1), iodolactonization (Step 2), and nucleophilic amidation (Step 3).

Scheme 18

[Chem. 23]

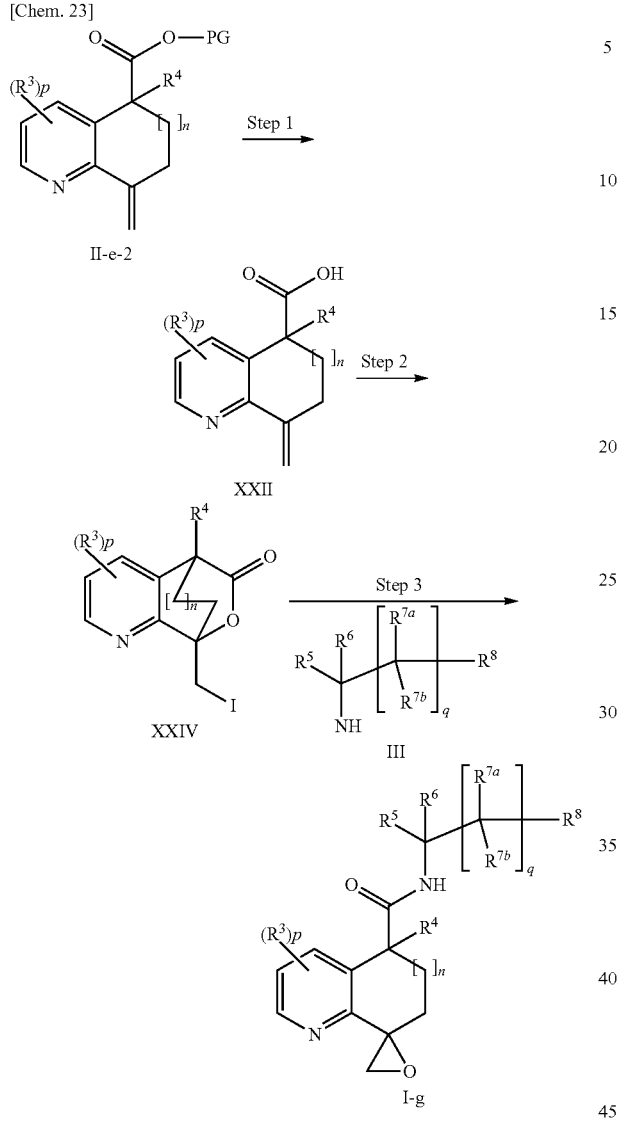

The compounds of formula XXIII can be prepared from the compounds of formula II-e-2 by hydrolysis with a base such as NaOH in a suitable solvent such as MeOH, THF at temperature 0 to 40° C. The compounds of formula XXIII also can be prepared by hydrolysis with an enzyme such as lipase in a suitable solvent such as phosphate buffer at temperature 20 to 40° C. (Step 1). The compounds of formula XXIV can be prepared from the compounds of formula XXIII by iodolactonization which is carried out in the presence of iodine or NIS and a base such as $K_2CO_3$ in a suitable solvent such as MeCN, DMF, DMSO at temperature 0 to 40° C. (Step 2). The Step 1 and Step 2 can be carried out in one-pot. The compounds of formula I-g can be prepared by nucleophilic amidation of the compounds of formula XXIV with an amine III in the presence of a base such as $K_2CO_3$ in a suitable solvent such as DMF, DMSO, MeCN at temperature of 0 to 40° C. (Step 3).

The following illustrates a preparation of the desired compounds of formula II-e-2 (Scheme 19). $R^4$ is fluoro, $R^3$, p, n, and PG are as defined above. The compounds of formula II-e-2 ($R^4$ is fluoro) also can be prepared from the compounds of formula V by the following steps; reduction (Step 1), organocatalytic fluorination (Step 2), oxidation (Step 3), protection (Step 4), and intramolecular Heck reaction (Step 5).

Scheme 19

[Chem. 24]

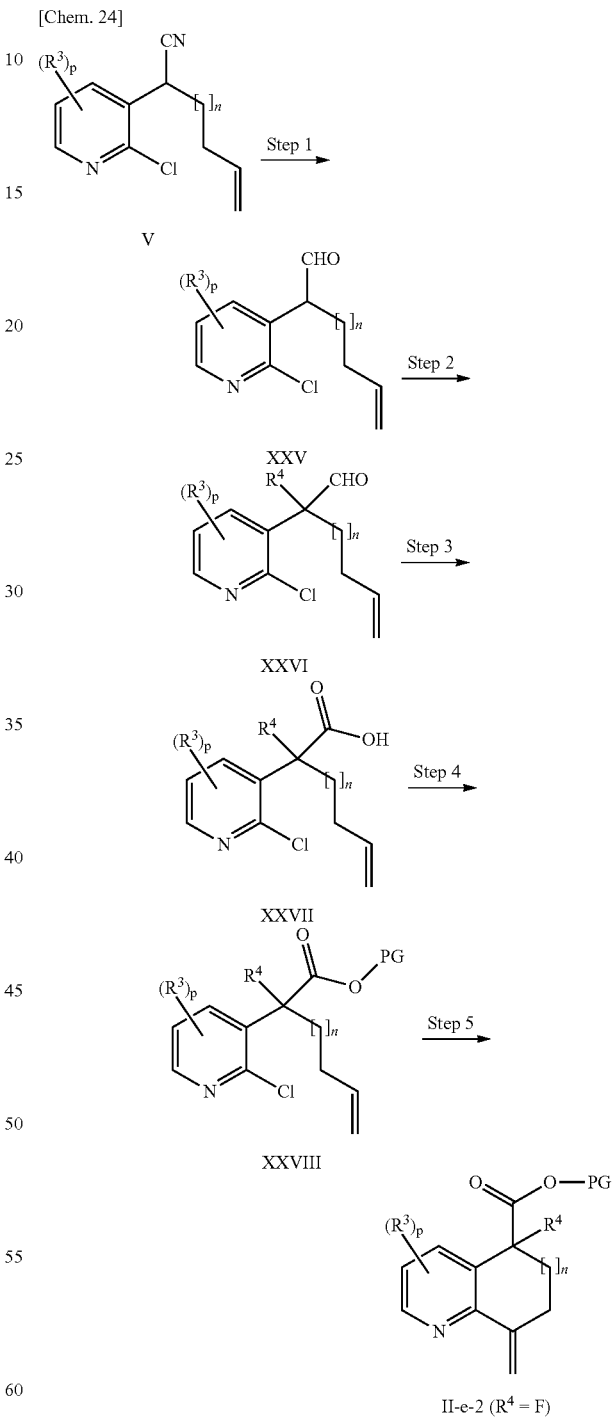

The compounds of formula XXV can be prepared by reduction of the compounds of formula V with a reducing reagent such as Diisobutylaluminium hydride in a suitable solvent such as toluene, THF at temperature of −78 to 0° C. (Step 1). The compounds of formula XXVI can be prepared by organocatalytic fluorination of the compounds of formula XXV, which is carried out with an organocatalyst and fluorination reagent such as proline, imidazolidinone organocatalysts and NFSI, Selectfluor (registered trademark) in a suitable solvent such as DMF, THF, toluene, and ether at temperature −20 to 50° C. (Step 2). The compounds of formula XXVII can be prepared by oxidation of the compounds of formula XXVI with an oxidizing reagent such as sodium chlorite in a suitable solvent such as tert-BuOH at temperature of −10 to 40° C. (Step 3). The compound of formula XXVIII can be prepared by protection of the compound of formula XXVII (Step 4). The compound of formula II-e-2 ($R^4$ is fluoro) can be prepared from the compounds of formula XXVIII by cyclization with a palladium catalyst and a base such as $Pd(OAc)_2$ and N,N-Diisopropylethylamine in the presence of a phosphine ligand such as BINAP, Xantphos in a suitable solvent such as DMF at temperature of 50 to 150° C. as described in the Step 5. The compound of formula II-e-2 ($R^4$ is fluoro) can be also prepared from the compounds of formula V by the same procedure as described in the Step 2, Step 3, and Step 4 in Scheme 2.

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (TLC) and reaction times are given for illustration only; the structure and purity of all isolated compounds were assured by at least one of the following techniques: TLC (Merck silica gel 60 $F_{254}$ precoated TLC plates or Merck $NH_2$ $F_{254s}$ precoated HPTLC plates), mass spectrometry or nuclear magnetic resonance (NMR). Yields are given for illustrative purposes only. Flash column chromatography was carried out using Merck silica gel 60 (230-400 mesh ASTM) or Fuji Silysia Chromatorex (trademark) DU3050 (Amino Type, 30-50 microm) or Biotage silica (32-63 mm, KP-Sil) or Biotage amino bounded silica (35-75 mm, KP—NH). SCX cartridge column chromatography was carried out using Biotage ISO-LUTE (trademark) SCX-2 (1 g, 6 mL) SPE column. The purification of compounds using HPLC was performed by the following apparatus and conditions; Apparatus; Waters MS-trigger AutoPurification (trademark) system Column; Waters XTerra C18, 19×50 mm, 5 mm particle, solvent systems; Methanol or acetonitrile/0.05% (v/v) formic acid aqueous solution, or; methanol or acetonitrile/0.01% (v/v) ammonia aqueous solution. Low-resolution mass spectral data (ESI) were obtained by the following apparatus and conditions: Apparatus; Waters Alliance HPLC system on ZQ or ZMD mass spectrometer and UV detector. NMR data was determined at 270 MHz (JEOL JNM-LA 270 spectrometer), 300 MHz (JEOL JNM-LA300), 400 MHz (JEOL ECZ 400S) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quin=quintet, m=multiplet, br=broad, etc. Chemical symbols have their usual meanings; microL (microliter(s)), microg (microgram(s)), M (mol(s) per liter), L (liter(s)), mL (milliliter(s)), g (gram(s)), mg (milligram(s)), mol (moles), mmol (millimoles).

Conditions for determining HPLC retention time:
Method A:
  Apparatus: Waters ACQUITY UPLC/ACQUITY PDA Detector/ZQ 2000
  Column: Waters ACQUITY BEH C18, 2.1×100 mm
  Column temperature: 60° C.
  PDA detection (scan range): 200-400 nm
  MS detection: ESI positive/negative mode
Solvents:
  A1: 10 mM ammonium acetate aqueous solution
  B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| Run time | 3 min | |
| Flow rate | 0.7 mL/min | |

Method B:
  Apparatus: Waters ACQUITY UPLC/ACQUITY PDA Detector/ZQ 2000
  Column: YMC Meteoric core C18, 2.1×100 mm
  Column temperature: 60° C.
  PDA detection (scan range): 200-400 nm
  MS detection: ESI positive/negative mode
Solvents:
  A1: 10 mM ammonium acetate aqueous solution
  B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 5 | 95 |
| 2.31 | 95 | 5 |
| Run time | 3 min | |
| Flow rate | 0.7 mL/min | |

Method C:
  Apparatus: Waters ACQUITY UPLC/ACQUITY PDA Detector/ZQ 2000
  Column: Waters ACQUITY BEH C18, 2.1×100 mm
  Column temperature: 60° C.
  PDA detection (scan range): 200-400 nm
  MS detection: ESI positive/negative mode
Solvents:
  A1: 10 mM ammonium acetate aqueous solution
  B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 5 | 95 |
| 2.31 | 95 | 5 |
| Run time | 3 min | |
| Flow rate | 0.7 mL/min | |

Method D:
- Apparatus: Waters ACQUITY UPLC/ACQUITY PDA Detector/ZQ 2000
- Column: YMC Triart C18, 2.1×100 mm, 1.9 microm particle
- Column temperature: 60° C.
- PDA detection (scan range): 200-400 nm MS detection: ESI positive/negative mode
- Solvents:
  - A1: 10 mM ammonium acetate aqueous solution
  - B1: acetonitrile

| Time(min) | A1(%) | B1(%) |
|---|---|---|
| 0 | 80 | 10 |
| 0.05 | 90 | 10 |
| 1.9 | 5 | 95 |
| 2.5 | 5 | 95 |
| 2.51 | 90 | 10 |
| Run time | 3 min | |
| Flow rate | 0.75 mL/min | |

Method E
- Apparatus: Waters Alliance 2695/2996 PDA
- Column: DAICEL CHIRALCEL OJ-H, 4.6 mm×250 mm
- Column temperature: 40° C.
- UV detection: 270 nm
- Solvents: n-hexane/2-propanol/diethylamine=95/5/0.1
- Flow rate: 1 mL/min
- Run time: 40 min Method F
- Apparatus: Waters Alliance 2695/2996 PDA
- Column: DAICEL CHIRALPAK IC-3, 4.6 mm×250 mm
- Column temperature: 40° C.
- UV detection: 265 nm
- Solvents:
  - A2: 0.1% diethylamine in n-hexane
  - B2: 0.1% diethylamine in 2-propanol

| Time(min) | A2(%) | B2(%) |
|---|---|---|
| 0 | 85 | 15 |
| 15 | 85 | 15 |
| 30 | 50 | 50 |
| 40 | 50 | 50 |
| 40.01 | 85 | 15 |
| Run time | 60 min | |
| Flow rate | 1 mL/min | |

Method G
- Apparatus: Waters Alliance 2695/2996 PDA
- Column: DAICEL CHIRALPAK AD-H 4.6 mm×250 mm
- Column temperature: 40° C.
- UV detection: 265 nm
- Solvents: n-hexane/ethanol/diethylamine=94/6/0.1
- Flow rate: 1 mL/min
- Run time: 30 min Method H
- Apparatus: Waters Alliance 2695/2996 PDA
- Column: DAICEL CHIRALCEL OD-H, 4.6 mm×250 mm
- Column temperature: 40° C.
- UV detection: 270 nm
- Solvents: n-hexane/2-propanol/diethylamine=95/5/0.1
- Flow rate: 1 mL/min
- Run time: 20 min Method I
- Apparatus: Waters Alliance 2695/2996 PDA
- Column: DAICEL CHIRALPAK AD-H, 4.6×250 mm
- Column temperature: 40° C.
- UV Detection: 265 nm
- Solvents: n-hexane/ethanol/diethylamine=88/12/0.1
- Flow rate: 1 mL/min
- Run time: 30 min Method J
- Apparatus: Waters Alliance 2695/2996 PDA
- Column: DAICEL CHIRALCEL OD-H, 4.6 mm×250 mm
- Column temperature: 40° C.
- UV detection: 265 nm
- Solvents: n-hexane/2-propanol/diethylamine=85/15/0.1
- Flow rate: 1 mL/min
- Run time: 50 min Method K
- Apparatus: Waters Alliance 2695/2996 PDA
- Column: DAICEL CHIRALCEL OJ-H, 4.6 mm×250 mm
- Column temperature: 40° C.
- UV detection: 265 nm
- Solvents: n-hexane/ethanol/diethylamine=90/10/0.1
- Flow rate: 1 mL/min
- Run time: 45 min Method L
- Apparatus: Waters Alliance 2695/2996 PDA
- Column: Daicel CHIRALPAK IC
- Column Temperature: 40° C.
- UV detection: 245 nm
- Solvents: n-hexane/2-propanol=90/10
- Flow rate: 1 mL/min
- Run time: 35 min Preparation of Intermediates II General Procedure: Scheme 2, Step 1

To a solution of substrate (1.0 eq.) in THF was added dropwise 1.1 M NaHMDS in THF solution (1.2 eq.) at −78° C. under $N_2$ atmosphere. After addition, the mixture was stirred at −78° C. for 2 h. A THF solution of alkenylalkylhalide was added dropwise to the mixture at −78° C. and the mixture was stirred at this temperature for 1 h. The mixture was warmed to room temperature. After being stirred at room temperature until complete reaction, the mixture was quenched with water. The mixture was extracted with EtOAc twice and washed successively with 10% aq. citric acid, aq. $NaHCO_3$, and brine. The extracts were combined, dried over $Na_2SO_4$, and concentrated in vacuo. The resulting residue was purified by silica gel column chromatography to afford the following intermediates (Table 1).

TABLE 1

| Intermediates | Structure | Chemical Name | Substrate | alkenylalkylhalide |
|---|---|---|---|---|
| V-1 | 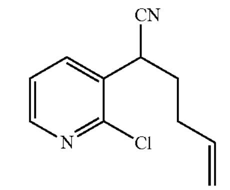 | 2-(2-chloropyridin-3-yl)hex-5-enenitrile | | Br⟶⟶= (4-bromobut-1-ene) |
| V-2 | 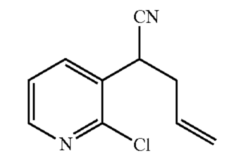 | 2-(2-chloropyridin-3yl)pent-4-enenitrile | | Br⟶= (allyl bromide) |
| V-3 | 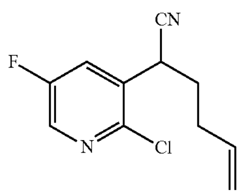 | 2-(2-chloro-5-fluoropyridin-3-yl)hex-5-enenitrile | | Br⟶⟶= |
| V-4 | 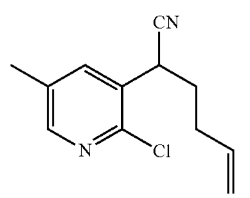 | 2-(2-chloro-5-methylpyridin-3-yl)hex-5-enenitrile | | Br⟶⟶= |

IM V-1

$^1$H NMR (CDCl$_3$) delta 8.40 (1H, dd, J=4.9, 1.8 Hz), 7.92 (1H, dd, J=7.3, 1.8 Hz), 7.34 (1H, dd, J=7.3, 4.9 Hz), 5.80 (1H, ddt, J=17.1, 10.4, 7.3 Hz), 5.16 (1H, br d, J=17.1 Hz), 5.11 (1H, br d, J=10.4 Hz), 4.27 (1H, dd, J=9.2, 4.9 Hz), 2.42-2.27 (2H, m), 2.04-1.90 (2H, m).

MS (ESI) m/z: 207.1 (M+H)$^+$.

IM V-2

$^1$H NMR (CDCl$_3$) delta 8.40 (1H, dd, J=4.9, 1.8 Hz), 7.89 (1H, dd, J=7.9, 1.8 Hz), 7.34 (1H, dd, J=7.9, 4.9 Hz), 5.83 (1H, ddt, J=17.1, 9.8, 7.3 Hz), 5.24 (1H, br d, J=9.8 Hz), 5.21 (1H, br d, J=17.1 Hz), 4.35 (1H, dd, J=7.9, 4.9 Hz), 2.73 (1H, m), 2.61 (1H, m).

MS (ESI) m/z: 193.2 (M+H)$^+$.

IM V-3

$^1$H NMR (CDCl$_3$) delta 8.28 (1H, dd, J=15.3, 3.1 Hz), 7.69 (1H, dd, J=7.9, 3.1 Hz), 5.79 (1H, ddt, J=17.1, 10.4, 6.1 Hz), 5.18 (1H, br dd, J=17.1, 1.2 Hz), 5.12 (1H, br dd, J=10.4, 1.2 Hz), 4.24 (1H, dd, J=9.8, 5.5 Hz), 2.44-2.28 (2H, m), 2.08-1.92 (2H, m).

MS (ESI) m/z: 225.0 (M+H)$^+$.

IM V-4

$^1$H NMR (CDCl$_3$) delta 8.19 (1H, d, J=1.8 Hz), 7.71 (1H, d, J=1.8 Hz), 5.80 (1H, ddt, J=17.1, 10.4, 6.1 Hz), 5.16 (1H, br d, J=17.1 Hz), 5.10 (1H, br d, J=10.4 Hz), 4.23 (1H, m), 2.41-2.25 (2H, m), 2.37 (3H, s), 2.06-1.90 (2H, m). MS (ESI) m/z: 221.2 (M+H)$^+$.

General Procedure: Scheme 2, Step 2

A mixture of substrate (1.0 eq.), triethylamine (3.0 eq.), (+/−)-BINAP (0.135 eq.), and Pd(OAc)$_2$ (0.135 eq.) in MeCN was heated at reflux until complete reaction. After cooling at room temperature, NH gel was added to the mixture and the mixture was filtered. The filter cake was washed with EtOAc. The filtrate was concentrated in vacuo. EtOAc was added to the resulting residue and the insoluble material was removed by filtration. Water was added to the filtrate, the mixture was extracted with EtOAc twice. The extracts were washed with brine, dried over Na$_2$SO$_4$, and concentrated in vacuo. The resulting residue was purified by silica gel column chromatography to afford the following intermediates (Table 2).

TABLE 2

| Intermediates | Structure | Chemical Name | Substrate |
|---|---|---|---|
| VI-1 | 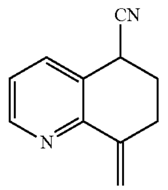 | 8-methylene-5,6,7,8-tetrahydroquinoline-5-carbonitrile | IM V-1 |
| VI-2 | 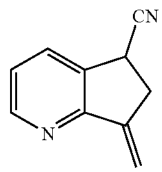 | 7-methylene-6,7-dihydro-5H-cyclopenta[b]pyridine-5-carbonitrile | IM V-2 |
| VI-3 | 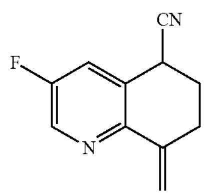 | 3-fluoro-8-methylene-5,6,7,8-tetrahydoquinoline-5-carbonitrile | IM V-3 |
| VI-4 | 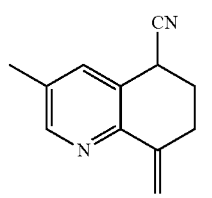 | 3-methyl-8-methylene-5,6,7,8-tetrahydroquinoline-5-carbonitrile | IM V-4 |

$^1$H NMR (CDCl$_3$) delta 8.57 (1H, dd, J=4.2, 1.8 Hz), 7.73 (1H, dd, J=7.9, 1.8 Hz), 7.23 (1H, dd, J=7.9, 4.2 Hz), 6.38 (1H, d, J=1.8 Hz), 5.25 (1H, d, J=1.8 Hz), 4.07 (1H, dd, J=7.9, 4.9 Hz), 2.92 (1H, m), 2.70 (1H, m), 2.32-2.15 (2H, m).

MS (ESI) m/z: 171.1 (M+H)$^+$.

IM VI-2

$^1$H NMR (CDCl$_3$) delta 8.60 (1H, br d, J=5.3 Hz), 7.81 (1H, dd, J=7.9, 1.3 Hz), 7.26 (1H, dd, J=7.9, 5.3 Hz), 6.11 (1H, br t, J=2.0 Hz), 5.51 (1H, br t, J=2.0 Hz), 4.22 (1H, dd, J=8.6, 5.9 Hz), 3.34 (1H, m), 3.17 (1H, m).

MS (ESI) m/z: 157.2 (M+H)$^+$.

IM VI-3

$^1$H NMR (CDCl$_3$) delta 8.44 (1H, d, J=15.9, 3.1 Hz), 7.47 (1H, dd, J=8.6, 3.1 Hz), 6.28 (1H, d, J=1.2 Hz), 5.24 (1H, d, 1.2 Hz), 4.07 (1H, dd, J=8.6, 4.9 Hz), 2.94-2.87 (1H, m), 2.73-2.64 (1H, m), 2.34-2.27 (1H, m), 2.23-2.15 (1H, m).

MS (ESI) m/z: 189.1 (M+H)$^+$.

IM VI-4

$^1$H NMR (CDCl$_3$) delta 8.38 (1H, d, J=1.2 Hz), 7.52 (1H, d, J=1.2 Hz), 6.29 (1H, d, J=1.2 Hz), 5.18 (1H, d, J=1.2 Hz), 4.02 (1H, m), 2.88 (1H, m), 2.66 (1H, m), 2.36 (3H, s), 2.31 (1H, m), 2.17 (1H, m).

MS (ESI) m/z: 185.2 (M+H)$^+$.

General Procedure: Scheme 2, Step 3

To a solution of substrate (1.0 eq.) in MeOH (0.2 M) was added TMSCl (30 eq.) at ambient temperature. The mixture was heated at reflux until complete reaction, and then cooled to room temperature. The mixture was basified with aq. NaHCO$_3$ and the mixture was concentrated in vacuo to remove volatile. The resulting residue was extracted with EtOAc twice and washed with brine. The extracts were combined, dried over Na$_2$SO$_4$, and concentrated in vacuo. The resulting residue was purified by silica gel column chromatography to afford the following intermediates (Table 3).

TABLE 3

| Intermediates | Structure | Chemical Name | Substrate |
|---|---|---|---|
| II-e-1-1 | 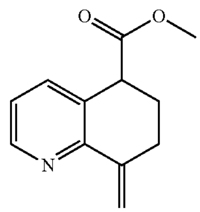 | methyl 8-methylene-5,6,7,8-tetrahydroquinoline-5-carboxylate | IM VI-1 |
| II-e-1-2 | 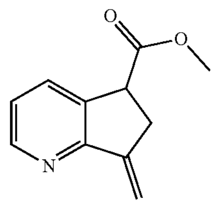 | methyl 7-methylene-6,7-dihydro-5H-cyclopenta[b]pyridine-5-carboxylate | IM VI-2 |
| II-e-1-3 | 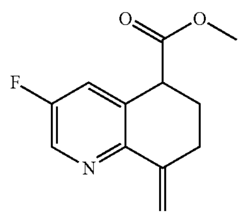 [SMILES: C=C1CCC(C(=O)OC)c2cc(F)cnc21] | methyl 3-fluoro-8-methylene-5,6,7,8-tetrahydroquinoline-5-carboxylate | IM VI-3 |
| II-e-1-4 | 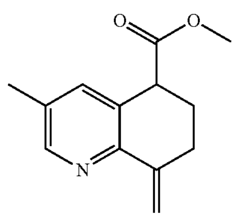 | methyl 3-methyl-8-methylene-5,6,7,8-tetrahydroquinoline-5-carboxylate | IM VI-4 |

IM II-e-1-1

$^1$H NMR (CDCl$_3$) delta 8.51 (1H, dd, J=4.3, 1.8 Hz), 7.52 (1H, dd, J=7.9, 1.8 Hz), 7.14 (1H, dd, J=7.9, 4.3 Hz), 6.29 (1H, d, J=1.8 Hz), 5.18 (1H, d, J=1.8 Hz), 3.88 (1H, dd, J=5.5, 5.5 Hz), 3.73 (3H, s), 2.81 (1H, m), 2.65 (1H, m), 2.30 (1H, in), 2.07 (1H, m).

MS (ESI) m/z: 204.1 (M+H)$^+$.

IM II-e-1-2

$^1$H NMR (CDCl$_3$) delta 8.52 (1H, dd, J=4.9, 1.8 Hz), 7.79 (1H, dd, J=7.3, 1.8 Hz), 7.16 (1H, dd, J=7.3, 4.9 Hz), 6.04 (1H, br t, J=2.4 Hz), 5.25 (1H, br t, J=2.4 Hz), 4.13 (1H, dd, J=9.2, 5.5 Hz), 3.76 (3H, s), 3.27 (1H, m), 3.09 (1H, m).

MS (ESI) m/z: 190.2 (M+H)$^+$.

IM II-e-1-3

$^1$H NMR (CDCl$_3$) delta 8.35 (1H, dd, J=15.3, 3.1 Hz), 7.26 (1H, dd, J=7.9, 3.1 Hz), 6.19 (1H, s), 5.15 (1H, d, J=1.8 Hz), 3.87 (1H, dd, J=5.5, 5.5 Hz), 3.73 (3H, s), 2.77 (1H, m), 2.63 (1H, m), 2.28 (1H, m), 2.06 (1H, m).

MS (ESI) m/z: 222.1 (M+H)$^+$.

IM II-e-1-4

$^1$H NMR (CDCl$_3$) delta 8.32 (1H, br s), 7.29 (1H, br s), 6.21 (1H, br s), 5.10 (1H, br s), 3.83 (1H, m), 3.71 (3H, s), 2.78 (1H, m), 2.60 (1H, m), 2.30 (3H, s), 2.24 (1H, m), 2.03 (1H, m).

MS (ESI) m/z: 218.1 (M+H)$^+$.

General Procedure: Scheme 2, Step 4-A

To a stirred solution of substrate (1.0 eq.) in THF was added 1.1 M THF solution of NaHMDS (1.3 eq.) at −78° C. under N$_2$ atmosphere. After being stirred at −78° C. for 30 min, NFSI (1.3 eq.) was added to the mixture. The mixture was stirred at −78° C. until complete reaction and then warmed to room temperature. The mixture was poured into water and extracted with EtOAc. The extract was dried over Na$_2$SO$_4$ and concentrated in vacuo. The resulting residue was purified by silica gel column chromatography to afford the following intermediates (Table 4).

General Procedure: Scheme 2, Step 4-B

To a stirred solution of substrate (1.0 eq.) in THF was added 1.1 M THF solution of NaHMDS (1.2 eq.) at 0° C. under N$_2$ atmosphere. After being stirred at 0° C. for 20 min, Togni reagent (1.2 eq.) in THF was added to the mixture. The mixture was warmed to room temperature and stirred until complete reaction. The mixture was poured into water and extracted with EtOAc. The extract was dried over Na$_2$SO$_4$, and concentrated in vacuo. The residue was purified by silica gel column chromatography to afford the following intermediates (Table 4).

TABLE 4

| Intermediates | Structure | Chemical Name | Substrate | General Procedure: Step 4 |
|---|---|---|---|---|
| II-e-2-1 | 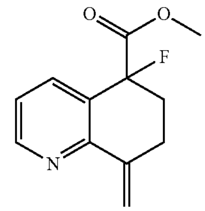 [SMILES: C=C1CCC(F)(C(=O)OC)c2cccnc21] | methyl 5-fluoro-8-methylene-5,6,7,8-tetrahydroquinoline-5-carboxylate | IM II-e-1-1 | A |
| II-e-2-2 | 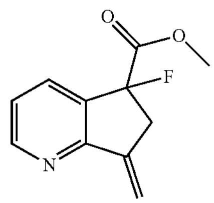 | methyl 5-fluoro-7-methylene-6,7-dihydro-5H-cyclopenta[b]pyridine-5-carboxylate | IM II-e-1-2 | A |
| II-e-2-3 | 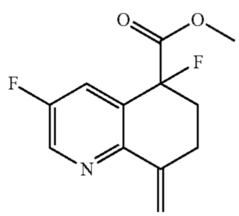 [SMILES: C=C1CCC(F)(C(=O)OC)c2cc(F)cnc21] | methyl 3,5-difluoro-8-methylene-5,6,7,8-tetrahydroquinoline-5-carboxylate | IM II-e-1-3 | A |
| II-e-2-4 | 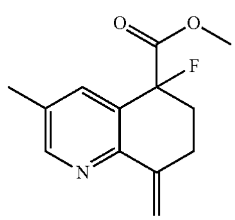 | methyl 5-fluoro-3-methyl-8-methylene-5,6,7,8-tetrahydroquinoline-5-carboxylate | IM II-e-1-4 | A |
| II-e-2-5 | 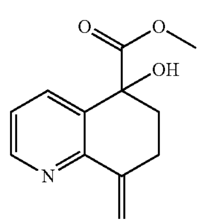 [SMILES: C=C1CCC(O)(C(=O)OC)c2cccnc21] | methyl 5-hydroxy-8-methylene-5,6,7,8-tetrahydroquinoline-5-carboxylate | IM II-e-1-1 | B |

IM II-e-2-1
¹H NMR (CDCl₃) delta 8.63 (1H, ddd, J=4.3, 1.8, 1.2 Hz), 7.68 (1H, dd, J=7.9, 1.8 Hz), 7.24 (1H, ddd, J=7.9, 4.3, 1.8 Hz), 6.37 (1H, br s), 5.31 (1H, d, J=1.2 Hz), 3.81 (3H, s), 2.89-2.73 (2H, m), 2.48 (1H, m), 2.32 (1H, m).
MS (ESI) m/z: 222.1 (M+H)⁺.

IM II-e-2-2
¹H NMR (CDCl₃) delta 8.70 (1H, ddd, J=4.9, 1.8, 1.2 Hz), 7.83 (1H, ddd, J=7.9, 1.8, 1.2 Hz), 7.27 (1H, dd, J=7.9, 4.9 Hz), 6.20 (1H, br t, J=2.4 Hz), 5.36 (1H, dd, J=1.8, 1.2 Hz), 3.83 (3H, s), 3.58 (1H, m), 3.20 (1H, m).
MS (ESI) m/z: 208.2 (M+H)⁺.

IM II-e-2-3
¹H NMR (CDCl₃) delta 8.48 (1H, m), 7.42 (1H, dd, J=8.6, 1.8 Hz), 6.27 (1H, s), 5.28 (1H, s), 3.83 (3H, s), 2.82 (2H, m), 2.45 (1H, m), 2.29 (1H, m).
MS (ESI) m/z: 240.0 (M+H)⁺.

IM II-e-2-4
¹H NMR (CDCl₃) delta 8.37 (1H, br s), 7.36 (1H, br s), 6.23 (1H, br s), 5.19 (1H, br s), 3.76 (3H, s), 3.73 (1H, m), 2.40-2.24 (2H, m), 2.30 (3H, s), 2.08 (1H, m).
MS (ESI) m/z: 236.2 (M+H)⁺.

IM II-e-2-5

¹H NMR (CDCl₃) delta 8.55 (1H, dd, J=4.6, 2.0 Hz), 7.55 (1H, dd, J=7.9, 2.0 Hz), 7.19 (1H, dd, J=7.9, 4.6 Hz), 6.31 (1H, br s), 5.26 (1H, d, J=2.0 Hz), 3.93 (1H, br), 3.77 (3H, s), 2.92-2.73 (2H, m), 2.30 (1H, ddd, J=13.2, 8.6, 4.3 Hz), 2.10 (1H, ddd, J=13.2, 7.9, 4.6 Hz).

MS (ESI) m/z: 220.2 (M+H)⁺.

General Procedure: Scheme 2, Step 5

O₃ was bubbled into a solution of substrate (1.0 eq.) in 50% CH₂Cl₂-MeOH at −78° C. until starting material consumed. N₂ was bubbled into the mixture to remove the excess of O₃ at −78° C. The mixture was quenched with Me₂S (2.0 eq.) and the mixture was warmed to room temperature. The mixture was concentrated in vacuo and the resulting residue was purified by silica gel column chromatography to afford the following Intermediates (Table 5).

IM II-c-1

¹H NMR (CDCl₃) delta 8.79 (1H, dd, J=4.6, 1.3 Hz), 7.78 (1H, br d, J=7.9 Hz), 7.46 (1H, dd, J=7.9, 4.6 Hz), 4.05 (1H, dd, J=5.2, 4.6 Hz), 3.76 (3H, s), 3.04 (1H, in), 2.82 (1H, m), 2.59 (1H, m), 2.43 (1H, m).

MS (ESI) m/z: 206.1 (M+H)⁺.

IM II-c-2

¹H NMR (CDCl₃) delta 8.91 (1H, dd, J=4.3, 1.2 Hz), 7.96 (1H, dd, J=7.9, 1.2 Hz), 7.57 (1H, dd, J=7.9, 4.3 Hz), 3.85 (3H, s), 3.06-3.03 (2H, m), 2.85 (1H, m), 2.63 (1H, m).

MS (ESI) m/z: 224.1 (M+H)⁺.

IM II-c-3

¹H NMR (CDCl₃) delta 8.73 (1H, dd, J=14.6, 2.4 Hz), 7.66 (1H, dd, J=7.9, 2.4 Hz), 3.86 (3H, s), 3.06-2.99 (2H, m), 2.85 (1H, m), 2.62 (1H, m).

MS (ESI) m/z: 242.0 (M+H)⁺.

TABLE 5

| Intermediates | Structure | Chemical Name | Substrate |
|---|---|---|---|
| II-c-1 | 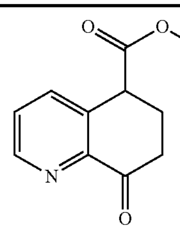 | methyl 8-oxo-5,6,7,8-tetrahydroquinoline-5-carboxylate | IM II-e-1-1 |
| II-c-2 | 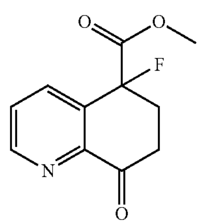 [SMILES: COC(=O)C1(F)CCC(=O)c2ncccc21] | methyl 5-fluoro-8-oxo-5,6,7,8-tetrahydroquinoline-5-carboxylate | IM II-e-2-1 |
| II-c-3 | 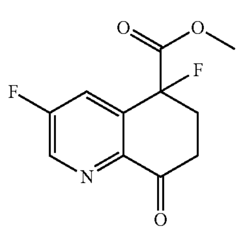 [SMILES: COC(=O)C1(F)CCC(=O)c2ncc(F)cc21] | methyl 3,5-difluoro-8-oxo-5,6,7,8-tetrahydroquinoline-5-carboxylate | IM II-e-2-3 |
| II-c-4 | 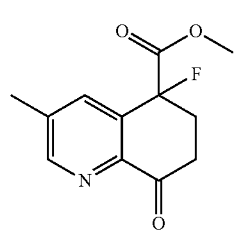 | methyl 5-fluoro-3-methyl-8-oxo-5,6,7,8-tetrahydroquinoline-5-carboxylate | IM II-e-2-4 |

IM II-c-4

$^1$H NMR (CDCl$_3$) delta 8.72 (1H, d, J=1.4 Hz), 7.73 (1H, d, J=1.4 Hz), 3.86 (3H, s), 3.03-2.99 (2H, m), 2.82 (1H, m), 2.61 (1H, m), 2.48 (3H, s).

MS (ESI) m/z: 238.2 (M+H)$^+$.

General Procedure: Scheme 2, Step 6

NaBH$_4$ (1.5 eq.) was added to a solution of substrate (1.0 eq.) in MeOH and the mixture was stirred at room temperature until complete reaction. The mixture was poured into water and extracted with EtOAc. The extract was dried over Na$_2$SO$_4$ and concentrated in vacuo. The resulting residue was purified by silica gel column chromatography to afford the following intermediates (Table 6).

IM II-d-2

$^1$H NMR (CDCl$_3$) delta 8.64 (1H, dd, J=4.6, 1.3 Hz), 7.80 (0.5H, d, J=8.6 Hz), 7.69 (0.5H, dd, J=7.9, 1.3 Hz), 7.31 (1H, dd, J=7.9, 4.6 Hz), 4.80-4.71 (1H, m), 4.31 (0.5H, br), 3.84 (2H, s), 3.80 (1.5H, s), 2.75-2.63 (0.5H, m), 2.53-2.00 (3.5H, m).

MS (ESI) m/z: 226.2 (M+H)$^+$.

General Procedure: Scheme 3, Step 1

To a stirred solution of tert-butyl 2-(diethoxyphosphoryl)acetate (1.0 eq.) in THF was added NaH (60% oil dispersant,

TABLE 6

| Intermediates | Structure | Chemical Name | Substrate |
|---|---|---|---|
| II-d-1 | (structure) | methyl 8-hydroxy-5,6,7,8-tetrahydroquinoline-5-carboxylate | (structure) IM II-c-1 |
| II-d-2 | (structure) | methyl 5-fluoro-8-hydroxy-5,6,7,8-tetrahydroquinoline-5-carboxylate | (structure) IM II-c-2 |

IM II-d-1

$^1$H NMR (CDCl$_3$) delta 8.49 (1H, d, J=4.6 Hz), 7.61 (0.5H, d, J=7.9 Hz), 7.57 (0.5H, d, J=7.9 Hz), 7.20 (1H, dd, J=7.9, 5.3 Hz), 4.75 (0.5H, dd, J=8.6, 5.3 Hz), 4.67 (0.5H, dd, J=9.3, 5.3 Hz), 4.10 (1H, br), 3.91 (0.5H, dd, J=7.9, 6.6 Hz), 3.82 (0.5H, br), 3.75 (1.5H, s), 3.72 (1.5H, s), 2.44-1.99 (3.5H, m), 1.81 (0.5H, m).

MS (ESI) m/z: 208.2 (M+H)$^+$.

1.0 eq.) at 0° C. After being stirred at this temperature for 1 h, a solution of substrate (1.0 eq.) in THF was added to the mixture. The mixture was warmed to room temperature and stirred until complete reaction. The reaction mixture was poured into water and extracted with EtOAc. The extract was dried over Na$_2$SO$_4$ and concentrated in vacuo. The resulting residue was purified by silica gel column chromatography to afford the following intermediates (Table 7).

TABLE 7

| Intermediates | Structure | Chemical Name | Substrate |
|---|---|---|---|
| VII-1 | (structure) | methyl 8-(2-(tert-butoxy)-2-oxoethylidene)-5,6,7,8-tetrahydroquinoline-5-carboxylate | (structure) IM II-c-1 |

TABLE 7-continued

| Intermediates | Structure | Chemical Name | Substrate |
|---|---|---|---|
| VII-2 | 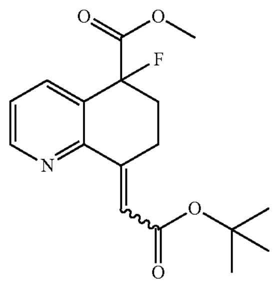 [SMILES: COC(=O)C1(F)CCC(=CC(=O)OC(C)(C)C)c2ncccc21] | methyl 8-(2-(tert-butoxy)-2-oxoethylidene)-5-fluoro-5,6,7,8-tetra-hydroquinoline-5-carboxylate | IM II-c-2 |

IM VII-1; isomer A $^1$H NMR (CDCl$_3$) delta 8.54 (1H, dd, J=4.6, 1.3 Hz), 7.54 (1H, br d, J=7.9 Hz), 7.23 (1H, dd, J=7.9, 4.6 Hz), 7.15 (1H, s), 3.87 (1H, t, J=5.3 Hz), 3.72 (3H, s), 3.39 (1H, m), 3.19 (1H, m), 2.29 (1H, m), 2.05 (1H, m), 1.51 (9H, s).

MS (ESI) m/z: 304.2 (M+H)$^+$.

IM VII-1; isomer B $^1$H NMR (CDCl$_3$) delta 8.42 (1H, dd, J=4.6, 1.3 Hz), 7.54 (1H, br d, J=7.9 Hz), 7.15 (1H, dd, J=7.9, 4.6 Hz), 5.86 (1H, s), 3.86 (1H, t, J=5.3 Hz), 3.70 (3H, s), 2.80 (1H, m), 2.56 (1H, m), 2.32 (1H, m), 2.13 (1H, m), 1.56 (9H, s).

MS (ESI) m/z: 304.2 (M+H)$^+$.

IM VII-2

$^1$H NMR (CDCl$_3$) delta 8.65 (0.25H, br d, J=3.3 Hz), 8.54 (0.75H, dd, J=4.6, 2.0 Hz), 7.77 (0.25H, br d, J=7.9 Hz), 7.69 (0.75H, br d, J=7.3 Hz), 7.33 (0.25H, dd, J=7.9, 4.6 Hz), 7.24 (0.75H, br d, J=4.6 Hz), 5.98 (0.75H, s), 5.30 (0.25H, s), 3.81 (0.75H, s), 3.80 (2.25H, s), 3.42 (0.5H, m), 2.78 (1.5H, m), 2.30-2.10 (2H, m), 1.58 (6.75H, s), 1.52 (2.25H, s).

MS (ESI) m/z: 322.1 (M+H)$^+$.

General Procedure: Scheme 3, Step 2

10% Pd—C (0.2 eq.) was added to a solution of substrate (1.0 eq.) in MeOH and the mixture was stirred until complete reaction at room temperature under H$_2$ atmosphere. The reaction mixture was filtrated through a pad of cerite and the filtrate was concentrated in vacuo. The resulting residue was purified by silica gel column chromatography to afford the following intermediates (Table 8).

TABLE 8

| Intermediates | Structure | Chemical Name | Substrate |
|---|---|---|---|
| II-v-1 | 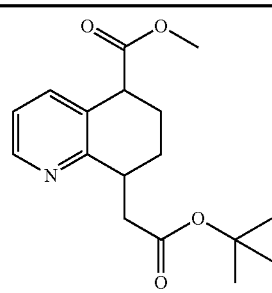 | methyl 8-(2-tert-butoxy)-2-oxoethyl)-5,6,7,8-tetrahydro-quinoline-5-carboxylate | IM VII-1 |
| II-v-2 | 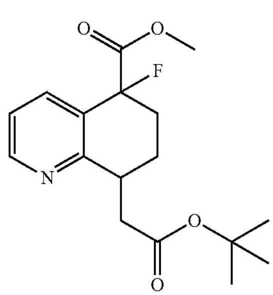 [SMILES: COC(=O)C1(F)CCC(CC(=O)OC(C)(C)C)c2ncccc21] | methyl 8-(2-(tert-butoxy)-2-oxoethyl)-5-fluoro-5,6,7,8-tetrahydroquinoline-5-carboxylate | IM VII-2 |

IM II-v-1

$^1$H NMR (CDCl$_3$) delta 8.45 (1H, dd, J=4.6, 1.3 Hz), 7.50 (1H, br d, J=7.3 Hz), 7.09 (1H, dd, J=7.3, 4.6 Hz), 3.81 (1H, t, J=5.3 Hz), 3.72 (3H, s), 3.34 (1H, m), 3.13 (1H, dd, J=10.5, 4.6 Hz), 2.41 (1H, dd, J=15.8, 9.9 Hz), 2.31-1.72 (4H, m), 1.46 (9H, s).

MS (ESI) m/z: 306.1 (M+H)$^+$.

IM II-v-2

$^1$H NMR (CDCl$_3$) delta 8.58 (0.5H, d, J=4.6 Hz), 8.49 (0.5H, d, J=4.6 Hz), 7.70 (0.5H, d, J=7.3 Hz), 7.53 (0.5H, d, J=7.9 Hz), 7.20 (0.5H, dd, J=7.9, 4.6 Hz), 7.13 (0.5H, dd, J=7.3, 4.6 Hz), 3.83 (1H, t, J=5.3 Hz), 3.74 (1.5H, s), 3.72 (1.5H, s), 3.55-3.30 (1H, m), 3.15-2.94 (1H, m), 2.57-2.41 (1H, m), 2.4-1.7 (3H, m), 1.47 (4.5H, s), 1.45 (4.5H, s).

MS (ESI) m/z: 324.1 (M+H)$^+$.

Preparation of Intermediates III

General Procedure: Scheme 5, Step 1

To a solution of the substrate (1.0 eq.) in CCl$_4$ were added NBS (1.2 eq.) and AIBN (0.1 eq.) at 50° C. under N$_2$ atmosphere. The reaction mixture was heated at reflux and stirred for 2 h, another portion of AIBN (0.1 eq.) was added to the mixture. After being stirred at reflux for 16 h, the mixture was cooled to room temperature. The mixture was concentrated in vacuo and diethylether was added to the resulting residue. The insoluble materials were removed by filtration. The filtrate was washed with 2 N hydrochloric acid and brine. The extract was dried over Na$_2$SO$_4$ and concentrated in vacuo. The resulting residue was purified and separated by column chromatography to afford the following intermediates, di-bromide IX and mono-bromide X (Table 9).

TABLE 9

| Intermediates | Structure | Chemical Name | Substrate |
|---|---|---|---|
| IX-1 | 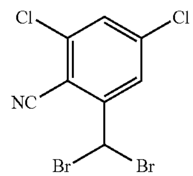 [SMILES: N#Cc1c(Cl)cc(Cl)cc1C(Br)Br] | 2,4-dichloro-6-(dibromomethyl)benzonitrile | |
| X-1 | 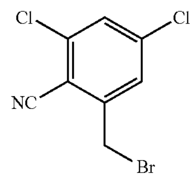 [SMILES: N#Cc1c(Cl)cc(Cl)cc1CBr] | 2-(bromomethyl)-4,6-dichlorobenzonitrile | |
| IX-2 | 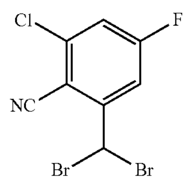 [SMILES: N#Cc1c(Cl)cc(F)cc1C(Br)Br] | 2-chloro-6-(dibromomethyl)-4-fluorobenzonitrile | |
| X-2 | 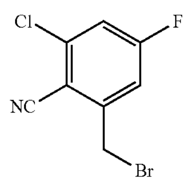 [SMILES: N#Cc1c(Cl)cc(F)cc1CBr] | 2-(bromomethyl)-6-chloro-4-fluorobenzonitrile | |

IM IX1

$^1$H NMR (CDCl$_3$) delta 7.93 (1H, d, J=2.0 Hz), 7.52 (1H, d, J=2.0 Hz), 6.90 (1H, s).

IM X-1

$^1$H NMR (CDCl$_3$) delta 7.49 (1H, d, J=2.0 Hz), 7.47 (1H, d, J=2.0 Hz), 4.57 (2H, s).

IM IX-2

$^1$H NMR (CDCl$_3$) delta 7.69 (1H, dd, J=9.2, 2.4 Hz), 7.26 (1H, dd, J=9.2, 2.4 Hz), 6.93 (1H, d, J=1.2 Hz).

IM X-2

$^1$H NMR (CDCl$_3$) delta 7.23 (1H, dd, J=7.9, 2.4 Hz), 7.22 (1H, dd, J=7.9, 2.4 Hz), 4.59 (2H, s).

MS (ESI) m/z: 250.9 (M+H)$^+$.

Procedure: Scheme 5, Step 2

Intermediate (IM) XI-1,
2,4-dichloro-6-(difluoromethyl)benzonitrile

[Chem. 25]

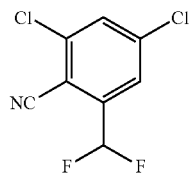

To a solution of 2,4-dichloro-6-(dibromomethyl)benzonitrile (350 mg, 1.018 mmol, IM IX-1) in $CH_2Cl_2$ (5 mL) was added silver tetrafluoroborate (495 mg, 2.54 mmol) at ambient temperature under $N_2$ atmosphere. After being stirred at room temperature for 3 h, the insoluble material was removed by filtration. The filtrate was concentrated in vacuo to afford 204 mg (90%) of the title compound.

$^1$H NMR (CDCl$_3$) delta 7.68 (2H, br s), 6.89 (1H, dd, J=54.7, 54.0 Hz).

Procedure: Scheme 5, Step 4

Intermediate (IM) XII-1,
3-chloro-2-cyano-5-fluorobenzyl acetate

[Chem. 26]

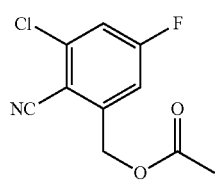

To a solution of the 2-(bromomethyl)-4,6-dichlorobenzonitrile (609 mg, 2.451 mmol, IM X-2) in AcOH (6.0 mL) was added NaOAc (1.0 g, 12.25 mmol) at ambient temperature. The mixture was heated at 100° C. for 6 h. The mixture was concentrated in vacuo and aq. NaHCO$_3$ was added to the resulting residue. The mixture was extracted with EtOAc and washed with brine. The extracts were dried over Na$_2$SO$_4$ and concentrated in vacuo. The resulting residue was purified by silica gel column chromatography (5% EtOAc/n-hexane) to afford 505 mg (91%) of the title compound.

MS (ESI) m/z: 245.0 (M+H$_3$O)$^+$.

General Procedure: Scheme 5, Step 3

To a solution of the substrate (1.0 eq.) in AcOH was added NaOAc (5.0 eq.) at ambient temperature. The resulting mixture was heated at 100° C. until complete reaction. The mixture was concentrated in vacuo and aq. NaHCO$_3$ was added to the resulting residue. The mixture was extracted with EtOAc and washed with brine. The extracts were dried over Na$_2$SO$_4$ and concentrated in vacuo. The resulting residue was purified by silica gel column chromatography to afford the following intermediates (Table 10).

TABLE 10

| Intermediates | Structure | Chemical Name | Substrate |
|---|---|---|---|
| III-a-1 | (structure) | (2,4-dichloro-6-(difluoromethyl)phenyl)methanamine | (structure) IM XI-1 |
| III-b-1 | (structure) | (2-(aminomethyl)-3-chloro-5-fluorophenyl)methanol | (structure) IM XII-1 |

IM III-a-1
$^1$H NMR (CDCl$_3$) delta 7.53 (1H, br s), 7.48 (1H, br s), 6.91 (1H, dd, J=82.0, 81.0 Hz), 4.02 (2H, s), 1.48 (2H, s).
MS (ESI) m/z: 226.0 (M+H)$^+$.
IM III-b-1
$^1$H NMR (CDCl$_3$) delta 7.09 (1H, dd, J=8.6, 2.4 Hz), 7.03 (1H, dd, J=8.6, 2.4 Hz), 4.64 (2H, s), 4.16 (2H, s), 2.35 (3H, br).
MS (ESI) m/z: 190.1 (M+H)$^+$.
The following Examples and Intermediates were prepared by General Procedure A (Tables 11 and 13).

General Procedure A

A mixture of substrate (1.0 eq.) and 2 N aq. NaOH (2.0 eq.) in MeOH was stirred at room temperature for 1.5 h, 2 N hydrochloric acid (2.2 eq.) was added to the mixture. The mixture was concentrated in vacuo to afford a glass. Toluene and MeCN were added to the mixture and concentrated in vacuo. This procedure was repeated 3 times to remove remaining water. The residual powder was dissolved with DMF and amine (1.5 eq.), triethylamine (3.0 eq.), and HBTU (1.3 eq.) were added to the mixture at ambient temperature. After overnight stirring, the mixture was poured into water and the mixture was extracted with $CH_2Cl_2$. The extract was concentrated in vacuo and the resulting residue was purified by silica gel column chromatography, and/or SCX cartridge column, preparative HPLC to afford the following Examples and Intermediates.

TABLE 11

| Examples | Structure | Chemical Name | Substrate | Amine |
|---|---|---|---|---|
| 1 | 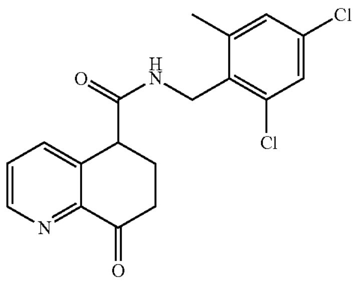 [SMILES: Cc1cc(Cl)cc(Cl)c1CNC(=O)C1CCC(=O)c2ncccc21] | N-(2,4-dichloro-6-methylbenzyl)-8-oxo-5,6,7,8-tetrahydroquinoline-5-carboxamide | IM II-c-1 | |
| 2 | 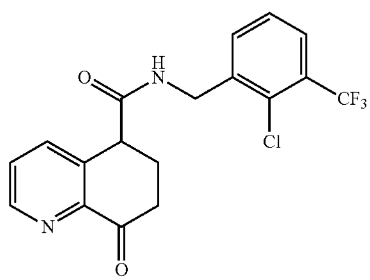 [SMILES: O=C1CCC(C(=O)NCc2cccc(C(F)(F)F)c2Cl)c2cccnc21] | N-(2-chloro-3-(trifluoromethyl)benzyl)-8-oxo-5,6,7,8-tetrahydroquinoline-5-carboxamide | IM II-c-1 | |
| 3 | 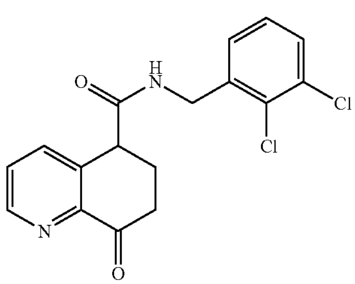 [SMILES: O=C1CCC(C(=O)NCc2cccc(Cl)c2Cl)c2cccnc21] | N-(2,3-dichlorobenzyl)-8-oxo-5,6,7,8-tetrahydroquinoline-5-carboxamide | IM II-c-1 | |
| 4 | 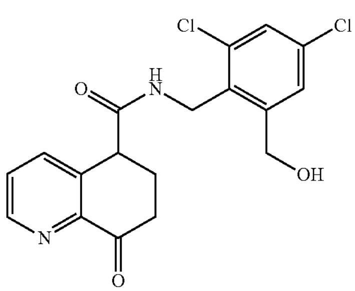 [SMILES: O=C1CCC(C(=O)NCc2c(Cl)cc(Cl)cc2CO)c2cccnc21] | N-(2,4-dichloro-6-(hydroxymethyl)benzyl)-8-oxo-5,6,7,8-tetrahydroquinoline-5-carboxamide | IM II-c-1 | |
| 5 | 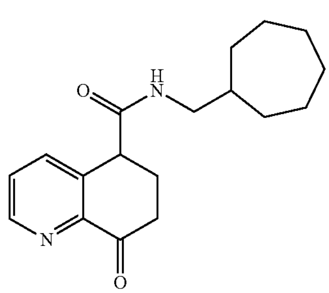 [SMILES: O=C1CCC(C(=O)NCC2CCCCCC2)c2cccnc21] | N-(cycloheptylmethyl)-8-oxo-5,6,7,8-tetrahydroquinoline-5-carboxamide | IM II-c-1 | |

TABLE 11-continued

| Examples | Structure | Chemical Name | Substrate | Amine |
|---|---|---|---|---|
| 6 | 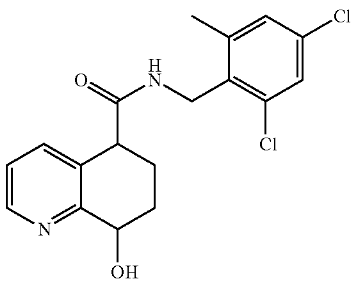 [SMILES: Cc1cc(Cl)cc(Cl)c1CNC(=O)C1CCC(O)c2ncccc21] | N-(2,4-dichloro-6-methylbenzyl)-8-hydroxy-5,6,7,8-tetrahydroquinoline-5-carboxamide | IM II-d-1 | |
| 7 | 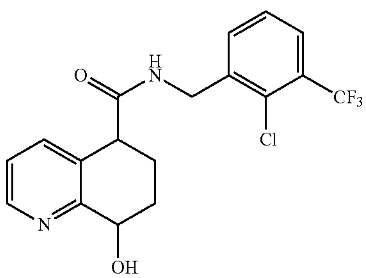 [SMILES: O=C(NCc1cccc(C(F)(F)F)c1Cl)C1CCC(O)c2ncccc21] | N-(2-chloro-3-(trifluoromethyl)benzyl)-8-hydroxy-5,6,7,8-tetrahydroquinoline-5-carboxamide | IM II-d-1 | |
| 8 | 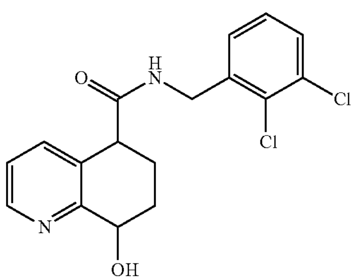 [SMILES: O=C(NCc1cccc(Cl)c1Cl)C1CCC(O)c2ncccc21] | N-(2,3-dichlorobenzyl)-8-hydroxy-5,6,7,8-tetrahydroquinoline-5-carboxamide | IM II-d-1 | |
| 9 | 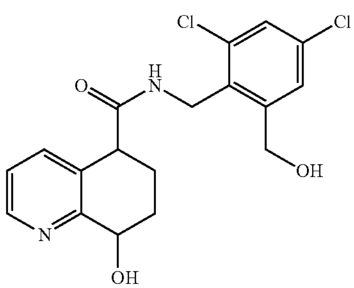 [SMILES: O=C(NCc1c(Cl)cc(Cl)cc1CO)C1CCC(O)c2ncccc21] | N-(2,4-dichloro-6-(hydroxymethyl)benzyl)-8-hydroxy-5,6,7,8-tetrahydroquinoline-5-carboxamide | IM II-d-1 | |
| 10 | 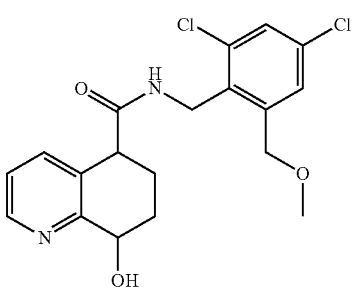 [SMILES: COCc1cc(Cl)cc(Cl)c1CNC(=O)C1CCC(O)c2ncccc21] | N-(2,4-dichloro-6-(methoxymethyl)benzyl)-8-hydroxy-5,6,7,8-tetrahydroquinoline-5-carboxamide | IM II-d-1 | |

TABLE 11-continued

| Examples | Structure | Chemical Name | Substrate | Amine |
|---|---|---|---|---|
| 11 | 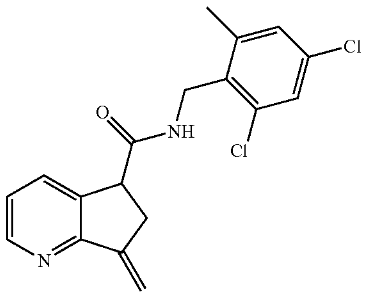 [SMILES: C=C1CC(C(=O)NCc2c(C)cc(Cl)cc2Cl)c2cccnc21] | N-(2,4-dichloro-6-methylbenzyl)-7-methylene-6,7-dihydro-5H-cyclopenta[b]pyridine-5-carboxamide | IM II-e-1-2 | |

TABLE 12

| | LC MS | | |
|---|---|---|---|
| Examples | Method | tR (min) | [M + H]+ |
| 1 | D | 1.53 | 363.0 |
| 2 | D | 1.47 | 383.0 |
| 3 | D | 1.40 | 349.0 |
| 4 | A | 1.25 | 379.3 |
| 5 | D | 1.45 | 301.2 |
| 6 | D | 1.53 | 365.0 |
| 7 | D | 1.46 | 385.0 |
| 8 | D | 1.40 | 351.0 |
| 9 | A | 1.26 | 381.3 |
| 10 | A | 1.44 | 395.1 |
| 11 | D | 1.79 | 347.0 |

Ex 2

$^1$H NMR (DMSO d6) delta 9.00 (1H, br), 8.67 (1H, m), 7.79 (2H, br d, J=7.9 Hz), 7.68 (1H, d, J=7.3 Hz). 7.68-7.54 (2H, m). 4.48 (2H, m). 4.12 (1H, dd, J=5.9, 5.2 Hz), 2.84 (1H, m), 2.66 (1H, m), 2.38-2.32 (2H, m).

Ex 6

$^1$H NMR (DMSO d6) delta 8.42 (1H, d, J=4.6 Hz), 8.37 (1H, br), 7.50 (1H, s), 7.40-7.36 (2H, m), 7.23 (1H, dd, J=7.9, 4.6 Hz), 5.18 (0.7H, d, J=4.0 Hz), 5.13 (0.3H, d, J=4.0 Hz), 4.51 (1H, br), 4.44 (0.7H, s), 4.42 (0.7H, s), 4.39 (0.3H, s), 4.37 (0.3H, s), 3.74 (0.3H, br), 3.65 (0.7H, br), 2.40 (2.1H, s), 2.37 (0.9H, s), 2.20-1.90 (2H, m), 1.82-1.76 (2H, m).

Ex 7

$^1$H NMR (DMSO d6) delta 8.79 (1H, br), 8.43 (1H, d, J=4.6 Hz), 7.80 (1H, d, J=7.9 Hz), 7.68 (1H, dd, J=8.6, 6.6 Hz), 7.58 (1H, dd, J=7.9, 7.3 Hz), 7.46 (1H, d, J=7.3 Hz), 7.23 (1H, dd, J=8.6, 5.3 Hz), 5.18 (1H, br), 4.54 (1H, br), 4.47 (2H, m), 3.75 (1H, m), 2.22-1.80 (4H, m).

TABLE 13

| Intermediates | Structure | Chemical Name | Substrate | Amine |
|---|---|---|---|---|
| I-e-1 | 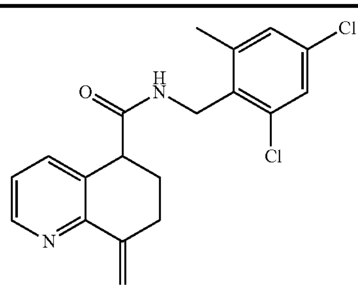 | N-(2,4-dichloro-6-methyl)benzyl)-8-methylene-5,6,7,8-tetrahydroquinoline-5-carboxamide | IM II-e-1-1 | |
| I-e-2 | 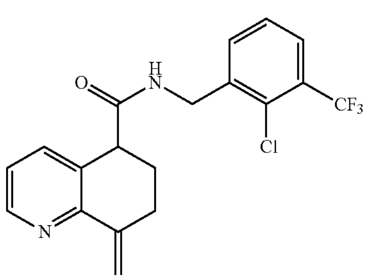 [SMILES: C=C1CCC(C(=O)NCc2cccc(C(F)(F)F)c2Cl)c2cccnc21] | N-(2-chloro-3-(trifluoromethyl)benzyl)-8-methylene-5,6,7,8-tetrahydroquinoline-5-carboxamide | IM II-e-1-1 | |

TABLE 13-continued

| Intermediates | Structure | Chemical Name | Substrate | Amine |
|---|---|---|---|---|
| I-e-3 | 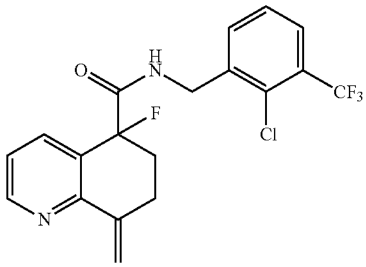 [SMILES: C=C1CCC(F)(C(=O)NCc2cccc(C(F)(F)F)c2Cl)c2cccnc21] | N-(2-chloro-3-(trifluoromethyl)benzyl)-5-fluoro-8-methylene-5,6,7,8-tetrahydroquinoline-5-carboxamide | IM II-e-2-1 | |
| I-e-4 | 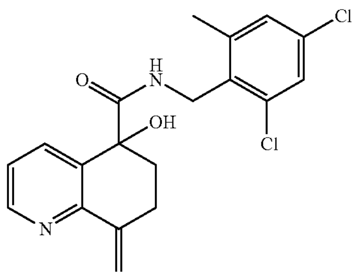 [SMILES: C=C1CCC(O)(C(=O)NCc2c(C)cc(Cl)cc2Cl)c2cccnc21] | N-(2,4-dichloro-6-methylbenzyl)-5-hydroxy-8-methylene-5,6,7,8-tetrahydroquinoline-5-carboxamide | IM II-e-2-5 | |
| I-e-5 | 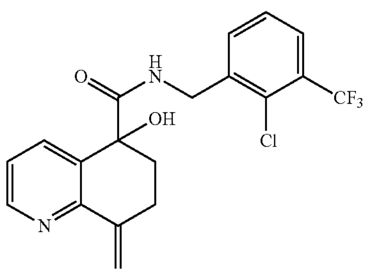 [SMILES: C=C1CCC(O)(C(=O)NCc2cccc(C(F)(F)F)c2Cl)c2cccnc21] | N-(2-chloro-3-(trifluoromethyl)benzyl)-5-hydroxy-8-methylene-5,6,7,8-tetrahydroquinoline-5-carboxamide | IM II-e-2-5 | |
| I-e-6 | 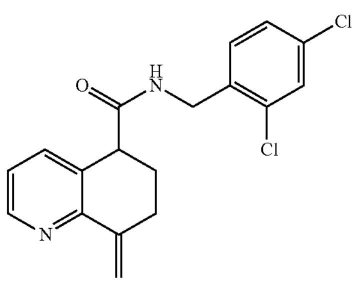 [SMILES: C=C1CCC(C(=O)NCc2ccc(Cl)cc2Cl)c2cccnc21] | N-(2,4-dichlorobenzyl)-8-methylene-5,6,7,8-tetrahydroquinoline-5-carboxamide | IM II-e-1-1 | |
| I-e-7 | 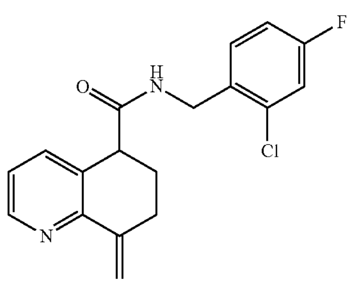 [SMILES: C=C1CCC(C(=O)NCc2ccc(F)cc2Cl)c2cccnc21] | N-(2-chloro-4-fluorobenzyl)-8-methylene-5,6,7,8-tetrahydroquinoline-5-carboxamide | IM II-e-1-1 | |

TABLE 13-continued

| Intermediates | Structure | Chemical Name | Substrate | Amine |
|---|---|---|---|---|
| I-e-8 | 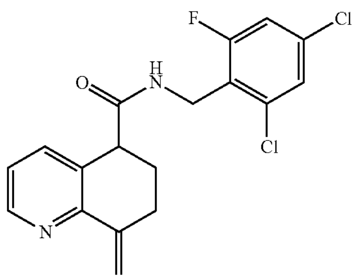 [SMILES: C=C1CCC(C(=O)NCc2c(F)cc(Cl)cc2Cl)c2cccnc21] | N-(2,4-dichloro-6-fluorobenzyl)-8-methylene-5,6,7,8-tetrahydroquinoline-5-carboxamide | IM II-e-1-1 | |
| I-e-9 | 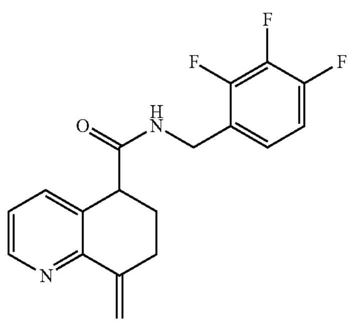 [SMILES: C=C1CCC(C(=O)NCc2ccc(F)c(F)c2F)c2cccnc21] | 8-methylene-N-(2,3,4-trifluorobenzyl)-5,6,7,8-tetrahydroquinoline-5-carboxamide | IM II-e-1-1 | |
| I-e-10 | 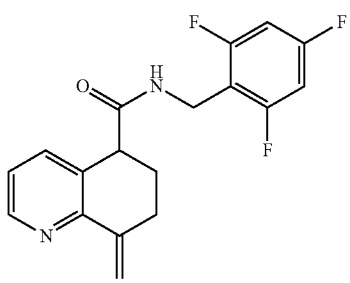 [SMILES: C=C1CCC(C(=O)NCc2c(F)cc(F)cc2F)c2cccnc21] | 8-methylene-N-(2,4,6-trifluorobenzyl)-5,6,7,8-tetrahydroquinoline-5-carboxamide | IM II-e-1-1 | |
| I-e-11 | 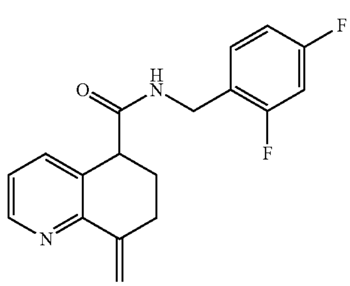 [SMILES: C=C1CCC(C(=O)NCc2ccc(F)cc2F)c2cccnc21] | N-(2,4-difluorobenzyl)-8-methylene-5,6,7,8-tetrahydroquinoline-5-carboxamide | IM II-e-1-1 | |
| I-e-12 | 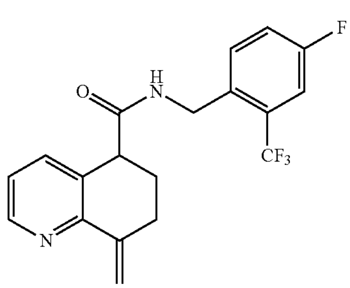 [SMILES: C=C1CCC(C(=O)NCc2ccc(F)cc2C(F)(F)F)c2cccnc21] | N-(4-fluoro-2-(trifluoromethyl)benzyl)-8-methylene-5,6,7,8-tetrahydroquinoline-5-carboxamide | IM II-e-1-1 | |

TABLE 13-continued

| Intermediates | Structure | Chemical Name | Substrate | Amine |
|---|---|---|---|---|
| I-e-13 | 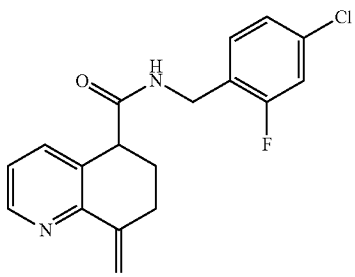 [SMILES: C=C1CCC(C(=O)NCc2ccc(Cl)cc2F)c2cccnc21] | N-(4-chloro-2-fluorobenzyl)-8-methylene-5,6,7,8-tetrahydroquinoline-5-carboxamide | IM II-e-1-1 | |
| I-e-14 | 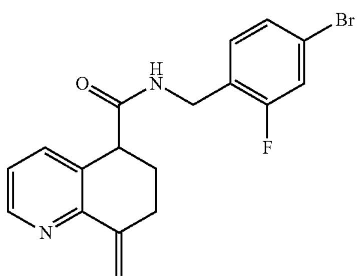 [SMILES: C=C1CCC(C(=O)NCc2ccc(Br)cc2F)c2cccnc21] | N-(4-bromo-2-fluorobenzyl)-8-methylene-5,6,7,8-tetrahydroquinoline-5-carboxamide | IM II-e-1-1 | |
| I-e-15 | 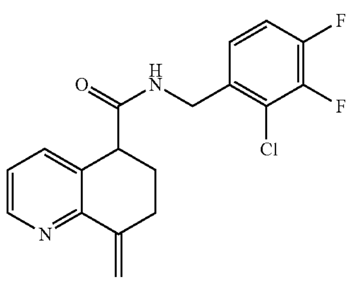 [SMILES: C=C1CCC(C(=O)NCc2ccc(F)c(F)c2Cl)c2cccnc21] | N-(2-chloro-3,4-difluorobenzyl)-8-methylene-5,6,7,8-tetrahydroquinoline-5-carboxamide | IM II-e-1-1 | |
| I-e-16 | 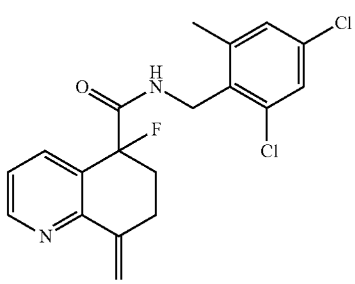 [SMILES: C=C1CCC(F)(C(=O)NCc2c(C)cc(Cl)cc2Cl)c2cccnc21] | N-(2,4-dichloro-6-methylbenzyl)-5-fluoro-8-methylene-5,6,7,8-tetrahydroquinoline-5-carboxamide | IM II-e-2-1 | |
| I-e-17 | 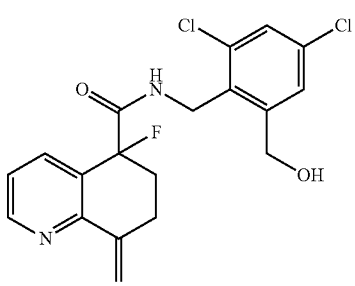 [SMILES: C=C1CCC(F)(C(=O)NCc2c(Cl)cc(Cl)cc2CO)c2cccnc21] | N-(2,4-dichloro-6-(hydroxymethyl)benzyl)-5-fluoro-8-methylene-5,6,7,8-tetrahydroquinoline-5-carboxamide | IM II-e-2-1 | |

TABLE 13-continued

| Intermediates | Structure | Chemical Name | Substrate | Amine |
|---|---|---|---|---|
| I-e-18 | 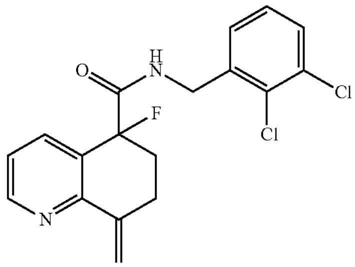 [SMILES: C=C1CCC(F)(C(=O)NCc2cccc(Cl)c2Cl)c2cccnc21] | N-(2,3-dichlorobenzyl)-5-fluoro-8-methylene-5,6,7,8-tetrahydroquinoline-5-carboxamide | IM II-e-2-1 | |
| I-e-19 | 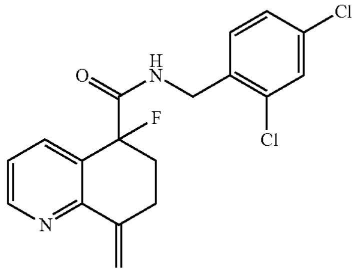 [SMILES: C=C1CCC(F)(C(=O)NCc2ccc(Cl)cc2Cl)c2cccnc21] | N-(2,4-dichlorobenzyl)-5-fluoro-8-methylene-5,6,7,8-tetrahydroquinoline-5-carboxamide | IM II-e-2-1 | |
| I-e-20 | 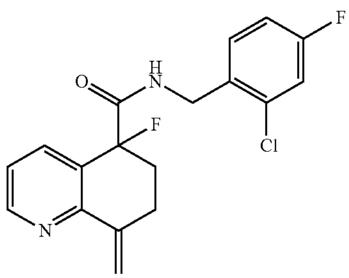 [SMILES: C=C1CCC(F)(C(=O)NCc2ccc(F)cc2Cl)c2cccnc21] | N-(2-chloro-4-fluorobenzyl)-5-fluoro-8-methylene-5,6,7,8-tetrahydroquinoline-5-carboxamide | IM II-e-2-1 | |
| I-e-21 | 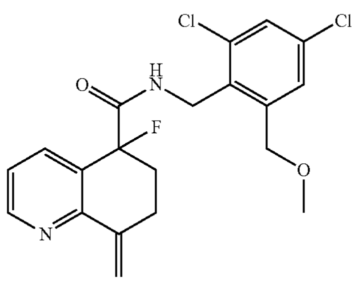 [SMILES: C=C1CCC(F)(C(=O)NCc2c(Cl)cc(Cl)cc2COC)c2cccnc21] | N-(2,4-dichloro-6-(methoxymethyl)benzyl)-5-fluoro-8-methylene-5,6,7,8-tetrahydroquinoline-5-carboxamide | IM II-e-2-1 | |
| I-e-22 | 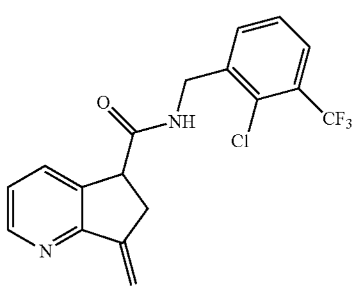 [SMILES: C=C1CC(C(=O)NCc2cccc(C(F)(F)F)c2Cl)c2cccnc21] | N-(2-chloro-3-(trifluoromethyl)benzyl)-7-methylene-6,7-dihydro-5H-cyclopenta[b]pyridine-5-carboxamide | IM II-e-1-2 | |

TABLE 13-continued

| Intermediates | Structure | Chemical Name | Substrate | Amine |
|---|---|---|---|---|
| I-e-23 | 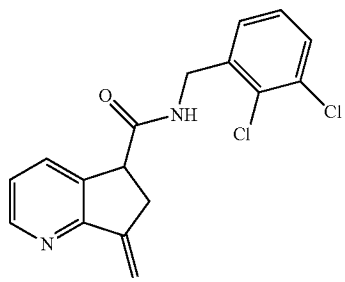 [SMILES: C=C1CC(C(=O)NCc2cccc(Cl)c2Cl)c2cccnc21] | N-(2,3-dichlorobenzyl)-7-methylene-6,7-dihydro-5H-cyclopenta[b]pyridine-5-carboxamide | IM II-e-1-2 | |
| I-e-24 | 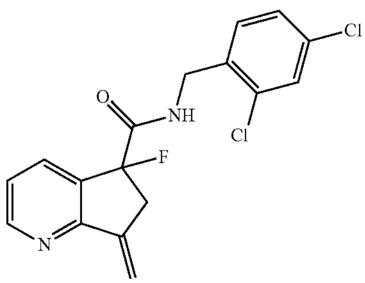 [SMILES: C=C1CC(F)(C(=O)NCc2ccc(Cl)cc2Cl)c2cccnc21] | N-(2,4-dichlorobenzyl)-5-fluoro-7-methylene-6,7-dihydro-5H-cyclopenta[b]pyridine-5-carboxamide | IM II-e-2-2 | |
| I-v-1 | 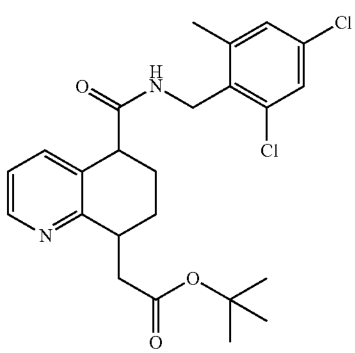 [SMILES: Cc1cc(Cl)cc(Cl)c1CNC(=O)C1CCC(CC(=O)OC(C)(C)C)c2ncccc21] | tert-butyl 2-(5-((2,4-dichloro-6-methylbenzyl)carbamoyl)-5,6,7,8-tetrahydroquinolin-8-yl)acetate | IM II-v-1 | |
| I-v-2 | 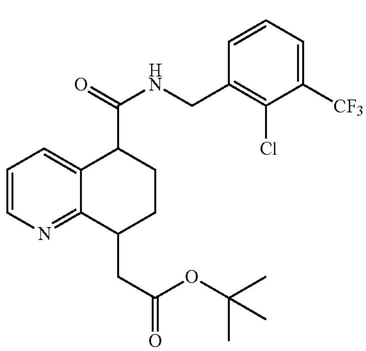 [SMILES: CC(C)(C)OC(=O)CC1CCC(C(=O)NCc2cccc(C(F)(F)F)c2Cl)c2cccnc21] | tert-butyl 2-(5-((2-chloro-3-(trifluoromethyl)benzyl)carbamoyl)-5,6,7,8-tetrahydroquinolin-8-yl)acetate | IM II-v-1 | |

| Intermediates | Structure | Chemical Name | Substrate | Amine |
|---|---|---|---|---|
| I-v-3 | 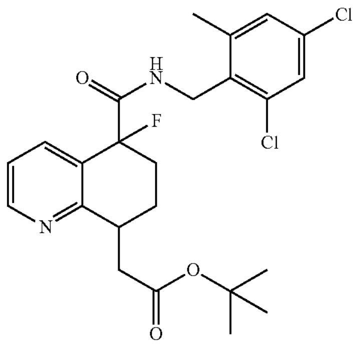 [SMILES: Cc1cc(Cl)cc(Cl)c1CNC(=O)C1(F)CCC(CC(=O)OC(C)(C)C)c2ncccc21] | tert-butyl 2-(5-((2,4-dichloro-6-methylbenzyl)carbamoyl)-5-fluoro-5,6,7,8-tetrahydroquinolin-8-yl)acetate | IM II-v-2 | |

IM I-e-1

$^1$H NMR (CDCl$_3$) delta 8.54 (1H, dd, J=4.6, 2.0 Hz), 7.40 (1H, d, J=9.2 Hz), 7.21 (1H, d, J=2.0 Hz), 7.15 (1H, dd, J=9.2, 4.6 Hz), 7.09 (1H, d, J=2.0 Hz), 6.31 (1H, s), 5.66 (1H, br), 5.19 (1H, s), 4.56 (1H, dd, J=14.5, 5.9 Hz), 4.44 (1H, dd, J=14.5, 5.9 Hz), 3.71 (1H, br t, J=5.3 Hz), 2.63 (2H, m), 2.45 (3H, s), 2.35 (1H, m), 2.04 (1H, m).

MS (ESI) m/z: 361.7 (M+H)$^+$.

IM I-e-2

$^1$H NMR (CDCl$_3$) delta 8.56 (1H, d, J=4.6 Hz), 7.64 (1H, d, J=7.3 Hz), 7.55 (1H, d, J=7.3 Hz), 7.42 (1H, d, J=8.6 Hz), 7.35 (1H, br t, J=7.3 Hz), 7.17 (1H, dd, J=7.3, 4.6 Hz), 6.34 (1H, s), 5.86 (1H, br), 5.22 (1H, s), 4.59 (1H, dd, J=14.5, 5.9 Hz), 4.51 (1H, dd, J=14.5, 5.9 Hz), 3.77 (1H, br t, J=5.3 Hz), 2.66 (2H, m), 2.18 (1H, m), 2.06 (1H, m).

MS (ESI) m/z: 381.7 (M+H)$^+$.

IM I-e-3

$^1$H NMR (CDCl$_3$) delta 8.60 (1H, br dd, J=4.6, 1.3 Hz), 7.70 (1H, d, J=7.9 Hz), 7.65 (1H, d, J=7.3 Hz), 7.47 (1H, br dd, J=7.9, 1.3 Hz), 7.40 (1H, dd, J=7.9, 7.3 Hz), 7.30 (1H, br), 7.18 (1H, dd, J=7.9, 4.6 Hz), 6.35 (1H, br s), 5.31 (1H, d, J=2.6 Hz), 4.73 (2H, d, J=5.9 Hz), 2.88-2.83 (2H, m), 2.60-2.20 (2H, m).

MS (ESI) m/z: 399.0 (M+H)$^+$.

IM I-e-4

$^1$H NMR (DMSO d6) delta 8.48 (1H, dd, J=4.6, 2.0 Hz), 8.12 (1H, br t, J=5.3 Hz), 7.53 (1H, dd, J=7.9, 2.0 Hz), 7.47 (1H, d, J=2.0 Hz), 7.32 (1H, d, J=2.0 Hz), 7.26 (1H, dd, J=7.9, 4.6 Hz), 6.26 (1H, s), 6.18 (1H, s), 5.15 (1H, br), 4.44 (2H, d, J=5.3 Hz), 2.74 (2H, m), 2.40 (3H, s), 2.15 (1H, m), 1.86 (1H, m).

MS (ESI) m/z: 377.3 (M+H)$^+$.

IM I-e-5

$^1$H NMR (DMSO d6) delta 8.90 (1H, br t, J=6.6 Hz), 8.49 (1H, dd, J=4.6, 2.0 Hz), 7.78 (1H, br d, J=7.9 Hz), 7.67-7.54 (3H, m), 7.29 (1H, dd, J=7.9, 4.6 Hz), 6.43 (1H, s), 6.18 (1H, br s), 5.17 (1H, br s), 4.47 (2H, d, J=6.6 Hz), 2.78 (2H, m), 2.23 (1H, m), 1.96 (1H, m).

MS (ESI) m/z: 397.3 (M+H)$^+$.

IM I-e-6

$^1$H NMR (CDCl$_3$) delta 8.55 (1H, dd, J=4.9, 1.8 Hz), 7.43 (1H, dd, J=7.9, 1.8 Hz), 7.36 (1H, d, J=2.4 Hz), 7.30-7.26 (1H, m), 7.21 (1H, dd, J=7.9, 4.9 Hz), 7.17 (1H, dd, J=8.0, 4.9 Hz), 6.33 (1H, d, J=1.8 Hz), 5.77 (1H, br), 5.21 (1H, d, J=1.8 Hz), 4.47 (1H, dd, J=15.3, 6.1 Hz), 4.41 (1H, dd, J=15.3, 6.1 Hz), 3.75 (1H, t, J=4.9 Hz), 3.75 (2H, br t, J=4.9 Hz), 2.34 (1H, m), 2.05 (1H, m).

MS (ESI) m/z: 346.7 (M+H)$^+$.

IM I-e-7

$^1$H NMR (CDCl$_3$) delta 8.55 (1H, dd, J=4.9, 1.2 Hz), 7.43 (1H, dd, J=7.9, 1.2 Hz), 7.32 (1H, dd, J=8.6, 6.1 Hz), 7.16 (1H, dd, J=7.9, 4.9 Hz), 7.09 (1H, dd, J=8.6, 2.4 Hz), 6.94 (1H, ddd, J=8.6, 7.9, 2.4 Hz), 6.33 (1H, d, J=1.8 Hz), 5.76 (1H, br), 5.21 (1H, d, J=1.8 Hz), 4.47 (1H, dd, J=15.3, 6.1 Hz), 4.41 (1H, dd, J=15.3, 6.1 Hz), 3.75 (1H, t, J=4.9 Hz), 2.66-2.62 (2H, m), 2.34 (1H, m), 2.05 (1H, m).

MS (ESI) m/z: 330.8 (M+H)$^+$.

IM I-e-8

$^1$H NMR (CDCl$_3$) delta 8.54 (1H, dd, J=4.9, 1.8 Hz), 7.42 (1H, dd, J=7.9, 1.8 Hz), 7.20 (1H, m), 7.16 (1H, dd, J=7.9, 4.9 Hz), 7.03 (1H, dd, J=9.2, 1.8 Hz), 6.32 (1H, d, J=1.8 Hz), 5.64 (1H, br), 5.20 (1H, d, J=1.8 Hz), 4.58 (1H, ddd, J=14.7, 5.5, 1.2 Hz), 4.49 (1H, dd, J=14.7, 5.5, 1.8 Hz), 3.74 (1H, m), 2.65-2.61 (2H, m), 2.31 (1H, m), 2.03 (1H, m).

MS (ESI) m/z: 364.7 (M+H)$^+$.

IM I-e-9

$^1$H NMR (CDCl$_3$) delta 8.46 (1H, dd, J=4.8, 1.2 Hz), 7.39 (1H, dd, J=7.9, 1.2 Hz), 7.13 (1H, dd, J=7.9, 4.8 Hz), 6.99 (1H, m), 6.89 (1H, m), 6.27 (1H, d, J=1.8 Hz), 6.13 (1H, br t, J=5.5 Hz), 5.18 (1H, d, J=1.8 Hz), 4.41 (2H, br d, J=6.1 Hz), 3.73 (1H, br t, J=5.5 Hz), 2.65-2.61 (2H, m), 2.26 (1H, m), 2.03 (1H, m).

MS (ESI) m/z: 333.2 (M+H)$^+$.

IM I-e-10

$^1$H NMR (CDCl$_3$) delta 8.53 (1H, dd, J=4.3, 1.2 Hz), 7.41 (1H, dd, J=7.9, 1.2 Hz), 7.16 (1H, dd, J=7.9, 4.3 Hz), 6.64 (2H, m), 6.31 (1H, d, J=1.8 Hz), 5.56 (1H, br), 5.19 (1H, d, J=1.8 Hz), 4.49 (1H, dd, J=14.7, 6.1 Hz), 4.43 (1H, dd, J=14.7, 5.5 Hz), 3.73 (1H, br t, J=5.5 Hz), 2.65-2.61 (2H, m), 2.31 (1H, m), 2.04 (1H, m).

MS (ESI) m/z: 333.1 (M+H)$^+$.

IM I-e-11

$^1$H NMR (CDCl$_3$) delta 8.54 (1H, dd, J=4.9, 1.2 Hz), 7.42 (1H, dd, J=7.9, 1.2 Hz), 7.29-7.22 (1H, m), 7.16 (1H, dd, J=7.9, 4.9 Hz), 6.85-6.74 (2H, m), 6.32 (1H, d, J=1.8 Hz), 5.66 (1H, br), 5.20 (1H, d, J=1.8 Hz), 4.42 (2H, br d, J=5.5 Hz), 3.75 (1H, br t, J=5.5 Hz), 2.66-2.63 (2H, m), 2.33 (1H, m), 2.06 (1H, m).

MS (ESI) m/z: 315.2 (M+H)$^+$.

IM I-e-12

¹H NMR (CDCl₃) delta 8.48 (1H, dd, J=4.2, 1.2 Hz), 7.45 (1H, dd, J=8.6, 5.5 Hz), 7.38 (1H, dd, J=7.9, 1.2 Hz), 7.30 (1H, dd, J=8.6, 2.4 Hz), 7.17 (1H, dt, J=8.6, 2.4 Hz), 7.12 (1H, dd, J=7.9, 4.2 Hz), 6.27 (1H, d, J=1.2 Hz), 6.07 (1H, br t, J=6.1 Hz), 5.16 (1H, d, J=1.2 Hz), 4.51 (2H, br d, J=6.1 Hz), 3.72 (1H, br t, J=5.5 Hz), 2.72-2.60 (2H, m), 2.27 (1H, m), 2.02 (1H, m).

MS (ESI) m/z: 365.1 (M+H)⁺.

IM I-e-13

¹H NMR (CDCl₃) delta 8.44 (1H, dd, J=4.9, 1.8 Hz), 7.39 (1H, dd, J=7.9, 1.8 Hz), 7.18 (1H, t, J=7.9 Hz), 7.11 (1H, dd, J=7.9, 4.9 Hz), 7.08-7.00 (2H, m), 6.25 (1H, d, J=1.2 Hz), 6.17 (1H, br t, J=5.5 Hz), 5.16 (1H, d, J=1.2 Hz), 4.38 (2H, br d, J=6.1 Hz), 3.71 (1H, br t, J=5.5 Hz), 2.69-2.55 (2H, m), 2.24 (1H, m), 2.02 (1H, m).

MS (ESI) m/z: 331.1 (M+H)⁺.

IM I-e-14

¹H NMR (CDCl₃) delta 8.46 (1H, dd, J=4.9, 1.8 Hz), 7.38 (1H, dd, J=7.9, 1.8 Hz), 7.22-7.10 (4H, m), 6.26 (1H, d, J=1.2 Hz), 6.16 (1H, br t, J=5.5 Hz), 5.17 (1H, d, J=1.2 Hz), 4.37 (2H, br d, J=5.5 Hz), 3.71 (1H, br t, J=5.5 Hz), 2.69-2.55 (2H, m), 2.24 (1H, m), 2.02 (1H, m).

MS (ESI) m/z: 375.0 (M+H)⁺.

IM I-e-15

¹H NMR (CDCl₃) delta 8.52 (1H, dd, J=4.9, 1.8 Hz), 7.42 (1H, dd, J=7.9, 1.8 Hz), 7.16 (1H, dd, J=7.9, 4.9 Hz), 7.09-7.01 (2H, m), 6.31 (1H, d, J=1.8 Hz), 5.92 (1H, br t, J=5.5 Hz), 5.20 (1H, d, J=1.8 Hz), 4.47 (1H, dd, J=15.3, 6.1 Hz), 4.41 (1H, dd, J=15.5, 6.1 Hz), 3.75 (1H, br t, J=5.5 Hz), 2.64 (2H, m), 2.31 (1H, m), 2.05 (1H, m).

MS (ESI) m/z: 349.0 (M+H)⁺.

IM I-e-16

¹H NMR (CDCl₃) delta 8.61 (1H, dd, J=4.6, 2.0 Hz), 7.47 (1H, ddd, J=7.9, 2.0, 1.3 Hz), 7.32 (1H, d, J=1.3 Hz), 7.19 (1H, dd, J=7.9, 4.6 Hz), 7.16 (1H, d, J=1.3 Hz), 7.04 (1H, br d, J=5.3 Hz), 6.34 (1H, s), 5.31 (1H, s), 4.72 (1H, dd, J=13.8, 5.3 Hz), 4.63 (1H, dd, J=13.8, 5.3 Hz), 2.84 (2H, m), 2.45 (1H, m), 2.48 (3H, s), 2.25 (1H, m).

MS (ESI) m/z: 379.0 (M+H)⁺.

IM I-e-17

¹H NMR (CDCl₃) delta 8.58 (1H, dd, J=4.6, 2.0 Hz), 7.62 (1H, br d, J=5.3 Hz), 7.44 (1H, d, J=2.0 Hz), 7.40 (1H, ddd, J=7.9, 2.0, 1.3 Hz), 7.34 (1H, d, J=2.0 Hz), 7.16 (1H, dd, J=7.9, 4.6 Hz), 6.33 (1H, s), 5.30 (1H, s), 4.81-4.65 (4H, m), 3.96 (1H, br), 2.80 (2H, m), 2.86-2.14 (2H, m).

MS (ESI) m/z: 394.9 (M+H)⁺.

IM I-e-18

¹H NMR (CDCl₃) delta 8.61 (1H, br dd, J=4.6, 1.3 Hz), 7.51-7.45 (2H, m), 7.35 (1H, dd, J=7.9, 1.3 Hz), 7.26-7.20 (2H, m), 7.19 (1H, dd, J=7.9, 4.6 Hz), 6.35 (1H, s), 5.31 (1H, s), 4.69 (1H, d, J=5.9 Hz), 2.88-2.83 (2H, m), 2.61-2.20 (2H, m).

MS (ESI) m/z: 364.9 (M+H)⁺.

IM I-e-19

¹H NMR (CDCl₃) delta 8.61 (1H, br dd, J=4.9, 1.8 Hz), 7.47 (1H, br dd, J=7.9, 1.8 Hz), 7.45 (1H, d, J=1.8 Hz), 7.37 (1H, d, J=7.9 Hz), 7.26 (1H, d, J=7.9, 1.8 Hz), 7.19 (1H, br), 7.18 (1H, dd, J=7.9, 4.9 Hz), 6.35 (1H, s), 5.31 (1H, s), 4.65 (1H, dd, J=14.7, 5.5 Hz), 4.60 (1H, dd, J=14.7, 5.5 Hz), 2.86-2.83 (2H, m), 2.46 (1H, m), 2.26 (1H, m).

MS (ESI) m/z: 365.0 (M+H)⁺.

IM I-e-20

¹H NMR (CDCl₃) delta 8.61 (1H, ddd, J=4.9, 1.8, 1.8 Hz), 7.47 (1H, ddd, J=7.9, 1.8, 1.8 Hz), 7.42 (1H, dd, J=8.6, 6.1 Hz), 7.24-7.13 (3H, m), 7.00 (1H, ddd, J=8.6, 3.1, 3.1 Hz), 6.35 (1H, s), 5.31 (1H, s), 4.65 (1H, dd, J=15.3, 6.1 Hz), 4.60 (1H, dd, J=15.3, 6.1 Hz), 2.90-2.79 (2H, m), 2.48 (1H, m), 2.25 (1H, m).

MS (ESI) m/z: 348.9 (M+H)⁺.

IM I-e-21

¹H NMR (CDCl₃) delta 8.60 (1H, dd, J=4.6, 2.0 Hz), 7.48 (1H, dd, J=7.3, 2.0 Hz), 7.45 (1H, d, J=2.0 Hz), 7.33 (1H, d, J=2.0 Hz), 7.29 (1H, m), 7.18 (1H, dd, J=7.3, 4.6 Hz), 6.34 (1H, s), 5.30 (1H, s), 4.79 (1H, dd, J=14.5, 6.6 Hz), 4.60 (1H, m), 4.58 (1H, d, J=11.2 Hz), 4.55 (1H, d, J=11.2 Hz), 3.44 (3H, s), 2.83 (2H, m), 2.59-2.15 (2H, m).

MS (ESI) m/z: 408.9 (M+H)⁺.

IM I-e-22

MS (ESI) m/z: 367.0 (M+H)⁺.

IM I-e-23

MS (ESI) m/z: 333.1 (M+H)⁺.

IM I-e-24

¹H NMR (CDCl₃) delta 8.68 (1H, ddd, J=4.9, 4.0, 1.8 Hz), 7.61 (1H, br dt, J=7.9, 1.8 Hz), 7.45 (1H, d, J=1.8 Hz), 7.40-7.35 (1H, m), 7.29-7.15 (3H, m), 6.19 (1H, br d, J=1.8 Hz), 5.35 (1H, br d, J=1.8 Hz), 4.67 (1H, dd, J=14.7, 6.1 Hz), 4.59 (1H, dd, J=14.7, 6.1 Hz), 3.58 (1H, m), 3.12 (1H, m).

MS (ESI) m/z: 351.1 (M+H)⁺.

IM I-v-1

¹H NMR (CDCl₃) delta 8.44 (1H, m), 7.36 (1H, m), 7.28-7.02 (3H, m), 6.34 (0.5H, br), 5.73 (0.5H, br), 4.59-4.39 (2H, m), 3.75 (0.5H, br), 3.66 (0.5H, br t, J=6.6 Hz), 3.40 (0.5H, m), 3.15 (0.5H, m), 3.10-2.91 (1.5H, m), 2.73-2.65 (0.5H, m), 2.50-2.20 (2H, m), 2.55 (1.5H, s), 2.37 (1.5H, s), 2.07-1.95 (2H, m), 1.44 (4.5H, s), 1.26 (4.5H, s).

MS (ESI) m/z: 463.1 (M+H)⁺.

IM I-v-2

¹H NMR (CDCl₃) delta 8.47 (1H, m), 7.62 (0.5H, d, J=8.6 Hz), 7.58 (0.5H, d, J=7.9 Hz), 7.46-7.24 (3H, m), 7.09 (1H, m), 6.88 (0.5H, br), 5.90 (0.5H, br), 4.68 (0.5H, dd, J=15.2, 6.6 Hz), 4.59-4.51 (1H, m), 4.39 (0.5H, dd, J=15.8, 5.2 Hz), 3.75 (0.5H, br d, J=2.6 Hz), 3.72 (0.5H, br t, J=7.3 Hz), 3.40 (0.5H, br), 3.28 (0.5H, dd, J=16.4, 6.0 Hz), 3.19 (0.5H, br), 2.94 (0.5H, m), 2.68 (0.5H, dd, J=16.4, 2.6 Hz), 2.46 (0.5H, dd, J=15.8, 9.2 Hz), 2.37-2.30 (0.5H, m), 2.16-1.97 (3H, m), 1.80-1.67 (0.5H, m), 1.44 (4.5H, s), 1.28 (4.5H, s).

MS (ESI) m/z: 483.0 (M+H)⁺.

IM I-v-3

¹H NMR (CDCl₃) delta 8.55 (1H, m), 7.47 (1H, d, J=7.9 Hz), 7.30 (1H, d, J=2.0 Hz), 7.14 (2H, m), 7.02 (1H, br), 4.69 (1H, dd, J=13.8, 5.3 Hz), 4.61 (1H, dd, J=14.5, 5.3 Hz), 3.45 (1H, br), 2.92 (1H, dd, J=16.5, 4.6 Hz), 2.61-2.48 (1.5H, m), 2.45 (3H, s), 2.26-2.05 (2.5H, m), 1.45 (9H, s).

MS (ESI) m/z: 481.0 (M+H)⁺.

The following Examples and Intermediates were prepared by General Procedure B (Tables 14 and 16).

General Procedure B

The General Procedure B was carried out by the same procedure described in General Procedure: Scheme 2, Step 5 with/without following purification; SCX cartridge column, preparative HPLC to afford the following Examples and Intermediates.

TABLE 14

| Examples | Structure | Chemical Name | Substrate |
|---|---|---|---|
| 12 | 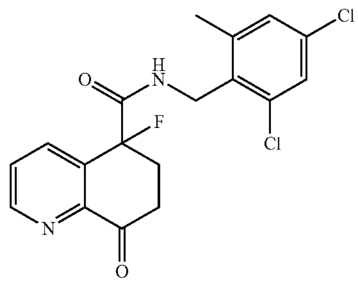 [SMILES: Cc1cc(Cl)cc(Cl)c1CNC(=O)C1(F)CCC(=O)c2ncccc21] | N-(2,4-dichloro-6-methylbenzyl)-5-fluoro-8-oxo-5,6,7,8-tetrahydro-quinoline-5-carboxamide | IM I-e-16 |
| 13 | 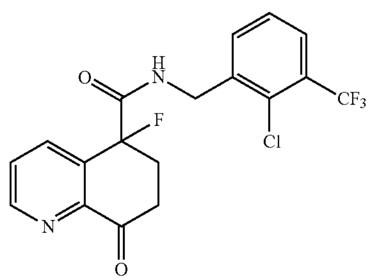 [SMILES: O=C1CCC(F)(C(=O)NCc2cccc(C(F)(F)F)c2Cl)c2cccnc21] | N-(2-chloro-3-(trifluoromethyl)benzyl)-5-fluoro-8-oxo-5,6,7,8-tetrahydro-quinoline-5-carboxamide | IM I-e-3 |
| 14 | 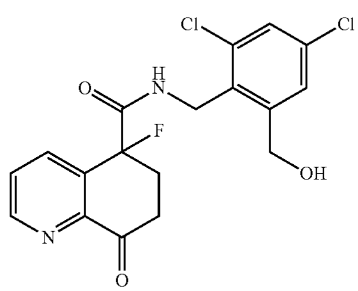 [SMILES: O=C1CCC(F)(C(=O)NCc2c(Cl)cc(Cl)cc2CO)c2cccnc21] | N-(2,4-dichloro-6-(hydroxymethyl)benzyl)-5-fluoro-8-oxo-5,6,7,8-tetrahydroquinoline-5-carboxamide | IM I-e-17 |
| 15 | 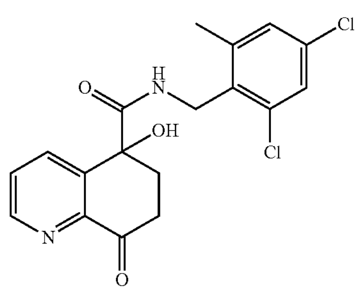 [SMILES: Cc1cc(Cl)cc(Cl)c1CNC(=O)C1(O)CCC(=O)c2ncccc21] | N-(2,4-dichloro-6-methylbenzyl)-5-hydroxy-8-oxo-5,6,7,8-tetrahydro-quinoline-5-carboxamide | IM I-e-4 |

TABLE 14-continued

| Examples | Structure | Chemical Name | Substrate |
|---|---|---|---|
| 16 | 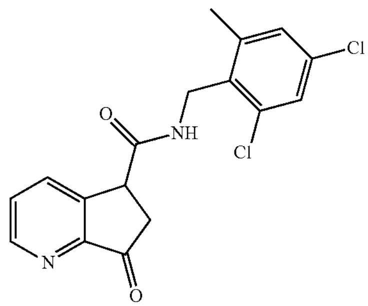 [SMILES: Cc1cc(Cl)cc(Cl)c1CNC(=O)C1CC(=O)c2ncccc21] | N-(2,4-dichloro-6-methylbenzyl)-7-oxo-6,7-dihydro-5H-cyclopenta[b]pyridine-5-carboxamide | Ex 11 |
| 17 | 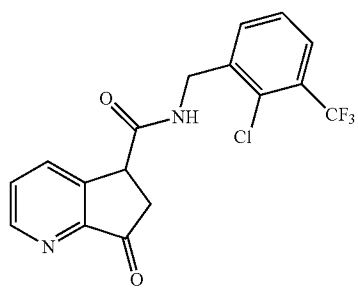 [SMILES: O=C1CC(C(=O)NCc2cccc(C(F)(F)F)c2Cl)c2cccnc21] | N-(2-chloro-3-(trifluoromethyl)benzyl)-7-oxo-6,7-dihydro-5H-cyclopenta[b]pyridine-5-carboxamide | IM I-e-22 |

TABLE 15

| | LC MS | | |
|---|---|---|---|
| Examples | Method | tR (min) | [M + H]+ |
| 12 | D | 1.68 | 381.0 |
| 13 | D | 1.59 | 401.0 |
| 14 | A | 1.35 | 397.2 |
| 15 | A | 1.47 | 379.3 |
| 16 | D | 1.55 | 349.0 |
| 17 | D | 1.48 | 369.0 |

Ex 12

$^1$H NMR (CDCl$_3$) delta 8.87 (1H, d, J=4.6 Hz), 7.73 (1H, d, J=7.9 Hz), 7.52 (1H, dd, J=7.9, 4.6 Hz), 7.33 (1H, d, J=1.3 Hz), 7.16 (1H, d, J=1.3 Hz), 7.05 (1H, br d, J=5.9 Hz), 4.71 (1H, dd, J=14.5, 5.9 Hz), 4.64 (1H, dd, J=14.5, 5.9 Hz), 3.17 (1H, m), 3.00 (1H, m), 2.79 (1H, m), 2.52 (1H, m), 2.46 (3H, s).

Ex 13

$^1$H NMR (CDCl$_3$) delta 8.88 (1H, dd, J=4.6, 1.3 Hz), 7.74 (1H, d, J=7.9 Hz), 7.71 (1H, d, J=7.9 Hz), 7.63 (1H, d, J=7.9 Hz), 7.51 (1H, dd, J=7.9, 4.6 Hz), 7.40 (1H, dd, J=7.9, 7.9 Hz), 7.33 (1H, br d, J=5.9 Hz), 4.72 (2H, d, J=5.9 Hz), 3.17 (1H, m), 3.01 (1H, m), 2.59 (1H, m).

Ex 14

$^1$H NMR (CDCl$_3$) delta 8.88 (1H, br dd, J=4.6, 1.3 Hz), 7.69 (1H, d, J=7.9 Hz), 7.59 (1H, br), 7.50 (1H, dd, J=7.9, 4.6 Hz), 7.45 (1H, d, J=2.0 Hz), 7.34 (1H, d, J=2.0 Hz), 4.85-4.64 (4H, m), 3.60 (1H, br), 3.18-2.92 (2H, m), 2.76 (1H, m), 2.54 (1H, m).

Ex 15

$^1$H NMR (DMSO d6) delta 8.70 (1H, br dd, J=4.6, 2.0 Hz), 8.23 (1H, br), 7.86 (1H, dd, J=7.9, 2.0 Hz), 7.60 (1H, dd, J=7.9, 4.6 Hz), 7.46 (1H, d, J=2.0 Hz), 7.30 (1H, d, J=2.0 Hz), 6.64 (1H, s), 4.42 (2H, m), 2.89-2.69 (2H, m), 2.43 (1H, m), 2.37 (3H, s), 2.22 (1H, m).

Ex 16

$^1$H NMR (DMSO d6) delta 8.82 (1H, br), 8.77 (1H, d, J=4.6 Hz), 8.00 (1H, d, J=7.9 Hz), 7.63 (1H, dd, J=7.9, 4.6 Hz), 7.50 (1H, br s), 7.36 (1H, br s), 4.39 (2H, br d J=4.6 Hz), 4.29 (1H, m), 2.80 (2H, m), 2.37 (3H, s).

TABLE 16

| Intermediates | Structure | Chemical Name | Substrate |
|---|---|---|---|
| I-c-1 | 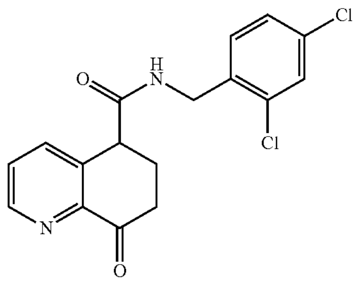 | N-(2,4-dichlorobenzyl)-8-oxo-5,6,7,8-tetrahydroquinoline-5-carboxamide | IM I-e-6 |
| I-c-2 | 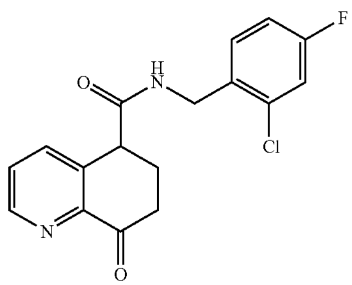 [SMILES: O=C1CCC(C(=O)NCc2ccc(F)cc2Cl)c2cccnc21] | N-(2-chloro-4-fluorobenzyl)-8-oxo-5,6,7,8-tetrahydroquinoline-5-carboxamide | IM I-e-7 |
| I-c-3 | 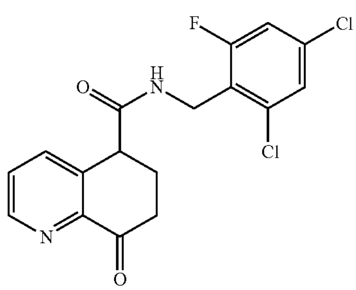 [SMILES: O=C1CCC(C(=O)NCc2c(F)cc(Cl)cc2Cl)c2cccnc21] | N-(2,4-dichloro-6-fluorobenzyl)-8-oxo-5,6,7,8-tetrahydroquinoline-5-carboxamide | IM I-e-8 |
| I-c-4 | 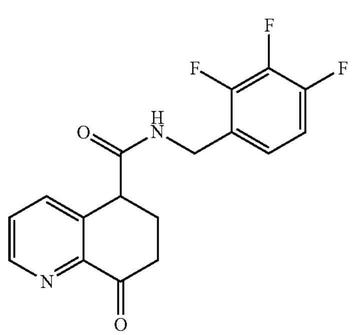 [SMILES: O=C1CCC(C(=O)NCc2ccc(F)c(F)c2F)c2cccnc21] | 8-oxo-N-(2,3,4-trifluorobenzyl)-5,6,7,8-tetrahydroquinoline-5-carboxamide | IM I-e-9 |

TABLE 16-continued

| Intermediates | Structure | Chemical Name | Substrate |
|---|---|---|---|
| I-c-5 | 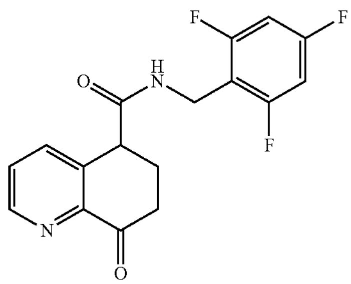 [SMILES: O=C1CCC(C(=O)NCc2c(F)cc(F)cc2F)c2cccnc21] | 8-oxo-N-(2,4,6-trifluorobenzyl)-5,6,7,8-tetrahydroquinoline-5-carboxamide | IM I-e-10 |
| I-c-6 | 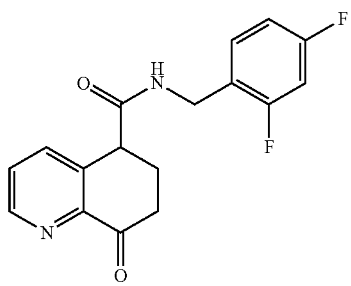 [SMILES: O=C1CCC(C(=O)NCc2ccc(F)cc2F)c2cccnc21] | N-(2,4-difluorobenzyl)-8-oxo-5,6,7,8-tetrahydroquinoline-5-carboxamide | IM I-e-11 |
| I-c-7 | 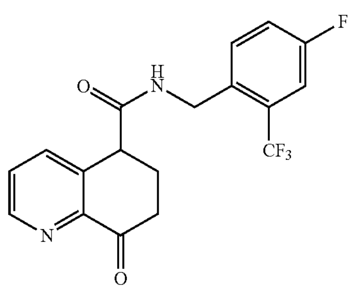 [SMILES: O=C1CCC(C(=O)NCc2ccc(F)cc2C(F)(F)F)c2cccnc21] | N-(4-fluoro-2-(trifluoromethyl)benzyl)-8-oxo-5,6,7,8-tetrahydroquinoline-5-carboxamide | IM I-e-12 |
| I-c-8 | 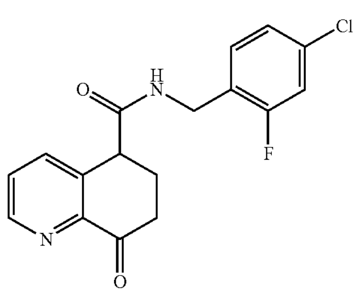 [SMILES: O=C1CCC(C(=O)NCc2ccc(Cl)cc2F)c2cccnc21] | N-(4-chloro-2-fluorobenzyl)-8-oxo-5,6,7,8-tetrahydroquinoline-5-carboxamide | IM I-e-13 |

TABLE 16-continued

| Intermediates | Structure | Chemical Name | Substrate |
|---|---|---|---|
| I-c-9 | 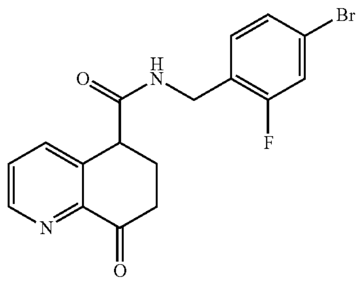 [SMILES: O=C1CCC(C(=O)NCc2ccc(Br)cc2F)c2cccnc21] | N-(4-bromo-2-fluorobenzyl)-8-oxo-5,6,7,8-tetrahydroquinoline-5-carboxamide | IM I-e-14 |
| I-c-10 | 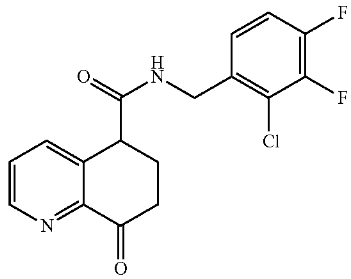 [SMILES: O=C1CCC(C(=O)NCc2ccc(F)c(F)c2Cl)c2cccnc21] | N-(2-chloro-3,4-difluorobenzyl)-8-oxo-5,6,7,8-tetrahydroquinoline-5-carboxamide | IM I-e-15 |
| I-c-11 | 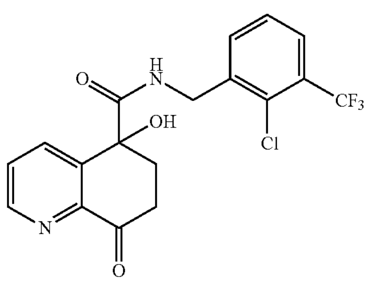 [SMILES: O=C1CCC(O)(C(=O)NCc2cccc(C(F)(F)F)c2Cl)c2cccnc21] | N-(2-chloro-3-(trifluoromethyl)benzyl)-5-hydroxy-8-oxo-5,6,7,8-tetrahydroquinoline-5-carboxamide | IM I-e-5 |
| I-c-12 | 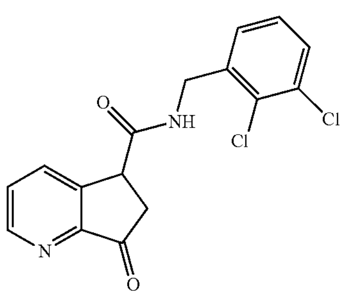 [SMILES: O=C1CC(C(=O)NCc2cccc(Cl)c2Cl)c2cccnc21] | N-(2,3-dichlorobenzyl)-7-oxo-6,7-dihydro-5H-cyclopenta[b]pyridine-5-carboxamide | IM I-e-23 |

IM I-c-1

$^1$H NMR (CDCl$_3$) delta 8.60 (1H, dd, J=4.3, 1.8 Hz), 7.67 (1H, dd, J=7.9, 1.8 Hz), 7.40 (1H, dd, J=7.9, 4.9 Hz), 7.34 (1H, d, J=1.8 Hz), 7.29 (1H, d, J=7.9 Hz), 7.19 (1H, dd, J=7.9, 1.8 Hz), 6.94 (1H, t, J=5.5 Hz), 4.53 (1H, dd, J=14.6, 5.5 Hz), 4.47 (1H, dd, J=14.6, 5.5 Hz), 3.96 (1H, t, J=5.5 Hz), 2.96 (1H, ddd, J=17.7, 10.4, 4.9 Hz), 2.70 (1H, ddd, J=17.7, 7.3, 4.9 Hz), 2.53 (1H, m), 2.40 (1H, m).

MS (ESI) m/z: 349.0 (M+H)$^+$.

IM I-c-2

$^1$H NMR (CDCl$_3$) delta 8.53 (1H, dd, J=4.3, 1.2 Hz), 7.69 (1H, dd, J=7.9, 1.2 Hz), 7.55 (1H, br), 7.37 (1H, dd, J=7.9, 4.3 Hz), 7.30 (1H, dd, J=8.5, 6.1 Hz), 7.06 (1H, dd, J=8.5, 2.4 Hz), 6.89 (1H, dt, J=8.5, 2.4 Hz), 4.48 (1H, dd, J=9.8, 5.5 Hz), 4.47 (1H, dd, J=9.8, 5.5 Hz), 4.03 (1H, br t, J=5.5 Hz), 2.99 (1H, ddd, J=17.7, 9.8, 4.9 Hz), 2.67 (1H, m), 2.48 (1H, m), 2.36 (1H, m).

MS (ESI) m/z: 333.1 (M+H)$^+$.

IM I-c-3

¹H NMR (CDCl₃) delta 8.52 (1H, m), 7.69 (1H, dd, J=7.9, 1.2 Hz), 7.38 (1H, dd, J=7.9, 4.3 Hz), 7.26 (1H, br), 7.16 (1H, d, J=1.8 Hz), 6.97 (1H, dd, J=8.6, 1.8 Hz), 4.59 (1H, dd, J=15.9, 4.9 Hz), 4.55 (1H, dd, J=15.9, 4.9 Hz), 3.98 (1H, br t, J=5.5 Hz), 3.19 (1H, ddd, J=17.7, 10.4, 4.9 Hz), 2.66 (1H, m), 2.48 (1H, m), 2.36 (1H, m).

MS (ESI) m/z: 367.0 (M+H)⁺.

IM I-c-4

¹H NMR (CDCl₃) delta 8.53 (1H, dd, J=4.9, 1.2 Hz), 7.99 (1H, br t, J=5.5 Hz), 7.70 (1H, d, J=7.9 Hz), 7.39 (1H, dd, J=7.9, 4.9 Hz), 7.06 (1H, m), 6.89 (1H, m), 4.45 (2H, m), 4.04 (1H, br t, J=5.5 Hz), 3.03 (1H, ddd, J=17.7, 10.4, 4.9 Hz), 2.65 (1H, m), 2.50-2.34 (2H, m).

MS (ESI) m/z: 335.1 (M+H)⁺.

IM I-c-5

¹H NMR (CDCl₃) delta 8.49 (1H, dd, J=4.3, 1.2 Hz), 8.07 (1H, br t, J=5.5 Hz), 7.69 (1H, d, J=7.9 Hz), 7.39 (1H, dd, J=7.9, 4.3 Hz), 6.62 (2H, m), 4.46 (2H, m), 4.01 (1H, br t, J=5.5 Hz), 2.99 (1H, m), 2.64 (1H, m), 2.42-2.28 (2H, m).

MS (ESI) m/z: 335.1 (M+H)⁺.

IM I-c-6

¹H NMR (CDCl₃) delta 8.50 (1H, dd, J=4.9, 1.2 Hz), 7.68 (1H, dd, J=7.9, 1.2 Hz), 7.60 (1H, br t, J=5.5 Hz), 7.36 (1H, dd, J=7.9, 4.9 Hz) 7.26, (1H, ddd, J=15.3, 8.6, 6.7 Hz), 6.80-6.70 (2H, m), 4.45 (1H, dd, J=15.9, 5.5 Hz), 4.41 (1H, dd, J=15.9, 5.5 Hz), 4.02 (1H, br t, J=5.5 Hz), 2.99 (1H, ddd, J=17.7, 10.4, 4.9 Hz), 2.66 (1H, ddd, J=17.7, 7.3, 4.9 Hz), 2.50-2.32 (2H, m).

MS (ESI) m/z: 317.1 (M+H)⁺.

IM I-c-7

¹H NMR (CDCl₃) delta 8.55 (1H, dd, J=4.9, 1.2 Hz), 7.66 (1H, dd, J=7.9, 1.2 Hz), 7.51 (1H, dd, J=8.5, 5.5 Hz), 7.38 (1H, dd, J=7.9, 4.9 Hz), 7.31 (1H, dd, J=8.5, 2.4 Hz), 7.18 (1H, ddd, J=8.5, 7.9, 2.4 Hz), 7.12 (1H, br t, J=6.1 Hz), 4.60 (1H, dd, J=15.9, 6.1 Hz), 4.55 (1H, dd, J=15.9, 6.1 Hz), 3.99 (1H, br t, J=5.5 Hz), 2.97 (1H, ddd, J=17.7, 9.8, 4.9 Hz), 2.68 (1H, ddd, J=17.7, 6.7, 4.9 Hz), 2.53-2.34 (2H, m).

MS (ESI) m/z: 367.1 (M+H)⁺.

IM I-c-8

¹H NMR (CDCl₃) delta 8.49 (1H, dd, J=4.9, 1.2 Hz), 7.67 (1H, dd, J=7.9, 1.2 Hz), 7.63 (1H, br t, J=6.1 Hz), 7.36 (1H, dd, J=7.9, 4.9 Hz), 7.21 (1H, dd, J=8.5, 7.3 Hz), 7.02 (1H, dd, J=8.9, 2.4 Hz), 6.99 (1H, dd, J=7.3, 2.4 Hz), 4.43 (1H, dd, J=15.3, 6.1 Hz), 4.38 (1H, dd, J=15.3, 6.1 Hz), 4.00 (1H, br t, J=5.5 Hz), 2.99 (1H, ddd, J=17.7, 9.8, 4.9 Hz), 2.65 (1H, ddd, J=17.7, 6.7, 5.5 Hz), 2.46-2.31 (2H, m).

MS (ESI) m/z: 333.1 (M+H)⁺.

IM I-c-9

¹H NMR (CDCl₃) delta 8.50 (1H, dd, J=4.9, 1.2 Hz), 7.68 (1H, dd, J=7.9, 1.2 Hz), 7.60 (1H, br t, J=6.1 Hz), 7.37 (1H, dd, J=7.9, 4.9 Hz), 7.22-7.14 (3H, m), 4.42 (2H, m), 4.00 (1H, br t, J=5.5 Hz), 2.99 (1H, ddd, J=17.7, 10.4, 4.9 Hz), 2.66 (1H, ddd, J=17.7, 7.3, 4.9 Hz), 2.49-2.31 (2H, m).

MS (ESI) m/z: 377.0 (M+H)⁺.

IM I-c-10

¹H NMR (CDCl₃) delta 8.69 (1H, d, J=4.3 Hz), 7.65 (1H, d, J=7.9 Hz), 7.44 (1H, dd, J=7.9, 4.3 Hz), 7.15 (1H, m), 7.07 (1H, dd, J=8.6, 7.3 Hz), 6.35 (1H, br), 4.57 (1H, dd, J=15.3, 6.1 Hz), 4.49 (1H, dd, J=15.3, 5.5 Hz), 3.91 (1H, br t, J=5.5 Hz), 2.94 (1H, ddd, J=17.7, 10.4, 4.9 Hz), 2.75 (1H, ddd, J=17.7, 6.1, 4.9 Hz), 2.56 (1H, ddd, J=17.7, 11.7, 6.1 Hz), 2.42 (1H, ddd, J=17.7, 10.4, 4.9 Hz).

MS (ESI) m/z: 351.0 (M+H)⁺.

IM I-c-11

¹H NMR (DMSO d6) delta 8.97 (1H, br t, J=5.9 Hz), 8.71 (1H, d, J=4.6 Hz), 7.98 (1H, d, J=7.9 Hz), 7.77 (1H, dd, J=5.9, 2.6 Hz), 7.64 (1H, dd, J=7.9, 4.6 Hz), 7.66-7.50 (2H, m), 6.81 (1H, s), 4.45 (2H, br d J=5.9 Hz), 2.88-2.70 (2H, m), 2.50 (1H, m), 2.34 (1H, m).

MS (ESI) m/z: 399.3 (M+H)⁺.

IM I-c-12 MS (ESI) m/z: 335.5 (M+H)⁺.

The following Examples and Intermediates were prepared by General Procedure C, D, or E (Tables 17 and 19).

General Procedure C $O_3$ was bubbled into a solution of substrate (1.0 eq.) in 50% $CH_2Cl_2$-MeOH at −78° C. until starting material consumed. $N_2$ were bubbled into the mixture to remove the excess of $O_3$ at −78° C. The mixture was quenched with $NaBH_4$ (10.0 eq.) and the mixture was warmed to room temperature gradually. After being stirred at room temperature for 1 h, 10% aq. citric acid was added to the mixture. The mixture extracted with $CH_2Cl_2$ 3 times and the extracts were washed with water. The extracts were combined, dried over $Na_2SO_4$, and concentrated in vacuo. The resulting residue was purified by NH gel column chromatography and/or SCX cartridge column, preparative HPLC to afford the following Examples and Intermediates.

General Procedure D

Sodium borohydride (1.5 eq.) was added to a solution of substrate (1.0 eq.) in MeOH and the mixture was stirred at room temperature until complete reaction. Water was added to the mixture and the volatile was removed by evaporation. The residue was extracted with EtOAc and washed with brine. The extract was dried over $Na_2SO_4$ and concentrated in vacuo. The resulting residue was purified by NH gel column chromatography and/or SCX cartridge column, preparative HPLC to afford the following Examples and Intermediates.

General Procedure E

To a solution of substrate in $CH_2Cl_2$ (0.065 M) was added TFA (0.065 M) at room temperature. The mixture was stirred at room temperature until complete reaction, the mixture was poured into water. The mixture was extracted with $CH_2Cl_2$. The extract was washed with water, dried over $Na_2SO_4$ and concentrated in vacuo to afford the following Examples and Intermediates.

TABLE 17

| Examples | Structure | Chemical Name | Substrate | General Procedure |
|---|---|---|---|---|
| 18 | 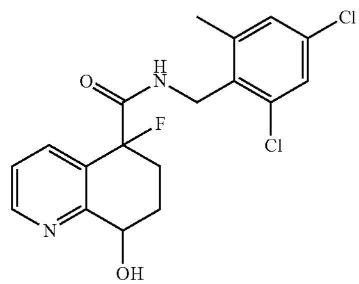 [SMILES: Cc1cc(Cl)cc(Cl)c1CNC(=O)C1(F)CCC(O)c2ncccc21] | N-(2,4-dichloro-6-methyl-benzyl)-5-fluoro-8-hydroxy-5,6,7,8-tetrahydroquinoline-5-carboxamide | Ex 12 | D |
| 19 | 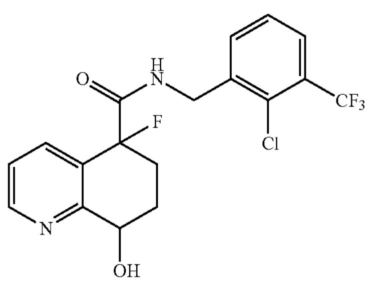 [SMILES: O=C(NCc1cccc(C(F)(F)F)c1Cl)C1(F)CCC(O)c2ncccc21] | N-(2-chloro-3-(trifluoromethyl)benzyl)-5-fluoro-6-hydroxy-5,6,7,8-tetrahydroquinoline-5-carboxamide | Ex 13 | D |
| 20 | 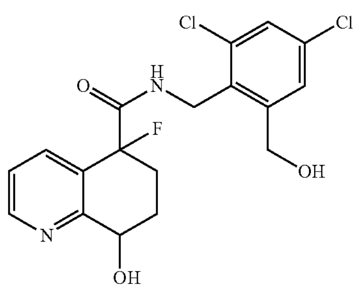 [SMILES: O=C(NCc1c(Cl)cc(Cl)cc1CO)C1(F)CCC(O)c2ncccc21] | N-(2,4-dichloro-6-(hydroxymethyl)benzyl)-5-fluoro-8-hydroxy-5,6,7,8-tetrahydroquinoline-5-carboxamide | Ex 14 | D |
| 21 | 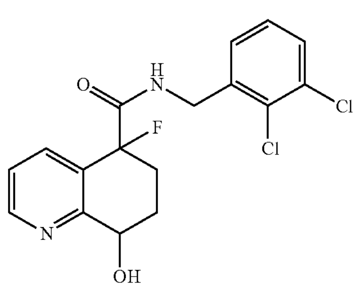 [SMILES: O=C(NCc1cccc(Cl)c1Cl)C1(F)CCC(O)c2ncccc21] | N-(2,3-dichlorobenzyl)-5-fluoro-8-hydroxy-5,6,7,8-tetrahydroquinoline-5-carboxamide | IM I-e-18 | C |

TABLE 17-continued

| Examples | Structure | Chemical Name | Substrate | General Procedure |
|---|---|---|---|---|
| 22 | 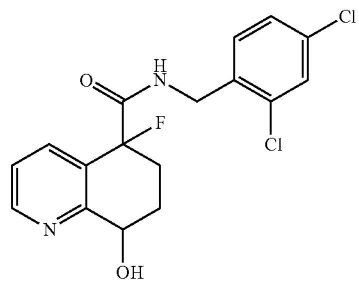 [SMILES: O=C(NCc1ccc(Cl)cc1Cl)C1(F)CCC(O)c2ncccc21] | N-(2,4-dichlorobenzyl)-5-fluoro-8-hydroxy-5,6,7,8-tetrahydroquinoline-5-carboxamide | IM I-e-19 | C |
| 23 | 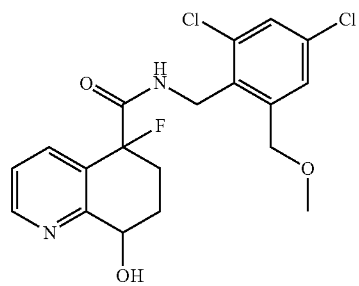 [SMILES: COCc1cc(Cl)cc(Cl)c1CNC(=O)C1(F)CCC(O)c2ncccc21] | N-(2,4-dichloro-6-(methoxymethyl)benzyl)-5-fluoro-8-hydroxy-5,6,7,8-tetrahydroquinoline-5-carboxamide | IM I-e-21 | C |
| 24 | 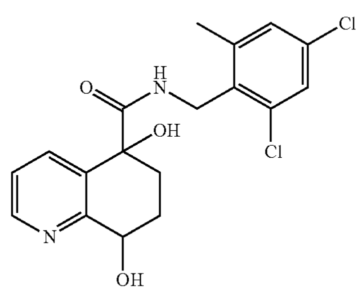 [SMILES: Cc1cc(Cl)cc(Cl)c1CNC(=O)C1(O)CCC(O)c2ncccc21] | N-(2,4-dichloro-6-methylbenzyl)-5,8-dihydroxy-5,6,7,8-tetrahydroquinoline-5-carboxamide | Ex 15 | D |
| 25 | 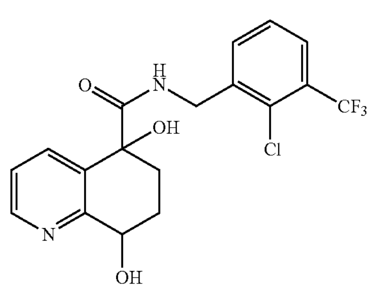 [SMILES: O=C(NCc1cccc(C(F)(F)F)c1Cl)C1(O)CCC(O)c2ncccc21] | N-(2-chloro-3-(trifluoromethyl)benzyl)-5,8-dihydroxy-5,6,7,8-tetrahydroquinoline-5-carboxamide | IM I-c-11 | D |

TABLE 17-continued

| Examples | Structure | Chemical Name | Substrate | General Procedure |
|---|---|---|---|---|
| 26 | 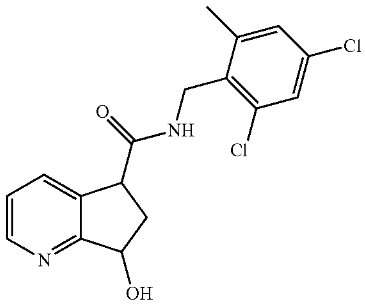 [SMILES: Cc1cc(Cl)cc(Cl)c1CNC(=O)C1CC(O)c2ncccc21] | N-(2,4-dichloro-6-methylbenzyl)-7-hydroxy-6,7-dihydro-5H-cyclopenta[b]pyridine-5-carboxamide | Ex 16 | D |
| 27 | 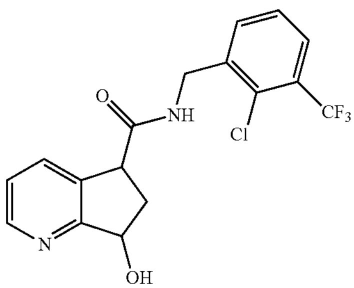 [SMILES: O=C(NCc1cccc(C(F)(F)F)c1Cl)C1CC(O)c2ncccc21] | N-(2-chloro-3-(trifluoromethyl)benzyl)-7-hydroxy-6,7-dihydro-5H-cyclopenta[b]pyridine-5-carboxamide | Ex 17 | D |
| 28 | 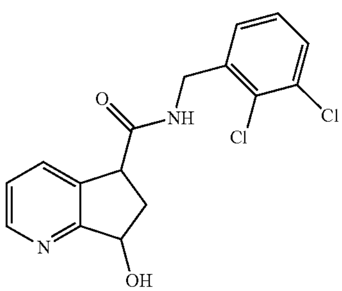 [SMILES: O=C(NCc1cccc(Cl)c1Cl)C1CC(O)c2ncccc21] | N-(2,3-dichlorobenzyl)-7-hydroxy-6,7-dihydro-5H-cyclopenta[b]pyridine-5-carboxamide | IM I-c-12 | D |
| 29 | 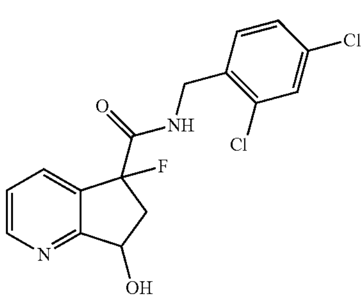 [SMILES: O=C(NCc1ccc(Cl)cc1Cl)C1(F)CC(O)c2ncccc21] | N-(2,4-dichlorobenzyl)-5-fluoro-7-hydroxy-6,7-dihydro-5H-cyclopenta[b]pyridine-5-carboxamide | IM I-e-24 | C |

TABLE 17-continued

| Examples | Structure | Chemical Name | Substrate | General Procedure |
|---|---|---|---|---|
| 30 | 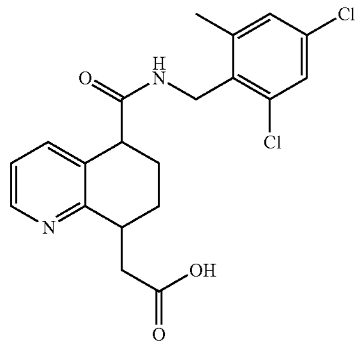 [SMILES: Cc1cc(Cl)cc(Cl)c1CNC(=O)C1CCC(CC(=O)O)c2ncccc21] | 2-(5-((2,4-dichloro-6-methylbenzyl)carbamoyl)-5,6,7,8-tetrahydroquinolin-8-yl)acetic acid | IM I-v-1 | E |
| 31 | 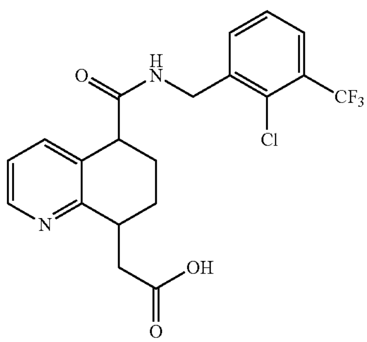 [SMILES: O=C(O)CC1CCC(C(=O)NCc2cccc(C(F)(F)F)c2Cl)c2cccnc21] | 2-(5-((2-chloro-3-(trifluoromethyl)benzyl)carbamoyl)-5,6,7,8-tetrahydroquinolin-8-yl)acetic acid | IM I-v-2 | E |

TABLE 18

| | LC MS | | |
|---|---|---|---|
| Examples | Method | tR (min) | [M + H]+ |
| 18 | D | 1.66, 1.69 | 383.0 |
| 19 | D | 1.56, 1.59 | 403.0 |
| 20 | A | 1.35 | 399.2 |
| 21 | A | 1.45 | 369.1 |
| 22 | A | 1.49 | 369.1 |
| 23 | A | 1.57 | 413.1 |
| 24 | A | 1.46 | 381.3 |
| 25 | A | 1.40 | 401.3 |
| 26 | D | 1.51 | 351.0 |
| 27 | D | 1.40, 1.45 | 371.0 |
| 28 | D | 1.33, 1.38 | 337.0 |
| 29 | D | 1.52 | 355.1 |
| 30 | A | 1.27 | 407.1 |
| 31 | A | 1.23 | 427.2 |

Ex 18

$^1$H NMR (DMSO d6) delta 8.74 (1H, m), 8.60 (1H, br s), 7.58 (0.4H, d, J=7.9 Hz), 7.55 (0.6H, d, J=7.9 Hz), 7.46 (1H, br s), 7.38 (1H, dd, J=7.9, 4.6 Hz), 7.35 (1H, br s), 5.41 (1H, br s), 4.61 (1H, m), 4.48 (0.8H, d, J=4.6 Hz), 4.43 (1.2H, d, J=4.6 Hz), 2.80-1.75 (4H, m), 2.42 (1.2H, s), 2.38 (1.8H, s).

Ex 19

$^1$H NMR (CDCl$_3$) delta 8.60 (1H, br), 7.71-7.62 (2H, m), 7.51 (1H, m), 7.39 (1H, m), 7.30 (1H, br), 7.30-7.20 (1H, m), 4.78-4.69 (3H, m), 4.33 (0.5H, br s), 3.75 (0.5H, br s), 2.76-1.80 (4H, m).

Ex 20

$^1$H NMR (DMSO d6) delta 8.69 (1H, br), 8.62 (1H, br), 7.58 (1H, m), 7.56 (1H, d, J=2.6 Hz), 7.48 (1H, d, J=2.6 Hz), 7.38 (1H, dd, J=7.9, 4.6 Hz), 5.53 (1H, br), 5.43 (1H, m), 4.71-4.55 (3H, m), 4.52-4.40 (2H, m), 2.40-1.72 (4H, m).

Ex 24

$^1$H NMR (DMSO d6) delta 8.48 (1H, br dd, J=4.6, 2.0 Hz), 8.07 (1H, m), 7.52-7.45 (2H, m), 7.32 (1H, J=2.6 Hz), 7.26 (1H, dd, J=7.9, 4.6 Hz), 6.23 (0.5H, s), 6.11 (0.5H, s), 5.16 (1H, m), 4.54-4.42 (3H, m), 2.41 (1.5H, s), 2.39 (1.5H, s), 2.30-1.64 (4H, m).

Ex 25

$^1$H NMR (DMSO d6) delta 8.86 (1H, t, J=6.6 Hz), 8.49 (1H, br d, J=4.6 Hz), 7.78 (1H, m), 7.66-7.57 (3H, m), 7.30 (1H, dd, J=7.9, 4.6 Hz), 6.39 (0.5H, br), 6.27 (0.5H, br), 5.20 (0.5H, d, J=2.6 Hz), 5.16 (0.5H, d, J=3.3 Hz), 4.56-4.44 (3H, m), 2.33-1.75 (4H, m).

Ex 26

$^1$H NMR (DMSO d6) delta 8.53 (1H, br), 8.44 (1H, d, J=4.6 Hz), 7.52 (1H, d, J=7.9 Hz), 7.50 (1H, d, J=2.0 Hz), 7.36 (1H, d, J=2.0 Hz), 7.23 (1H, dd, J=7.9, 4.6 Hz), 5.48 (1H, d, J=6.6 Hz), 4.90 (1H, m), 4.44 (1H, d, J=4.6 Hz), 4.42 (1H, d, J=4.6 Hz), 3.82 (1H, m), 2.54 (1H, m), 2.39 (3H, s), 2.02 (1H, m).

Ex 29

$^1$H NMR (CDCl$_3$) delta 8.69 (1H, br dd, J=4.9, 1.2 Hz), 7.62 (1H, br dd, J=7.9, 1.2 Hz), 7.44 (1H, d, J=1.8 Hz), 7.35-7.16 (4H, m), 5.33 (1H, dd, J=6.1, 2.4 Hz), 4.63 (1H, dd, J=14.7, 6.1 Hz), 4.57 (1H, dd, J=14.7, 6.1 Hz), 3.94 (1H, d, J=5.5 Hz), 2.83-2.66 (2H, m).

TABLE 19

| Intermediate | Structure | Chemical Name | Substrate | General Procedure |
|---|---|---|---|---|
| I-w-1 | (structure) | 2-(5-((2,4-dichloro-6-methylbenzyl)carbamoyl)-5-fluoro-5,6,7,8-tetrahydroquinolin-8-yl)acetic acid | (structure) IM I-v-3 | E |

IM I-w-1

MS (ESI) m/z: 425.0 (M+H)$^+$.

The following Example was prepared by General Procedure A (Table 20).

TABLE 20

| Example | Structure | Chemical Name | Substrate | Amine |
|---|---|---|---|---|
| 32 | (structure) | (2-amino-2-oxoethyl)-N-(2-chloro-3-(trifluoromethyl)benzyl)-5,6,7,8-tetrahydroquinoline-5-carboxamide | (structure) Ex 30 | NH$_4$Cl |

Ex 32

LCMS (ESI) m/z: 426.2 (M+H)$^+$, tR 1.39 min (Method A).

The following Examples were prepared by General Procedure F (Table 21).

General Procedure F

A mixture of substrate (1.0 eq.), 4% aq. OsO$_4$ (1.0 eq.), and NMO (15.0 eq.) in 50% aq. THF was stirred at room temperature until complete reaction. Aq. Na$_2$S$_2$O$_3$ was added to the mixture and the mixture was stirred for 10 min. The mixture was extracted with EtOAc twice. The extracts were washed with brine, dried over $Na_2SO_4$, and concentrated in vacuo. The resulting residue was purified by silica gel column chromatography and/or SCX column, preparative HPLC to afford the following Examples.

TABLE 21

| Examples | Structure | Chemical Name | Substrate |
|---|---|---|---|
| 33 | 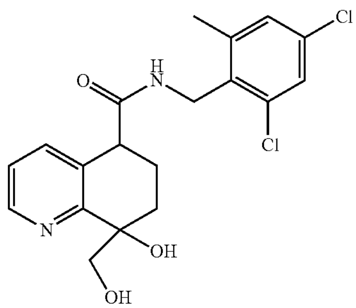 [SMILES: Cc1cc(Cl)cc(Cl)c1CNC(=O)C1CCC(O)(CO)c2ncccc21] | N-(2,4-dichloro-6-methylbenzyl)-8-hydroxy-8-(hydroxymethyl)-5,6,7,8-tetrahydroquinoline-5-carboxamide | IM Ie-1 |
| 34 | 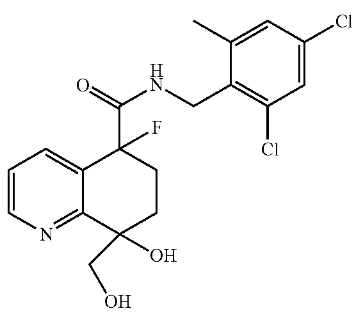 [SMILES: Cc1cc(Cl)cc(Cl)c1CNC(=O)C1(F)CCC(O)(CO)c2ncccc21] | N-(2,4-dichloro-6-methylbenzyl)-5-fluoro-8-hydroxy-8-(hydroxymethyl)-5,6,7,8-tetrahydroquinoline-5-carboxamide | IM Ie-16 |
| 35 | 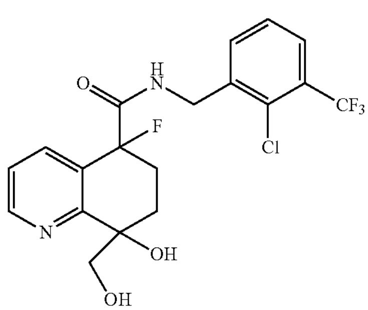 [SMILES: O=C(NCc1cccc(C(F)(F)F)c1Cl)C1(F)CCC(O)(CO)c2ncccc21] | N-(2-chloro-3-(trifluoromethyl)benzyl)-5-fluoro-8-hydroxy-8-(hydroxymethyl)-5,6,7,8-tetrahydroquinoline-5-carboxamide | IM Ie-3 |
| 36 | 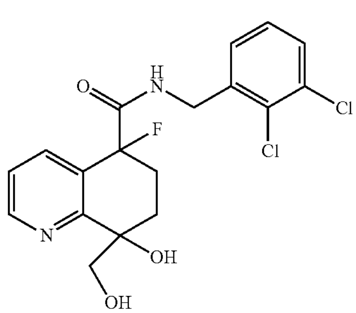 [SMILES: O=C(NCc1cccc(Cl)c1Cl)C1(F)CCC(O)(CO)c2ncccc21] | N-(2,3-dichlorobenzyl)-5-fluoro-8-hydroxy-8-(hydroyxmethyl)-5,6,7,8-tetrahydroquinoline-5-carboxamide | IM Ie-18 |

TABLE 21-continued

| Examples | Structure | Chemical Name | Substrate |
|---|---|---|---|
| 37 | 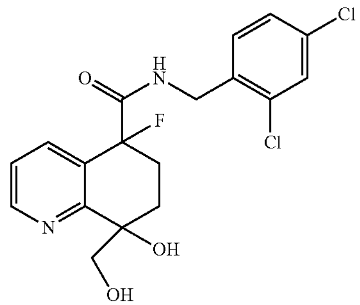 [SMILES: O=C(NCc1ccc(Cl)cc1Cl)C1(F)CCC(O)(CO)c2ncccc21] | N-(2,4-dichlorobenzyl)-5-fluoro-8-hydroxy-8-(hydroxymethyl)-5,6,7,8-tetrahydroquinoline-5-carboxamide | IM Ie-19 |
| 38 | 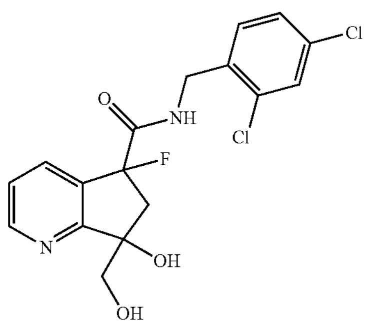 [SMILES: O=C(NCc1ccc(Cl)cc1Cl)C1(F)CC(O)(CO)c2ncccc21] | N-(2,4-dichlorobenzyl)-5-fluoro-7-hydroxy-7-(hydroxymethyl)-6,7-dihydro-5H-cyclopenta[b]pyridine-5-carboxamide | IM I-e-24 |

TABLE 22

LC MS

| Examples | Method | tR (min) | [M + H]$^+$ |
|---|---|---|---|
| 33 | A | 1.41 | 395.3 |
| 34 | A | 1.52 | 413.1 |
| 35 | A | 1.44 | 433.1 |
| 36 | A | 1.39 | 399.1 |
| 37 | A | 1.42 | 399.1 |
| 38 | D | 1.41 | 385.1 |

The following Intermediates were prepared by General Procedure G or H (Table 23).

General Procedure G

A substrate (1.0 eq.) and trimethylsulfoxonium iodide (1.2 eq.) were dissolved in DMSO. A solution of KOBu$^t$ (1.2 eq.) in DMSO was added to the mixture at ambient temperature. After being stirred at room temperature until complete reaction, the mixture was poured into ice-water. The mixture was extracted with EtOAc twice and washed with brine. The extracts were combined, dried over Na$_2$SO$_4$, and concrete in vacuo. The resulting residue was purified by silica gel column chromatography to afford the following Intermediates. The each diastero isomer can be separated by silica gel column chromatography.

General Procedure H

To a solution of substrate (1.0 eq.) in water-tert-BuOH-THF (2:1:1) was added NBS (2.0 eq.) in portions at ambient temperature and then the mixture was heated at 50° C. until starting material consumed. After cooling to 0° C., the reaction mixture was basified with 5 M aqueous NaOH and stirred at 0° C. until complete reaction. The reaction mixture was poured into water and extract with EtOAc twice. The extracts were washed with brine, and dried over Na$_2$SO$_4$. The combined extracts were evaporated and the resulting residue was purified by silica gel column chromatography to afford the following Intermediates. The each diastereo isomer can be separated by silica gel column chromatography.

TABLE 23

| Intermediates | Structure | Chemical Name | Substrate | General Procedure |
|---|---|---|---|---|
| I-g-1 | 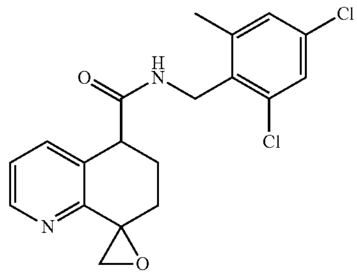 [SMILES: Cc1cc(Cl)cc(Cl)c1CNC(=O)C1CCC2(CO2)c2ncccc21] | N-(2,4-dichloro-6-methylbenzyl)-6',7'-dihydro-5'H-spiro[oxirane-2,8'-quinoline]-5'-carboxamide | Ex 1 | G |
| I-g-2 | 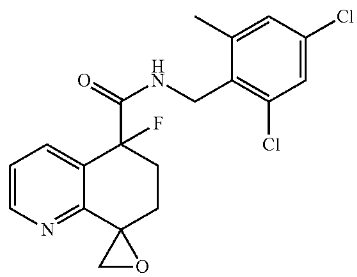 [SMILES: Cc1cc(Cl)cc(Cl)c1CNC(=O)C1(F)CCC2(CO2)c2ncccc21] | N-(2,4-dichloro-6-methylbenzyl)-5'-fluoro-6',7'-dihydro-5'H-spiro[oxirane-2,8'-quinoline]-5'-carboxamide | Ex 12 | G |
| I-g-3 | 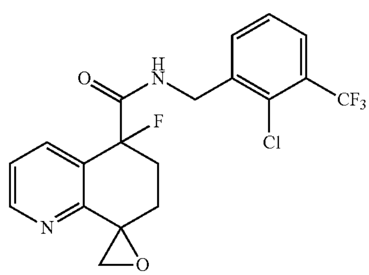 [SMILES: O=C(NCc1cccc(C(F)(F)F)c1Cl)C1(F)CCC2(CO2)c2ncccc21] | N-(2-chloro-3-(trifluoromethyl)benzyl)-5'-fluoro-6',7'-dihydro-5'H-spiro[oxirane-2,8'-quinoline]-5'-carboxamide | Ex 13 | G |
| I-g-4 | 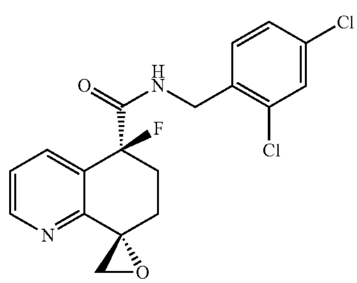 | (2S*,5'S*)-N-(2,4-dichlorobenzyl)-5'-fluoro-6',7'-dihydro-5'H-spiro[oxirane-2,8'-quinoline]-5'-carboxamide | IM I-e-19 | H |
| I-g-5 | 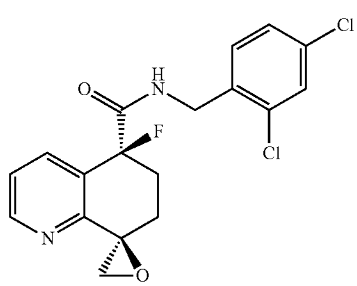 [SMILES: O=C(NCc1ccc(Cl)cc1Cl)[C@]1(F)CC[C@]2(CO2)c2ncccc21] | (2R*,5'S*)-N-(2,4-dichlorobenzyl)-5'-fluoro-6',7'-dihydro-5'H-spiro[oxirane-2,8'-quinoline]-5'-carboxamide | | |

TABLE 23-continued

| Inter-mediates | Structure | Chemical Name | Substrate | General Procedure |
|---|---|---|---|---|
| I-g-6 | 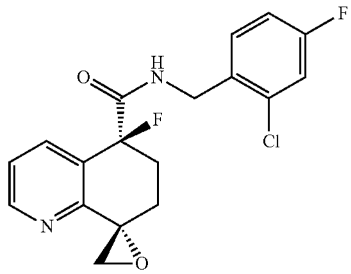 [SMILES: O=C(NCc1ccc(F)cc1Cl)[C@]1(F)CC[C@@]2(CO2)c2ncccc21] | (2S*,5'S*)-N-(2-chloro-4-fluorobenzyl)-5'-fluoro-6',7'-dihydro-5'H-spiro[oxirane-2,8'-quinoline]-5'-carboxamide | IM I-e-20 | H |
| I-g-7 | 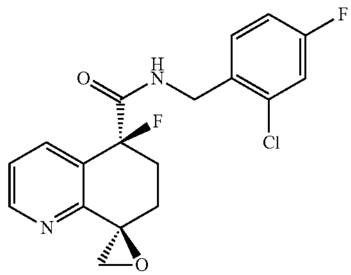 [SMILES: O=C(NCc1ccc(F)cc1Cl)[C@]1(F)CC[C@]2(CO2)c2ncccc21] | (2R*,5'S*)-N-(2-chloro-4-fluorobenzyl)-5'-fluoro-6',7'-dihydro-5'H-spiro[oxirane-2,8'-quinoline]-5'-carboxamide | | |

IM I-g-1

$^1$H NMR (CDCl$_3$) delta 8.53 (1H, dd, J=4.6, 1.3 Hz), 7.45 (0.5H, d, J=7.9 Hz), 7.42 (0.5H, dd, J=7.9, 1.3 Hz), 7.24 (0.5H, d, J=2.0 Hz), 7.22 (0.5H, d, J=2.0 Hz), 7.18 (1H, dd, J=7.9, 4.6 Hz), 7.11 (0.5H, d, J=2.0 Hz), 7.10 (0.5H, d, J=2.0 Hz), 5.94 (0.5H, br t, J=5.9 Hz), 5.79 (0.5H, br t, J=5.9 Hz), 4.63-4.41 (2H, m), 3.75 (1H, m), 3.73 (0.5H, d, J=5.9 Hz), 3.62 (0.5H, d, J=5.9 Hz), 2.98 (0.5H, d, J=5.9 Hz), 2.97 (0.5H, d, J=5.9 Hz), 2.47 (1.5H, s), 2.46 (1.5H, s), 2.50-1.80 (4H, m).

MS (ESI) m/z: 377.0 (M+H)$^+$.

IM I-g-2 MS (ESI) m/z: 395.0 (M+H)$^+$.

IM I-g-3

$^1$H NMR (CDCl$_3$) delta 8.63 (1H, dd, J=4.6, 2.0 Hz), 7.67 (2H, m), 7.44 (2H, m), 7.30-7.04 (2H, m), 4.75 (2H, d, J=5.9 Hz), 3.86 (1H, d, J=5.9 Hz), 3.03 (1H, d, J=5.9 Hz), 2.99-2.00 (4H, m).

MS (ESI) m/z: 414.9 (M+H)$^+$.

IM I-g-4

$^1$H NMR (CDCl$_3$) delta 8.63 (1H, br dd, J=4.9, 1.8 Hz), 7.50 (1H, br dd, J=7.9, 1.8 Hz), 7.46 (1H, d, J=2.4 Hz), 7.39 (1H, d, J=8.6 Hz), 7.27 (1H, br dd, J=7.9, 1.8 Hz), 7.23 (1H, dd, J=7.9, 4.9 Hz), 7.19 (1H, br), 4.67 (1H, dd, J=14.7, 6.1 Hz), 4.62 (1H, dd, J=14.7, 6.1 Hz), 3.86 (1H, d, J=6.1 Hz), 3.03 (1H, d, J=6.1 Hz), 2.76 (1H, m), 2.57 (1H, m), 2.32 (1H, m), 2.14 (1H, m).

MS (ESI) m/z: 380.9 (M+H)$^+$.

IM I-g-5

$^1$H NMR (CDCl$_3$) delta 8.63 (1H, ddd, J=4.9, 1.8, 1.2 Hz), 7.51 (1H, ddd, J=7.9, 1.8, 1.2 Hz), 7.46 (1H, d, J=1.8 Hz), 7.37 (1H, d, J=7.9 Hz), 7.27 (1H, dd, J=7.9, 1.8 Hz), 7.24 (1H, br), 7.22 (1H, dd, J=7.9, 4.9 Hz), 4.65 (1H, dd, J=14.7, 6.1 Hz), 4.60 (1H, dd, J=14.7, 6.1 Hz), 3.51 (1H, d, J=6.1 Hz), 3.06 (1H, d, J=6.1 Hz), 2.65 (1H, m), 2.50-2.39 (2H, m), 2.19 (1H, m).

MS (ESI) m/z: 380.9 (M+H)$^+$.

IM I-g-6

$^1$H NMR (CDCl$_3$) delta 8.63 (1H, ddd, J=4.9, 1.8, 1.2 Hz), 7.49 (1H, ddd, J=7.9, 1.8, 1.2 Hz), 7.44 (1H, dd, J=8.6, 5.5 Hz), 7.23 (1H, dd, J=7.9, 4.9 Hz), 7.18 (1H, dd, J=8.6, 2.4 Hz), 7.17 (1H, br), 7.01 (1H, ddd, J=8.6, 7.9, 2.4 Hz), 4.67 (1H, dd, J=14.7, 6.1 Hz), 4.62 (1H, dd, J=14.7, 6.1 Hz), 3.86 (1H, d, J=6.1 Hz), 3.03 (1H, d, J=6.1 Hz), 2.77 (1H, m), 2.57 (1H, m), 2.32 (1H, m), 2.13 (1H, m).

MS (ESI) m/z: 365.1 (M+H)$^+$.

IM I-g-7

$^1$H NMR (CDCl$_3$) delta 8.62 (1H, br dd, J=4.9, 1.8 Hz), 7.51 (1H, br dd, J=7.9, 1.8 Hz), 7.42 (1H, dd, J=8.5, 6.1 Hz), 7.23-7.18 (3H, m), 7.00 (1H, m), 4.66 (1H, dd, J=14.7, 6.1 Hz), 4.60 (1H, dd, J=14.7, 6.1 Hz), 3.51 (1H, d, J=6.1 Hz), 3.06 (1H, d, J=6.1 Hz), 2.66 (1H, m), 2.51-2.39 (2H, m), 2.19 (1H, m).

MS (ESI) m/z: 364.7 (M+H).

The following Examples were prepared by General Procedure I, J, or K (Table 24).

General Procedure I

A solution of 1.0 M NaOMe in MeOH (1.3 eq.) was added to substrate (1.0 eq.) in small portions at ambient temperature. After being stirred at room temperature until complete reaction, the mixture was concentrated in vacuo to afford a glass. The residual glass was distributed between EtOAc and water. The extract was dried over Na$_2$SO$_4$ and concentrated in vacuo. The resulting residue was purified by SCX cartridge column and preparative HPLC to afford the following Examples.

General Procedure J

A solution of substrate (1.0 eq.) in MeOH was treated with amine (45 eq.) at room temperature until complete reaction. The mixture was concentrated in vacuo and the resulting residue was distributed between EtOAc and water. The extract was dried over Na$_2$SO$_4$ and concentrated in vacuo.

The resulting residue was purified by silica gel column chromatography and/or SCX column and preparative HPLC to afford the following Examples.

General Procedure K

To a stirred solution of substrate (1.0 eq.) in EtOH was added NaBH$_4$ (6.0 eq.) at ambient temperature. The mixture was stirred at room temperature until complete reaction, water was added to the mixture. The mixture was extracted with EtOAc and washed with aq. NaHCO$_3$. The extract was dried over Na$_2$SO$_4$ and concentrated in vacuo. The resulting residue was purified by SCX cartridge column and preparative HPLC to afford the following Examples.

TABLE 24

| Examples | Structure | Chemical Name | Substrate | General Procedure (/Amine) |
|---|---|---|---|---|
| 39 | 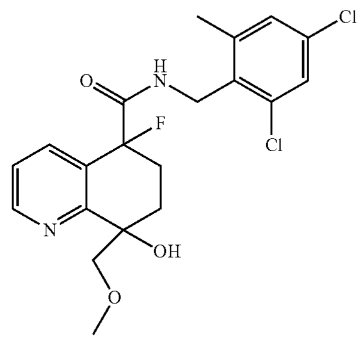 [SMILES: COCC1(O)CCC(F)(C(=O)NCc2c(C)cc(Cl)cc2Cl)c2cccnc21] | N-(2,4-dichloro-6-methylbenzyl)-5-fluoro-8-hydroxy-8-(methoxymethyl)-5,6,7,8-tetrahydroquinoline-5-carboxamide | IM I-g-2 | I |
| 40 | 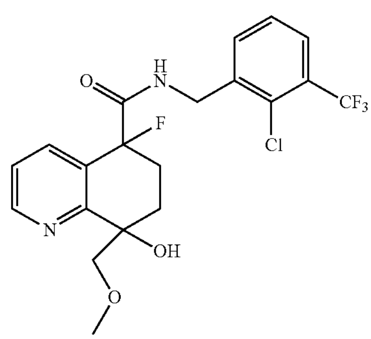 [SMILES: COCC1(O)CCC(F)(C(=O)NCc2cccc(C(F)(F)F)c2Cl)c2cccnc21] | N-(2-chloro-3-(trifluoromethyl)benzyl)-5-fluoro-8-hydroxy-8-(methoxymethyl)-5,6,7,8-tetrahydroquinoline-5-carboxamide | IM I-g-3 | I |
| 41 | 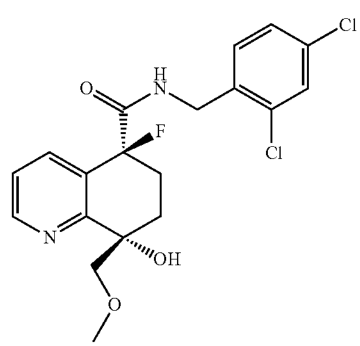 [SMILES: COC[C@]1(O)CC[C@@](F)(C(=O)NCc2ccc(Cl)cc2Cl)c2cccnc21] | (5S*,8S*)-N-(2,4-dichlorobenzyl)-5-fluoro-8-hydroxy-8-(methoxymethyl)-5,6,7,8-tetrahydroquinoline-5-carboxamide | IM I-g-4 | I |

TABLE 24-continued

| Examples | Structure | Chemical Name | Substrate | General Procedure (/Amine) |
|---|---|---|---|---|
| 42 | 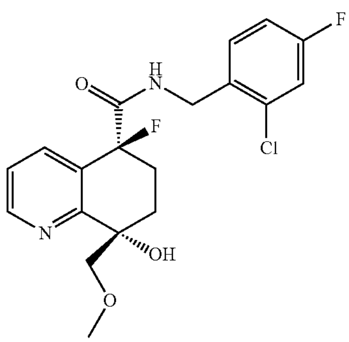 [SMILES: COC[C@]1(O)CC[C@@](F)(C(=O)NCc2ccc(F)cc2Cl)c2cccnc21] | (5S*,8S*)-N-(2-chloro-4-fluorobenzyl)-5-fluoro-8-hydroxy-8-(methoxymethyl)-5,6,7,8-tetrahydroquinoline-5-carboxamide | IM I-g-6 | I |
| 43 | 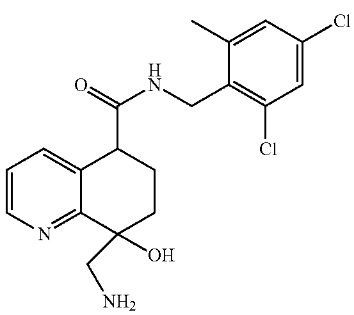 [SMILES: Cc1cc(Cl)cc(Cl)c1CNC(=O)C1CCC(O)(CN)c2ncccc21] | 8-(aminomethyl)-N-(2,4-dichloro-6-methylbenzyl)-8-hydroxy-5,6,7,8-tetrahydroquinolin-5-carboxamide | IM I-g-1 | J/ NH$_4$OH |
| 44 | 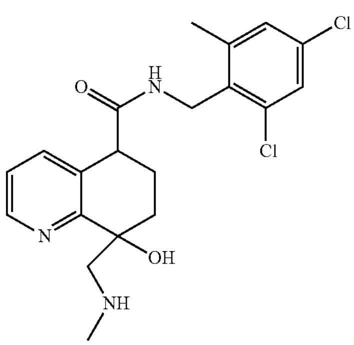 [SMILES: CNCC1(O)CCC(C(=O)NCc2c(C)cc(Cl)cc2Cl)c2cccnc21] | N-(2,4-dichloro-6-methylbenzyl)-8-hydroxy-8-((methylamino)methyl)-5,6,7,8-tetrahydroquinoline-5-carboxamide | | J/ MeNH$_2$ in MeOH |
| 45 | 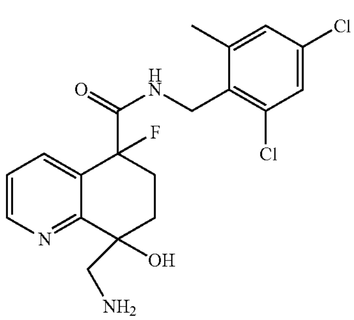 [SMILES: Cc1cc(Cl)cc(Cl)c1CNC(=O)C1(F)CCC(O)(CN)c2ncccc21] | 8-(aminomethyl)-N-(2,4-dichloro-6-methylbenzyl)-5-fluoro-8-hydroxy-5,6,7,8-tetrahydroquinoline-5-carboxamide | | J/ NH$_4$OH |

TABLE 24-continued

| Examples | Structure | Chemical Name | Substrate | General Procedure (/Amine) |
|---|---|---|---|---|
| 46 | 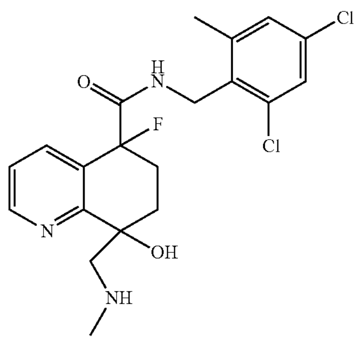 [SMILES: CNCC1(O)CCC(F)(C(=O)NCc2c(C)cc(Cl)cc2Cl)c2cccnc21] | N-(2,4-dichloro-6-methylbenzyl)-5-fluoro-8-hydroxy-8-((methylamino)methyl)-5,6,7,8-tetrahydroquinoline-5-carboxamide | | J/ MeNH$_2$ in MeOH |
| 47 | 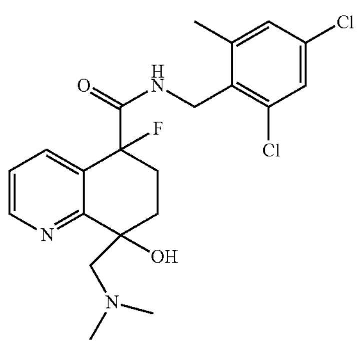 [SMILES: Cc1cc(Cl)cc(Cl)c1CNC(=O)C1(F)CCC(O)(CN(C)C)c2ncccc21] | N-(2,4-dichloro-6-methylbenzyl)-8-((dimethylamino)methyl)-5-fluoro-8-hydroxy-5,6,7,8-tetrahydroquinoline-5-carboxamide | | J/ Me$_2$NH in THF |
| 48 | 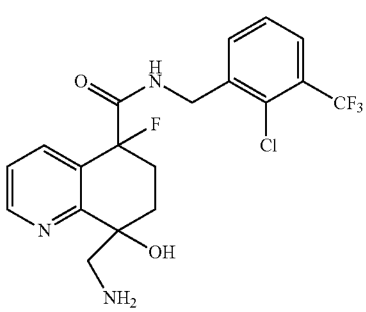 [SMILES: NCC1(O)CCC(F)(C(=O)NCc2cccc(C(F)(F)F)c2Cl)c2cccnc21] | 8-(aminomethyl)-N-(2-chloro-3-(trifluoromethyl)benzyl)-5-fluoro-8-hydroxy-5,6,7,8-tetrahydroquinoline-5-carboxamide | IM I-g-3 | J/ NH$_4$OH |
| 49 | 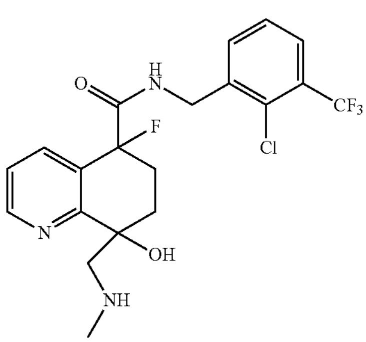 [SMILES: CNCC1(O)CCC(F)(C(=O)NCc2cccc(C(F)(F)F)c2Cl)c2cccnc21] | N-(2-chloro-3-(trifluoromethyl)benzyl)-5-fluoro-8-hydroxy-8-((methylamino)methyl)-5,6,7,8-tetrahydroquinoline-5-carboxamide | | J/ MeNH$_2$ in MeOH |

TABLE 24-continued

| Examples | Structure | Chemical Name | Substrate | General Procedure (/Amine) |
|---|---|---|---|---|
| 50 | 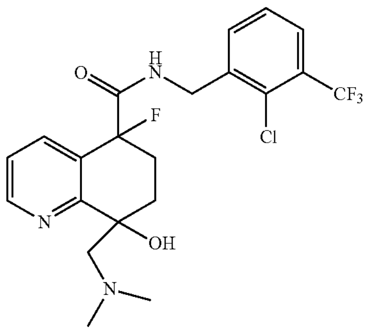 [SMILES: CN(C)CC1(O)CCC(F)(C(=O)NCc2cccc(C(F)(F)F)c2Cl)c2cccnc21] | N-(2-chloro-3-(trifluoromethyl)benzyl)-8-((dimethylamino)methyl)-5-fluoro-8-hydroxy-5,6,7,8-tetrahydroquinoline-5-carboxamide | | J/ Me$_2$NH in THF |
| 51 | 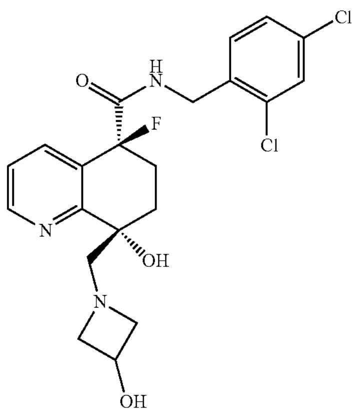 [SMILES: O=C(NCc1ccc(Cl)cc1Cl)[C@]1(F)CC[C@@](O)(CN2CC(O)C2)c2ncccc21] | (5S*,8R*)-N-(2,4-dichlorobenzyl)-5-fluoro-8-hydroxy-8-((3-hydroxyazetidin-1-yl)methyl)-5,6,7,8-tetrahydroquinoline-5-carboxamide | IM I-g-4 | J/ |
| 52 | 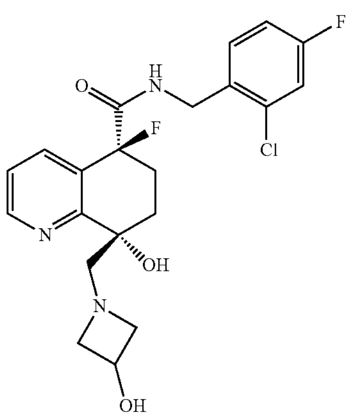 [SMILES: O=C(NCc1ccc(F)cc1Cl)[C@]1(F)CC[C@@](O)(CN2CC(O)C2)c2ncccc21] | (5S*,8R*)-N-(2-chloro-4-fluorobenzyl)-5-fluoro-8-hydroxy-8-((3-hydroxyazetidin-1-yl)methyl)-5,6,7,8-tetrahydroquinoline-5-carboxamide | IM I-g-6 | J/ |
| 53 | 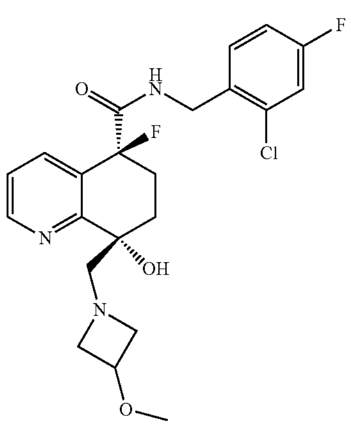 [SMILES: COC1CN(C[C@]2(O)CC[C@@](F)(C(=O)NCc3ccc(F)cc3Cl)c3cccnc32)C1] | (5S*,8R*)-N-(2-chloro-4-fluorobenzyl)-5-fluoro-8-hydroxy-8-((3-methoxyazetidin-1-yl)methyl)-5,6,7,8-tetrahydroquinoline-5-carboxamide | | J/ |

TABLE 24-continued

| Examples | Structure | Chemical Name | Substrate | General Procedure (/Amine) |
|---|---|---|---|---|
| 54 | 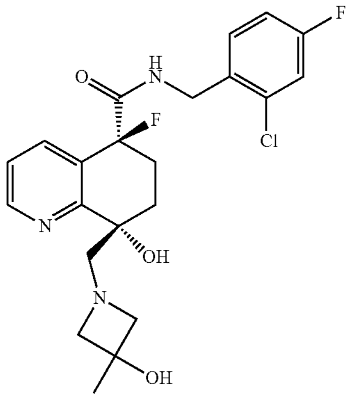 [SMILES: CC1(O)CN(C[C@]2(O)CC[C@@](F)(C(=O)NCc3ccc(F)cc3Cl)c3cccnc32)C1] | (5S*,8R*)-N-(2-chloro-4-fluorobenzyl)-5-fluoro-8-hydroxy-8-((3-hydroxy-3-methylazetidin-1-yl)methyl)-5,6,7,8-tetrahydroquinoline-5-carboxamide | | J/ |
| 55 | 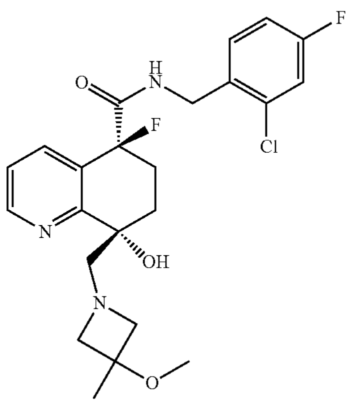 [SMILES: COC1(C)CN(C[C@]2(O)CC[C@@](F)(C(=O)NCc3ccc(F)cc3Cl)c3cccnc32)C1] | (5S*,8R*)-N-(2-chloro-4-fluorobenzyl)-5-fluoro-8-hydroxy-8-((3-methoxy-3-methyl-azetidin-1-yl)methyl)-5,6,7,8-tetrahydro-quinoline-5-carboxamide | | J/ |
| 56 | 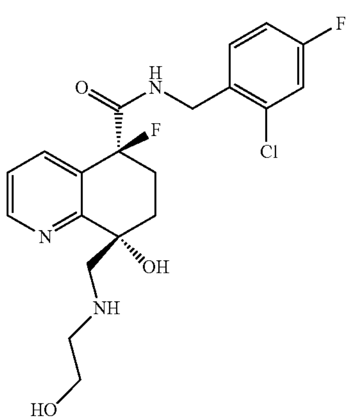 [SMILES: O=C(NCc1ccc(F)cc1Cl)[C@]1(F)CC[C@@](O)(CNCCO)c2ncccc21] | (5S*,8R*)-N-(2-chloro-4-fluorobenzyl)-5-fluoro-8-hydroxy-8-(((2-hydroxyethyl)amino)methyl)-5,6,7,8-tetrahydroquinoline-5-carboxamide | | J/ |

TABLE 24-continued

| Examples | Structure | Chemical Name | Substrate | General Procedure (/Amine) |
|---|---|---|---|---|
| 57 | 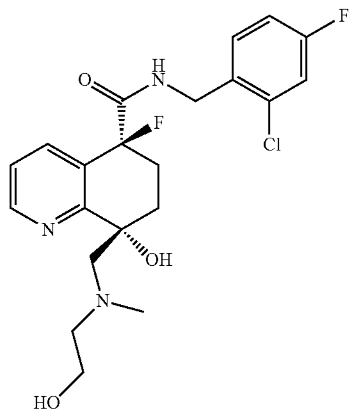 [SMILES: CN(CCO)C[C@]1(O)CC[C@@](F)(C(=O)NCc2ccc(F)cc2Cl)c2cccnc21] | (5S*,8R*)-N-(2-chloro-4-fluorobenzyl)-5-fluoro-8-hydroxy-8-(((2-hydroxyethyl)(methyl)amino)methyl)-5,6,7,8-tetrahydroquinoline-5-carboxamide | | J/ |
| 58 | 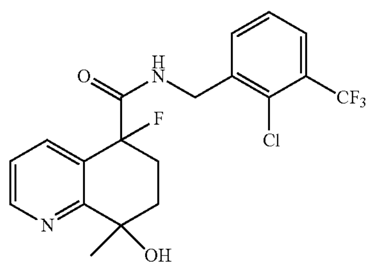 [SMILES: CC1(O)CCC(F)(C(=O)NCc2cccc(C(F)(F)F)c2Cl)c2cccnc21] | N-(2-chloro-3-(trifluoromethyl)benzyl)-5-fluoro-8-hydroxy-8-methyl-5,6,7,8-tetrahydroquinoline-5-carboxamide | IM I-g-3 | K |

TABLE 25

| | LC MS | | |
|---|---|---|---|
| Examples | Method | tR (min) | [M + H]$^+$ |
| 39 | A | 1.67 | 427.1 |
| 40 | A | 1.57 | 447.1 |
| 43 | A | 1.35 | 394.2 |
| 44 | A | 1.36 | 408.1 |
| 45 | A | 1.42 | 412.2 |
| 46 | A | 1.45 | 426.2 |
| 47 | A | 1.50 | 440.2 |
| 48 | A | 1.36 | 432.1 |
| 49 | A | 1.38 | 446.1 |
| 50 | A | 1.43 | 460.1 |
| 58 | A | 1.58 | 417.1 |

Ex 41

$^1$H NMR (DMSO d6) delta 9.27 (1H, br s), 8.74 (1H, d, J=4.5 Hz), 7.75-7.80 (2H, m), 7.62 (1H, d, J=2.0 Hz), 7.53 (1H, dd, J=8.0, 4.7 Hz), 7.45 (1H, dd, J=8.4, 2.1 Hz), 7.36 (1H, d, J=8.3 Hz), 4.40 (2H, t, J=5.3 Hz), 3.88 (1H, d, J=8.6 Hz), 3.53 (1H, d, J=8.4 Hz) 2.29-2.48 (5H, m).

MS (ESI) m/z: 413.2 (M+H)$^+$.

Ex 42

$^1$H NMR (CDCl$_3$) delta 8.61 (1H, dt, J=4.7, 1.6 Hz), 7.51 (1H, dt, J=7.8, 1.5 Hz), 7.40 (1H, dd, J=8.5, 6.1 Hz), 7.14-7.25 (3H, m), 6.99 (1H, td, J=8.3, 2.6 Hz), 4.51-4.68 (2H, m), 3.76 (2H, dd, J=9.5, 8.4 Hz), 3.34-3.37 (4H, m), 2.57-2.72 (1H, m), 2.38-2.49 (1H, m) 2.18-2.32 (2H, m).

MS (ESI) m/z: 397.2 (M+H)$^+$.

Ex 51

$^1$H NMR (CDCl$_3$) delta 8.61 (1H, br d, J=4.7 Hz), 7.54 (1H, d, J=8.0 Hz), 7.44 (1H, d, J=2.1 Hz), 7.34 (1H, d, J=7.7 Hz), 7.27-7.30 (1H, m), 7.19-7.25 (1H, m), 4.48-4.65 (3H, m), 3.99-4.13 (4H, m), 3.89 (2H, br s), 3.56 (1H, br d, J=13.0 Hz), 3.18 (1H, br d, J=13.1 Hz), 2.67-2.82 (1H, m), 2.16-2.28 (3H, m).

MS (ESI) m/z: 454.2 (M+H)$^+$.

Ex 52

$^1$H NMR (CDCl$_3$) delta 8.62 (1H, dt, J=4.7, 1.6 Hz), 7.49 (1H, dt, J=7.8, 1.5 Hz), 7.41 (1H, dd, J=8.5, 6.1 Hz), 7.09-7.25 (3H, m), 6.99 (1H, td, J=8.3, 2.6 Hz), 4.53-4.67 (2H, m), 4.41 (1H, quin, J=5.78 Hz), 3.74-3.82 (1H, m), 3.57 (1H, br s), 3.07-3.16 (2H, m), 3.00 (1H, br t, J=6.4 Hz), 2.85 (1H, d, J=12.8 Hz), 2.56-2.77 (1H, m), 2.13-2.37 (4H, m).

MS (ESI) m/z: 438.3 (M+H)$^+$.

Ex 53

$^1$H NMR (CDCl$_3$) delta 8.61-8.64 (1H, m), 7.49 (1H, d, J=7.6 Hz), 7.41 (1H, dd, J=8.6, 6.0 Hz), 7.09-7.25 (3H, m), 6.99 (1H, td, J=8.3, 2.6 Hz), 4.54-4.66 (2H, m), 4.03 (1H, br t, J=5.8 Hz), 3.66-3.84 (1H, m), 3.58 (1H, br s), 3.15-3.24 (4H, m), 2.95-3.10 (1H, m), 2.85 (1H, br d, J=12.8 Hz), 2.58-2.72 (1H, m), 2.08-2.35 (3H, m).

MS (ESI) m/z: 452.0 (M+H)$^+$.

Ex 54

¹H NMR (CDCl₃) delta 8.62 (1H, d, J=5.0 Hz), 7.50 (1H, d, J=7.6 Hz), 7.41 (1H, dd, J=8.6, 6.0 Hz), 7.10-7.25 (3H, m), 6.99 (1H, td, J=8.3, 2.6 Hz), 4.54-4.67 (2H, m), 3.46 (1H, d, J=8.0 Hz), 3.22-3.39 (4H, m), 2.90 (1H, d, J=12.8 Hz), 2.59-2.74 (1H, m), 2.14-2.27 (3H, m), 1.45 (3H, s).

MS (ESI) m/z: 452.3 (M+H)⁺.

Ex 55

¹H-NMR (CDCl₃) delta 8.62 (1H, dt, J=4.7, 1.6 Hz), 7.48 (1H, d, J=7.6 Hz), 7.41 (1H, t, J=7.0 Hz), 7.08-7.24 (3H, m), 6.99 (1H, td, J=8.3, 2.6 Hz), 4.53-4.67 (2H, m), 3.14-3.41 (6H, m), 3.10 (2H, br s), 2.83 (1H, br d, J=12.6 Hz), 2.49-2.76 (1H, m), 2.13-2.37 (3H, m), 1.43 (3H, s).

MS (ESI) m/z: 466.3 (M+H)⁺.

Ex 56

¹H-NMR (CDCl₃) delta 8.59 (1H, dt, J=4.7, 1.7 Hz), 7.50 (1H, dt, J=7.9, 1.5 Hz), 7.41 (1H, dd, J=8.4, 6.0 Hz), 7.13-7.25 (3H, m), 6.99 (1H, td, J=8.3, 2.6 Hz), 4.55-4.67 (2H, m), 3.64 (2H, t, J=5.2 Hz), 3.12 (1H, d, J=12.0 Hz), 2.92 (1H, d, J=12.0 Hz), 2.68-2.83 (2H, m), 2.28-2.36 (1H, m), 2.13-2.25 (3H, m).

MS (ESI) m/z: 426.3 (M+H)⁺.

Ex 57

¹H-NMR (CDCl₃) delta 8.62 (1H, dt, J=4.7, 1.7 Hz), 7.51 (1H, d, J=7.6 Hz), 7.41 (1H, dd, J=8.5, 6.1 Hz), 7.10-7.25 (3H, m), 6.99 (1H, td, J=8.3, 2.6 Hz), 4.54-4.67 (2H, m), 3.43-3.66 (3H, m), 3.03 (1H, d, J=14.1 Hz), 2.87 (1H, br d, J=14.2 Hz), 2.57-2.73 (3H, m), 2.14-2.41 (6H, m).

MS (ESI) m/z: 440.0 (M+H)⁺.

The following Intermediates were prepared by General Procedure L (Table 26).

General Procedure L

NaN₃ (3.0 eq.) and NH₄Cl (3.0 eq.) were added to a solution of substrate (1.0 eq.) in MeOH, and the mixture was stirred at 60° C. until complete reaction. The reaction was quenched with aq. NaHCO₃, and the resulting mixture was extracted with CHCl₃. The extract was concentrated under reduced pressure to afford the following Intermediates.

TABLE 26

| Intermediates | Structure | Chemical Name | Substrate |
|---|---|---|---|
| I-h-3-1 | (structure) | (5S*,8R*)-8-(azidomethyl)-N-(2,4-dichlorobenzyl)-5-fluoro-8-hydroxy-5,6,7,8-tetrahydroquinoline-5-carboxamide | IM I-g-4 |
| I-h-3-2 | (structure) | (5S*,8S*)-8-(azidomethyl)-N-(2,4-dichlorobenzyl)-5-fluoro-8-hydroxy-5,6,7,8-tetrahydroquinoline-5-carboxamide | IM I-g-6 |

IM I-h-3-1

¹H-NMR (CDCl₃) delta 8.65 (1H, dt, J=4.7, 1.71 Hz), 7.53 (1H, dt, J=7.9, 1.5 Hz), 7.45 (1H, d, J=2.1 Hz), 7.36 (1H, d, J=8.2 Hz), 7.27-7.31 (2H, m), 7.16 (1H, br d, J=5.3 Hz), 4.54-4.67 (2H, m), 3.70 (2H, d, J=1.1 Hz), 3.20 (s, 1H), 2.59-2.74 (1H, m), 2.36-2.46 (1H, m), 2.13-2.33 (2H, m).

MS (ESI) m/z: 424.2 (M+H)⁺.

IM I-h-3-2

¹H-NMR (CDCl₃) delta 8.60-8.66 (1H, m), 7.52 (1H, d, J=8.2 Hz), 7.46 (1H, s), 7.17-7.39 (6H, m), 4.54-4.68 (2H, m), 3.53-3.60 (1H, m), 3.41 (1H, d, J=13.0 Hz), 2.41-2.55 (2H, m), 2.26-2.39 (1H, m), 2.01-2.21 (1H, m).

MS (ESI) m/z: 424.2 (M+H)⁺.

General Procedure: Scheme 11, Step 1

To a stirred solution of substrate (1.0 eq.) in MeCN and water (100 eq.) at 60° C. was added portion wise triphenyl phosphine (2.0 eq.). The mixture was stirred at that temperature until complete reaction. The mixture was purified by silica gel column chromatography to afford the following Intermediates (Table 27).

TABLE 27

| Intermediates | Structure | Chemical Name | Substrate |
|---|---|---|---|
| I-m-1 | 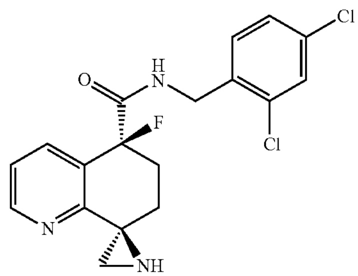 | (2S*,5'S*)-N-(2,4-dichlorobenzyl)-5'-fluoro-6',7'-dihydro-5'H-spiro[aziridine-2,8'-quinoline]-5'-carboxamide | IM I-h-3-1 |
| I-m-2 | 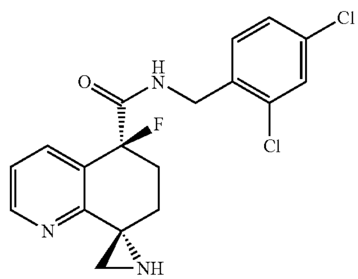 | (2R*,5'S*)-N-(2,4-dichlorobenzyl)-5'-fluoro-6',7'-dihydro-5'H-spiro[aziridine-2,8'-quinoline]-5'-carboxamide | IM I-h-3-2 |

IM I-m-1

$^1$H-NMR (CDCl$_3$) delta 8.46 (1H, dt, J=4.7, 1.9 Hz), 7.21-7.48 (6H, m), 7.13 (1H, ddd, J=7.8, 4.8, 0.9 Hz), 4.57-4.72 (2H, m), 2.57-2.78 (1H, m), 2.45-2.55 (1H, m), 2.34 (1H, tdd, J=14.1, 14.1, 4.3, 2.9 Hz), 2.16 (1H, s) 1.91 (1H, s), 1.71 (1H, dt, J=13.6, 3.7 Hz).

MS (ESI) m/z: 380.1 (M+H)$^+$.

IM I-m-2

$^1$H-NMR (CDCl$_3$) delta 8.47 (1H, dt, J=4.7, 1.7 Hz), 7.63-7.70 (1H, m), 7.32-7.49 (4H, m), 7.19-7.29 (2H, m), 7.13 (1H, ddd, J=7.9, 4.7, 0.7 Hz), 4.54-4.68 (2H, m), 2.49-2.70 (3H, m), 2.23-2.36 (2H, m), 2.09-2.20 (1H, m).

MS (ESI) m/z: 380.1 (M+H)$^+$.

General Procedure: Scheme 11, Step 2

Triethylamine (1.5 eq.) and 2-nitrophenylsulfonyl chloride (1.2 eq.) were successively added to a dichloromethane solution of substrate (1.0 eq.) at 0° C. After stirring at ambient temperature until complete reaction, the reaction was quenched with aq. NH$_4$Cl. The mixture was extracted with CHCl$_3$, dried over Na$_2$SO$_4$, and concentrated under reduced pressure to afford the following Intermediates (Table 28).

TABLE 28

| Intermediates | Structure | Chemical Name | Substrate |
|---|---|---|---|
| XIV-1 | 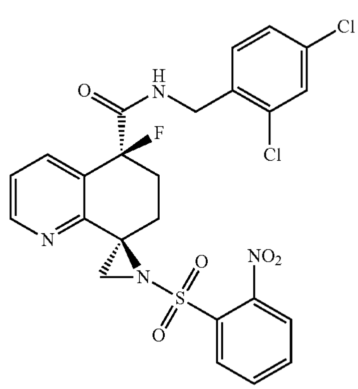 | (2S*,5'S*)-N-(2,4-dichlorobenzyl)-5'-fluoro-1-((2-nitrophenyl)sulfonyl)-6',7'-dihydro-5'H-spiro[aziridine-2,8'-quinoline]-5'-carboxamide | IM I-m-1 |

TABLE 28-continued

| Intermediates | Structure | Chemical Name | Substrate |
|---|---|---|---|
| XIV-2 | 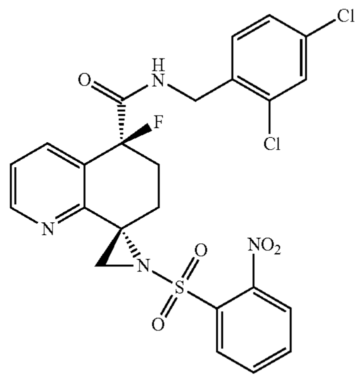 | (2R*,5'S*)-N-(2,4-dichlorobenzyl)-5'-fluoro-1-((2-nitrophenyl)sulfonyl)-6',7'-dihydro-5'H-spiro[aziridine-2,8'-quinoline]-5'-carboxamide | IM I-m-2 |

IM XIV-1
MS (ESI) m/z: 565.0 (M+H)+
IM XIV-2
MS (ESI) m/z: 565.0 (M+H)+.

General Procedure: Scheme 11, Step 3

To a solution of substrate (1.0 eq.) in DMF was added NaOAc (10 eq.) and the mixture was stirred at 100° C. until starting material consumed. Aq. NaOH (5 N, 5 eq.) was added to the mixture and stirred at ambient temperature until complete reaction. The reaction was quenched with aq. $NH_4Cl$, extracted with $CHCl_3$. The extract was concentrated under reduced pressure. The residue was purified by silica gel column chromatography to afford the following Intermediates (Table 29).

TABLE 29

| Intermediates | Structure | Chemical Name | Substrate |
|---|---|---|---|
| XV-1 | 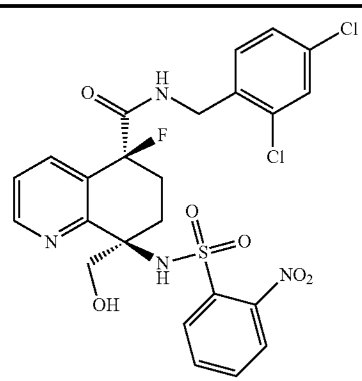 | (5S*,8R*)-N-(2,4-dichlorobenzyl)-5-fluoro-8-(hydroxymethyl)-8-(2-nitrophenylsulfonamido)-5,6,7,8-tetrahydroquinoline-5-carboxamide | |
| XV-2 | 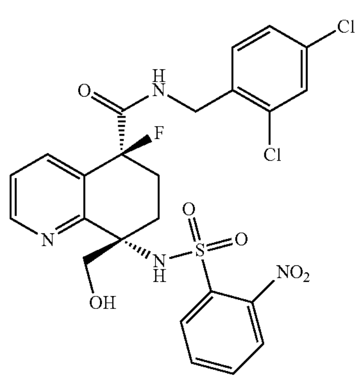 [SMILES: O=C(NCc1ccc(Cl)cc1Cl)[C@]1(F)CC[C@](CO)(NS(=O)(=O)c2ccccc2[N+](=O)[O-])c2ncccc21] | (5S*,8S*)-N-(2,4-dichlorobenzyl)-5-fluoro-8-(hydroxymethyl)-8-(2-nitrophenylsulfonamido)-5,6,7,8-tetrahydroquinoline-5-carboxamide | |

IM XVI-1
 MS (ESI) m/z: 583.1 (M+H)+.

IM XV-2
 MS (ESI) m/z: 583.1 (M+H)+.

General Procedure: Scheme 11, Step 4

The mixture of substrate (1.0 eq.), 4-mercaptobenzoic acid (2.0 eq.), and $K_2CO_3$ (4.0 eq.) in DMF was stirred at 80° C. until complete reaction. The solvent of the mixture was removed under reduced pressure. The residue was purified by SCX cartridge column to afford the following Examples (Table 30).

Ex 59

$^1$H-NMR (CDCl$_3$) delta 8.56-8.65 (1H, m), 7.50 (1H, br d, J=8.1 Hz), 7.45 (1H, d, J=2.2 Hz), 7.30-7.39 (1H, m), 7.13-7.29 (3H, m), 4.60 (2H, dd, J=10.0, 5.9 Hz), 2.90-3.09 (2H, m), 2.29-2.45 (2H, m), 2.05-2.17 (2H, m).
 MS (ESI) m/z: 398.2 (M+H)+.

EX 60

$^1$H-NMR (CDCl$_3$) delta 8.54 (1H, dd, J=2.7, 1.3 Hz), 7.52 (1H, d, J=7.3 Hz) 7.40-7.44 (1H, m), 7.27-7.36 (2H, m), 7.12-7.25 (3H, m), 4.51-4.65 (2H, m), 3.14-3.31 (2H, m), 2.67-3.00 (2H, m), 2.17-2.31 (2H, m).
 MS (ESI) m/z: 398.2 (M+H)+.

General Procedure: Scheme 12, Step 1

Chloroacetyl chloride (1.1 eq.) was added dropwise to a biphasic solution of substrate (1.0 eq.) in dichloromethane

TABLE 30

| Examples | Structure | Chemical Name | Substrate |
| --- | --- | --- | --- |
| 59 | 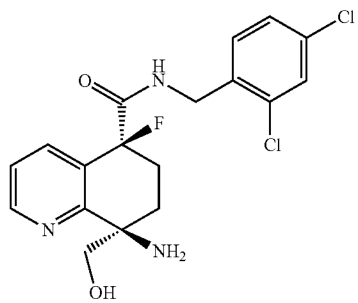 [SMILES: N[C@]1(CO)CC[C@@](F)(C(=O)NCc2ccc(Cl)cc2Cl)c2cccnc21] | (5S*,8R*)-8-amino-N-(2,4-dichloro-benzyl)-5-fluoro-8-(hydroxymethyl)-5,6,7,8-tetrahydroquinoline-5-carboxamide | IM XV-1 |
| 60 | 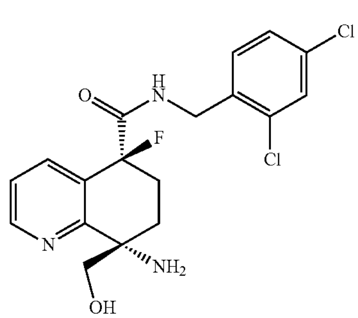 [SMILES: N[C@@]1(CO)CC[C@@](F)(C(=O)NCc2ccc(Cl)cc2Cl)c2cccnc21] | (5S*,8S*)-8-amino-N-(2,4-dichloro-benzyl)-5-fluoro-8-(hydroxymethyl)-5,6,7,8-tetrahydroquinoline-5-carboxamide | IM XV-2 |

(0.3 M) and 0.5 N aq. NaOH (2.0 eq) at 0° C. The reaction mixture was warmed up to ambient temperature and stirred at that temperature until complete reaction. The mixture was extracted with dichloromethane 3 times, dried over Na₂SO₄, and concentrated under reduced pressure to afford the following Intermediates (Table 31).

TABLE 31

| Intermediates | Structure | Chemical Name | Substrate |
|---|---|---|---|
| XVI-1 | 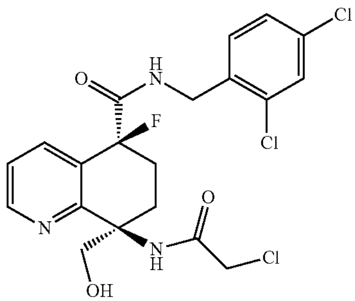 [SMILES: O=C(CCl)N[C@]1(CO)CC[C@@](F)(C(=O)NCc2ccc(Cl)cc2Cl)c2cccnc21] | (5S*,8R*)-8-(2-chloroacetamido)-N-(2,4-dichlorobenzyl)-5-fluoro-8-(hydroxymethyl)-5,6,7,8-tetrahydroquinoline-5-carboxamide | Ex 59 |
| XVI-2 | 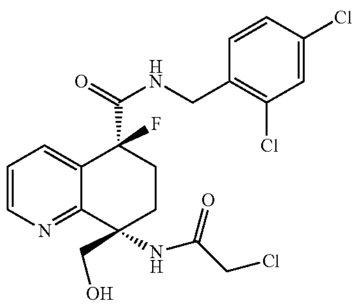 [SMILES: O=C(CCl)N[C@@]1(CO)CC[C@@](F)(C(=O)NCc2ccc(Cl)cc2Cl)c2cccnc21] | (5S*,8S*)-8-(2-chloroacetamido)-N-(2,4-dichlorobenzyl)-5-fluoro-8-(hydroxymethyl)-5,6,7,8-tetrahydroquinoline-5-carboxamide | Ex 60 |

IM XVI-1
MS (ESI) m/z: 474.1 (M+H)⁺.
IM XVI-2
MS (ESI) m/z: 474.1 (M+H)⁺.

General Procedure: Scheme 12, Step 2

To a solution of substrate (1.0 eq.) in 50% dichloromethane/2-propanol was added portion wise tert-BuOK (4.0 eq.) at 0° C. The solution was allowed to warm to ambient temperature and stirred until complete reaction. The solvent was removed under reduced pressure and the resulting crude residue was purified by preparative HPLC to afford the following Examples (Table 32).

TABLE 32

| Examples | Structure | Chemical Name | Substrate |
|---|---|---|---|
| 61 | 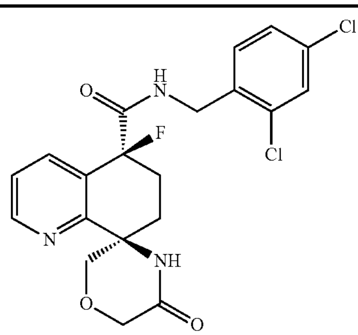 | (3R*,5'S*)-N-(2,4-dichlorobenzyl)-5'-fluoro-5-oxo-6',7'-dihydro-5'H-spiro[morpholine-3,8'-quinoline]-5'-carboxamide | IM XVI-1 |

TABLE 32-continued

| Examples | Structure | Chemical Name | Substrate | |
|---|---|---|---|---|
| 62 | 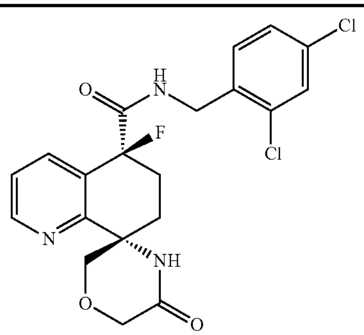 | (3S*,5'S*)-N-(2,4-dichlorobenzyl)-5'-fluoro-5-oxo-6',7'-dihydro-5'H-spiro[morpholine-3,8'-quinoline]-5'-carboxamide | | IM XVI-2 |

Ex 61

$^1$H-NMR (CDCl$_3$) delta 8.61-8.69 (1H, m), 7.54 (1H, d, J=7.7 Hz), 7.46 (1H, d, J=2.0 Hz), 7.16-7.40 (6H, m), 6.18 (1H, br s), 4.56-4.69 (2H, m), 4.34 (1H, dd, J=12.2, 2.2 Hz), 4.17 (2H, dd, J=17.5, 16.6 Hz), 3.37 (1H, dd, J=12.2, 2.9 Hz), 2.77-2.95 (1H, m), 2.40-2.50 (1H, m), 2.12-2.32 (2H, m).

MS (ESI) m/z: 438.1 (M+H)$^+$.

Ex 62

$^1$H-NMR (CDCl$_3$) delta 8.70 (1H, d, J=4.7 Hz), 7.57 (1H, d, J=8.2 Hz), 7.46 (1H, d, J=2.1 Hz), 7.27-7.35 (3H, m), 7.14-7.22 (1H, m), 5.95 (1H, br s), 4.53-4.65 (2H, m), 4.25-4.42 (2H, m), 4.20 (1H, d, J=11.4 Hz), 3.43 (1H, dd, J=12.4, 4.0 Hz), 2.54-2.64 (1H, m) 2.29-2.53 (3H, m), 1.25 (1H, s).

MS (ESI) m/z: 438.1 (M+H)$^+$.

The following Examples and Intermediates were prepared by General Procedure M (Tables 33 and 35).

General Procedure M

To a mixture of substrate (1.0 eq.), Chiral Ru Catalyst (5 mol %) and triethylamine (2.0 eq.) in DMF was added formic acid (5.0 eq.) at 0° C. The mixture was stirred at 0° C. for 10 min, and then warm to room temperature. After being stirred at room temperature until complete reaction, aq. NaHCO$_3$ was added to the mixture. The mixture was extracted with EtOAc twice and washed with water and brine. The extracts were combined, dried over Na$_2$SO$_4$, and concentrated in vacuo. The resulting residue was purified by silica gel column chromatography and the each diastereo isomer was separated by silica gel column chromatography and/or preparative TLC to afford following Examples.

TABLE 33

| Examples | Structure | Chemical Name | Substrate | Chiral Ru Catalyst |
|---|---|---|---|---|
| 63 | 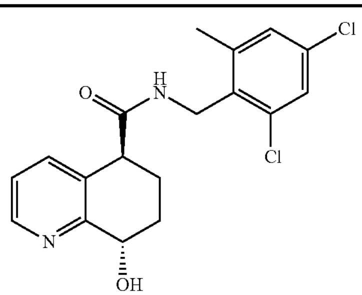 | (5S,8S)-N-(2,4-dichloro-6-methylbenzyl)-8-hydroxy-5,6,7,8-tetrahydroquinoline-5-carboxamide | Ex 1 | RuCl(p-cymene)[(S,S)-Ts-DPEN] |
| 64 | 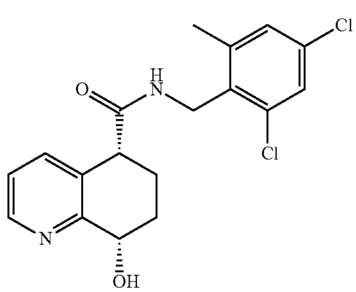 | (5R,8S)-N-(2,4-dichloro-6-methylbenzyl)-8-hydroxy-5,6,7,8-tetrahydroquinoline-5-carboxamide | | |

TABLE 33-continued

| Examples | Structure | Chemical Name | Substrate | Chiral Ru Catalyst |
|---|---|---|---|---|
| 65 | 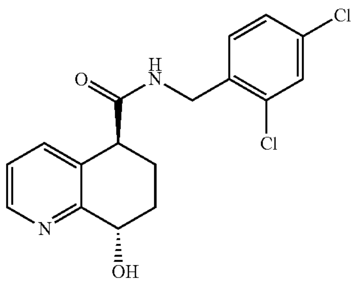 [SMILES: O=C(NCc1ccc(Cl)cc1Cl)[C@H]1CC[C@H](O)c2ncccc21] | (5S,8S)-N-(2,4-dichlorobenzyl)-8-hydroxy-5,6,7,8-tetrahydroquinoline-5-carboxamide | IM I-c-1 | RuCl(p-cymene) [(S,S)-Ts-DPEN] |
| 66 | 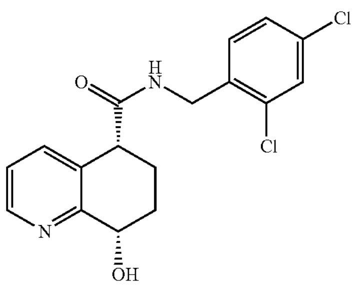 [SMILES: O=C(NCc1ccc(Cl)cc1Cl)[C@@H]1CC[C@H](O)c2ncccc21] | (5R,8S)-N-(2,4-dichlorobenzyl)-8-hydroxy-5,6,7,8-tetrahydroquinoline-5-carboxamide | | |
| 67 | 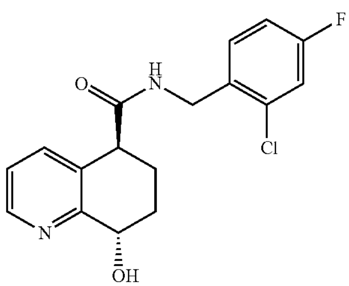 [SMILES: O=C(NCc1ccc(F)cc1Cl)[C@H]1CC[C@H](O)c2ncccc21] | (5S,8S)-N-(2-chloro-4-fluorobenzyl)-8-hydroxy-5,6,7,8-tetrahydroquinoline-5-carboxamide | IM I-c-2 | RuCl(p-cymene) [(S,S)-Ts-DPEN] |
| 68 | 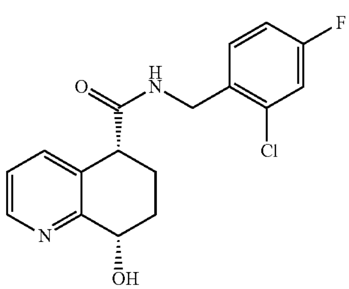 [SMILES: O=C(NCc1ccc(F)cc1Cl)[C@@H]1CC[C@H](O)c2ncccc21] | (5R,8S)-N-(2-chloro-4-fluorobenzyl)-8-hydroxy-5,6,7,8-tetrahydroquinoline-5-carboxamide | | |
| 69 | 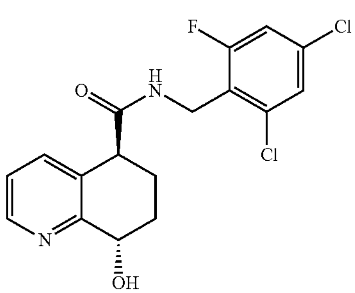 [SMILES: O=C(NCc1c(F)cc(Cl)cc1Cl)[C@H]1CC[C@H](O)c2ncccc21] | (5S,8S)-N-(2,4-dichloro-6-fluorobenzyl)-8-hydroxy-5,6,7,8-tetrahydroquinoline-5-carboxamide | IM I-c-3 | RuCl(p-cymene) [(S,S)-Ts-DPEN] |

TABLE 33-continued

| Examples | Structure | Chemical Name | Substrate | Chiral Ru Catalyst |
|---|---|---|---|---|
| 70 | 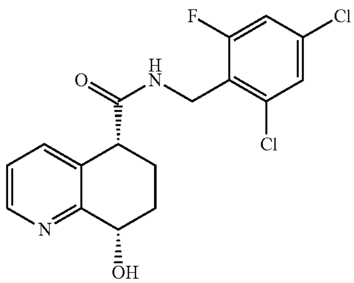 [SMILES: O=C(NCc1c(F)cc(Cl)cc1Cl)[C@@H]1CC[C@H](O)c2ncccc21] | (5R,8S)-N-(2,4-dichloro-6-fluorobenzyl)-8-hydroxy-5,6,7,8-tetrahydroquinoline-5-carboxamide | | |
| 71 | 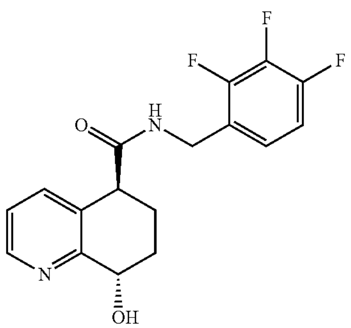 [SMILES: O=C(NCc1ccc(F)c(F)c1F)[C@H]1CC[C@H](O)c2ncccc21] | (5S,8S)-8-hydroxy-N-(2,3,4-trifluorobenzyl)-5,6,7,8-tetrahydroquinoline-5-carboxamide | IM I-c-4 | RuCl(p-cymene)[(S,S)-Ts-DPEN] |
| 72 | 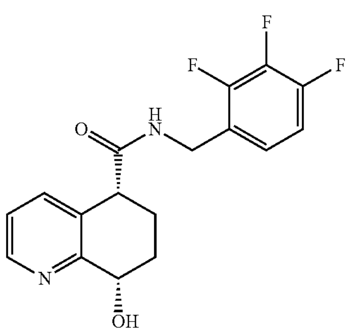 [SMILES: O=C(NCc1ccc(F)c(F)c1F)[C@@H]1CC[C@H](O)c2ncccc21] | (5R,8S)-8-hydroxy-N-(2,3,4-trifluorobenzyl)-5,6,7,8-tetrahydroquinoline-5-carboxamide | | |
| 73 | 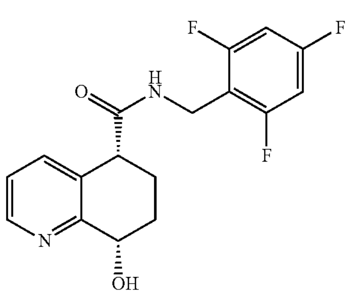 [SMILES: O=C(NCc1c(F)cc(F)cc1F)[C@@H]1CC[C@H](O)c2ncccc21] | (5R,8S)-8-hydroxy-N-(2,4,6-trifluorobenzyl)-5,6,7,8-tetrahydroquinoline-5-carboxamide | IM I-c-5 | RuCl(p-cymene)[(S,S)-Ts-DPEN] |

TABLE 33-continued

| Examples | Structure | Chemical Name | Substrate | Chiral Ru Catalyst |
|---|---|---|---|---|
| 74 | 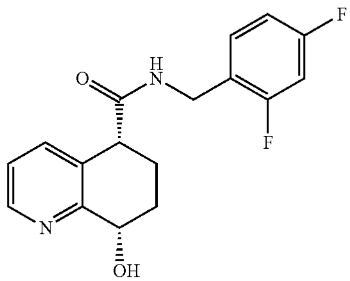 [SMILES: O=C(NCc1ccc(F)cc1F)[C@@H]1CC[C@H](O)c2ncccc21] | (5R,8S)-N-(2,4-difluorobenzyl)-8-hydroxy-5,6,7,8-tetrahydroquinoline-5-carboxamide | IM I-c-6 | RuCl(p-cymene)[(S,S)-Ts-DPEN] |
| 75 | 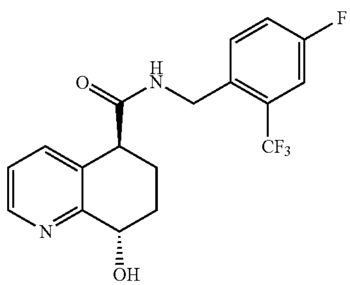 [SMILES: O=C(NCc1ccc(F)cc1C(F)(F)F)[C@H]1CC[C@H](O)c2ncccc21] | (5S,8S)-N-(4-fluoro-2-(trifluoromethyl)benzyl)-8-hydroxy-5,6,7,8-tetrahydroquinoline-5-carboxamide | IM I-c-7 | RuCl(p-cymene)[(S,S)-Ts-DPEN] |
| 76 | 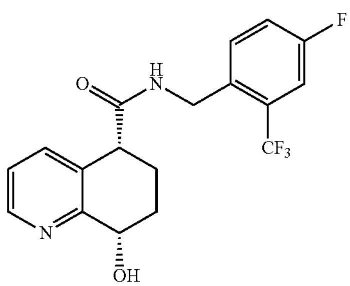 [SMILES: O=C(NCc1ccc(F)cc1C(F)(F)F)[C@@H]1CC[C@H](O)c2ncccc21] | (5R,8S)-N-(4-fluoro-2-(trifluoromethyl)benzyl)-8-hydroxy-5,6,7,8-tetrahydroquinoline-5-carboxamide | | |
| 77 | 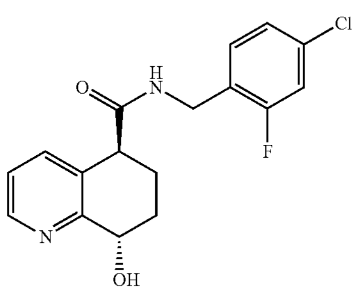 [SMILES: O=C(NCc1ccc(Cl)cc1F)[C@H]1CC[C@H](O)c2ncccc21] | (5S,8S)-N-(4-chloro-2-fluorobenzyl)-8-hydroxy-5,6,7,8-tetrahydroquinoline-5-carboxamide | IM I-c-8 | RuCl(p-cymene)[(S,S)-Ts-DPEN] |
| 78 | 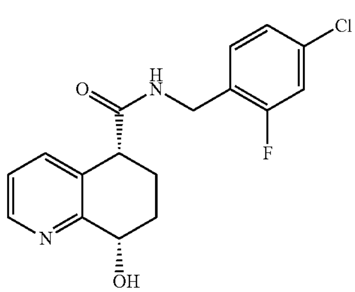 [SMILES: O=C(NCc1ccc(Cl)cc1F)[C@@H]1CC[C@H](O)c2ncccc21] | (5R,8S)-N-(4-chloro-2-fluorobenzyl)-8-hydroxy-5,6,7,8-tetrahydroquinoline-5-carboxamide | | |

TABLE 33-continued

| Examples | Structure | Chemical Name | Substrate | Chiral Ru Catalyst |
|---|---|---|---|---|
| 79 | 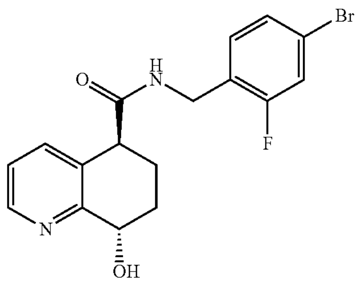 [SMILES: O=C(NCc1ccc(Br)cc1F)[C@H]1CC[C@H](O)c2ncccc21] | (5S,8S)-N-(4-bromo-2-fluorobenzyl)-8-hydroxy-5,6,7,8-tetrahydroquinoline-5-carboxamide | IM I-c-9 | RuCl(p-cymene)[(S,S)-Ts-DPEN] |
| 80 | 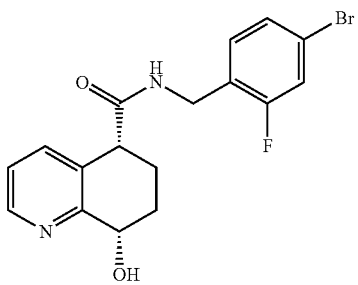 [SMILES: O=C(NCc1ccc(Br)cc1F)[C@@H]1CC[C@H](O)c2ncccc21] | (5R,8S)-N-(4-bromo-2-fluorobenzyl)-8-hydroxy-5,6,7,8-tetrahydroquinoline-5-carboxamide | | |
| 81 | 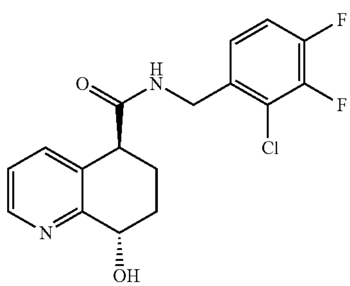 [SMILES: O=C(NCc1ccc(F)c(F)c1Cl)[C@H]1CC[C@H](O)c2ncccc21] | (5S,8S)-N-(2-chloro-3,4-difluorobenzyl)-8-hydroxy-5,6,7,8-tetrahydroquinoline-5-carboxamide | IM I-c-10 | RuCl(p-cymene)[(S,S)-Ts-DPEN] |
| 82 | 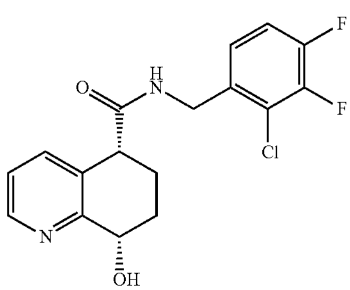 [SMILES: O=C(NCc1ccc(F)c(F)c1Cl)[C@@H]1CC[C@H](O)c2ncccc21] | (5R,8S)-N-(2-chloro-3,4-difluorobenzyl)-8-hydroxy-5,6,7,8-tetrahydroquinoline-5-carboxamide | | |
| 83 | 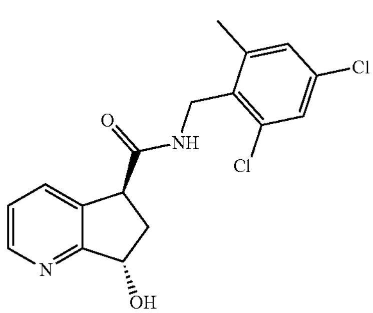 [SMILES: Cc1cc(Cl)cc(Cl)c1CNC(=O)[C@H]1C[C@H](O)c2ncccc21] | (5S,7S)-N-(2,4-dichloro-6-methylbenzyl)-7-hydroxy-6,7-dihydro-5H-cyclopenta[b]pyridine-5-carboxamide | Ex 16 | RuCl(p-cymene)[(S,S)-Ts-DPEN] |

TABLE 33-continued

| Examples | Structure | Chemical Name | Substrate | Chiral Ru Catalyst |
|---|---|---|---|---|
| 84 | 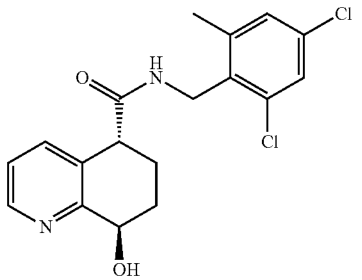 [SMILES: Cc1cc(Cl)cc(Cl)c1CNC(=O)[C@@H]1CC[C@@H](O)c2ncccc21] | (5R,8R)-N-(2,4-dichloro-6-methylbenzyl)-8-hydroxy-5,6,7,8-tetrahydroquinoline-5-carboxamide | Ex 1 | RuCl(p-cymene)[(R,R)-Ts-DPEN] |
| 85 | 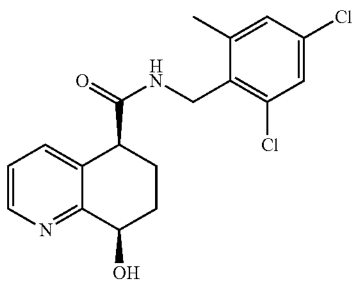 [SMILES: Cc1cc(Cl)cc(Cl)c1CNC(=O)[C@H]1CC[C@@H](O)c2ncccc21] | (5S,8R)-N-(2,4-dichloro-6-methylbenzyl)-8-hydroxy-5,6,7,8-tetrahydroquinoline-5-carboxamide | | |
| 86 | 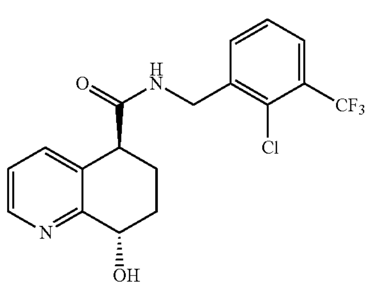 [SMILES: O=C(NCc1cccc(C(F)(F)F)c1Cl)[C@H]1CC[C@H](O)c2ncccc21] | (5S,8S)-N-(2-chloro-3-(trifluoromethyl)benzyl)-8-hydroxy-5,6,7,8-tetrahydroquinoline-5-carboxamide | Ex 2 | RuCl(p-cymene)[(S,S)-Ts-DPEN] |
| 87 | 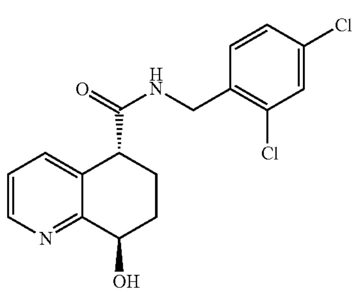 [SMILES: O=C(NCc1ccc(Cl)cc1Cl)[C@@H]1CC[C@@H](O)c2ncccc21] | (5R,8R)-N-(2,4-dichlorobenzyl)-8-hydroxy-5,6,7,8-tetrahydroquinoline-5-carboxamide | IM I-c-1 | RuCl(p-cymene)[(R,R)-Ts-DPEN] |
| 88 | 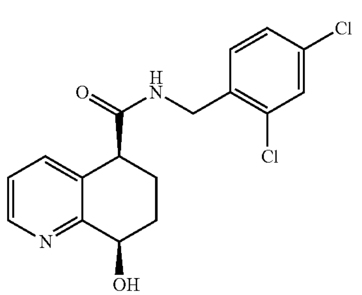 [SMILES: O=C(NCc1ccc(Cl)cc1Cl)[C@H]1CC[C@@H](O)c2ncccc21] | (5S,8R)-N-(2,4-dichlorobenzyl)-8-hydroxy-5,6,7,8-tetrahydroquinoline-5-carboxamide | | |

TABLE 33-continued

| Examples | Structure | Chemical Name | Substrate | Chiral Ru Catalyst |
|---|---|---|---|---|
| 89 | 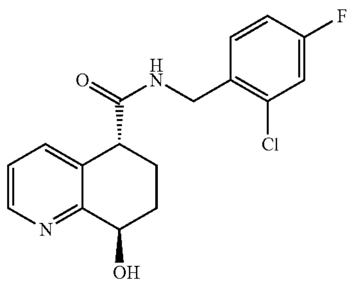 [SMILES: O=C(NCc1ccc(F)cc1Cl)[C@@H]1CC[C@@H](O)c2ncccc21] | (5R,8R)-N-(2-chloro-4-fluorobenzyl)-8-hydroxy-5,6,7,8-tetrahydro-quinoline-5-carboxamide | IM I-c-2 | RuCl(p-cymene)[(R,R)-Ts-DPEN] |
| 90 | 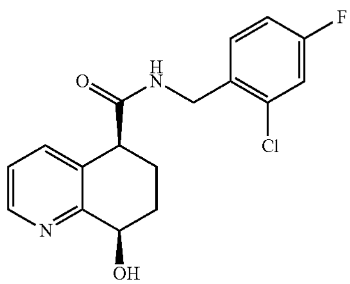 [SMILES: O=C(NCc1ccc(F)cc1Cl)[C@H]1CC[C@@H](O)c2ncccc21] | (5S,8R)-N-(2-chloro-4-fluorobenzyl)-8-hydroxy-5,6,7,8-tetrahydro-quinoline-5-carboxamide | | |
| 91 | 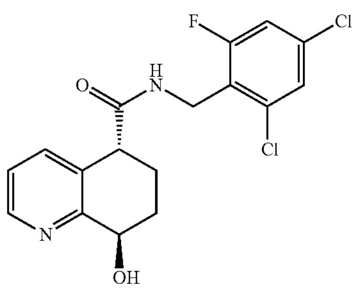 | (5R,8R)-N-(2,4-dichloro-6-fluorobenzyl)-8-hydroxy-5,6,7,8-tetrahydro-quinoline-5-carboxamide | IM I-c-3 | RuCl(p-cymene)[(R,R)-Ts-DPEN] |
| 92 | 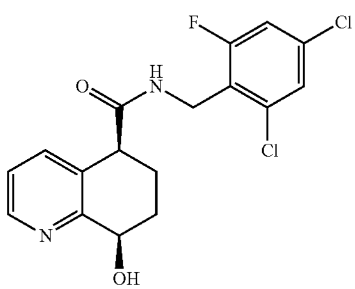 | (5S,8R)-N-(2,4-dichloro-6-fluorobenzyl)-8-hydroxy-5,6,7,8-tetrahydro-quinoline-5-carboxamide | | |
| 93 | 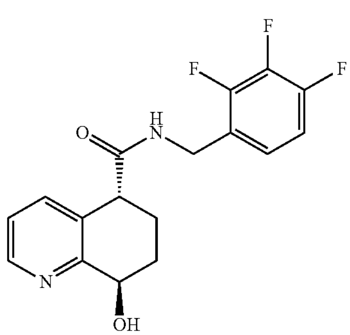 [SMILES: O=C(NCc1ccc(F)c(F)c1F)[C@@H]1CC[C@@H](O)c2ncccc21] | (5R,8R)-8-hydroxy-N-(2,3,4-trifluorobenzyl)-5,6,7,8-tetrahydro-quinoline-5-carboxamide | IM I-c-4 | RuCl(p-cymene)[(R,R)-Ts-DPEN] |

TABLE 33-continued

| Examples | Structure | Chemical Name | Substrate | Chiral Ru Catalyst |
|---|---|---|---|---|
| 94 | 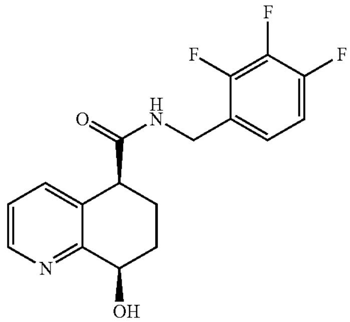 [SMILES: O=C(NCc1ccc(F)c(F)c1F)[C@H]1CC[C@@H](O)c2ncccc21] | (5S,8R)-8-hydroxy-N-(2,3,4-trifluorobenzyl)-5,6,7,8-tetrahydro-quinoline-5-carboxamide | | |
| 95 | 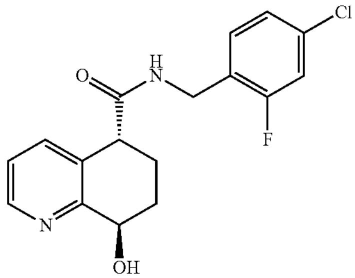 [SMILES: O=C(NCc1ccc(Cl)cc1F)[C@@H]1CC[C@@H](O)c2ncccc21] | (5R,8R)-N-(4-chloro-2-fluorobenzyl)-8-hydroxy-5,6,7,8-tetrahydro-quinoline-5-carboxamide | IM I-c-8 | RuCl(p-cymene) [(R,R)-Ts-DPEN] |
| 96 | 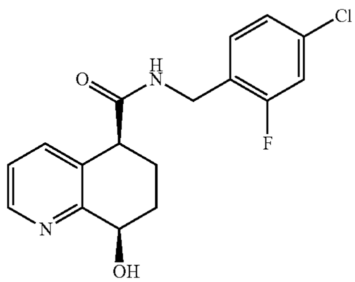 [SMILES: O=C(NCc1ccc(Cl)cc1F)[C@H]1CC[C@@H](O)c2ncccc21] | (5S,8R)-N-(4-chloro-2-fluorobenzyl)-8-hydroxy-5,6,7,8-tetrahydro-quinoline-5-carboxamide | | |
| 97 | 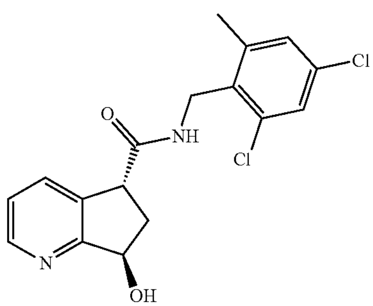 [SMILES: Cc1cc(Cl)cc(Cl)c1CNC(=O)[C@@H]1C[C@@H](O)c2ncccc21] | (5R,7R)-N-(2,4-dichloro-6-methylbenzyl)-7-hydroxy-6,7-dihydro-5H-cyclopenta[b]pyridine-5-carboxamide | Ex 16 | RuCl(p-cymene) [(R,R)-Ts-DPEN] |
| 98 | 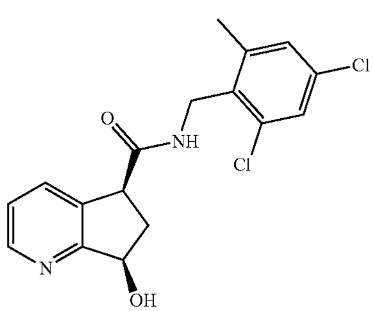 [SMILES: Cc1cc(Cl)cc(Cl)c1CNC(=O)[C@H]1C[C@@H](O)c2ncccc21] | (5S,7R)-N-(2,4-dichloro-6-methylbenzyl)-7-hydroxy-6,7-dihydro-5H-cyclopenta[b]pyridine-5-carboxamide | | |

TABLE 34

| | | LC MS | |
|---|---|---|---|
| Examples | Method | tR (min) | [M + H]+ |
| 63 | A | 1.48 | 365.3 |
| 64 | A | 1.47 | 365.3 |
| 65 | C | 1.40 | 351.0 |
| 66 | C | 1.39 | 351.0 |
| 67 | C | 1.28 | 335.0 |
| 68 | C | 1.28 | 335.0 |
| 69 | C | 1.39 | 369.0 |
| 70 | C | 1.39 | 369.0 |
| 71 | C | 1.25 | 337.0 |
| 72 | C | 1.25 | 337.0 |
| 73 | C | 1.20 | 337.0 |
| 74 | C | 1.19 | 319.0 |
| 75 | C | 1.36 | 369.0 |
| 76 | C | 1.36 | 369.0 |
| 77 | C | 1.30 | 335.0 |
| 78 | C | 1.30 | 335.0 |
| 79 | C | 1.33 | 378.9 |
| 80 | C | 1.33 | 378.9 |
| 81 | C | 1.31 | 352.9 |
| 82 | C | 1.31 | 352.9 |
| 83 | D | 1.46 | 351.0 |
| 84 | A | 1.48 | 365.3 |
| 85 | A | 1.47 | 365.2 |
| 86 | A | 1.42 | 385.3 |
| 87 | C | 1.40 | 351.0 |
| 88 | C | 1.40 | 351.0 |
| 89 | C | 1.28 | 335.0 |
| 90 | C | 1.28 | 335.0 |
| 91 | C | 1.39 | 369.0 |
| 92 | C | 1.38 | 369.0 |
| 93 | C | 1.25 | 337.0 |
| 94 | C | 1.25 | 337.0 |
| 95 | C | 1.30 | 335.0 |
| 96 | C | 1.30 | 335.0 |
| 97 | D | 1.46 | 351.0 |

Ex 63

$^1$H NMR (DMSO d6) delta 8.42 (1H, d, J=4.6 Hz), 8.37 (1H, br), 7.49 (1H, br s), 7.37 (1H, d, J=7.9 Hz), 7.36 (1H, br s), 7.23 (1H, dd, J=7.9, 4.6 Hz), 5.18 (1H, d, J=4.0 Hz), 4.52 (1H, d, J=4.0 Hz), 4.43 (2H, d, J=4.0 Hz), 3.66 (1H, dd, J=8.6, 5.9 Hz), 2.40 (3H, s), 2.18-1.99 (2H, m), 1.84-1.79 (2H, m).

Chiral HPLC tR: 28.1 min (Method E), >99% e.e., d.e.

Ex 64

$^1$H NMR (DMSO d6) delta 8.42 (1H, d, J=4.6 Hz), 8.34 (1H, br), 7.48 (1H, br s), 7.39 (1H, d, J=7.9 Hz), 7.34 (1H, br s), 7.22 (1H, dd, J=7.9, 4.6 Hz), 5.11 (1H, d, J=3.3 Hz), 4.55 (1H, br), 4.37 (2H, d, J=4.6 Hz), 3.73 (1H, dd, J=5.9, 5.9 Hz), 2.36 (3H, s), 2.22 (1H, m), 2.05 (1H, m), 1.84 (1H, m), 1.65 (1H, m).

Chiral HPLC tR: 15.0 min (Method E), >99% e.e., d.e.

Ex 65

$^1$H NMR (CDCl$_3$) delta 8.49 (1H, dd, J=4.9, 1.2 Hz), 7.42 (1H, dd, J=7.9, 1.2 Hz), 7.39 (1H, d, J=1.8 Hz), 7.31 (1H, d, J=8.6 Hz), 7.22 (1H, dd, J=8.6, 1.8 Hz), 7.18 (1H, dd, J=7.9, 4.9 Hz), 6.03 (1H, br), 4.74 (1H, dd, J=8.6, 5.5 Hz), 4.51 (1H, dd, J=15.3, 6.1 Hz), 4.46 (1H, dd, J=15.3, 6.1 Hz), 3.72 (1H, dd, J=9.2, 6.1 Hz), 2.38-2.26 (2H, m), 2.06 (1H, m), 1.78 (1H, m). A signal due to OH was not observed.

Ex 66

$^1$H NMR (CDCl$_3$) delta 8.52 (1H, dd, J=4.9, 1.2 Hz), 7.47 (1H, dd, J=7.9, 1.2 Hz), 7.36 (1H, d, J=1.8 Hz), 7.26 (1H, d, J=8.6 Hz), 7.21 (1H, m), 7.20 (1H, dd, J=7.9, 4.9 Hz), 5.84 (1H, br), 4.70 (1H, dd, J=9.2, 5.5 Hz), 4.49 (1H, dd, J=14.7, 6.1 Hz), 4.39 (1H, dd, J=14.7, 6.1 Hz), 3.72 (1H, dd, J=6.1, 4.3 Hz), 2.37 (1H, m), 2.21 (1H, m), 2.10 (1H, m), 1.90 (1H, m). A signal due to OH was not observed.

Ex 67

$^1$H NMR (CDCl$_3$) delta 8.49 (1H, dd, J=4.9, 1.2 Hz), 7.42 (1H, d, J=7.9 Hz), 7.37 (1H, dd, J=8.6, 6.1 Hz), 7.18 (1H, dd, J=7.9, 4.9 Hz), 7.13 (1H, dd, J=7.9, 2.4 Hz), 6.96 (1H, ddd, J=8.6, 7.9, 2.4 Hz), 6.00 (1H, br), 4.74 (1H, dd, J=9.2, 5.5 Hz), 4.51 (1H, dd, J=15.3, 6.1 Hz), 4.47 (1H, dd, J=15.3, 5.5 Hz), 4.12 (1H, br), 3.73 (1H, dd, J=9.2, 6.1 Hz), 2.38-2.23 (2H, m), 2.07 (1H, m), 1.80 (1H, m).

Ex 68

$^1$H NMR (CDCl$_3$) delta 8.52 (1H, dd, J=4.9, 1.8 Hz), 7.47 (1H, dd, J=7.9, 1.8 Hz), 7.32 (1H, dd, J=8.6, 6.1 Hz), 7.21 (1H, dd, J=7.9, 4.9 Hz), 7.09 (1H, dd, J=8.6, 2.4 Hz), 6.94 (1H, ddd, J=8.6, 7.9, 2.4 Hz), 5.87 (1H, br), 4.70 (1H, dd, J=8.6, 5.5 Hz), 4.49 (1H, dd, J=14.7, 6.1 Hz), 4.39 (1H, dd, J=14.7, 6.1 Hz), 4.10 (1H, br), 3.71 (1H, dd, J=6.1, 4.9 Hz), 2.36 (1H, m), 2.20 (1H, m), 2.10 (1H, m), 1.90 (1H, m).

Ex 69

$^1$H NMR (CDCl$_3$) delta 8.49 (1H, dd, J=4.9, 1.8 Hz), 7.43 (1H, d, J=7.3 Hz), 7.24 (1H, d, J=1.8 Hz), 7.18 (1H, dd, J=7.3, 4.9 Hz), 7.06 (1H, dd, J=9.2, 1.8 Hz), 5.90 (1H, br), 4.73 (1H, dd, J=9.2, 5.5 Hz), 4.63-4.54 (2H, m), 4.12 (1H, br), 3.70 (1H, dd, J=7.9, 7.3 Hz), 2.37-2.21 (2H, m), 2.06 (1H, m), 1.77 (1H, m).

Ex 70

$^1$H NMR (CDCl$_3$) delta 8.51 (1H, dd, J=4.9, 1.2 Hz), 7.47 (1H, dd, J=7.9, 1.2 Hz), 7.22-7.19 (2H, m), 7.03 (1H, dd, J=9.2, 1.8 Hz), 5.74 (1H, br), 4.68 (1H, dd, J=9.2, 5.5 Hz), 4.60 (1H, ddd, J=14.7, 6.1, 1.2 Hz), 4.46 (1H, ddd, J=14.7, 5.5, 1.2 Hz), 4.03 (1H, br), 3.69 (1H, dd, J=6.1, 4.3 Hz), 2.35 (1H, m), 2.19 (1H, m), 2.08 (1H, m), 1.89 (1H, m).

Ex 71

$^1$H NMR (CDCl$_3$) delta 8.50 (1H, d, J=4.9 Hz), 7.41 (1H, d, J=7.9 Hz), 7.19 (1H, dd, J=7.9, 4.9 Hz), 7.07 (1H, m), 6.94 (1H, ddd, J=9.2, 6.7, 1.8 Hz), 5.94 (1H, br), 4.74 (1H, dd, J=9.2, 5.5 Hz), 4.50 (1H, dd, J=14.7, 6.1 Hz), 4.46 (1H, dd, J=14.7, 6.1 Hz), 4.09 (1H, br), 3.73 (1H, dd, J=9.2, 6.1 Hz), 2.39-2.23 (2H, m), 2.06 (1H, m), 1.79 (1H, m).

Ex 72

$^1$H NMR (CDCl$_3$) delta 8.51 (1H, dd, J=4.9, 1.8 Hz), 7.47 (1H, d, J=7.3 Hz), 7.22 (1H, dd, J=7.3, 4.9 Hz), 7.01 (1H, m), 6.93 (1H, m), 5.97 (1H, br), 4.71 (1H, dd, J=8.6, 5.5 Hz), 4.46 (1H, dd, J=15.3, 6.1 Hz), 4.40 (1H, dd, J=15.3, 6.1 Hz), 4.12 (1H, br), 3.73 (1H, dd, J=6.1, 4.9 Hz), 2.34 (1H, m), 2.22-2.04 (2H, m), 1.93 (1H, m).

Ex 73

$^1$H NMR (CDCl$_3$) delta 8.52 (1H, d, J=4.9 Hz), 7.47 (1H, d, J=7.9 Hz), 7.21 (1H, dd, J=7.9, 4.9 Hz), 6.66 (2H, dd, J=8.6, 7.9 Hz), 5.75 (1H, br), 4.69 (1H, dd, J=8.6, 5.5 Hz), 4.52 (1H, ddd, J=14.7, 5.5 Hz), 4.42 (1H, dd, J=14.7, 5.5 Hz), 4.10 (1H, br s), 3.70 (1H, dd, J=5.5, 5.5 Hz), 2.34 (1H, m), 2.22 (1H, m), 2.09 (1H, m), 1.91 (1H, m).

Ex 74

$^1$H NMR (CDCl$_3$) delta 8.46 (1H, dd, J=4.9, 1.8 Hz), 7.46 (1H, d, J=7.9 Hz), 7.25 (1H, m), 7.18 (1H, dd, J=7.9, 4.9 Hz), 6.84-6.74 (2H, m), 6.02 (1H, dd, J=5.5, 5.5 Hz), 4.69 (1H, dd, J=7.9, 4.9 Hz), 4.43 (1H, dd, J=15.3, 6.1 Hz), 4.37 (1H, dd, J=15.3, 6.1 Hz), 4.16 (1H, br), 3.70 (1H, dd, J=5.5, 5.5 Hz), 2.33 (1H, m), 2.17-2.04 (2H, m), 1.94 (1H, m).

Ex 75

$^1$H NMR (CDCl$_3$) delta 8.50 (1H, dd, J=4.9, 1.2 Hz), 7.57 (1H, dd, J=8.6, 5.5 Hz), 7.40 (1H, dd, J=7.9, 1.2 Hz), 7.37 (1H, dd, J=8.6, 2.4 Hz), 7.23 (1H, ddd, J=8.6, 8.6, 2.4 Hz), 7.18 (1H, dd, J=7.9, 4.9 Hz), 6.03 (1H, br), 4.74 (1H, dd, J=8.6, 5.5 Hz), 4.62 (1H, dd, J=15.3, 6.7 Hz), 4.58 (1H, dd, J=15.3, 6.1 Hz), 4.03 (1H, br), 3.72 (1H, dd, J=8.6, 6.1 Hz), 2.35 (1H, m), 2.26 (1H, m), 2.07 (1H, m), 1.79 (1H, m).

Ex 76

$^1$H NMR (CDCl$_3$) delta 8.52 (1H, dd, J=4.9, 1.2 Hz), 7.51 (1H, dd, J=8.6, 5.5 Hz), 7.45 (1H, d, J=7.9 Hz), 7.33 (1H, dd, J=8.6, 2.4 Hz), 7.23-7.19 (2H, m), 5.74 (1H, br), 4.70 (1H, dd, J=8.6, 5.5 Hz), 4.57 (1H, dd, J=15.3, 6.1 Hz), 4.52 (1H, dd, J=15.3, 6.1 Hz), 3.71 (1H, dd, J=6.1, 4.3 Hz), 2.37 (1H, m), 2.21 (1H, m), 2.10 (1H, m), 1.89 (1H, m). A signal due to OH was not observed.

Ex 77

$^1$H NMR (CDCl$_3$) delta 8.47 (1H, dd, J=4.9, 1.2 Hz), 7.41 (1H, d, J=7.9 Hz), 7.25 (1H, dd, J=7.9, 6.7 Hz), 7.17 (1H, dd, J=7.9, 4.9 Hz), 7.10 (1H, dd, J=7.9, 1.8 Hz), 7.08 (1H, dd, J=7.9, 1.8 Hz), 6.14 (1H, dd, J=6.1, 5.3 Hz), 4.73 (1H, dd, J=9.2, 5.5 Hz), 4.46 (1H, dd, J=15.3, 6.1 Hz), 4.43 (1H, dd, J=15.3, 6.1 Hz), 4.26 (1H, br), 3.71 (1H, dd, J=8.6, 6.1 Hz), 2.37-2.21 (2H, m), 2.05 (1H, m), 1.76 (1H, m).

Ex 78

$^1$H NMR (CDCl$_3$) delta 8.51 (1H, dd, J=4.9, 1.8 Hz), 7.47 (1H, d, J=7.9 Hz), 7.22 (1H, dd, J=7.9, 5.5 Hz), 7.20 (1H, dd, J=7.9, 1.8 Hz), 7.10-7.04 (2H, m), 5.80 (1H, br), 4.70 (1H, dd, J=8.6, 5.5 Hz), 4.45 (1H, dd, J=14.7, 6.1 Hz), 4.38 (1H, dd, J=14.7, 6.1 Hz), 4.11 (1H, br), 3.71 (1H, dd, J=5.5, 4.9 Hz), 2.35 (1H, m), 2.19 (1H, m), 2.09 (1H, m), 1.91 (1H, m).

Ex 79

$^1$H NMR (CDCl$_3$) delta 8.49 (1H, dd, J=4.9, 1.2 Hz), 7.42 (1H, d, J=7.3 Hz), 7.27-7.18 (3H, m), 7.18 (1H, dd, J=7.3, 4.9 Hz), 6.01 (1H, br), 4.74 (1H, dd, J=8.6, 5.5 Hz), 4.47 (1H, dd, J=14.7, 6.1 Hz), 4.43 (1H, dd, J=14.7, 6.1 Hz), 4.15 (1H, s), 3.72 (1H, dd, J=8.6, 6.1 Hz), 2.38-2.22 (2H, m), 2.06 (1H, m), 1.77 (1H, m).

Ex 80

$^1$H NMR (CDCl$_3$) delta 8.50 (1H, dd, J=4.9, 1.2 Hz), 7.46 (1H, d, J=7.3 Hz), 7.26-7.13 (4H, m), 5.83 (1H, br), 4.69 (1H, dd, J=8.6, 7.9 Hz), 4.43 (1H, dd, J=15.3, 6.1 Hz), 4.36 (1H, dd, J=15.3, 6.1 Hz), 4.14 (1H, s), 3.71 (1H, dd, J=5.5, 4.9 Hz), 2.35 (1H, m), 2.24-2.04 (2H, m), 1.90 (1H, m).

Ex 81

$^1$H NMR (CDCl$_3$) delta 8.51 (1H, d, J=4.9 Hz), 7.44 (1H, d, J=7.9 Hz), 7.21 (1H, dd, J=7.9, 4.9 Hz), 7.16 (1H, m), 7.09 (1H, m), 5.95 (1H, br), 4.76 (1H, dd, J=8.6, 4.9 Hz), 4.54 (1H, dd, J=14.7, 6.1 Hz), 4.50 (1H, dd, J=14.7, 6.1 Hz), 3.75 (1H, dd, J=8.6, 6.1 Hz), 3.49 (1H, s), 2.39-2.25 (2H, m), 2.07 (1H, m), 1.81 (1H, m).

Ex 82

$^1$H NMR (CDCl$_3$) delta 8.53 (1H, dd, J=4.9, 1.8 Hz), 7.48 (1H, d, J=7.9 Hz), 7.23 (1H, dd, J=7.9, 4.9 Hz), 7.12-7.02 (2H, m), 5.86 (1H, br), 4.72 (1H, dd, J=9.2, 5.5 Hz), 4.45 (1H, dd, J=15.3, 6.7 Hz), 4.40 (1H, dd, J=15.3, 6.1 Hz), 3.73 (1H, dd, J=6.1, 4.2 Hz), 2.90 (1H, br), 2.36 (1H, m), 2.28-2.09 (2H, m), 1.92 (1H, m).

Ex 83

$^1$H NMR (DMSO d6) delta 8.44 (1H, br), 8.43 (1H, d, J=4.6 Hz), 7.56 (1H, d, J=7.3 Hz), 7.49 (1H, d, J=2.0 Hz), 7.35 (1H, d, J=2.0 Hz), 7.22 (1H, dd, J=7.3, 4.6 Hz), 5.41 (1H, d, J=5.3 Hz), 5.09 (1H, dd, J=11.9, 5.3 Hz), 4.38 (2H, d, J=4.6 Hz), 4.08 (1H, dd, J=7.9, 5.3 Hz), 2.47 (1H, m), 2.36 (3H, s), 1.97 (1H, m).

Ex 84

$^1$H NMR was identified with the Example 63.
Chiral HPLC tR: 25.1 min (Method E), >99% e.e., d.e.

Ex 85

$^1$H NMR was identified with the Example 64.
Chiral HPLC tR: 17.9 min (Method E), >99% e.e., d.e.

Ex 86

1H NMR (DMSO d6) delta 8.73 (1H, br), 8.45 (1H, d, J=4.6 Hz), 7.79 (1H, dd, J=7.9, 1.3 Hz), 7.66 (1H, d, J=7.9 Hz), 7.57 (1H, dd, J=7.9, 7.3 Hz), 7.49 (1H, d, J=7.3 Hz), 7.24 (1H, dd, J=7.9, 4.6 Hz), 5.14 (1H, d, J=4.0 Hz), 4.56 (1H, br), 4.52-4.43 (2H, m), 3.85 (1H, dd, J=5.9, 5.3 Hz), 2.25-2.18 (2H, m), 1.92 (1H, m), 1.69 (1H, m).

Ex 87

$^1$H NMR was identified with the Example 65.

Ex 88

$^1$H NMR was identified with the Example 66.

Ex 89

$^1$H NMR was identified with the Example 67.

Ex 90

$^1$H NMR was identified with the Example 68.

Ex 91

$^1$H NMR was identified with the Example 69.

Ex 92

¹H NMR was identified with the Example 70.

Ex 93

¹H NMR was identified with the Example 71.

Ex 94

¹H NMR was identified with the Example 72.

Ex 95

¹H NMR was identified with the Example 77.

Ex 96

¹H NMR was identified with the Example 78.

Ex 97

¹H NMR was identified with the Example 83.

Ex 98

¹H NMR (DMSO d6) delta 8.53 (1H, br), 8.44 (1H, d, J=4.6 Hz), 7.52 (1H, d, J=7.9 Hz), 7.50 (1H, d, J=2.0 Hz), 7.36 (1H, d, J=2.0 Hz), 7.24 (1H, dd, J=7.9, 4.6 Hz), 5.48 (1H, d, J=7.33 Hz), 4.90 (1H, dd, J=13.8, 6.6 Hz), 4.47 (1H, dd, J=14.5, 4.6 Hz), 4.40 (1H, dd, J=14.5, 4.6 Hz), 3.82 (1H, dd, J=7.3, 7.3 Hz), 2.57 (1H, m), 2.39 (3H, s), 2.02 (1H, m).

TABLE 35

| Intermediates | Structure | Chemical Name | Substrate | Chiral Ru Catalyst |
|---|---|---|---|---|
| II-d-3 | 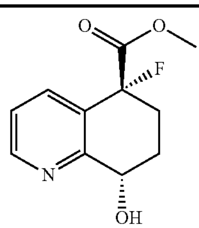 | (5R,8S)-methyl 5-fluoro-8-hydroxy-5,6,7,8-tetrahydroquinoline-5-carboxylate | IM II-c-2 | RuCl(p-cymene) [(S,S)-Ts-DPEN] |
| II-d-4 | 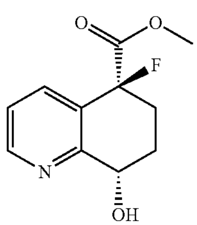 [SMILES: COC(=O)[C@]1(F)CC[C@H](O)c2ncccc21] | (5S,8S)-methyl 5-fluoro-8-hydroxy-5,6,7,8-tetrahydroquinoline-5-carboxylate | | |
| II-d-5 | 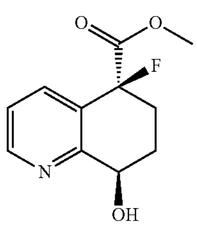 [SMILES: COC(=O)[C@]1(F)CC[C@@H](O)c2ncccc21] | (5S,8R)-methyl 5-fluoro-8-hydroxy-5,6,7,8-tetrahydroquinoline-5-carboxylate | | RuCl(p-cymene) [(R,R)-Ts-DPEN] |
| II-d-6 | 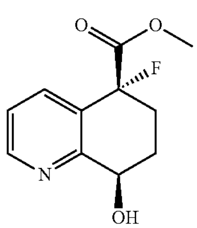 [SMILES: COC(=O)[C@@]1(F)CC[C@@H](O)c2ncccc21] | (5R,8R)-methyl 5-fluoro-8-hydroxy-5,6,7,8-tetrahydroquinoline-5-carboxylate | | |
| II-d-7 | 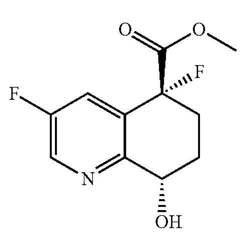 [SMILES: COC(=O)[C@@]1(F)CC[C@H](O)c2ncc(F)cc21] | (5R,8S)-methyl 3,5-difluoro-8-hydroxy-5,6,7,8-tetrahydroquinoline-5-carboxylate | IM II-c-3 | RuCl(p-cymene) [(S,S)-Ts-DPEN] |

TABLE 35-continued

| Intermediates | Structure | Chemical Name | Substrate | Chiral Ru Catalyst |
|---|---|---|---|---|
| II-d-8 | 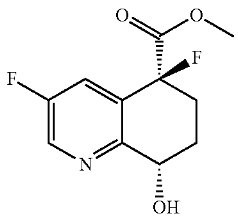 [SMILES: COC(=O)[C@]1(F)CC[C@H](O)c2ncc(F)cc21] | (5S,8S)-methyl 3,5-difluoro-8-hydroxy-5,6,7,8-tetrahydro-quinoline-5-carboxylate | | |
| II-d-9 | 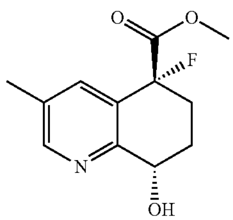 | (5R,8S)-methyl 5-fluoro-8-hydroxy-3-methyl-5,6,7,8-tetrahydro-quinoline-5-carboxylate | IM II-c-4 | RuCl(p-cymene) [(S,S)-Ts-DPEN] |
| II-d-10 | 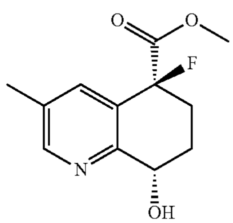 | (5S,8S)-methyl 5-fluoro-8-hydroxy-3-methyl-5,6,7,8-tetrahydro-quinoline-5-carboxylate | | |

IM II-d-3

$^1$H NMR (CDCl$_3$) delta 8.64 (1H, br dd, J=4.9, 1.2 Hz), 7.69 (1H, br dd, J=7.9, 1.2 Hz), 7.31 (1H, dd, J=7.9, 4.9 Hz), 4.74 (1H, m), 4.32 (1H, br), 3.83, (3H, s), 2.53-2.34 (3H, m), 2.08-1.98 (1H, m).

MS (ESI) m/z: 226.1 (M+H)$^+$.

Chiral HPLC tR: 16.7 min (Method F), >99% e.e., d.e.

IM II-d-4

$^1$H NMR (CDCl$_3$) delta 8.62 (1H, br d, J=4.3 Hz), 7.79 (1H, d, J=7.9 Hz), 7.31 (1H, dd, J=7.9, 4.3 Hz), 4.80 (1H, m), 4.06 (1H, br), 3.81, (3H, s), 2.74-2.65 (1H, m), 2.45-2.39 (1H, m), 2.27-2.13 (2H, m).

MS (ESI) m/z: 226.1 (M+H)$^+$.

Chiral HPLC tR: 34.6 min (Method F), >99% e.e., d.e.

IM II-d-5

$^1$H NMR and LCMS were identified with the IM JJ-d-3.

Chiral HPLC tR: 12.2 min (Method F), >99% e.e., d.e.

IM II-d-6

$^1$H NMR and LCMS were identified with the IM II-d-4.

Chiral HPLC tR: 13.9 min (Method F), >99% e.e., d.e.

IM II-d-7

$^1$H NMR (CDCl$_3$) delta 8.50 (1H, m), 7.43 (1H, dd, J=7.3, 2.4 Hz), 4.72 (1H, m), 3.97 (1H, br), 3.85 (3H, s), 2.52-2.33 (3H, m), 2.03 (1H, m).

MS (ESI) m/z: 244.0 (M+H)$^+$.

Chiral HPLC tR: 7.3 min (Method H), 98.8% e.e., >99% d.e

IM II-d-8

$^1$H NMR (CDCl$_3$) delta 8.49 (1H, m), 7.52 (1H, dd, J=8.5, 2.4 Hz), 4.78 (1H, m), 3.83 (3H, s), 3.69 (1H, s), 2.54 (1H, m), 2.41 (1H, m), 2.26-2.11 (2H, m).

MS (ESI) m/z: 244.0 (M+H)$^+$.

Chiral HPLC tR: 9.6 min (Method H), 97.5% e.e., 97.1% d.e.

IM II-d-9

$^1$H NMR (CDCl$_3$) delta 8.44 (1H, s), 7.49 (1H, s), 4.73 (1H, m), 4.34 (1H, br), 3.83 (3H, s), 2.48-2.32 (3H, m), 2.35 (3H, s), 2.02 (1H, m).

MS (ESI) m/z: 238.2 (M+H)$^+$.

Chiral HPLC tR: 15.4 min (Method G), 98.6% e.e., 97.0% d.e.

IM II-d-10

$^1$H NMR (CDCl$_3$) delta 8.43 (1H, s), 7.56 (1H, s), 4.79 (1H, m), 3.82 (3H, s), 2.68 (1H, m), 2.37 (1H, m), 2.35 (3H, s), 2.24-2.11 (2H, m), 1.86 (1H, br).

MS (ESI) m/z: 238.2 (M+H)$^+$.

Chiral HPLC tR: 10.4 min (Method G), >99% e.e., 96.4% d.e.

The following Examples were prepared by General Procedure A (Table 36).

TABLE 36

| Examples | Structure | Chemical Name | Substrate | Amine |
|---|---|---|---|---|
| 99 | 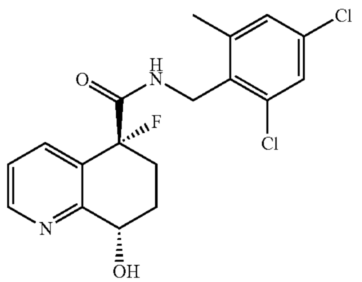 [SMILES: Cc1cc(Cl)cc(Cl)c1CNC(=O)[C@@]1(F)CC[C@H](O)c2ncccc21] | (5R,8S)-N-(2,4-dichloro-6-methylbenzyl)-5-fluoro-8-hydroxy-5,6,7,8-tetrahydroquinoline-5-carboxamide | IM II-d-3 | |
| 100 | 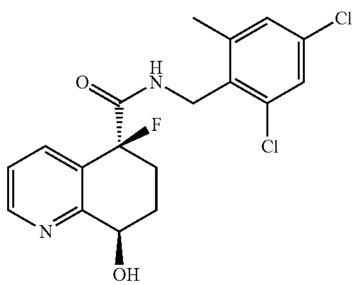 | (5S,8R)-N-(2,4-dichloro-6-methylbenzyl)-5-fluoro-8-hydroxy-5,6,7,8-tetrahydroquinoline-5-carboxamide | IM II-d-5 | |
| 101 | 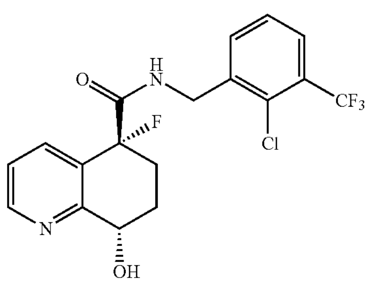 [SMILES: O=C(NCc1cccc(C(F)(F)F)c1Cl)[C@@]1(F)CC[C@H](O)c2ncccc21] | (5R,8S)-N-(2-chloro-3-(trifluoromethyl)benzyl)-5-fluoro-8-hydroxy-5,6,7,8-tetrahydroquinoline-5-carboxamide | IM II-d-3 | |
| 102 | 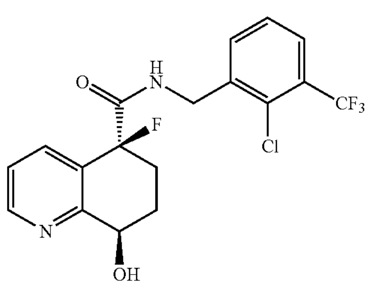 [SMILES: O=C(NCc1cccc(C(F)(F)F)c1Cl)[C@]1(F)CC[C@@H](O)c2ncccc21] | (5S,8R)-N-(2-chloro-3-(trifluoromethyl)benzyl)-5-fluoro-8-hydroxy-5,6,7,8-tetrahydroquinoline-5-carboxamide | IM II-d-5 | |
| 103 | 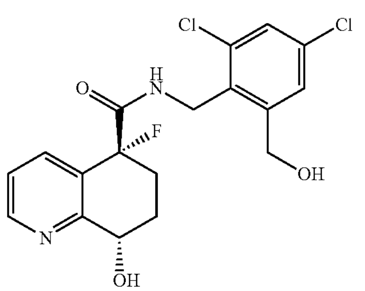 [SMILES: O=C(NCc1c(Cl)cc(Cl)cc1CO)[C@@]1(F)CC[C@H](O)c2ncccc21] | (5R,8S)-N-(2,4-dichloro-6-(hydroxymethyl)benzyl)-5-fluoro-8-hydroxy-5,6,7,8-tetrahydroquinoline-5-carboxamide | IM II-d-3 | |

TABLE 36-continued

| Examples | Structure | Chemical Name | Substrate | Amine |
|---|---|---|---|---|
| 104 | 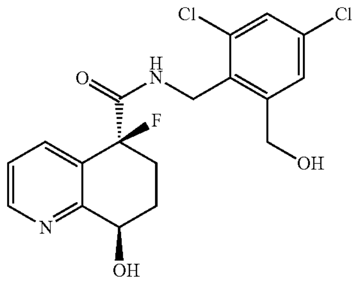 [SMILES: O=C(NCc1c(Cl)cc(Cl)cc1CO)[C@]1(F)CC[C@@H](O)c2ncccc21] | (5S,8R)-N-(2,4-dichloro-6-(hydroxymethyl)benzyl)-5-fluoro-8-hydroxy-5,6,7,8-tetrahydroquinoline-5-carboxamide | IM II-d-5 | |
| 105 | 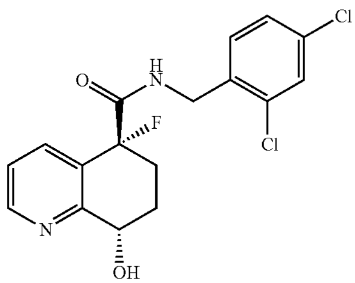 [SMILES: O=C(NCc1ccc(Cl)cc1Cl)[C@@]1(F)CC[C@H](O)c2ncccc21] | (5R,8S)-N-(2,4-dichlorobenzyl)-5-fluoro-8-hydroxy-5,6,7,8-tetrahydroquinoline-5-carboxamide | IM II-d-3 | |
| 106 | 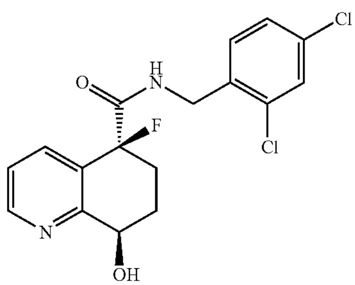 | (5S,8R)-N-(2,4-dichlorobenzyl)-5-fluoro-8-hydroxy-5,6,7,8-tetrahydroquinoline-5-carboxamide | IM II-d-5 | |
| 107 | 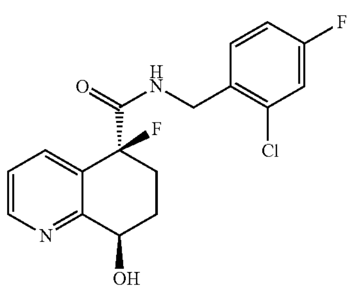 [SMILES: O=C(NCc1ccc(F)cc1Cl)[C@]1(F)CC[C@@H](O)c2ncccc21] | (5S,8R)-N-(2-chloro-4-fluorobenzyl)-5-fluoro-8-hydroxy-5,6,7,8-tetrahydroquinoline-5-carboxamide | IM II-d-5 | |
| 108 | 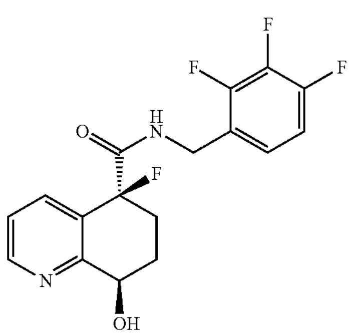 [SMILES: O=C(NCc1ccc(F)c(F)c1F)[C@]1(F)CC[C@@H](O)c2ncccc21] | (5S,8R)-5-fluoro-8-hydroxy-N-(2,3,4-trifluorobenzyl)-5,6,7,8-tetrahydroquinoline-5-carboxamide | IM II-d-5 | |

TABLE 36-continued

| Examples | Structure | Chemical Name | Substrate | Amine |
|---|---|---|---|---|
| 109 | 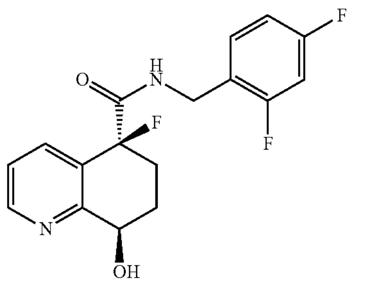 [SMILES: O=C(NCc1ccc(F)cc1F)[C@]1(F)CC[C@@H](O)c2ncccc21] | (5S,8R)-N-(2,4-difluorobenzyl)-5-fluoro-8-hydroxy-5,6,7,8-tetrahydroquinoline-5-carboxamide | IM II-d-5 | |
| 110 | 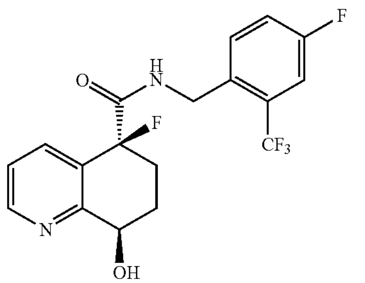 [SMILES: O=C(NCc1ccc(F)cc1C(F)(F)F)[C@]1(F)CC[C@@H](O)c2ncccc21] | (5S,8R)-5-fluoro-N-(4-fluoro-2-(trifluoromethyl)benzyl)-8-hydroxy-5,6,7,8-tetrahydroquinoline-5-carboxamide | IM II-d-5 | |
| 111 | 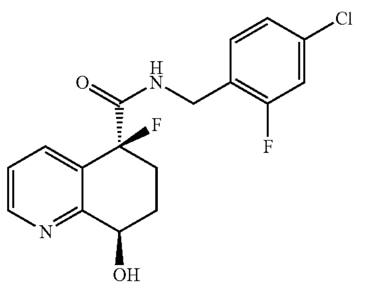 [SMILES: O=C(NCc1ccc(Cl)cc1F)[C@]1(F)CC[C@@H](O)c2ncccc21] | (5S,8R)-N-(4-chloro-2-fluorobenzyl)-5-fluoro-8-hydroxy-5,6,7,8-tetrahydroquinoline-5-carboxamide | IM II-d-5 | |
| 112 | 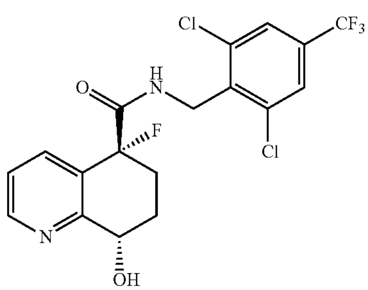 [SMILES: O=C(NCc1c(Cl)cc(C(F)(F)F)cc1Cl)[C@@]1(F)CC[C@H](O)c2ncccc21] | (5R,8S)-N-(2,6-dichloro-4-(trifluoromethyl)benzyl)-5-fluoro-8-hydroxy-5,6,7,8-tetrahydroquinoline-5-carboxamide | IM II-d-3 | |
| 113 | 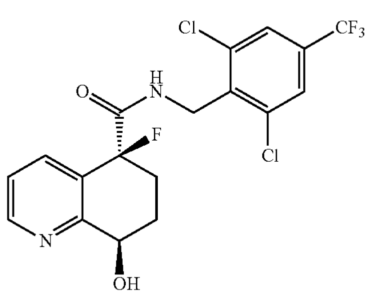 [SMILES: O=C(NCc1c(Cl)cc(C(F)(F)F)cc1Cl)[C@]1(F)CC[C@@H](O)c2ncccc21] | (5S,8R)-N-(2,6-dichloro-4-(trifluoromethyl)benzyl)-5-fluoro-8-hydroxy-5,6,7,8-tetrahydroquinoline-5-carboxamide | IM II-d-5 | |

TABLE 36-continued

| Examples | Structure | Chemical Name | Substrate | Amine |
|---|---|---|---|---|
| 114 | 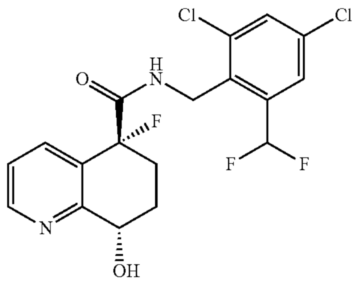 [SMILES: O=C(NCc1c(Cl)cc(Cl)cc1C(F)F)[C@@]1(F)CC[C@H](O)c2ncccc21] | (5R,8S)-N-(2,4-dichloro-6-(difluoromethyl)benzyl)-5-fluoro-8-hydroxy-5,6,7,8-tetrahydroquinoline-5-carboxamide | IM II-d-3 | IM III-a-1 |
| 115 | 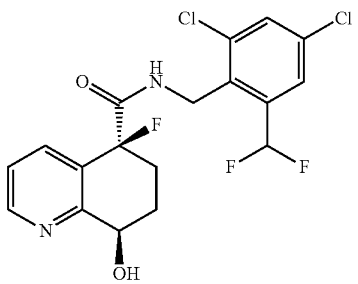 [SMILES: O=C(NCc1c(Cl)cc(Cl)cc1C(F)F)[C@]1(F)CC[C@@H](O)c2ncccc21] | (5S,8R)-N-(2,4-dichloro-6-(difluoromethyl)benzyl)-5-fluoro-8-hydroxy-5,6,7,8-tetrahydroquinoline-5-carboxamide | IM II-d-5 | |
| 116 | 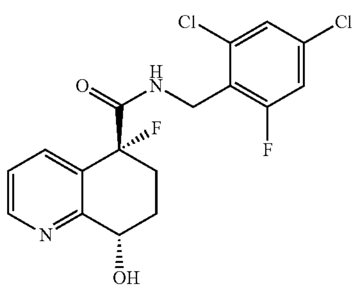 [SMILES: O=C(NCc1c(F)cc(Cl)cc1Cl)[C@@]1(F)CC[C@H](O)c2ncccc21] | (5R,8S)-N-(2,4-dichloro-6-fluorobenzyl)-5-fluoro-8-hydroxy-5,6,7,8-tetrahydroquinoline-5-carboxamide | IM II-d-3 | |
| 117 | 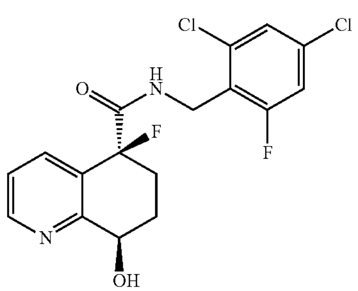 [SMILES: O=C(NCc1c(F)cc(Cl)cc1Cl)[C@]1(F)CC[C@@H](O)c2ncccc21] | (5S,8R)-N-(2,4-dichloro-6-fluorobenzyl)-5-fluoro-8-hydroxy-5,6,7,8-tetrahydroquinoline-5-carboxamide | IM II-d-5 | |
| 118 | 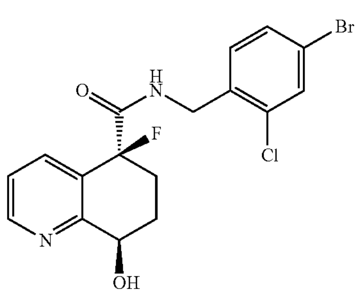 [SMILES: O=C(NCc1ccc(Br)cc1Cl)[C@]1(F)CC[C@@H](O)c2ncccc21] | (5S,8R)-N-(4-bromo-2-chlorobenzyl)-5-fluoro-8-hydroxy-5,6,7,8-tetrahydroquinoline-5-carboxamide | IM II-d-5 | |

TABLE 36-continued

| Examples | Structure | Chemical Name | Substrate | Amine |
|---|---|---|---|---|
| 119 | 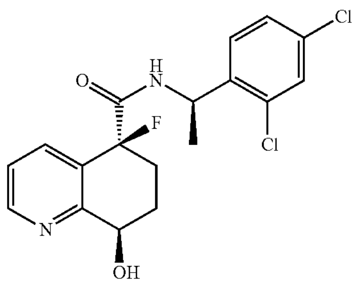 [SMILES: C[C@@H](NC(=O)[C@]1(F)CC[C@@H](O)c2ncccc21)c1ccc(Cl)cc1Cl] | (5S,8R)-N-((R)-1-(2,4-dichlorophenyl)ethyl)-5-fluoro-8-hydroxy-5,6,7,8-tetrahydroquinoline-5-carboxamide | IM II-d-5 | |
| 120 | 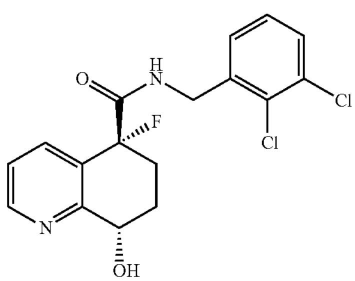 [SMILES: O=C(NCc1cccc(Cl)c1Cl)[C@@]1(F)CC[C@H](O)c2ncccc21] | (5R,8S)-N-(2,3-dichlorobenzyl)-5-fluoro-8-hydroxy-5,6,7,8-tetrahydroquinoline-5-carboxamide | IM II-d-3 | |
| 121 | 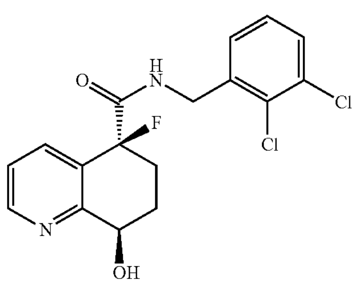 [SMILES: O=C(NCc1cccc(Cl)c1Cl)[C@]1(F)CC[C@@H](O)c2ncccc21] | (5S,8R)-N-(2,3-dichlorobenzyl)-5-fluoro-8-hydroxy-5,6,7,8-tetrahydroquinoline-5-carboxamide | IM II-d-5 | |
| 122 | 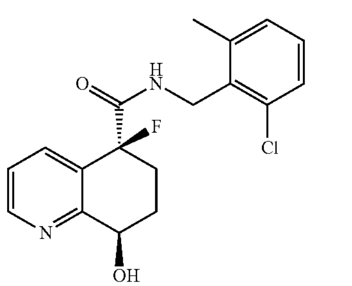 [SMILES: Cc1cccc(Cl)c1CNC(=O)[C@]1(F)CC[C@@H](O)c2ncccc21] | (5S,8R)-N-(2-chloro-6-methylbenzyl)-5-fluoro-8-hydroxy-5,6,7,8-tetrahydroquinoline-5-carboxamide | IM II-d-5 | |
| 123 | 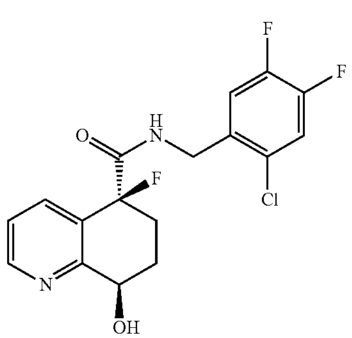 [SMILES: O=C(NCc1cc(F)c(F)cc1Cl)[C@]1(F)CC[C@@H](O)c2ncccc21] | (5S,8R)-N-(2-chloro-4,5-difluorobenzyl)-5-fluoro-8-hydroxy-5,6,7,8-tetrahydroquinoline-5-carboxamide | IM II-d-5 | |

TABLE 36-continued

| Examples | Structure | Chemical Name | Substrate | Amine |
|---|---|---|---|---|
| 124 | 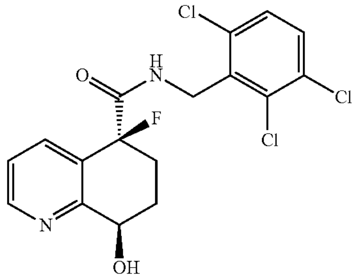 [SMILES: O=C(NCc1c(Cl)ccc(Cl)c1Cl)[C@]1(F)CC[C@@H](O)c2ncccc21] | (5S,8R)-5-fluoro-8-hydroxy-N-(2,3,6-trichlorobenzyl)-5,6,7,8-tetrahydroquinoline-5-carboxamide | IM II-d-5 | |
| 125 | 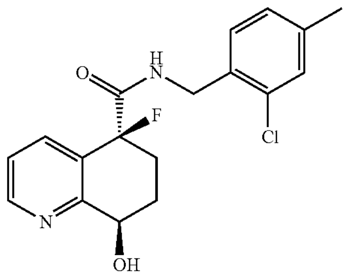 [SMILES: Cc1ccc(CNC(=O)[C@]2(F)CC[C@@H](O)c3ncccc32)c(Cl)c1] | (5S,8R)-N-(2-chloro-4-methylbenzyl)-5-fluoro-8-hydroxy-5,6,7,8-tetrahydroquinoline-5-carboxamide | IM II-d-5 | |

TABLE 37

LC MS

| Examples | Method | tR (min) | [M + H]$^+$ |
|---|---|---|---|
| 99 | A | 1.61 | 383.0 |
| 101 | A | 1.52 | 403.1 |
| 102 | A | 1.52 | 403.1 |
| 105 | A | 1.51 | 369.1 |
| 106 | A | 1.51 | 369.1 |
| 107 | A | 1.39 | 353.1 |
| 108 | C | 1.35 | 354.9 |
| 109 | C | 1.30 | 337.0 |
| 110 | C | 1.47 | 386.9 |
| 111 | C | 1.41 | 352.9 |
| 112 | A | 1.62 | 437.0 |
| 113 | A | 1.62 | 437.1 |
| 114 | A | 1.61 | 419.1 |
| 115 | A | 1.61 | 419.1 |
| 116 | C | 1.50 | 386.9 |
| 117 | C | 1.49 | 386.9 |
| 118 | A | 1.54 | 413.0 |
| 119 | A | 1.58 | 383.2 |
| 120 | A | 1.47 | 369.1 |
| 121 | A | 1.47 | 369.1 |
| 122 | A | 1.45 | 349.2 |
| 123 | A | 1.42 | 371.2 |
| 124 | A | 1.54 | 403.1 |
| 125 | A | 1.47 | 349.2 |

Ex 99

$^1$H NMR (CDCl$_3$) delta 8.60 (1H, ddd, J=4.6, 2.0, 1.3 Hz), 7.49 (1H, ddd, J=7.9, 2.0, 1.3 Hz), 7.33 (1H, d, J=2.0 Hz), 7.25 (1H, dd, J=7.9, 4.6 Hz), 7.16 (1H, d, J=2.0 Hz), 7.08 (1H, br), 4.76 (1H, dd, J=5.3, 5.3 Hz), 4.73 (1H, dd, J=13.8, 5.3 Hz), 4.63 (1H, dd, J=13.8, 5.3 Hz), 4.35 (1H, s), 2.66-2.23 (3H, m), 2.48 (3H, s), 2.00 (1H, m).

Chiral HPLC tR: 11.5 min (Method I), >99% e.e., d.e.

Ex 100

$^1$H NMR and LCMS were identified with the Example 99.
Chiral HPLC tR: 15.2 min (Method I), >99% e.e., d.e.

Ex 101

$^1$H NMR (CDCl$_3$) delta 8.61 (1H, br d, J=4.6 Hz), 7.71 (1H, d, J=7.3 Hz), 7.65 (1H, d, J=7.9 Hz), 7.49 (1H, ddd, J=7.9, 2.0, 1.3 Hz), 7.41 (1H, dd, J=7.9, 7.3 Hz), 7.32 (1H, br), 7.24 (1H, dd, J=7.9, 4.6 Hz), 4.79-4.71 (3H, m), 4.35 (1H, s), 2.57 (1H, m), 2.44-2.27 (2H, m), 2.03 (1H, m).

Chiral HPLC tR: 20.7 min (Method K), >99% e.e., d.e.

Ex 102

$^1$H NMR was identified with the Example 101.
Chiral HPLC tR: 29.8 min (Method K), >99% e.e., d.e.

Ex 103

$^1$H NMR (CDCl$_3$) delta 8.60 (1H, br d, J=4.6 Hz), 7.65 (1H, br), 7.45 (1H, d, J=2.0 Hz), 7.42 (1H, d, J=7.9 Hz), 7.34 (1H, d, J=2.0 Hz), 7.23 (1H, dd, J=7.9, 4.6 Hz), 4.83-4.65 (5H, m), 4.32 (1H, s), 3.82 (1H, br), 2.52 (1H, m), 2.42-2.21 (2H, m), 2.00 (1H, m).

MS (ESI) m/z: 399.0 (M+H)$^+$.
Chiral HPLC tR: 12.2 min (Method J), >99% e.e., d.e.

Ex 104

$^1$H NMR and LCMS were identified with the Example 103.
Chiral HPLC tR: 16.4 min (Method J), >99% e.e., d.e.

Ex 107

$^1$H NMR (CDCl$_3$) delta 8.60 (1H, ddd, J=4.9, 1.8, 1.2 Hz), 7.49 (1H, ddd, J=7.9, 1.8, 1.2 Hz), 7.41 (1H, dd, J=8.6, 6.1

Hz), 7.25-7.22 (1H, br), 7.24 (1H, dd, J=7.9, 4.9 Hz), 7.19 (1H, dd, J=8.6, 2.4 Hz), 7.00 (1H, ddd, J=8.6, 7.9, 2.4 Hz), 4.74 (1H, m), 4.65 (1H, dd, J=14.7, 6.1 Hz), 4.59 (1H, dd, J=14.7, 6.1 Hz), 4.46 (1H, br s), 2.61-2.28 (3H, m), 2.02 (1H, m).

Ex 108

$^1$H NMR (CDCl$_3$) delta 8.61 (1H, br d, J=4.9 Hz), 7.48 (1H, br d, J=7.9 Hz), 7.26 (1H, dd, J=7.9, 4.9 Hz), 7.23 (1H, br), 7.12 (1H, m), 6.98 (1H, m), 4.75 (1H, m), 4.65 (1H, dd, J=14.7, 6.1 Hz), 4.57 (1H, dd, J=14.7, 6.1 Hz), 4.40 (1H, br s), 2.61-2.28 (3H, m), 2.02 (1H, m).

Ex 109

$^1$H NMR (CDCl$_3$) delta 8.60 (1H, br d, J=4.9 Hz), 7.48 (1H, br d, J=7.9 Hz), 7.36 (1H, m), 7.26-7.23 (1H, br), 7.24 (1H, dd, J=7.9, 4.9 Hz), 6.91-6.84 (2H, m), 4.75 (1H, m), 4.62 (1H, dd, J=14.7, 6.1 Hz), 4.53 (1H, dd, J=14.7, 5.5 Hz), 4.49 (1H, br s), 2.61-2.27 (3H, m), 2.02 (1H, m).

Ex 111

$^1$H NMR (CDCl$_3$) delta 8.60 (1H, br d, J=4.9 Hz), 7.48 (1H, br d, J=7.9 Hz), 7.32 (1H, dd, J=7.9, 7.9 Hz), 7.25 (1H, dd, J=7.9, 4.9 Hz), 7.21 (1H, br), 7.16-7.14 (2H, m), 4.74 (1H, m), 4.62 (1H, dd, J=15.3, 6.1 Hz), 4.54 (1H, dd, J=15.3, 5.5 Hz), 4.43 (1H, br s), 2.61-2.27 (3H, m), 2.01 (1H, m).

Ex 116

$^1$H NMR (CDCl$_3$) delta 8.60 (1H, ddd, J=4.9, 1.8, 1.2 Hz), 7.52 (1H, ddd, J=7.9, 1.8, 1.2 Hz), 7.29 (1H, dd, J=1.8, 1.8 Hz), 7.25 (1H, dd, J=7.9, 4.9 Hz), 7.14-7.08 (1H, br), 7.11 (1H, ddd, J=9.2, 1.8, 1.8 Hz), 4.79-4.63 (3H, m), 4.46 (1H, br), 2.61-2.26 (3H, m), 2.02 (1H, m).

Ex 117

$^1$H NMR was identified with the Example 116.

EX 119

$^1$H NMR (CDCl$_3$) delta 8.57 (1H, br d, J=4.9 Hz), 7.44 (1H, d, J=1.8 Hz), 7.43 (1H, br d, J=7.9 Hz), 7.37 (1H, d, J=8.6 Hz), 7.30 (1H, dd, J=8.6, 1.8 Hz), 7.20 (1H, dd, J=7.9, 4.9 Hz), 7.17 (1H, br), 5.45 (1H, m), 4.73 (1H, m), 4.38 (1H, br), 2.62-2.30 (3H, m), 2.02 (1H, m), 1.59 (3H, d, J=7.3 Hz).

The following Examples and Intermediates were prepared by General Procedure N (Tables 38 and 40).

General Procedure N

A mixture of substrate (1.0 eq.) and 2 N aq. NaOH (2.0 eq.) in MeOH was stirred at room temperature for 1.5 h, 2 N hydrochloric acid (2.2 eq.) was added to the mixture. The mixture was concentrated in vacuo. Toluene and MeCN was added to the resulting mixture and concentrated in vacuo. This procedure was repeated 3 times to remove remaining water. The residual powder was dissolved with THF and amine (1.1 eq.), triethylamine (1.3 eq.), and DMT-MM (1.8 eq.) were added to the mixture at ambient temperature. After being stirred until complete reaction, the insoluble material was removed by filtration, and the filtrate was concentrated in vacuo. The resulting residue was purified by silica gel column chromatography, and/or SCX cartridge column, and then preparative HPLC to afford the following Examples and Intermediates.

TABLE 38

| Examples | Structure | Chemical Name | Substrate | Amine |
| --- | --- | --- | --- | --- |
| 126 | 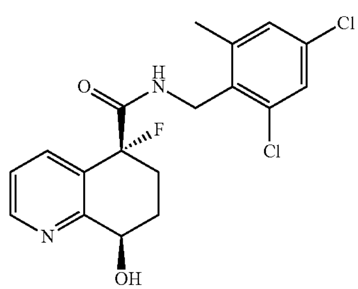 [SMILES: Cc1cc(Cl)cc(Cl)c1CNC(=O)[C@@]1(F)CC[C@@H](O)c2ncccc21] | (5R,8R)-N-(2,4-dichloro-6-methylbenzyl)-5-fluoro-8-hydroxy-5,6,7,8-tetrahydroquinoline-5-carboxamide | IM II-d-6 | |
| 127 | 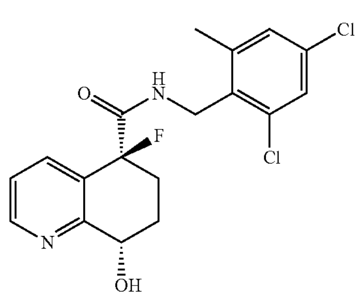 [SMILES: Cc1cc(Cl)cc(Cl)c1CNC(=O)[C@]1(F)CC[C@H](O)c2ncccc21] | (5S,8S)-N-(2,4-dichloro-6-methylbenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 128 | 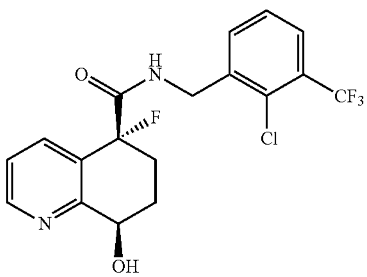 [SMILES: O=C(NCc1cccc(C(F)(F)F)c1Cl)[C@@]1(F)CC[C@@H](O)c2ncccc21] | (5R,8R)-N-(2-chloro-3-(trifluoromethyl)benzyl)-5-fluoro-8-hydroxy-5,6,7,8-tetrahydroquinoline-5-carboxamide | IM II-d-6 | |
| 129 | 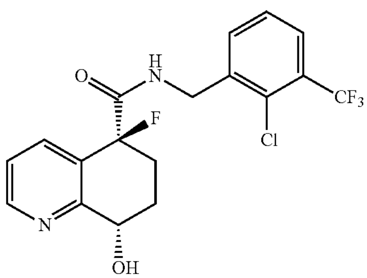 [SMILES: O=C(NCc1cccc(C(F)(F)F)c1Cl)[C@]1(F)CC[C@H](O)c2ncccc21] | (5S,8S)-N-(2-chloro-3-(trifluoromethyl)benzyl)-5-fluoro-8-hydroxy-5,6,7,8-tetrahydroquinoline-5-carboxamide | IM II-d-4 | |
| 130 | 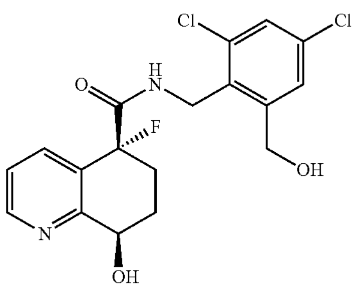 [SMILES: O=C(NCc1c(Cl)cc(Cl)cc1CO)[C@@]1(F)CC[C@@H](O)c2ncccc21] | (5R,8R)-N-(2,4-dichloro-6-(hydroxymethyl)benzyl)-5-fluoro-8-hydroxy-5,6,7,8-tetrahydroquinoline-5-carboxamide | IM II-d-6 | |
| 131 | 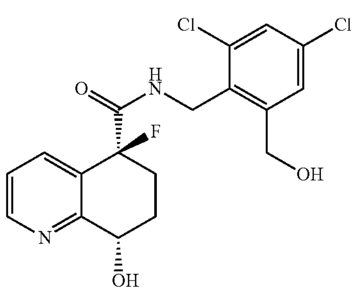 [SMILES: O=C(NCc1c(Cl)cc(Cl)cc1CO)[C@]1(F)CC[C@H](O)c2ncccc21] | (5S,8S)-N-(2,4-dichloro-6-(hydroxymethyl)benzyl)-5-fluoro-8-hydroxy-5,6,7,8-tetrahydroquinoline-5-carboxamide | IM II-d-4 | |
| 132 | 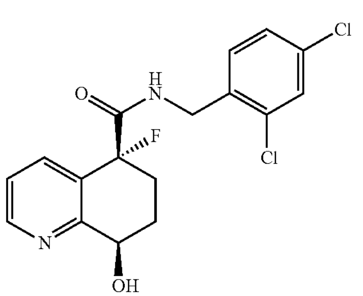 [SMILES: O=C(NCc1ccc(Cl)cc1Cl)[C@@]1(F)CC[C@@H](O)c2ncccc21] | (5R,8R)-N-(2,4-dichlorobenzyl)-5-fluoro-8-hydroxy-5,6,7,8-tetrahydroquinoline-5-carboxamide | IM II-d-6 | |

TABLE 38-continued

| Examples | Structure | Chemical Name | Substrate | Amine |
|---|---|---|---|---|
| 133 | 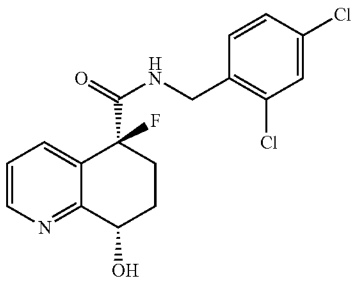 | (5S,8S)-N-(2,4-dichlorobenzyl)-5-fluoro-8-hydroxy-5,6,7,8-tetrahydroquinoline-5-carboxamide | IM II-d-4 | |
| 134 | 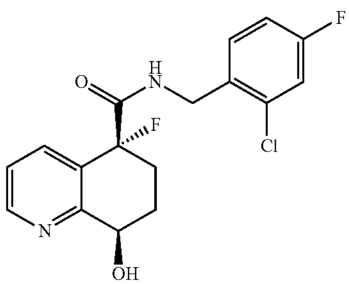 [SMILES: O=C(NCc1ccc(F)cc1Cl)[C@@]1(F)CC[C@@H](O)c2ncccc21] | (5R,8R)-N-(2-chloro-4-fluorobenzyl)-5-fluoro-8-hydroxy-5,6,7,8-tetrahydroquinoline-5-carboxamide | IM II-d-6 | |
| 135 | 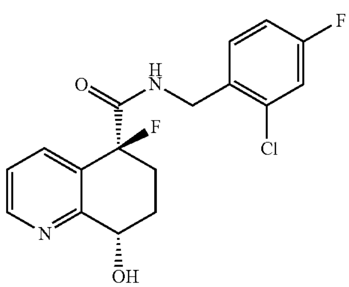 [SMILES: O=C(NCc1ccc(F)cc1Cl)[C@]1(F)CC[C@H](O)c2ncccc21] | (5S,8S)-N-(2-chloro-4-fluorobenzyl)-5-fluoro-8-hydroxy-5,6,7,8-tetrahydroquinoline-5-carboxamide | IM II-d-4 | |
| 136 | 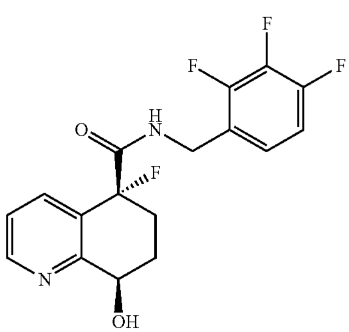 [SMILES: O=C(NCc1ccc(F)c(F)c1F)[C@@]1(F)CC[C@@H](O)c2ncccc21] | (5R,8R)-5-fluoro-8-hydroxy-N-(2,3,4-trifluorobenzyl)-5,6,7,8-tetrahydroquinoline-5-carboxamide | IM II-d-6 | |
| 137 | 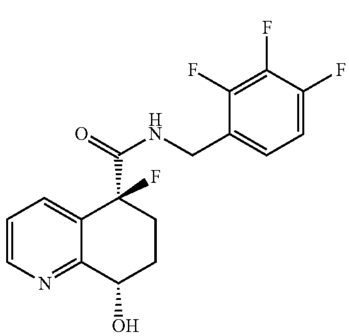 [SMILES: O=C(NCc1ccc(F)c(F)c1F)[C@]1(F)CC[C@H](O)c2ncccc21] | (5S,8S)-5-fluoro-8-hydroxy-N-(2,3,4-trifluorobenzyl)-5,6,7,8-tetrahydroquinoline-5-carboxamide | IM II-d-4 | |

TABLE 38-continued

| Examples | Structure | Chemical Name | Substrate | Amine |
|---|---|---|---|---|
| 138 | 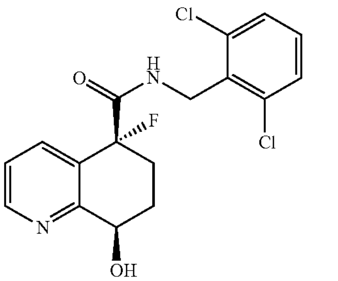 [SMILES: O=C(NCc1c(Cl)cccc1Cl)[C@@]1(F)CC[C@@H](O)c2ncccc21] | (5R,8R)-N-(2,6-dichloro-benzyl)-5-fluoro-8-hydroxy-5,6,7,8-tetrahydroquinoline-5-carboxamide | IM II-d-6 | |
| 139 | 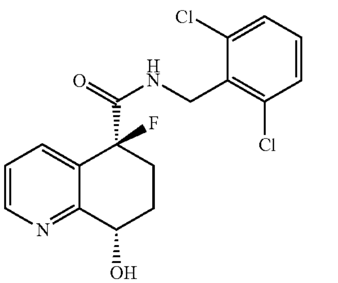 | (5S,8S)-N-(2,6-dichloro-benzyl)-5-fluoro-8-hydroxy-5,6,7,8-tetrahydroquinoline-5-carboxamide | IM II-d-4 | |
| 140 | 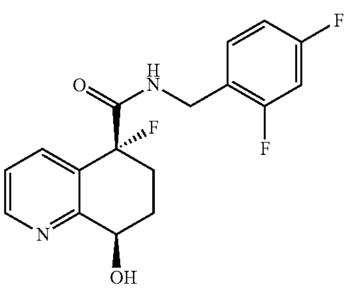 [SMILES: O=C(NCc1ccc(F)cc1F)[C@@]1(F)CC[C@@H](O)c2ncccc21] | (5R,8R)-N-(2,4-difluoro-benzyl)-5-fluoro-8-hydroxy-5,6,7,8-tetrahydroquinoline-5-carboxamide | IM II-d-6 | |
| 141 | 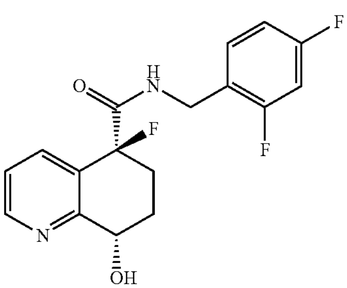 [SMILES: O=C(NCc1ccc(F)cc1F)[C@]1(F)CC[C@H](O)c2ncccc21] | (5S,8S)-N-(2,4-difluoro-benzyl)-5-fluoro-8-hydroxy-5,6,7,8-tetrahydroquinoline-5-carboxamide | IM II-d-4 | |
| 142 | 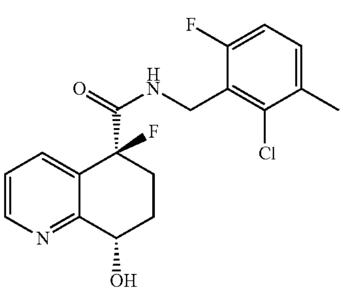 [SMILES: Cc1ccc(F)c(CNC(=O)[C@]2(F)CC[C@H](O)c3ncccc32)c1Cl] | (5S,8S)-N-(2-chloro-6-fluoro-3-methylbenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 143 | 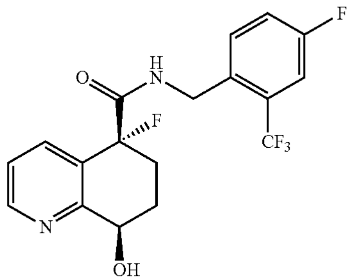 [SMILES: O=C(NCc1ccc(F)cc1C(F)(F)F)[C@@]1(F)CC[C@@H](O)c2ncccc21] | (5R,8R)-5-fluoro-N-(4-fluoro-2-(trifluoromethyl)benzyl)-8-hydroxy-5,6,7,8-tetrahydroquinoline-5-carboxamide | IM II-d-6 | |
| 144 | 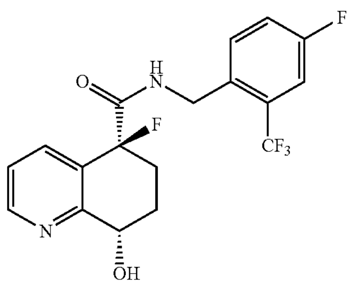 | (5S,8S)-5-fluoro-N-(4-fluoro-2-(trifluoromethyl)benzyl)-8-hydroxy-5,6,7,8-tetrahydroquinoline-5-carboxamide | IM II-d-4 | |
| 145 | 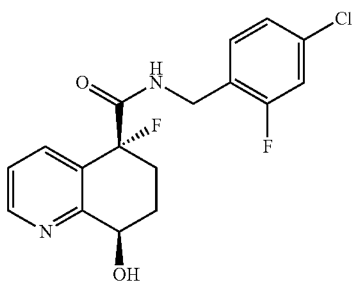 [SMILES: O=C(NCc1ccc(Cl)cc1F)[C@@]1(F)CC[C@@H](O)c2ncccc21] | (5R,8R)-N-(4-chloro-2-fluorobenzyl)-5-fluoro-8-hydroxy-5,6,7,8-tetrahydroquinoline-5-carboxamide | IM II-d-6 | |
| 146 | 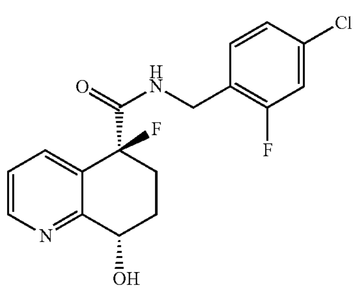 [SMILES: O=C(NCc1ccc(Cl)cc1F)[C@]1(F)CC[C@H](O)c2ncccc21] | (5S,8S)-N-(4-chloro-2-fluorobenzyl)-5-fluoro-8-hydroxy-5,6,7,8-tetrahydroquinoline-5-carboxamide | IM II-d-4 | |
| 147 | 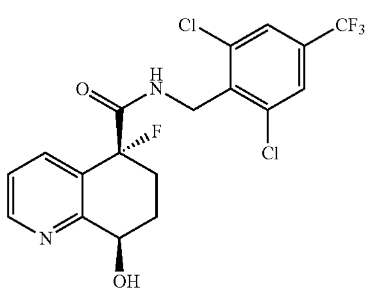 [SMILES: O=C(NCc1c(Cl)cc(C(F)(F)F)cc1Cl)[C@@]1(F)CC[C@@H](O)c2ncccc21] | (5R,8R)-N-(2,6-dichloro-4-(trifluoromethyl)benzyl)-5-fluoro-8-hydroxy-5,6,7,8-tetrahydroquinoline-5-carboxamide | IM II-d-6 | |

TABLE 38-continued

| Examples | Structure | Chemical Name | Substrate | Amine |
|---|---|---|---|---|
| 148 | 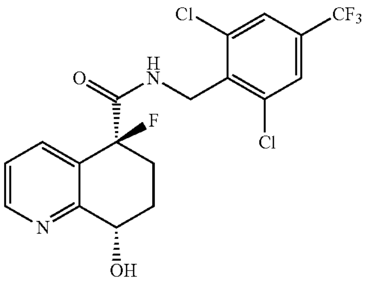 [SMILES: O=C(NCc1c(Cl)cc(C(F)(F)F)cc1Cl)[C@]1(F)CC[C@H](O)c2ncccc21] | (5S,8S)-N-(2,6-dichloro-4-(trifluoromethyl)benzyl)-5-fluoro-8-hydroxy-5,6,7,8-tetrahydroquinoline-5-carboxamide | IM II-d-4 | |
| 149 | 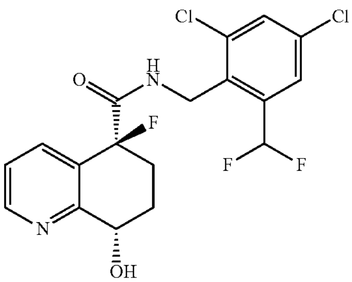 [SMILES: O=C(NCc1c(Cl)cc(Cl)cc1C(F)F)[C@]1(F)CC[C@H](O)c2ncccc21] | (5S,8S)-N-(2,4-dichloro-6-(difluoromethyl)benzyl)-5-fluoro-8-hydroxy-5,6,7,8-tetrahydroquinoline-5-carboxamide | IM II-d-4 | IM III-a-1 |
| 150 | 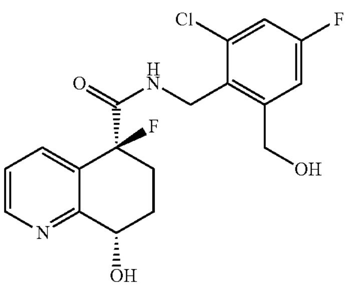 [SMILES: O=C(NCc1c(Cl)cc(F)cc1CO)[C@]1(F)CC[C@H](O)c2ncccc21] | (5S,8S)-N-(2-chloro-4-fluoro-6-(hydroxymethyl)benzyl)-5-fluoro-8-hydroxy-5,6,7,8-tetrahydroquinoline-5-carboxamide | IM II-d-4 | IM III-b-1 |
| 151 | 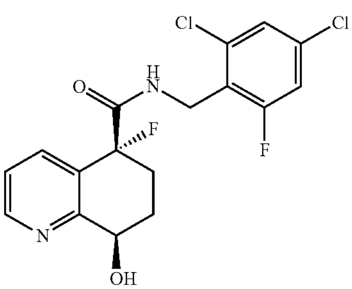 | (5R,8R)-N-(2,4-dichloro-6-fluorobenzyl)-5-fluoro-8-hydroxy-5,6,7,8-tetrahydroquinoline-5-carboxamide | IM II-d-6 | |
| 152 | 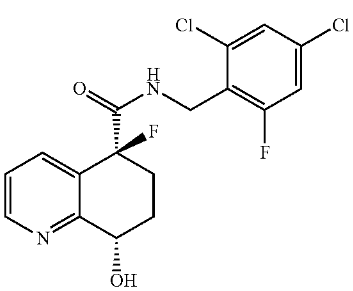 [SMILES: O=C(NCc1c(F)cc(Cl)cc1Cl)[C@]1(F)CC[C@H](O)c2ncccc21] | (5S,8S)-N-(2,4-dichloro-6-fluorobenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 153 | 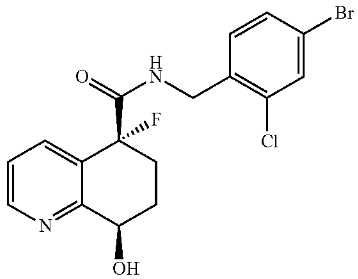 [SMILES: O=C(NCc1ccc(Br)cc1Cl)[C@@]1(F)CC[C@@H](O)c2ncccc21] | (5R,8R)-N-(4-bromo-2-chlorobenzyl)-5-fluoro-8-hydroxy-5,6,7,8-tetrahydroquinoline-5-carboxamide | IM II-d-6 | |
| 154 | 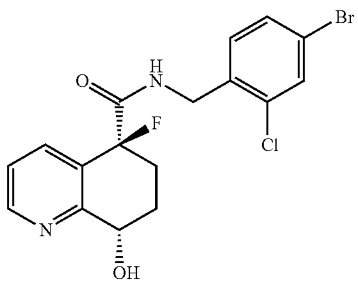 [SMILES: O=C(NCc1ccc(Br)cc1Cl)[C@]1(F)CC[C@H](O)c2ncccc21] | (5S,8S)-N-(4-bromo-2-chlorobenzyl)-5-fluoro-8-hydroxy-5,6,7,8-tetrahydroquinoline-5-carboxamide | IM II-d-4 | |
| 155 | 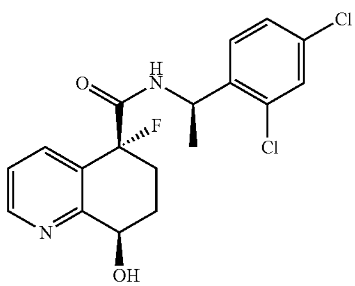 [SMILES: C[C@@H](NC(=O)[C@@]1(F)CC[C@@H](O)c2ncccc21)c1ccc(Cl)cc1Cl] | (5R,8R)-N-((R)-1-(2,4-dichlorophenyl)ethyl)-5-fluoro-8-hydroxy-5,6,7,8-tetrahydroquinoline-5-carboxamide | IM II-d-6 | |
| 156 | 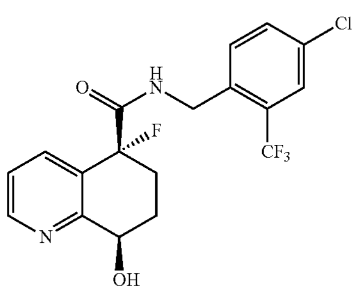 | (5R,8R)-N-(4-chloro-2-(trifluoromethyl)benzyl)-5-fluoro-8-hydroxy-5,6,7,8-tetrahydroquinoline-5-carboxamide | IM II-d-6 | |
| 157 | 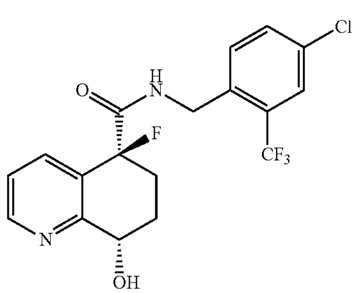 [SMILES: O=C(NCc1ccc(Cl)cc1C(F)(F)F)[C@]1(F)CC[C@H](O)c2ncccc21] | (5S,8S)-N-(4-chloro-2-(trifluoromethyl)benzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 158 | 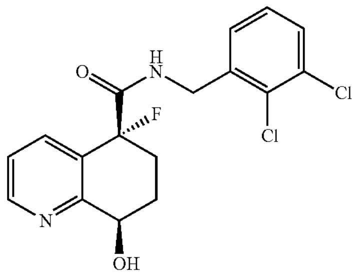 [SMILES: O=C(NCc1cccc(Cl)c1Cl)[C@@]1(F)CC[C@@H](O)c2ncccc21] | (5R,8R)-N-(2,3-dichlorobenzyl)-5-fluoro-8-hydroxy-5,6,7,8-tetrahydroquinoline-5-carboxamide | IM II-d-6 | |
| 159 | 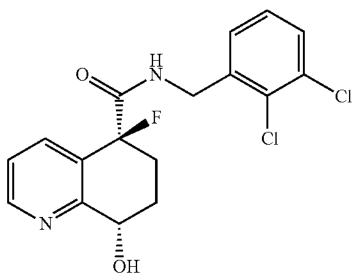 | (5S,8S)-N-(2,3-dichlorobenzyl)-5-fluoro-8-hydroxy-5,6,7,8-tetrahydroquinoline-5-carboxamide | IM II-d-4 | |
| 160 | 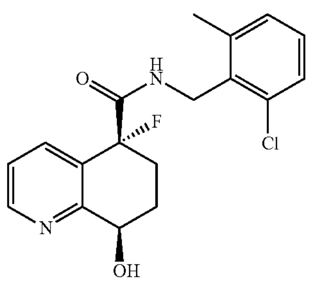 [SMILES: Cc1cccc(Cl)c1CNC(=O)[C@@]1(F)CC[C@@H](O)c2ncccc21] | (5R,8R)-N-(2-chloro-6-methylbenzyl)-5-fluoro-8-hydroxy-5,6,7,8-tetrahydroquinoline-5-carboxamide | IM II-d-6 | |
| 161 | 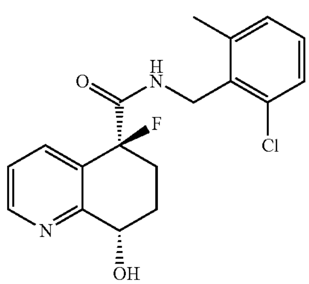 [SMILES: Cc1cccc(Cl)c1CNC(=O)[C@]1(F)CC[C@H](O)c2ncccc21] | (5S,8S)-N-(2-chloro-6-methylbenzyl)-5-fluoro-8-hydroxy-5,6,7,8-tetrahydroquinoline-5-carboxamide | IM II-d-4 | |
| 162 | 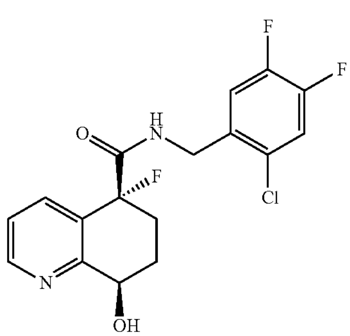 [SMILES: O=C(NCc1cc(F)c(F)cc1Cl)[C@@]1(F)CC[C@@H](O)c2ncccc21] | (5R,8R)-N-(2-chloro-4,5-difluorobenzyl)-5-fluoro-8-hydroxy-5,6,7,8-tetrahydroquinoline-5-carboxamide | IM II-d-6 | |

TABLE 38-continued

| Examples | Structure | Chemical Name | Substrate | Amine |
|---|---|---|---|---|
| 163 | 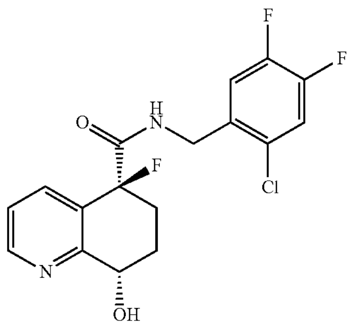 [SMILES: O=C(NCc1cc(F)c(F)cc1Cl)[C@]1(F)CC[C@H](O)c2ncccc21] | (5S,8S)-N-(2-chloro-4,5-difluorobenzyl)-5-fluoro-8-hydroxy-5,6,7,8-tetrahydroquinoline-5-carboxamide | IM II-d-4 | |
| 164 | 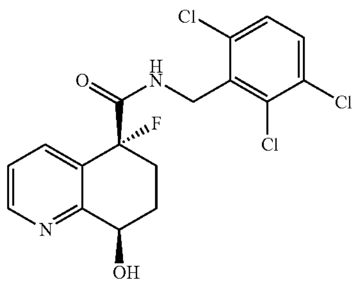 [SMILES: O=C(NCc1c(Cl)ccc(Cl)c1Cl)[C@@]1(F)CC[C@@H](O)c2ncccc21] | (5R,8R)-5-fluoro-8-hydroxy-N-(2,3,6-trichlorobenzyl)-5,6,7,8-tetrahydroquinoline-5-carboxamide | IM II-d-6 | |
| 165 | 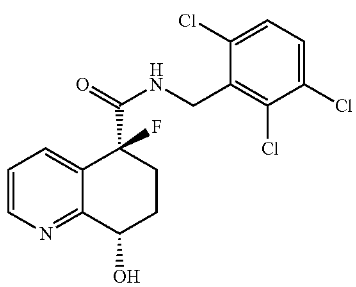 [SMILES: O=C(NCc1c(Cl)ccc(Cl)c1Cl)[C@]1(F)CC[C@H](O)c2ncccc21] | (5S,8S)-5-fluoro-8-hydroxy-N-(2,3,6-trichlorobenzyl)-5,6,7,8-tetrahydroquinoline-5-carboxamide | IM II-d-4 | |
| 166 | 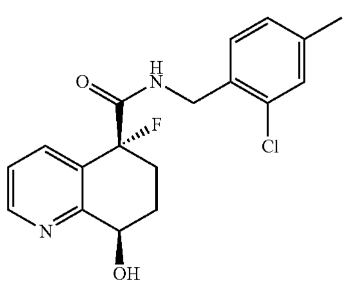 [SMILES: Cc1ccc(CNC(=O)[C@@]2(F)CC[C@@H](O)c3ncccc32)c(Cl)c1] | (5R,8R)-N-(2-chloro-4-methylbenzyl)-5-fluoro-8-hydroxy-5,6,7,8-tetrahydroquinoline-5-carboxamide | IM II-d-6 | |
| 167 | 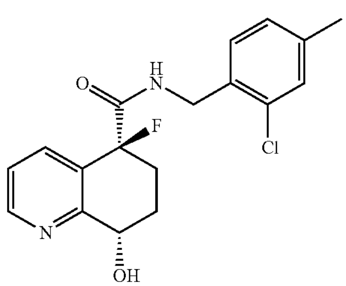 [SMILES: Cc1ccc(CNC(=O)[C@]2(F)CC[C@H](O)c3ncccc32)c(Cl)c1] | (5S,8S)-N-(2-chloro-4-methylbenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 168 | 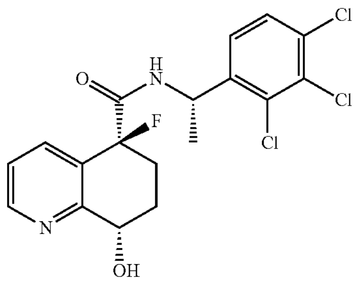 [SMILES: C[C@H](NC(=O)[C@]1(F)CC[C@H](O)c2ncccc21)c1ccc(Cl)c(Cl)c1Cl] | (5S,8S)-5-fluoro-8-hydroxy-N-((S)-1-(2,3,4-trichlorophenyl)ethyl)-5,6,7,8-tetrahydroquinoline-5-carboxamide | IM II-d-4 | |
| 169 | 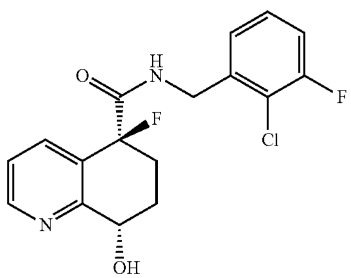 [SMILES: O=C(NCc1cccc(F)c1Cl)[C@]1(F)CC[C@H](O)c2ncccc21] | (5S,8S)-N-(2-chloro-3-fluorobenzyl)-5-fluoro-8-hydroxy-5,6,7,8-tetrahydroquinoline-5-carboxamide | IM II-d-4 | |
| 170 | 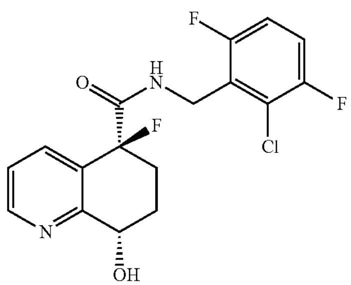 [SMILES: O=C(NCc1c(F)ccc(F)c1Cl)[C@]1(F)CC[C@H](O)c2ncccc21] | (5S,8S)-N-(2-chloro-3,6-difluorobenzyl)-5-fluoro-8-hydroxy-5,6,7,8-tetrahydroquinoline-5-carboxamide | IM II-d-4 | |
| 171 | 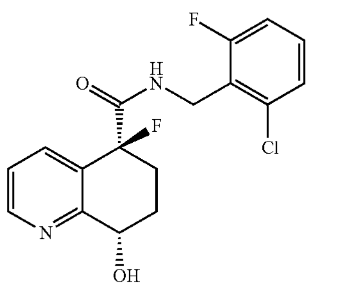 [SMILES: O=C(NCc1c(F)cccc1Cl)[C@]1(F)CC[C@H](O)c2ncccc21] | (5S,8S)-N-(2-chloro-6-fluorobenzyl)-5-fluoro-8-hydroxy-5,6,7,8-tetrahydroquinoline-5-carboxamide | IM II-d-4 | |
| 172 | 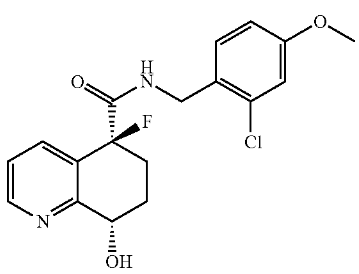 [SMILES: COc1ccc(CNC(=O)[C@]2(F)CC[C@H](O)c3ncccc32)c(Cl)c1] | (5S,8S)-N-(2-chloro-4-methoxybenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 173 | 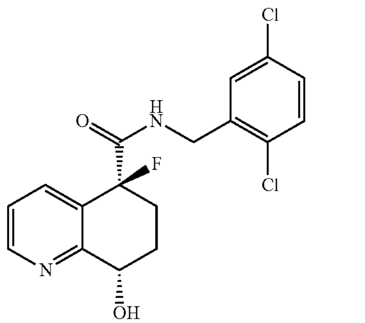 [SMILES: O=C(NCc1cc(Cl)ccc1Cl)[C@]1(F)CC[C@H](O)c2ncccc21] | (5S,8S)-N-(2,5-dichloro-benzyl)-5-fluoro-8-hydroxy-5,6,7,8-tetrahydroquinoline-5-carboxamide | IM II-d-4 | |
| 174 | 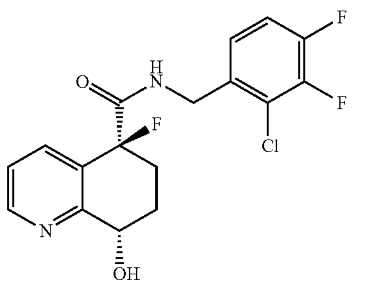 [SMILES: O=C(NCc1ccc(F)c(F)c1Cl)[C@]1(F)CC[C@H](O)c2ncccc21] | (5S,8S)-N-(2-chloro-3,4-difluorobenzyl)-5-fluoro-8-hydroxy-5,6,7,8-tetrahydroquinoline-5-carboxamide | IM II-d-4 | |
| 175 | 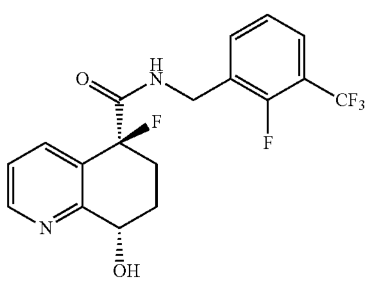 [SMILES: O=C(NCc1cccc(C(F)(F)F)c1F)[C@]1(F)CC[C@H](O)c2ncccc21] | (5S,8S)-5-fluoro-N-(2-fluoro-3-(trifluoromethyl)benzyl)-8-hydroxy-5,6,7,8-tetrahydroquinoline-5-carboxamide | IM II-d-4 | |
| 176 | 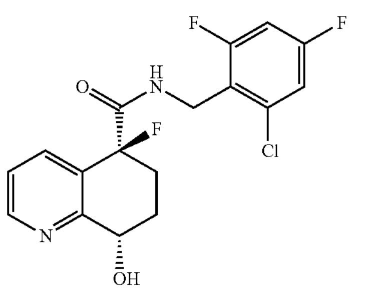 [SMILES: O=C(NCc1c(F)cc(F)cc1Cl)[C@]1(F)CC[C@H](O)c2ncccc21] | (5S,8S)-N-(2-chloro-4,6-difluorobenzyl)-5-fluoro-8-hydroxy-5,6,7,8-tetrahydroquinoline-5-carboxamide | IM II-d-4 | |
| 177 | 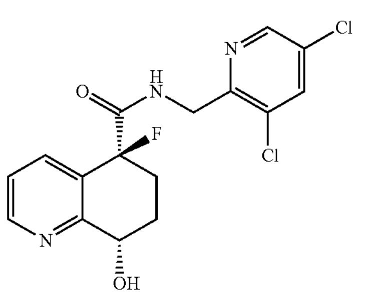 [SMILES: O=C(NCc1ncc(Cl)cc1Cl)[C@]1(F)CC[C@H](O)c2ncccc21] | (5S,8S)-N-((3,5-dichloropyridin-2-yl)methyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 178 | 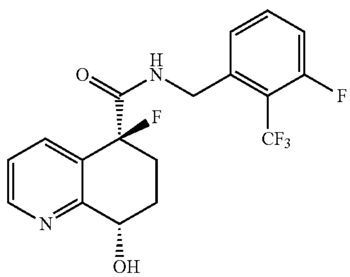 [SMILES: O=C(NCc1cccc(F)c1C(F)(F)F)[C@]1(F)CC[C@H](O)c2ncccc21] | (5S,8S)-5-fluoro-N-(3-fluoro-2-(trifluoromethyl)benzyl)-8-hydroxy-5,6,7,8-tetrahydroquinoline-5-carboxamide | IM II-d-4 | |
| 179 | 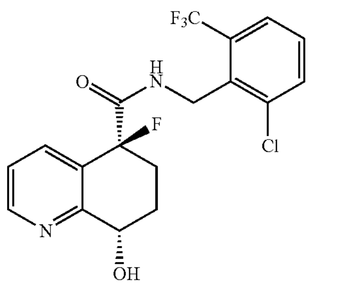 [SMILES: O=C(NCc1c(Cl)cccc1C(F)(F)F)[C@]1(F)CC[C@H](O)c2ncccc21] | (5S,8S)-N-(2-chloro-6-(trifluoromethyl)benzyl)-5-fluoro-8-hydroxy-5,6,7,8-tetrahydroquinoline-5-carboxamide | IM II-d-4 | |
| 180 | 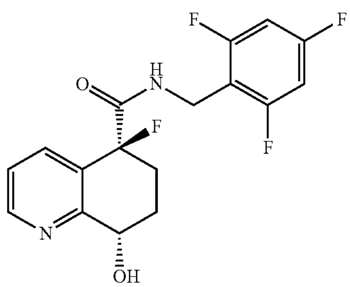 [SMILES: O=C(NCc1c(F)cc(F)cc1F)[C@]1(F)CC[C@H](O)c2ncccc21] | (5S,8S)-5-fluoro-8-hydroxy-N-(2,4,6-trifluorobenzyl)-5,6,7,8-tetrahydroquinoline-5-carboxamide | IM II-d-4 | |
| 181 | 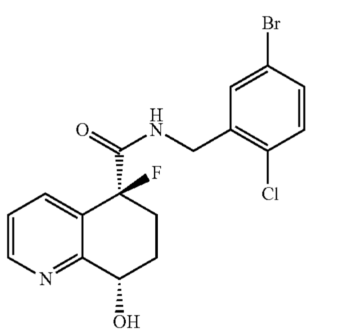 [SMILES: O=C(NCc1cc(Br)ccc1Cl)[C@]1(F)CC[C@H](O)c2ncccc21] | (5S,8S)-N-(5-bromo-2-chlorobenzyl)-5-fluoro-8-hydroxy-5,6,7,8-tetrahydroquinoline-5-carboxamide | IM II-d-4 | |
| 182 | 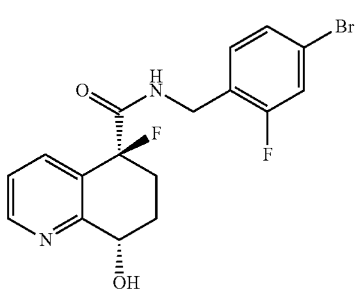 [SMILES: O=C(NCc1ccc(Br)cc1F)[C@]1(F)CC[C@H](O)c2ncccc21] | (5S,8S)-N-(4-bromo-2-fluorobenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 183 | 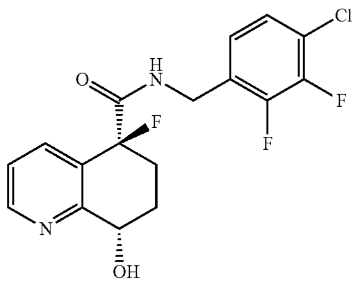 [SMILES: O=C(NCc1ccc(Cl)c(F)c1F)[C@]1(F)CC[C@H](O)c2ncccc21] | (5S,8S)-N-(4-chloro-2,3-difluorobenzyl)-5-fluoro-8-hydroxy-5,6,7,8-tetrahydroquinoline-5-carboxamide | IM II-d-4 | |
| 184 | 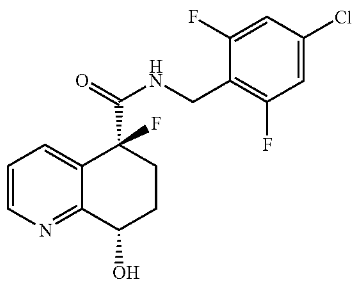 [SMILES: O=C(NCc1c(F)cc(Cl)cc1F)[C@]1(F)CC[C@H](O)c2ncccc21] | (5S,8S)-N-(4-chloro-2,6-difluorobenzyl)-5-fluoro-8-hydroxy-5,6,7,8-tetrahydroquinoline-5-carboxamide | IM II-d-4 | |
| 185 | 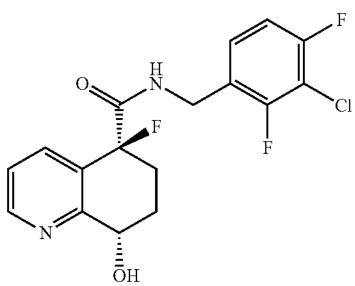 [SMILES: O=C(NCc1ccc(F)c(Cl)c1F)[C@]1(F)CC[C@H](O)c2ncccc21] | (5S,8S)-N-(3-chloro-2,4-difluorobenzyl)-5-fluoro-8-hydroxy-5,6,7,8-tetrahydroquinoline-5-carboxamide | IM II-d-4 | |
| 186 | 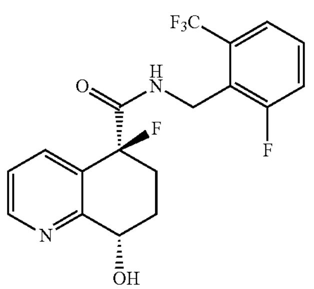 [SMILES: O=C(NCc1c(F)cccc1C(F)(F)F)[C@]1(F)CC[C@H](O)c2ncccc21] | (5S,8S)-5-fluoro-N-(2-fluoro-6-(trifluoromethyl)benzyl)-8-hydroxy-5,6,7,8-tetrahydroquinoline-5-carboxamide | IM II-d-4 | |
| 187 | 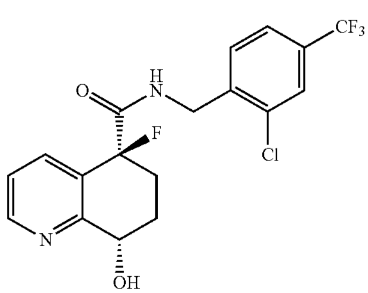 | (5S,8S)-N-(2-chloro-4-(trifluoromethyl)benzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 188 | 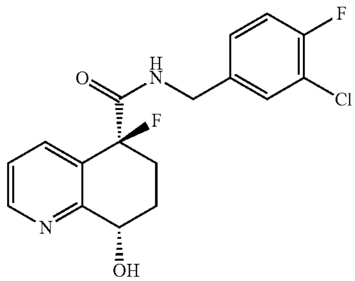 | (5S,8S)-N-(3-chloro-4-fluorobenzyl)-5-fluoro-8-hydroxy-5,6,7,8-tetrahydroquinoline-5-carboxamide | IM II-d-4 | |
| 189 | 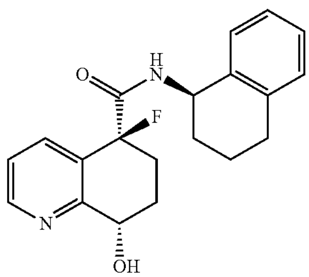 [SMILES: O=C(N[C@@H]1CCCc2ccccc21)[C@]1(F)CC[C@H](O)c2ncccc21] | (5S,8S)-5-fluoro-8-hydroxy-N-((R)-1,2,3,4-tetrahydronaphthalen-1-yl)-5,6,7,8-tetrahydroquinoline-5-carboxamide | IM II-d-4 | |
| 190 | 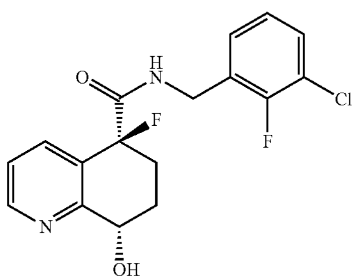 [SMILES: O=C(NCc1cccc(Cl)c1F)[C@]1(F)CC[C@H](O)c2ncccc21] | (5S,8S)-N-(3-chloro-2-fluorobenzyl)-5-fluoro-8-hydroxy-5,6,7,8-tetrahydroquinoline-5-carboxamide | IM II-d-4 | |
| 191 | 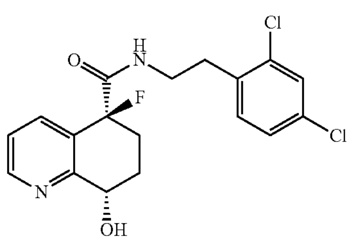 [SMILES: O=C(NCCc1ccc(Cl)cc1Cl)[C@]1(F)CC[C@H](O)c2ncccc21] | (5S,8S)-N-(2,4-dichlorophenethyl)-5-fluoro-8-hydroxy-5,6,7,8-tetrahydroquinoline-5-carboxamide | IM II-d-4 | |
| 192 | 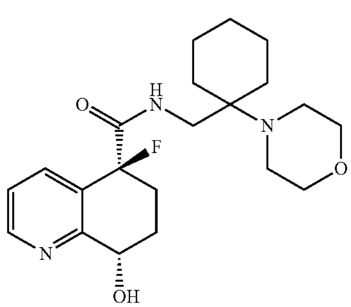 [SMILES: O=C(NCC1(N2CCOCC2)CCCCC1)[C@]1(F)CC[C@H](O)c2ncccc21] | (5S,8S)-5-fluoro-8-hydroxy-N-((1-morpholinocyclohexyl)methyl)-5,6,7,8-tetrahydroquinoline-5-carboxamide | IM II-d-4 | |

TABLE 38-continued

| Examples | Structure | Chemical Name | Substrate | Amine |
|---|---|---|---|---|
| 193 | 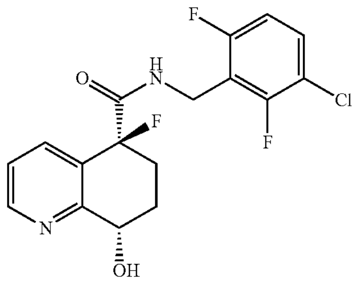 [SMILES: O=C(NCc1c(F)ccc(Cl)c1F)[C@]1(F)CC[C@H](O)c2ncccc21] | (5S,8S)-N-(3-chloro-2,6-difluorobenzyl)-5-fluoro-8-hydroxy-5,6,7,8-tetrahydroquinoline-5-carboxamide | IM II-d-4 | |
| 194 | 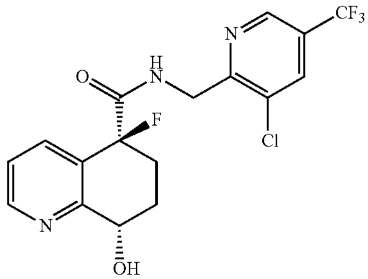 [SMILES: O=C(NCc1ncc(C(F)(F)F)cc1Cl)[C@]1(F)CC[C@H](O)c2ncccc21] | (5S,8S)-N-((3-chloro-5-(trifluoromethyl)pyridin-2-yl)methyl-5-fluoro-8-hydroxy-5,6,7,8-tetrahydroquinoline-5-carboxamide | IM II-d-4 | |
| 195 | 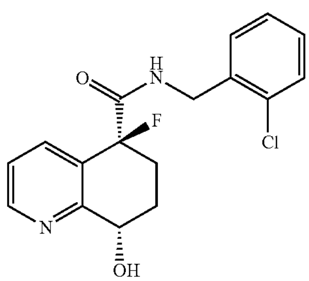 [SMILES: O=C(NCc1ccccc1Cl)[C@]1(F)CC[C@H](O)c2ncccc21] | (5S,8S)-N-(2-chlorobenzyl)-5-fluoro-8-hydroxy-5,6,7,8-tetrahydroquinoline-5-carboxamide | IM II-d-4 | |
| 196 | 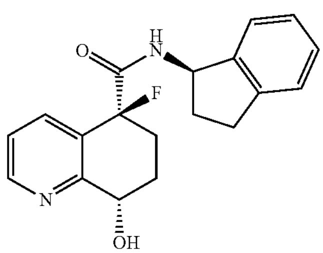 [SMILES: O=C(N[C@@H]1CCc2ccccc21)[C@]1(F)CC[C@H](O)c2ncccc21] | (5S,8S)-N-((R)-2,3-dihydro-1H-inden-1-yl)-5-fluoro-8-hydroxy-5,6,7,8-tetrahydroquinoline-5-carboxamide | IM II-d-4 | |
| 197 | 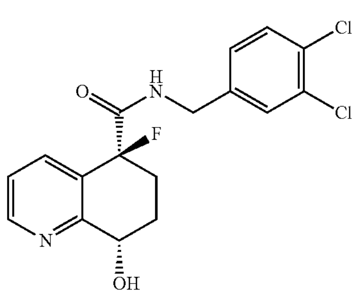 [SMILES: O=C(NCc1ccc(Cl)c(Cl)c1)[C@]1(F)CC[C@H](O)c2ncccc21] | (5S,8S)-N-(3,4-dichlorobenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 198 | 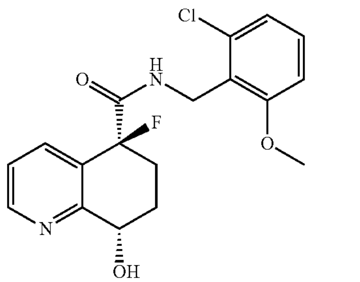 [SMILES: COc1cccc(Cl)c1CNC(=O)[C@]1(F)CC[C@H](O)c2ncccc21] | (5S,8S)-N-(2-chloro-6-methoxybenzyl)-5-fluoro-8-hydroxy-5,6,7,8-tetrahydroquinoline-5-carboxamide | IM II-d-4 | |
| 199 | 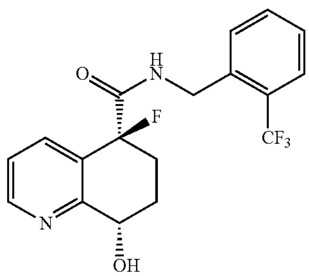 [SMILES: O=C(NCc1ccccc1C(F)(F)F)[C@]1(F)CC[C@H](O)c2ncccc21] | (5S,8S)-5-fluoro-8-hydroxy-N-(2-(trifluoromethyl)benzyl)-5,6,7,8-tetrahydroquinoline-5-carboxamide | IM II-d-4 | |
| 200 | 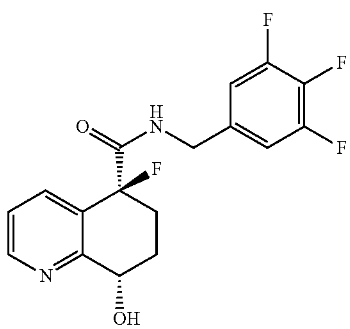 [SMILES: O=C(NCc1cc(F)c(F)c(F)c1)[C@]1(F)CC[C@H](O)c2ncccc21] | (5S,8S)-5-fluoro-8-hydroxy-N-(3,4,5-trifluorobenzyl)-5,6,7,8-tetrahydroquinoline-5-carboxamide | IM II-d-4 | |
| 201 | 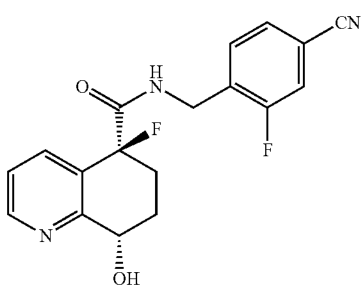 [SMILES: N#Cc1ccc(CNC(=O)[C@]2(F)CC[C@H](O)c3ncccc32)c(F)c1] | (5S,8S)-N-(4-cyano-2-fluorobenzyl)-5-fluoro-8-hydroxy-5,6,7,8-tetrahydroquinoline-5-carboxamide | IM II-d-4 | |
| 202 | 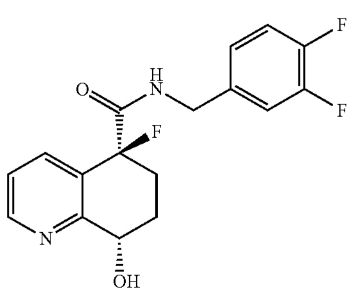 [SMILES: O=C(NCc1ccc(F)c(F)c1)[C@]1(F)CC[C@H](O)c2ncccc21] | (5S,8S)-N-(3,4-difluorobenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 203 | 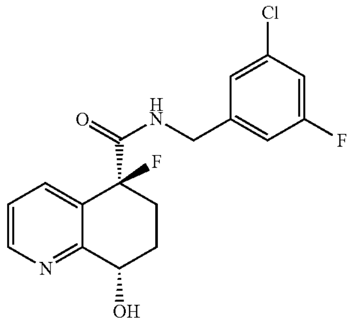 | (5S,8S)-N-(3-chloro-5-fluorobenzyl)-5-fluoro-8-hydroxy-5,6,7,8-tetrahydroquinoline-5-carboxamide | IM II-d-4 | |
| 204 | 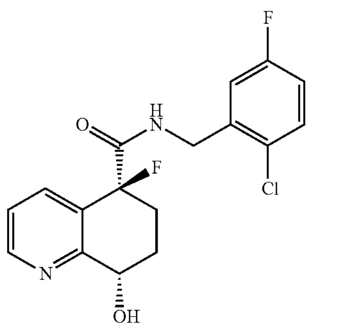 [SMILES: O=C(NCc1cc(F)ccc1Cl)[C@]1(F)CC[C@H](O)c2ncccc21] | (5S,8S)-N-(2-chloro-5-fluorobenzyl)-5-fluoro-8-hydroxy-5,6,7,8-tetrahydroquinoline-5-carboxamide | IM II-d-4 | |
| 205 | 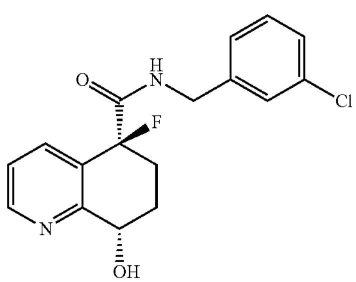 [SMILES: O=C(NCc1cccc(Cl)c1)[C@]1(F)CC[C@H](O)c2ncccc21] | (5S,8S)-N-(3-chlorobenzyl)-5-fluoro-8-hydroxy-5,6,7,8-tetrahydroquinoline-5-carboxamide | IM II-d-4 | |
| 206 | 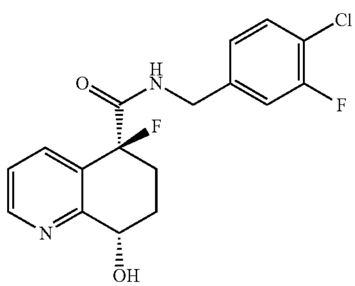 | (5S,8S)-N-(4-chloro-3-fluorobenzyl)-5-fluoro-8-hydroxy-5,6,7,8-tetrahydroquinoline-5-carboxamide | IM II-d-4 | |
| 207 | 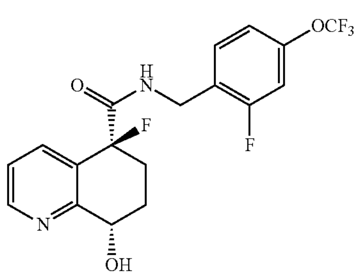 [SMILES: O=C(NCc1ccc(OC(F)(F)F)cc1F)[C@]1(F)CC[C@H](O)c2ncccc21] | (5S,8S)-5-fluoro-N-(2-fluoro-4-(trifluoromethoxy)benzyl)-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 208 | 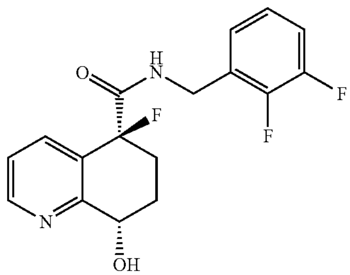 [SMILES: O=C(NCc1cccc(F)c1F)[C@]1(F)CC[C@H](O)c2ncccc21] | (5S,8S)-N-(2,3-difluorobenzyl)-5-fluoro-8-hydroxy-5,6,7,8-tetrahydroquinoline-5-carboxamide | IM II-d-4 | |
| 209 | 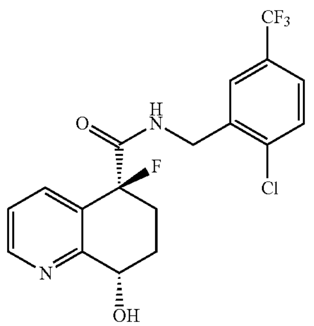 [SMILES: O=C(NCc1cc(C(F)(F)F)ccc1Cl)[C@]1(F)CC[C@H](O)c2ncccc21] | (5S,8S)-N-(2-chloro-5-(trifluoromethyl)benzyl)-5-fluoro-8-hydroxy-5,6,7,8-tetrahydroquinoline-5-carboxamide | IM II-d-4 | |
| 210 | 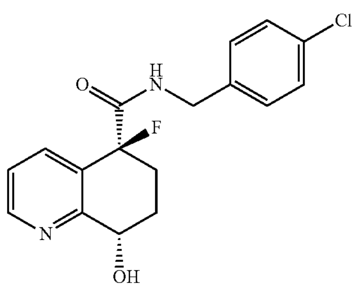 [SMILES: O=C(NCc1ccc(Cl)cc1)[C@]1(F)CC[C@H](O)c2ncccc21] | (5S,8S)-N-(4-chlorobenzyl)-5-fluoro-8-hydroxy-5,6,7,8-tetrahydroquinoline-5-carboxamide | IM II-d-4 | |
| 211 | 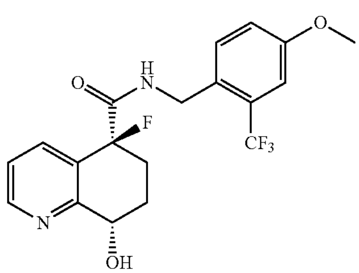 [SMILES: COc1ccc(CNC(=O)[C@]2(F)CC[C@H](O)c3ncccc32)c(C(F)(F)F)c1] | (5S,8S)-5-fluoro-8-hydroxy-N-(4-methoxy-2-(trifluoromethyl)benzyl)-5,6,7,8-tetrahydroquinoline-5-carboxamide | IM II-d-4 | |
| 212 | 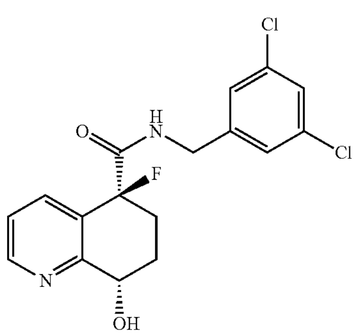 [SMILES: O=C(NCc1cc(Cl)cc(Cl)c1)[C@]1(F)CC[C@H](O)c2ncccc21] | (5S,8S)-N-(3,5-dichlorobenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 213 | 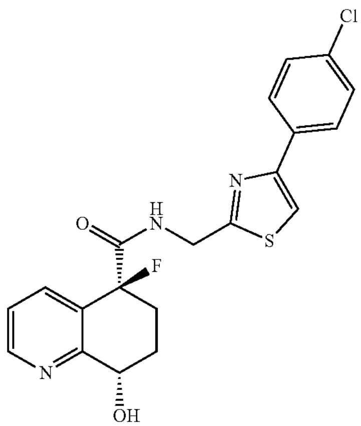 [SMILES: O=C(NCc1nc(-c2ccc(Cl)cc2)cs1)[C@]1(F)CC[C@H](O)c2ncccc21] | (5S,8S)-N-((4-(4-chlorophenyl)thiazol-2-yl)methyl)-5-fluoro-8-hydroxy-5,6,7,8-tetrahydroquinoline-5-carboxamide | IM II-d-4 | |
| 214 | 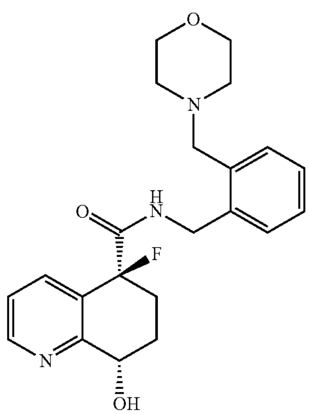 [SMILES: O=C(NCc1ccccc1CN1CCOCC1)[C@]1(F)CC[C@H](O)c2ncccc21] | (5S,8S)-5-fluoro-8-hydroxy-N-(2-(morpholinomethyl)benzyl)-5,6,7,8-tetrahydroquinoline-5-carboxamide | IM II-d-4 | |
| 215 | 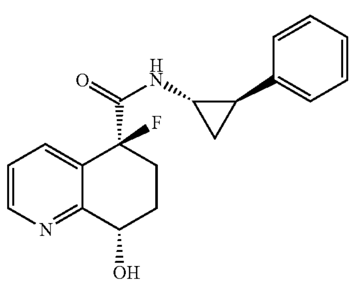 [SMILES: O=C(N[C@H]1C[C@@H]1c1ccccc1)[C@]1(F)CC[C@H](O)c2ncccc21] | (5S,8S)-5-fluoro-8-hydroxy-N-((1S,2R)-2-phenylcyclopropyl)-5,6,7,8-tetrahydroquinoline-5-carboxamide | IM II-d-4 | |
| 216 | 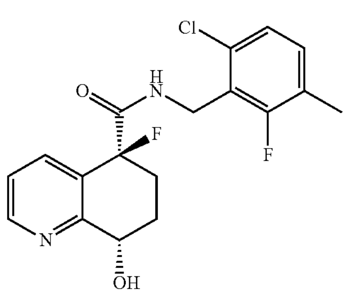 | (5S,8S)-N-(6-chloro-2-fluoro-3-methylbenzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 217 | 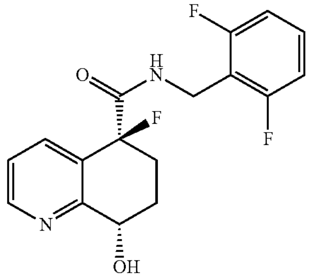 [SMILES: O=C(NCc1c(F)cccc1F)[C@]1(F)CC[C@H](O)c2ncccc21] | (5S,8S)-N-(2,6-difluoro-benzyl)-5-fluoro-8-hydroxy-5,6,7,8-tetrahydroquinoline-5-carboxamide | IM II-d-4 | |
| 218 | 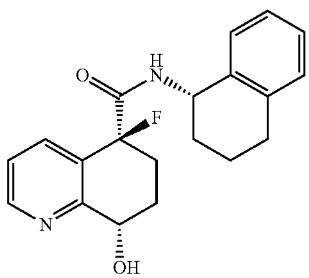 [SMILES: O=C(N[C@H]1CCCc2ccccc21)[C@]1(F)CC[C@H](O)c2ncccc21] | (5S,8S)-5-fluoro-8-hydroxy-N-((S)-1,2,3,4-tetrahydronaphthalen-1-yl)-5,6,7,8-tetrahydroquinoline-5-carboxamide | IM II-d-4 | |
| 219 | 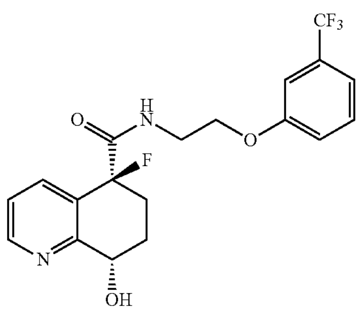 [SMILES: O=C(NCCOc1cccc(C(F)(F)F)c1)[C@]1(F)CC[C@H](O)c2ncccc21] | (5S,8S)-5-fluoro-8-hydroxy-N-(2-(3-(tri-fluoromethyl)phenoxy)ethyl)-5,6,7,8-tetrahydroquinoline-5-carboxamide | IM II-d-4 | |
| 220 | 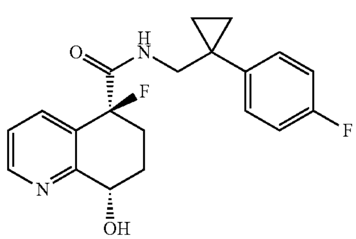 [SMILES: O=C(NCC1(c2ccc(F)cc2)CC1)[C@]1(F)CC[C@H](O)c2ncccc21] | (5S,8S)-5-fluoro-N-((1-(4-fluorophenyl)cyclo-propyl)methyl)-8-hydroxy-5,6,7,8-tetrahydroquinoline-5-carboxamide | IM II-d-4 | |
| 221 | 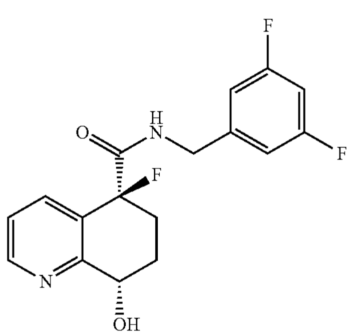 [SMILES: O=C(NCc1cc(F)cc(F)c1)[C@]1(F)CC[C@H](O)c2ncccc21] | (5S,8S)-N-(3,5-difluoro-benzyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 222 | 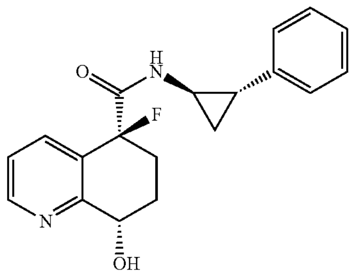 [SMILES: O=C(N[C@@H]1C[C@H]1c1ccccc1)[C@]1(F)CC[C@H](O)c2ncccc21] | (5S,8S)-5-fluoro-8-hydroxy-N-((1R,2S)-2-phenylcyclopropyl)-5,6,7,8-tetrahydroquinoline-5-carboxamide | IM II-d-4 | |
| 223 | 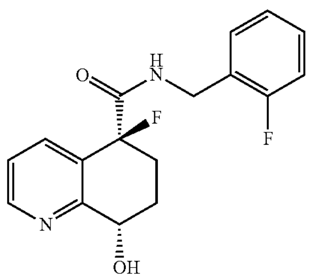 [SMILES: O=C(NCc1ccccc1F)[C@]1(F)CC[C@H](O)c2ncccc21] | (5S,8S)-5-fluoro-N-(2-fluorobenzyl)-8-hydroxy-5,6,7,8-tetrahydroquinoline-5-carboxamide | IM II-d-4 | |
| 224 | 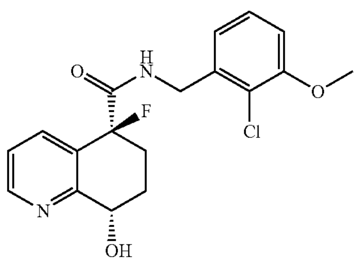 [SMILES: COc1cccc(CNC(=O)[C@]2(F)CC[C@H](O)c3ncccc32)c1Cl] | (5S,8S)-N-(2-chloro-3-methoxybenzyl)-5-fluoro-8-hydroxy-5,6,7,8-tetrahydroquinoline-5-carboxamide | IM II-d-4 | |
| 225 | 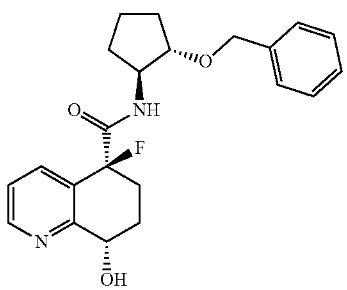 [SMILES: O=C(N[C@H]1CCC[C@@H]1OCc1ccccc1)[C@]1(F)CC[C@H](O)c2ncccc21] | (5S,8S)-N-((1S,2S)-2-(benzyloxy)cyclopentyl)-5-fluoro-8-hydroxy-5,6,7,8-tetrahydroquinoline-5-carboxamide | IM II-d-4 | |
| 226 | 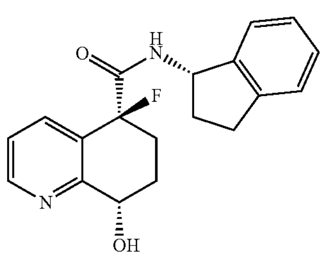 [SMILES: O=C(N[C@H]1CCc2ccccc21)[C@]1(F)CC[C@H](O)c2ncccc21] | (5S,8S)-N-((S)-2,3-dihydro-1H-inden-1-yl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 227 | 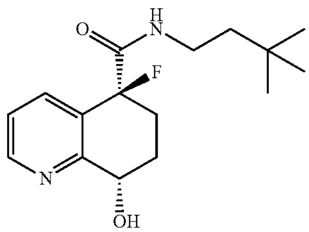 [SMILES: CC(C)(C)CCNC(=O)[C@]1(F)CC[C@H](O)c2ncccc21] | (5S,8S)-N-(3,3-dimethyl-butyl)-5-fluoro-8-hydroxy-5,6,7,8-tetrahydro-quinoline-5-carboxamide | IM II-d-4 | |
| 228 | 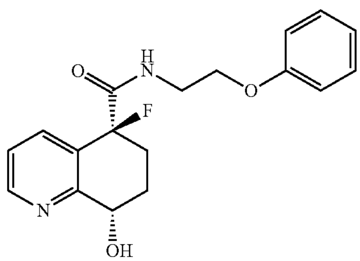 [SMILES: O=C(NCCOc1ccccc1)[C@]1(F)CC[C@H](O)c2ncccc21] | (5S,8S)-5-fluoro-8-hydroxy-N-(2-phenoxyethyl)-5,6,7,8-tetrahydroquinoline-5-carboxamide | IM II-d-4 | |
| 229 | 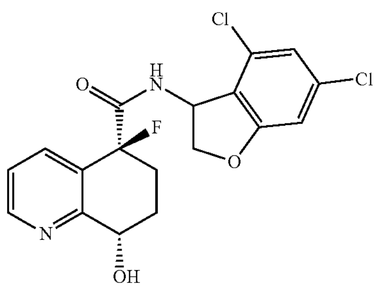 [SMILES: O=C(NC1COc2cc(Cl)cc(Cl)c21)[C@]1(F)CC[C@H](O)c2ncccc21] | (5S,8S)-N-(4,6-dichloro-2,3-dihydrobenzofuran-3-yl)-5-fluoro-8-hydroxy-5,6,7,8-tetrahydro-quinoline-5-carboxamide | IM II-d-4 | |
| 230 | 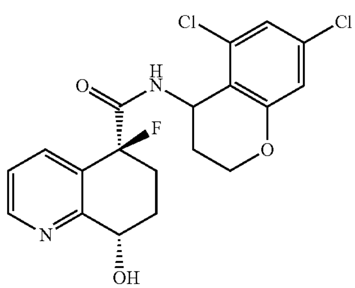 [SMILES: O=C(NC1CCOc2cc(Cl)cc(Cl)c21)[C@]1(F)CC[C@H](O)c2ncccc21] | (5S,8S)-N-(5,7-dichloro-chroman-4-yl)-5-fluoro-8-hydroxy-5,6,7,8-tetra-hydroquinoline-5-carbox-amide | IM II-d-4 | |
| 231 | 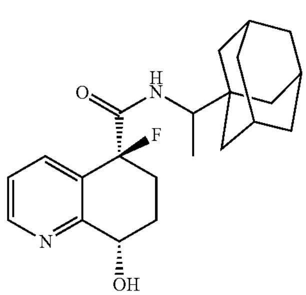 [SMILES: CC(NC(=O)[C@]1(F)CC[C@H](O)c2ncccc21)C12CC3CC(CC(C3)C1)C2] | (5S,8S)-N-(1-(adamantan-1-yl)ethyl)-5-fluoro-8-hydroxy-5,6,7,8-tetra-hydroquinoline-5-carbox-amide | IM II-d-4 | |

TABLE 38-continued

| Examples | Structure | Chemical Name | Substrate | Amine |
|---|---|---|---|---|
| 232 | 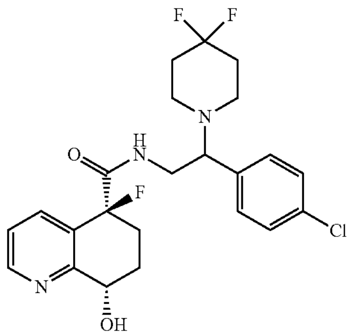 [SMILES: O=C(NCC(c1ccc(Cl)cc1)N1CCC(F)(F)CC1)[C@]1(F)CC[C@H](O)c2ncccc21] | (5S,8S)-N-(2-(4-chlorophenyl)-2-(4,4-difluoropiperidin-1-yl)ethyl)-5-fluoro-8-hydroxy-5,6,7,8-tetrahydroquinoline-5-carboxamide | IM II-d-4 | |
| 233 | 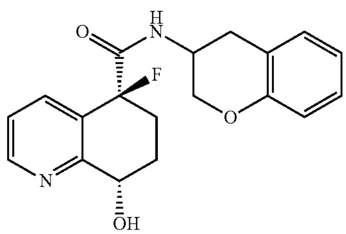 [SMILES: O=C(NC1COc2ccccc2C1)[C@]1(F)CC[C@H](O)c2ncccc21] | (5S,8S)-N-(chroman-3-yl)-5-fluoro-8-hydroxy-5,6,7,8-tetrahydroquinoline-5-carboxamide | IM II-d-4 | |
| 234 | 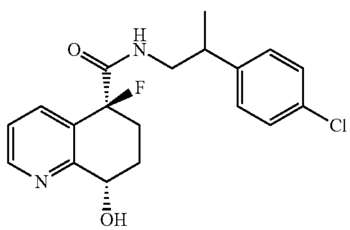 [SMILES: CC(CNC(=O)[C@]1(F)CC[C@H](O)c2ncccc21)c1ccc(Cl)cc1] | (5S,8S)-N-(2-(4-chlorophenyl)propyl)-5-fluoro-8-hydroxy-5,6,7,8-tetrahydroquinoline-5-carboxamide | IM II-d-4 | |
| 235 | 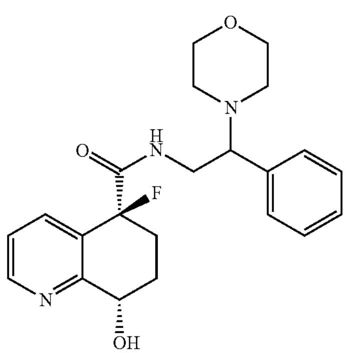 [SMILES: O=C(NCC(c1ccccc1)N1CCOCC1)[C@]1(F)CC[C@H](O)c2ncccc21] | (5S,8S)-5-fluoro-8-hydroxy-N-((rac)-2-morpholino)-2-phenylethyl)-5,6,7,8-tetrahydroquinoline-5-carboxamide | IM II-d-4 | |
| 236 | 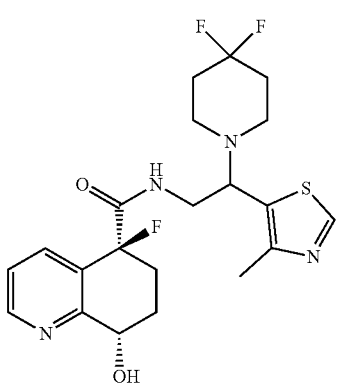 [SMILES: Cc1ncsc1C(CNC(=O)[C@]1(F)CC[C@H](O)c2ncccc21)N1CCC(F)(F)CC1] | (5S,8S)-N-(2-(4,4-difluoropiperidin-1-yl)-2-(4-methylthiazol-5-yl)ethyl)-5-fluoro-8-hydroxy-5,6,7,8-tetrahydroquinoline-5-carboxamide | IM II-d-4 | |

TABLE 38-continued

| Examples | Structure | Chemical Name | Substrate | Amine |
|---|---|---|---|---|
| 237 | 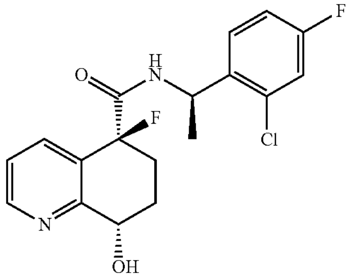 [SMILES: C[C@@H](NC(=O)[C@]1(F)CC[C@H](O)c2ncccc21)c1ccc(F)cc1Cl] | (5S,8S)-N-((R)-1-(2-chloro-4-fluorophenyl)ethyl)-5-fluoro-8-hydroxy-5,6,7,8-tetrahydroquinoline-5-carboxamide | IM II-d-4 | |
| 238 | 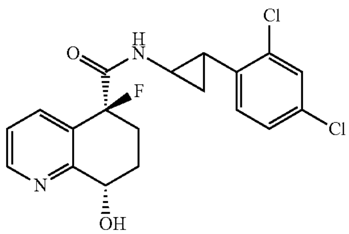 [SMILES: O=C(NC1CC1c1ccc(Cl)cc1Cl)[C@]1(F)CC[C@H](O)c2ncccc21] | (5S,8S)-N-((trans)-2-(2,4-dichlorophenyl)cyclopropyl)-5-fluoro-8-hydroxy-5,6,7,8-tetrahydroquinoline-5-carboxamide | IM II-d-4 | |
| 239 | 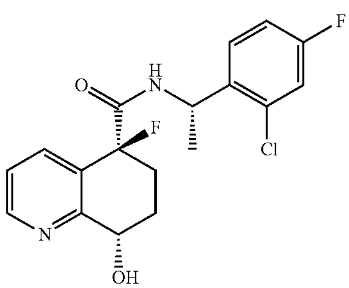 [SMILES: C[C@H](NC(=O)[C@]1(F)CC[C@H](O)c2ncccc21)c1ccc(F)cc1Cl] | (5S,8S)-N-((S)-1-(2-chloro-4-fluorophenyl)ethyl)-5-fluoro-8-hydroxy-5,6,7,8-tetrahydroquinoline-5-carboxamide | IM II-d-4 | |
| 240 | 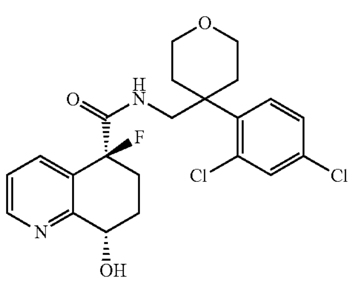 [SMILES: O=C(NCC1(c2ccc(Cl)cc2Cl)CCOCC1)[C@]1(F)CC[C@H](O)c2ncccc21] | (5S,8S)-N-((4-(2,4-dichlorophenyl)tetrahydro-2H-pyran-4-yl)methyl)-5-fluoro-8-hydroxy-5,6,7,8-tetrahydroquinoline-5-carboxamide | IM II-d-4 | |
| 241 | 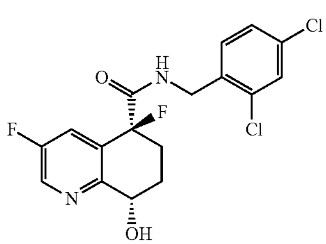 [SMILES: O=C(NCc1ccc(Cl)cc1Cl)[C@]1(F)CC[C@H](O)c2ncc(F)cc21] | (5S,8S)-N-(2,4-dichlorobenzyl)-3,5-difluoro-8-hydroxy-5,6,7,8-tetrahydroquinoline-5-carboxamide | IM II-d-8 | |
| 242 | 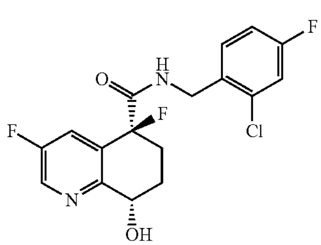 [SMILES: O=C(NCc1ccc(F)cc1Cl)[C@]1(F)CC[C@H](O)c2ncc(F)cc21] | (5S,8S)-N-(2-chloro-4-fluorobenzyl)-3,5-difluoro-8-hydroxy-5,6,7,8-tetrahydroquinoline-5-carboxamide | IM II-d-8 | |

TABLE 38-continued

| Examples | Structure | Chemical Name | Substrate | Amine |
|---|---|---|---|---|
| 243 | 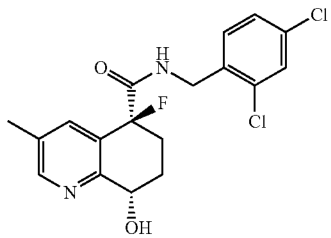 [SMILES: Cc1cnc2c(c1)[C@](F)(C(=O)NCc1ccc(Cl)cc1Cl)CC[C@@H]2O] | (5S,8S)-N-(2,4-dichlorobenzyl)-5-fluoro-8-hydroxy-3-methyl-5,6,7,8-tetrahydroquinoline-5-carboxamide | IM II-d-10 | |
| 244 | 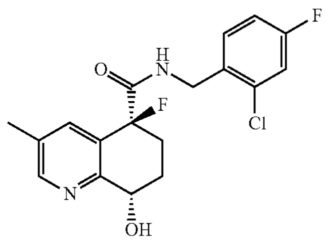 [SMILES: Cc1cnc2c(c1)[C@](F)(C(=O)NCc1ccc(F)cc1Cl)CC[C@@H]2O] | (5S,8S)-N-(2-chloro-4-fluorobenzyl)-5-fluoro-8-hydroxy-3-methyl-5,6,7,8-tetrahydroquinoline-5-carboxamide | IM II-d-10 | |

TABLE 39

LC MS

| Examples | Method | tR (min) | [M + H]+ |
|---|---|---|---|
| 127 | A | 1.59 | 383.0 |
| 128 | A | 1.50 | 403.1 |
| 129 | A | 1.50 | 403.1 |
| 132 | A | 1.49 | 369.1 |
| 133 | A | 1.49 | 369.1 |
| 134 | A | 1.38 | 353.1 |
| 135 | A | 1.38 | 353.1 |
| 136 | C | 1.34 | 355.0 |
| 137 | B | 1.27 | 355.1 |
| 138 | A | 1.41 | 369.1 |
| 139 | A | 1.41 | 369.1 |
| 140 | C | 1.29 | 337.1 |
| 141 | B | 1.22 | 337.1 |
| 142 | A | 1.45 | 367.2 |
| 143 | C | 1.45 | 387.0 |
| 144 | A | 1.45 | 387.0 |
| 145 | C | 1.40 | 353.0 |
| 146 | A | 1.40 | 353.0 |
| 147 | A | 1.60 | 437.1 |
| 148 | A | 1.60 | 437.0 |
| 149 | A | 1.58 | 419.1 |
| 150 | D | 1.26 | 383.1 |
| 151 | C | 1.48 | 386.9 |
| 152 | B | 1.41 | 387.0 |
| 153 | A | 1.52 | 413.0 |
| 154 | A | 1.52 | 413.0 |
| 155 | A | 1.56 | 383.2 |
| 156 | C | 1.55 | 403.0 |
| 157 | B | 1.49 | 403.0 |
| 158 | A | 1.45 | 369.1 |
| 159 | A | 1.46 | 369.1 |
| 160 | A | 1.44 | 349.2 |
| 161 | A | 1.44 | 349.2 |
| 162 | A | 1.41 | 371.2 |
| 163 | A | 1.41 | 371.2 |
| 164 | A | 1.51 | 403.1 |
| 165 | A | 1.52 | 403.0 |
| 166 | A | 1.46 | 349.2 |
| 167 | A | 1.46 | 349.2 |
| 168 | A | 1.64 | 417.1 |
| 169 | A | 1.36 | 353.2 |
| 170 | A | 1.35 | 371.2 |
| 171 | A | 1.34 | 353.1 |
| 172 | A | 1.38 | 365.2 |
| 173 | A | 1.45 | 369.1 |
| 174 | B | 1.34 | 370.9 |
| 175 | A | 1.44 | 387.0 |
| 176 | C | 1.37 | 370.9 |
| 177 | B | 1.29 | 370.0 |
| 178 | C | 1.42 | 387.1 |
| 179 | A | 1.46 | 403.0 |
| 180 | B | 1.22 | 355.1 |
| 181 | A | 1.48 | 413.0 |
| 182 | B | 1.35 | 397.0 |
| 183 | C | 1.42 | 370.9 |
| 184 | C | 1.40 | 370.9 |
| 185 | C | 1.41 | 370.9 |
| 186 | B | 1.33 | 387.0 |
| 187 | A | 1.45 | 387.0 |
| 188 | B | 1.31 | 353.1 |
| 189 | C | 1.46 | 341.1 |
| 190 | A | 1.37 | 353.1 |
| 191 | B | 1.46 | 383.0 |
| 192 | C | 1.44 | 392.2 |
| 193 | B | 1.30 | 371.0 |
| 194 | C | 1.43 | 404.0 |
| 195 | A | 1.34 | 335.0 |
| 196 | C | 1.38 | 327.1 |
| 197 | A | 1.47 | 369.0 |
| 198 | A | 1.40 | 365.2 |
| 199 | B | 1.35 | 369.1 |
| 200 | C | 1.35 | 355.1 |
| 201 | B | 1.12 | 344.1 |
| 202 | A | 1.30 | 337.1 |
| 203 | B | 1.33 | 353.1 |
| 204 | A | 1.36 | 353.2 |
| 205 | A | 1.35 | 335.1 |
| 206 | B | 1.32 | 353.1 |
| 207 | B | 1.43 | 403.0 |
| 208 | A | 1.28 | 337.1 |
| 209 | A | 1.50 | 403.1 |
| 210 | B | 1.29 | 335.1 |
| 211 | B | 1.39 | 399.1 |
| 212 | B | 1.43 | 369.0 |
| 213 | C | 1.52 | 418.0 |
| 214 | C | 1.36 | 400.1 |
| 215 | C | 1.35 | 327.1 |
| 216 | A | 1.45 | 367.2 |

TABLE 39-continued

| | LC MS | | |
|---|---|---|---|
| Examples | Method | tR (min) | [M + H]+ |
| 217 | B | 1.18 | 337.1 |
| 218 | C | 1.46 | 341.1 |
| 219 | C | 1.48 | 399.1 |
| 220 | C | 1.44 | 359.1 |
| 221 | B | 1.23 | 337.1 |
| 222 | C | 1.35 | 327.1 |
| 223 | B | 1.18 | 319.1 |
| 224 | B | 1.24 | 365.0 |
| 225 | C | 1.48 | 385.2 |
| 226 | C | 1.38 | 327.1 |
| 227 | C | 1.40 | 295.2 |
| 228 | C | 1.29 | 331.1 |
| 229 | C | 1.49 | 397.1 |
| 230 | C | 1.55 | 411.0 |
| 231 | C | 1.78 | 373.2 |
| 232 | D | 1.69 | 468.1 |
| 233 | C | 1.34 | 343.1 |
| 234 | C | 1.48 | 363.1 |
| 235 | C | 1.23 | 400.2 |
| 236 | D | 1.30 | 455.2 |
| 237 | D | 1.50 | 367.1 |
| 238 | D | 1.68 | 395.1 |
| 239 | D | 1.51 | 367.1 |
| 240 | D | 1.57 | 453.1 |
| 241 | C | 1.56 | 387.0 |
| 242 | C | 1.45 | 371.1 |
| 243 | D | 1.67 | 383.1 |
| 244 | D | 1.54 | 367.1 |

Ex 126

$^1$H NMR (CDCl$_3$) delta 8.59 (1H, d, J=4.6 HL), 7.53 (1H, d, J=7.9 HL), 7.31 (1H, br s), 7.25 (1H, m), 7.14 (1H, br s), 6.98 (1H, br d, J=5.3 Hz), 4.80 (1H, dd, J=5.3, 5.3 Hz), 4.70 (1H, dd, J=13.8, 5.9 Hz), 4.60 (1H, dd, J=13.8, 5.9 Hz), 3.79 (1H, br s), 2.65 (1H, m), 2.46 (3H, s), 2.40-2.28 (2H, m), 2.16 (1H, m).

MS (ESI) m/z: 382.9 (M+H)+.

Chiral HPLC tR: 13.6 min (Method I), 99.0% e.e., >99% d.e.

Ex 127

$^1$H NMR was identified with the Example 126.
Chiral HPLC tR: 17.0 min (Method I), 98.2% e.e., >99% d.e.

Ex 128

$^1$H NMR (CDCl$_3$) delta 8.58 (1H, ddd, J=4.6, 2.0, 1.3 Hz), 7.70 (1H, d, J=7.9 Hz), 7.64 (1H, d, J=7.2 Hz), 7.54 (1H, d, J=7.9 Hz), 7.39 (1H, dd, J=7.9, 7.2 Hz), 7.24 (1H, br), 7.23 (1H, dd, J=7.9, 4.6 Hz), 4.81 (1H, dd, J=5.3, 4.6 Hz), 4.71 (2H, d, J=5.9 Hz), 3.87 (1H, br), 2.68 (1H, m), 2.42-2.08 (3H, m).

Chiral HPLC tR: 35.1 min (Method K), >99% e.e., d.e.

Ex 129

$^1$H NMR was identified with the Example 128.
Chiral HPLC tR: 23.9 min (Method K), >99% e.e., d.e.

Ex 130

$^1$H NMR (DMSO d6) delta 8.69 (1H, br), 8.61 (1H, d, J=4.6 Hz), 7.56 (1H, d, J=2.0 Hz), 7.55 (1H, d, J=7.9 Hz), 7.48 (1H, d, J=2.0 Hz), 7.38 (1H, dd, J=7.9, 4.6 Hz), 5.54 (1H, t, J=5.3 Hz), 5.43 (1H, d, J=4.0 Hz), 4.70 (2H, d, J=5.3 Hz), 4.63 (1H, d, J=4.0 Hz), 4.50 (2H, m), 2.76-2.55 (1H, m), 2.14-1.90 (3H, m).

MS (ESI) m/z: 398.9 (M+H)+.

Chiral HPLC tR: 14.1 min (Method J), 98.2% e.e., >99% d.e.

Ex 131

$^1$H NMR and MS were identified with the Example 130.
Chiral HPLC tR: 39.1 min (Method J), >99% e.e., d.e.

Ex 132

$^1$H NMR (CDCl$_3$) delta 8.59 (1H, ddd, J=4.9, 1.8, 1.2 Hz), 7.54 (1H, dd, J=7.9, 1.2 Hz), 7.45 (1H, d, J=1.8 Hz), 7.36 (1H, d, J=7.9 Hz), 7.31-7.23 (2H, m), 7.18 (1H, br), 4.80 (1H, ddd, J=6.7, 6.0, 1.2 Hz), 4.63 (1H, dd, J=14.7, 6.1 Hz), 4.57 (1H, dd, J=14.7, 6.1 Hz), 3.79 (1H, br s), 2.67 (1H, m), 2.41-2.25 (2H, m), 2.15 (1H, m).

Ex 133

$^1$H NMR was identified with the Example 132.

Ex 134

$^1$H NMR (CDCl$_3$) delta 8.60 (1H, ddd, J=4.9, 1.8, 1.2 Hz), 7.54 (1H, ddd, J=7.9, 1.8, 1.2 Hz), 7.41 (1H, dd, J=8.6, 6.1 Hz), 7.25 (1H, dd, J=7.9, 4.9 Hz), 7.19 (1H, dd, J=7.9, 2.4 Hz), 7.13 (1H, br d, J=5.5 Hz), 7.00 (1H, ddd, J=8.6, 7.9, 2.4 Hz), 4.81 (1H, dd, J=5.5, 4.9 Hz), 4.63 (1H, dd, J=14.7, 6.1 Hz), 4.57 (1H, dd, J=14.7, 5.5 Hz), 3.74 (1H, br s), 2.67 (1H, m), 2.41-2.25 (2H, m), 2.15 (1H, m).

Ex 135

$^1$H NMR was identified with the Example 134.

Ex 150

$^1$H NMR (CDCl$_3$) delta 8.58 (1H, ddd, J=4.9, 1.8, 1.2 Hz), 7.52 (1H, br d, J=4.9 Hz), 7.48 (1H, ddd, J=7.9, 1.8, 1.2 Hz), 7.23 (1H, dd, J=7.9, 4.9 Hz), 7.17 (1H, dd, J=7.9, 2.4 Hz), 7.09 (1H, dd, J=8.6, 2.4 Hz), 4.79-4.73 (4H, m), 4.65 (1H, dd, J=14.7, 6.1 Hz), 3.82 (1H, br), 3.67 (1H, br), 2.61 (1H, m), 2.37-2.21 (2H, m), 2.11 (1H, m).

Ex 158

$^1$H NMR (CDCl$_3$) delta 8.61 (1H, br dd, J=4.9, 1.6 Hz), 7.56 (1H, d, J=7.9 Hz), 7.41 (1H, dd, J=7.9, 1.6 Hz), 7.34 (1H, dd, J=7.6, 1.3 Hz), 7.28-7.15 (3H, m), 4.81 (1H, dd, J=6.3, 4.9 Hz), 4.70 (1H, dd, J=14.5, 5.9 Hz), 4.63 (1H, dd, J=14.5, 6.3 Hz), 3.62 (1H, s), 2.66 (1H, m), 2.44-2.08 (3H, m).

Ex 159

$^1$H NMR was identified with the Example 158.

Ex 191

$^1$H NMR (CDCl$_3$) delta 8.58 (1H, m), 7.42 (1H, d, J=1.8 Hz), 7.39 (1H, d, J=7.9 Hz), 7.25-7.20 (2H, m), 7.19 (1H, d, J=7.9 Hz), 6.79 (1H, br), 4.80 (1H, ddd, J=6.4, 5.2, 1.2 Hz), 3.80 (1H, br), 3.75-3.59 (2H, m), 3.03 (2H, dt, J=6.7, 1.8 Hz), 2.62 (1H, m), 2.38-2.22 (2H, m), 2.10 (1H, m).

Ex 192

¹H NMR (CDCl₃) delta 8.61 (1H, br d, J=4.9 Hz), 7.60 (1H, d, J=7.9 Hz), 7.28 (2H, dd, J=7.9, 4.9 Hz), 4.83 (1H, dd, J=6.1, 5.5 Hz), 3.76 (1H, br), 3.69 (4H, dd, J=4.9, 4.3 Hz), 3.48 (1H, dd, J=14.1, 6.1 Hz), 3.41 (1H, dd, J=14.1, 5.5 Hz), 2.70 (1H, m), 2.63 (4H, dd, J=4.9, 4.3 Hz), 2.38 (1H, m), 2.28 (1H, m), 2.16 (1H, m), 1.70-1.52 (5H, m), 1.47-1.37 (4H, m), 1.24 (1H, m).

Ex 237

¹H NMR (CDCl₃) delta 8.56 (1H, br dd, J=4.3, 1.8 Hz), 7.50 (1H, br dd, J=7.9, 1.8 Hz), 7.39 (1H, dd, J=8.6, 6.1 Hz), 7.21 (1H, dd, J=7.9, 4.3 Hz), 7.16 (1H, dd, J=7.9, 3.1 Hz), 7.08 (1H, m), 7.02 (1H, ddd, J=8.6, 7.9, 3.1 Hz), 5.43 (1H, m), 4.81 (1H, br t, J=5.8 Hz), 2.90 (1H, br), 2.69 (1H, m), 2.41-2.26 (2H, m), 2.17 (1H, m), 1.60 (3H, d, J=7.3 Hz).

Ex 238

¹H NMR (CDCl₃) delta 8.63 (1H, m), 7.62 (1H, br d, J=7.3 Hz), 7.40 (0.5H, d, J=1.8 Hz), 7.39 (0.5H, d, J=1.8 Hz), 7.30 (0.5H, dd, J=7.9, 4.3 Hz), 7.29 (0.5H, dd, J=7.9, 4.3 Hz), 7.180 (0.5H, dd, J=8.6, 1.8 Hz), 7.179 (0.5H, dd, J=8.6, 1.8 Hz), 7.12 (0.5H, d, J=8.6 Hz), 7.11 (0.5H, d, J=8.6 Hz), 6.98 (1H, br), 4.82 (1H, br), 3.68 (1H, br), 3.05 (1H, m), 2.69 (1H, m), 2.42-2.25 (3H, m), 2.17 (1H, m), 1.41-1.24 (2H, m).

Ex 239

¹H NMR (CDCl₃) delta 8.61 (1H, br dd, J=4.9, 1.8 Hz), 7.65 (1H, br dd, J=7.9, 1.8 Hz), 7.35 (1H, dd, J=8.6, 6.1 Hz), 7.30 (1H, dd, J=7.9, 4.9 Hz), 7.16 (1H, dd, J=8.6, 2.4 Hz), 7.08 (1H, br), 7.02 (1H, ddd, J=8.6, 6.1, 2.4 Hz), 5.41 (1H, m), 4.80 (1H, br), 3.75 (1H, br), 2.60 (1H, m), 2.37-2.07 (3H, m), 1.60 (3H, d, J=7.3 Hz).

Ex 240

¹H NMR (CDCl₃) delta 8.58 (1H, br dd, J=4.9, 1.8 Hz), 7.47 (1H, d, J=1.8 Hz), 7.33 (1H, dd, J=8.6, 1.8 Hz), 7.29 (1H, d, J=8.6 Hz), 7.21 (1H, dd, J=7.9, 4.9 Hz), 7.15 (1H, br d, J=7.9 Hz), 6.32 (1H, br), 4.75 (1H, br dd, J=5.5, 4.9 Hz), 4.18 (1H, dd, J=14.1, 6.1 Hz), 3.95 (1H, dd, J=14.1, 6.1 Hz), 3.92-3.83 (2H, m), 3.74-3.55 (3H, m), 2.49 (1H, m), 2.40-2.55 (3H, m), 2.24-2.08 (3H, m), 2.01 (1H, m).

TABLE 40

| Intermediates | Structure | Chemical Name | Substrate | Amine |
|---|---|---|---|---|
| I-d-1 | 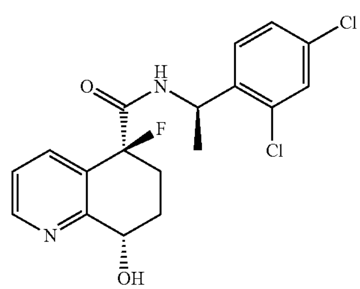 [SMILES: C[C@@H](NC(=O)[C@]1(F)CC[C@H](O)c2ncccc21)c1ccc(Cl)cc1Cl] | (5S,8S)-N-((R)-1-(2,4-dichlorophenyl)ethyl)-5-fluoro-8-hydroxy-5,6,7,8-tetrahydroquinoline-5-carboxamide | IM II-d-4 | |
| I-d-2 | 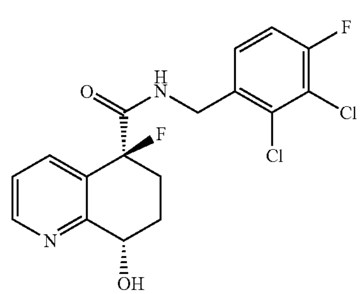 | (5S,8S)-N-(2,3-dichloro-4-fluorobenzyl)-5-fluoro-8-hydroxy-5,6,7,8-tetrahydroquinoline-5-carboxamide | IM II-d-4 | |
| I-d-3 | 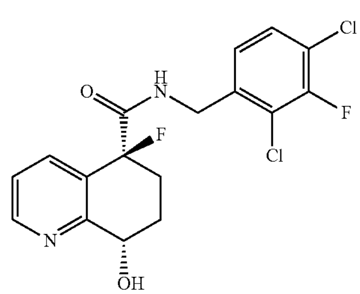 | (5S,8S)-N-(2,4-dichloro-3-fluorobenzyl)-5-fluoro-8-hydroxy-5,6,7,8-tetrahydroquinoline-5-carboxamide | IM II-d-4 | |

TABLE 40-continued

| Intermediates | Structure | Chemical Name | Substrate | Amine |
|---|---|---|---|---|
| I-d-4 | 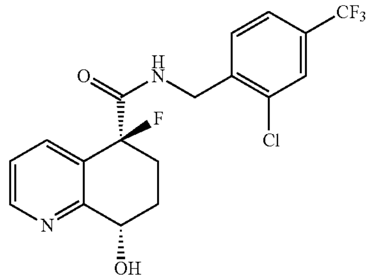 [SMILES: O=C(NCc1ccc(C(F)(F)F)cc1Cl)[C@]1(F)CC[C@H](O)c2ncccc21] | (5S,8S)-N-(2-chloro-4-(trifluoromethyl)benzyl)-5-fluoro-8-hydroxy-5,6,7,8-tetrahydroquinoline-5-carboxamide | IM II-d-4 | |
| I-d-5 | 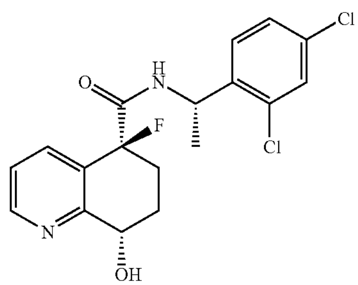 [SMILES: C[C@H](NC(=O)[C@]1(F)CC[C@H](O)c2ncccc21)c1ccc(Cl)cc1Cl] | (5S,8S)-N-((S)-1-(2,4-dichlorophenyl)ethyl)-5-fluoro-8-hydroxy-5,6,7,8-tetrahydroquinoline-5-carboxamide | IM II-d-4 | |

IM I-d-1
  MS (ESI) m/z: 383.2 (M+H)⁺.
IM I-d-2
  MS (ESI) m/z: 386.9 (M+H)⁺.
IM I-d-3
  MS (ESI) m/z: 386.9 (M+H)⁺.
IM I-d-4
  MS (ESI) m/z: 403.0 (M+H)⁺.
IM I-d-5
  MS (ESI) m/z: 383.2 (M+H)⁺.

Intermediate (IM) I-d-6

(5S,8S)—N-(2-(((tert-butyldimethylsilyl)oxy)methyl)-6-chloro-4-fluorobenzyl)-5-fluoro-8-hydroxy-5,6,7,8-tetrahydroquinoline-5-carboxamide

[Chem. 27]

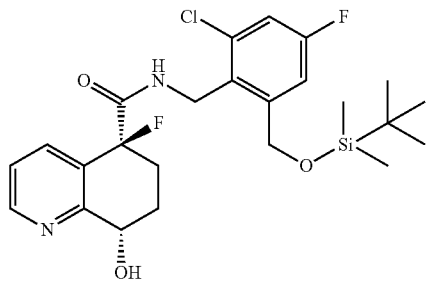

To a solution of (5S,8S)—N-(2-chloro-4-fluoro-6-(hydroxymethyl)benzyl)-5-fluoro-8-hydroxy-5,6,7,8-tetrahydroquinoline-5-carboxamide (174 mg, 0.455 mmol, Ex 150) in CH$_2$Cl$_2$ (1.0 mL) was added imidazole (93 mg, 1.364 mmol) at 0° C. After 10 min stirring, TBSCl (82 mg, 0.545 mmol) was added to the mixture at 0° C. Then the mixture was allowed to warm to room temperature and stirred for 3 h. The mixture was diluted with cold water and extracted with CH$_2$Cl$_2$. The extracts were washed with brine, dried over Na$_2$SO$_4$, and then concentrated in vacuo. The resulting residue was purified by silica gel column chromatography (30- to 100% EtOAc/n-hexane, gradient) to afford 165 mg (73%) of the title compound.

IM I-d-6
  $^1$H NMR (CDCl$_3$) delta 8.58 (1H, br d, J=4.9 Hz), 7.55 (1H, br d, J=7.9 Hz), 7.24 (1H, dd, J=7.9, 4.9 Hz), 7.15 (1H, dd, J=9.8, 3.1 Hz), 7.12 (1H, dd, J=8.6, 3.1 Hz), 7.05 (1H, br d, J=5.5 Hz), 4.89 (1H, d, J=13.4 Hz), 4.82 (1H, d, J=13.4 Hz), 4.80 (1H, m), 4.70 (1H, dd, J=14.1, 6.1 Hz), 4.57 (1H, dd, J=14.1, 5.5 Hz), 3.80 (1H, br), 2.66 (1H, m), 2.39-2.25 (2H, m), 2.12 (1H, m), 0.94 (9H, s), 0.12 (3H, s), 0.11 (3H, s).
  MS (ESI) m/z: 496.8 (M+H)⁺.

Example 245

(5S,8S)-5-((2,4-dichlorobenzyl)carbamoyl)-5-fluoro-8-hydroxy-5,6,7,8-tetrahydroquinoline-1-oxide

[Chem. 28]

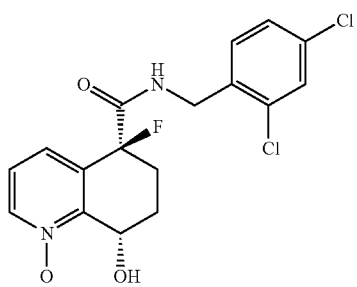

To a stirred solution of (5S,8S)—N-(2,4-dichlorobenzyl)-5-fluoro-8-hydroxy-5,6,7,8-tetrahydroquinoline-5-carboxamide (30 mg, 0.081 mmol, Ex 133) in CH$_2$Cl$_2$ (2 mL) was added mCPBA (17 mg, 0.099 mmol) at 0° C. The mixture was stirred at 0° C. for 2 h, and then warmed to room temperature. After being stirred at room temperature for 16 h, aq. Na$_2$S$_2$O$_3$ was added to the mixture. The resulting mixture was stirred for 30 min vigorously, and then extracted with EtOAc. The extract was washed with aq. NaHCO$_3$, water, and brine. The extract was dried over Na$_2$SO$_4$ and concentrated in vacuo. The resulting solid was washed with EtOAc to afford 22 mg (70%) of the title compound.

Ex 245

$^1$H NMR (CDCl$_3$) delta 8.27 (1H, ddd, J=4.9, 1.8, 1.2 Hz), 7.46 (1H, d, J=1.8 Hz), 7.38 (1H, d, J=7.9 Hz), 7.28-7.25 (2H, m), 7.16-7.14 (2H, m), 5.23 (1H, br), 5.15 (1H, br), 4.65 (1H, dd, J=14.7, 6.1 Hz), 4.59 (1H, dd, J=14.7, 6.1 Hz), 2.61 (1H, m), 2.33-2.28 (2H, m), 2.11 (1H, m).

LCMS (ESI) m/z: 385.0 (M+H)$^+$, tR 1.40 min (Method D).

Intermediate (IM) II-e-2-6

(5R)-Methyl 5-fluoro-8-methylene-5,6,7,8-tetrahydroquinoline-5-carboxylate Intermediate (IM) II-e-2-7

(5S)-Methyl 5-fluoro-8-methylene-5,6,7,8-tetrahydroquinoline-5-carboxylate

[Chem. 29]

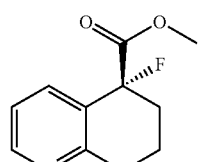

II-e-2-6

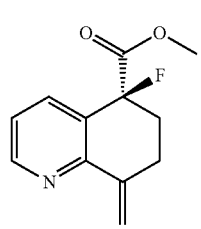

II-e-2-7

The title compounds were prepared by chiral HPLC separation of methyl 5-fluoro-8-methylene-5,6,7,8-tetrahydroquinoline-5-carboxylate (IM IJ-e-2-1).

IM II-e-2-6
Chiral HPLC tR: 15.1 min (Method L), >98% e.e.

IM II-e-2-7
Chiral HPLC tR: 17.8 min (Method L), >98% e.e.

The following Intermediates were prepared by General Procedure A (Table 41), except Intermediate I-e-35.

The Intermediate I-e-35 was prepared by General Procedure N (Table 41).

TABLE 41

| Intermediates | Structure | Chemical Name | Substrate | Amine |
|---|---|---|---|---|
| I-e-25 | (structure shown) | (R)-N-(2-chloro-3-(trifluoro-methyl)benzyl)-5-fluoro-8-methylene-5,6,7,8-tetrahydroquinoline-5-carboxamide | IM II-e-2-6 | (structure shown) |

TABLE 41-continued

| Intermediates | Structure | Chemical Name | Substrate | Amine |
|---|---|---|---|---|
| I-e-26 | 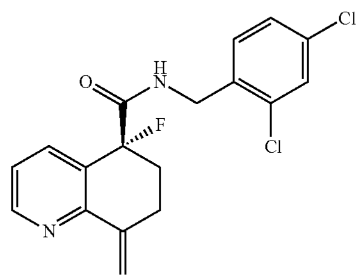 [SMILES: C=C1CC[C@](F)(C(=O)NCc2ccc(Cl)cc2Cl)c2cccnc21] | (R)-N-(2,4-dichlorobenzyl)-5-fluoro-8-methylene-5,6,7,8-tetrahydroquinoline-5-carboxamide | IM II-e-2-6 | |
| I-e-27 | 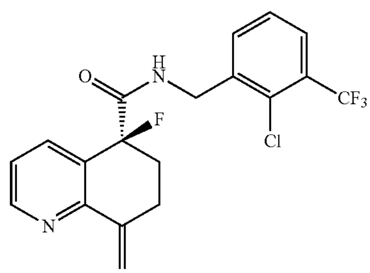 [SMILES: C=C1CC[C@@](F)(C(=O)NCc2cccc(C(F)(F)F)c2Cl)c2cccnc21] | (S)-N-(2-chloro-3-(trifluoro-methyl)benzyl)-5-fluoro-8-methylene-5,6,7,8-tetrahydroquinoline-5-carboxamide | IM II-e-2-7 | |
| I-e-28 | 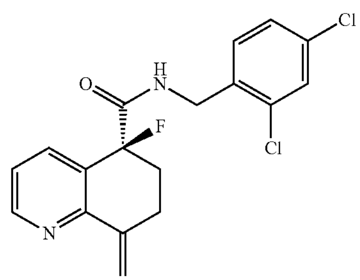 [SMILES: C=C1CC[C@@](F)(C(=O)NCc2ccc(Cl)cc2Cl)c2cccnc21] | (S)-N-(2,4-dichlorobenzyl)-5-fluoro-8-methylene-5,6,7,8-tetrahydroquinoline-5-carboxamide | IM II-e-2-7 | |
| I-e-29 | 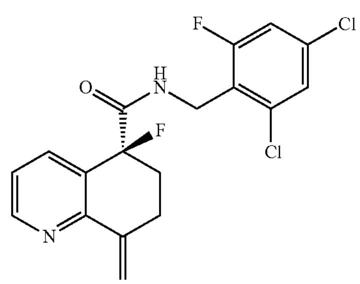 [SMILES: C=C1CC[C@@](F)(C(=O)NCc2c(F)cc(Cl)cc2Cl)c2cccnc21] | (S)-N-(2,4-dichloro-6-fluorobenzyl)-5-fluoro-8-methylene-5,6,7,8-tetrahydroquinoline-5-carboxamide | IM II-e-2-7 | |
| I-e-30 | 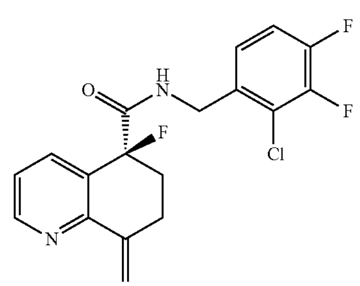 [SMILES: C=C1CC[C@@](F)(C(=O)NCc2ccc(F)c(F)c2Cl)c2cccnc21] | (S)-N-(2-chloro-3,4-difluorobenzyl)-5-fluoro-8-methylene-5,6,7,8-tetrahydroquinoline-5-carboxamide | IM II-e-2-7 | |

TABLE 41-continued

| Intermediates | Structure | Chemical Name | Substrate | Amine |
|---|---|---|---|---|
| I-e-31 | 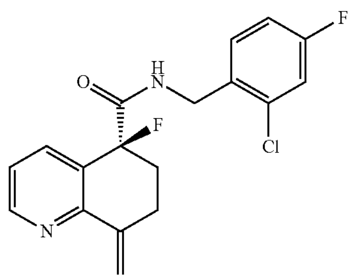 [SMILES: C=C1CC[C@@](F)(C(=O)NCc2ccc(F)cc2Cl)c2cccnc21] | (S)-N-(2-chloro-4-fluorobenzyl)-5-fluoro-8-methylene-5,6,7,8-tetrahydroquinoline-5-carboxamide | IM II-e-2-7 | |
| I-e-32 | 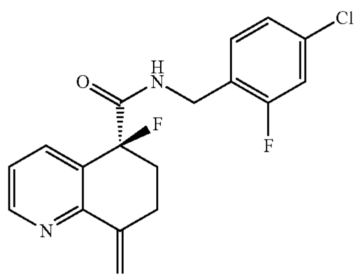 [SMILES: C=C1CC[C@@](F)(C(=O)NCc2ccc(Cl)cc2F)c2cccnc21] | (S)-N-(4-chloro-2-fluorobenzyl)-5-fluoro-8-methylene-5,6,7,8-tetrahydroquinoline-5-carboxamide | IM II-e-2-7 | |
| I-e-33 | 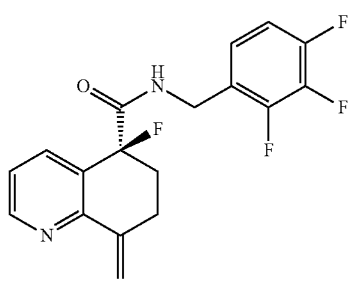 [SMILES: C=C1CC[C@@](F)(C(=O)NCc2ccc(F)c(F)c2F)c2cccnc21] | (S)-5-fluoro-8-methylene-N-(2,3,4-trifluorobenzyl)-5,6,7,8-tetrahydroquinoline-5-carboxamide | IM II-e-2-7 | |
| I-e-34 | 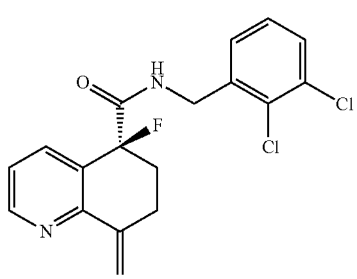 [SMILES: C=C1CC[C@@](F)(C(=O)NCc2cccc(Cl)c2Cl)c2cccnc21] | (S)-N-(2,3-dichlorobenzyl)-5-fluoro-8-methylene-5,6,7,8-tetrahydroquinoline-5-carboxamide | IM II-e-2-7 | |
| I-e-35 | 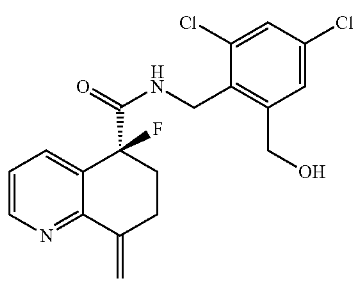 [SMILES: C=C1CC[C@@](F)(C(=O)NCc2c(Cl)cc(Cl)cc2CO)c2cccnc21] | (S)-N-(2,4-dichloro-6-(hydroxymethyl)benzyl)-5-fluoro-8-methylene-5,6,7,8-tetrahydroquinoline-5-carboxamide | IM II-e-2-7 | |

IM I-e-25
¹H NMR and MS were identified with the IM I-e-3.
IM I-e-26
¹H NMR and MS were identified with the IM I-e-19.
IM I-e-27
¹H NMR and MS were identified with the IM I-e-3.
IM I-e-28
¹H NMR and MS were identified with the IM I-e-19.
IM I-e-29
MS (ESI) m/z: 384.6 (M+H)⁺.
IM I-e-30
¹H NMR (CDCl₃) delta 8.61 (1H, br dd, J=4.3, 1.8 Hz), 7.48 (1H, br dd, J=7.9, 1.8 Hz), 7.24 (1H, br), 7.24-7.17 (2H, m), 7.10 (1H, m), 6.35 (1H, s), 5.31 (1H, s), 4.66 (1H, dd, J=15.3, 6.1 Hz), 4.62 (1H, dd, J=15.3, 6.1 Hz), 2.88-2.82 (2H, m), 2.47 (1H, m), 2.27 (1H, m).
MS (ESI) m/z: 367.1 (M+H)⁺.
IM I-e-31
¹H NMR and MS were identified with the IM I-e-20.
IM I-e-32
MS (ESI) m/z: 348.8 (M+H)⁺.
IM I-e-33
¹H NMR (CDCl₃) delta 8.61 (1H, br dd, J=4.9, 1.8 Hz), 7.46 (1H, br dd, J=7.9, 1.8 Hz), 7.21-7.10 (3H, m), 6.98 (1H, m), 6.36 (1H, s), 5.31 (1H, s), 4.63 (1H, dd, J=14.7, 6.1 Hz), 4.58 (1H, dd, J=14.7, 6.1 Hz), 2.90-2.79 (2H, m), 2.47 (1H, m), 2.26 (1H, m).
MS (ESI) m/z: 350.8 (M+H)⁺.
IM I-e-34
¹H NMR and MS were identified with the IM I-e-18.
IM I-e-35
¹H NMR and MS were identified with the IM I-e-17.

The following Examples and Intermediates were prepared by General Procedure B or O (Tables 42 and 44).

General Procedure O

To a solution of substrate (1.0 eq.) in CH₂Cl₂ was added Dess-Martin Periodinane (1.5 eq.) at ambient temperature. After being stirred until complete reaction, aq. Na₂S₂O₃ and aq. NaHCO₃ were added to the mixture. The mixture was extracted with CH₂Cl₂ and washed with water. The extract was dried over Na₂SO₄ and concentrated in vacuo to afford a solid. The residual solid was purified by silica gel column chromatography and preparative HPLC to afford following Examples and Intermediates.

TABLE 42

| Examples | Structure | Chemical Name | Substrate | General Procedure |
|---|---|---|---|---|
| 246 | 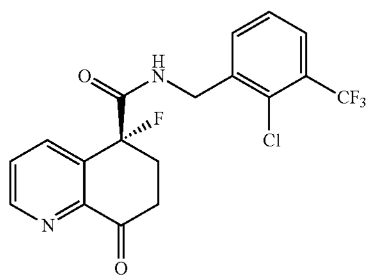 [SMILES: O=C1CC[C@](F)(C(=O)NCc2cccc(C(F)(F)F)c2Cl)c2cccnc21] | (R)-N-(2-chloro-3-(trifluoromethyl)benzyl)-5-fluoro-8-oxo-5,6,7,8-tetrahydroquinoline-5-carboxamide | IM I-e-25 | B |
| 247 | 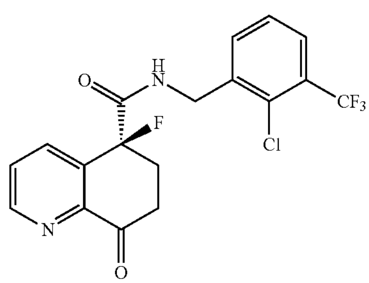 [SMILES: O=C1CC[C@@](F)(C(=O)NCc2cccc(C(F)(F)F)c2Cl)c2cccnc21] | (S)-N-(2-chloro-3-(trifluoromethyl)benzyl)-5-fluoro-8-oxo-5,6,7,8-tetrahydroquinoline-5-carboxamide | IM I-e-27 | B |
| 248 | 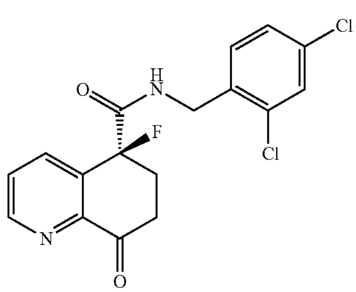 [SMILES: O=C1CC[C@@](F)(C(=O)NCc2ccc(Cl)cc2Cl)c2cccnc21] | (S)-N-(2,4-dichlorobenzyl)-5-fluoro-8-oxo-5,6,7,8-tetrahydroquinoline-5-carboxamide | IM I-e-28 | B |

TABLE 42-continued

| Examples | Structure | Chemical Name | Substrate | General Procedure |
|---|---|---|---|---|
| 249 | 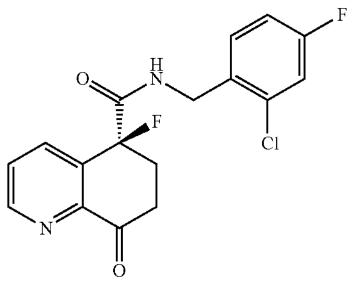 | (S)-N-(2-chloro-4-fluorobenzyl)-5-fluoro-8-oxo-5,6,7,8-tetrahydroquinoline-5-carboxamide | Ex 107 | O |
| 250 | 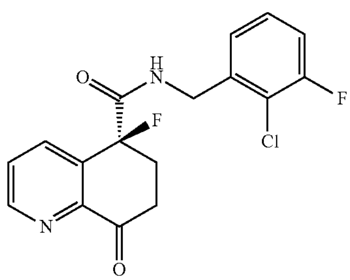 [SMILES: O=C1CC[C@@](F)(C(=O)NCc2cccc(F)c2Cl)c2cccnc21] | (S)-N-(2-chloro-3-fluorobenzyl)-5-fluoro-8-oxo-5,6,7,8-tetrahydroquinoline-5-carboxamide | Ex 169 | O |
| 251 | 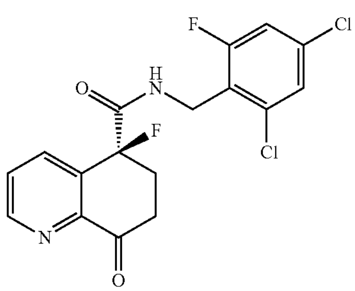 [SMILES: O=C1CC[C@@](F)(C(=O)NCc2c(F)cc(Cl)cc2Cl)c2cccnc21] | (S)-N-(2,4-dichloro-6-fluorobenzyl)-5-fluoro-8-oxo-5,6,7,8-tetrahydroquinoline-5-carboxamide | Ex 117 | O |
| 252 | 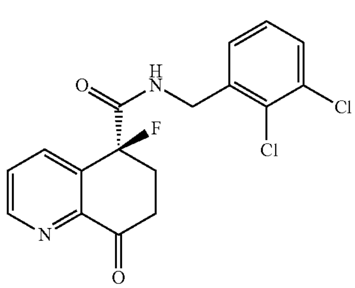 [SMILES: O=C1CC[C@@](F)(C(=O)NCc2cccc(Cl)c2Cl)c2cccnc21] | (S)-N-(2,3-dichlorobenzyl)-5-fluoro-8-oxo-5,6,7,8-tetrahydroquinoline-5-carboxamide | IM I-e-34 | B |

TABLE 42-continued

| Examples | Structure | Chemical Name | Substrate | General Procedure |
|---|---|---|---|---|
| 253 | 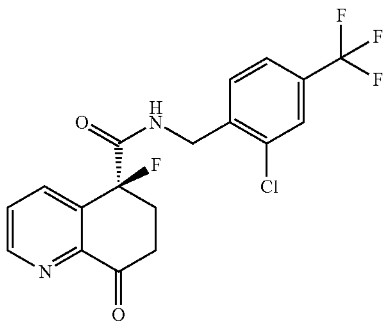 [SMILES: O=C1CC[C@@](F)(C(=O)NCc2ccc(C(F)(F)F)cc2Cl)c2cccnc21] | (S)-N-(2-chloro-4-(trifluoromethyl)benzyl)-5-fluoro-8-oxo-5,6,7,8-tetra-hydroquinoline-5-carboxamide | IM I-d-4 | O |
| 254 | 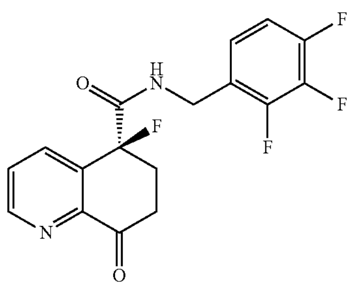 [SMILES: O=C1CC[C@@](F)(C(=O)NCc2ccc(F)c(F)c2F)c2cccnc21] | (S)-5-fluoro-8-oxo-N-(2,3,4-trifluoro-benzyl)-5,6,7,8-tetrahydroquinoline-5-carboxamide | Ex 108 | O |
| 255 | 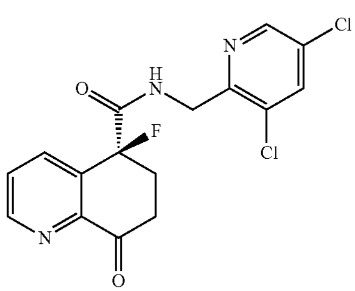 | (S)-N-((3,5-dichloropyridin-2-yl)methyl)-5-fluoro-8-oxo-5,6,7,8-tetrahydro-quinoline-5-carboxamide | Ex 177 | O |

TABLE 43

| LC MS | | | |
|---|---|---|---|
| Examples | Method | tR (min) | [M + H]$^+$ |
| 246 | A | 1.51 | 401.1 |
| 247 | A | 1.51 | 401.1 |
| 248 | B | 1.44 | 367.0 |
| 249 | B | 1.33 | 351.0 |
| 250 | B | 1.31 | 351.0 |
| 251 | B | 1.44 | 384.9 |
| 252 | B | 1.40 | 366.9 |
| 253 | B | 1.49 | 400.9 |
| 254 | C | 1.35 | 353.0 |
| 255 | D | 1.43 | 368.0 |

Ex 246

$^1$H NMR was identified with the Example 13.

Ex 247

$^1$H NMR was identified with the Example 13.

Ex 248

$^1$H NMR (DMSO d6) delta 9.35 (1H, br), 8.85 (1H, d, J=4.9 Hz), 7.95 (1H, dd, J=7.9, 1.8 Hz), 7.73 (1H, dd, J=7.9, 4.9 Hz), 7.62 (1H, d, J=1.8 Hz), 7.44 (1H, dd, J=7.9, 1.8 Hz), 7.34 (1H, d, J=7.9 Hz), 4.44 (1H, dd, J=15.9, 6.1 Hz), 4.39 (1H, dd, J=15.9, 5.5 Hz), 2.89-2.85 (2H, m), 2.77-2.58 (2H, m).

Ex 249

¹H NMR (DMSO d6) delta 9.31 (1H, br), 8.85 (1H, dd, J=4.9, 1.8 Hz), 7.95 (1H, dd, J=7.9, 1.8 Hz), 7.73 (1H, dd, J=7.9, 4.9 Hz), 7.45 (1H, dd, J=8.6, 3.1 Hz), 7.38 (1H, dd, J=8.6, 6.1 Hz), 7.23 (1H, ddd, J=8.6, 8.6, 3.1 Hz), 4.44 (1H, dd, J=15.9, 6.1 Hz), 4.39 (1H, dd, J=15.9, 5.5 Hz), 2.94-2.81 (2H, m), 2.77-2.54 (2H, m).

Ex 252

¹H NMR (CDCl₃) delta 8.90 (1H, dd, J=4.6, 1.3 Hz), 7.75 (1H, dd, J=7.9, 1.3 Hz), 7.52 (1H, dd, J=7.9, 4.6 Hz), 7.48 (1H, dd, J=7.9, 2.0 Hz), 7.33 (1H, dd, J=7.9, 2.0 Hz), 7.23-7.20 (1H, br), 7.22 (1H, dd, J=7.9, 7.9 Hz), 4.68 (2H, d, J=5.9 Hz), 3.17 (1H, m), 3.02 (1H, m), 2.81 (1H, m), 2.58 (1H, m).

Ex 253

¹H NMR (DMSO d6) delta 9.35 (1H, br), 8.84 (1H, d, J=4.3 Hz), 7.90 (1H, dd, J=7.9, 1.2 Hz), 7.71 (1H, dd, J=7.9, 4.3 Hz), 7.29 (1H, m), 7.19 (1H, m), 4.43 (1H, dd, J=15.3, 5.5 Hz), 4.39 (1H, dd, J=15.3, 5.5 Hz), 2.88-2.84 (2H, m), 2.73-2.56 (2H, m).

TABLE 44

| Intermediates | Structure | Chemical Name | Substrate | General Procedure |
|---|---|---|---|---|
| I-c-13 | 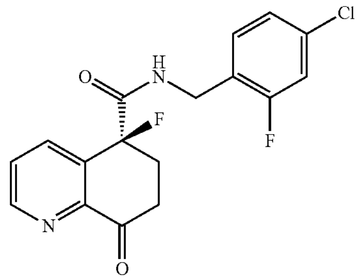 | (S)-N-(4-chloro-2-fluorobenzyl)-5-fluoro-8-oxo-5,6,7,8-tetrahydroquinoline-5-carboxamide | Ex 111 | O |
| I-c-14 | 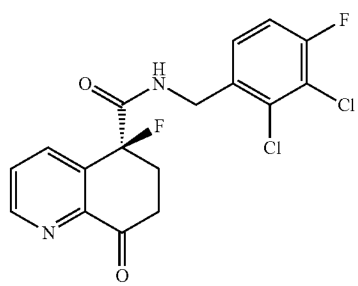 [SMILES: O=C1CC[C@@](F)(C(=O)NCc2ccc(F)c(Cl)c2Cl)c2cccnc21] | (S)-N-(2,3-dichloro-4-fluorobenzyl)-5-fluoro-8-oxo-5,6,7,8-tetrahydroquinoline-5-carboxamide | IM I-d-2 | O |
| I-c-15 | 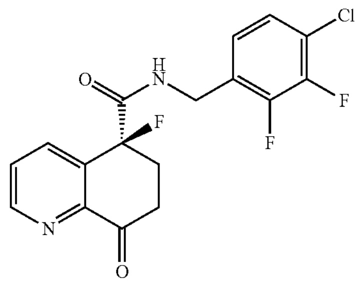 | (S)-N-(4-chloro-2,3-difluorobenzyl)-5-fluoro-8-oxo-5,6,7,8-tetrahydroquinoline-5-carboxamide | Ex 183 | O |

TABLE 44-continued

| Intermediates | Structure | Chemical Name | Substrate | General Procedure |
|---|---|---|---|---|
| I-c-16 | 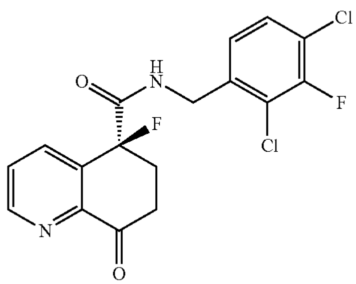 [SMILES: O=C1CC[C@@](F)(C(=O)NCc2ccc(Cl)c(F)c2Cl)c2cccnc21] | (S)-N-(2,4-dichloro-3-fluorobenzyl)-5-fluoro-8-oxo-5,6,7,8-tetrahydroquinoline-5-carboxamide | IM I-d-3 | O |
| I-c-17 | 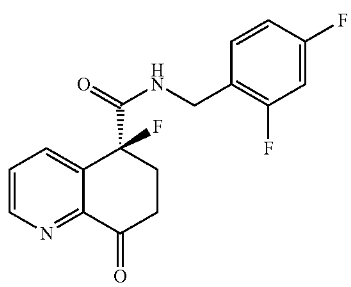 [SMILES: O=C1CC[C@@](F)(C(=O)NCc2ccc(F)cc2F)c2cccnc21] | (S)-N-(2,4-difluorobenzyl)-5-fluoro-8-oxo-5,6,7,8-tetrahydroquinoline-5-carboxamide | Ex 109 | O |
| I-c-18 | 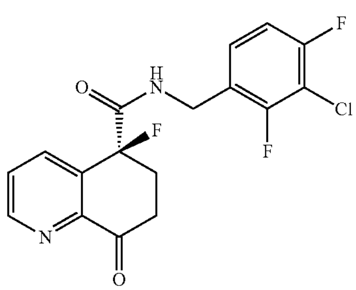 [SMILES: O=C1CC[C@@](F)(C(=O)NCc2ccc(F)c(Cl)c2F)c2cccnc21] | (S)-N-(3-chloro-2,4-difluorobenzyl)-5-fluoro-8-oxo-5,6,7,8-tetrahydroquinoline-5-carboxamide | Ex 185 | O |
| I-c-19 | 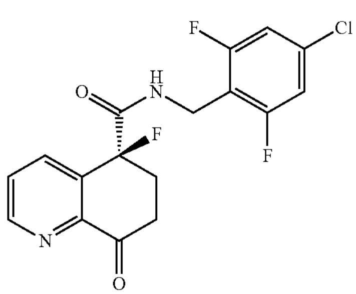 | (S)-N-(4-chloro-2,6-difluorobenzyl)-5-fluoro-8-oxo-5,6,7,8-tetrahydroquinoline-5-carboxamide | Ex 184 | O |

TABLE 44-continued

| Intermediates | Structure | Chemical Name | Substrate | General Procedure |
|---|---|---|---|---|
| I-c-20 | 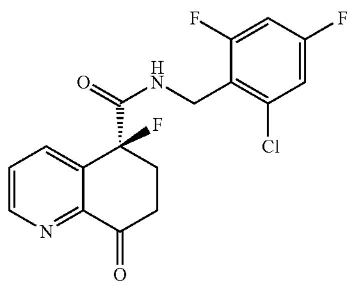 [SMILES: O=C1CC[C@@](F)(C(=O)NCc2c(F)cc(F)cc2Cl)c2cccnc21] | (S)-N-(2-chloro-4,6-difluorobenzyl)-5-fluoro-8-oxo-5,6,7,8-tetrahydroquinoline-5-carboxamide | Ex 176 | O |
| I-c-21 | 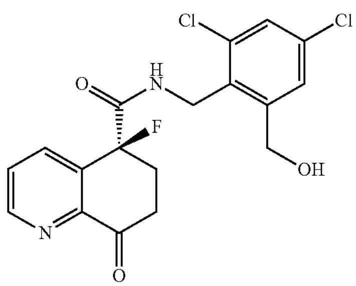 [SMILES: O=C1CC[C@@](F)(C(=O)NCc2c(Cl)cc(Cl)cc2CO)c2cccnc21] | (S)-N-(2,4-dichloro-6-(hydroxymethyl)benzyl)-5-fluoro-8-oxo-5,6,7,8-tetrahydroquinoline-5-carboxamide | IM I-e-35 | B |
| I-c-22 | 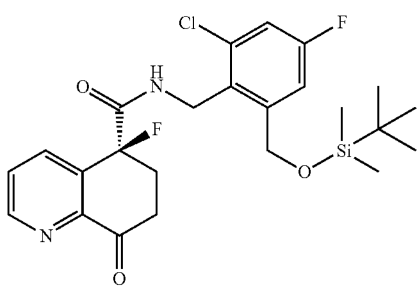 [SMILES: CC(C)(C)[Si](C)(C)OCc1cc(F)cc(Cl)c1CNC(=O)[C@]1(F)CCC(=O)c2ncccc21] | (S)-N-(2-(((tert-butyldimethylsilyl)oxy)methyl)-6-chloro-4-fluorobenzyl)-5-fluoro-8-oxo-5,6,7,8-tetrahydroquinoline-5-carboxamide | IM I-d-6 | O |
| I-c-23 | 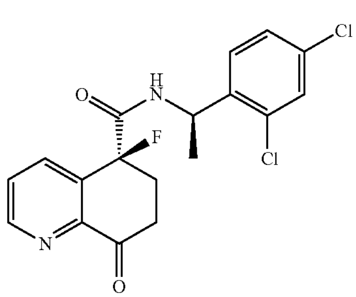 [SMILES: C[C@@H](NC(=O)[C@]1(F)CCC(=O)c2ncccc21)c1ccc(Cl)cc1Cl] | (S)-N-((R)-1-(2,4-dichlorophenyl)ethyl)-5-fluoro-8-oxo-5,6,7,8-tetrahydroquinoline-5-carboxamide | IM I-d-1 | O |

TABLE 44-continued

| Intermediates | Structure | Chemical Name | Substrate | General Procedure |
|---|---|---|---|---|
| I-c-24 | 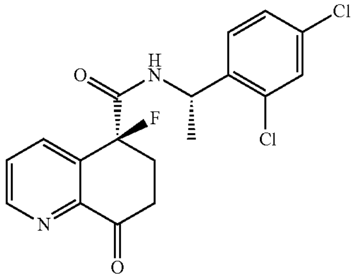 [SMILES: C[C@H](NC(=O)[C@]1(F)CCC(=O)c2ncccc21)c1ccc(Cl)cc1Cl] | (S)-N-((S)-1-(2,4-dichlorophenyl)ethyl)-5-fluoro-8-oxo-5,6,7,8-tetrahydroquinoline-5-carboxamide | IM I-d-5 | O |
| I-c-25 | 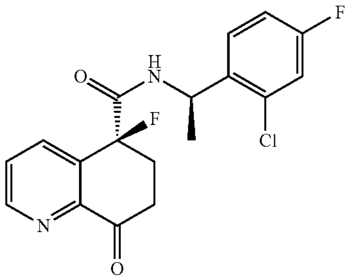 [SMILES: C[C@@H](NC(=O)[C@]1(F)CCC(=O)c2ncccc21)c1ccc(F)cc1Cl] | (S)-N-((R)-1-(2-chloro-4-fluorophenyl)ethyl)-5-fluoro-8-oxo-5,6,7,8-tetrahydroquinoline-5-carboxamide | Ex 237 | O |
| I-c-26 | 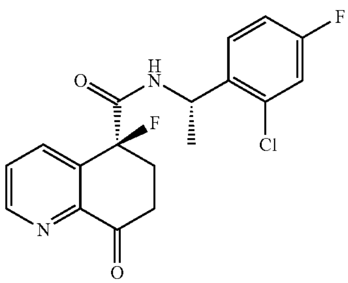 [SMILES: C[C@H](NC(=O)[C@]1(F)CCC(=O)c2ncccc21)c1ccc(F)cc1Cl] | (S)-N-((S)-1-(2-chloro-4-fluorophenyl)ethyl)-5-fluoro-8-oxo-5,6,7,8-tetrahydroquinoline-5-carboxamide | Ex 239 | O |
| I-c-27 | 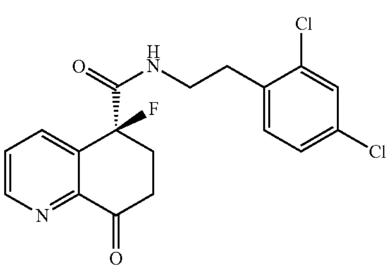 [SMILES: O=C1CC[C@@](F)(C(=O)NCCc2ccc(Cl)cc2Cl)c2cccnc21] | (S)-N-(2,4-dichlorophenyl)-5-fluoro-8-oxo-5,6,7,8-tetrahydroquinoline-5-carboxamide | Ex 191 | O |
| I-c-28 | 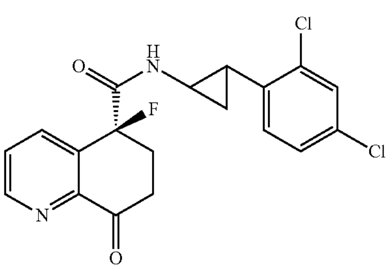 [SMILES: O=C1CC[C@@](F)(C(=O)NC2CC2c2ccc(Cl)cc2Cl)c2cccnc21] | (S)-N-((trans)-2-(2,4-dichlorophenyl)cyclopropyl)-5-fluoro-8-oxo-5,6,7,8-tetrahydroquinoline-5-carboxamide | Ex 238 | O |

TABLE 44-continued

| Intermediates | Structure | Chemical Name | Substrate | General Procedure |
|---|---|---|---|---|
| I-c-29 | 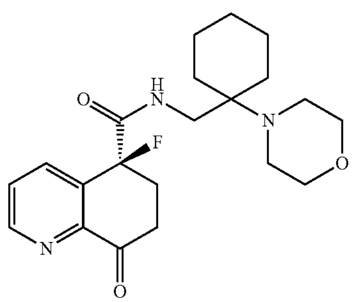 [SMILES: O=C1CC[C@@](F)(C(=O)NCC2(N3CCOCC3)CCCCC2)c2cccnc21] | (S)-5-fluoro-N-((1-morpholinocyclohexyl)methyl)-8-oxo-5,6,7,8-tetrahydroquinoline-5-carboxamide | Ex 192 | O |
| I-c-30 | 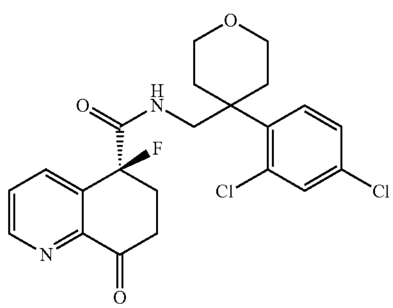 [SMILES: O=C1CC[C@@](F)(C(=O)NCC2(c3ccc(Cl)cc3Cl)CCOCC2)c2cccnc21] | (S)-N-((4-(2,4-dichlorophenyl)tetrahydro-2H-pyran-4-yl)methyl)-5-fluoro-8-oxo-5,6,7,8-tetrahydroquinoline-5-carboxamide | Ex 240 | O |
| I-c-31 | 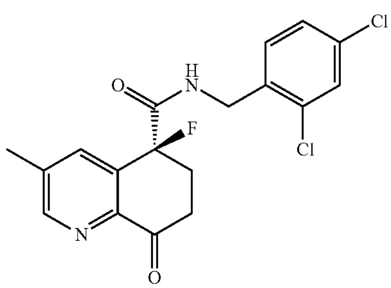 [SMILES: Cc1cnc2c(c1)[C@](F)(C(=O)NCc1ccc(Cl)cc1Cl)CCC2=O] | (S)-N-(2,4-dichlorobenzyl)-5-fluoro-3-methyl-8-oxo-5,6,7,8-tetrahydroquinoline-5-carboxamide | Ex 243 | O |
| I-c-32 | 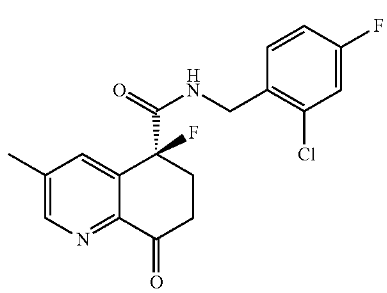 [SMILES: Cc1cnc2c(c1)[C@](F)(C(=O)NCc1ccc(F)cc1Cl)CCC2=O] | (S)-N-(2-chloro-4-fluorobenzyl)-5-fluoro-3-methyl-8-oxo-5,6,7,8-tetrahydroquinoline-5-carboxamide | Ex 244 | O |

IM I-c-13
  MS (ESI) m/z: 350.8 (M+H)$^+$.
IM I-c-14
  MS (ESI) m/z: 384.8 (M+H)$^+$.
IM I-c-15
  MS (ESI) m/z: 368.8 (M+H)$^+$.
IM I-c-16
  MS (ESI) m/z: 384.8 (M+H)$^+$.

IM I-c-17
  MS (ESI) m/z: 334.8 (M+H)$^+$.
IM I-c-18
  MS (ESI) m/z: 368.8 (M+H)$^+$.
IM I-c-19
  MS (ESI) m/z: 368.8 (M+H)$^+$.
IM I-c-20
  MS (ESI) m/z: 368.8 (M+H)$^+$.

IM I-c-21
¹H NMR and MS were identified with the Ex 14.
IM I-c-22
¹H NMR (CDCl₃) delta 8.88 (1H, ddd, J=4.3, 1.8, 1.2 Hz), 7.74 (1H, br d, J=7.9 Hz), 7.50 (1H, dd, J=7.9, 4.3 Hz), 7.14 (3H, br d, J=7.9 Hz), 4.88 (1H, d, J=13.4 Hz), 4.82 (1H, d, J=13.4 Hz), 4.71 (1H, dd, J=14.1, 5.5 Hz), 4.62 (1H, dd, J=14.1, 5.5 Hz), 3.16 (1H, m), 2.99 (1H, m), 2.79 (1H, m), 2.54 (1H, m), 0.94 (9H, s), 0.12 (3H, s), 0.11 (3H, s).
MS (ESI) m/z: 494.8 (M+H)⁺.
IM I-c-23
¹H NMR (CDCl₃) delta 8.87 (1H, ddd, J=4.3, 1.8, 1.2 Hz), 7.67 (1H, dd, J=7.9, 2.4 Hz), 7.48 (1H, dd, J=7.9, 4.3 Hz), 7.43 (1H, d, J=1.8 Hz), 7.33 (1H, d, J=8.6 Hz), 7.29 (1H, dd, J=8.6, 2.4 Hz), 7.12 (1H, br), 5.42 (1H, m), 3.18 (1H, m), 3.02 (1H, m), 2.83 (1H, m), 2.59 (1H, m), 1.62 (3H, d, J=6.7 Hz).
MS (ESI) m/z: 381.4 (M+H)⁺.
IM I-c-24
¹H NMR (DMSO d6) delta 9.34 (1H, br d, J=6.1 Hz), 8.85 (1H, br d, J=4.3 Hz), 7.97 (1H, dd, J=7.9, 1.8 Hz), 7.74 (1H, dd, J=7.9, 4.9 Hz), 7.59 (1H, d, J=1.8 Hz), 7.57 (1H, d, J=7.9 Hz), 7.48 (1H, dd, J=7.9, 1.8 Hz), 5.23 (1H, m), 2.83 (1H, m), 2.74-2.50 (3H, m), 1.44 (3H, d, J=7.3 Hz).
MS (ESI) m/z: 381.0 (M+H)⁺.
IM I-c-25
¹H NMR (DMSO d6) delta 9.28 (1H, br d, J=7.3 Hz), 8.81 (1H, br d, J=4.3 Hz), 7.84 (1H, dd, J=7.9, 1.8 Hz), 7.69 (1H, dd, J=7.9, 4.3 Hz), 7.59 (1H, dd, J=8.6, 6.1 Hz), 7.37 (1H, dd, J=8.6, 2.4 Hz), 7.24 (1H, dt, J=8.6, 2.4 Hz), 5.26 (1H, m), 2.98-2.80 (2H, m), 2.77-2.54 (2H, m), 1.43 (3H, d, J=6.7 Hz).
MS (ESI) m/z: 365.0 (M+H)⁺.
IM I-c-26
¹H NMR (DMSO d6) delta 9.32 (1H, br d, J=7.3 Hz), 8.85 (1H, d, J=4.3 Hz), 7.98 (1H, br d, J=7.9 Hz), 7.74 (1H, dd, J=7.9, 4.3 Hz), 7.60 (1H, dd, J=8.6, 6.1 Hz), 7.40 (1H, br d, J=9.2 Hz), 7.28 (1H, dt, J=8.6, 2.4 Hz), 5.26 (1H, m), 2.83 (1H, m), 2.76-2.51 (3H, m), 1.44 (3H, d, J=7.3 Hz).
MS (ESI) m/z: 365.0 (M+H)⁺.
IM I-c-27
¹H NMR (CDCl₃) delta 8.88 (1H, br d, J=4.3 Hz), 7.57 (1H, d, J=7.9 Hz), 7.49 (1H, dd, J=7.9, 4.3 Hz), 7.43 (1H, d, J=1.8 Hz), 7.23 (1H, dd, J=7.9, 1.8 Hz), 7.18 (1H, d, J=7.9 Hz), 6.85 (1H, br), 3.77-3.62 (2H, m), 3.17-2.94 (4H, m), 2.74 (1H, m), 2.52 (1H, m).
MS (ESI) m/z: 381.0 (M+H)⁺.

IM I-c-28
¹H NMR (CDCl₃) delta 8.91 (1H, m), 7.81 (1H, dd, J=7.9, 1.8 Hz), 7.57-7.53 (1H, m), 7.403 (0.5H, d, J=2.4 Hz), 7.397 (0.5H, d, J=2.4 Hz), 7.189 (0.5H, dd, J=8.6, 1.8 Hz), 7.185 (0.5H, dd, J=8.6, 1.8 Hz), 7.09 (0.5H, d, J=8.6 Hz), 7.08 (0.5H, d, J=8.6 Hz), 7.06 (1H, br), 3.23-3.14 (1H, m), 3.10-2.96 (2H, m), 2.89-2.76 (1H, m), 2.64-2.54 (1H, m), 2.36-2.29 (1H, m), 1.44-1.30 (2H, m).
MS (ESI) m/z: 393.3 (M+H)⁺.
IM I-c-29
¹H NMR (CDCl₃) delta 8.90 (1H, ddd, J=4.3, 1.8, 1.2 Hz), 7.77 (1H, dd, J=7.9, 1.2 Hz), 7.53 (1H, dd, J=7.9, 4.3 Hz), 7.46 (1H, br), 3.73 (4H, dd, J=4.9, 4.3 Hz), 3.48 (1H, dd, J=13.8, 4.9 Hz), 3.45 (1H, dd, J=13.8, 4.9 Hz), 3.17 (1H, m), 3.02 (1H, m), 2.83 (1H, m), 2.66 (4H, dd, J=4.9, 4.3 Hz), 2.57 (1H, m), 1.76-1.22 (10H, m).
MS (ESI) m/z: 390.4 (M+H)⁺.
IM I-c-30
¹H NMR (CDCl₃) delta 8.87 (1H, ddd, J=4.9, 1.8, 1.2 Hz), 7.48 (1H, d, J=1.8 Hz), 7.46 (1H, dd, J=7.9, 4.9 Hz), 7.35-7.32 (2H, m), 7.29 (1H, d, J=8.6 Hz), 6.40 (1H, brd, J=6.1 Hz), 4.16 (1H, dd, J=14.1, 6.1 Hz), 3.98 (1H, dd, J=14.1, 6.1 Hz), 3.92-3.83 (2H, m), 3.73-3.61 (2H, m), 3.06 (1H, m), 2.93 (1H, m), 2.61 (1H, m), 2.47-2.36 (3H, m), 2.13-2.08 (2H, m).
MS (ESI) m/z: 450.9 (M+H)⁺.
IM I-c-31
¹H NMR (CDCl₃) delta 8.68 (1H, br s), 7.462 (1H, d, J=1.8 Hz), 7.456 (1H, d, J=2.4 Hz), 7.37 (1H, d, J=7.9 Hz), 7.27 (1H, dd, J=7.9, 1.8 Hz), 7.23 (1H, br), 4.64 (1H, dd, J=15.3, 6.1 Hz), 4.61 (1H, dd, J=15.3, 6.1 Hz), 3.11 (1H, m), 2.97 (1H, m), 2.79 (1H, m), 2.54 (1H, m), 2.40 (3H, s).
MS (ESI) m/z: 381.0 (M+H)⁺.
IM I-c-32
¹H NMR (CDCl₃) delta 8.69 (1H, br s), 7.46 (1H, d, J=1.2 Hz), 7.42 (1H, dd, J=8.6, 6.1 Hz), 7.20 (1H, dd, J=7.9, 2.4 Hz), 7.20 (1H, br), 7.01 (1H, dt, J=8.6, 2.4 Hz), 4.64 (1H, dd, J=14.7, 6.1 Hz), 4.61 (1H, dd, J=14.7, 6.1 Hz), 3.10 (1H, m), 2.97 (1H, m), 2.79 (1H, m), 2.54 (1H, m), 2.40 (3H, s).
MS (ESI) m/z: 365.2 (M+H)⁺.

The following Intermediates were prepared by General Procedure G or H (Table 45).

In the preparation of the Intermediate (IM) I-g-16, the TBS group was removed under this reaction condition.

TABLE 45

| Intermediates | Structure | Chemical Name | Substrate | General Procedure |
|---|---|---|---|---|
| I-g-8 | [structure] | (2S,5'S)-N-(2,4-dichlorobenzyl)-5'-fluoro-6',7'-dihydro-5'H-spiro[oxirane-2,8'-quinoline]-5'-carboxamide | [structure] Ex 284 | G |

TABLE 45-continued

| Intermediates | Structure | Chemical Name | Substrate | General Procedure |
|---|---|---|---|---|
| I-g-9 | 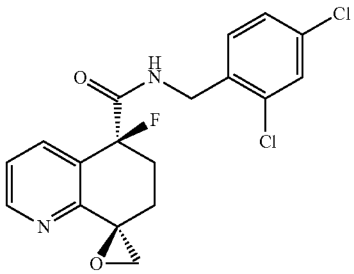 [SMILES: O=C(NCc1ccc(Cl)cc1Cl)[C@]1(F)CC[C@]2(CO2)c2ncccc21] | (2R,5'S)-N-(2,4-dichlorobenzyl)-5'-fluoro-6',7'-dihydro-5'H-spiro[oxirane-2,8'-quinoline]-5'-carboxamide | | |
| I-g-10 | 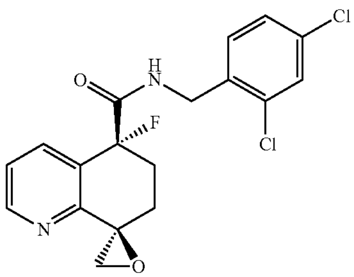 [SMILES: O=C(NCc1ccc(Cl)cc1Cl)[C@@]1(F)CC[C@]2(CO2)c2ncccc21] | (2R,5'R)-N-(2,4-dichlorobenzyl)-5'-fluoro-6',7'-dihydro-5'H-spiro[oxirane-2,8'-quinoline]-5'-carboxamide | IM I-e-26 | H |
| I-g-11 | 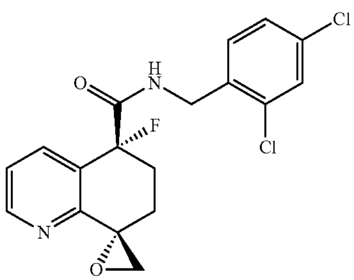 [SMILES: O=C(NCc1ccc(Cl)cc1Cl)[C@@]1(F)CC[C@@]2(CO2)c2ncccc21] | (2S,5'R)-N-(2,4-dichlorobenzyl)-5'-fluoro-6',7'-dihydro-5'H-spiro[oxirane-2,8'-quinoline]-5'-carboxamide | | |
| I-g-12 | 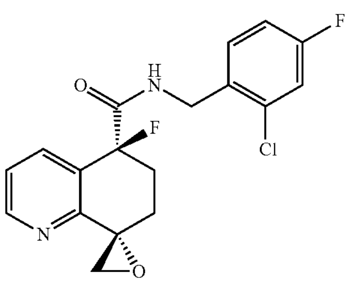 [SMILES: O=C(NCc1ccc(F)cc1Cl)[C@]1(F)CC[C@@]2(CO2)c2ncccc21] | (2S,5'S)-N-(2-chloro-4-fluoro-benzyl)-5'-fluoro-6',7'-dihydro-5'H-spiro[oxirane-2,8'-quinoline]-5'-carboxamide | Ex 249 | G |
| I-g-13 | 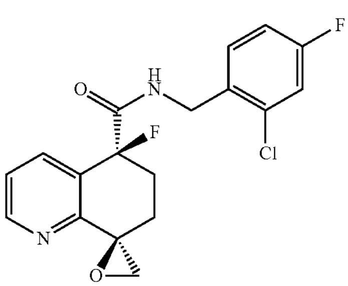 [SMILES: O=C(NCc1ccc(F)cc1Cl)[C@]1(F)CC[C@]2(CO2)c2ncccc21] | (2R,5'S)-N-(2-chloro-4-fluoro-benzyl)-5'-fluoro-6',7'-dihydro-5'H-spiro[oxirane-2,8'-quinoline]-5'-carboxamide | | |

TABLE 45-continued

| Intermediates | Structure | Chemical Name | Substrate | General Procedure |
|---|---|---|---|---|
| I-g-14 | 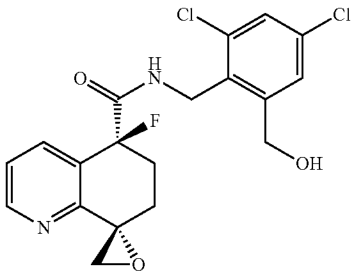 [SMILES: O=C(NCc1c(Cl)cc(Cl)cc1CO)[C@]1(F)CC[C@@]2(CO2)c2ncccc21] | (2S,5'S)-N-(2,4-dichloro-6-(hydroxymethyl)benzyl)-5'-fluoro-6',7'-dihydro-5'H-spiro[oxirane-2,8'-quinoline]-5'-carboxamide | IM I-c-21 | G |
| I-g-15 | 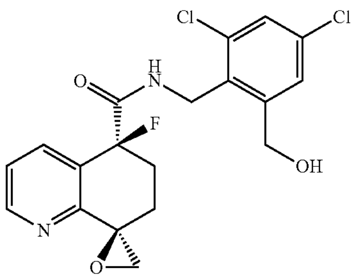 [SMILES: O=C(NCc1c(Cl)cc(Cl)cc1CO)[C@]1(F)CC[C@]2(CO2)c2ncccc21] | (2S,5'S)-N-(2,4-dichloro-6-(hydroxymethyl)benzyl)-5'-fluoro-6',7'-dihydro-5'H-spiro[oxirane-2,8'-quinoline]-5'-carboxamide | | |
| I-g-16 | 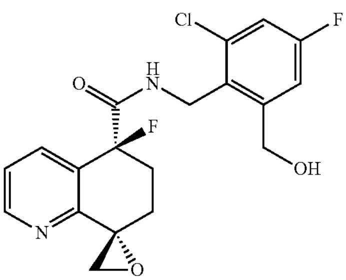 [SMILES: O=C(NCc1c(Cl)cc(F)cc1CO)[C@]1(F)CC[C@@]2(CO2)c2ncccc21] | (2S,5'S)-N-(2-chloro-4-fluoro-6-(hydroxymethyl)benzyl)-5'-fluoro-6',7'-dihydro-5'H-spiro[oxirane-2,8'-quinoline]-5'-carboxamide | IM I-c-22 | G |
| I-g-17 | 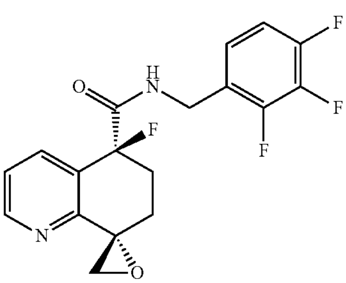 [SMILES: O=C(NCc1ccc(F)c(F)c1F)[C@]1(F)CC[C@@]2(CO2)c2ncccc21] | (2S,5'S)-5'-fluoro-N-(2,3,4-trifluorobenzyl)-6',7'-dihydro-5'H-spiro[oxirane-2,8'-quinoline]-5'-carboxamide | Ex 254 | G |
| I-g-18 | 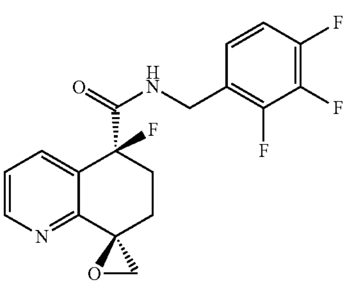 [SMILES: O=C(NCc1ccc(F)c(F)c1F)[C@]1(F)CC[C@]2(CO2)c2ncccc21] | (2S,5'S)-5'-fluoro-N-(2,3,4-trifluorobenzyl)-6',7'-dihydro-5'H-spiro[oxirane-2,8'-quinoline]-5'-carboxamide | | |

TABLE 45-continued

| Intermediates | Structure | Chemical Name | Substrate | General Procedure |
|---|---|---|---|---|
| I-g-19 | 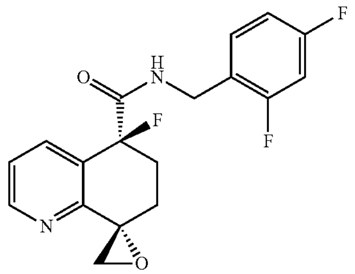 [SMILES: O=C(NCc1ccc(F)cc1F)[C@]1(F)CC[C@@]2(CO2)c2ncccc21] | (2S,5'S)-N-(2,4-difluorobenzyl)-5'-fluoro-6',7'-dihydro-5'H-spiro[oxirane-2,8'-quinoline]-5'-carboxamide | IM I-c-17 | G |
| I-g-20 | 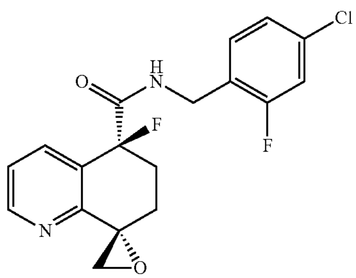 [SMILES: O=C(NCc1ccc(Cl)cc1F)[C@]1(F)CC[C@@]2(CO2)c2ncccc21] | (2S,5'S)-N-(4-chloro-2-fluorobenzyl)-5'-fluoro-6',7'-dihydro-5'H-spiro[oxirane-2,8'-quinoline]-5'-carboxamide | IM I-c-13 | G |
| I-g-21 | 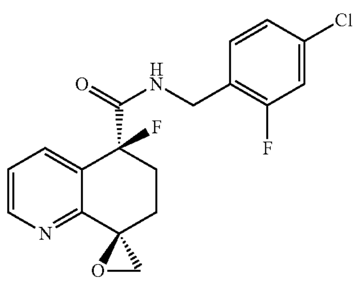 [SMILES: O=C(NCc1ccc(Cl)cc1F)[C@]1(F)CC[C@]2(CO2)c2ncccc21] | (2R,5'S)-N-(4-chloro-2-fluorobenzyl)-5'-fluoro-6',7'-dihydro-5'H-spiro[oxirane-2,8'-quinoline]-5'-carboxamide | | |
| I-g-22 | 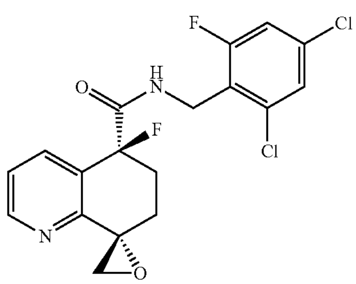 [SMILES: O=C(NCc1c(F)cc(Cl)cc1Cl)[C@]1(F)CC[C@@]2(CO2)c2ncccc21] | (2S,5'S)-N-(2,4-dichloro-6-fluorobenzyl)-5'-fluoro-6',7'-dihydro-5'H-spiro[oxirane-2,8'-quinoline]-5'-carboxamide | Ex 251 | G |
| I-g-23 | 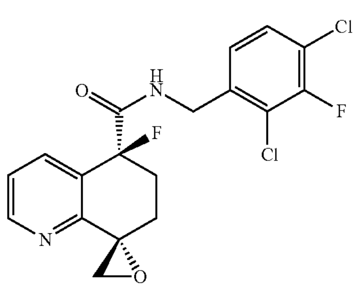 [SMILES: O=C(NCc1ccc(Cl)c(F)c1Cl)[C@]1(F)CC[C@@]2(CO2)c2ncccc21] | (2S,5'S)-N-(2,4-dichloro-3-fluorobenzyl)-5'-fluoro-6',7'-dihydro-5'H-spiro[oxirane-2,8'-quinoline]-5'-carboxamide | IM I-c-16 | G |

TABLE 45-continued

| Intermediates | Structure | Chemical Name | Substrate | General Procedure |
|---|---|---|---|---|
| I-g-24 | 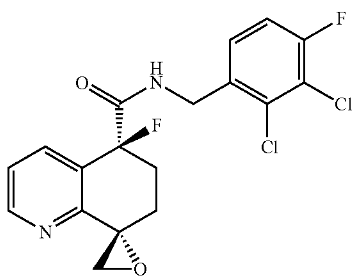 [SMILES: O=C(NCc1ccc(F)c(Cl)c1Cl)[C@]1(F)CC[C@@]2(CO2)c2ncccc21] | (2S,5'S)-N-(2,3-dichloro-4-fluorobenzyl)-5'-fluoro-6',7'-dihydro-5'H-spiro[oxirane-2,8'-quinoline]-5'-carboxamide | IM I-c-14 | G |
| I-g-25 | 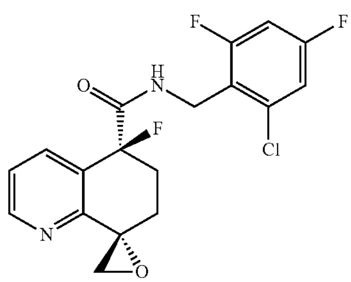 [SMILES: O=C(NCc1c(F)cc(F)cc1Cl)[C@]1(F)CC[C@@]2(CO2)c2ncccc21] | (2S,5'S)-N-(2-chloro-4,6-difluorobenzyl)-5'-fluoro-6',7'-dihydro-5'H-spiro[oxirane-2,8'-quinoline]-5'-carboxamide | IM I-c-20 | G |
| I-g-26 | 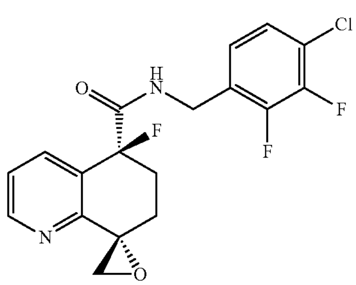 [SMILES: O=C(NCc1ccc(Cl)c(F)c1F)[C@]1(F)CC[C@@]2(CO2)c2ncccc21] | (2S,5'S)-N-(4-chloro-2,3-difluorobenzyl)-5'-fluoro-6',7'-dihydro-5'H-spiro[oxirane-2,8'-quinoline]-5'-carboxamide | IM I-c-15 | G |
| I-g-27 | 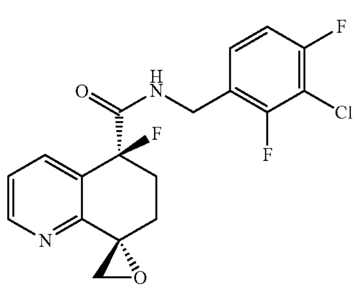 [SMILES: O=C(NCc1ccc(F)c(Cl)c1F)[C@]1(F)CC[C@@]2(CO2)c2ncccc21] | (2S,5'S)-N-(3-chloro-2,4-difluorobenzyl)-5'-fluoro-6',7'-dihydro-5'H-spiro[oxirane-2,8'-quinoline]-5'-carboxamide | IM I-c-18 | G |

TABLE 45-continued

| Intermediates | Structure | Chemical Name | Substrate | General Procedure |
|---|---|---|---|---|
| I-g-28 | 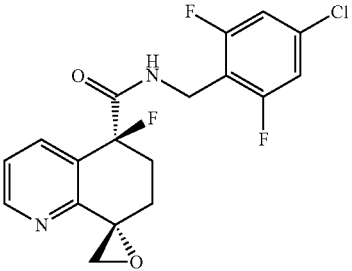 [SMILES: O=C(NCc1c(F)cc(Cl)cc1F)[C@]1(F)CC[C@@]2(CO2)c2ncccc21] | (2S,5'S)-N-(4-chloro-2,6-difluorobenzyl)-5'-fluoro-6',7'-dihydro-5'H-spiro[oxirane-2,8'-quinoline]-5'-carboxamide | 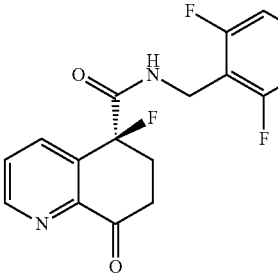

IM I-c-19 | G |
| I-g-29 | 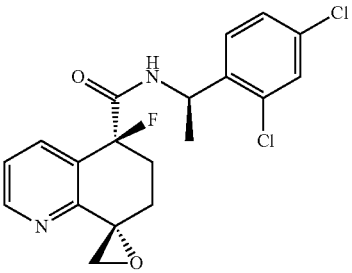 [SMILES: C[C@@H](NC(=O)[C@]1(F)CC[C@@]2(CO2)c2ncccc21)c1ccc(Cl)cc1Cl] | (2S,5'S)-N-((R)-1-(2,4-dichlorophenyl)ethyl)-5'-fluoro-6',7'-dihydro-5'H-spiro[oxirane-2,8'-quinoline]-5'-carboxamide | 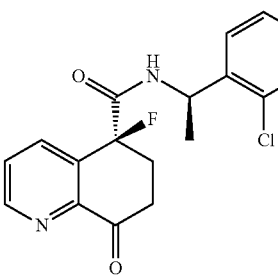

IM I-c-23 | G |
| I-g-30 | 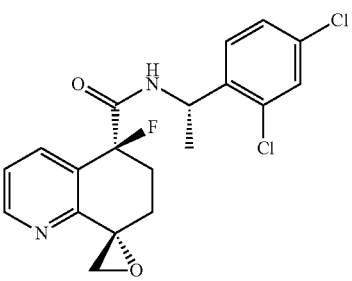 [SMILES: C[C@H](NC(=O)[C@]1(F)CC[C@@]2(CO2)c2ncccc21)c1ccc(Cl)cc1Cl] | (2S,5'S)-N-((S)-1-(2,4-dichlorophenyl)ethyl)-5'-fluoro-6',7'-dihydro-5'H-spiro[oxirane-2,8'-quinoline]-5'-carboxamide | 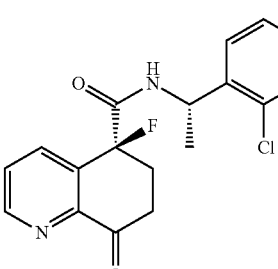

IM I-c-24 | G |
| I-g-31 | 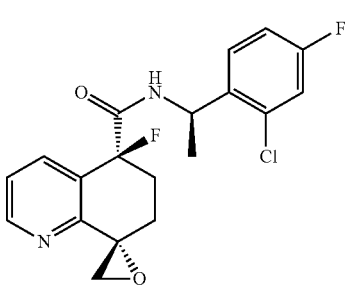 [SMILES: C[C@@H](NC(=O)[C@]1(F)CC[C@@]2(CO2)c2ncccc21)c1ccc(F)cc1Cl] | (2S,5'S)-N-((R)-1-(2-chloro-4-fluorophenyl)ethyl)-5'-fluoro-6',7'-dihydro-5'H-spiro[oxirane-2,8'-quinoline]-5'-carboxamide | 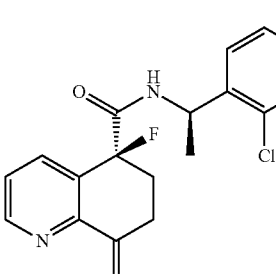

IM I-c-25 | G |
| I-g-32 | 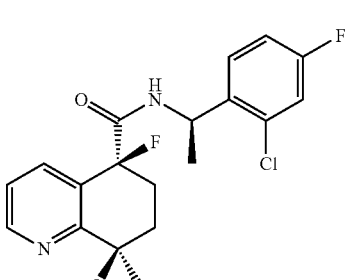 | (2R,5'S)-N-((R)-1-(2-chloro-4-fluorophenyl)ethyl)-5'-fluoro-6',7'-dihydro-5'H-spiro[oxirane-2,8'-quinoline]-5'-carboxamide | | |

TABLE 45-continued

| Intermediates | Structure | Chemical Name | Substrate | General Procedure |
|---|---|---|---|---|
| I-g-33 | 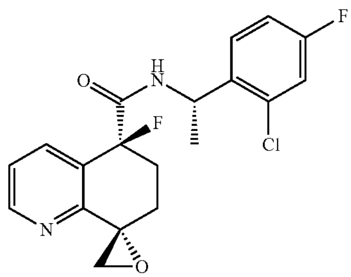 [SMILES: C[C@H](NC(=O)[C@]1(F)CC[C@@]2(CO2)c2ncccc21)c1ccc(F)cc1Cl] | (2S,5'S)-N-((S)-1-(2-chloro-4-fluorophenyl)ethyl)-5'-fluoro-6',7'-dihydro-5'H-spiro[oxirane-2,8'-quinoline]-5'-carboxamide | IM I-c-26 | G |
| I-g-34 | 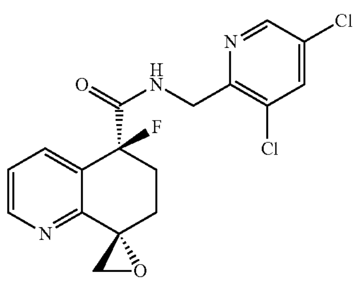 [SMILES: O=C(NCc1ncc(Cl)cc1Cl)[C@]1(F)CC[C@@]2(CO2)c2ncccc21] | (2S,5'S)-N-((3,5-dichloropyridin-2-yl)methyl)-5'-fluoro-6',7'-dihydro-5'H-spiro[oxirane-2,8'-quinoline]-5'-carboxamide | Ex 255 | G |
| I-g-35 | 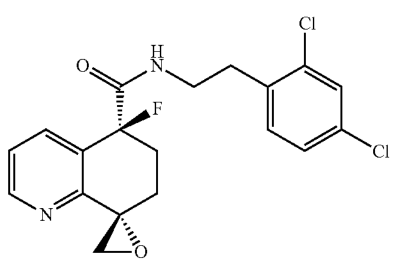 [SMILES: O=C(NCCc1ccc(Cl)cc1Cl)[C@]1(F)CC[C@@]2(CO2)c2ncccc21] | (2S,5'S)-N-(2,4-dichlorophenethyl)-5'-fluoro-6',7'-dihydro-5'H-spiro[oxirane-2,8'-quinoline]-5'-carboxamide | IM I-c-27 | G |
| I-g-36 | 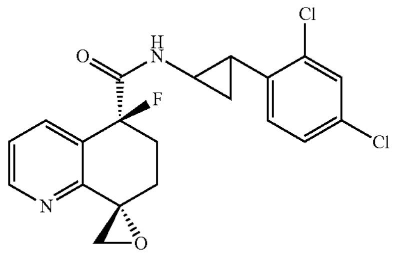 [SMILES: O=C(NC1CC1c1ccc(Cl)cc1Cl)[C@]1(F)CC[C@@]2(CO2)c2ncccc21] | (2S,5'S)-N-(2-(2,4-dichlorophenyl)cyclopropyl)-5'-fluoro-6',7'-dihydro-5'H-spiro[oxirane-2,8'-quinoline]-5'-carboxamide | IM I-c-28 | G |

TABLE 45-continued

| Intermediates | Structure | Chemical Name | Substrate | General Procedure |
|---|---|---|---|---|
| I-g-37 | 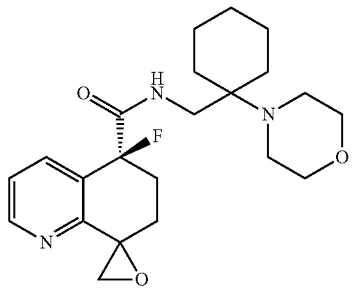 [SMILES: O=C(NCC1(N2CCOCC2)CCCCC1)[C@]1(F)CCC2(CO2)c2ncccc21] | (5'S)-5'-fluoro-N-((1-morpholinocyclohexyl)methyl)-6',7'-dihydro-5'H-spiro[oxirane-2,8'-quinoline]-5'-carboxamide | IM I-c-29 | G |
| I-g-38 | 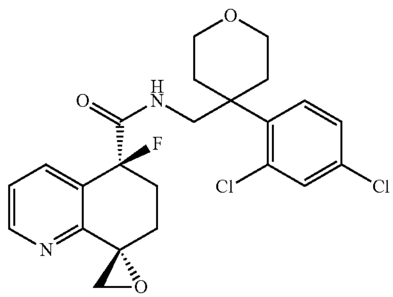 [SMILES: O=C(NCC1(c2ccc(Cl)cc2Cl)CCOCC1)[C@]1(F)CC[C@@]2(CO2)c2ncccc21] | (2S,5'S)-N-((4-(2,4-dichlorophenyl)tetrahydro-2H-pyran-4-yl)methyl)-5'-fluoro-6',7'-dihydro-5'H-spiro[oxirane-2,8'-quinoline]-5'-carboxamide | IM I-c-30 | G |
| I-g-39 | 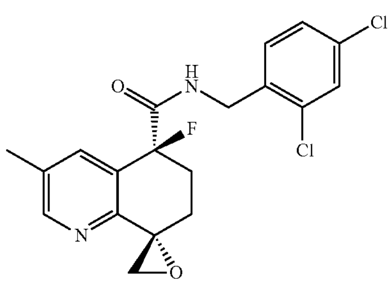 [SMILES: Cc1cnc2c(c1)[C@](F)(C(=O)NCc1ccc(Cl)cc1Cl)CC[C@@]21CO1] | (2S,5'S)-N-(2,4-dichlorobenyl)-5'-fluoro-3'-methyl-6',7'-dihydro-5'H-spiro[oxirane-2,8'-quinoline]-5'-carboxamide | IM I-c-31 | G |
| I-g-40 | 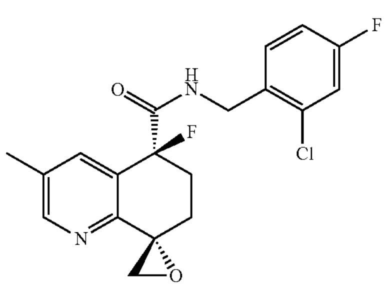 [SMILES: Cc1cnc2c(c1)[C@](F)(C(=O)NCc1ccc(F)cc1Cl)CC[C@@]21CO1] | (2S,5'S)-N-(2-chloro-4-fluorobenzyl)-5'-fluoro-3'-methyl-6',7'-dihydro-5'H-spiro[oxirane-2,8'-quinoline]-5'-carboxamide | IM I-c-32 | G |

IM I-g-8
$^1$H NMR and LCMS were identified with the IM I-g-4.
IM I-g-9
$^1$H NMR and LCMS were identified with the IM I-g-5.
IM I-g-10
$^1$H NMR and LCMS were identified with the IM I-g-4.
IM I-g-11
$^1$H NMR and LCMS were identified with the IM I-g-5.
IM I-g-12
$^1$H NMR and LCMS were identified with the IM I-g-6.
IM I-g-13
$^1$H NMR and LCMS were identified with the IM I-g-7.
IM I-g-14
$^1$H NMR (CDCl$_3$) delta 8.61 (1H, br dd, J=4.9, 1.8 Hz), 7.59 (1H, br), 7.45 (1H, d, J=1.8 Hz), 7.43 (1H, br dd, J=7.9, 1.8 Hz), 7.36 (1H, d, J=1.8 Hz), 7.21 (1H, dd, J=7.9, 4.9 Hz), 4.80 (1H, dd, J=14.7, 6.1 Hz), 4.78 (2H, d, J=6.1 Hz), 4.71 (1H, dd, J=14.7, 6.1 Hz), 3.85 (1H, d, J=6.1 Hz), 3.73 (1H, t, J=6.1 Hz), 3.02 (1H, d, J=6.1 Hz), 2.71 (1H, m), 2.54 (1H, m), 2.29 (1H, m), 2.10 (1H, m).

MS (ESI) m/z: 411.1 (M+H)$^+$.

IM I-g-15

$^1$H NMR (DMSO-d6) delta 8.77 (1H, br), 8.60 (1H, d, J=4.9 Hz), 7.64 (1H, d, J=7.9 Hz), 7.55 (1H, d, J=1.8 Hz), 7.48 (1H, d, J=1.8 Hz), 7.41 (1H, dd, J=7.9, 4.9 Hz), 5.52 (1H, t, J=5.5 Hz), 4.68 (2H, d, J=5.5 Hz), 4.51 (1H, d, J=14.7 Hz), 4.46 (1H, d, J=14.7 Hz), 3.43 (1H, d, J=6.1 Hz), 3.05 (1H, d, J=6.1 Hz), 2.50 (1H, m), 2.33-2.23 (2H, m), 2.13 (1H, m).

MS (ESI) m/z: 410.7 (M+H)$^+$.

IM I-g-16

$^1$H NMR (CDCl$_3$) delta 8.61 (1H, ddd, J=4.9, 1.8, 1.2 Hz), 7.57 (1H, br d, J=6.1 Hz), 7.43 (1H, ddd, J=7.9, 1.8, 1.2 Hz), 7.20 (1H, dd, J=7.9, 4.9 Hz), 7.18 (1H, dd, J=7.9, 2.4 Hz), 7.10 (1H, dd, J=8.6, 2.4 Hz), 4.82-4.77 (3H, m), 4.71 (1H, dd, J=14.7, 6.1 Hz), 3.85 (1H, d, J=6.1 Hz), 3.74 (1H, t, J=6.1 Hz), 3.02 (1H, d, J=6.1 Hz), 2.72 (1H, m), 2.54 (1H, m), 2.29 (1H, m), 2.10 (1H, m).

MS (ESI) m/z: 394.8 (M+H)$^+$.

IM I-g-17

$^1$H NMR (DMSO d6) delta 9.32 (1H, br), 8.61 (1H, br dd, J=4.9, 1.8 Hz), 7.80 (1H, br dd, J=7.9, 1.8 Hz), 7.61 (1H, dd, J=7.9, 4.9 Hz), 7.35-7.16 (2H, m), 4.45 (2H, m), 3.72 (1H, d, J=6.1 Hz), 3.03 (1H, d, J=6.1 Hz), 2.60-2.41 (2H, m), 2.27 (1H, m), 1.90 (1H, m).

MS (ESI) m/z: 367.0 (M+H)$^+$.

IM I-g-18

$^1$H NMR (DMSO-d6) delta 9.31 (1H, br), 8.61 (1H, br d, J=4.9 Hz), 7.64 (1H, d, J=7.9 Hz), 7.41 (1H, dd, J=7.9, 4.9 Hz), 7.32 (1H, m), 7.22 (1H, m), 4.45 (1H, dd, J=15.3, 5.5 Hz), 4.41 (1H, dd, J=15.3, 5.5 Hz), 3.43 (1H, d, J=6.1 Hz), 3.05 (1H, d, J=6.1 Hz), 2.50 (1H, m), 2.38-2.23 (2H, m), 2.12 (1H, m).

MS (ESI) m/z: 367.0 (M+H)$^+$.

IM I-g-19

$^1$H NMR (CDCl$_3$) delta 8.65 (1H, br dd, J=4.9, 1.8 Hz), 7.52 (1H, br dd, J=7.9, 1.8 Hz), 7.41 (1H, m), 7.25 (1H, br dd, J=7.9, 4.9 Hz), 7.17 (1H, br d, J=6.1 Hz), 6.96-6.87 (2H, m), 4.66 (1H, dd, J=14.7, 6.1 Hz), 4.58 (1H, dd, J=14.7, 6.1 Hz), 3.89 (1H, d, J=6.1 Hz), 3.05 (1H, d, J=6.1 Hz), 2.79 (1H, m), 2.60 (1H, m), 2.34 (1H, m), 2.15 (1H, m).

MS (ESI) m/z: 349.9 (M+H)$^+$.

IM I-g-20

$^1$H NMR (CDCl$_3$) delta 8.63 (1H, br dd, J=4.9, 1.8 Hz), 7.49 (1H, br dd, J=7.9, 1.8 Hz), 7.35 (1H, m), 7.23 (1H, br dd, J=7.9, 4.9 Hz), 7.19-7.11 (3H, m), 4.64 (1H, dd, J=14.7, 6.1 Hz), 4.56 (1H, dd, J=14.7, 6.1 Hz), 3.87 (1H, d, J=6.1 Hz), 3.03 (1H, d, J=6.1 Hz), 2.77 (1H, m), 2.58 (1H, m), 2.32 (1H, m), 2.13 (1H, m).

MS (ESI) m/z: 364.8 (M+H)$^+$.

IM I-g-21

$^1$H NMR (CDCl$_3$) delta 8.65 (1H, br dd, J=4.9, 1.8 Hz), 7.53 (1H, br dd, J=7.9, 1.8 Hz), 7.34 (1H, d, J=7.9, 6.7 Hz), 7.25 (1H, dd, J=7.9, 4.9 Hz), 7.26-7.13 (3H, m), 4.65 (1H, dd, J=14.7, 6.1 Hz), 4.57 (1H, dd, J=14.7, 6.1 Hz), 3.52 (1H, d, J=6.1 Hz), 3.08 (1H, d, J=6.1 Hz), 2.67 (1H, m), 2.53-2.40 (2H, m), 2.19 (1H, m).

MS (ESI) m/z: 364.8 (M+H)$^+$.

IM I-g-22

$^1$H NMR (CDCl$_3$) delta 8.62 (1H, br dd, J=4.9, 1.8 Hz), 7.53 (1H, br dd, J=7.9, 1.8 Hz), 7.31 (1H, d, J=1.8 Hz), 7.24 (1H, br dd, J=7.9, 4.9 Hz), 7.12 (1H, dd, J=8.6, 1.8 Hz), 7.02 (1H, br), 4.78 (1H, dd, J=14.7, 6.1 Hz), 4.69 (1H, dd, J=14.7, 6.1 Hz), 3.85 (1H, d, J=6.1 Hz), 3.02 (1H, d, J=6.1 Hz), 2.76 (1H, m), 2.56 (1H, m), 2.31 (1H, m), 2.14 (1H, m).

MS (ESI) m/z: 398.7 (M+H)$^+$.

IM I-g-23

$^1$H NMR (CDCl$_3$) delta 8.63 (1H, br dd, J=4.9, 1.8 Hz), 7.50 (1H, br dd, J=7.9, 1.8 Hz), 7.34 (1H, br dd, J=7.9, 4.9 Hz), 7.26-7.18 (3H, m), 4.69 (1H, dd, J=14.7, 6.1 Hz), 4.65 (1H, dd, J=14.7, 6.1 Hz), 3.86 (1H, d, J=6.1 Hz), 3.03 (1H, d, J=6.1 Hz), 2.76 (1H, m), 2.57 (1H, m), 2.33 (1H, m), 2.14 (1H, m).

MS (ESI) m/z: 398.8 (M+H)$^+$.

IM I-g-24

$^1$H NMR (CDCl$_3$) delta 8.63 (1H, br dd, J=4.9, 1.8 Hz), 7.49 (1H, br dd, J=7.9, 1.8 Hz), 7.38 (1H, dd, J=8.6, 5.5 Hz), 7.24 (1H, br dd, J=7.9, 4.9 Hz), 7.25-7.22 (1H, br), 7.12 (1H, dd, J=8.6, 7.9 Hz), 4.69 (1H, dd, J=15.3, 6.1 Hz), 4.65 (1H, dd, J=15.3, 6.1 Hz), 3.86 (1H, d, J=6.1 Hz), 3.03 (1H, d, J=6.1 Hz), 2.76 (1H, m), 2.57 (1H, m), 2.32 (1H, m), 2.14 (1H, m).

MS (ESI) m/z: 398.8 (M+H)$^+$.

IM I-g-25

$^1$H NMR (CDCl$_3$) delta 8.62 (1H, br dd, J=4.9, 1.8 Hz), 7.54 (1H, br dd, J=7.9, 1.8 Hz), 7.24 (1H, m), 7.06 (1H, br dd, J=7.9, 4.9 Hz), 7.01 (1H, br), 6.86 (1H, m), 4.78 (1H, dd, J=14.7, 5.5 Hz), 4.68 (1H, dd, J=14.7, 5.5 Hz), 3.86 (1H, d, J=6.1 Hz), 3.02 (1H, d, J=6.1 Hz), 2.76 (1H, m), 2.56 (1H, m), 2.32 (1H, m), 2.14 (1H, m).

MS (ESI) m/z: 382.8 (M+H)$^+$.

IM I-g-26

$^1$H NMR (CDCl$_3$) delta 8.63 (1H, br dd, J=4.9, 1.8 Hz), 7.50 (1H, br dd, J=7.9, 1.8 Hz), 7.28-7.08 (4H, m), 4.66 (1H, dd, J=14.7, 6.7 Hz), 4.61 (1H, dd, J=14.7, 6.7 Hz), 3.87 (1H, br d, J=6.1 Hz), 3.03 (1H, br d, J=6.1 Hz), 2.76 (1H, m), 2.57 (1H, m), 2.33 (1H, m), 2.15 (1H, m).

MS (ESI) m/z: 382.8 (M+H)$^+$.

IM I-g-27

$^1$H NMR (CDCl$_3$) delta 8.63 (1H, br dd, J=4.9, 1.8 Hz), 7.49 (1H, br dd, J=7.9, 1.8 Hz), 7.31 (1H, m), 7.24 (1H, br dd, J=7.9, 4.9 Hz), 7.19 (1H, br), 7.00 (1H, ddd, J=8.6, 4.3, 1.8 Hz), 4.64 (1H, dd, J=14.7, 6.1 Hz), 4.59 (1H, dd, J=14.7, 6.1 Hz), 3.87 (1H, d, J=6.1 Hz), 3.03 (1H, d, J=6.1 Hz), 2.76 (1H, m), 2.57 (1H, m), 2.32 (1H, m), 2.13 (1H, m).

MS (ESI) m/z: 382.8 (M+H)$^+$.

IM I-g-28

$^1$H NMR (CDCl$_3$) delta 8.62 (1H, br dd, J=4.3, 1.8 Hz), 7.51 (1H, br dd, J=7.9, 1.8 Hz), 7.24 (1H, br dd, J=7.9, 4.3 Hz), 7.06-6.99 (3H, m), 4.71 (1H, dd, J=14.7, 5.5 Hz), 4.61 (1H, dd, J=14.7, 4.9 Hz), 3.86 (1H, d, J=6.1 Hz), 3.02 (1H, d, J=6.1 Hz), 2.74 (1H, m), 2.56 (1H, m), 2.30 (1H, m), 2.13 (1H, m).

MS (ESI) m/z: 382.8 (M+H)$^+$.

IM I-g-29

$^1$H NMR (CDCl$_3$) delta 8.60 (1H, br dd, J=4.9, 1.8 Hz), 7.45 (1H, d, J=1.8 Hz), 7.44 (1H, br dd, J=7.9, 1.8 Hz), 7.37 (1H, d, J=8.6 Hz), 7.30 (1H, dd, J=8.6, 1.8 Hz), 7.19 (1H, dd, J=7.9, 4.9 Hz), 7.13 (1H, br), 5.47 (1H, m), 3.85 (1H, d, J=6.1 Hz), 3.02 (1H, d, J=6.1 Hz), 2.78 (1H, m), 2.58 (1H, m), 2.35 (1H, m), 2.16 (1H, m), 1.60 (3H, d, J=7.3 Hz).

MS (ESI) m/z: 395.3 (M+H)$^+$.

IM I-g-30

$^1$H NMR (CDCl$_3$) delta 8.64 (1H, br dd, J=4.9, 1.8 Hz), 7.61 (1H, br dd, J=7.9, 1.8 Hz), 7.42 (1H, d, J=1.8 Hz), 7.31-7.26 (3H, m), 7.17 (1H, dd, J=6.7, 6.1 Hz), 5.45 (1H, m), 3.86 (1H, d, J=6.1 Hz), 3.01 (1H, d, J=6.1 Hz), 2.77-2.51 (2H, m), 2.27 (1H, m), 2.10 (1H, m), 1.62 (3H, d, J=7.3 Hz).

MS (ESI) m/z: 395.2 (M+H)$^+$.

IM I-g-31

$^1$H NMR (CDCl$_3$) delta 8.59 (1H, br dd, J=4.3, 1.8 Hz), 7.45 (1H, br dd, J=7.9, 1.8 Hz), 7.41 (1H, dd, J=8.6, 6.1 Hz), 7.18 (1H, dd, J=7.9, 4.3 Hz), 7.16 (1H, dd, J=6.1, 3.1 Hz), 7.14 (1H, br), 7.03 (1H, ddd, J=8.5, 7.9, 3.1 Hz), 5.46 (1H, m), 3.85 (1H, d, J=6.1 Hz), 3.02 (1H, d, J=6.1 Hz), 2.77 (1H, m), 2.57 (1H, m), 2.34 (1H, m), 2.15 (1H, m), 1.60 (3H, d, J=6.7 Hz).

MS (ESI) m/z: 379.2 (M+H)$^+$.

IM I-g-32

$^1$H NMR (CDCl$_3$) delta 8.59 (1H, br dd, J=4.9, 1.8 Hz), 7.45 (1H, ddd, J=7.9, 1.8, 1.2 Hz), 7.40 (1H, dd, J=8.6, 6.1 Hz), 7.18 (1H, dd, J=8.6, 2.4 Hz), 7.16 (1H, dd, J=7.9, 4.9 Hz), 7.14 (1H, br), 7.04 (1H, ddd, J=8.6, 7.9, 2.4 Hz), 5.45 (1H, m), 3.50 (1H, d, J=6.1 Hz), 3.05 (1H, d, J=6.1 Hz), 2.67 (1H, m), 2.50-2.42 (2H, m), 2.22 (1H, m), 1.60 (3H, d, J=6.7 Hz).

MS (ESI) m/z: 379.2 (M+H)$^+$.

IM I-g-33

$^1$H NMR (CDCl$_3$) delta 8.64 (1H, ddd, J=4.9, 1.8, 1.2 Hz), 7.61 (1H, ddd, J=7.9, 1.8, 1.2 Hz), 7.36 (1H, dd, J=8.6, 6.1 Hz), 7.28 (1H, dd, J=7.9, 4.9 Hz), 7.16 (1H, dd, J=8.6, 3.1 Hz), 7.13 (1H, br), 7.02 (1H, dt, J=8.6, 3.1 Hz), 5.46 (1H, m), 3.86 (1H, d, J=6.1 Hz), 3.02 (1H, d, J=6.1 Hz), 2.78-2.52 (2H, m), 2.28 (1H, m), 2.10 (1H, m), 1.63 (3H, d, J=6.7 Hz).

MS (ESI) m/z: 378.9 (M+H)$^+$.

IM I-g-34

$^1$H NMR (CDCl$_3$) delta 8.64 (1H, br dd, J=4.3, 1.8 Hz), 8.47 (1H, d, J=2.4 Hz), 8.10 (1H, br), 7.78 (1H, d, J=2.4 Hz), 7.74 (1H, dd, J=7.9, 1.8 Hz), 7.26 (1H, dd, J=7.9, 4.3 Hz), 4.83 (1H, dd, J=18.3, 4.9 Hz), 4.71 (1H, dd, J=18.3, 4.9 Hz), 3.89 (1H, d, J=6.1 Hz), 3.05 (1H, d, J=6.1 Hz), 2.83 (1H, m), 2.62 (1H, m), 2.40 (1H, m), 2.16 (1H, m).

MS (ESI) m/z: 382.5 (M+H)$^+$.

IM I-g-35

$^1$H NMR (CDCl$_3$) delta 8.61 (1H, br d, J=4.3 Hz), 7.43 (1H, s), 7.33 (1H, d, J=7.9 Hz), 7.25-7.19 (2H, m), 7.21 (1H, dd, J=7.9, 4.3 Hz), 6.86 (1H, br d, J=4.9 Hz), 3.86 (1H, d, J=6.1 Hz), 3.79-3.63 (2H, m), 3.08-3.04 (2H, m), 3.02 (1H, d, J=6.1 Hz), 2.72 (1H, m), 2.55 (1H, m), 2.26 (1H, m), 2.12 (1H, m).

MS (ESI) m/z: 395.0 (M+H)$^+$.

IM I-g-36

$^1$H NMR (CDCl$_3$) delta 8.65 (1H, m), 7.59 (1H, m), 7.40 (1H, d, J=1.8 Hz), 7.27 (1H, m), 7.19 (1H, m), 7.12 (1H, d, J=8.6 Hz), 7.03 (1H, br), 3.88 (0.5H, d, J=6.1 Hz), 3.87 (0.5H, d, J=6.1 Hz), 3.10 (1H, m), 3.03 (1H, d, J=6.1 Hz), 2.79 (1H, m), 2.60 (1H, m), 2.39-2.29 (2H, m), 2.15 (1H, m), 1.43-1.31 (2H, m).

MS (ESI) m/z: 407.3 (M+H)$^+$.

IM I-g-37

$^1$H NMR (CDCl$_3$) delta 8.63 (1H, ddd, J=4.3, 1.8, 1.8 Hz), 7.55 (1H, dd, J=7.9, 1.8 Hz), 7.39 (1H, br), 7.25 (1H, m), 3.87 (0.7H, d, J=6.1 Hz), 3.7-3.69 (4H, m), 3.54-3.42 (2.3H, m), 3.06 (0.3H, d, J=6.1 Hz), 3.03 (0.7H, d, J=6.1 Hz), 2.85-2.38 (6H, m), 2.31 (1H, m), 2.15 (1H, m), 1.76-1.46 (10H, m).

MS (ESI) m/z: 404.2 (M+H)$^+$.

IM I-g-38

$^1$H NMR (CDCl$_3$) delta 8.60 (1H, br d, J=4.9 Hz), 7.47 (1H, d, J=1.8 Hz), 7.34-7.29 (2H, m), 7.18 (1H, dd, J=7.9, 4.9 Hz), 7.10 (1H, br d, J=7.9 Hz), 6.40 (1H, br d, J=6.7 Hz), 4.21 (1H, dd, J=14.1, 6.7 Hz), 3.99 (1H, dd, J=14.1, 6.1 Hz), 3.93-3.84 (2H, m), 3.81 (1H, d, J=6.1 Hz), 3.74-3.62 (2H, m), 2.99 (1H, d, J=6.1 Hz), 2.60 (1H, m), 2.50-2.34 (3H, m), 2.19-2.04 (4H, m).

MS (ESI) m/z: 465.0 (M+H)$^+$.

IM I-g-39

$^1$H NMR (CDCl$_3$) delta 8.44 (1H, br), 7.46 (1H, d, J=1.8 Hz), 7.39 (1H, m), 7.29-7.22 (3H, m), 4.71-4.59 (2H, m), 3.85 (1H, d, J=6.1 Hz), 3.00 (1H, d, J=6.1 Hz), 2.76 (1H, m), 2.57 (1H, m), 2.29 (1H, m), 2.27 (3H, s), 2.09 (1H, m).

MS (ESI) m/z: 395.0 (M+H)$^+$.

IM I-g-40

$^1$H NMR (CDCl$_3$) delta 8.44 (1H, br), 7.46 (1H, dd, J=8.6, 6.1 Hz), 7.20-7.14 (3H, m), 7.02 (1H, ddd, J=8.6, 7.9, 3.1 Hz), 4.69 (1H, dd, J=14.7, 6.1 Hz), 4.62 (1H, dd, J=14.7, 6.1 Hz), 3.86 (1H, d, J=6.1 Hz), 3.01 (1H, d, J=6.1 Hz), 2.76 (1H, m), 2.58 (1H, m), 2.29 (1H, m), 2.27 (3H, s), 2.07 (1H, m).

MS (ESI) m/z: 379.4 (M+H)$^+$.

The following Examples and Intermediates were prepared by General Procedure J, K, P, Q, R, or S (Tables 46 and 48).

General Procedure P

A mixture of substrate (1.0 eq.), LiClO$_4$ (1.5 eq.), and KCN (1.5 eq.) in MeCN was heated at reflux. After being stirred at reflux until complete reaction, the mixture was cooled to room temperature. Water was added to the mixture, and the mixture was extracted with EtOAc twice. The extracts were washed with brine, dried over Na$_2$SO$_4$, and concentrated in vacuo. The residue was purified by silica gel column chromatography and preparative HPLC to afford following Examples.

General Procedure Q

The substrate (1.0 eq.) was dissolved with 1.0 M TBAF in THF (12.0 eq.) and the mixture was heated at 70° C. until complete reaction. The mixture was cooled to room temperature and water was added to the mixture. The mixture was extracted with EtOAc and washed with brine. The extract was dried over Na$_2$SO$_4$ and concentrated in vacuo. The resulting mixture was purified by silica gel column chromatography and preparative HPLC to afford the following Examples.

General Procedure R

Fifteen percent of sodium thiomethoxide in water (3.0 eq.) was added to the solution of substrate (1.0 eq.) in THF. The mixture was stirred at 60° C. until complete reaction and then cooled to room temperature. Water was added to the mixture and extracted with EtOAc twice. The extracts were dried over Na$_2$SO$_4$ and concentrated in vacuo. The resulting residue was purified by silica gel column chromatography and preparative HPLC to afford the following Examples and Intermediates.

General Procedure S

To a mixture of substrate (1.0 eq.) and K$_2$CO$_3$ (2.0 eq.) in acetone was added mercaptoethanol (4.4 eq.) at ambient temperature. The mixture was stirred at 70° C. until complete reaction and cooled to room temperature. The volatile was removed under reduced pressure and water was added to the mixture. The mixture was extracted with EtOAc, dried over Na$_2$SO$_4$, and concentrated in vacuo. The resulting residue was purified by silica gel column chromatography and preparative HPLC to afford the following Examples and Intermediates.

TABLE 46

| Examples | Structure | Chemical Name | Substrate | General Procedure (/Amine) |
|---|---|---|---|---|
| 256 | 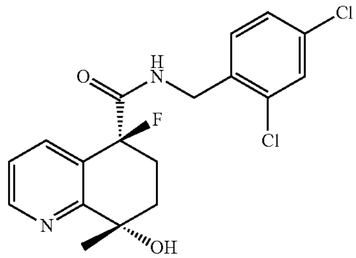 [SMILES: C[C@]1(O)CC[C@@](F)(C(=O)NCc2ccc(Cl)cc2Cl)c2cccnc21] | (5S,8S)-N-(2,4-dichloro-benzyl)-5-fluoro-8-hydroxy-8-methyl-5,6,7,8-tetrahydro-quinoline-5-carboxamide | IM I-g-8 | K |
| 257 | 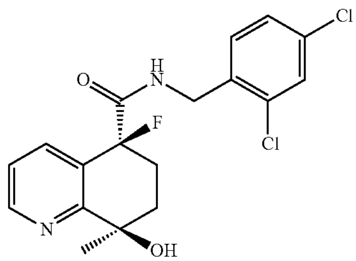 [SMILES: C[C@@]1(O)CC[C@@](F)(C(=O)NCc2ccc(Cl)cc2Cl)c2cccnc21] | (5S,8R)-N-(2,4-dichloro-benzyl)-5-fluoro-8-hydroxy-8-methyl-5,6,7,8-tetrahydro-quinoline-5-carboxamide | IM I-g-9 | K |
| 258 | 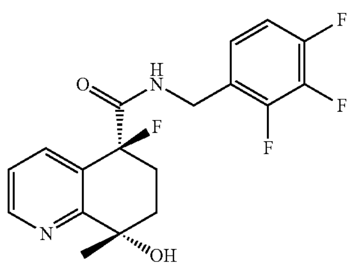 [SMILES: C[C@]1(O)CC[C@@](F)(C(=O)NCc2ccc(F)c(F)c2F)c2cccnc21] | (5S,8S)-5-fluoro-8-hydroxy-8-methyl-N-(2,3,4-trifluorobenzyl)-5,6,7,8-tetrahydro-quinoline-5-carboxamide | IM I-g-17 | K |
| 259 | 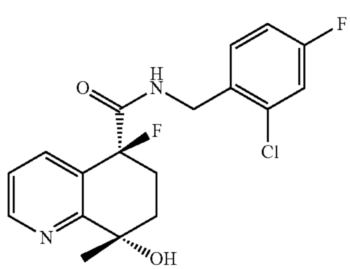 [SMILES: C[C@]1(O)CC[C@@](F)(C(=O)NCc2ccc(F)cc2Cl)c2cccnc21] | (5S,8S)-N-(2-chloro-4-fluorobenzyl)-5-fluoro-8-hydroxy-8-methyl-5,6,7,8-tetra-hydroquinoline-5-carboxamide | IM I-g-12 | K |
| 260 | 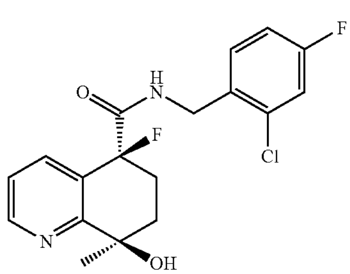 [SMILES: C[C@@]1(O)CC[C@@](F)(C(=O)NCc2ccc(F)cc2Cl)c2cccnc21] | (5S,8R)-N-(2-chloro-4-fluorobenzyl)-5-fluoro-8-hydroxy-8-methyl-5,6,7,8-tetra-hydroquinoline-5-carboxamide | IM I-g-13 | K |

TABLE 46-continued

| Examples | Structure | Chemical Name | Substrate | General Procedure (/Amine) |
|---|---|---|---|---|
| 261 | 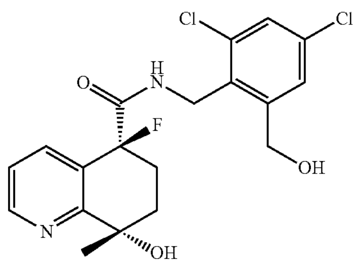 [SMILES: C[C@]1(O)CC[C@@](F)(C(=O)NCc2c(Cl)cc(Cl)cc2CO)c2cccnc21] | (5S,8S)-N-(2,4-dichloro-6-(hydroxymethyl)benzyl)-5-fluoro-8-hydroxy-8-methyl-5,6,7,8-tetrahydroquinoline-5-carboxamide | IM I-g-14 | K |
| 262 | 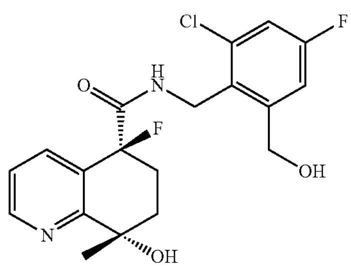 [SMILES: C[C@]1(O)CC[C@@](F)(C(=O)NCc2c(Cl)cc(F)cc2CO)c2cccnc21] | (5S,8S)-N-(2-chloro-4-fluoro-6-(hydroxymethyl)benzyl)-5-fluoro-8-hydroxy-8-methyl-5,6,7,8-tetrahydroquinoline-5-carboxamide | IM I-g-16 | K |
| 263 | 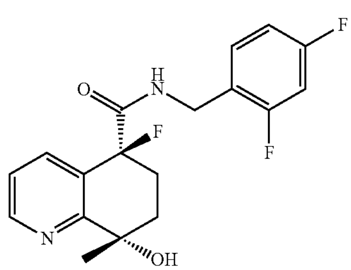 [SMILES: C[C@]1(O)CC[C@@](F)(C(=O)NCc2ccc(F)cc2F)c2cccnc21] | (5S,8S)-N-(2,4-difluorobenzyl)-5-fluoro-8-hydroxy-8-methyl-5,6,7,8-tetrahydroquinoline-5-carboxamide | IM I-g-19 | K |
| 264 | 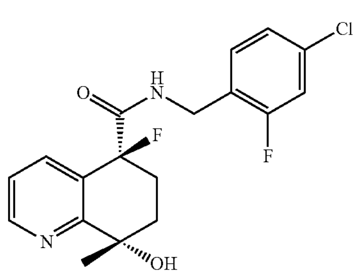 [SMILES: C[C@]1(O)CC[C@@](F)(C(=O)NCc2ccc(Cl)cc2F)c2cccnc21] | (5S,8S)-N-(4-chloro-2-fluorobenzyl)-5-fluoro-8-hydroxy-8-methyl-5,6,7,8-tetrahydroquinoline-5-carboxamide | IM I-g-20 | K |

TABLE 46-continued

| Examples | Structure | Chemical Name | Substrate | General Procedure (/Amine) |
|---|---|---|---|---|
| 265 | 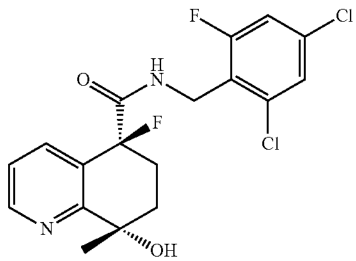 [SMILES: C[C@]1(O)CC[C@@](F)(C(=O)NCc2c(F)cc(Cl)cc2Cl)c2cccnc21] | (5S,8S)-N-(2,4-dichloro-6-fluorobenzyl)-5-fluoro-8-hydroxy-8-methyl-5,6,7,8-tetrahydroquinoline-5-carboxamide | IM-I-g-22 | K |
| 266 | 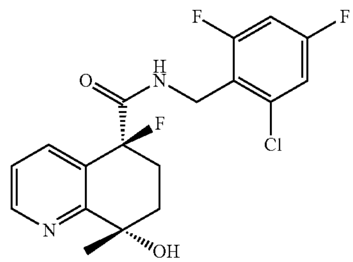 [SMILES: C[C@]1(O)CC[C@@](F)(C(=O)NCc2c(F)cc(F)cc2Cl)c2cccnc21] | (5S,8S)-N-(2-chloro-4,6-difluorobenzyl)-5-fluoro-8-hydroxy-8-methyl-5,6,7,8-tetrahydroquinoline-5-carboxamide | IM-I-g-25 | K |
| 267 | 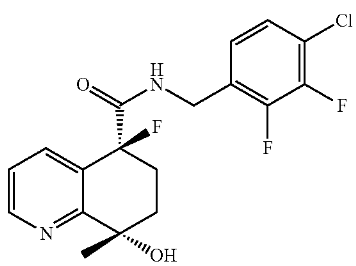 | (5S,8S)-N-(4-chloro-2,3-difluorobenzyl)-5-fluoro-8-hydroxy-8-methyl-5,6,7,8-tetrahydroquinoline-5-carboxamide | IM I-g-26 | K |
| 268 | 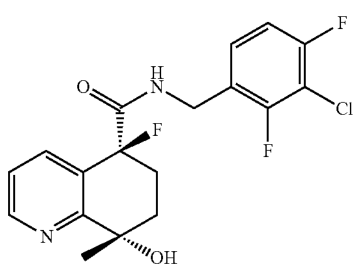 [SMILES: C[C@]1(O)CC[C@@](F)(C(=O)NCc2ccc(F)c(Cl)c2F)c2cccnc21] | (5S,8S)-N-(3-chloro-2,4-difluorobenzyl)-5-fluoro-8-hydroxy-8-methyl-5,6,7,8-tetrahydroquinoline-5-carboxamide | IM I-g-27 | K |
| 269 | 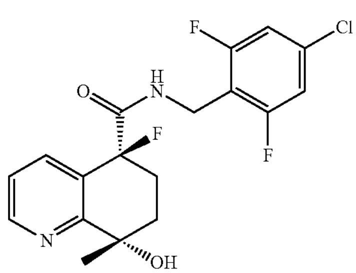 [SMILES: C[C@]1(O)CC[C@@](F)(C(=O)NCc2c(F)cc(Cl)cc2F)c2cccnc21] | (5S,8S)-N-(4-chloro-2,6-difluorobenzyl)-5-fluoro-8-hydroxy-8-methyl-5,6,7,8-tetrahydroquinoline-5-carboxamide | IM I-g-28 | K |

TABLE 46-continued

| Examples | Structure | Chemical Name | Substrate | General Procedure (/Amine) |
|---|---|---|---|---|
| 270 | 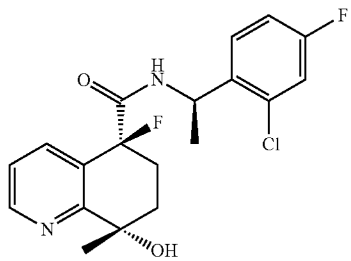 [SMILES: C[C@@H](NC(=O)[C@]1(F)CC[C@](C)(O)c2ncccc21)c1ccc(F)cc1Cl] | (5S,8S)-N-((R)-1-(2-chloro-4-fluorophenyl)ethyl)-5-fluoro-8-hydroxy-8-methyl-5,6,7,8-tetrahydroquinoline-5-carboxamide | IM-I-g-31 | K |
| 271 | 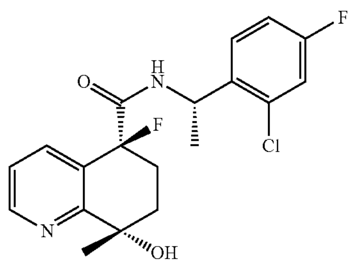 [SMILES: C[C@H](NC(=O)[C@]1(F)CC[C@](C)(O)c2ncccc21)c1ccc(F)cc1Cl] | (5S,8S)-N-((S)-1-(2-chloro-4-fluorophenyl)ethyl)-5-fluoro-8-hydroxy-8-methyl-5,6,7,8-tetrahydroquinoline-5-carboxamide | IM I-g-33 | K |
| 272 | 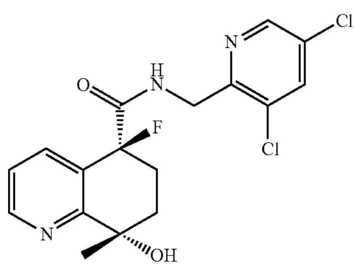 [SMILES: C[C@]1(O)CC[C@@](F)(C(=O)NCc2ncc(Cl)cc2Cl)c2cccnc21] | (5S,8S)-N-((3,5-dichloropyridin-2-yl)methyl)-5-fluoro-8-hydroxy-8-methyl-5,6,7,8-tetrahydroquinoline-5-carboxamide | IM I-g-34 | K |
| 273 | 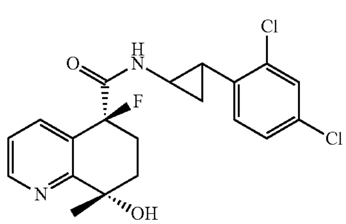 [SMILES: C[C@]1(O)CC[C@@](F)(C(=O)NC2CC2c2ccc(Cl)cc2Cl)c2cccnc21] | (5S,8S)-N-((trans)-2-(2,4-dichlorophenyl)cyclopropyl)-5-fluoro-8-hydroxy-8-methyl-5,6,7,8-tetrahydroquinoline-5-carboxamide | IM I-g-36 | K |
| 274 | 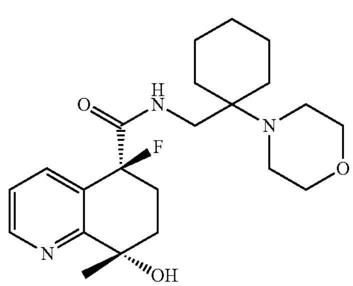 [SMILES: C[C@]1(O)CC[C@@](F)(C(=O)NCC2(N3CCOCC3)CCCCC2)c2cccnc21] | (5S,8S)-5-fluoro-8-hydroxy-8-methyl-N-((1-morpholinocyclohexyl)methyl)-5,6,7,8-tetrahydroquinoline-5-carboxamide | IM I-g-37 | K |

TABLE 46-continued

| Examples | Structure | Chemical Name | Substrate | General Procedure (/Amine) |
|---|---|---|---|---|
| 275 | 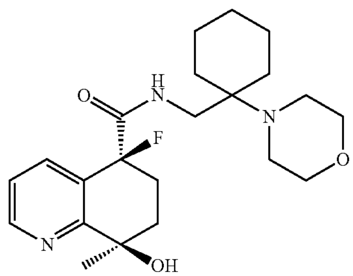 [SMILES: C[C@@]1(O)CC[C@@](F)(C(=O)NCC2(N3CCOCC3)CCCCC2)c2cccnc21] | (5S,8R)-5-fluoro-8-hydroxy-8-methyl-N-((1-morpholinocyclohexyl)methyl)-5,6,7,8-tetrahydroquinoline-5-carboxamide | | |
| 276 | 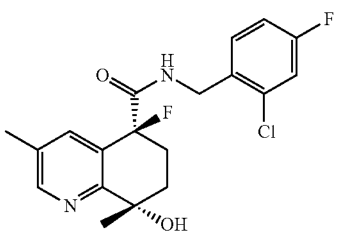 [SMILES: Cc1cnc2c(c1)[C@](F)(C(=O)NCc1ccc(F)cc1Cl)CC[C@]2(C)O] | (5S,8S)-N-(2-chloro-4-fluorobenzyl)-5-fluoro-8-hydroxy-3,8-dimethyl-5,6,7,8-tetrahydroquinoline-5-carboxamide | IM I-g-40 | K |
| 277 | 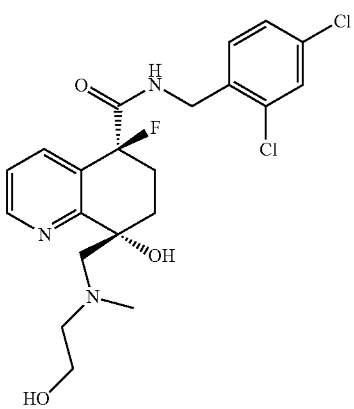 [SMILES: CN(CCO)C[C@]1(O)CC[C@@](F)(C(=O)NCc2ccc(Cl)cc2Cl)c2cccnc21] | (5S,8R)-N-(2,4-dichlorobenzyl)-5-fluoro-8-hydroxy-8-(((2-hydroxyethyl)(methyl)amino)methyl)-5,6,7,8-tetrahydroquinoline-5-carboxamide | IM I-g-8 | J/ |
| 278 | 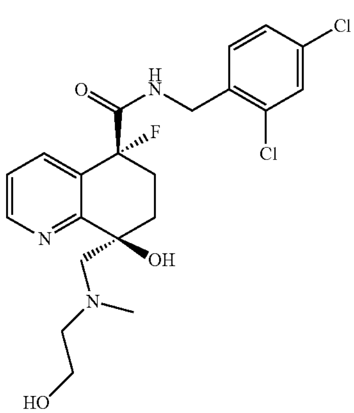 [SMILES: CN(CCO)C[C@@]1(O)CC[C@](F)(C(=O)NCc2ccc(Cl)cc2Cl)c2cccnc21] | (5R,8S)-N-(2,4-dichlorobenzyl)-5-fluoro-8-hydroxy-8-(((2-hydroxyethyl)(methyl)amino)methyl)-5,6,7,8-tetrahydroquinoline-5-carboxamide | IM I-g-9 | J/ |

TABLE 46-continued

| Examples | Structure | Chemical Name | Substrate | General Procedure (/Amine) |
|---|---|---|---|---|
| 279 | 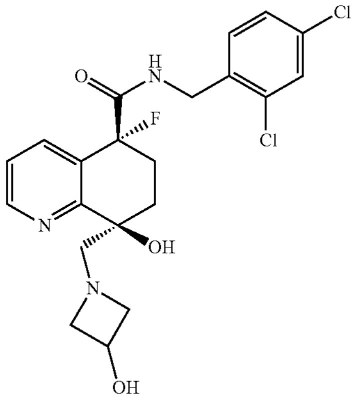 [SMILES: O=C(NCc1ccc(Cl)cc1Cl)[C@@]1(F)CC[C@](O)(CN2CC(O)C2)c2ncccc21] | (5R,8S)-N-(2,4-dichlorobenzyl)-5-fluoro-8-hydroxy-8-((3-hydroxyazetidin-1-yl)methyl)-5,6,7,8-tetrahydroquinoline-5-carboxamide | IM I-g-8 | J/ |
| 280 | 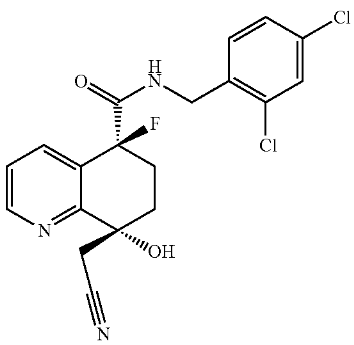 [SMILES: N#CC[C@]1(O)CC[C@@](F)(C(=O)NCc2ccc(Cl)cc2Cl)c2cccnc21] | (5S,6R)-8-(cyanomethyl)-N-(2,4-dichlorobenzyl)-5-fluoro-8-hydroxy-5,6,7,8-tetrahydroquinoline-5-carboxamide | IM I-g-8 | P |
| 281 | 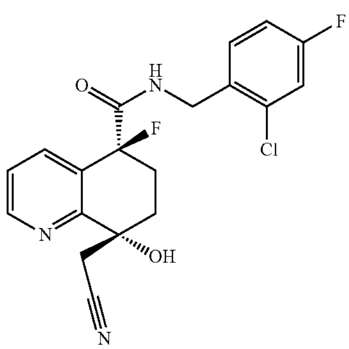 [SMILES: N#CC[C@]1(O)CC[C@@](F)(C(=O)NCc2ccc(F)cc2Cl)c2cccnc21] | (5S,6R)-N-(2-chloro-4-fluorobenzyl)-8-(cyanomethyl)-5-fluoro-8-hydroxy-5,6,7,8-tetrahydroquinoline-5-carboxamide | IM I-g-12 | P |
| 282 | 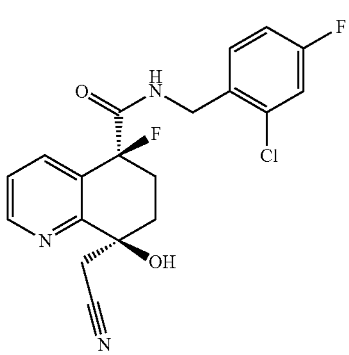 [SMILES: N#CC[C@@]1(O)CC[C@@](F)(C(=O)NCc2ccc(F)cc2Cl)c2cccnc21] | (5S,8S)-N-(2-chloro-4-fluorobenzyl)-8-(cyanomethyl)-5-fluoro-8-hydroxy-5,6,7,8-tetrahydroquinoline-5-carboxamide | IM I-g-13 | P |

TABLE 46-continued

| Examples | Structure | Chemical Name | Substrate | General Procedure (/Amine) |
|---|---|---|---|---|
| 283 | 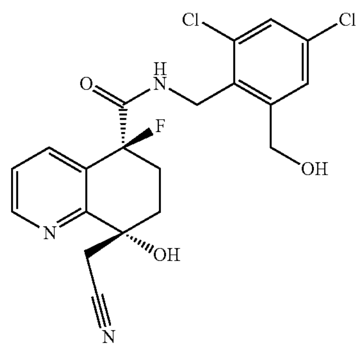 [SMILES: N#CC[C@]1(O)CC[C@@](F)(C(=O)NCc2c(Cl)cc(Cl)cc2CO)c2cccnc21] | (5S,8R)-8-(cyanomethyl)-N-(2,4-dichloro-6-(hydroxymethyl)benzyl)-5-fluoro-8-hydroxy-5,6,7,8-tetrahydroquinoline-5-carboxamide | IM I-g-14 | P |
| 284 | 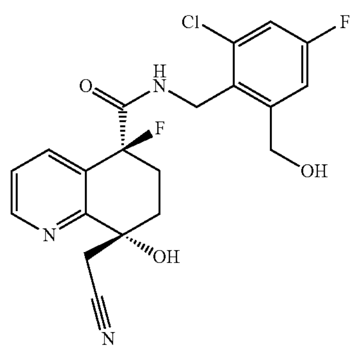 [SMILES: N#CC[C@]1(O)CC[C@@](F)(C(=O)NCc2c(Cl)cc(F)cc2CO)c2cccnc21] | (5S,8R)-N-(2-chloro-4-fluoro-6-(hydroxymethyl)benzyl)-8-(cyanomethyl)-5-fluoro-8-hydroxy-5,6,7,8-tetrahydroquinoline-5-carboxamide | IM I-g-16 | P |
| 285 | 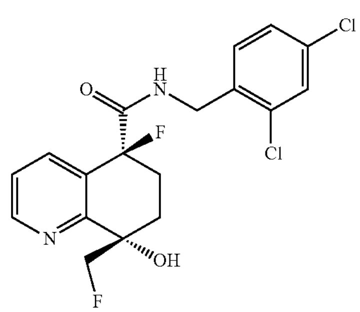 [SMILES: O=C(NCc1ccc(Cl)cc1Cl)[C@]1(F)CC[C@@](O)(CF)c2ncccc21] | (5S,8S)-N-(2,4-dichlorobenzyl)-5-fluoro-8-(fluoromethyl)-8-hydroxy-5,6,7,8-tetrahydroquinoline-5-carboxamide | IM I-g-8 | Q |
| 286 | 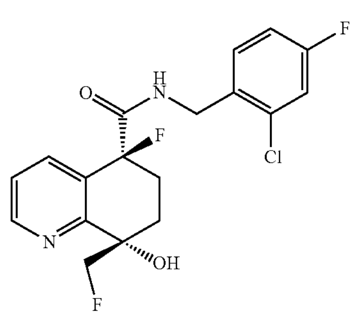 [SMILES: O=C(NCc1ccc(F)cc1Cl)[C@]1(F)CC[C@@](O)(CF)c2ncccc21] | (5S,8S)-N-(2-chloro-4-fluorobenzyl)-5-fluoro-8-(fluoromethyl)-8-hydroxy-5,6,7,8-tetrahydroquinoline-5-carboxamide | IM I-g-12 | Q |

TABLE 46-continued

| Examples | Structure | Chemical Name | Substrate | General Procedure (/Amine) |
|---|---|---|---|---|
| 287 | 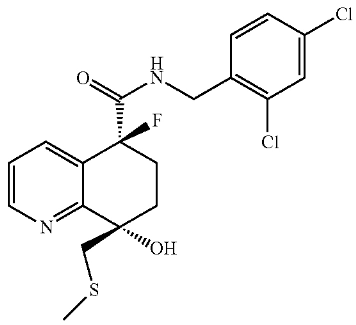 [SMILES: CSC[C@]1(O)CC[C@@](F)(C(=O)NCc2ccc(Cl)cc2Cl)c2cccnc21] | (5S,8S)-N-(2,4-dichlorobenzyl)-5-fluoro-8-hydroxy-8-((methylthio)methyl)-5,6,7,8-tetrahydroquinoline-5-carboxamide | IM I-g-8 | R |
| 288 | 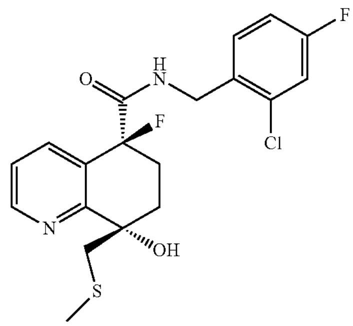 [SMILES: CSC[C@]1(O)CC[C@@](F)(C(=O)NCc2ccc(F)cc2Cl)c2cccnc21] | (5S,8S)-N-(2-chloro-4-fluorobenzyl)-5-fluoro-8-hydroxy-8-((methylthio)methyl)-5,6,7,8-tetrahydroquinoline-5-carboxamide | IM I-g-12 | R |
| 289 | 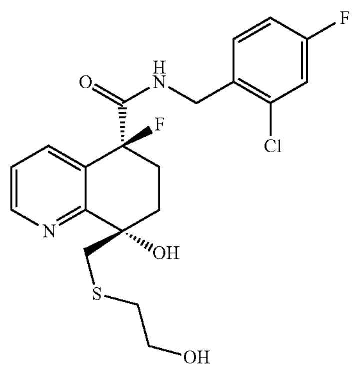 [SMILES: O=C(NCc1ccc(F)cc1Cl)[C@]1(F)CC[C@@](O)(CSCCO)c2ncccc21] | (5S,8S)-N-(2-chloro-4-fluorobenzyl)-5-fluoro-8-hydroxy-8-(((2-hydroxyethyl)thio)methyl)-5,6,7,8-tetrahydroquinoline-5-carboxamide | IM I-g-12 | S |

TABLE 47

| | LC MS | | |
|---|---|---|---|
| Examples | Method | tR (min) | [M + H]+ |
| 256 | C | 1.57 | 382.9 |
| 257 | C | 1.57 | 383.0 |
| 258 | C | 1.43 | 369.0 |
| 259 | C | 1.47 | 367.0 |
| 260 | C | 1.45 | 366.9 |
| 261 | C | 1.43 | 412.9 |
| 262 | D | 1.37 | 397.1 |
| 263 | C | 1.37 | 351.1 |
| 264 | C | 1.48 | 367.1 |
| 265 | C | 1.57 | 401.0 |
| 266 | D | 1.54 | 385.0 |
| 267 | D | 1.59 | 385.0 |
| 268 | D | 1.58 | 385.0 |
| 269 | D | 1.57 | 385.0 |
| 270 | D | 1.61 | 381.1 |
| 271 | D | 1.62 | 381.1 |
| 272 | D | 1.54 | 384.0 |
| 273 | D | 1.79 | 409.1 |
| 274 | D | 1.61 | 406.2 |
| 275 | D | 1.58 | 406.2 |
| 276 | D | 1.63 | 381.1 |
| 280 | D | 1.66 | 408.0 |
| 281 | D | 1.55 | 392.1 |
| 282 | D | 1.54 | 392.1 |
| 283 | D | 1.49 | 438.1 |
| 284 | D | 1.37 | 422.0 |
| 285 | D | 1.70 | 401.0 |
| 286 | D | 1.58 | 385.1 |
| 287 | D | 1.78 | 429.0 |
| 288 | D | 1.67 | 413.1 |
| 289 | D | 1.44 | 443.1 |

Ex 256

¹H NMR (CDCl₃) delta 8.60 (1H, ddd, J=4.9, 1.8, 1.2 Hz), 7.49 (1H, ddd, J=7.9, 1.8, 1.2 Hz), 7.44 (1H, d, J=2.4 Hz), 7.36 (1H, d, J=7.9 Hz), 7.23 (1H, dd, J=7.9, 2.4 Hz), 7.21 (1H, dd, J=7.9, 4.9 Hz), 7.13 (1H, br d, J=5.5, Hz), 4.62 (1H, dd, J=14.7, 6.1 Hz), 4.57 (1H, dd, J=14.7, 6.1 Hz), 3.26 (1H, br s), 2.65 (1H, m), 2.38 (1H, m), 2.22-2.11 (2H, m), 1.63 (3H, s).

Ex 257

¹H NMR (CDCl₃) delta 8.60 (1H, br dd, J=4.9, 1.8 Hz), 7.46 (1H, d, J=1.8 Hz), 7.45 (1H, ddd, J=7.9, 1.8, 1.2 Hz), 7.39-7.20 (4H, m), 4.66 (1H, dd, J=14.7, 6.1 Hz), 4.59 (1H, dd, J=14.7, 6.1 Hz), 4.00 (1H, br s), 2.60 (1H, m), 2.36-2.23 (2H, m), 2.16 (1H, m), 1.56 (3H, s).

Ex 258

¹H NMR (CDCl₃) delta 8.61 (1H, ddd, J=4.9, 1.8, 1.2 Hz), 7.49 (1H, ddd, J=7.9, 1.8, 1.2 Hz), 7.22 (1H, dd, J=7.9, 4.9 Hz), 7.14-7.08 (2H, m), 6.97 (1H, m), 4.61 (1H, dd, J=14.7, 6.1 Hz), 4.55 (1H, dd, J=14.7, 6.1 Hz), 3.30 (1H, br s), 2.65 (1H, m), 2.37 (1H, m), 2.22-2.11 (2H, m), 1.63 (3H, s).

Ex 259

¹H NMR (CDCl₃) delta 8.61 (1H, ddd, J=4.9, 1.8, 1.2 Hz), 7.50 (1H, ddd, J=7.9, 1.8, 1.2 Hz), 7.41 (1H, dd, J=8.6, 5.5 Hz), 7.22 (1H, dd, J=7.9, 4.9 Hz), 7.18 (1H, dd, J=8.6, 2.4 Hz), 7.11 (1H, br d, J=5.5 Hz), 6.99 (1H, ddd, J=8.6, 7.9, 2.4, Hz), 4.63 (1H, dd, J=14.7, 6.1 Hz), 4.57 (1H, dd, J=14.7, 6.1 Hz), 3.18 (1H, br s), 2.65 (1H, m), 2.39 (1H, m), 2.23-2.10 (2H, m), 1.63 (3H, s).

Ex 260

¹H NMR (CDCl₃) delta 8.60 (1H, br dd, J=4.9, 1.8 Hz), 7.45-7.41 (2H, m), 7.26-7.18 (3H, m), 7.00 (1H, ddd, J=8.6, 7.9, 2.4 Hz), 4.66 (1H, dd, J=14.7, 6.1 Hz), 4.59 (1H, dd, J=14.7, 5.5 Hz), 4.03 (1H, s), 2.59 (1H, m), 2.36-2.23 (2H, m), 2.14 (1H, m), 1.56 (3H, s).

Ex 261

¹H NMR (CDCl₃) delta 8.57 (1H, ddd, J=4.9, 1.8, 1.2 Hz), 7.52 (1H, br d, J=5.5 Hz), 7.43-7.41 (2H, m), 7.33 (1H, d, J=1.8 Hz), 7.18 (1H, dd, J=7.9, 4.9 Hz), 4.76-4.69 (3H, m), 4.64 (1H, dd, J=14.7, 6.1 Hz), 3.99 (1H, br), 3.43 (1H, br), 2.60 (1H, m), 2.32 (1H, m), 2.17-2.04 (2H, m), 1.61 (3H, s).

Ex 262

¹H NMR (CDCl₃) delta 8.60 (1H, ddd, J=4.9, 1.8, 1.2 Hz), 7.51 (1H, br d, J=5.5 Hz), 7.43 (1H, br d, J=7.9 Hz), 7.19 (1H, dd, J=7.9, 4.9 Hz), 7.17 (1H, dd, J=7.9, 2.4 Hz), 7.09 (1H, dd, J=8.6, 2.4 Hz), 4.79-4.62 (3H, m), 4.66 (1H, dd, J=14.7, 6.1 Hz), 3.79 (1H, br), 3.21 (1H, br), 2.60 (1H, m), 2.33 (1H, m), 2.19-2.08 (2H, m), 1.63 (3H, s).

Ex 263

¹H NMR (CDCl₃) delta 8.60 (1H, ddd, J=4.9, 1.8, 1.2 Hz), 7.49 (1H, d, J=7.9 Hz), 7.36 (1H, dd, J=8.6, 6.1 Hz), 7.21 (1H, dd, J=7.9, 4.9 Hz), 7.07 (1H, br d, J=4.9 Hz), 6.90-6.84 (2H, m), 4.59 (1H, dd, J=14.7, 6.1 Hz), 4.52 (1H, dd, J=14.7, 6.1 Hz), 3.28 (1H, br), 2.66 (1H, m), 2.38 (1H, m), 2.22-2.11 (2H, m), 1.63 (3H, s).

Ex 264

¹H NMR (CDCl₃) delta 8.60 (1H, ddd, J=4.9, 1.8, 1.2 Hz), 7.49 (1H, ddd, J=7.9, 1.8, 1.2 Hz), 7.31 (1H, t, J=7.9 Hz), 7.21 (1H, dd, J=7.9, 4.9 Hz), 7.16-7.08 (3H, m), 4.59 (1H, dd, J=14.7, 6.1 Hz), 4.52 (1H, dd, J=14.7, 6.1 Hz), 3.31 (1H, br s), 2.66 (1H, m), 2.38 (1H, m), 2.22-2.11 (2H, m), 1.63 (3H, s).

Ex 265

¹H NMR (CDCl₃) delta 8.60 (1H, ddd, J=4.9, 1.8, 1.2 Hz), 7.51 (1H, ddd, J=7.9, 1.8, 1.2 Hz), 7.29 (1H, dd, J=1.8, 1.2 Hz), 7.21 (1H, dd, J=7.9, 4.9 Hz), 7.10 (1H, dd, J=9.2, 1.8 Hz), 6.97 (1H, br d, J=5.5 Hz), 4.74 (1H, dd, J=14.7, 6.1 Hz), 4.64 (1H, dd, J=14.7, 5.5 Hz), 3.29 (1H, br s), 2.66 (1H, m), 2.38 (1H, m), 2.21-2.10 (2H, m), 1.63 (3H, s).

Ex 266

¹H NMR (CDCl₃) delta 8.59 (1H, ddd, J=4.9, 1.8, 1.2 Hz), 7.52 (1H, ddd, J=7.9, 1.8, 1.2 Hz), 7.21 (1H, dd, J=7.9, 4.9 Hz), 7.04 (1H, br dd, J=7.9, 2.4 Hz), 6.96 (1H, br d, J=5.5 Hz), 6.84 (1H, br dt, J=8.6, 2.4 Hz), 4.74 (1H, dd, J=14.7, 6.1 Hz), 4.64 (1H, dd, J=14.7, 5.5 Hz), 3.32 (1H, br s), 2.67 (1H, m), 2.32 (1H, m), 2.21-2.10 (2H, m), 1.63 (3H, s).

Ex 267

¹H NMR (CDCl₃) delta 8.61 (1H, m), 7.49 (1H, dd, J=7.9, 1.2 Hz), 7.25-7.08 (4H, m), 4.62 (1H, dd, J=15.3, 6.1 Hz), 4.56 (1H, dd, J=15.3, 6.7 Hz), 3.30 (1H, br), 2.64 (1H, m), 2.38 (1H, m), 2.22-2.11 (2H, m), 1.63 (3H, s).

Ex 268

¹H NMR (CDCl₃) delta 8.61 (1H, ddd, J=4.9, 1.8, 1.2 Hz), 7.49 (1H, ddd, J=7.9, 1.8, 1.2 Hz), 7.28 (1H, m), 7.22 (1H, dd, J=7.9, 4.9 Hz), 7.11 (1H, br), 6.98 (1H, dt, J=8.6, 1.8 Hz), 4.60 (1H, dd, J=14.7, 6.1 Hz), 4.55 (1H, dd, J=14.7, 6.1 Hz), 3.29 (1H, br s), 2.65 (1H, m), 2.38 (1H, m), 2.25-2.11 (2H, m), 1.63 (3H, s).

Ex 269

¹H NMR (CDCl₃) delta 8.60 (1H, ddd, J=4.9, 1.8, 1.2 Hz), 7.50 (1H, d, J=7.9 Hz), 7.22 (1H, dd, J=7.9, 4.9 Hz), 7.04-6.95 (3H, m), 4.66 (1H, dd, J=14.7, 6.1 Hz), 4.57 (1H, dd, J=14.7, 5.5 Hz), 3.30 (1H, br s), 2.65 (1H, m), 2.37 (1H, m), 2.20-2.09 (2H, m), 1.63 (3H, s).

Ex 270

¹H NMR (CDCl₃) delta 8.57 (1H, br d, J=4.9 Hz), 7.45 (1H, ddd, J=7.9, 1.8, 1.2 Hz), 7.39 (1H, dd, J=8.6, 6.1 Hz), 7.17-7.14 (2H, m), 7.06 (1H, dd, J=6.7, 5.5 Hz), 7.02 (1H, ddd, J=8.6, 7.9, 2.4 Hz), 5.42 (1H, dq, J=6.7, 6.7 Hz), 3.33 (1H, br s), 2.68 (1H, m), 2.39 (1H, m), 2.24-2.13 (2H, m), 1.63 (3H, s), 1.59 (3H, d, J=6.7 Hz).

Ex 271

¹H NMR (CDCl₃) delta 8.62 (1H, ddd, J=4.9, 1.8, 1.2 Hz), 7.60 (1H, ddd, J=7.9, 1.8, 1.2 Hz), 7.34 (1H, dd, J=8.6, 5.5

Hz), 7.26 (1H, dd, J=7.9, 4.9 Hz), 7.15 (1H, dd, J=8.6, 2.4 Hz), 7.07 (1H, dd, J=6.7, 5.5 Hz), 7.01 (1H, ddd, J=8.6, 7.9, 2.4 Hz), 5.41 (1H, dq, J=7.3, 6.7 Hz), 3.28 (1H, br s), 2.59 (1H, m), 2.33 (1H, m), 2.19-2.08 (2H, m), 1.63 (3H, s), 1.59 (3H, d, J=7.3 Hz).

Ex 272

¹H NMR (CDCl₃) delta 8.63 (1H, br d, J=4.9 Hz), 8.48 (1H, d, J=2.4 Hz), 8.03 (1H, br d, J=4.3 Hz), 7.77 (1H, d, J=2.4 Hz), 7.72 (1H, d, J=7.9 Hz), 7.24 (1H, dd, J=7.9, 4.9 Hz), 4.78 (1H, dd, J=18.3, 4.9 Hz), 4.67 (1H, dd, J=18.3, 4.3 Hz), 3.27 (1H, br s), 2.72 (1H, m), 2.40 (1H, m), 2.29-2.18 (2H, m), 1.66 (3H, s).

Ex 277

¹H NMR (CDCl₃) delta 8.61 (1H, dt, J=4.7, 1.6 Hz), 7.51 (1H, dt, J=8.0, 1.5 Hz), 7.44 (1H, s), 7.35 (1H, d, J=8.19 Hz), 7.16-7.29 (3H, m), 4.53-4.66 (2H, m), 3.46-3.64 (2H, m), 3.03 (1H, d, J=14.1 Hz), 2.85 (1H, d, J=14.1 Hz), 2.49-2.75 (3H, m), 2.13-2.40 (6H, m) 1.99-2.10 (1H, m).
MS (ESI) m/z: 456.2 (M+H)⁺.

Ex 278

¹H NMR and LCMS were identified with the Ex 277.

Ex 279

¹H NMR (CDCl₃) delta 8.61 (1H, br d, J=4.7 Hz), 7.54 (1H, d, J=8.0 Hz), 7.44 (1H, d, J=2.1 Hz), 7.34 (1H, d, J=7.7 Hz), 7.27-7.30 (1H, m), 7.19-7.25 (1H, m), 4.48-4.65 (3H, m), 3.96-4.16 (2H, m), 3.89 (1H, br s), 3.56 (1H, br d, J=13.0 Hz), 3.18 (1H, br d, J=13.1 Hz), 2.67-2.82 (1H, m), 2.16-2.28 (3H, m).
MS (ESI) m/z: 454.2 (M+H)⁺.

Ex 280

¹H NMR (DMSO d6) delta 9.25 (1H, br), 8.70 (1H, ddd, J=4.9, 1.8, 1.2 Hz), 7.67 (1H, dd, J=7.9, 1.8 Hz), 7.64 (1H, d, J=1.8 Hz), 7.50-7.42 (2H, m), 7.39 (1H, d, J=6.7 Hz), 5.98 (1H, s), 4.53 (1H, dd, J=15.3, 6.1 Hz), 4.44 (1H, dd, J=15.3, 5.5 Hz), 3.35 (1H, d, J=16.5 Hz), 3.24 (1H, d, J=16.5 Hz), 2.82-2.64 (2H, m), 2.30-2.17 (2H, m).

Ex 282

¹H NMR (CDCl₃) delta 8.63 (1H, ddd, J=4.9, 1.8, 1.2 Hz), 7.56 (1H, ddd, J=7.9, 1.8, 1.2 Hz), 7.40 (1H, dd, J=8.6, 5.5 Hz), 7.32 (1H, dd, J=7.9, 4.9 Hz), 7.23 (1H, br), 7.20 (1H, dd, J=8.6, 2.4 Hz), 7.01 (1H, ddd, J=8.6, 7.9, 2.4 Hz), 4.63 (1H, dd, J=14.7, 6.1 Hz), 4.57 (1H, dd, J=14.7, 6.1 Hz), 4.29 (1H, s), 2.98 (1H, d, J=16.5 Hz), 2.89 (1H, d, J=16.5 Hz), 2.82-2.27 (4H, m).

Ex 283

¹H NMR (CDCl₃) delta 8.60 (1H, ddd, J=4.9, 1.8, 1.2 Hz), 7.60 (1H, br), 7.45 (1H, ddd, J=7.9, 1.8, 1.2 Hz), 7.44 (1H, d, J=1.8 Hz), 7.33 (1H, d, J=1.8 Hz), 7.26 (1H, m), 4.80-4.62 (4H, m), 3.78 (1H, dd, J=6.1, 5.5 Hz), 3.71 (1H, br s), 3.20 (1H, d, J=16.5 Hz), 3.06 (1H, d, J=16.5 Hz), 2.71 (1H, m), 2.40-2.37 (2H, m), 2.19 (1H, m).

Ex 284

¹H NMR (CDCl₃) delta 8.60 (1H, ddd, J=4.9, 1.8, 1.2 Hz), 7.59 (1H, br d, J=6.1 Hz), 7.45 (1H, ddd, J=7.9, 1.8, 1.2 Hz), 7.26 (1H, m), 7.18 (1H, dd, J=7.9, 2.4 Hz), 7.08 (1H, dd, J=8.6, 2.4 Hz), 4.87-4.71 (3H, m), 4.65 (1H, dd, J=14.7, 6.1 Hz), 3.77 (1H, br), 3.62 (1H, br), 3.20 (1H, d, J=17.1 Hz), 3.06 (1H, d, J=17.1 Hz), 2.73 (1H, m), 2.43-2.37 (2H, m), 2.18 (1H, m).

Ex 287

¹H NMR (CDCl₃) delta 8.62 (1H, br d, J=4.3 Hz), 7.49 (1H, dd, J=7.9, 1.2 Hz), 7.45 (1H, d, J=2.4 Hz), 7.37 (1H, d, J=7.9 Hz), 7.27 (1H, dd, J=7.9, 2.4 Hz), 7.26 (1H, dd, J=7.9, 4.3 Hz), 7.18 (1H, br d, J=5.5 Hz), 4.65 (1H, dd, J=14.7, 6.1 Hz), 4.58 (1H, dd, J=14.7, 6.1 Hz), 3.33 (1H, br), 3.16 (1H, d, J=13.5 Hz), 3.12 (1H, d, J=13.5 Hz), 2.68 (1H, m), 2.52 (1H, m), 2.30 (1H, m), 2.18 (1H, m), 2.10 (3H, s).

Ex 289

¹H NMR (CDCl₃) delta 8.62 (1H, ddd, J=4.9, 1.8, 1.2 Hz), 7.51 (1H, ddd, J=7.9, 1.8, 1.2 Hz), 7.41 (1H, dd, J=8.6, 6.1 Hz), 7.24 (1H, dd, J=7.9, 4.9 Hz), 7.19 (1H, dd, J=7.9, 3.1 Hz), 7.19 (1H, br), 7.00 (1H, ddd, J=8.6, 7.9, 3.1 Hz), 4.64 (1H, dd, J=14.7, 6.1 Hz), 4.58 (1H, dd, J=14.7, 6.1 Hz), 3.73 (2H, t, J=6.1 Hz), 3.71 (1H, br), 3.23 (1H, d, J=13.4 Hz), 3.18 (1H, d, J=13.4 Hz), 2.82-2.63 (3H, m), 2.45 (1H, m), 2.31 (1H, m), 2.17 (1H, m), 1.69 (1H, br).

TABLE 48

| Intermediates | Structure | Chemical Name | Substrate | General Procedure (/Amine) |
|---|---|---|---|---|
| I-h-2-1 | (structure) | (5S,8R)-N-(2,4-(dichlorobenzyl)-5-fluoro-8-hydroxy-8-((methylthio)methyl)-5,6,7,8-tetrahydroquinoline-5-carboxamide | IM I-g-9 | R |

TABLE 48-continued

| Intermediates | Structure | Chemical Name | Substrate | General Procedure (/Amine) |
|---|---|---|---|---|
| I-h-2-2 | 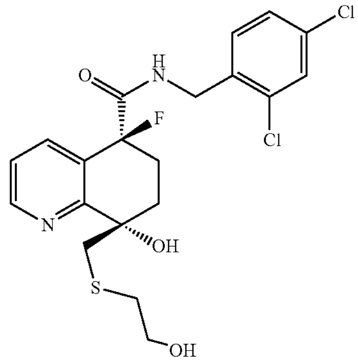 [SMILES: O=C(NCc1ccc(Cl)cc1Cl)[C@]1(F)CC[C@@](O)(CSCCO)c2ncccc21] | (5S,8S)-N-(2,4-dichloro benzyl)-5-fluoro-8-hydroxy-8-(((2-hydroxyethyl)thio)methyl)-5,6,7,8-tetrahydroquinoline-5-carboxamid | IM I-g-8 | S |
| I-h-1-1 | 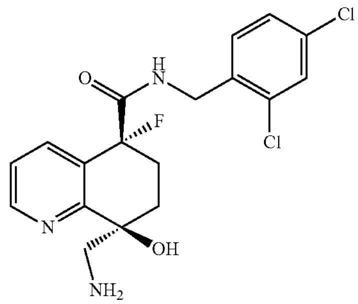 [SMILES: NC[C@@]1(O)CC[C@](F)(C(=O)NCc2ccc(Cl)cc2Cl)c2cccnc21] | (5R,8S)-8-(aminomethyl)-N-(2,4-dichlorobenzyl)-5-fluoro-8-hydroxy-5,6,7,8-tetrahydroquinoline-5-carboxamide | IM I-g-10 | J/ NH$_4$Cl |
| I-h-1-2 | 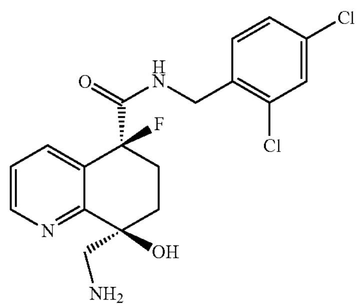 [SMILES: NC[C@@]1(O)CC[C@@](F)(C(=O)NCc2ccc(Cl)cc2Cl)c2cccnc21] | (5S,8S)-8-(aminomethyl)-N-(2,4-dichlorobenzyl)-5-fluoro-8-hydroxy-5,6,7,8-tetrahydroquinoline-5-carboxamide | IM I-g-9 | J/ NH$_4$Cl |
| I-h-1-3 | 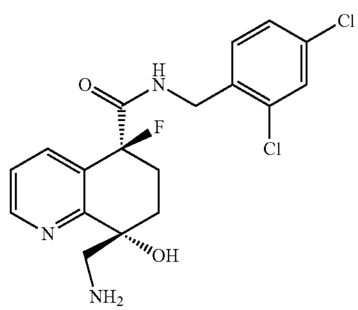 [SMILES: NC[C@]1(O)CC[C@@](F)(C(=O)NCc2ccc(Cl)cc2Cl)c2cccnc21] | (5S,8R)-8-(aminomethyl)-N-(2,4-dichlorobenzyl)-5-fluoro-8-hydroxy-5,6,7,8-tetrahydroquinoline-5-carboxamide | IM I-g-8 | J/ NH$_4$Cl |

IM I-h-2-1

$^1$H NMR (CDCl$_3$) delta 8.62 (1H, ddd, J=4.3, 1.8, 1.2 Hz), 7.49 (1H, ddd, J=7.9, 1.8, 1.2 Hz), 7.45 (1H, d, J=1.8 Hz), 7.36 (1H, d, J=8.6 Hz), 7.28-7.21 (3H, m), 4.63 (1H, dd, J=14.7, 6.1 Hz), 4.58 (1H, dd, J=14.7, 6.1 Hz), 4.12 (1H, s), 2.97 (2H, s), 2.65-2.43 (2H, m), 2.30 (1H, m), 2.18 (3H, s), 2.14 (1H, m).

MS (ESI) m/z: 429.1 (M+H)$^+$.

IM I-h-2-2

$^1$H NMR (CDCl$_3$) delta 8.61 (1H, br dd, J=4.9, 1.8 Hz), 7.50 (1H, br dd, J=7.9, 1.8 Hz), 7.45 (1H, d, J=1.8 Hz), 7.36 (1H, d, J=7.9 Hz), 7.27-7.22 (2H, m), 7.20 (1H, br), 4.64 (1H, dd, J=14.7, 6.1 Hz), 4.58 (1H, dd, J=14.7, 6.1 Hz), 3.82 (1H, br), 3.72 (2H, t, J=5.5 Hz), 3.47 (1H, s), 3.24 (1H, d, J=13.5 Hz), 3.17 (1H, d, J=13.5 Hz), 2.81-2.62 (3H, m), 2.44 (1H, m), 2.30 (1H, m), 2.17 (1H, m).

MS (ESI) m/z: 459.2 (M+H)$^+$.

IM I-h-1-1
  MS (ESI) m/z: 398.1 (M+H)+.
IM I-h-1-2
  MS (ESI) m/z: 398.1 (M+H)+.
IM I-h-1-3
  MS (ESI) m/z: 398.1 (M+H)+.

Example 290

(2R,5'S)—N-(2,4-dichlorobenzyl)-5'-fluoro-4-methyl-6',7'-dihydro-5'H-spiro[morpholine-2,8'-quinoline]-5'-carboxamide

[Chem. 30]

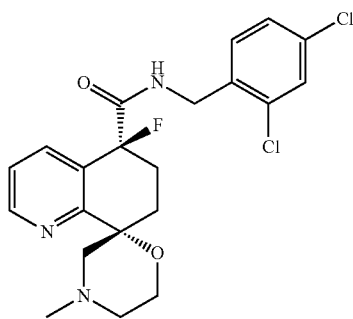

To a stirred solution of substrate (1.0 eq.) and TMAD (1.5 eq.) in THF was added nBu₃P (1.5 eq.) at ambient temperature. After being stirred at ambient temperature until complete reaction, the mixture was concentrated under reduced pressure. The crude residue was purified by silica gel column chromatography (EtOAc) to afford the title compound.

Ex 290

$^1$H NMR (DMSO d6) delta 9.22 (1H, br s), 8.65 (1H, dt, J=4.6, 1.6 Hz), 7.60-7.70 (2H, m), 7.36-7.49 (3H, m), 4.35-4.53 (2H, m), 3.79 (1H, td, J=11.7, 2.5 Hz), 3.61 (1H, dd, J=11.6, 3.1 Hz), 3.08 (1H, d, J=11.3 Hz), 2.84 (1H, dt, J=11.8, 2.5 Hz), 2.66 (1H, br d, J=11.1 Hz), 2.52-2.58 (1H, m), 2.32-2.47 (1H, m), 2.21 (3H, s), 1.90-2.16 (3H, m).

MS (ESI) m/z: 438.1 (M+H)+.

The following Examples were prepared by General Procedure T (Table 49).

General Procedure T

The mixture of substrate (1.0 eq.) and 1,1'-carbonylbis-1H-imidazole (1.1 eq.) in THF was stirred at ambient temperature until complete reaction. The reaction mixture was purified by silica gel column chromatography (10% MeOH/EtOAc) to afford the following Examples.

TABLE 49

| Examples | Structure | Chemical Name | Substrate |
| --- | --- | --- | --- |
| 291 | 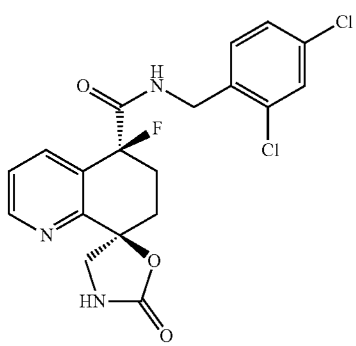 [SMILES: O=C1NC[C@]2(CC[C@@](F)(C(=O)NCc3ccc(Cl)cc3Cl)c3cccnc32)O1] | (5S,5'S)-N-(2,4-dichlorobenzyl)-5'-fluoro-2-oxo-6',7'-dihydro-5'H-spiro[oxazolidine-5,8'-quinoline]-5'-carboxamide | IM I-h-1-2 |
| 292 | 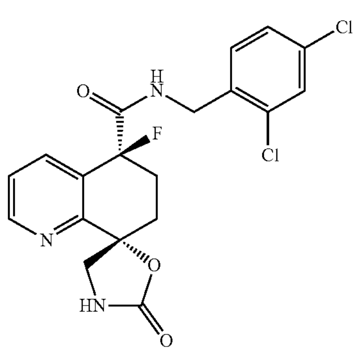 [SMILES: O=C1NC[C@@]2(CC[C@@](F)(C(=O)NCc3ccc(Cl)cc3Cl)c3cccnc32)O1] | (5R,5'S)-N-(2,4-dichlorobenzyl)-5'-fluoro-2-oxo-6',7'-dihydro-5'H-spiro[oxazolidine-5,8'-quinoline]-5'-carboxamide | IM I-h-1-3 |

Ex 291

¹H NMR (DMSO d6) delta 9.27 (1H, br s), 8.74 (1H, d, J=4.5 Hz), 7.75-7.80 (2H, m), 7.62 (1H, d, J=2.1 Hz), 7.53 (1H, dd, J=8.0, 4.7 Hz), 7.45 (1H, dd, J=8.4, 2.1 Hz), 7.36 (1H, d, J=8.3 Hz), 4.40 (2H, t, J=5.3 Hz), 3.88 (1H, d, J=8.6 Hz), 3.53 (1H, d, J=8.4 Hz), 2.29-2.48 (5H, m).

MS (ESI) m/z: 424.1 (M+H)⁺.

Ex 292

¹H NMR (DMSO d6) delta 9.30 (1H, br s), 8.76 (1H, d, J=4.8 Hz), 7.79 (1H, s), 7.71 (1H, d, J=8.2 Hz), 7.64 (1H, d, J=2.1 Hz), 7.54 (1H, t, J=6.2 Hz), 7.47 (1H, d, J=8.1 Hz), 7.40 (1H, d, J=8.1 Hz), 4.40-4.53 (2H, m), 4.16 (1H, d, J=8.2 Hz), 3.45 (1H, d, J=8.7 Hz), 2.57-2.68 (1H, m), 2.39-2.45 (1H, m), 2.24-2.38 (2H, m).

MS (ESI) m/z: 424.1 (M+H)⁺.

The following Intermediates were prepared by General Procedure U (Table 50).

General Procedure U

Chloroacetyl chloride (1.1 eq.) was added dropwise to a biphasic solution of substrate (1.0 eq.) in dichloromethane and 0.5 N aq. NaOH (2.0 eq.) at 0° C. The reaction mixture was warmed up to ambient temperature and stirred until complete reaction. The mixture was extracted with dichloromethane 3 times, and the combined extracts were dried over Na₂SO₄ and concentrated under reduced pressure to afford the following Intermediates.

TABLE 50

| Intermediates | Structure | Chemical Name | Substrate |
|---|---|---|---|
| I-i-1 | (structure) | (5R,8S)-8-((2-chloroacetamido)methyl)-N-(2,4-dichlorobenzyl)-5-fluoro-8-hydroxy-5,6,7,8-tetrahydroquinoline-5-carboxamide | IM I-h-1-1 |
| I-i-2 | (structure) | (5S,8S)-8-((2-chloroacetamido)methyl)-N-(2,4-dichlorobenzyl)-5-fluoro-8-hydroxy-5,6,7,8-tetrahydroquinoline-5-carboxamide | IM I-h-1-2 |
| I-i-3 | (structure) | (5S,8R)-8-((2-chloroacetamido)methyl)-N-(2,4-dichlorobenzyl)-5-fluoro-8-hydroxy-5,6,7,8-tetrahydroquinoline-5-carboxamide | IM I-h-1-3 |

IM I-i-1
MS (ESI) m/z: 474.1 (M+H)+.
IM I-i-2
MS (ESI) m/z: 474.1 (M+H)+.
IM I-i-3
MS (ESI) m/z: 474.1 (M+H)+.

The following Examples were prepared by General Procedure V (Table 51).

General Procedure V

To a solution of substrate (1.0 eq.) in 50% dichloromethane/2-propanol was added portion wise tert-BuOK (4.0 eq.) at 0° C. The solution was allowed to warm to ambient temperature and stirred until complete reaction. The solvent of the reaction mixture was removed by evaporation. The crude residue was purified by silica gel column chromatography to afford the following Examples.

TABLE 51

| Examples | Structure | Chemical Name | Substrate |
|---|---|---|---|
| 293 | 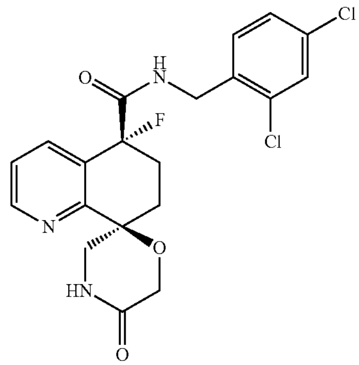 [SMILES: O=C1CO[C@@]2(CC[C@](F)(C(=O)NCc3ccc(Cl)cc3Cl)c3cccnc32)CN1] | (2S,5'R)-N-(2,4-dichlorobenzyl)-5'-fluoro-5-oxo-6',7'-dihydro-5'H-spiro[morpholine-2,8'-quinoline]-5'-carboxamide | IM I-i-1 |
| 294 | 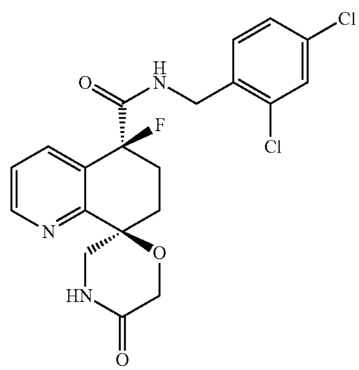 [SMILES: O=C1CO[C@@]2(CC[C@@](F)(C(=O)NCc3ccc(Cl)cc3Cl)c3cccnc32)CN1] | (2S,5'S)-N-(2,4-dichlorobenzyl)-5'-fluoro-5-oxo-6',7'-dihydro-5'H-spiro[morpholine-2,8'-quinoline]-5'-carboxamide | IM I-i-2 |
| 295 | 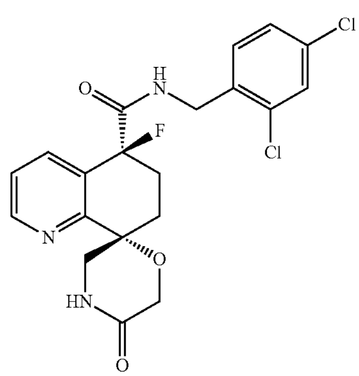 [SMILES: O=C1CO[C@]2(CC[C@@](F)(C(=O)NCc3ccc(Cl)cc3Cl)c3cccnc32)CN1] | (2R,5'S)-N-(2,4-dichlorobenzyl)-5'-fluoro-5-oxo-6',7'-dihydro-5'H-spiro[morpholine-2,8'-quinoline]-5'-carboxamide | IM I-i-3 |

Ex 293

¹H NMR (CDCl₃) delta 8.64-8.72 (1H, m), 7.54 (1H, d, J=7.5 Hz), 7.27-7.47 (4H, m), 7.09-7.25 (1H, m), 4.56-4.70 (2H, m), 4.34 (1H, dd, J=12.2, 2.3 Hz), 4.11-4.23 (2H, m), 3.37 (1H, dd, J=12.2, 3.1 Hz), 2.77-2.99 (1H, m), 2.40-2.51 (1H, m), 2.09-2.28 (2H, m).

MS (ESI) m/z: 438.1 (M+H)⁺.

Ex 294

¹H NMR (CDCl₃) delta 8.70 (1H, dt, J=4.7, 1.6 Hz), 7.57 (1H, d, J=7.6 Hz), 7.46 (1H, d, J=2.0 Hz), 7.19-7.35 (6H, m), 6.04 (1H, br s), 4.53-4.64 (2H, m), 4.39 (1H, d, J=16.8 Hz), 4.28 (1H, d, J=15.2 Hz), 4.19 (1H, dd, J=12.5, 1.5 Hz), 3.43 (1H, dd, J=12.5, 3.9 Hz), 2.56-2.64 (1H, m), 2.29-2.53 (3H, m).

MS (ESI) m/z: 438.1 (M+H)⁺.

Ex 295

¹H NMR (CDCl₃) delta 8.66 (1H, dt, J=4.7, 1.8 Hz), 7.54 (1H, d, J=7.6 Hz), 7.46 (1H, d, J=2.1 Hz), 7.39 (1H, d, J=8.2 Hz), 7.27-7.33 (2H, m), 7.13-7.25 (1H, m), 6.10 (1H, br s), 4.58-4.69 (2H, m), 4.34 (1H, dd, J=12.2, 2.3 Hz), 4.17 (2H, dd, J=16.8, 15.5 Hz), 3.37 (1H, dd, J=12.2, 3.0 Hz) 2.77-2.95 (1H, m), 2.41-2.49 (1H, m), 2.08-2.30 (2H, m).

MS (ESI) m/z: 438.1 (M+H)⁺.

The following Examples were prepared by General Procedure W or X (Table 52).

General Procedure W

To a solution of substrate (1.0 eq.) in dichloromethane was added mCPBA (1.05 eq.) at 0° C. The mixture was stirred at 0° C. until complete reaction, 1:1 mixture of aq. Na₂S₂O₃ and aq. NaHCO₃ was added to the mixture. The resulting mixture was extracted with CH₂Cl₂ and the extract was dried over Na₂SO₄. The extract was concentrated in vacuo, and the resulting residue was purified by silica gel column chromatography and preparative HPLC to afford the following Examples.

General Procedure X

To a solution of substrate (1.0 eq.) in dichloromethane was added mCPBA (2.5 eq.) at 0° C. The mixture was stirred at 0° C. until complete reaction, 1:1 mixture of aq. Na₂S₂O₃ and aq. NaHCO₃ was added to the mixture. The resulting mixture was extracted with CH₂Cl₂ and the extract was dried over Na₂SO₄. The extract was concentrated in vacuo, and the resulting residue was purified by silica gel column chromatography and preparative HPLC to afford the following Examples.

TABLE 52

| Examples | Structure | Chemical Name | Substrate | General Procedure |
|---|---|---|---|---|
| 296 | 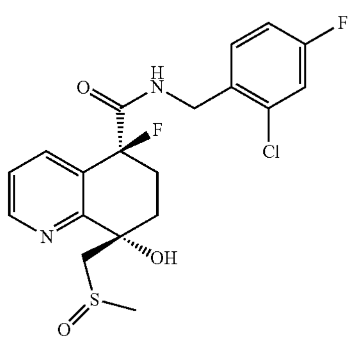 [SMILES: CS(=O)C[C@]1(O)CC[C@@](F)(C(=O)NCc2ccc(F)cc2Cl)c2cccnc21] | (5S,8S)-N-(2-chloro-4-fluorobenzyl)-5-fluoro-8-hydroxy-8-((methylsulfinyl)methyl)-5,6,7,8-tetrahydroquinoline-5-carboxamide | Ex 288 | W |
| 297 | 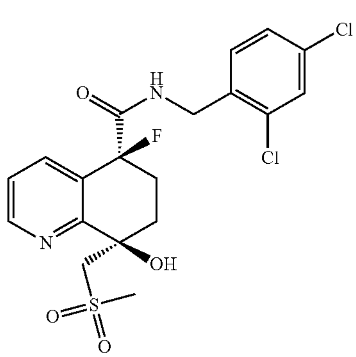 [SMILES: CS(=O)(=O)C[C@@]1(O)CC[C@@](F)(C(=O)NCc2ccc(Cl)cc2Cl)c2cccnc21] | (5S,8R)-N-(2,4-dichlorobenzyl)-5-fluoro-8-hydroxy-8-((methylthio)methyl)-5,6,7,8-tetrahydroquinoline-5-carboxamide | IM I-h-2-1 | X |

TABLE 52-continued

| Examples | Structure | Chemical Name | Substrate | General Procedure |
|---|---|---|---|---|
| 298 | 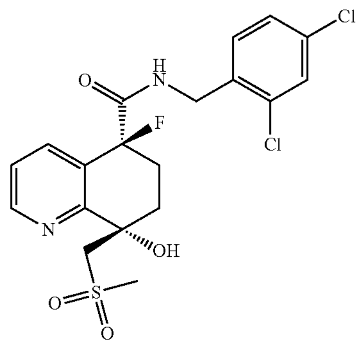 [SMILES: CS(=O)(=O)C[C@]1(O)CC[C@@](F)(C(=O)NCc2ccc(Cl)cc2Cl)c2cccnc21] | (5S,8S)-N-(2,4-dichlorobenzyl)-5-fluoro-8-hydroxy-8-((methylsulfonyl)methyl)-5,6,7,8-tetrahydroquinoline-5-carboxamide | Ex 287 | X |
| 299 | 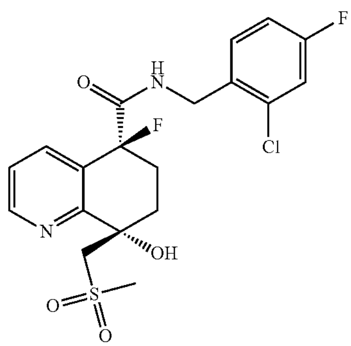 [SMILES: CS(=O)(=O)C[C@]1(O)CC[C@@](F)(C(=O)NCc2ccc(F)cc2Cl)c2cccnc21] | (5S,8S)-N-(2-chloro-4-fluorobenzyl)-5-fluoro-8-hydroxy-8-((methylsulfonyl)methyl)-5,6,7,8-tetrahydroquinoline-5-carboxamide | Ex 288 | X |
| 300 | 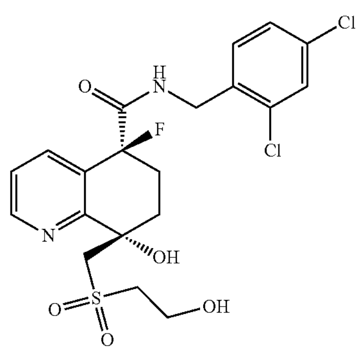 [SMILES: O=C(NCc1ccc(Cl)cc1Cl)[C@]1(F)CC[C@@](O)(CS(=O)(=O)CCO)c2ncccc21] | (5S,8S)-N-(2,4-dichlorobenzyl)-5-fluoro-8-hydroxy-8-(((2-hydroxyethyl)sulfonyl)methyl)-5,6,7,8-tetrahydroquinoline-5-carboxamide | IM I-h-2-2 | X |
| 301 | 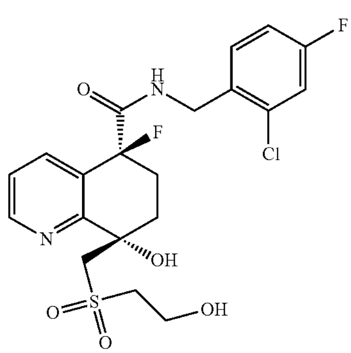 [SMILES: O=C(NCc1ccc(F)cc1Cl)[C@]1(F)CC[C@@](O)(CS(=O)(=O)CCO)c2ncccc21] | (5S,8S)-N-(2-chloro-4-fluorobenzyl)-5-fluoro-8-hydroxy-8-(((2-hydroxyethyl)sulfonyl)methyl)-5,6,7,8-tetrahydroquinoline-5-carboxamide | Ex 289 | X |

TABLE 53

| | | LC MS | |
|---|---|---|---|
| Examples | Method | tR (min) | [M + H]$^+$ |
| 296 | D | 1.29 | 429.0 |
| 297 | D | 1.58 | 461.0 |
| 298 | D | 1.56 | 461.0 |
| 299 | D | 1.44 | 445.0 |
| 300 | D | 1.47 | 491.0 |
| 301 | D | 1.36 | 475.0 |

Ex 296

$^1$H NMR (CDCl$_3$) delta 8.65-8.60 (1H, m), 7.56-7.51 (1H, m), 7.43-7.37 (1H, m), 7.31-7.26 (1H, m), 7.24-7.17 (2H, m), 7.02-6.97 (1H, m), 4.68-4.54 (2H, m), 4.08 (1H, br), 3.77 (0.5H, d, J=12.8 Hz), 3.58 (0.5H, d, J=13.5 Hz), 3.35 (0.5H, d, J=12.8 Hz), 3.11 (0.5H, d, J=13.5 Hz), 2.86 (0.5H, m), 2.74 (1.5H, s), 2.69 (1.5H, s), 2.69 (0.5H, m), 2.61-2.46 (2H, m), 2.32-2.19 (1H, m).

Ex 297

$^1$H NMR (CDCl$_3$) delta 8.62 (1H, ddd, J=4.9, 1.8, 1.2 Hz), 7.57 (1H, dd, J=7.9, 1.2 Hz), 7.45 (1H, d, J=1.8 Hz), 7.35-7.31 (2H, m), 7.27 (1H, dd, J=7.9, 4.9 Hz), 7.19 (1H, br d, J=4.9 Hz), 4.62 (1H, dd, J=14.7, 6.1 Hz), 4.573 (1H, s), 4.566 (1H, dd, J=14.7, 6.1 Hz), 3.55 (1H, d, J=16.5 Hz), 3.51 (1H, d, J=16.5 Hz), 3.14 (3H, s), 3.07 (1H, m), 2.63 (1H, m), 2.40 (1H, m), 2.18 (1H, m).

Ex 298

$^1$H NMR (CDCl$_3$) delta 8.62 (1H, br d, J=4.9 Hz), 7.55 (1H, dd, J=7.9, 1.2 Hz), 7.45 (1H, d, J=1.8 Hz), 7.35 (1H, d, J=7.9 Hz), 7.30 (1H, dd, J=7.9, 4.9 Hz), 7.26 (1H, dd, J=7.9, 1.8 Hz), 7.21 (1H, br), 4.64 (1H, dd, J=14.7, 6.1 Hz), 4.57 (1H, dd, J=14.7, 6.1 Hz), 4.12 (1H, d, J=15.3 Hz), 4.03 (1H, br), 3.37 (1H, d, J=15.3 Hz), 3.11 (3H, s), 2.79-2.64 (3H, m), 2.24 (1H, m).

Ex 299

$^1$H NMR (CDCl$_3$) delta 8.62 (1H, br d, J=4.9 Hz), 7.55 (1H, d, J=7.9 Hz), 7.40 (1H, dd, J=8.6, 6.1 Hz), 7.30 (1H, dd, J=7.9, 4.9 Hz), 7.21 (1H, br), 7.19 (1H, dd, J=8.6, 2.4 Hz), 7.00 (1H, ddd, J=8.6, 7.9, 1.8 Hz), 4.64 (1H, dd, J=14.7, 6.1 Hz), 4.57 (1H, dd, J=14.7, 6.1 Hz), 4.12 (1H, d, J=15.3 Hz), 4.02 (1H, br), 3.37 (1H, d, J=15.3 Hz), 3.11 (3H, s), 2.79-2.64 (3H, m), 2.24 (1H, m).

Ex 300

$^1$H NMR (CDCl$_3$) delta 8.58 (1H, br s), 7.53 (1H, d, J=7.9 Hz), 7.44 (1H, br s), 7.34-7.22 (4H, m), 4.72 (1H, br), 4.62 (1H, dd, J=15.3, 6.1 Hz), 4.34 (1H, dd, J=15.3, 6.1 Hz), 4.34 (1H, d, J=15.3 Hz), 4.09 (2H, br), 3.62 (1H, m), 3.43 (1H, d, J=15.3 Hz), 3.42 (1H, br s), 3.25 (1H, m), 2.77-2.66 (3H, m), 2.21 (1H, m).

Ex 301

$^1$H NMR (CDCl$_3$) delta 8.60 (1H, br s), 7.54 (1H, d, J=7.9 Hz), 7.39 (1H, dd, J=7.9, 6.1 Hz), 7.29 (1H, m), 7.26 (1H, br), 7.19 (1H, dd, 8.6, 2.4 Hz), 7.00 (1H, dd, J=8.6, 7.9 Hz), 4.63 (1H, dd, J=14.7, 6.1 Hz), 4.55 (1H, dd, J=14.7, 6.1 Hz), 4.54 (1H, br), 4.34 (1H, d, J=15.3 Hz), 4.12 (2H, br), 3.62 (1H, m), 3.46 (1H, d, J=15.3 Hz), 3.44 (1H, br s), 3.29 (1H, m), 3.03-2.71 (3H, m), 2.22 (1H, m).

The following Examples were prepared by General Procedure Y or Z (Table 54).

General Procedure Y

To stirred solution of the substrate (1.0 eq.) in MeOH-tert-BuOH-water (1:1:1) was added AD-Mix alpha and/or beta (4 times weight of substrate) at ambient temperature. The mixture was stirred at room temperature until complete reaction, aq. Na$_2$S$_2$O$_3$ was added to the mixture and then the mixture was stirred for 2 h. The mixture was extracted with CH$_2$Cl$_2$ twice and the extracts were combined. The extracts were dried over Na$_2$SO$_4$ and concentrated in vacuo. The resulting residue was purified and each diastereo isomer was separated by silica gel column chromatography to afford the following Examples.

General Procedure Z

A mixture of substrate (1.0 eq.) and 2 N aq. NaOH (15.0 eq.) in 50% 1,4-dioxane-water (0.02 M) was heated at 65° C. until complete reaction. The mixture was extracted with CH$_2$Cl$_2$ twice and the extracts were combined. The extracts were dried over Na$_2$SO$_4$ and concentrated in vacuo to afford a glass. The residual glass was purified by silica gel column chromatography and preparative HPLC to afford following Examples.

TABLE 54

| Examples | Structure | Chemical Name | Substrate | General Procedure |
|---|---|---|---|---|
| 302 | (structure) | (5R,8R)-N-(2,4-dichlorobenzyl)-5-fluoro-8-hydroxy-8-(hydroxymethyl)-5,6,7,8-tetrahydroquinoline-5-carboxamide | IM I-e-26 | Y |

TABLE 54-continued

| Examples | Structure | Chemical Name | Substrate | General Procedure |
|---|---|---|---|---|
| 303 | 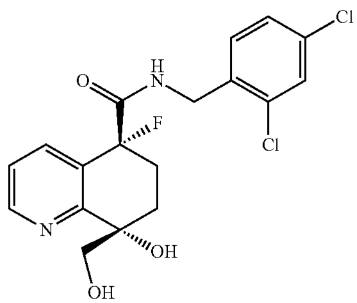 [SMILES: O=C(NCc1ccc(Cl)cc1Cl)[C@@]1(F)CC[C@@](O)(CO)c2ncccc21] | (5R,8S)-N-(2,4-dichloro benzyl)-5-fluoro-8-hydroxy-8-(hydroxymethyl)-5,6,7,8-tetrahydroquinoline-5-carboxamide | | |
| 304 | 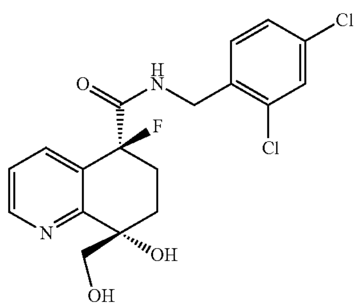 [SMILES: O=C(NCc1ccc(Cl)cc1Cl)[C@]1(F)CC[C@@](O)(CO)c2ncccc21] | (5S,8S)-N-(2,4-dichloro benzyl)-5-fluoro-8-hydroxy-8-(hydroxymethyl)-5,6,7,8-tetrahydroquinoline-5-carboxamide | IM I-e-28 | Y |
| 305 | 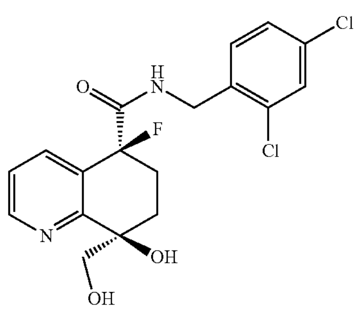 [SMILES: O=C(NCc1ccc(Cl)cc1Cl)[C@]1(F)CC[C@](O)(CO)c2ncccc21] | (5S,8R)-N-(2,4-dichloro benzyl)-5-fluoro-8-hydroxy-8-(hydroxymethyl)-5,6,7,8-tetrahydroquinoline-5-carboxamide | | |
| 306 | 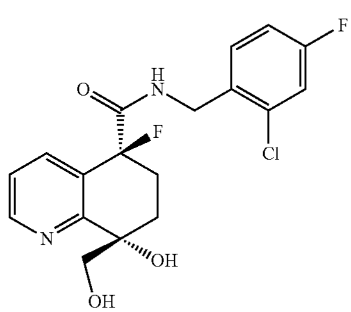 [SMILES: O=C(NCc1ccc(F)cc1Cl)[C@]1(F)CC[C@@](O)(CO)c2ncccc21] | (5S,8S)-N-(2-chloro-4-fluorobenzyl)-5-fluoro-8-hydroxy-8-(hydroxymethyl)-5,6,7,8-tetrahydroquinoline-5-carboxamide | IM I-e-31 | Y |
| 307 | 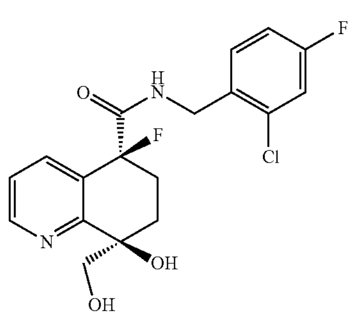 [SMILES: O=C(NCc1ccc(F)cc1Cl)[C@]1(F)CC[C@](O)(CO)c2ncccc21] | (5S,8R)-N-(2-chloro-4-fluorobenzyl)-5-fluoro-8-hydroxy-8-(hydroxymethyl)-5,6,7,8-tetrahydroquinoline-5-carboxamide | | |

TABLE 54-continued

| Examples | Structure | Chemical Name | Substrate | General Procedure |
|---|---|---|---|---|
| 308 | 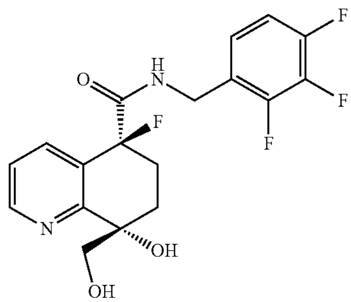 [SMILES: O=C(NCc1ccc(F)c(F)c1F)[C@]1(F)CC[C@@](O)(CO)c2ncccc21] | (5S,8S)-5-fluoro-8-hydroxy-8-(hydroxymethyl)-N-(2,3,4-trifluorobenzyl)-5,6,7,8-tetrahydroquinoline-5-carboxamide | IM I-e-33 | Y |
| 309 | 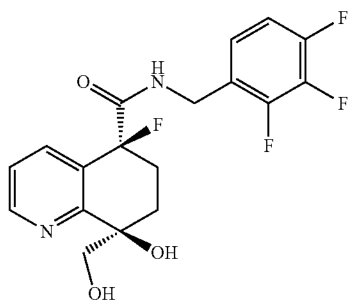 [SMILES: O=C(NCc1ccc(F)c(F)c1F)[C@]1(F)CC[C@](O)(CO)c2ncccc21] | (5S,8R)-5-fluoro-8-hydroxy-8-(hydroxymethyl)-N-(2,3,4-trifluorobenzyl)-5,6,7,8-tetrahydroquinoline-5-carboxamide | | |
| 310 | 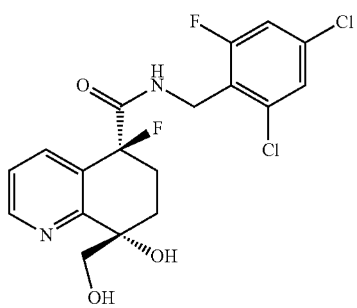 [SMILES: O=C(NCc1c(F)cc(Cl)cc1Cl)[C@]1(F)CC[C@@](O)(CO)c2ncccc21] | (5S,8S)-N-(2,4-dichloro-6-fluorobenzyl)-5-fluoro-8-hydroxy-8-(hydroxymethyl)-5,6,7,8-tetrahydroquinoline-5-carboxamide | IM I-e-29 | Y |
| 311 | 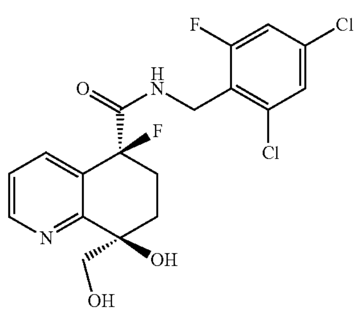 [SMILES: O=C(NCc1c(F)cc(Cl)cc1Cl)[C@]1(F)CC[C@](O)(CO)c2ncccc21] | (5S,8R)-N-(2,4-dichloro-6-fluorobenzyl)-5-fluoro-8-hydroxy-8-(hydroxymethyl)-5,6,7,8-tetrahydroquinoline-5-carboxamide | | |
| 312 | 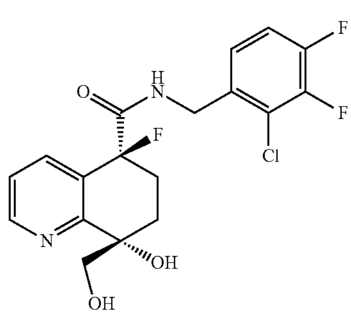 [SMILES: O=C(NCc1ccc(F)c(F)c1Cl)[C@]1(F)CC[C@@](O)(CO)c2ncccc21] | (5S,8S)-N-(2-chloro-3,4-difluorobenzyl)-5-fluoro-8-hydroxy-8-(hydroxymethyl)-5,6,7,8-tetrahydroquinoline-5-carboxamide | IM I-e-30 | Y |

TABLE 54-continued

| Examples | Structure | Chemical Name | Substrate | General Procedure |
|---|---|---|---|---|
| 313 | 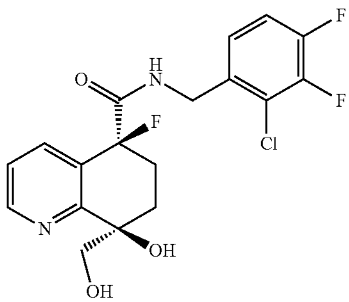 [SMILES: O=C(NCc1ccc(F)c(F)c1Cl)[C@]1(F)CC[C@](O)(CO)c2ncccc21] | (5S,8R)-N-(2-chloro-3,4-difluorobenzyl)-5-fluoro-8-hydroxy-8-(hydroxymethyl)-5,6,7,8-tetrahydroquinoline-5-carboxamide | | |
| 314 | 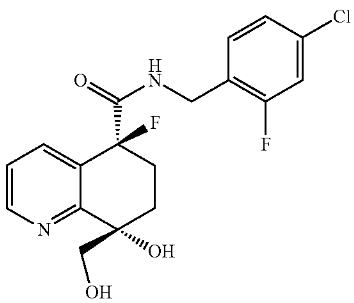 [SMILES: O=C(NCc1ccc(Cl)cc1F)[C@]1(F)CC[C@@](O)(CO)c2ncccc21] | (5S,8S)-N-(4-chloro-2-fluorobenzyl)-5-fluoro-8-hydroxy-8-(hydroxymethyl)-5,6,7,8-tetrahydroquinoline-5-carboxamide | IM I-e-32 | Y |
| 315 | 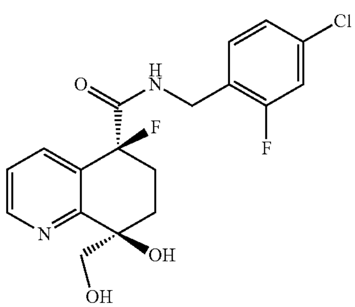 [SMILES: O=C(NCc1ccc(Cl)cc1F)[C@]1(F)CC[C@](O)(CO)c2ncccc21] | (5S,8R)-N-(4-chloro-2-fluorobenzyl)-5-fluoro-8-hydroxy-8-(hydroxymethyl)-5,6,7,8-tetrahydroquinoline-5-carboxamide | | |
| 316 | 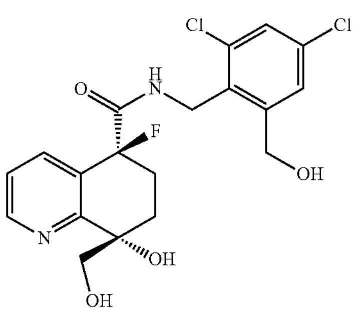 [SMILES: O=C(NCc1c(Cl)cc(Cl)cc1CO)[C@]1(F)CC[C@@](O)(CO)c2ncccc21] | (5S,8S)-N-(2,4-dichloro-6-(hydroxymethyl)benzyl)-5-fluoro-8-hydroxy-8-(hydroxymethyl)-5,6,7,8-tetrahydroquinoline-5-carboxamide | IM I-g-14 | Z |
| 317 | 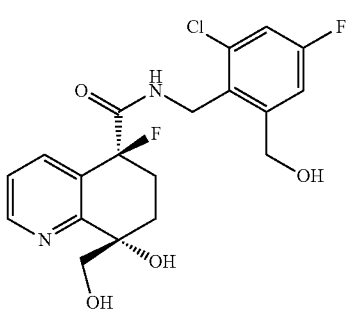 [SMILES: O=C(NCc1c(Cl)cc(F)cc1CO)[C@]1(F)CC[C@@](O)(CO)c2ncccc21] | (5S,8S)-N-(2-chloro-4-fluoro-6-(hydroxymethyl)benzyl)-5-fluoro-8-hydroxy-8-(hydroxymethyl)-5,6,7,8-tetrahydroquinoline-5-carboxamide | IM I-g-16 | Z |

TABLE 54-continued

| Examples | Structure | Chemical Name | Substrate | General Procedure |
|---|---|---|---|---|
| 318 | 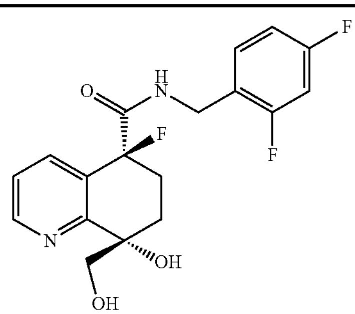 | (5S,8S)-N-(2,4-difluorobenzyl)-5-fluoro-8-hydroxy-8-(hydroxymethyl)-5,6,7,8-tetrahydroquinoline-5-carboxamide | IM I-g-19 | Z |
| 319 | 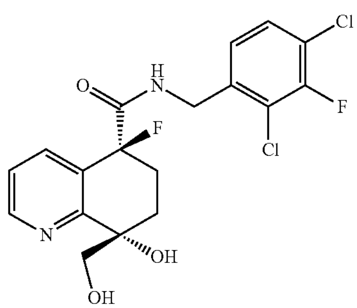 [SMILES: O=C(NCc1ccc(Cl)c(F)c1Cl)[C@]1(F)CC[C@@](O)(CO)c2ncccc21] | (5S,8S)-N-(2,4-dichloro-3-fluorobenzyl)-5-fluoro-8-hydroxy-8-(hydroxymethyl)-5,6,7,8-tetrahydroquinoline-5-carboxamide | IM I-g-23 | Z |
| 320 | 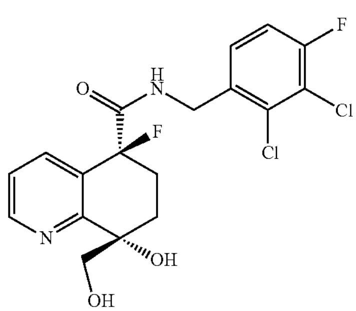 [SMILES: O=C(NCc1ccc(F)c(Cl)c1Cl)[C@]1(F)CC[C@@](O)(CO)c2ncccc21] | (5S,8S)-N-(2,3-dichloro-4-fluorobenzyl)-5-fluoro-8-hydroxy-8-(hydroxymethyl)-5,6,7,8-tetrahydroquinoline-5-carboxamide | IM I-g-24 | Z |
| 321 | 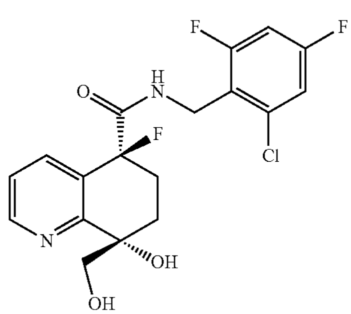 [SMILES: O=C(NCc1c(F)cc(F)cc1Cl)[C@]1(F)CC[C@@](O)(CO)c2ncccc21] | (5S,8S)-N-(2-chloro-4,6-difluorobenzyl)-5-fluoro-8-hydroxy-8-(hydroxymethyl)-5,6,7,8-tetrahydroquinoline-5-carboxamide | IM I-g-25 | Z |
| 322 | 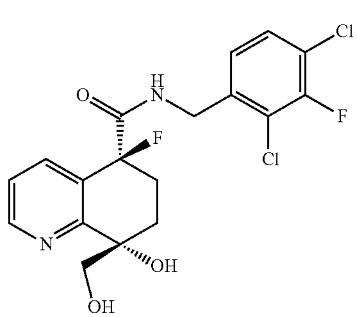 [SMILES: O=C(NCc1ccc(Cl)c(F)c1Cl)[C@]1(F)CC[C@@](O)(CO)c2ncccc21] | (5S,8S)-N-(4-chloro-2,3-difluorobenzyl)-5-fluoro-8-hydroxy-8-(hydroxymethyl)-5,6,7,8-tetrahydroquinoline-5-carboxamide | IM I-g-26 | Z |

TABLE 54-continued

| Examples | Structure | Chemical Name | Substrate | General Procedure |
|---|---|---|---|---|
| 323 | 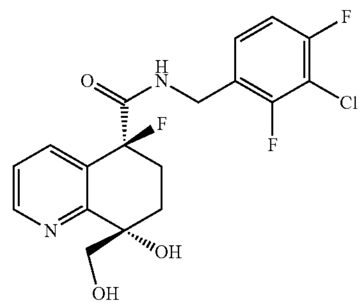 [SMILES: O=C(NCc1ccc(F)c(Cl)c1F)[C@]1(F)CC[C@@](O)(CO)c2ncccc21] | (5S,8S)-N-(3-chloro-2,4-difluorobenzyl)-5-fluoro-8-hydroxy-8-(hydroxymethyl)-5,6,7,8-tetrahydroquinoline-5-carboxamide | IM I-g-27 | Z |
| 324 | 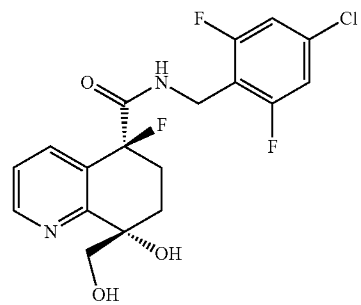 [SMILES: O=C(NCc1c(F)cc(Cl)cc1F)[C@]1(F)CC[C@@](O)(CO)c2ncccc21] | (5S,8S)-N-(4-chloro-2,6-difluorobenzyl)-5-fluoro-8-hydroxy-8-(hydroxymethyl)-5,6,7,8-tetrahydroquinoline-5-carboxamide | IM I-g-28 | Z |
| 325 | 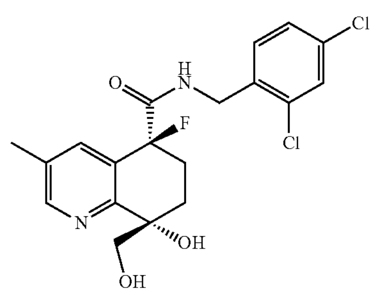 [SMILES: Cc1cnc2c(c1)[C@](F)(C(=O)NCc1ccc(Cl)cc1Cl)CC[C@@]2(O)CO] | (5S,8S)-N-(2,4-dichlorobenzyl)-5-fluoro-8-hydroxy-8-(hydroxymethyl)-3-methyl-5,6,7,8-tetrahydroquinoline-5-carboxamide | IM I-g-39 | Z |
| 326 | 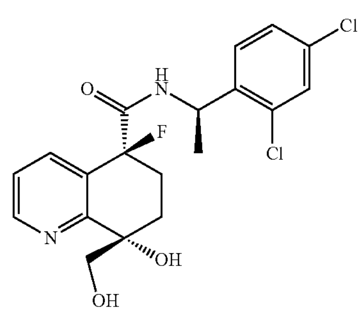 [SMILES: C[C@@H](NC(=O)[C@]1(F)CC[C@@](O)(CO)c2ncccc21)c1ccc(Cl)cc1Cl] | (5S,8S)-N-((R)-1-(2,4-dichlorophenyl)ethyl)-5-fluoro-8-hydroxy-8-(hydroxymethyl)-5,6,7,8-tetrahydroquinoline-5-carboxamide | IM I-g-29 | Z |
| 327 | 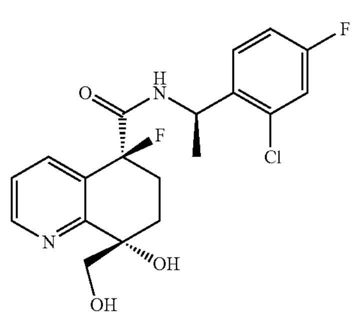 [SMILES: C[C@@H](NC(=O)[C@]1(F)CC[C@@](O)(CO)c2ncccc21)c1ccc(F)cc1Cl] | (5S,8S)-N-((R)-1-(2-chloro-4-fluorophenyl)ethyl)-5-fluoro-8-hydroxy-8-(hydroxymethyl)-5,6,7,8-tetrahydroquinoline-5-carboxamide | IM I-g-31 | Z |

TABLE 54-continued

| Examples | Structure | Chemical Name | Substrate | General Procedure |
|---|---|---|---|---|
| 328 | 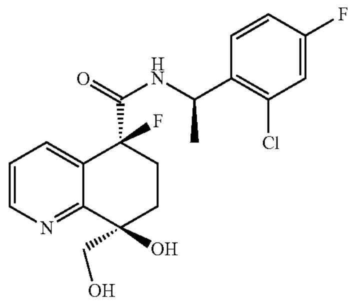 [SMILES: C[C@@H](NC(=O)[C@]1(F)CC[C@](O)(CO)c2ncccc21)c1ccc(F)cc1Cl] | (5S,8R)-N-((R)-1-(2-chloro-4-fluorophenyl)ethyl)-5-fluoro-8-hydroxy-8-(hydroxymethyl)-5,6,7,8-tetrahydroquinoline-5-carboxamide | IM I-g-32 | Z |
| 329 | 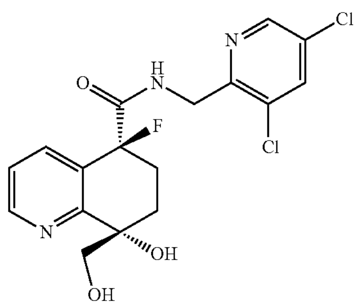 [SMILES: O=C(NCc1ncc(Cl)cc1Cl)[C@]1(F)CC[C@@](O)(CO)c2ncccc21] | (5S,8S)-N-((3,5-dichloropyridin-2-yl)methyl)-5-fluoro-8-hydroxy-8-(hydroxymethyl)-5,6,7,8-tetrahydroquinoline-5-carboxamide | IM I-g-34 | Z |
| 330 | 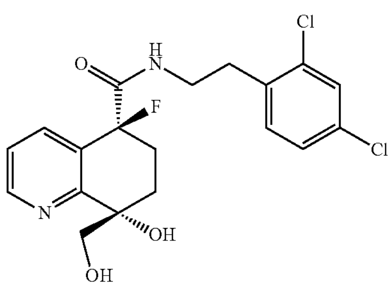 [SMILES: O=C(NCCc1ccc(Cl)cc1Cl)[C@]1(F)CC[C@@](O)(CO)c2ncccc21] | (5S,8S)-N-(2,4-dichlorophenethyl)-5-fluoro-8-hydroxy-8-(hydroxymethyl)-5,6,7,8-tetrahydroquinoline-5-carboxamide | IM I-g-35 | Z |
| 331 | 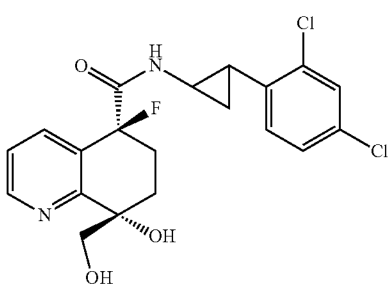 [SMILES: O=C(NC1CC1c1ccc(Cl)cc1Cl)[C@]1(F)CC[C@@](O)(CO)c2ncccc21] | (5S,8S)-N-((trans)-2-(2,4-dichlorophenyl)cyclopropyl)-5-fluoro-8-hydroxy-8-(hydroxymethyl)-5,6,7,8-tetrahydroquinoline-5-carboxamide | IM I-g-36 | Z |
| 332 | 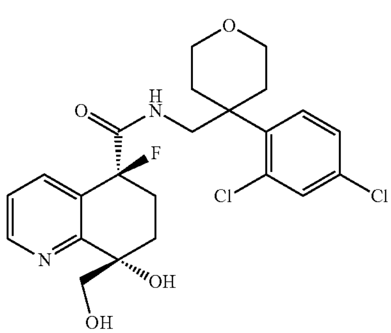 [SMILES: O=C(NCC1(c2ccc(Cl)cc2Cl)CCOCC1)[C@]1(F)CC[C@@](O)(CO)c2ncccc21] | (5S,8S)-N-((4-(2,4-dichlorophenyl)tetrahydro-2H-pyran-4-yl)methyl)-5-fluoro-8-hydroxy-8-(hydroxymethyl)-5,6,7,8-tetrahydroquinoline-5-carboxamide | IM I-g-38 | Z |

TABLE 55

| | LC MS | | |
|---|---|---|---|
| Examples | Method | tR (min) | [M + H]$^+$ |
| 302 | C | 1.42 | 398.8 |
| 303 | C | 1.41 | 398.8 |
| 304 | C | 1.41 | 398.9 |
| 305 | C | 1.42 | 398.9 |
| 306 | C | 1.31 | 382.9 |
| 307 | C | 1.30 | 382.9 |
| 308 | C | 1.27 | 384.9 |
| 309 | C | 1.27 | 385.0 |
| 310 | C | 1.40 | 416.8 |
| 311 | C | 1.40 | 416.8 |
| 312 | C | 1.34 | 401.0 |
| 313 | C | 1.34 | 401.0 |
| 314 | C | 1.32 | 382.8 |
| 315 | C | 1.32 | 382.8 |
| 316 | C | 1.28 | 428.9 |
| 317 | D | 1.18 | 413.0 |
| 318 | C | 1.22 | 366.9 |
| 319 | D | 1.47 | 417.0 |
| 320 | D | 1.46 | 417.0 |
| 321 | D | 1.33 | 401.0 |
| 322 | D | 1.40 | 401.0 |
| 323 | D | 1.38 | 401.0 |
| 324 | D | 1.36 | 401.0 |
| 325 | D | 1.54 | 413.1 |
| 326 | D | 1.54 | 413.1 |
| 327 | D | 1.41 | 397.1 |
| 328 | D | 1.42 | 397.1 |
| 329 | D | 1.31 | 400.0 |
| 330 | D | 1.51 | 413.0 |
| 331 | D | 1.59 | 425.0 |
| 332 | D | 1.47 | 483.0 |

Ex 302

$^1$H NMR (CDCl$_3$) delta 8.54 (1H, br dd, J=4.9, 1.8 Hz), 7.53 (1H, br dd, J=7.9, 1.8 Hz Hz), 7.45 (1H, d, J=1.8 Hz), 7.38 (1H, d, J=8.6 Hz), 7.29 (1H, dd, J=7.9, 4.9 Hz), 7.20-7.14 (2H, m), 5.00 (1H, br), 4.66 (1H, dd, J=14.7, 6.1 Hz), 4.60 (1H, dd, J=14.7, 6.1 Hz), 3.99 (1H, d, J=11.6 Hz), 3.76-3.64 (2H, m), 2.88 (1H, m), 2.24-1.99 (3H, m).

Ex 303

$^1$H NMR (DMSO d6) delta 9.16 (1H, br), 8.64 (1H, br d, J=4.9 Hz), 7.66 (1H, d, J=7.9 Hz), 7.62 (1H, d, J=2.4 Hz), 7.46 (1H, dd, J=7.9, 2.4 Hz), 7.39 (1H, dd, J=7.9, 4.9 Hz), 7.36 (1H, J=7.9 Hz), 4.93 (1H, s), 4.75 (1H, br), 4.44 (1H, dd, J=15.9, 6.1 Hz), 4.38 (1H, dd, J=15.9, 6.1 Hz), 3.68 (1H, dd, J=11.0, 6.1 Hz), 3.56 (1H, dd, J=11.0, 4.3 Hz), 2.54-2.22 (3H, m), 1.87 (1H, m).

Ex 304

$^1$H NMR was identified with the Example 302.

Ex 305

$^1$H NMR was identified with the Example 303.

Ex 306

$^1$H NMR (CDCl$_3$) delta 8.54 (1H, br dd, J=4.5, 1.8 Hz), 7.53 (1H, br dd, J=7.9, 1.8 Hz), 7.43 (1H, dd, J=8.6, 6.1 Hz), 7.28 (1H, br dd, J=4.9, 1.2 Hz), 7.19 (1H, dd, J=8.6, 2.4 Hz), 7.17 (1H, br), 7.00 (1H, dt, J=7.9, 2.4 Hz), 5.01 (1H, br d, J=9.8 Hz), 4.66 (1H, dd, J=14.7, 6.1 Hz), 4.60 (1H, dd, J=14.7, 5.5 Hz), 3.99 (1H, d, J=11.6 Hz), 3.79-3.63 (2H, m), 2.88 (1H, m), 2.36-1.99 (3H, m).

Ex 307

$^1$H NMR (CDCl$_3$) delta 8.57 (1H, br dd, J=4.3, 1.8 Hz), 7.56 (1H, d, J=7.9 Hz), 7.39 (1H, dd, J=8.5, 6.1 Hz), 7.28 (1H, dd, J=7.9, 4.3 Hz), 7.19 (1H, dd, J=8.5, 2.4 Hz), 7.16 (1H, br), 6.99 (1H, ddd, J=8.5, 7.9, 2.4 Hz), 4.62 (1H, dd, J=14.7, 6.1 Hz), 4.55 (1H, dd, J=14.7, 6.1 Hz), 4.01 (1H, br), 3.85 (1H, d, J=11.6 Hz), 3.79 (1H, br), 3.71 (1H, d, J=11.6 Hz), 2.54-2.36 (3H, m), 2.02 (1H, m).

Ex 308

$^1$H NMR (CDCl$_3$) delta 8.54 (1H, br dd, J=4.5, 1.8 Hz), 7.53 (1H, br dd, J=7.9, 1.8 Hz), 7.30 (1H, dd, J=7.9, 4.9 Hz), 7.20 (1H, br d, J=4.9 Hz), 7.13 (1H, m), 6.98 (1H, m), 5.02 (1H, br), 4.64 (1H, dd, J=14.7, 6.1 Hz), 4.57 (1H, dd, J=14.7, 6.1 Hz), 3.97 (1H, d, J=11.6 Hz), 3.85 (1H, br), 3.68 (1H, d, J=11.6 Hz), 2.87 (1H, m), 2.23-1.99 (3H, m).

Ex 309

$^1$H NMR (CDCl$_3$) delta 8.57 (1H, br dd, J=4.9, 1.2 Hz), 7.56 (1H, br dd, J=7.9, 1.2 Hz), 7.29 (1H, dd, J=7.9, 4.9 Hz), 7.16 (1H, br), 7.09 (1H, m), 6.97 (1H, m), 4.60 (1H, dd, J=15.3, 6.1 Hz), 4.53 (1H, dd, J=15.3, 6.1 Hz), 4.01 (1H, br), 3.84 (1H, d, J=11.0 Hz), 3.82 (1H, br), 3.71 (1H, d, J=11.6 Hz), 2.44-2.04 (3H, m), 2.04 (1H, m).

Ex 310

$^1$H NMR (CDCl$_3$) delta 8.53 (1H, m), 7.56 (1H, d, J=7.9 Hz), 7.33-7.28 (2H, m), 7.11 (1H, dd, J=9.2, 1.8 Hz), 7.02 (1H, br), 5.01 (1H, br), 4.78 (1H, dd, J=14.7, 5.5 Hz), 4.66 (1H, dd, J=14.7, 5.5 Hz), 3.97 (1H, d, J=11.6 Hz), 3.76 (1H, br), 3.68 (1H, d, J=11.6 Hz), 2.88 (1H, m), 2.23-1.98 (3H, m).

Ex 311

$^1$H NMR (CDCl$_3$) delta 8.56 (1H, dd, J=4.9, 1.2 Hz), 7.57 (1H, dd, J=7.9, 1.2 Hz), 7.29-7.27 (2H, m), 7.11 (1H, dd, J=9.2, 2.4 Hz), 7.04 (1H, br), 4.73 (1H, dd, J=14.7, 6.1 Hz), 4.63 (1H, dd, J=14.7, 5.5 Hz), 4.00 (1H, br s), 3.84 (1H, d, J=11.6 Hz), 3.79 (1H, br), 3.70 (1H, d, J=11.6 Hz), 2.52-2.37 (3H, m), 2.02 (1H, m).

Ex 312

$^1$H NMR (CDCl$_3$) delta 8.53 (1H, dd, J=4.9, 1.8 Hz), 7.52 (1H, ddd, J=7.9, 1.8, 1.2 Hz), 7.29 (1H, dd, J=7.9, 4.9 Hz), 7.25-7.08 (3H, m), 4.99 (1H, br d, J=10.4 Hz), 4.67 (1H, dd, J=14.7, 6.1 Hz), 4.62 (1H, dd, J=14.7, 5.5 Hz), 3.99 (1H, d, J=10.4 Hz), 3.71 (1H, br s), 3.67 (1H, d, J=10.4 Hz), 2.88 (1H, m), 2.24-1.99 (3H, m).

Ex 313

$^1$H NMR (CDCl$_3$) delta 8.57 (1H, ddd, J=4.9, 1.8, 1.2 Hz), 7.56 (1H, d, J=7.9, 1.8 Hz), 7.29 (1H, dd, J=7.9, 4.9 Hz), 7.19-7.08 (3H, m), 4.63 (1H, dd, J=14.7, 6.1 Hz), 4.57 (1H, dd, J=14.7, 5.5 Hz), 3.99 (1H, s), 3.85 (1H, d, J=11.0 Hz), 3.76 (1H, br s), 3.72 (1H, d, J=11.0 Hz), 2.50-2.40 (3H, m), 2.03 (1H, m).

Ex 314

¹H NMR (CDCl₃) delta 8.53 (1H, br dd, J=4.9, 1.8 Hz), 7.53 (1H, br dd, J=7.9, 1.8 Hz), 7.33 (1H, t, J=7.9 Hz), 7.29 (1H, dd, J=7.9, 4.9 Hz), 7.27-7.10 (2H, m), 7.15 (1H, d, J=7.9 Hz), 5.02 (1H, br), 4.63 (1H, dd, J=14.7, 6.1 Hz), 4.54 (1H, dd, J=14.7, 6.1 Hz), 3.98 (1H, d, J=11.6 Hz), 3.82 (1H, br), 3.68 (1H, d, J=11.6 Hz), 2.87 (1H, m), 2.18 (1H, m), 2.09-1.99 (2H, m).

Ex 315

¹H NMR (CDCl₃) delta 8.56 (1H, br dd, J=4.9, 1.8 Hz), 7.55 (1H, d, J=7.9 Hz), 7.35-7.27 (2H, m), 7.18-7.09 (3H, m), 4.57 (1H, dd, J=14.7, 6.1 Hz), 4.50 (1H, dd, J=14.7, 6.1 Hz), 4.06 (1H, br), 3.83 (2H, d, J=11.0 Hz), 3.70 (1H, d, J=11.0 Hz), 2.52-2.34 (3H, m), 2.04 (1H, m).

Ex 316

¹H NMR (CDCl₃) delta 8.51 (1H, br dd, J=4.9, 1.8 Hz), 7.58 (1H, br d, J=5.5 Hz), 7.46 (1H, br dd, J=7.9, 1.8 Hz), 7.43 (1H, d, J=2.4 Hz), 7.34 (1H, d, J=2.4 Hz), 7.26 (1H, dd, J=7.9, 4.9 Hz), 5.03 (1H, br), 4.82-4.64 (4H, m), 3.97 (1H, d, J=11.0 Hz), 3.87 (2H, br), 3.66 (1H, d, J=11.0 Hz), 2.81 (1H, m), 2.19-1.95 (3H, m).

Ex 317

¹H NMR (CDCl₃) delta 8.52 (1H, br d, J=4.9 Hz), 7.56 (1H, br), 7.46 (1H, dd, J=7.9, 1.8 Hz), 7.25 (1H, dd, J=7.9, 4.9 Hz), 7.17 (1H, dd, J=8.6, 2.4 Hz), 7.10 (1H, dd, J=8.6, 2.4 Hz), 5.06 (1H, br), 4.82-4.62 (4H, m), 3.98 (1H, d, J=11.0 Hz), 3.81 (1H, br), 3.66 (1H, d, J=11.0 Hz), 2.81 (1H, m), 2.11 (1H, m), 2.07-1.96 (2H, m), 1.65 (1H, br).

Ex 318

¹H NMR (CDCl₃) delta 8.53 (1H, br dd, J=4.9, 1.8 Hz), 7.53 (1H, d, J=7.9 Hz), 7.34 (1H, m), 7.28 (1H, dd, J=7.9, 4.9 Hz), 7.16 (1H, br), 6.90-6.85 (2H, m), 5.30 (1H, br), 4.62 (1H, dd, J=14.7, 6.1 Hz), 4.53 (1H, dd, J=14.7, 6.1 Hz), 3.97 (1H, d, J=11.6 Hz), 3.87 (1H, br), 3.67 (1H, d, J=11.6 Hz), 2.88 (1H, m), 2.23-1.99 (3H, m).

Ex 319

¹H NMR (CDCl₃) delta 8.54 (1H, br dd, J=4.9, 1.8 Hz), 7.54 (1H, br dd, J=7.9, 1.8 Hz), 7.33 (1H, dd, J=8.6, 6.7 Hz), 7.30 (1H, dd, J=7.9, 4.9 Hz), 7.23 (1H, br), 7.20 (1H, dd, J=8.6, 1.8 Hz), 4.99 (1H, br d, J=9.2 Hz), 4.68 (1H, dd, J=14.7, 6.1 Hz), 4.63 (1H, dd, J=14.7, 6.1 Hz), 4.00 (1H, d, J=11.0 Hz), 3.77 (1H, br s), 3.68 (1H, br), 2.87 (1H, m), 2.24-1.99 (3H, m).

Ex 320

¹H NMR (CDCl₃) delta 8.54 (1H, br dd, J=4.9, 1.8 Hz), 7.53 (1H, br dd, J=7.9, 1.8 Hz), 7.37 (1H, dd, J=8.6, 5.5 Hz), 7.29 (1H, dd, J=7.9, 4.9 Hz), 7.21 (1H, br d J=6.1 Hz), 7.11 (1H, dd, J=8.6, 7.9 Hz), 5.00 (1H, br), 4.68 (1H, dd, J=15.3, 6.1 Hz), 4.63 (1H, dd, J=14.7, 6.1 Hz), 3.99 (1H, d, J=11.0 Hz), 3.74 (1H, br s), 3.68 (1H, d, J=11.0 Hz), 2.87 (1H, m), 2.24-1.99 (3H, m).

Ex 321

¹H NMR (CDCl₃) delta 8.54 (1H, br dd, J=4.9, 1.8 Hz), 7.57 (1H, br dd, J=7.9, 1.8 Hz), 7.29 (1H, dd, J=7.9, 4.9 Hz), 7.05 (1H, ddd, J=7.9, 2.4, 1.8 Hz), 6.99 (1H, br), 6.85 (1H, ddd, J=9.8, 8.6, 2.4 Hz), 4.80 (1H, br), 4.77 (1H, dd, J=14.7, 6.1 Hz), 4.66 (1H, dd, J=14.7, 6.1 Hz), 3.98 (1H, d, J=11.6 Hz), 3.74 (1H, br), 3.68 (1H, d, J=11.6 Hz), 2.88 (1H, m), 2.23-1.99 (3H, m).

Ex 322

¹H NMR (CDCl₃) delta 8.55 (1H, br dd, J=4.9, 1.8 Hz), 7.54 (1H, br dd, J=7.9, 1.8 Hz), 7.30 (1H, dd, J=8.0, 5.5 Hz), 7.21-7.10 (3H, m), 5.00 (1H, br), 4.66 (1H, dd, J=14.7, 6.9 Hz), 4.59 (1H, dd, J=14.7, 6.9 Hz), 3.99 (1H, d, J=11.6 Hz), 3.78 (1H, br), 3.68 (1H, d, J=11.6 Hz), 2.87 (1H, m), 2.24-1.99 (3H, m).

Ex 323

¹H NMR (CDCl₃) delta 8.55 (1H, br dd, J=4.3, 1.8 Hz), 7.53 (1H, br dd, J=7.9, 1.8 Hz), 7.34-7.28 (2H, m), 7.16 (1H, m), 6.99 (1H, dt, J=8.6, 1.8 Hz), 5.01 (1H, br), 4.64 (1H, dd, J=14.7, 6.1 Hz), 4.50 (1H, dd, J=14.7, 6.1 Hz), 3.99 (1H, d, J=11.6 Hz), 3.77 (1H, br), 3.68 (1H, d, J=11.6 Hz), 2.87 (1H, m), 2.24-1.99 (3H, m).

Ex 324

¹H NMR (CDCl₃) delta 8.54 (1H, ddd, J=4.3, 1.8, 1.2 Hz), 7.55 (1H, ddd, J=7.9, 1.8, 1.2 Hz), 7.30 (1H, dd J=7.9, 4.9 Hz), 7.02 (1H, br), 7.01 (2H, d, J=7.3 Hz), 5.00 (1H, br), 4.70 (1H, dd, J=14.7, 6.1 Hz), 4.60 (1H, dd, J=14.7, 5.5 Hz), 3.98 (1H, d, J=11.6 Hz), 3.71 (1H, br), 3.68 (1H, d, J=11.6 Hz), 2.87 (1H, m), 2.22-1.98 (3H, m).

Ex 325

¹H NMR (CDCl₃) delta 8.35 (1H, s), 7.46 (1H, d, J=2.4 Hz), 7.40 (1H, d J=7.9 Hz), 7.28-7.25 (2H, m), 7.19 (1H, br d, J=5.5 Hz), 5.10 (1H, br), 4.67 (1H, dd, J=14.7, 6.1 Hz), 4.60 (1H, dd, J=14.7, 6.1 Hz), 3.97 (1H, d, J=11.6 Hz), 3.67 (1H, d, J=11.6 Hz), 3.65 (1H, br s), 2.87 (1H, m), 2.27 (3H, s), 2.22-1.96 (3H, m).

Ex 326

¹H NMR (CDCl₃) delta 8.54 (1H, br dd, J=4.3, 1.8 Hz), 7.47 (1H, ddd, J=7.9, 1.8, 1.2 Hz), 7.44 (1H, d J=1.8 Hz), 7.37 (1H, d, J=8.6 Hz), 7.30 (1H, dd, J=8.6, 1.8 Hz), 7.25 (1H, dd, J=7.9, 4.3 Hz), 7.12 (1H, dd, J=6.7, 6.1 Hz), 5.46 (1H, dq, J=7.3, 6.7 Hz), 3.98 (1H, d, J=11.6 Hz), 3.75 (1H, br), 3.69 (1H, d, J=11.6 Hz), 3.48 (1H, d, J=1.8 Hz), 2.88 (1H, m), 2.26-2.01 (3H, m), 1.59 (3H, d, J=7.3 Hz).

Ex 327

¹H NMR (CDCl₃) delta 8.51 (1H, ddd, J=4.3, 1.8, 1.2 Hz), 7.48 (1H, ddd, J=7.9, 1.8, 1.2 Hz), 7.41 (1H, dd, J=8.6, 6.1 Hz), 7.24 (1H, dd, J=7.9, 4.3 Hz), 7.18 (1H, dd, J=8.6, 2.4 Hz), 7.14 (1H, br), 7.04 (1H, ddd, J=8.6, 7.9, 2.4 Hz), 5.48 (1H, dq, J=7.3, 6.7 Hz), 3.98 (1H, d, J=11.6 Hz), 3.69 (1H, d, J=11.6 Hz), 2.90 (1H, m), 2.48 (2H, br), 2.26-1.99 (3H, m), 1.60 (3H, d, J=7.3 Hz).

Ex 328

¹H NMR (CDCl₃) delta 8.53 (1H, ddd, J=4.9, 1.8, 1.2 Hz), 7.53 (1H, ddd, J=7.9, 1.8, 1.2 Hz), 7.38 (1H, dd, J=8.6, 6.1 Hz), 7.24 (1H, dd, J=7.9, 4.9 Hz), 7.16 (1H, dd, J=8.6, 3.1

Hz), 7.10 (1H, br), 7.02 (1H, dt, J=8.6, 3.1 Hz), 5.39 (1H, m), 4.00 (1H, br), 3.83 (1H, d, J=11.6 Hz), 3.69 (1H, d, J=11.6 Hz), 2.56-2.38 (3H, m), 2.03 (1H, m), 1.66 (1H, br), 1.59 (3H, d, J=7.3 Hz).

Ex 329

$^1$H NMR (CDCl$_3$) delta 8.55 (1H, br d, J=4.3 Hz), 8.48 (1H, d, J=2.4 Hz), 8.08 (1H, br d, J=4.3 Hz), 7.79 (1H, dd, J=7.9, 1.8 Hz), 7.78 (1H, d, J=2.4 Hz), 7.31 (1H, dd, J=7.9, 4.3 Hz), 4.83 (1H, dd, J=18.3, 4.9 Hz), 4.70 (1H, dd, J=18.3, 4.3 Hz), 4.02 (1H, d, J=11.6 Hz), 3.72 (1H, d, J=11.6 Hz), 2.94 (1H, m), 2.32-2.02 (3H, m). The signals due to OH were not observed.

Ex 330

$^1$H NMR (CDCl$_3$) delta 8.54 (1H, br dd, J=4.9, 1.8 Hz), 7.42 (1H, d, J=1.8 Hz), 7.36 (1H, br dd, J=7.9, 1.8 Hz), 7.28-7.20 (3H, m), 6.86 (1H, br d, J=5.5 Hz), 5.00 (1H, br), 3.98 (1H, d, J=11.0 Hz), 3.77-3.62 (2H, m), 3.68 (1H, d, J=11.0 Hz), 3.48 (1H, s), 3.07-3.03 (2H, m), 2.83 (1H, m), 2.18-1.98 (3H, m).

Ex 331

$^1$H NMR (CDCl$_3$) delta 8.57-8.54 (1H, m), 7.63 (1H, br d, J=7.9, 1.8 Hz), 7.39 (1H, d, J=1.8 Hz), 7.33 (1H, dd, J=7.9, 4.9 Hz), 7.20-7.11 (2H, m), 7.03 (1H, br), 4.90 (1H, br), 3.99 (1H, d, J=11.6 Hz), 3.74 (1H, br), 3.70 (1H, d, J=11.6 Hz), 3.08 (1H, m), 2.90 (1H, m), 2.3-2.01 (4H, m), 1.42-1.29 (2H, m).

The following Intermediates were prepared by General Procedure AA (Table 56).

General Procedure AA

To a stirred solution of substrate (1.0 eq.), iodomethane (15 eq.), and silver(I)oxide (10 eq.) in THF was added one drop of dimethyl sulfide at ambient temperature in the dark. The mixture was stirred at room temperature for 1 h, and then heated to 50° C. After being stirred at 50° C. until complete reaction, the mixture was cooled to room temperature. The insoluble material was removed by filtration, the resulting filtrate was concentrated in vacuo. The residue was purified by silica gel column chromatography to afford following Intermediates.

TABLE 56

| Intermediates | Structure | Chemical Name | Substrate |
|---|---|---|---|
| II-s-1 | 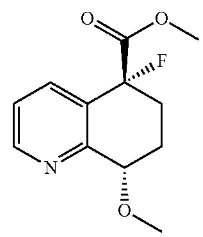 [SMILES: COC(=O)[C@@]1(F)CC[C@H](OC)c2ncccc21] | (5R,8S)-methyl 5-fluoro-8-methoxy-5,6,7,8-tetrahydroquinoline-5-carboxylate | IM II-d-3 |
| II-s-2 | 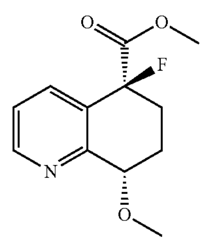 [SMILES: COC(=O)[C@]1(F)CC[C@H](OC)c2ncccc21] | (5S,8S)-methyl 5-fluoro-8-methoxy-5,6,7,8-tetrahydroquinoline-5-carboxylate | IM II-d-4 |
| II-s-3 | 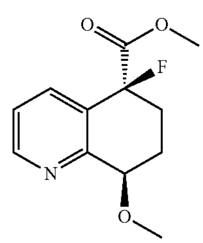 [SMILES: COC(=O)[C@]1(F)CC[C@@H](OC)c2ncccc21] | (5S,8R)-methyl 5-fluoro-8-methoxy-5,6,7,8-tetrahydroquinoline-5-carboxylate | IM II-d-5 |

IM II-s-1

¹H NMR (CDCl₃) delta 8.69 (1H, d, J=4.6 Hz), 7.79 (1H, d, J=7.9 Hz), 7.31 (1H, dd, J=7.9, 4.6 Hz), 4.42 (1H, m), 3.79 (3H, s), 3.57, (3H, s), 2.55 (1H, m), 2.43-2.24 (3H, m).

MS (ESI) m/z: 240.2 (M+H)⁺.

IM II-s-2

¹H NMR (CDCl₃) delta 8.69 (1H, br dd, J=4.6, 1.3 Hz), 7.68 (1H, dd, J=7.9, 1.3 Hz), 7.32 (1H, dd, J=7.9, 4.6 Hz), 4.41 (1H, m), 3.82 (3H, s), 3.54 (3H, s), 2.78 (1H, m), 2.36-2.04 (3H, m).

MS (ESI) m/z: 240.1 (M+H)⁺.

IM II-s-3

¹H NMR (CDCl₃) delta 8.69 (1H, br dd, J=4.6, 1.3 Hz), 7.79 (1H, dd, J=7.9, 1.3 Hz), 7.31 (1H, dd, J=7.9, 4.6 Hz), 4.42 (1H, m), 3.79 (3H, s), 3.57, (3H, s), 2.55 (1H, m), 2.43-2.24 (3H, m).

MS (ESI) m/z: 240.1 (M+H)⁺.

The following Examples were prepared by General Procedure A (Table 57).

TABLE 57

| Examples | Structure | Chemical Name | Substrate | Amine |
|---|---|---|---|---|
| 333 | 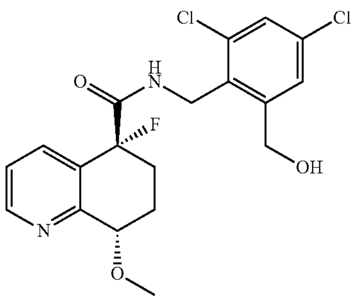 [SMILES: CO[C@H]1CC[C@](F)(C(=O)NCc2c(Cl)cc(Cl)cc2CO)c2cccnc21] | (5R,8S)-N-(2,4-dichloro-6-(hydroxymethyl)benzyl)-5-fluoro-8-methoxy-5,6,7,8-tetrahydroquinoline-5-carboxamide | IM II-s-1 | |
| 334 | 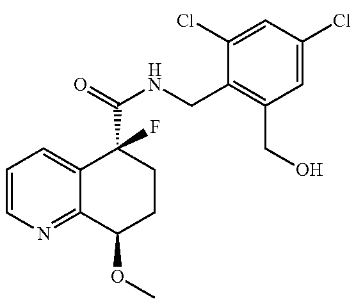 [SMILES: CO[C@@H]1CC[C@@](F)(C(=O)NCc2c(Cl)cc(Cl)cc2CO)c2cccnc21] | (5S,8R)-N-(2,4-dichloro-6-(hydroxymethyl)benzyl)-5-fluoro-8-methoxy-5,6,7,8-tetrahydroquinoline-5-carboxamide | IM II-s-3 | |
| 335 | 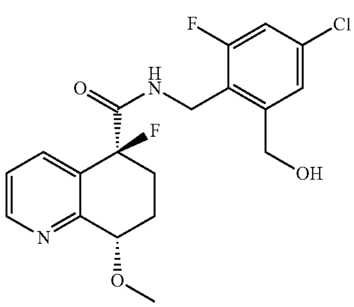 [SMILES: CO[C@H]1CC[C@@](F)(C(=O)NCc2c(F)cc(Cl)cc2CO)c2cccnc21] | (5S,8S)-N-(2,4-dichloro-6-fluorobenzyl)-5-fluoro-8-methoxy-5,6,7,8-tetrahydroquinoline-5-carboxamide | IM II-s-2 | |
| 336 | 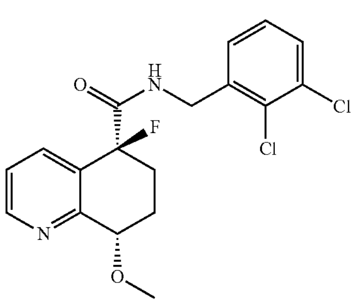 [SMILES: CO[C@H]1CC[C@@](F)(C(=O)NCc2cccc(Cl)c2Cl)c2cccnc21] | (5S,8S)-N-(2,3-dichlorobenzyl)-5-fluoro-8-hydroxy-5,6,7,8-tetrahydroquinoline-5-carboxamide | IM II-s-2 | |

TABLE 57-continued

| Examples | Structure | Chemical Name | Substrate | Amine |
|---|---|---|---|---|
| 337 | 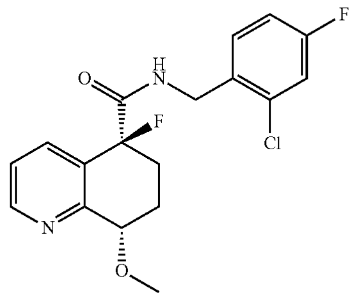 [SMILES: CO[C@H]1CC[C@@](F)(C(=O)NCc2ccc(F)cc2Cl)c2cccnc21] | (5S,8S)-N-(2-chloro-4-fluorobenzyl)-5-fluoro-8-methoxy-5,6,7,8-tetrahydroquinoline-5-carboxamide | IM II-s-2 | |
| 338 | 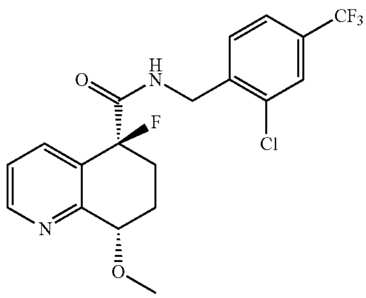 [SMILES: CO[C@H]1CC[C@@](F)(C(=O)NCc2ccc(C(F)(F)F)cc2Cl)c2cccnc21] | (5S,8S)-N-(2-chloro-4-(trifluoromethyl)benzyl)-5-fluoro-8-methoxy-5,6,7,8-tetrahydroquinoline-5-carboxamide | IM II-s-2 | |
| 339 | 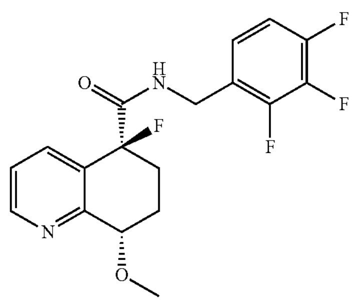 [SMILES: CO[C@H]1CC[C@@](F)(C(=O)NCc2ccc(F)c(F)c2F)c2cccnc21] | (5S,8S)-5-fluoro-8-methoxy-N-(2,3,4-trifluorobenzyl)-5,6,7,8-tetrahydroquinoline-5-carboxamide | IM II-s-2 | |
| 340 | 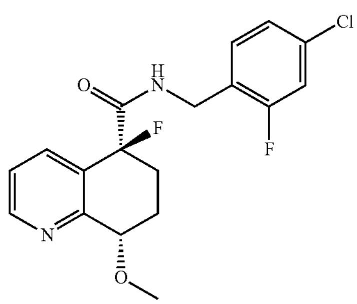 [SMILES: CO[C@H]1CC[C@@](F)(C(=O)NCc2ccc(Cl)cc2F)c2cccnc21] | (5S,8S)-N-(4-chloro-2-fluorobenzyl)-5-fluoro-8-methoxy-5,6,7,8-tetrahydroquinoline-5-carboxamide | IM II-s-2 | |
| 341 | 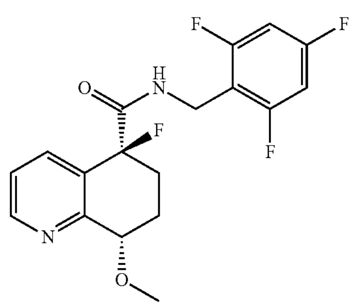 [SMILES: CO[C@H]1CC[C@@](F)(C(=O)NCc2c(F)cc(F)cc2F)c2cccnc21] | (5S,8S)-5-fluoro-8-methoxy-N-(2,4,6-trifluorobenzyl)-5,6,7,8-tetrahydroquinoline-5-carboxamide | IM II-s-2 | |

TABLE 57-continued

| Examples | Structure | Chemical Name | Substrate | Amine |
|---|---|---|---|---|
| 342 | 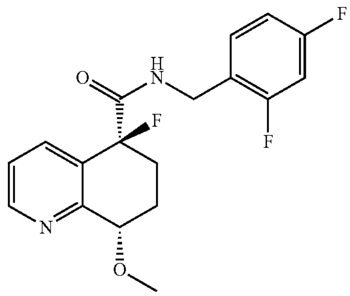 [SMILES: CO[C@H]1CC[C@@](F)(C(=O)NCc2ccc(F)cc2F)c2cccnc21] | (5S,8S)-N-(2,4-difluoro benzyl)-5-fluoro-8-methoxy-5,6,7,8-tetrahydroquinoline-5-carboxamide | 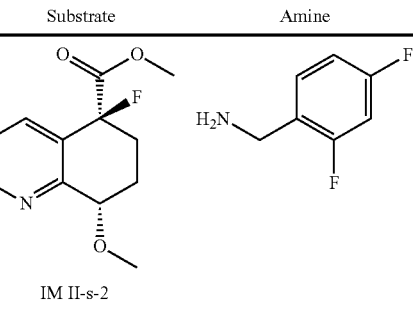 IM II-s-2 | |

TABLE 58

LC MS

| Examples | Method | tR (min) | [M + H]+ |
|---|---|---|---|
| 333 | A | 1.45 | 413.1 |
| 334 | A | 1.44 | 413.1 |
| 335 | B | 1.58 | 400.9 |
| 337 | B | 1.54 | 383.0 |
| 337 | B | 1.47 | 367.1 |
| 338 | B | 1.63 | 417.0 |
| 339 | C | 1.46 | 368.9 |
| 340 | C | 1.52 | 366.9 |
| 341 | C | 1.42 | 368.9 |
| 342 | C | 1.41 | 351.0 |

Ex 333

¹H NMR (CDCl₃) delta 8.66 (1H, br d, J=4.6 Hz), 7.57 (1H, br d, J=5.9 Hz), 7.49 (1H, d, J=7.9 Hz), 7.44 (1H, d, J=2.0 Hz), 7.33 (1H, d, J=2.0 Hz), 7.23 (1H, dd, J=7.9, 4.6 Hz), 4.73-4.67 (4H, m), 4.43 (1H, m), 3.90 (1H, br), 3.57 (3H, s), 2.80-2.11 (4H, m).

Ex 334

¹H NMR was identified with the Example 333.

Intermediate (IM) II-s-4

(5S,8S)-allyl 8-(allyloxy)-5-fluoro-5,6,7,8-tetrahydroquinoline-5-carboxylate

[Chem. 31]

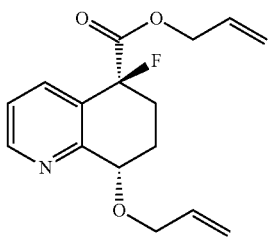

A mixture of (5S,8S)-methyl 5-fluoro-8-hydroxy-5,6,7,8-tetrahydroquinoline-5-carboxylate (100 mg, 0.444 mmol, IM II-d-4) and 2 N aq. NaOH in MeOH (2.0 mL) was stirred at room temperature for 1 h, the resulting solution was concentrated in vacuo. The residue was added NMP (1.0 mL) and the mixture was added sodium hydride (60% oil dispersant, 5 mg, 0.222 mmol) at 0° C. The mixture was warmed to room temperature and stirred for 20 min. Allyl bromide (0.192 mL, 2.22 mmol) was added to the reaction mixture and the mixture was heated at 60° C. for 6 h. The mixture was cooled to room temperature and stirred further 9 h. Water was added to the mixture and the mixture was extracted with EtOAc. The extract was washed with brine, dried over Na₂SO₄, and concentrated in vacuo. The residue was purified by silica gel column chromatography (0- to 50% EtOAc/n-hexane, gradient) to afford 25 mg (19%) of the title compound.

¹H NMR (CDCl₃) delta 8.67 (1H, br dd, J=4.6, 1.8 Hz), 7.68 (1H, br dd, J=7.9, 1.8 Hz), 7.31 (1H, dd, J=7.9, 4.9 Hz), 5.95 (1H, ddt, J=17.1, 10.4, 5.5 Hz), 5.88 (1H, ddt, J=17.1, 10.4, 5.5 Hz), 5.32 (1H, ddt, J=17.1, 4.9, 1.8 Hz), 5.30 (1H, ddt, J=17.1, 3.1, 1.2 Hz), 5.25 (1H, br d J=10.4 Hz), 5.17 (1H, ddt, J=10.4, 3.1, 1.2 Hz), 4.76-4.66 (2H, m), 4.56 (1H, m), 4.30-4.21 (2H, m), 2.89 (1H, m), 2.33-2.15 (3H, m).

MS (ESI) m/z: 291.9 (M+H)⁺.

Intermediate (IM) I-s-1

(5R,8R)-8-(allyloxy)-N-(2,4-dichlorobenzyl)-5-fluoro-5,6,7,8-tetrahydroquinoline-5-carboxamide

[Chem. 32]

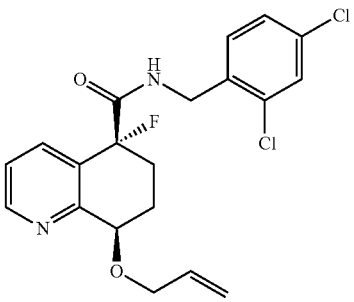

60% oil dispersant NaH (6 mg, 0.244 mmol) was added to a solution of (5R,8R)-methyl 5-fluoro-8-hydroxy-5,6,7,8-tetrahydroquinoline-5-carboxylate (25 mg, 0.111 mmol, IM II-d-6) in THF (1.0 mL) under N₂ atmosphere at 0° C. After being stirred at 0° C., allyl iodide (0.025 mL, 0.278 mmol) was added to the mixture and the mixture was stirred for 1 h. 60% oil dispersant NaH (6 mg, 0.244 mmol) and allyl iodide (0.025 mL, 0.278 mmol) was added to the mixture and the mixture was stirred further 1 h. Water was added to the mixture and acidified with 2 N hydrochloric acid. The mixture was concentrated in vacuo. The resulting residue was diluted with MeCN and toluene and the mixture was concentrated in vacuo. This procedure was repeated 3 times to remove remaining water. The residue was dissolved in 25% MeOH-THF (2.0 mL) and 2,4-dichlorobenzylamine (20 mg, 0.111 mmol), triethylamine (0.025 mL, 0.179 mmol), and DMT-MM (40 mg, 0.167 mmol) were added to the mixture. After being stirred at room temperature for 16 h, water was added to the mixture. The mixture was extracted with EtOAc and washed with brine. The extract was dried over $Na_2SO_4$ and concentrated in vacuo to afford glass. The residual glass was purified by preparative TLC (70% EtOAc/n-hexane) to afford 15 mg (33%) of the title compound as a white solid.

$^1$H NMR (CDCl$_3$) delta 8.64 (1H, br dd, J=4.9, 1.8 Hz), 7.51 (1H, br dd, J=7.9, 1.8 Hz), 7.44 (1H, d, J=1.8 Hz), 7.37 (1H, br d, J=7.9 Hz), 7.27-7.22 (2H, m), 7.16 (1H, br), 5.92 (1H, ddt, J=17.1, 10.4, 5.5 Hz), 5.29 (1H, ddt, J=17.1, 3.7, 1.8 Hz), 5.14 (1H, ddt, J=17.1, 3.7, 1.8 Hz), 4.71-4.51 (3H, m), 4.27-4.17 (2H, m), 2.92 (1H, m), 2.33-2.06 (3H, m).

MS (ESI) m/z: 408.7 (M+H)$^+$.

The following Intermediates were prepared from IM II-s-4 by General Procedure A (Table 59).

TABLE 59

| Intermediates | Structure | Chemical Name | Amine |
| --- | --- | --- | --- |
| I-s-2 | 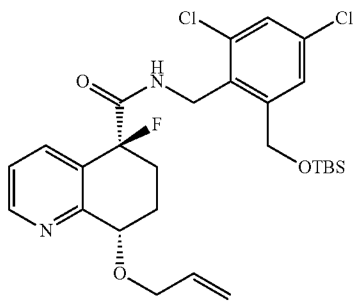 [SMILES: C=CCO[C@H]1CC[C@@](F)(C(=O)NCc2c(Cl)cc(Cl)cc2CO[Si](C)(C)C(C)(C)C)c2cccnc21] | (5S,8S)-8-(allyloxy)-N-(2-(((tert-butyl dimethylsilyl)oxy)methyl)-4,6-dichloro benzyl)-5-fluoro-5,6,7,8-tetrahydroquinoline-5-carboxamide | |
| I-s-3 | 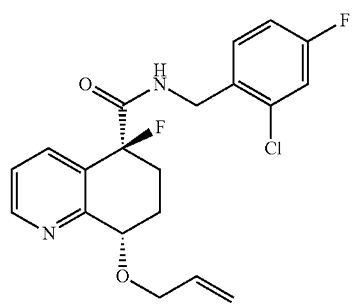 [SMILES: C=CCO[C@H]1CC[C@@](F)(C(=O)NCc2ccc(F)cc2Cl)c2cccnc21] | (5S,8S)-8-(allyloxy)-N-(2-chloro-4-fluorobenzyl)-5-fluoro-5,6,7,8-tetrahydroquinoline-5-carboxamide | |
| I-s-4 | 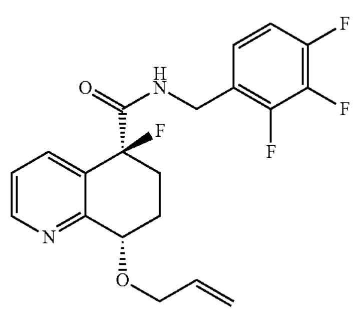 [SMILES: C=CCO[C@H]1CC[C@@](F)(C(=O)NCc2ccc(F)c(F)c2F)c2cccnc21] | (5S,8S)-8-(allyloxy)-5-fluoro-N-(2,3,4-trifluorobenzyl)-5,6,7,8-tetrahydroquinoline-5-carboxamide | |
| I-s-5 | 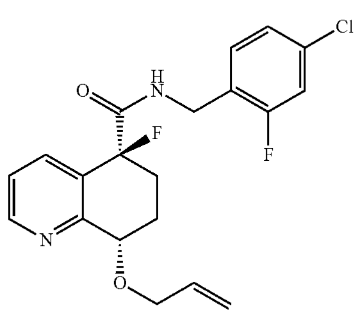 [SMILES: C=CCO[C@H]1CC[C@@](F)(C(=O)NCc2ccc(Cl)cc2F)c2cccnc21] | (5S,8S)-8-(allyloxy)-N-(4-chloro-2-fluorobenzyl)-5-fluoro-5,6,7,8-tetrahydroquinoline-5-carboxamide | |

TABLE 59-continued

| Intermediates | Structure | Chemical Name | Amine |
|---|---|---|---|
| I-s-6 | 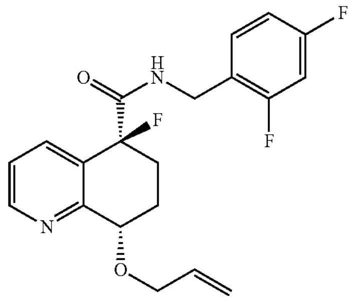 [SMILES: C=CCO[C@H]1CC[C@@](F)(C(=O)NCc2ccc(F)cc2F)c2cccnc21] | (5S,8S)-8-(allyloxy)-N-(2,4-difluorobenzyl)-5-fluoro-5,6,7,8-tetrahydroquinoline-5-carboxamide | |
| I-s-7 | 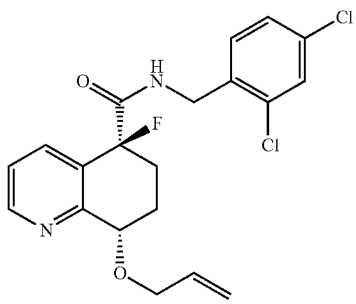 | (5S,8S)-8-(allyloxy)-N-(2,4-dichlorobenzyl)-5-fluoro-5,6,7,8-tetrahydroquinoline-5-carboxamide | |

IM I-s-2
  MS (ESI) m/z: 552.4 (M+H)$^+$.
IM I-s-3
  MS (ESI) m/z: 392.7 (M+H)$^+$.
IM I-s-4
  MS (ESI) m/z: 394.8 (M+H)$^+$.
IM I-s-5
  MS (ESI) m/z: 392.8 (M+H)$^+$.
IM I-s-6
  MS (ESI) m/z: 376.8 (M+H)$^+$.
IM I-s-7
  MS (ESI) m/z: 408.7 (M+H)$^+$.

The following Examples were prepared by General Procedure C (Table 60).

In preparation of Example 343, the TBS group was deprotected on the SCX cartridge column.

TABLE 60

| Examples | Structure | Chemical Name | Substrate |
|---|---|---|---|
| 343 | 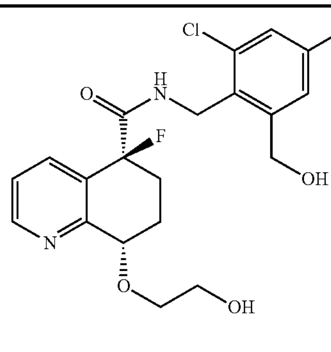 | (5S,8S)-N-(2,4-dichloro-6-(hydroxymethyl)benzyl)-5-fluoro-8-(2-hydroxyethoxy)-5,6,7,8-tetrahydroquinoline-5-carboxamide | IM I-s-2 |

TABLE 60-continued

| Examples | Structure | Chemical Name | Substrate |
|---|---|---|---|
| 344 | 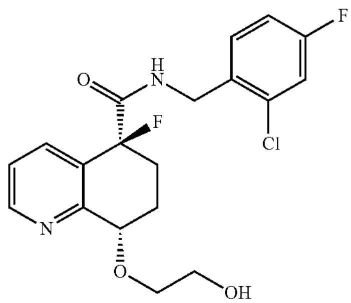 [SMILES: O=C(NCc1ccc(F)cc1Cl)[C@]1(F)CC[C@H](OCCO)c2ncccc21] | (5S,8S)-N-(2-chloro-4-fluorobenzyl)-5-fluoro-8-(2-hydroxyethoxy)-5,6,7,8-tetrahydroquinoline-5-carboxamide | IM I-s-3 |
| 345 | 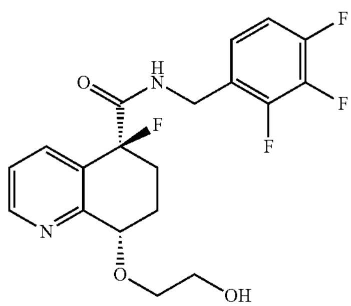 [SMILES: O=C(NCc1ccc(F)c(F)c1F)[C@]1(F)CC[C@H](OCCO)c2ncccc21] | (5S,8S)-5-fluoro-8-(2-hydroxyethoxy)-N-(2,3,4-trifluorobenzyl)-5,6,7,8-tetrahydroquinoline-5-carboxamide | IM I-s-4 |
| 346 | 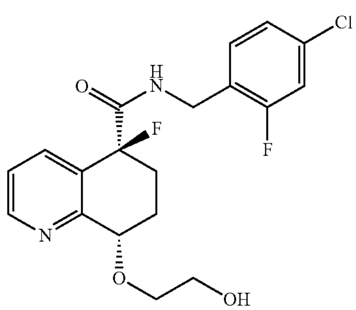 [SMILES: O=C(NCc1ccc(Cl)cc1F)[C@]1(F)CC[C@H](OCCO)c2ncccc21] | (5S,8S)-N-(4-chloro-2-fluorobenzyl)-5-fluoro-8-(2-hydroxyethoxy)-5,6,7,8-tetrahydroquinoline-5-carboxamide | IM I-s-5 |
| 347 | 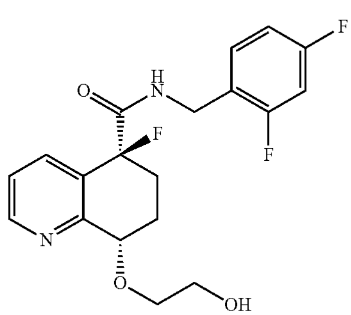 [SMILES: O=C(NCc1ccc(F)cc1F)[C@]1(F)CC[C@H](OCCO)c2ncccc21] | (5S,8S)-N-(2,4-difluorobenzyl)-5-fluoro-8-(2-hydroxyethoxy)-5,6,7,8-tetrahydroquinoline-5-carboxamide | IM I-s-6 |

TABLE 60-continued

| Examples | Structure | Chemical Name | Substrate |
|---|---|---|---|
| 348 | 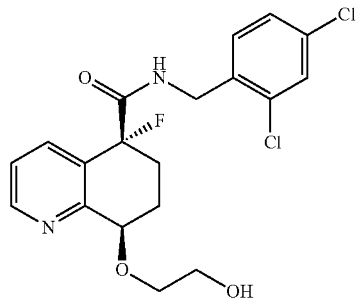 [SMILES: O=C(NCc1ccc(Cl)cc1Cl)[C@@]1(F)CC[C@@H](OCCO)c2ncccc21] | (5R,8R)-N-(2,4-dichlorobenzyl)-5-fluoro-8-(2-hydroxyethoxy)-5,6,7,8-tetrahydroquinoline-5-carboxamide | IM I-s-1 |

TABLE 61

| | LC MS | | |
|---|---|---|---|
| Examples | Method | tR (min) | [M + H]⁺ |
| 343 | C | 1.37 | 442.9 |
| 344 | C | 1.39 | 397.0 |
| 345 | C | 1.36 | 399.0 |
| 346 | C | 1.41 | 397.1 |
| 347 | C | 1.31 | 381.0 |
| 348 | C | 1.49 | 413.0 |

Example 349

(5S,8S)—N-(2,4-dichlorobenzyl)-8-(2,3-dihydroxypropoxy)-5-fluoro-5,6,7,8-tetrahydroquinoline-5-carboxamide

[Chem. 33]

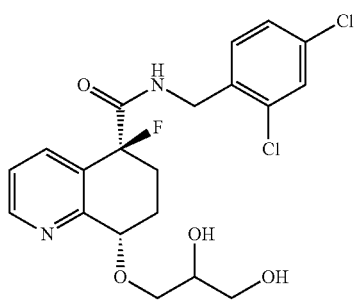

A mixture of AD-Mix beta (250 mg) in 50% tert-BuOH-water (3.0 mL) was stirred at room temperature until the two clear phases formed. After cooling to 0° C., a solution of (5S,8S)-8-(allyloxy)-N-(2,4-dichlorobenzyl)-5-fluoro-5,6,7,8-tetrahydroquinoline-5-carboxamide (24 mg, 0.059 mmol, IM I-s-7) in THF (1.0 mL) was added to the mixture. The resulting mixture was stirred at 0° C. overnight. The mixture was filtered through a pad of celite, the filter cake was washed with THF. The filtrate was evaporated in vacuo to remove the volatile. The residue was diluted with brine and extracted with EtOAc twice. The extracts were combined and dried over Na$_2$SO$_4$. After removal of the solvent, the residue was purified by silica gel column chromatography (50% EtOAc/n-hexane then 5% MeOH/EtOAc) to afford 24 mg (92%) of the title compound.

¹H NMR (CDCl$_3$) delta 8.61 (1H, m), 7.55 (1H, m), 7.50 (1H, d, J=1.8 Hz), 7.36 (1H, br d, J=7.9 Hz), 7.31-7.23 (2H, m), 7.20 (1H, br d, J=5.5 Hz), 4.67-4.56 (3H, m), 3.92-3.52 (5H, m), 2.82 (1H, m), 2.7 (1H, br), 2.36-2.07 (3H, m), 1.8 (1H, br).

LCMS (ESI) m/z: 443.2 (M+H)⁺, tR 1.45 min (Method D).

Intermediate (IM) I-p-1

Procedure: Scheme 13, Step 1

S-((5S)-5-((2,4-dichlorobenzyl)carbamoyl)-5-fluoro-5,6,7,8-tetrahydroquinolin-8-yl) benzothioate

[Chem. 34]

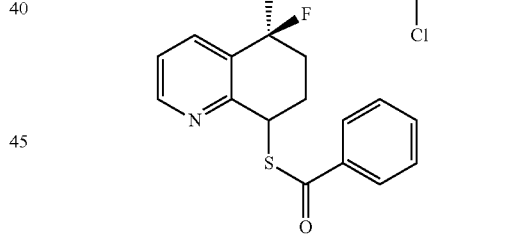

Bis(2-methoxyethyl) azodicarboxylate (57 mg, 0.244 mmol) was added to a solution of triphenylphosphine (64 mg, 0.244 mmol) in THF (2.0 mL) at 0° C. under N$_2$ atmosphere. The reaction mixture was stirred at 0° C. for 30 min, and then a solution of (5S,8S)—N-(2,4-dichlorobenzyl)-5-fluoro-8-hydroxy-5,6,7,8-tetrahydroquinoline-5-carboxamide (60 mg, 0.163 mmol, Ex 133) and thiobenzoic acid (34 mg, 0.244 mmol) in THF (1.0 mL) was added dropwise to the mixture. After being stirred at 0° C. for 20 h, water was added to the mixture and the mixture was extracted with EtOAc. The extract was washed with brine, dried over Na$_2$SO$_4$, and concentrated. The residue was purified by column chromatography (20- to 35% EtOAc/n-hexane, gradient) to afford 25 mg (31%) of the title compound.

¹H NMR (CDCl$_3$) delta 8.66-8.63 (1H, m), 8.01-7.96 (2H, m), 7.60-7.17 (9H, m), 5.30 (0.4H, br), 5.24 (0.6H, m), 4.75-4.56 (2H, m), 2.87-2.14 (4H, m).

MS (ESI) m/z: 488.6 (M+H)⁺.

Intermediate (IM) I-q-1

Procedure: Scheme 13, Step 2

(5S)—N-(2,4-dichlorobenzyl)-5-fluoro-8-(methylthio)-5,6,7,8-tetrahydroquinoline-5-carboxamide

[Chem. 35]

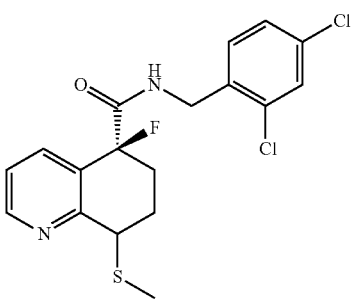

A solution of S-((5S)-5-((2,4-dichlorobenzyl)carbamoyl)-5-fluoro-5,6,7,8-tetrahydroquinolin-8-yl)benzothioate (25 mg, 0.051 mmol, IM I-p-1) in methanol (1.0 mL) was added 1 N aq. NaOH (0.06 mL, 0.06 mmol) and dimethyl sulfate (8 mg, 0.06 mmol) at room temperature. The mixture was stirred at room temperature for 2 h and concentrated in vacuo. Water was added to the resulting residue and extracted with EtOAc. The extract was washed with brine, dried over $Na_2SO_4$ and concentrated in vacuo. The residue was purified by SCX column to afford 18 mg (88%) of the title compound as a glass.

$^1$H NMR (CDCl$_3$) delta 8.67-8.58 (1H, m), 7.57-7.14 (6H, m), 4.68-4.53 (2H, m), 4.18-4.14 (1H, m), 3.49 (3H, s), 3.03-2.86 (0.4H, m), 2.72-2.64 (0.6H, m), 2.59-2.10 (3H, m).

MS (ESI) m/z: 400.5 (M+H)$^+$.

Intermediate (IM) I-q-2

Procedure: Scheme 13, Step 2

(5S)—N-(2,4-dichlorobenzyl)-5-fluoro-8-((2-hydroxyethyl)thio)-5,6,7,8-tetrahydroquinoline-5-carboxamide

[Chem. 36]

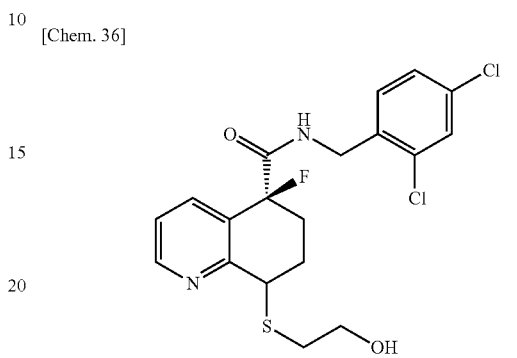

A solution of S-((5S)-5-((2,4-dichlorobenzyl)carbamoyl)-5-fluoro-5,6,7,8-tetrahydroquinolin-8-yl)benzothioate (24 mg, 0.049 mmol, IM I-p-1) in methanol (1.0 mL) was added 1 N aq. NaOH (0.06 mL, 0.06 mmol) and (2-bromoethoxy)(tert-butyl)dimethylsilane (18 mg, 0.074 mmol) at room temperature. The mixture was stirred at room temperature for 2 h and concentrated in vacuo. Water was added to the residue and the mixture was extracted with EtOAc. The extract was washed with brine, dried over $Na_2SO_4$, and concentrated in vacuo. The resulting residue was purified by SCX column to afford 16 mg (76%) of the title compound as a glass.

$^1$H NMR (CDCl$_3$) delta 8.57 (0.5H, dd, J=4.9, 1.8 Hz), 8.56 (0.5H, dd, J=4.9, 1.8 Hz), 7.53 (0.5H, d, J=7.9 Hz), 7.49 (0.5H, d, J=7.9 Hz), 7.45 (1H, d, J=1.8 Hz), 7.39 (0.5H, d, J=7.9 Hz), 7.34 (0.5H, d, J=7.9 Hz), 7.31-7.14 (3H, m), 4.68-4.53 (2H, m), 4.47 (0.5H, br), 4.29 (0.5H, br), 3.95-3.86 (2H, m), 3.48 (1H, br), 3.05-2.68 (3H, m), 2.53-2.12 (3H, m).

MS (ESI) m/z: 428.6 (M+H)$^+$.

General Procedure: Scheme 13, Step 3

The following Examples were prepared by General Procedure X (Table 62).

TABLE 62

| Examples | Structure | Chemical Name | Substrate |
|---|---|---|---|
| 350 | (structure) | (5S)-N-(2,4-dichlorobenzyl)-5-fluoro-8-(methylsulfonyl)-5,6,7,8-tetrahydroquinoline-5-carboxamide | (structure) IM I-q-1 |

TABLE 62-continued

| Examples | Structure | Chemical Name | Substrate |
|---|---|---|---|
| 351 | 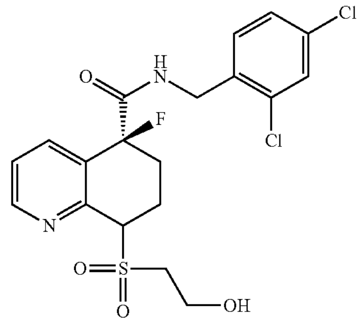 [SMILES: O=C(NCc1ccc(Cl)cc1Cl)[C@]1(F)CCC(S(=O)(=O)CCO)c2ncccc21] | (5S)-N-(2,4-dichlorobenzyl)-5-fluoro-8-((2-hydroxyethyl)sulfonyl)-5,6,7,8-tetrahydroquinoline-5-carboxamide | IM I-q-2 |

Ex 350

$^1$H NMR (CDCl$_3$) delta 8.66-8.60 (1H, m), 7.68 (1H, dd, J=7.9, 1.8 Hz), 7.45 (0.5H, d, J=1.8 Hz), 7.39 (0.5H, d, J=1.8 Hz), 7.37-7.21 (3H, m), 7.15 (0.5H, br), 7.00 (0.5H, br), 4.62-4.50 (2H, m), 4.44 (1H, m), 3.30 (1.5H, s), 3.16 (1.5H, s), 3.03-2.62 (3H, m), 2.42-2.27 (1H, m).

LCMS (ESI) m/z: 430.5 (M+H)$^+$, tR 1.58 min (Method C).

Ex 351

$^1$H NMR (CDCl$_3$) delta 8.59 (1H, dd, J=4.9, 1.2 Hz), 7.72 (1H, dd, J=7.9, 1.2 Hz), 7.45 (1H, d, J=2.4 Hz), 7.41-7.22 (3H, m), 7.14 (1H, br), 4.80 (1H, m), 4.70 (1H, br), 4.62-4.49 (2H, m), 4.24-4.17 (2H, m), 3.95-3.89 (1H, m), 3.42-3.36 (1H, m), 3.07-2.66 (3H, m), 2.43-2.30 (1H, m).

LCMS (ESI) m/z: 460.8 (M+H)$^+$, tR 1.50 min (Method C).

The following Intermediate was prepared by General Procedure AB (Table 63).

General Procedure AB

Deoxo-Fluor (Trademark) (2.0 eq.) was added to a solution of substrate (1.0 eq.) in CH$_2$Cl$_2$ (0.15 M) and stirred for 1 h. The mixture was poured into water and extracted with EtOAc. The extract was dried over Na$_2$SO$_4$ and concentrated in vacuo. The resulting residue was purified by silica gel column chromatography.

TABLE 63

| Intermediate | Structure | Chemical Name | Substrate |
|---|---|---|---|
| II-y-1 | 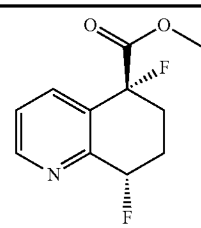 | (5R,8S)-methyl 5,8-difluoro-5,6,7,8-tetrahydroquinoline-5-carboxylate | II-d-6 |

IM II-y-1

$^1$H NMR (CDCl$_3$) delta 8.74 (1H, d, J=4.6 Hz), 7.87 (1H, d, J=7.9 Hz), 7.39 (1H, in), 5.61 (1H, br d, J=49.4 Hz), 3.80 (3H, s), 2.57-2.40 (4H, m).

MS (ESI) m/z: 228.1 (M+H).

The following Examples were prepared by General Procedure A (Table 64).

TABLE 64

| Examples | Structure | Chemical Name | Substrate | Amine |
|---|---|---|---|---|
| 352 | 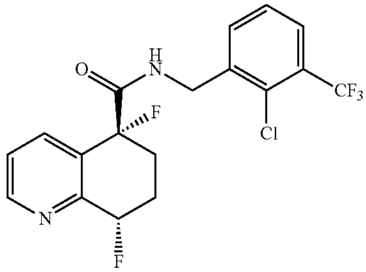 [SMILES: O=C(NCc1cccc(C(F)(F)F)c1Cl)[C@@]1(F)CC[C@H](F)c2ncccc21] | (5R,8S)-N-(2-chloro-3-(trifluoromethyl)benzyl)-5,8-difluoro-5,6,7,8-tetrahydroquinoline-5-carboxamide | IM II-y-1 | |
| 353 | 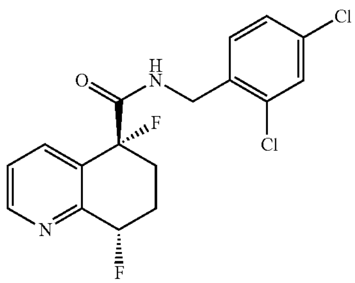 | (5R,8S)-N-(2,4-dichlorobenzyl)-5,8-difluoro-5,6,7,8-tetrahydroquinoline-5-carboxamide | | |
| 354 | 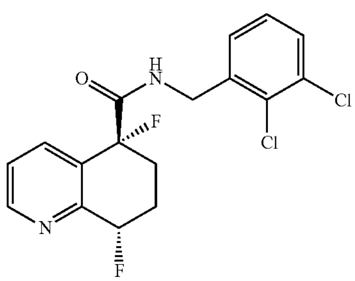 | (5R,8S)-N-(2,3-dichlorobenzyl)-5,8-difluoro-5,6,7,8-tetrahydroquinoline-5-carboxamide | | |

TABLE 65

| | LC MS | | |
|---|---|---|---|
| Examples | Method | tR (min) | [M + H]⁺ |
| 352 | A | 1.64 | 405.1 |
| 353 | A | 1.64 | 371.1 |
| 354 | A | 1.61 | 371.1 |

Procedure: Scheme 16, Step 1

Intermediate (IM) XVIII-1, 1-(2-chloropyridin-3-yl)pent-4-en-1-one

[Chem. 37]

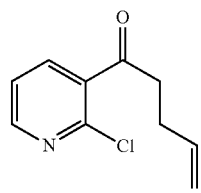

To a solution of 3-bromo-2-chloro pyridine (4.0 g, 20.8 mmol) in THF (100 mL) was added dropwise 1.3 M 2-propyl magnesium chloride lithium chloride complex in THF solution (18.5 ml, 25.0 mmol) at −10° C. under Ar atmosphere. The reaction mixture was stirred at the same temperature for 15 min. Then a THF solution of pent-4-enoyl chloride (3.2 g, 27.0 mmol) was added to the mixture at −40° C. After addition, the mixture was stirred at the same temperature for 1.5 h. The mixture was poured into aq. NH$_4$Cl at 0° C. The mixture was extracted with EtOAc twice and washed with aq. NaHCO$_3$ and brine. The combined extracts were dried over Na$_2$SO$_4$ and concentrated in vacuo. The insoluble material of the resulting residue was removed by filtration and washed with EtOAc. An activated charcoal was added to the filtrate. The mixture was stirred at 45° C. for 1.0 h and filtered through a pad of celite. The filtrate was distilled at reduced pressure to afford 2.9 g (72%) of the title compound.

$^1$H NMR (CDCl$_3$) delta 8.49 (1H, dd, J=4.9, 2.0 Hz), 7.81 (1H, dd, J=7.6, 2.0 Hz), 7.34 (1H, dd, J=7.6, 4.8 Hz), 5.77-5.91 (1H, m), 4.99-5.13 (3H, m), 3.11 (2H, t, J=7.3 Hz, 2H), 2.43-2.54 (2H, m).

MS (ESI) m/z: 196.3 (M+H)⁺.

Procedure: Scheme 16, Step 2

Intermediate (IM) XIX-1,
8-methylene-7,8-dihydroquinolin-5(6H)-one

[Chem. 38]

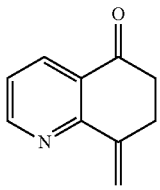

A mixture of 1-(2-chloropyridin-3-yl)pent-4-en-1-one (300 mg, 1.53 mmol, IM XVIII-1), triethylamine (0.64 mL, 4.61 mmol), Xantphos (17.7 mg, 0.031 mmol), and Pd(OAc)$_2$ (6.9 mg, 0.031 mmol) in MeCN (1.53 mL) was heated at reflux. After being refluxed for 15 h, the mixture was cooled to room temperature. The mixture was filtered with celite and the filtrate was concentrated in vacuo. To the residue was added EtOAc/n-hexane and the mixture was stirred for 15 min at room temperature. The mixture was filtered with celite and the filtrate was washed with water, dried over Na$_2$SO$_4$. The residue was distilled at reduced pressure to afford 238 mg (97%) of the title compound.
$^1$H NMR (CDCl$_3$) delta 8.76 (1H, dd, J=4.6, 1.8 Hz), 8.28 (1H, dd, J=8.0, 1.8 Hz), 7.34 (2H, dd, J=8.0, 4.7 Hz), 6.38 (1H, s), 5.47 (1H, d, J=1.3 Hz), 2.89-2.98 (2H, m), 2.75-2.85 (2H, m).
MS (ESI) m/z: 160.3 (M+H).

Procedure: Scheme 16, Step 3

Intermediate (IM) XX-1

5-fluoro-8-methylene-5,6,7,8-tetrahydroquinoline-5-carbonitrile

[Chem. 39]

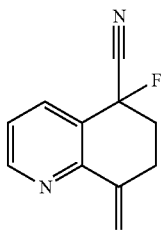

To a solution of 8-methylene-7,8-dihydroquinolin-5(6H)-one (300 mg, 1.9 mmol, IM XIX-1) in dichloromethane (15 mL) was added trimethylsilyl cyanide (243 microL, 2.45 mmol) and NMO (132 mg, 1.13 mmol) at 25° C. under Ar atmosphere. The reaction mixture was stirred at the same temperature for 4 h. Then DeoxoFluor (trademark) (382 microL, 2.07 mmol) was added to the mixture at 0° C. The mixture was stirred at the same temperature for 2 h and the mixture was poured into aq. NaHCO$_3$ at 0° C. The mixture was extracted with dichloromethane. The organic layer was dried over Na$_2$SO$_4$ and removed solvent in vacuo. The resulting residue was purified by silica gel column chromatography (30% EtOAc/n-hexane) to afford 256 mg (72%) of the title compound.
$^1$H NMR (CDCl$_3$) delta 8.70 (1H, dt, J=4.6, 1.6 Hz), 8.02 (1H, dt, J=8.0, 1.4 Hz), 7.35 (1H, dd, J=8.0, 4.7 Hz), 6.45 (1H, s), 5.37 (1H, s), 2.77-2.97 (3H, m), 2.42-2.62 (2H, m).
MS (ESI) m/z: 189.4 (M+H).

Procedure: Scheme 16, Step 4

Intermediate (IM) II-e-2-1, methyl 5-fluoro-8-methylene-5,6,7,8-tetrahydroquinoline-5-carboxylate

[Chem. 40]

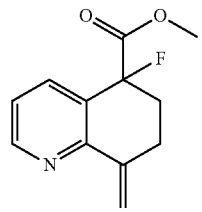

The title compound was prepared according to the procedure as described in General Procedure: Scheme 2, Step 3 using 5-fluoro-8-methylene-5,6,7,8-tetrahydroquinoline-5-carbonitrile (IM XX-1).

Procedure: Scheme 17, Step 1

Intermediate (IM) XXII-1, methyl 2-(2-chloropyridin-3-yl)-2-hydroxyhex-5-enoate

[Chem. 41]

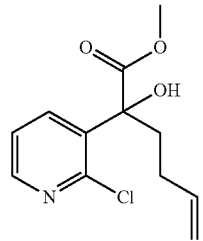

To a solution of 3-bromo-2-chloropyridine (1.79 g, 9.30 mmol) in THF (10 mL) was added dropwise 1.3 M 2-propylmagnesium chloride lithium chloride complex in THF (7.2 mL, 9.4 mmol) at −15° C. and the mixture was stirred at the same temperature for 1 h. A solution of methyl 2-oxohex-5-enoate (1.33 g, 9.36 mmol) in THF (3 mL) was added to the mixture at −40° C. The mixture was stirred at the same temperature for 2 h. Then the reaction was quenched with sat. aq. NH$_4$Cl. The mixture was extracted with EtOAc twice. The combined organic layer was washed with brine, dried over Na$_2$SO$_4$, and removed solvent in vacuo. The residue was purified by silica gel column chromatography (25% EtOAc/n-hexane) to afford 1.78 g (74%) of the title compound.

$^1$H NMR (CDCl$_3$) delta 8.35 (1H, dd, J=4.7, 1.8 Hz), 7.97 (1H, dd, J=7.8, 1.8 Hz), 7.26-7.33 (1H, m), 5.83 (1H, ddt, J=17.0, 10.4, 6.4, 6.4 Hz), 4.98-5.10 (2H, m), 3.84 (1H, s), 3.78 (3H, s), 2.14-2.40 (3H, m), 1.96-2.07 (1H, m).

Procedure: Scheme 17, Step 2

Intermediate (IM) II-e-2-5, methyl 5-hydroxy-8-methylene-5,6,7,8-tetrahydroquinoline-5-carboxylate

[Chem. 42]

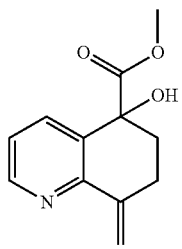

The title compound was prepared according to the procedure as described in General Procedure: Scheme 16, Step 2 using methyl 2-(2-chloropyridin-3-yl)-2-hydroxyhex-5-enoate (IM XXII-1).

Procedure: Scheme 18, Step 1

Intermediate (IM) XXIII-1

5-fluoro-8-methylene-5,6,7,8-tetrahydroquinoline-5-carboxylic acid

[Chem. 43]

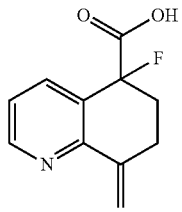

A mixture of methyl 5-fluoro-8-methylene-5,6,7,8-tetrahydroquinoline-5-carboxylate (3.0 g, 13.6 mmol, IM II-e-2-1) and 2 N aq. NaOH (14 mL, 28.0 mmol) in MeOH (67 mL) was stirred at room temperature for 1.5 h, and then the mixture was concentrated in vacuo. 10% aq. citric acid (90 mL) was added to the mixture. The mixture was extracted with EtOAc. The organic layer was dried over Na$_2$SO$_4$ and concentrated in vacuo to afford 1.57 g (56%) of the title compound.

$^1$H NMR (CDCl$_3$) delta 8.73 (1H, d, J=4.9 Hz), 8.28 (2H, br s), 7.95 (1H, d, J=7.6 Hz), 7.35 (1H, dd, J=7.9, 5.0 Hz), 6.24 (1H, s), 5.39 (1H, s), 2.75-2.91 (2H, m), 2.44-2.65 (1H, m), 2.26-2.40 (1H, m).

MS (ESI) m/z: 208.1 (M+H)$^+$.

Procedure: Scheme 18, Step 2

Intermediate (IM) XXIV 5-fluoro-8-(iodomethyl)-5,6,7,8-tetrahydro-8,5-(epoxymethano)quinolin-10-one

[Chem. 44]

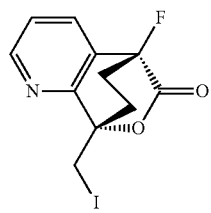

To a solution of 5-fluoro-8-methylene-5,6,7,8-tetrahydroquinoline-5-carboxylic acid (2.0 g, 9.65 mmol, IM XXIII-1) in MeCN (100 mL) was added NaHCO$_3$ (1.7 g, 19.6 mmol) and iodine (5.0 g, 19.6 mmol) at room temperature. The reaction mixture was stirred at the same temperature for 3 h. Then sat. aq. Na$_2$S$_2$O$_3$ was added to the mixture. The mixture was extracted with EtOAc and washed with brine. The extract was dried over Na$_2$SO$_4$ and concentrated in vacuo. The residue was purified by silica gel column chromatography (30% EtOAc/n-hexane) to afford 2.6 g (81%) of the title compound.

$^1$H NMR (CDCl$_3$) delta 8.59 (1H, dd, J=5.1, 1.5 Hz), 7.88 (1H, dd, J=7.6, 1.5 Hz), 7.43 (1H, dd, J=7.7, 5.0 Hz), 4.03-4.12 (2H, m), 2.71-2.81 (1H, m), 2.51 (1H, tdd, J=11.3, 11.3, 5.5, 3.4 Hz), 2.09 (1H, tdd, J=11.7, 11.7, 4.6, 3.2 Hz), 1.91-2.00 (1H, m).

MS (ESI) m/z: 333.9 (M+H)$^+$.

Pharmacological Assays

The ability of the 5,6,7,8-tetrahydroquinoline and 6,7-dihydro-5H-cyclopenta[b]pyridine derivatives of the formula (I) to inhibit the P2X7 channel was measured by Ca$^{2+}$ influx assay and electrophysiology assay described below.

Human P2X7 Functional Assay

The functional activity of compounds was determined by measuring changes in intracellular calcium concentration using a Ca$^{2+}$-sensitive fluorescent dye, Fluo-4 (Molecular Probes). The changes in fluorescent signal were monitored by the cell imaging technology by Hamamatsu Photonics's Functional Drug Screening System (FDSS). Increases in intracellular Ca$^{2+}$ concentration were readily detected upon activation with BzATP.

Cell Maintenance:

HEK293 cells stably expressing human P2X7 (GenBank accession number BC011913) carrying a C-terminal FLAG tag were grown in T225 flasks, in a 5% CO2 humidified incubator to about 80% confluence. Media composition consisted of Dulbecco's Modified Eagle Medium (high glucose), 10% fetal bovine serum (BSA), 100 units/microM Penicillin, 100 microg/mL Streptomycin and 250 microg/mL Geneticine.

Protocol:

Day One:
1. Plate-out HEK293-human P2X7 cells (40 microL medium containing 10,000 cells per well) into poly-D-lysine coated 384-well plates (Corning) at 24 h prior to assay.

2. Incubate at 37° C. in 5% $CO_2$.

Day Two:
1. Wash each well with 80 microL of assay buffer (20 mM HEPES, 1×HBSS, pH 7.4 adjusted with NaOH) three times and leave 20 microL using plate washer, ELx-405 Select CW (BIO-TEK).
2. Add 20 microL of assay buffer containing 2.5 mM probenecid, 0.5 microM Fluo-4-AM (Molecular Probes) and 0.1% Pluronic F-127 to each well.
3. Incubate the plate at 37° C. in 5% $CO_2$ for 1 h.
4. Wash each well with 80 microL of assay buffer (see below) three times and leave 20 microL using plate washer, ELx-405 Select CW (BIO-TEK).
5. Test compounds were prepared at 100× the test concentration in DMSO by serial dilution with Biomek-FX liquid handling instrument. 33× diluted compound solutions in assay buffer were prepared in intermediate compound plate with Biomek-NX liquid handling instrument. A further 3× dilution occurred in below steps 6 and 7.
6. Add 20 microL of 33× diluted compound solutions into each well and leave the plate for 10 min under the dark at room temperature.
7. Measure activity by FDSS as follows:
    Set the assay plate on the stacker of FDSS.
    Start the detection of fluorescence intensity at 540 nm by 480 nm excitation.
    After 30 seconds, add 20 microL of assay buffer containing 240 microM BzATP (final concentration 80 microM).

$IC_{50}$ values for compounds of the present invention were determined from 7-point dose-response studies. Curves were generated using the average of duplicate wells for each data point. Finally, the $IC_{50}$ values are calculated with the best-fit dose curve determined by XLfit (ID Business Solutions Ltd.).

Antagonistic activities with respect to the human P2X7 receptor ($IC_{50}$ values) of exemplified compounds are displayed in Table 66.

TABLE 66

| Examples | $IC_{50}$ |
|---|---|
| A: <50 nM, B: 50- to 100 nM, C: 101 - to 300 nM, D: 301- to 1,000 nM, E: 1,001 - to 3,000 nM | |
| 1 | A |
| 2 | A |
| 3 | D |
| 4 | A |
| 5 | E |
| 6 | A |
| 7 | A |
| 8 | A |
| 9 | A |
| 10 | A |
| 11 | A |
| 12 | A |
| 13 | A |
| 14 | A |
| 15 | D |
| 16 | A |
| 17 | B |
| 18 | A |
| 19 | A |
| 20 | A |
| 21 | A |
| 22 | A |
| 23 | A |
| 24 | A |

TABLE 66-continued

| Examples | $IC_{50}$ |
|---|---|
| A: <50 nM, B: 50- to 100 nM, C: 101 - to 300 nM, D: 301- to 1,000 nM, E: 1,001 - to 3,000 nM | |
| 25 | C |
| 26 | A |
| 27 | A |
| 28 | B |
| 29 | A |
| 30 | A |
| 31 | B |
| 32 | A |
| 33 | A |
| 34 | A |
| 35 | A |
| 36 | A |
| 37 | A |
| 38 | C |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | C |
| 61 | A |
| 62 | C |
| 63 | C |
| 64 | A |
| 65 | D |
| 66 | A |
| 67 | C |
| 68 | A |
| 69 | D |
| 70 | A |
| 71 | D |
| 72 | A |
| 73 | C |
| 74 | C |
| 75 | E |
| 76 | B |
| 77 | D |
| 78 | A |
| 79 | D |
| 80 | B |
| 81 | A |
| 82 | A |
| 83 | C |
| 84 | A |
| 85 | A |
| 86 | C |
| 87 | B |
| 88 | A |
| 89 | C |
| 90 | C |
| 91 | C |
| 92 | C |
| 93 | E |
| 94 | E |
| 95 | E |
| 96 | E |
| 97 | A |
| 98 | C |

TABLE 66-continued

A: <50 nM, B: 50- to 100 nM,
C: 101 - to 300 nM, D: 301- to
1,000 nM, E: 1,001 - to 3,000 nM

| Examples | IC$_{50}$ |
|---|---|
| 99 | A |
| 100 | A |
| 101 | C |
| 102 | A |
| 103 | C |
| 104 | A |
| 105 | D |
| 106 | A |
| 107 | C |
| 108 | D |
| 109 | D |
| 110 | D |
| 111 | D |
| 112 | C |
| 113 | A |
| 114 | C |
| 115 | A |
| 116 | D |
| 117 | A |
| 118 | A |
| 119 | A |
| 120 | E |
| 121 | B |
| 122 | B |
| 123 | C |
| 124 | C |
| 125 | C |
| 126 | A |
| 127 | A |
| 128 | A |
| 129 | A |
| 130 | A |
| 131 | A |
| 132 | A |
| 133 | A |
| 134 | C |
| 135 | A |
| 136 | C |
| 137 | A |
| 138 | C |
| 139 | A |
| 140 | D |
| 141 | A |
| 142 | A |
| 143 | D |
| 144 | A |
| 145 | C |
| 146 | A |
| 147 | A |
| 148 | A |
| 149 | A |
| 150 | A |
| 151 | A |
| 152 | A |
| 153 | A |
| 154 | A |
| 155 | B |
| 156 | C |
| 157 | A |
| 158 | A |
| 159 | A |
| 160 | C |
| 161 | A |
| 162 | C |
| 163 | A |
| 164 | C |
| 165 | A |
| 166 | C |
| 167 | A |
| 168 | C |
| 169 | A |
| 170 | A |
| 171 | A |
| 172 | C |

TABLE 66-continued

A: <50 nM, B: 50- to 100 nM,
C: 101 - to 300 nM, D: 301- to
1,000 nM, E: 1,001 - to 3,000 nM

| Examples | IC$_{50}$ |
|---|---|
| 173 | B |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | B |
| 200 | B |
| 201 | B |
| 202 | B |
| 203 | B |
| 204 | B |
| 205 | B |
| 206 | C |
| 207 | C |
| 208 | C |
| 209 | C |
| 210 | C |
| 211 | C |
| 212 | C |
| 213 | C |
| 214 | C |
| 215 | C |
| 216 | C |
| 217 | C |
| 218 | D |
| 219 | D |
| 220 | D |
| 221 | D |
| 222 | D |
| 223 | D |
| 224 | D |
| 225 | D |
| 226 | E |
| 227 | E |
| 228 | E |
| 229 | A |
| 230 | A |
| 231 | A |
| 232 | A |
| 233 | C |
| 234 | D |
| 235 | E |
| 236 | E |
| 237 | A |
| 238 | A |
| 239 | C |
| 240 | D |
| 241 | A |
| 242 | A |
| 243 | D |
| 244 | E |
| 245 | A |
| 246 | A |

TABLE 66-continued

A: <50 nM, B: 50- to 100 nM, C: 101 - to 300 nM, D: 301- to 1,000 nM, E: 1,001 - to 3,000 nM

| Examples | IC$_{50}$ |
|---|---|
| 247 | A |
| 248 | A |
| 249 | B |
| 250 | C |
| 251 | A |
| 252 | A |
| 253 | A |
| 254 | D |
| 255 | C |
| 256 | A |
| 257 | C |
| 258 | A |
| 259 | A |
| 260 | D |
| 261 | A |
| 262 | A |
| 263 | A |
| 264 | A |
| 265 | A |
| 266 | A |
| 267 | A |
| 268 | A |
| 269 | A |
| 270 | A |
| 271 | D |
| 272 | A |
| 273 | A |
| 274 | A |
| 275 | E |
| 276 | D |
| 277 | A |
| 278 | E |
| 279 | A |
| 280 | A |
| 281 | D |
| 282 | A |
| 283 | A |
| 284 | A |
| 285 | A |
| 286 | A |
| 287 | A |
| 288 | A |
| 289 | A |
| 290 | A |
| 291 | C |
| 292 | B |
| 293 | E |
| 294 | B |
| 295 | A |
| 296 | B |
| 297 | D |
| 298 | A |
| 299 | C |
| 300 | A |
| 301 | B |
| 302 | C |
| 303 | E |
| 304 | A |
| 305 | A |
| 306 | A |
| 307 | D |
| 308 | C |
| 309 | E |
| 310 | A |
| 311 | B |
| 312 | A |
| 313 | B |
| 314 | C |
| 315 | E |
| 316 | A |
| 317 | A |
| 318 | D |
| 319 | A |
| 320 | A |
| 321 | A |
| 322 | C |
| 323 | C |
| 324 | B |
| 325 | E |
| 326 | A |
| 327 | A |
| 328 | C |
| 329 | B |
| 330 | D |
| 331 | B |
| 332 | E |
| 333 | C |
| 334 | A |
| 335 | A |
| 336 | A |
| 337 | A |
| 338 | A |
| 339 | A |
| 340 | A |
| 341 | B |
| 342 | B |
| 343 | A |
| 344 | A |
| 345 | A |
| 346 | A |
| 347 | B |
| 348 | C |
| 349 | A |
| 350 | A |
| 351 | A |
| 352 | A |
| 353 | B |
| 354 | B |

Rat P2X7 Functional Assay

The functional activity of compounds was determined by measuring changes in intracellular calcium concentration using a $Ca^{2+}$-sensitive fluorescent dye, Fluo-4 (Molecular Probes). The changes in fluorescent signal were monitored by the cell imaging technology by Hamamatsu Photonics's Functional Drug Screening System (FDSS). Increases in intracellular $Ca^{2+}$ concentration were readily detected upon activation with BzATP.

Cell Maintenance:

HEK293 cells stably expressing rat P2X7 (GenBank accession number NM_019256) were grown in Corning CellBIND cell culture flasks, in a 5% $CO_2$ humidified incubator to about 80% confluence. Media composition consisted of Dulbecco's Modified Eagle Medium (high glucose), 10% fetal bovine serum (BSA), 100 units/microL Penicillin, 100 microg/mL Streptomycin and 250 microg/mL Geneticine.

Protocol:

Day One:
1. Plate-out HEK293-human P2X7 cells (40 microL medium containing 10,000 cells per well) into poly-D-lysine coated 384-well plates (Corning) at 24 h prior to assay. Plate-out HEK293-rat P2X7 cells (40 microL medium containing 5,000 cells per well) into poly-D-lysine coated 384-well plates (BD Falcon) at 24 h prior to assay.
2. Incubate at 37° C. in 5% $CO_2$.

Day Two:
1. Wash each well with 80 microL of assay buffer (20 mM HEPES, 1×HBSS, pH 7.4 adjusted with NaOH) three times and leave 20 microL using plate washer, ELx-405 Select CW (BIO-TEK).

2. Add 20 microL of assay buffer containing 2.5 mM probenecid, 0.5 microM Fluo-4-AM (Molecular Probes) and 0.1% Pluronic F-127 to each well.
3. Incubate the plate at 37° C. in 5% $CO_2$ for 1 h.
4. Wash each well with 80 microL of assay buffer (see below) three times and leave 20 microL using plate washer, ELx-405 Select CW (BIO-TEK).
5. Test compounds were prepared at 100× the test concentration in DMSO by serial dilution with Biomek-FX liquid handling instrument. 33× diluted compound solutions in assay buffer were prepared in intermediate compound plate with Biomek-NX liquid handling instrument. A further 3× dilution occurred in below steps 6 and 7.
6. Add 20 microL of 33× diluted compound solutions into each well and leave the plate for 10 min under the dark at room temperature.
7. Measure activity by FDSS as follows:
   Set the assay plate on the stacker of FDSS.
   Start the detection of fluorescence intensity at 540 nm by 480 nm excitation.
   After 30 seconds, add 20 microL of assay buffer containing 30 microM BzATP (final 10 microM).

$IC_{50}$ values for compounds of the present invention were determined from 7-point dose-response studies. Curves were generated using the average of duplicate wells for each data point. Finally, the $IC_{50}$ values are calculated with the best-fit dose curve determined by XLfit (ID Business Solutions Ltd.).

Antagonistic activities with respect to the rat P2X7 receptor ($IC_{50}$<1 uM) of exemplified compounds are displayed in Table 67.

TABLE 67

| Examples |
|---|
| 1 |
| 2 |
| 3 |
| 6 |
| 7 |
| 8 |
| 9 |
| 10 |
| 11 |
| 12 |
| 13 |
| 14 |
| 16 |
| 18 |
| 19 |
| 20 |
| 21 |
| 22 |
| 23 |
| 24 |
| 25 |
| 26 |
| 27 |
| 28 |
| 29 |
| 32 |
| 33 |
| 34 |
| 35 |
| 36 |
| 37 |
| 38 |
| 39 |
| 40 |
| 41 |
| 42 |
| 43 |

TABLE 67-continued

| Examples |
|---|
| 44 |
| 45 |
| 46 |
| 47 |
| 48 |
| 49 |
| 50 |
| 51 |
| 52 |
| 53 |
| 54 |
| 55 |
| 56 |
| 57 |
| 58 |
| 59 |
| 60 |
| 61 |
| 62 |
| 64 |
| 66 |
| 67 |
| 68 |
| 70 |
| 72 |
| 74 |
| 76 |
| 78 |
| 80 |
| 81 |
| 82 |
| 83 |
| 84 |
| 85 |
| 87 |
| 88 |
| 89 |
| 97 |
| 100 |
| 102 |
| 104 |
| 106 |
| 107 |
| 108 |
| 110 |
| 111 |
| 115 |
| 117 |
| 118 |
| 121 |
| 122 |
| 126 |
| 127 |
| 128 |
| 129 |
| 130 |
| 131 |
| 132 |
| 133 |
| 134 |
| 135 |
| 136 |
| 137 |
| 139 |
| 141 |
| 142 |
| 144 |
| 146 |
| 148 |
| 149 |
| 150 |
| 152 |
| 153 |
| 154 |
| 157 |
| 158 |
| 159 |
| 161 |

TABLE 67-continued

| Examples |
|---|
| 163 |
| 165 |
| 167 |
| 168 |
| 169 |
| 170 |
| 171 |
| 172 |
| 174 |
| 175 |
| 176 |
| 177 |
| 178 |
| 179 |
| 180 |
| 182 |
| 183 |
| 184 |
| 185 |
| 187 |
| 189 |
| 190 |
| 192 |
| 193 |
| 195 |
| 196 |
| 199 |
| 201 |
| 203 |
| 205 |
| 206 |
| 208 |
| 221 |
| 229 |
| 230 |
| 231 |
| 232 |
| 233 |
| 234 |
| 237 |
| 238 |
| 239 |
| 240 |
| 241 |
| 242 |
| 245 |
| 246 |
| 247 |
| 248 |
| 249 |
| 250 |
| 251 |
| 252 |
| 253 |
| 254 |
| 256 |
| 257 |
| 258 |
| 259 |
| 260 |
| 261 |
| 262 |
| 263 |
| 264 |
| 265 |
| 266 |
| 267 |
| 268 |
| 269 |
| 270 |
| 272 |
| 273 |
| 274 |
| 277 |
| 279 |
| 280 |
| 281 |
| 282 |
| 283 |
| 284 |
| 285 |
| 286 |
| 287 |
| 288 |
| 289 |
| 290 |
| 291 |
| 292 |
| 294 |
| 295 |
| 296 |
| 297 |
| 298 |
| 299 |
| 300 |
| 301 |
| 302 |
| 303 |
| 304 |
| 305 |
| 306 |
| 307 |
| 308 |
| 309 |
| 310 |
| 311 |
| 312 |
| 313 |
| 314 |
| 315 |
| 316 |
| 317 |
| 318 |
| 319 |
| 320 |
| 321 |
| 322 |
| 323 |
| 324 |
| 326 |
| 327 |
| 328 |
| 329 |
| 333 |
| 334 |
| 335 |
| 336 |
| 337 |
| 338 |
| 339 |
| 340 |
| 341 |
| 342 |
| 343 |
| 344 |
| 345 |
| 346 |
| 347 |
| 349 |
| 350 |
| 351 |
| 352 |

All tested compounds of the invention show higher $IC_{50}$ values in human dofetilide binding than $IC_{50}$ values in P2X7 functional assay described above.

Metabolic Stability Assay:

Human Liver Microsomal Clearance of Test Compounds.

The in vitro elimination half-life estimates ($t_{1/2}$) and in vitro intrinsic clearance values ($hCL_{int,u}$) were observed from metabolic stability in human liver microsomes.

Incubation with Liver Microsomes

Stock solutions of test compound were prepared at 10 mM (as active compound) in DMSO. The stock solution was diluted immediately before use to 50 microM using 50% acetonitrile-water mixture solution (v/v) to produce working solution. The NADPH-regenerating solution was prepared on the day of analysis by diluting 1 volume of 80 mM NADP+ (ORIENTAL YEAST) with 1 volume of 240 mM $MgCl_2$ (WAKO) and 1 volume of 320 mM of glucose-6-phosphate (Sigma-Aldrich) and 1 volume of 32 U/mL of glucose-6-phosphate dehydrogenase (Sigma-Aldrich) and 2 volume of 200 mM UDP-GA (Nacalai) and 2 volume of 6.6 mM beta-NAD (ORIENTAL YEAST), respectively. Immediately prior to use, the reaction mixture was produced mixing 1 volume of the NADPH-regenerating solution with 6.8 volume of 125 mM potassium phosphate assay buffer. Human liver microsomes (XenoTech, pooled, mixed-gender human microsomes) were diluted to 2.5 mg protein/mL using 125 mM potassium phosphate assay buffer. Two microliters of working solution of each test compound and 78 microL of reaction mixture were added to 96 well cluster tubes (Micronic) in duplicate.

The tubes were placed in an incubator at 37° C. for 5 minutes before adding the human liver microsomes. A 20 microL of aliquot of the human liver microsome solution (2.5 mg protein/mL) was added to each original well to initiate metabolism. Incubation was performed at 37° C. At 15 minutes, the plate was removed from the incubator and a solution containing internal standard (200 microL, 1 microM reserpine, 50 nM buspirone and 1 microM tolbutamide in 100% acetonitrile) was added to each well. The plate was then spun in a centrifuge at 3500 rpm for 15 minutes at 4° C. A supernatant was transferred from each well to a 96-well shallow plate and then diluted with 4 volume of the mobile phase (A).

LC-MS/MS Analysis

Quantitative analysis of test compound in quenched reaction mixture was performed using the LC-MS/MS system, which consisted of an Agilent 1100 series gradient HPLC pump (Agilent Technologies), a CTC HTS PAL Autosampler (AMR), and a Sciex API 3200 triple quadrupole mass spectrometer (Sciex) equipped with a turbo ionspray interface. The Chromatographic separation was achieved using reverse phase HPLC with an Inert Sustain RP C18 50×2.1 mm column (GL Science) or Capcell Pak RP C18 50×2.1 mm column (Shiseido). The column temperature was 40° C., and the flow rate was 0.4 mL/min. The mobile phase consisted of 2 solvents: (A) 0.1% formic acid in water and (B) acetonitrile or 0.1% formic acid in acetonitrile. The compounds were eluted with a step gradient achieving 5% to 90% of B in 0.7 min, 90% of B in 1.3 min and then returned to initial conditions for equilibration (1.5 or 1.6 min). The mass spectrometer was operated in multiple-reaction-monitoring mode. Integration of test compound and internal standard peak was performed using Analyst Software (version 1.6). The area ratio of each test compound was calculated by comparing the peak area of the compound to the peak area of an internal standard.

Calculation of Human Liver Microsomal Intrinsic Clearance ($hCL_{int,u}$)

The mean peak area ratios were calculated by averaging the peak area ratios (n=2) of a compound and internal standard for each sample. Metabolic stability was determined by plotting the natural logarithm of the mean peak area ratio of unchanged test compound as a function of time. Percent remaining was calculated by determining the ratio of the mean peak area ratio at incubation time to the mean peak area ratio of the time-zero samples. The rate of loss of test compound was calculated using the equation $k=[Ln(C_0)-Ln(C)]$/incubation time, where $C_0$ was the initial mean peak area ratio of the test compound, C was the mean peak area ratio of test compound remaining after incubation ($C=C_0\times$ remaining ratio), and the incubation time was 15 min. The $t_{1/2}$ was estimated using the equation $t_{1/2}=0.693/k$. The $hCL_{int,u}$ was estimated using the equation $hCL_{int,u}=k/$(microsomal protein concentration)×(microsomal protein per gram of liver)×(liver mass per kilogram of body mass)/ (human microsomal fu), where the microsomal protein concentration was 0.5 mg/mL, and the physical and physiological scaling factors were used such as the microsomal protein per gram of liver (48.8 mg) and, the liver mass per kilogram of body mass (25.7 g), and the human microsomal fu was determined experimentally from the human liver microsomal binding assay.

The compounds of this invention show preferable stability, which show the abovementioned practical use.

Drug-Drug Interaction Assay

Cytochrome P450 Inhibition of Test Compounds.

Incubation with Recombinant CYP and Chemiluminescent Probes

CYP inhibition assays (CYP1A2, 2B6, 2C8, 2C9, 2C19, 2D6 and 3A4) were performed with recombinant CYP enzyme (BD Gentest) and Promega assay kits (P450-Glo Assays) in 384 well plate (Corning). Each product's catalog number is shown in Table 68.

Stock solutions of test compound were prepared at 10 mM (as active compound) in DMSO. NADPH-regenerating solution for each well was prepared on the day of analysis by diluting 0.4 microL of NADPH-A reagent (BD Gentest), 0.08 microL of NADPH-B reagent (BD Gentest) and 3.52 microL of water, for CYP 1A2, 2B6, 2C8, 2C9, 2C19 and 2D6. For CYP3A4, 1.6 microL of 1 M $KPO_4$, 0.4 microL of NADPH-A reagent and 0.08 microL of NADPH-B reagent, and 1.92 microL of water was mixed for each well. CYP enzyme mixture was prepared by following mixing ratio: 0.96 microL of water, 0.8 microL of 1 M $KPO_4$, 0.16 microL of Luciferin-ME, CYP1A2 Enzyme 0.08 microL/well for CYP1A2, 1.176 microL of water, 0.8 microL of 1 M $KPO_4$, 0.008 microL of Luciferin-2B6, CYP2B6 Enzyme 0.016 microL/well for CYP2B6, 1.04 microL of water, 0.4 microL of 1 M $KPO_4$, 0.24 microL of Luciferin-ME, CYP2C8 Enzyme 0.32 microL/well for CYP2C8, 1.56 microL of water, 0.2 microL of 1 M $KPO_4$, 0.16 microL of Luciferin-H, CYP2C9 Enzyme 0.08 microL/well for CYP2C9, 1.552 microL of water, 0.4 microL of 1 M $KPO_4$, 0.008 microL of Luciferin-H EGE, CYP2C19 Enzyme 0.04 microL/well for CYP2C19, 1.136 microL of water, 0.8 microL of 1 M $KPO_4$, 0.024 microL of Luciferin-ME EGE, CYP2D6 Enzyme 0.04 microL/well for CYP2D6, 1.916 microL of 100 mM Tris-HCl, 0.004 microL of Luciferin-PPXE, CYP3A4 Enzyme 0.08 microL/well for CYP3A4. Four microL of NADPH-regenerating solution was placed in 384 well plate, and then 2 microL of stock solution of test compounds and 2 microL of CYP enzyme mixture were added into each well. The plate was spun down and incubated at each condition as shown in Table 69. After incubation, 8 microL of Luciferin Detection Reagent for each CYP enzyme was added into each well and stirred by plate shaker (BioShake XP, WAKEN B TECH) at 1000 rpm for 1 min. The plate was incubated for 30 min at room temperature, protected from light. Luminescence was measured by luminometer (Ultra, Tecan and EnVision, PerkinElmer). Luminescence signals were used to determine percent inhibition at 10 microM of test compound. A separate control incubation for chemiluminescence contained test compound (10 microM) and control CYPs.

TABLE 68

| CYP isoforms | P450-GloAssay Kit Cat No. | Human CYP Enzymes (BD Gentest) Cat No. |
|---|---|---|
| CYP1A2 | V8772 | 456203 |
| CYP2B6 | V8322 | 456255 |
| CYP2C8 | V8782 | 456252 |
| CYP2C9 | V8792 | 456258 |
| CYP2C19 | V8882 | 456259 |
| CYP2D6 | V8892 | 456217 |
| CYP3A4 | V8912 | 456202 |

TABLE 69

| CYP isoforms | Enzyme (pmol) | Substrate concentration (μM) | Incubation time(min)/ Temperature |
|---|---|---|---|
| CYP1A2 | 0.08 | 100 | 45/room temperature |
| CYP2B6 | 0.016 | 3 | 30/room temperature |
| CYP2C8 | 0.08 | 150 | 90/37° C. |
| CYP2C9 | 0.08 | 100 | 30/37° C. |
| CYP2C19 | 0.04 | 10 | 30/room temperature |
| CYP2D6 | 0.04 | 30 | 30/room temperature |
| CYP3A4 | 0.08 | 25 | 30/room temperature |

The compounds of this invention show preferable results, which show the abovementioned practical use.

To summarize the above metabolism assays, all the compounds of the present invention show unexpectedly preferable results in the HLM assay and/or in the drug-drug interaction assay comparing with the closest compounds. Therefore, all the compounds of the present invention have excellent pharmacokinetic properties.

hERG Assay

The hERG (Human ether-a-go-go-related gene) channel inhibitory activity and the QT prolonging action of the compound of the present invention can be confirmed in the suitable methods known to skilled in the art. For example, hERG channel inhibitory activity of compounds of the present invention have been confirmed in electrophysiology assay (Chanchin, M. et al., Folia Pharmacol. Jpn., 2002, 119, 345-351).

All tested compounds of the invention show higher $IC_{50}$ values in hERG assay than $IC_{50}$ values in P2X7 functional assay described above.

All publications, including but not limited to, issued patents, patent applications, and journal articles, cited in this application are each herein incorporated by reference in their entirety. Although the invention has been described above with reference to the disclosed embodiments, those skilled in the art would readily appreciate that the specific experiments detailed are only illustrative of the invention. It should be understood that various modifications can be made without departing from the spirit of the invention. Accordingly, the invention is limited only by the claims.

The invention claimed is:
1. A compound represented by the following formula (I):

or a pharmaceutically acceptable salt thereof,
wherein:
X is N or N-oxide;
n is 0 or 1;
$R^1$ is selected from the group consisting of:
(1) hydrogen, (2) halogen, (3) hydroxyl, (4) —$NH_2$, (5) —NH—$C_{1-6}$ alkyl and (6) —S(O)$_m$—$C_{1-6}$ alkyl;
wherein m is independently 0, 1 or 2;
$R^2$ is selected from the group consisting of:
(1) hydrogen, (2) halogen, (3) $C_{1-6}$ alkyl and (4) —O—$C_{1-6}$ alkyl; wherein the $C_{1-6}$ alkyl or the —O—$C_{1-6}$ alkyl is unsubstituted or substituted with one or more substituents independently selected from the group consisting of: halogen, hydroxyl, —O—$C_{1-6}$ alkyl, —CN, —$NR^{9a}R^{10a}$, —(C=O)—$R^{9a}$, —(C=O)—$NR^{9a}R^{10a}$ and —S(O)$_m$—$R^{9a}$; wherein m is independently 0, 1 or 2;
$R^1$ may form =$CH_2$ or =O with $R^2$;
$R^3$ is independently selected from the group consisting of:
(1) hydrogen, (2) halogen, (3) $C_{1-6}$ alkyl and (4) —O—$C_{1-6}$ alkyl;
p is 0, 1, 2 or 3;
when p is 2 or 3, each $R^3$ is the same or different;
$R^4$ is selected from the group consisting of:
(1) hydrogen, (2) halogen and (3) hydroxyl;
$R^5$ is hydrogen or $C_{1-6}$ alkyl;
$R^6$ is selected from the group consisting of:
(1) hydrogen, (2) $C_{1-6}$ alkyl, (3) hydroxy$C_{1-6}$ alkyl, (4) $C_{1-6}$ alkoxy $C_{1-6}$ alkyl and (5) heterocyclyl $C_{1-6}$ alkyl;
$R^5$ may form a saturated 3 to 7 membered ring with $R^6$ which may contain a nitrogen atom, an oxygen atom, a sulfur atom or a double bond; or a saturated or unsaturated bicyclic 9 to 10 membered ring with $R^6$ which may contain a nitrogen atom, an oxygen atom or a sulfur atom;
wherein the saturated 3 to 7 membered ring or the saturated or unsaturated bicyclic 9 to 10 membered ring is optionally substituted with 1 to 6 substituents independently selected from the group consisting of: (1) hydroxyl, (2) halogen, (3) —O-aryl and (4) —O—$C_{1-6}$ alkylaryl;
$R^{7a}$ and $R^{7b}$ are independently selected from the group consisting of:
(1) hydrogen, (2) halogen, (3) hydroxyl, (4) $C_{1-6}$ alkyl and (5) —$NR^{9b}R^{10b}$;
$R^{7a}$ may form a 3 to 7 membered ring with $R^5$ which may contain a nitrogen atom or an oxygen atom; or
$R^{7a}$ may form a 3 to 7 membered ring with $R^{7b}$ which may contain a nitrogen atom or an oxygen atom;

q is 0 or 1;
R$^8$ is
C$_{3-10}$ cycloalkyl, wherein the C$_{3-10}$ cycloalkyl is unsubstituted or substituted with one or more halogen or hydroxyl; or (7) heterocyclyl, (8) aryl, or (11) heteroaryl, wherein the heterocyclyl, aryl, or heteroaryl is unsubstituted or substituted with one or more substituents independently selected from the group consisting of: halogen, hydroxyl, —O—C$_{1-6}$ alkyl, —O—C$_{1-6}$ haloalkyl, —C$_{3-7}$ cycloalkyl, —O—C$_{3-7}$ cycloalkyl, hydroxyl-C$_{1-6}$ alkoxy, —CN, —NR$^{9b}$R$^{10b}$, —(C=O)—R$^{9b}$, —(C=O)—NR$^{9b}$R$^{10b}$, —NR$^{9b}$—(C=O)—R$^{10b}$, —NR$^{11}$—(C=O)—NR$^{9b}$R$^{10b}$, —NR$^{9b}$—(C=O)—OR$^{10b}$, —NR$^{9b}$—S(O)$_m$—R$^{10b}$, —NR$^{11}$—S(O)$_m$—NR$^{9b}$R$^{10b}$, —S(O)$_m$—R$^{9b}$ and C$_{1-6}$ alkyl which may be substituted one or more with halogen, hydroxyl, —O—C$_{1-6}$ alkyl or NR$^{9b}$R$^{10b}$, wherein m is independently 0, 1 or 2;
R$^{9a}$, R$^{9b}$, R$^{10a}$, R$^{10b}$ or R$^{11}$ is independently selected from the group consisting of:
(1) hydrogen, (2) hydroxyl, (3) C$_{1-6}$ alkyl and (4) hydroxyC$_{1-6}$ alkyl;
R$^{9a}$ may form a 4 to 7 membered ring with R$^{10a}$ which may contain one or more independently selected from the group consisting of: nitrogen atom, oxygen atom, sulfur atom and double bond, wherein the 4 to 7 membered ring is optionally substituted with 1 to 6 substituents independently selected from the group consisting of: (1) hydroxyl, (2) halogen, (3) C$_{1-6}$ alkyl and (4) —O—C$_{1-6}$ alkyl;
R$^{9b}$ may form a 4 to 7 membered ring with R$^{10b}$ which may contain one or more independently selected from the group consisting of: nitrogen atom, oxygen atom, sulfur atom and double bond, wherein the 4 to 7 membered ring is optionally substituted with 1 to 6 substituents independently selected from the group consisting of: (1) hydroxyl, (2) halogen and (3) C$_{1-6}$ alkyl.

2. The compound of claim 1:
or a pharmaceutically acceptable salt thereof,
wherein:
X is N;
R$^5$ is hydrogen or C$_{1-6}$ alkyl;
R$^6$ is selected from the group consisting of:
(1) hydrogen and (2) C$_{1-6}$ alkyl;
R$^5$ may form a saturated or unsaturated bicyclic 9 to 10 membered ring with R$^6$ which may contain a nitrogen atom, an oxygen atom or a sulfur atom; wherein the saturated or unsaturated bicyclic 9 to 10 membered ring is optionally substituted with 1 to 6 substituents independently selected from the group consisting of: (1) hydroxyl, (2) halogen and (3) —O-aryl;
R$^{7a}$ and R$^{7b}$ are independently selected from the group consisting of:
(1) hydrogen, (4) C$_{1-6}$ alkyl and (5) —NR$^{9b}$R$^{10b}$;
R$^{7a}$ may form a 3 to 7 membered ring with R$^5$ which may contain a nitrogen atom or an oxygen atom; or
R$^{7a}$ may form a 3 to 7 membered ring with R$^{7b}$ which may contain a nitrogen atom or an oxygen atom;
R$^8$ is
(5) C$_{3-10}$ cycloalkyl, wherein the C$_{3-10}$ cycloalkyl is unsubstituted or substituted with one or more halogen or hydroxyl; (7) heterocyclyl, (8) aryl, or (11) heteroaryl, wherein the heterocyclyl, aryl, or heteroaryl is unsubstituted or substituted with one or more substituents independently selected from the group consisting of: halogen, hydroxyl, —O—C$_{1-6}$ alkyl, —O—C$_{1-6}$ haloalkyl, —CN and C$_{1-6}$ alkyl which may be substituted one or more with halogen, hydroxyl, —O—C$_{1-6}$ alkyl or NR$^{9b}$R$^{10b}$.

3. A compound represented by the following formula (M):

(M)

or a pharmaceutically acceptable salt thereof,
wherein:
n is 0 or 1;
R$^1$ is selected from the group consisting of:
(1) hydrogen, (2) halogen, (3) hydroxyl, (4) —NH$_2$, (5) —NH—C$_{1-6}$ alkyl and (6) —S(O)$_m$—C$_{1-6}$ alkyl;
wherein m is independently 0, 1 or 2;
R$^2$ is selected from the group consisting of:
(1) hydrogen, (2) halogen, (3) C$_{1-6}$ alkyl and (4) —O—C$_{1-6}$ alkyl; wherein the C$_{1-6}$ alkyl or the —O—C$_{1-6}$ alkyl is unsubstituted or substituted with one or more substituents independently selected from the group consisting of: halogen, hydroxyl, —O—C$_{1-6}$ alkyl, —CN, —NR$^{9a}$R$^{10a}$, —(C=O)—R$^{9a}$, —(C=O)—NR$^{9a}$R$^{10a}$ and —S(O)$_m$—R$^{9a}$, wherein m is independently 0, 1 or 2;
R$^1$ may form =CH$_2$ or =O with R$^2$;
R$^3$ is independently selected from the group consisting of:
(1) hydrogen, (2) halogen, (3) C$_{1-6}$ alkyl and (4) —O—C$_{1-6}$ alkyl;
p is 0, 1, 2 or 3;
when p is 2 or 3, each R$^3$ is the same or different;
R$^4$ is selected from the group consisting of:
(1) hydrogen, (2) halogen and (3) hydroxyl;
R$^5$ is hydrogen or C$_{1-6}$ alkyl;
R$^6$ is selected from the group consisting of:
(1) hydrogen, (2) C$_{1-6}$ alkyl, (3) hydroxyC$_{1-6}$ alkyl, (4) C$_{1-6}$ alkoxy C$_{1-6}$ alkyl and (5) heterocyclyl C$_{1-6}$ alkyl;
R$^5$ may form a saturated 3 to 7 membered ring with R$^6$ which may contain a nitrogen atom, an oxygen atom, a sulfur atom or a double bond; wherein the saturated 3 to 7 membered ring is optionally substituted with 1 to 6 substituents independently selected from the group consisting of: (1) hydroxyl, (2) halogen, (3) —O-aryl and (4) —O—C$_{1-6}$ alkylaryl;
R$^{9a}$, R$^{9b}$, R$^{10a}$ or R$^{10b}$ is independently selected from the group consisting of:
(1) hydrogen, (2) hydroxyl, (3) C$_{1-6}$ alkyl and (4) hydroxyC$_{1-6}$ alkyl;
R$^{9a}$ may form a 4 to 7 membered ring with R$^{10a}$ which may contain a nitrogen atom or an oxygen atom; wherein the 4 to 7 membered ring is optionally substituted with 1 to 6 substituents independently selected from the group consisting of: (1) hydroxyl, (2) halogen, (3) C$_{1-6}$ alkyl and (4) —O—C$_{1-6}$ alkyl;

$R^{9b}$ may form a 4 to 7 membered ring with $R^{10b}$ which may contain a nitrogen atom or an oxygen atom; wherein the 4 to 7 membered ring is optionally substituted with 1 to 6 substituents independently selected from the group consisting of: (1) hydroxyl, (2) halogen and (3) $C_{1-6}$ alkyl;

$R^{12}$, $R^{13}$, $R^{14}$ and $R^{15}$ are independently selected from the group consisting of:

(1) hydrogen, (2) hydroxyl, (3) halogen, (4) $C_{1-6}$ alkyl, (5) —O—$C_{1-6}$ alkyl and (6) CN; wherein the $C_{1-6}$ alkyl or the —O—$C_{1-6}$ alkyl is unsubstituted or substituted with one or more substituents independently selected from the group consisting of: halogen, hydroxyl, —O—$C_{1-6}$ alkyl and $NR^{9b}R^{10b}$; or $R^{12}$ may form a 5 to 7 membered ring with $R^5$ which may contain one or more independently selected from the group consisting of: nitrogen atom and oxygen atom.

4. The compound of claim 3:
or a pharmaceutically acceptable salt thereof,
wherein:
n is 1;
$R^1$ is hydrogen or hydroxyl;
$R^2$ is methyl which is unsubstituted or substituted with one or more substituents independently selected from the group consisting of: halogen, hydroxyl, —O—$C_{1-6}$ alkyl, —CN and —$NR^{9a}R^{10a}$;
p is 0;
$R^4$ is hydrogen or fluoro;
$R^5$ and $R^6$ are independently selected from the group consisting of: (1) hydrogen and (2) $C_{1-6}$ alkyl;
$R^{12}$, $R^{13}$ and $R^{14}$ are independently selected from the group consisting of: (1) hydrogen, (3) halogen, and (4) $C_{1-3}$ alkyl which may be substituted one or more with hydroxyl;
$R^{15}$ is hydrogen.

5. A method of treating pain or neuropathic pain in a subject in need thereof, the method comprising:
administering to the subject in need thereof a therapeutically effective amount of the compound of claim 1, or a pharmaceutically acceptable salt thereof.

6. A method of treating pain or neuropathic pain in a subject in need thereof, the method comprising:
administering to the subject in need thereof a therapeutically effective amount of the compound of claim 3, or a pharmaceutically acceptable salt thereof.

* * * * *